United States Patent
Brown et al.

(10) Patent No.: US 8,748,462 B2
(45) Date of Patent: Jun. 10, 2014

(54) SPIROCYCLIC GPR40 MODULATORS

(75) Inventors: Sean P. Brown, San Francisco, CA (US); Paul Dransfield, San Francisco, CA (US); Xiaohui Du, Belmont, CA (US); Zice Fu, Foster City, CA (US); Jonathan Houze, San Mateo, CA (US); XianYun Jiao, Belmont, CA (US); Sujen Lai, Burlingame, CA (US); An-Rong Li, Foster City, CA (US); Jiwen Liu, Foster City, CA (US); Zhihua Ma, Foster City, CA (US); Julio C. Medina, San Carlos, CA (US); Vatee Pattaropong, Burlingame, CA (US); Wang Shen, San Mateo, CA (US); Marc Vimolratana, San Francisco, CA (US); Yingcai Wang, Millbrae, CA (US); Zhongyu Wang, Ewing, NJ (US); Ming Yu, Foster City, CA (US); Liusheng Zhu, Foster City, CA (US)

(73) Assignee: Amgen Inc., Thousand Oaks, CA (US)

(*) Notice: Subject to any disclaimer, the term of this patent is extended or adjusted under 35 U.S.C. 154(b) by 220 days.

(21) Appl. No.: 13/119,951

(22) PCT Filed: Oct. 13, 2009

(86) PCT No.: PCT/US2009/060549
§ 371 (c)(1),
(2), (4) Date: Mar. 18, 2011

(87) PCT Pub. No.: WO2010/045258
PCT Pub. Date: Apr. 22, 2010

(65) Prior Publication Data
US 2011/0190330 A1  Aug. 4, 2011

Related U.S. Application Data

(60) Provisional application No. 61/196,271, filed on Oct. 15, 2008.

(51) Int. Cl.
| | |
|---|---|
| A61K 31/19 | (2006.01) |
| C07C 69/76 | (2006.01) |
| C07D 211/72 | (2006.01) |
| C07D 211/84 | (2006.01) |
| C07D 213/62 | (2006.01) |
| A61K 31/44 | (2006.01) |

(52) U.S. Cl.
USPC ............. 514/345; 546/303; 560/56; 514/569

(58) Field of Classification Search
CPC .... A61K 31/44; C07D 211/00; C07D 213/00; C07D 215/00; C07D 217/00; C07D 219/00; C07D 221/00
See application file for complete search history.

(56) References Cited

U.S. PATENT DOCUMENTS 3,507,881 A    4/1970   Sandberg et al.
4,760,089 A    7/1988   Chambers et al.
(Continued)

FOREIGN PATENT DOCUMENTS

AU    A 27141/77    1/1979
AU    A 52306/93    6/1994
(Continued)

OTHER PUBLICATIONS

Carey, FA. Organic Chemistry 6th Ed. McGraw Hill. 2006, chapter 1, p. 9.*

(Continued)

*Primary Examiner* — Rita Desai
*Assistant Examiner* — Ben S Michelson
(74) *Attorney, Agent, or Firm* — Bernard P. Friedrichsen

(57) ABSTRACT

The present invention provides compounds useful, for example, for treating metabolic disorders in a subject. Such compounds have the general formula IA, IB, I'A or I'B:

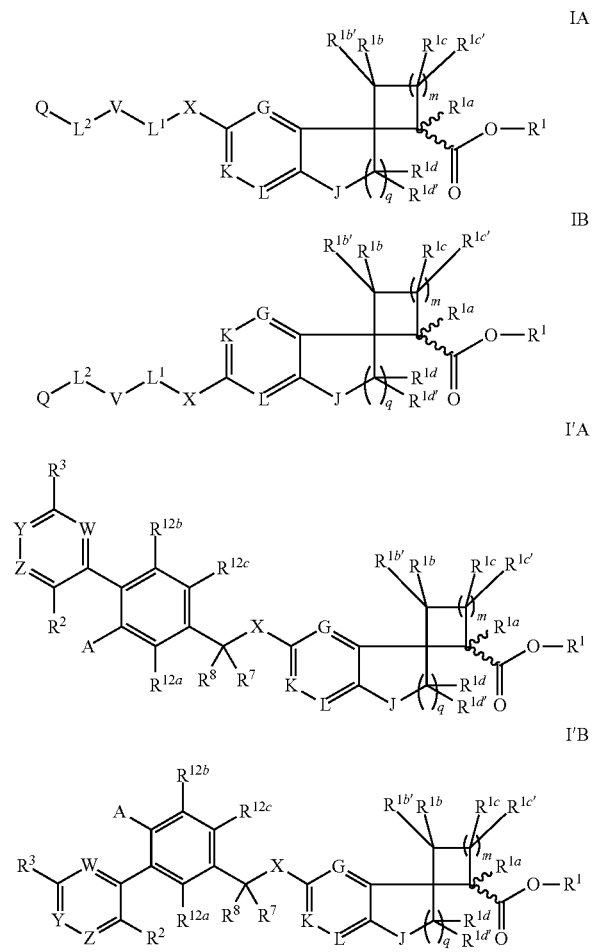

where the definitions of the variables are provided herein. The present invention also provides compositions that include, and methods for using, the compounds in preparing medicaments and for treating metabolic disorders such as, for example, type II diabetes.

25 Claims, No Drawings

(56) References Cited

U.S. PATENT DOCUMENTS

| | | | |
|---|---|---|---|
| 5,312,960 A | 5/1994 | Krämer et al. |
| 6,037,367 A | 3/2000 | Christensen, IV et al. |
| 6,506,757 B1 | 1/2003 | Tajima et al. |
| 6,620,832 B2 | 9/2003 | Eastwood |
| 6,645,939 B1 | 11/2003 | Durette et al. |
| 6,710,063 B1 | 3/2004 | Chao et al. |
| 6,723,740 B2 | 4/2004 | Chao et al. |
| 6,875,780 B2 | 4/2005 | Auerbach et al. |
| 6,906,046 B2 | 6/2005 | Jackson et al. |
| 6,939,875 B2 | 9/2005 | Auerbach et al. |
| 6,964,983 B2 | 11/2005 | Auerbach et al. |
| 7,326,732 B2 | 2/2008 | Oxford et al. |
| 7,338,960 B2 | 3/2008 | Bell et al. |
| 7,345,068 B2 | 3/2008 | Endou et al. |
| 2004/0058965 A1 | 3/2004 | Momose et al. |
| 2005/0089866 A1 | 4/2005 | Hinuma et al. |
| 2005/0119256 A1 | 6/2005 | Endo et al. |
| 2006/0003344 A1 | 1/2006 | Houseknecht et al. |
| 2006/0004012 A1 | 1/2006 | Akerman et al. |
| 2006/0270724 A1 | 11/2006 | Houze et al. |
| 2007/0066647 A1 | 3/2007 | Akerman et al. |
| 2007/0149608 A1 | 6/2007 | Yasuma et al. |
| 2007/0244155 A1 | 10/2007 | Sharma et al. |
| 2007/0265332 A1 | 11/2007 | Ge et al. |
| 2008/0090840 A1 | 4/2008 | Beck et al. |
| 2008/0119511 A1 | 5/2008 | Brown et al. |
| 2009/0111859 A1 | 4/2009 | Brown et al. |
| 2009/0137561 A1 | 5/2009 | Brown et al. |
| 2010/0144806 A1 | 6/2010 | Yasuma et al. |

FOREIGN PATENT DOCUMENTS

| | | | |
|---|---|---|---|
| CA | 2111035 | | 6/1994 |
| DE | 199 41 567 | A1 | 4/2000 |
| EP | 0 250 264 | A1 | 12/1987 |
| EP | 0 414 289 | B1 | 2/1994 |
| EP | 1 357 115 | A1 | 10/2003 |
| EP | 1 380 562 | A1 | 1/2004 |
| EP | 1 535 915 | A1 | 6/2005 |
| EP | 1 559 422 | A1 | 8/2005 |
| EP | 1 630 152 | A1 | 3/2006 |
| EP | 1 731 505 | A1 | 12/2006 |
| JP | 10316641 | A | 2/1998 |
| JP | 2001242165 | | 9/2001 |
| JP | 2002003368 | | 1/2002 |
| WO | WO 93/23040 | | 11/1993 |
| WO | WO 93/23041 | | 11/1993 |
| WO | WO 95/01326 | | 1/1995 |
| WO | WO 95/01348 | | 1/1995 |
| WO | WO 97/12867 | | 4/1997 |
| WO | WO 99/11255 | | 3/1999 |
| WO | WO 00/63196 | | 10/2000 |
| WO | WO 01/00603 | A1 | 1/2001 |
| WO | WO 01/36351 | A2 | 5/2001 |
| WO | WO 01/36365 | A2 | 5/2001 |
| WO | WO 02/057783 | A2 | 7/2002 |
| WO | WO 02/062774 | A1 | 8/2002 |
| WO | WO 02/100403 | A1 | 12/2002 |
| WO | WO 03/074050 | A1 | 9/2003 |
| WO | WO 03/099793 | A1 | 12/2003 |
| WO | WO 2004/000315 | A1 | 12/2003 |
| WO | WO 2004/092117 | A1 | 10/2004 |
| WO | WO 2004/106276 | A1 | 12/2004 |
| WO | WO 2005/051890 | A1 | 6/2005 |
| WO | WO 2005/058848 | A1 | 6/2005 |
| WO | WO 2005/063725 | A1 | 7/2005 |
| WO | WO 2005/063729 | A1 | 7/2005 |
| WO | WO 2005/086661 | A2 | 9/2005 |
| WO | WO 2005/087710 | A1 | 9/2005 |
| WO | WO 2006/001092 | A1 | 1/2006 |
| WO | WO 2006/011615 | A1 | 2/2006 |
| WO | WO 2006/083612 | A1 | 8/2006 |
| WO | WO 2006/083781 | A1 | 8/2006 |
| WO | WO 2007/008541 | A2 | 1/2007 |
| WO | WO 2007/013689 | A1 | 2/2007 |
| WO | WO 2007/049050 | A2 | 5/2007 |
| WO | WO 2007/123225 | A1 | 11/2007 |
| WO | WO 2007/131619 | A1 | 11/2007 |
| WO | WO 2007/131620 | A1 | 11/2007 |
| WO | WO 2007/131622 | A1 | 11/2007 |
| WO | WO 2008/001931 | A2 | 1/2008 |
| WO | WO 2008/054675 | A2 | 5/2008 |
| WO | WO 2008/130514 | A1 | 10/2008 |

OTHER PUBLICATIONS

Nakamura, I. et al. Transition-Metal-Catalyzed Reactions in Heterocyclic Synthesis. Chem. Rev. 2004, vol. 104, p. 2127.*

Chattopadhyay, SK. et al. Formation of medium-ring heterocycles by diene and enyne metathesis. Tetrahedron. 2007, vol. 63, p. 3919.*

Cho, HS. et al. Photophysical Properties of Porphyrin Tapes. JACS. 2002, vol. 124, p. 14643, chart 1.*

Dorwold, FZ. Side Reactions in Organic Synthesis. Wiley. 2005, preface.*

International Search Report from parent PCT Application No. PCT/US2009/060549 mailed on May 11, 2010.

Bachmann, W. E. et al., "The Synthesis of an Analog of the Sex Hormones," *J. Am. Chem. Soc.*, 64, 94-97 (1942).

Berthelot et al., "Synthesis and Pharmacological Evaluation of γ-Aminobutyric Acid Analogues. New Ligand for GABA$_B$ Sites," *J. Med. Chem.*, 30, 743-746 (1987).

Booth, C. J. et al., "The Synthesis and Transition Temperatures of Novel Low Molar Mass Chosesteric materials Derives from (R)-2-(4-Hydroxyphenoxy)propanoic Acid," Mol. Cryst. Liq. Cryst., vol. 210, pp. 31-57 (1992).

Booth, C. J. et al., "The Influence of the Liquid Crystalline Core Geometry on the Mesogenicity of Novel Chiral 2-(4-Substituted-phenoxy)propanonitriles," Liquid Crystals, vol. 16(6), pp. 925-940, (1994).

Boyle, Thomas F. et al., "Applications of the Spiroannulation of Tetralins with Alkynes; Towards New Anti-Estrogenic Compounds," *J. Chem. Soc. Perkin Trans. I: Organic and Bioorganic Chem.*, 18, 2707-2711 (1997).

Briscoe et al., "The Orphan G Protein-Coupled Receptor GPR40 is Activated by Medium and Long Chain Fatty Acids," *J. of Biol. Chem.*, 278(13), 11303-11311 (2003).

Briscoe, C. P. et al., "Pharmacological Regulation of Insulin Secretion in MIN6 Cells Through the Fatty Acid Receptor GPR40: Identification of Agonist and Antagonist Small Molecules," *Brit. J. of Pharmacology*, 148, 619-628 (2006).

Burnop, V.C.E. et al., "Fused Carbon Rings. Part XIX. Experiments on the Synthesis of Tetracyclic Compounds of the Sexual Hormonal Type," *J. Chem. Soc.*, 727-735 (1940).

Chatterjee, A., et al., "Studies on Nucleophilic Ring Opening of Some Epoxides in Polar Protic Solvents," *Tetrahedron*, 33, 85-94 (1977).

Collins, David J. et al., "The Structure and Function of Oestrogens. IX*. Synthesis of the trans Isomer of 5,5,10b-Trimtehyl-4b,5,6,10b,11,12-hexahydrocvhrysene-2,8-diol," *Aust. J. Chem.*, 41, 735-744 (1988).

Deb, Soumitra et al., "A Stereocontrolled Synthesis of (1'RS,2'SR)-3-oxo-3',4'-dihydrospiro[cyclopentane-1,1'(2'H)-naphthalen]-2-yl Acetic Acid and its Methoxy Derivatives," *J. Chem. Res. Synops.*, 12, 406 (1985).

DeWolf et al., "Inactivation of Dopamine β-Hydroxylase by β-Ethynyltyramine: Kinetic Characterization and Covalent Modification of an Active Site Peptide," *Biochemistry*, 28, 3833-3842 (1989).

Egan, R. W. et al., "Naphthalenes as Inhibitors of Myeloperoxidase: Direct and Indirect Mechanisms of Inhibition," *Agents and Actions*, 29 3/4 266-276 (1990).

Frey et al., "Total Synthesis of Pentacyclic Diterpenoid Tropone Hainanolidol," *Aust. J. Chem.*, 53, 819-830 (2000).

Galemmo et al., "The Development of a Novel Series of (Quinolin-2-ylmethoxy) phenyl-Containing Compounds as High-Affinity Leukotriene Receptor Antagonists. 3. Structural Variation of the Acidic Side Chain to Give Antagonists of Enhanced Potency," *J. Med. Chem.*, 33, 2828-2841 (1990).

(56) References Cited

OTHER PUBLICATIONS

Garrido, D. M., et al., "Synthesis and Activity of Small Molecule GPR40 Agonists," *Bioorg. and Med. Chem. Lett.*, 16, 1840-1845 (2006).
Ghosal, Probir Kumar, et al., "Stereospecific Synthesis of 9bβ-Carbomethoxy-7-methoxy-2,3,3aα,4,5,9bβ-Hexahydro-1H-Benz[e]-Inden-2-one; An Intermediate Towards Physiologically Active Compounds," *Tet. Lett.*, 17, 1463-1464 (1977).
Guthrie, R. W. et al., "Synthesis in the Series of Diterpene Alkaloids VI. A Simple Synthesis of Atisine," *Tet. Lett.*, 38, 4645-4654 (1966).
Haigh et al., "Non-thiazolidinedione Antihyperglycaemic Agents. Part 3: The Effects of Stereochemistry on the Potency of α-Methoxy-β-phenylpropanoic Acids," *Bioorg. and Med. Chem.*, 7, 821-830 (1999).
Hares, Owen et al., "Sythetic Studies of Tricyclospirodienones: Model Chemistry for Novel Mimics of Steroid Substrates," *J. Chem. Soc. Perkin Trans. I: Organic and Bioorganic Chem.*, 13, 1481-1492 (1993).
Houze, J. et al., "Beta-substituted Carboxylic Acids as Potent, Bioavailable Agonists of GPR40", 234th ACS National Meeting Boston, MA Aug. 19-23, 2007.
Iizuka et al., "β-Substituted Phenethylamines as High Affinity Mechanism-Based Inhibitors of Dopamine β-Hydroxylase," *J. Med. Chem.*, 31, 704-706 (1988).
Ishikawa et al., "Actions of the Novel Oral Antidiabetic Agent HQL-975 in Insulin-Resistant Non-Insulin—Dependent Diabetes Mellitus Model Animals," *Diabetes Res. and Clin. Pract.*, 41, 101-111 (1998).
Ishikawa et al., "Effects of the Novel Oral Antidiabetic Agent HQL-975 on Glucose and Lipid Metabolism in Diabetic db/db Mice," *Arzneim. Forsch. Drug Res.*, 48(3), 245-250 (1998).
Itoh et al., "Free Fatty Acids Regulate Insulin Secretion from Pancreatic β Cells Through GPR40," *Nature*, 422, 173-176 (2003).
Johns, William F. et al., "Total Synthesis of Estrajervatetraene," *J. Org. Chem.*, 44(6), 958-961 (1979).
Kao et al., "One-Pot Synthesis of the Hydroximoyl Chlorides and [3.3.0] Bicyclic Compounds from the Reactions of β-Nitrostyrenese with Stabilized Nucleophiles," *Tetrahedron*, 54(46), 13997-14014 (1998).
Kolasa et al., "Symmetrical Bis (heteroarylmethoxyphenyl) alkylcarboxylic Acids as Inhibitors of Leukotriene Biosynthesis," *J. Med. Chem.*, 43, 3322-3334 (2000).
Kotarsky et al., "A Human Cell Surface Receptor Activated by Free Fatty Acids and Thiazolidinedione Drugs", *Biochem. and Biophys. Res. Comm.*, 301, 406-410 (2003).
Kuchar et al., "Benzyloxyarylaliphatic Acids: Synthesis and Quantitative Relations Between Structure and Antiinflammatory Activity," *Collection Czechoslovak Chem, Comm.*, 47, 2514-2524 (1982).
Kuchar et al., "The Effects of Lopophilicity on the Inhibition of Denaturation of Serum Albumin and on the Activation of Fibrionolysis Observed with a Serixes of Benzyloxyarylaliphatic Acids," *Collection Czechoslovak Chem, Comm.*, 48, 1077-1088 (1983).
Lin, Llnus S. et al., "The Discovery of Acylated β-Amino Acids as Potent and Orally Bioavailable VLA-4 Antagonists," *Bioorg. and Med. Chem. Lett.*, 12, 611-614 (2002).
Liu et al., "Synthesis and Biological Activity of L-Tyrosine-based PPARγ Agonists with Reduced Molecular Weight," *Bioorg. and Med. Chem. Lett.*, 11, 3111-3113 (2001).
McKeown, S.C. et al., "Solid Phase Synthesis and SAR of Small Molecule Agonists for the GPR40 Receptor," Bioorg. and Med. Chem. Lett., 17, pp. 1584-1589 (2007).
Nilsson, N. E. et al., "Identification of a Free Fatty Acid Receptor, $FFA_2R$, Expressed on Leukocytes and Activated by Short-Chain Fatty Acids," *Biochem. and Biophys. Res. Comm.*, 303 1047-1052 (2003).
Oliver et al., "A Selective Peroxisome Proliferator-Activated Receptor δ Agonist Promotes Reverse Cholesterol Transport," *PNAS*, 98(9), 5306-5311 (2001).
Poitout, Vincent, "The Ins and Outs of Fatty Acids on the Pancreatic β Cells," *Trends in Endocrinology and Metabolism*, 14(5), 201-203 (2003).
Ray, Chhanda et al., "Synthesis of some angularly cyclopentanone fused hydrophenanthrene and hydrofluorene derivatives by acid-catalyzed intramolecular C-alkylation of γ, δ -unsaturated α'-diazomethyl ketones," *Synthetic Commun.*, 21(10-11), 1223-1242 (1991).
Sandberg, Rune et al., "N-Aminoalkylsuccinimides as Local Anaesthetics," *Acta Pharmaceutica Suecica*, 17(4) 169-176 (1980).
Sanyal, Utpal et al., "A Novel Synthesis of a Tricyclo $(7.5.0^{1,5}.0^{1,9})$ Tetradecane Ring System Related to Gascardic Acid," *Tet. Lett.*, 25, 2187-2190 (1978).
Sarma, Aluru Sudarsana et al., "Synthetic Studies on Terpenoids. Parts XVIII. Stereocontrolled Synthesis of (+/-)-1,2,3,4,4a,9,10,10aα-Octahydro-1α-methylenephenanthrene-1β,4aβ-dicarboxylic acid and the 7-Methoxy Analog: A Potential Intermediate for Diterpinoid Synthesis," *J. Chem. Soc. Perkin Trans. I: Organic and Bioorganic Chem.*, 7, 722-727 (1976).
Sawzdargo et al., "A Cluster of Four Novel Human G Protein-Coupled Receptor Genes Occurring in Close Proximity to CD22 Gene on Chromosome 19q13.1", *Biochem. and Biophys. Res. Comm.*, 239, 543-547 (1997).
Shaw et al., "Enantioselective Synthesis of (+)-(2S, 3S)-3-Ethyltyrosine," *Tet. Lett.*, 31(35), 5081-84 (1990).
Shiotani, Shunsaku et al., "Synthesis of 1,3-Bridged 1,2,3,4,5,6-Hexahydro-2,6-methano-3-benzazocine Derivatives," *Chem. Pharm. Bull.*, 28(6), 1928-1931 (1980).
Song, F. et al., "Synthesis and Biological Evaluation of 3-Aryl-3-(4-phenoxy)-propionic Acid as a Novel Series of G Protein-Coupled REceptor 40 Agonists," J. Med. Chem. 50 pp. 2807-2817 (2007).
Waid et al., "Constrained Amino Acids. An Approach to the Synthesis of 3-Substituted Prolines," *Tet. Lett.*, 37(24), 4091-4094 (1996).
Guldi, D. M. et al., "Fullerenes (C60) Versus Heteroazafullerenes ($C_{59}N$); A Photophysical Comparison of their Monoadducts and Hexaaducts," *Res. Chem. Intermed.*, 28(7-9), 817-830 (2002).
Hauke, F. et al., "Regioselective Formation of Highly Funcitionalized Heterofullerenes: Pentamaolonates of $RC_{59}N$ Involving an Octahedral Addition Pattern," *Chem. Comm.*, 14, 1316-1317 (2001).
Lamparth, I. et al., "Synthesis of [60]Fullerene Derivatives with an Octahedral Addition Pattern," *Tetrahedron* 52(14) 5065-5075 (1996).

\* cited by examiner

SPIROCYCLIC GPR40 MODULATORS

1. CROSS REFERENCES TO RELATED APPLICATIONS

This application is a national stage application under 35 U.S.C. 371 of International Application No. PCT/US2009/060549, having an international filing date of Oct. 13, 2009, which claims the benefit of, and priority to, U.S. Provisional Application No. 61/196,271, filed on Oct. 15, 2008, which is hereby incorporated by reference in its entirety and for all purposes as if fully set forth herein.

2. FIELD OF THE INVENTION

The present invention relates to compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

3. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al. (1997) Biochem. Biophys. Res. Commun 239: 543-547. GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al. (2003) Nature 422:173-176; Briscoe et al. (2003) J. Biol. Chem. 278: 11303-11311; Kotarsky et al. (2003) Biochem. Biophys. Res. Commun. 301: 406-410.

Various documents have disclosed compounds reportedly having activity with respect to GPR40. For example, WO 2004/041266 and EP 1559422 disclose compounds that purportedly act as GPR40 receptor function regulators. WO 2004/106276 and EP 1630152 are directed to condensed ring compounds that purportedly possess GPR40 receptor function modulating action. More recently, WO 2005/086661 U.S. Patent Publication No. 2006/0004012, US Patent Publication No. 2006/0270724, and US Patent Publication No. 2007/0066647 disclose compounds useful for modulating insulin levels in subjects and useful for treating type II diabetes.

Although a number of compounds have been disclosed that reportedly modulate GPR40 activity, the prevalence of type II diabetes, obesity, hypertension, cardiovascular disease and dyslipidemia underscores the need for new therapies to effectively treat these conditions.

4. SUMMARY OF THE INVENTION

Provided herein are compounds, pharmaceutical compositions, and methods useful for treating a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect, the present invention provides a compound having the formula I′A or I′B or a pharmaceutically acceptable salt, stereoisomer, or mixture thereof. Compounds of formula I′A or I′B have the following structures:

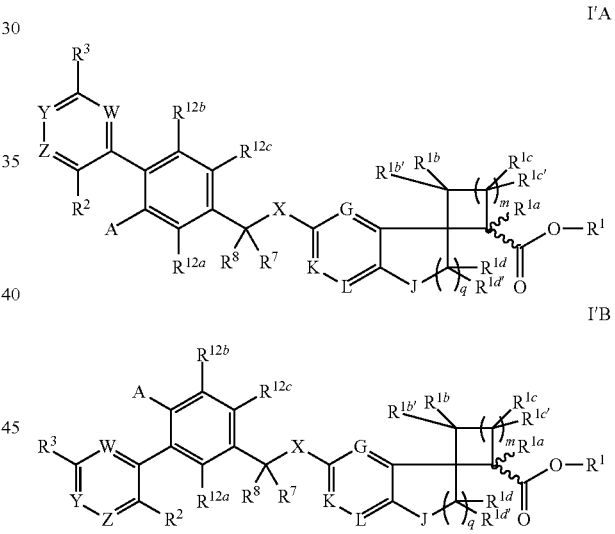

where
G is selected from N or $CR^{11a}$;
K is selected from N or $CR^{11b}$;
L is selected from N or $CR^{11c}$;
wherein 0 or 1 of G, L, and K is N;
X is O, S, or Me wherein $R^a$ is selected from —H or —($C_1$-$C_6$) alkyl groups;
J is selected from O, S, $NR^b$, $CR^cR^d$, C(=O), or —C(=O)—$NR^b$—; wherein $R^b$ is selected from H and ($C_1$-$C_4$)alkyl, and further wherein $R^c$ and $R^d$ are independently selected from H, F, and ($C_1$-$C_4$)alkyl;
W, Y, and Z are selected from N or $CR^{13}$; wherein 0, 1, or 2 of W, Y, and Z is N; and further wherein Z is not N if $R^2$ is —F; and A and W, when W is C, may join together to form a ring having 5 to 7 ring members of which 0 or 1 is a heteroatom selected from N, O, or S, and further wherein the ring having 5 to 7 ring members is optionally substituted with —(C$_1$-C$_8$)alkyl, —(C$_1$-C$_8$)alkenyl, —OH, —O—(C$_1$-C$_8$)alkyl, —O—(C$_1$-C$_8$)alkenyl, or halo;

A is selected from —H, —(C$_1$-C$_{12}$)alkyl; —(C$_2$-C$_{12}$)alkenyl; —(C$_1$-C$_{12}$)alkyl-O—(C$_1$-C$_4$)alkyl; —(C$_1$-C$_{12}$)alkyl-OH; —(C$_1$-C$_{12}$)alkyl-O—(C$_2$-C$_4$)alkenyl; —(C$_2$-C$_{12}$)alkenyl-O—(C$_1$-C$_4$)alkyl; —(C$_2$-C$_{12}$)alkenyl-OH; —(C$_2$-C$_{12}$)alkenyl-O—(C$_2$-C$_4$)alkenyl; —O—(C$_1$-C$_{12}$)alkyl; —O—(C$_2$-C$_{12}$)alkenyl; —O—(C$_1$-C$_4$)alkyl-aryl; —S—(C$_1$-C$_{12}$)alkyl; —S—(C$_2$-C$_{12}$)alkenyl; —S(O)—(C$_1$-C$_{12}$)alkyl; —S(O)—(C$_2$-C$_{12}$)alkenyl; —S(O)$_2$—(C$_1$-C$_{12}$)alkyl; —S(O)$_2$—(C$_2$-C$_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 (C$_1$-C$_2$)alkyl groups; a —(C$_1$-C$_4$)alkyl-heterocyclyl wherein the heterocyclyl of the —(C$_1$-C$_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 (C$_1$-C$_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 (C$_1$-C$_2$)alkyl groups; further wherein the alkyl and alkenyl groups of —(C$_1$-C$_{12}$)alkyl, —(C$_2$-C$_{12}$)alkenyl, —(C$_1$-C$_{12}$)alkyl-O—(C$_1$-C$_4$)alkyl, —(C$_1$-C$_{12}$)alkyl-O—H, —(C$_1$-C$_{12}$)alkyl-O—(C$_2$-C$_4$)alkenyl, —(C$_2$-C$_{12}$)alkenyl-O—(C$_1$-C$_4$)alkyl, —(C$_2$-C$_{12}$)alkenyl-OH, —(C$_2$-C$_{12}$)alkenyl-O—(C$_2$-C$_4$)alkenyl, —O—(C$_1$-C$_{12}$)alkyl, —O—(C$_2$-C$_{12}$)alkenyl, and —O—(C$_1$-C$_4$)alkyl-aryl are unsubstituted or are substituted with from 1 to 4 substituents selected from —F, —Cl, —OH, (=O), —NH$_2$, NH(C$_1$-C$_4$)alkyl, —N((C$_1$-C$_4$)alkyl)$_2$, aryl, unsubstituted —(C$_1$-C$_2$)alkyl, or unsubstituted —O—(C$_1$-C$_2$)alkyl;

$R^1$ is H or —(C$_1$-C$_6$)alkyl;

$R^{1a}$ is selected from —H and —(C$_1$-C$_4$)alkyl;

$R^{1b}$ is selected from —H and —(C$_1$-C$_4$)alkyl;

$R^{1b'}$ is selected from —H and —(C$_1$-C$_4$)alkyl;

$R^{1c}$ is selected from —H and —(C$_1$-C$_4$)alkyl;

$R^{1c'}$ is selected from —H and —(C$_1$-C$_4$)alkyl;

$R^{1d}$ is in each instance independently selected from —H, —F, and —(C$_1$-C$_4$)alkyl;

$R^{1d'}$ is in each instance independently selected from —H, —F, and —(C$_1$-C$_4$)alkyl;

$R^2$ is selected from —H, —F, —CF$_3$, —Cl, or —O—(C$_1$-C$_6$)alkyl;

$R^3$ is —H, —F, —Cl, —OH, —(C$_1$-C$_4$)alkyl, —O—(C$_1$-C$_3$)alkyl, or —S—(C$_1$-C$_2$)alkyl;

$R^7$ and $R^8$ are independently selected from —H and —(C$_1$-C$_4$)alkyl;

$R^{11a}$, $R^{11b}$, and $R^{11c}$ are independently selected from —H, —F, —Cl, —(C$_1$-C$_4$)alkyl, or —O(C$_1$-C$_4$)alkyl;

$R^{12a}$, $R^{12b}$ and $R^{12c}$ are independently selected from —H, —F, —Cl, —(C$_1$-C$_4$)alkyl, or —O(C$_1$-C$_4$)alkyl;

$R^{13}$ is selected from —H, —F, —(C$_1$-C$_4$)alkyl, and —O—(C$_1$-C$_4$)alkyl;

m is 0 or 1; and q is selected from 0, 1, 2, or 3, wherein the ⌇ bond indicates that the $R^{1a}$ and —C(=O)—O—R$^1$ may be attached to either side of the ring to which the ⌇ is attached and either R or S stereochemistry is allowed.

In some embodiments of the compound of formula I'A or I'B, $R^2$ is selected from —H, —F, —CF$_3$, or —O—(C$_1$-C$_6$)alkyl. In some embodiments $R^2$ is —F. In other embodiments, $R^2$ is —Cl.

In some embodiments of the compound of formula I'A or I'B, A is A is selected from —(C$_1$-C$_{12}$)alkyl; —(C$_2$-C$_{12}$)alkenyl; —(C$_1$-C$_{12}$)alkyl-O—(C$_1$-C$_4$)alkyl; —(C$_1$-C$_{12}$)alkyl-OH; —(C$_1$-C$_{12}$)alkyl-O—(C$_2$-C$_4$)alkenyl; —(C$_2$-C$_{12}$)alkenyl-O—(C$_1$-C$_4$)alkyl; —(C$_2$-C$_{12}$)alkenyl-OH; —(C$_2$-C$_{12}$)alkenyl-O—(C$_2$-C$_4$)alkenyl; —O—(C$_1$-C$_{12}$)alkyl; —O—(C$_2$-C$_{12}$)alkenyl; —O—(C$_1$-C$_4$)alkyl-aryl; —S—(C$_1$-C$_{12}$)alkyl; —S—(C$_2$-C$_{12}$)alkenyl; —S(O)—(C$_1$-C$_{12}$)alkyl; —S(O)—(C$_2$-C$_{12}$)alkenyl; —S(O)$_2$—(C$_1$-C$_{12}$)alkyl; —S(O)$_2$—(C$_2$-C$_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 (C$_1$-C$_2$)alkyl groups; a —(C$_1$-C$_4$)alkyl-heterocyclyl wherein the heterocyclyl of the —(C$_1$-C$_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 (C$_1$-C$_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 (C$_1$-C$_2$) alkyl groups; further wherein the alkyl and alkenyl groups of —(C$_1$-C$_{12}$)alkyl, —(C$_2$-C$_{12}$)alkenyl, —(C$_1$-C$_{12}$)alkyl-O—(C$_1$-C$_4$)alkyl, —(C$_1$-C$_{12}$)alkyl-O—H, —(C$_1$-C$_{12}$)alkyl-O—(C$_2$-C$_4$)alkenyl, —(C$_2$-C$_{12}$)alkenyl-O—(C$_1$-C$_4$)alkyl, —(C$_2$-C$_{12}$)alkenyl-OH, —(C$_2$-C$_{12}$)alkenyl-O—(C$_2$-C$_4$)alkenyl, —O—(C$_1$-C$_{12}$)alkyl, —O—(C$_2$-C$_{12}$)alkenyl, and —O—(C$_1$-C$_4$)alkyl-aryl are unsubstituted or are substituted with from 1 to 4 substituents selected from —F, —Cl, —OH, (=O), —NH$_2$, NH(C$_1$-C$_4$)alkyl, —N((C$_1$-C$_4$)alkyl)$_2$, aryl, unsubstituted —(C$_1$-C$_2$)alkyl, or unsubstituted —O—(C$_1$-C$_2$)alkyl.

In some embodiments, m is 0 such that the compound of formula I'A or I'B is a compound of formula II'A or II'B or a pharmaceutically acceptable salt, stereoisomer, or mixture thereof. The compounds of formula II'A or II'B have the following structures:

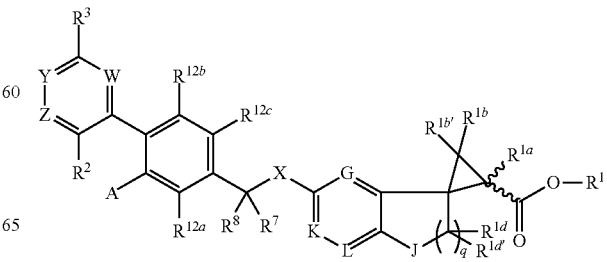

II'A

-continued

II'B

In some embodiments, $R^1$ is H such that the compound is a carboxylic acid. In other embodiments, $R^1$ is an unsubstituted —($C_1$-$C_6$) alkyl group such as a methyl, ethyl, propyl, butyl, pentyl, hexyl, or isopropyl group. Therefore, in some embodiments, $R^1$ is a —$CH_3$ or a —$CH_2CH_3$ group.

In another aspect, the invention provides a compound having the formula IA or IB or a pharmaceutically acceptable salt, stereoisomer, or mixture thereof. Compounds of formula IA and IB have the following structures:

IA

IB or a pharmaceutically acceptable salt, stereoisomer, or a mixture thereof, wherein G is selected from N or $CR^{11a}$;
K is selected from N or $CR^{11b}$;
L is selected from N or $CR^{11c}$;
wherein 0 or 1 of G, L, and K is N;
X is O, S, or $NR^a$ wherein $R^a$ is selected from —H or —($C_1$-$C_6$) alkyl groups;
J is selected from O, S, $NR^b$, $CR^cR^d$, C(═O), or —C(═O)—$NR^b$—; wherein $R^b$ is selected from H and ($C_1$-$C_4$)alkyl, and further wherein $R^c$ and $R^d$ are independently selected from H, F, and ($C_1$-$C_4$)alkyl;
$L^1$ is absent or is a ($C_1$-$C_4$) alkyl;
V is selected from a ($C_4$-$C_8$)cycloalkyl; a ($C_6$-$C_{10}$)aryl; a heteroaryl comprising from 5 to 10 ring members of which from 1 to 3 are heteroatoms selected from N, O, and S; a benzo-fused ($C_5$-$C_8$)cycloalkyl wherein the cycloalkyl group of the benzo-fused cycloalkyl is bonded to $L^1$, if present, or is bonded to X if $L^1$ is absent; a benzo-fused ($C_5$-$C_8$)cycloalkyl wherein the aromatic group of the benzo-fused cycloalkyl is bonded to $L^1$, if present, or is bonded to X if $L^1$ is absent; a heteroaryl-fused ($C_5$-$C_8$)cycloalkyl wherein the cycloalkyl group of the heteroaryl-fused cycloalkyl is bonded to $L^1$, if present, or is bonded to X if $L^1$ is absent; or a heteroaryl-fused ($C_5$-$C_8$)cycloalkyl wherein the heteroaryl group of the heteroaryl-fused cycloalkyl is bonded to $L^1$, if present, or is bonded to X if $L^1$ is absent; wherein the ($C_6$-$C_{10}$)aryl, heteroaryl, benzo-fused ($C_5$-$C_8$)cycloalkyl, and heteroaryl-fused ($C_5$-$C_8$)cycloalkyl group are optionally substituted with from 1 to 4 substituents independently selected from F, Cl, Br, OH, —O($C_1$-$C_6$)alkyl groups, —S($C_1$-$C_6$)alkyl groups ($C_1$-$C_6$)alkyl groups, —$CF_3$, or a group of formula A wherein A is selected from —($C_1$-$C_{12}$)alkyl; —($C_2$-$C_{12}$)alkenyl; —($C_1$-$C_{12}$)alkyl-O—($C_1$-$C_4$)alkyl; —($C_1$-$C_{12}$)alkyl-OH; —($C_1$-$C_{12}$)alkyl-O—($C_2$-$C_4$)alkenyl; —($C_2$-$C_{12}$)alkenyl-O—($C_1$-$C_4$)alkyl; —($C_2$-$C_{12}$)alkenyl-OH; —($C_2$-$C_{12}$)alkenyl-O—($C_2$-$C_4$)alkenyl; —O—($C_1$-$C_{12}$)alkyl; —O—($C_2$-$C_{12}$)alkenyl; —O—($C_1$-$C_4$)alkyl-aryl; —S—($C_1$-$C_{12}$)alkyl; —S—($C_2$-$C_{12}$)alkenyl; —S(O)—($C_1$-$C_{12}$)alkyl; —S(O)—($C_2$-$C_{12}$)alkenyl; —S(O)$_2$—($C_1$-$C_{12}$)alkyl; —S(O)$_2$—($C_2$-$C_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; a —($C_1$-$C_4$)alkyl-heterocyclyl wherein the heterocyclyl of the —($C_1$-$C_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 ($C_1$-$C_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$) alkyl groups; further wherein the alkyl and alkenyl groups of —($C_1$-$C_{12}$)alkyl, —($C_2$-$C_{12}$)alkenyl, —($C_1$-$C_{12}$)alkyl-O—($C_1$-$C_4$)alkyl, —($C_1$-$C_{12}$)alkyl-O—H, —($C_1$-$C_{12}$)alkyl-O—($C_2$-$C_4$)alkenyl, —($C_2$-$C_{12}$)alkenyl-O—($C_1$-$C_4$)alkyl, —($C_2$-$C_{12}$)alkenyl-OH, —($C_2$-$C_{12}$)alkenyl-O—($C_2$-$C_4$)alkenyl, —O—($C_1$-$C_{12}$)alkyl, —O—($C_2$-$C_{12}$)alkenyl, and —O—($C_1$-$C_4$)alkyl-aryl are unsubstituted or are substituted with from 1 to 4 substituents selected from —F, —Cl, —OH, (═O), —$NH_2$, NH($C_1$-$C_4$)alkyl, —N(($C_1$-$C_4$)alkyl)$_2$, aryl, unsubstituted —($C_1$-$C_2$)alkyl, or unsubstituted —O—($C_1$-$C_2$)alkyl;

$L^2$ is absent or is selected from O, S, SO, $SO_2$, C(═O), ($C_1$-$C_2$)alkyl, or $NR^x$ wherein $R^x$ is selected from —H or —($C_1$-$C_6$) alkyl groups;

Q is selected from H, a ($C_4$-$C_8$)cycloalkyl; a ($C_6$-$C_{10}$)aryl; or a heteroaryl comprising from 5 to 10 ring members of which from 1 to 3 are heteroatoms selected from N, O, and S; wherein the ($C_4$-$C_8$)cycloalkyl, ($C_6$-$C_{10}$)aryl, and heteroaryl groups are optionally substituted with from 1 to 5 substituents independently selected from F, Cl, Br, OH, —O($C_1$-$C_6$)alkyl groups, —S($C_1$-$C_6$)alkyl groups ($C_1$-$C_6$)alkyl groups, or —$CF_3$.

$R^1$ is H or —($C_1$-$C_6$)alkyl;
$R^{1a}$ is selected from —H and —($C_1$-$C_4$)alkyl;
$R^{1b}$ is selected from —H and —($C_1$-$C_4$)alkyl;
$R^{1b'}$ is selected from —H and —($C_1$-$C_4$)alkyl;
$R^{1c}$ is selected from —H and —($C_1$-$C_4$)alkyl;
$R^{1c'}$ is selected from —H and —($C_1$-$C_4$)alkyl;
$R^{1d}$ is in each instance independently selected from —H, —F, and —($C_1$-$C_4$)alkyl;
$R^{1d'}$ is in each instance independently selected from —H, —F and —($C_1$-$C_4$)alkyl;
$R^{11a}$, $R^{11b}$, and $R^{11c}$ are independently selected from —H, —F, —Cl, —($C_1$-$C_4$)alkyl, or —O($C_1$-$C_4$)alkyl;
m is 0 or 1; and
q is selected from 0, 1, 2, or 3,
wherein the ⁓ indicates that the $R^{1a}$ and —C(═O)—O—$R^1$ may be attached to either side of the ring to which the ⁓ is attached and either R or S stereochemistry is allowed.

In some embodiments of the compound of formula IA or IB,

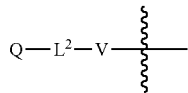

has the formula

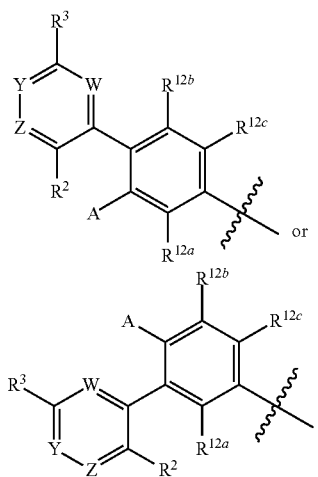

wherein

W, Y, and Z are selected from N or $CR^{13}$; wherein 0, 1, or 2 of W, Y, and Z is N; and further wherein Z is not N if $R^2$ is —F;

A is selected from —$(C_1\text{-}C_{12})$alkyl; —$(C_2\text{-}C_{12})$alkenyl; —$(C_1\text{-}C_{12})$alkyl-O—$(C_1\text{-}C_4)$alkyl; —$(C_1\text{-}C_{12})$alkyl-OH; —$(C_1\text{-}C_{12})$alkyl-O—$(C_2\text{-}C_4)$alkenyl; —$(C_2\text{-}C_{12})$alkenyl-O—$(C_1\text{-}C_4)$alkyl; —$(C_2\text{-}C_{12})$alkenyl-OH; —$(C_2\text{-}C_{12})$alkenyl-O—$(C_2\text{-}C_4)$alkenyl; —O—$(C_1\text{-}C_{12})$alkyl; —O—$(C_2\text{-}C_{12})$alkenyl; —O—$(C_1\text{-}C_4)$alkyl-aryl; —S—$(C_1\text{-}C_{12})$alkyl; —S—$(C_2\text{-}C_{12})$alkenyl; —S(O)—$(C_1\text{-}C_{12})$alkyl; —S(O)—$(C_2\text{-}C_{12})$alkenyl; —$S(O)_2$—$(C_1\text{-}C_{12})$alkyl; —$S(O)_2$—$(C_2\text{-}C_{12})$alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 $(C_1\text{-}C_2)$alkyl groups; a —$(C_1\text{-}C_4)$alkyl-heterocyclyl wherein the heterocyclyl of the —$(C_1\text{-}C_4)$alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 $(C_1\text{-}C_2)$alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 $(C_1\text{-}C_2)$alkyl groups; further wherein the alkyl and alkenyl groups of —$(C_1\text{-}C_{12})$alkyl, —$(C_2\text{-}C_{12})$alkenyl, —$(C_1\text{-}C_{12})$alkyl-O—$(C_1\text{-}C_4)$alkyl, —$(C_1\text{-}C_{12})$alkyl-O—H, —$(C_1\text{-}C_{12})$alkyl-O—$(C_2\text{-}C_4)$alkenyl, —$(C_2\text{-}C_{12})$alkenyl-O—$(C_1\text{-}C_4)$alkyl, —$(C_2\text{-}C_{12})$alkenyl-OH, —$(C_2\text{-}C_{12})$alkenyl-O—$(C_2\text{-}C_4)$alkenyl, —O—$(C_1\text{-}C_{12})$alkyl, —O—$(C_2\text{-}C_{12})$alkenyl, and —O—$(C_1\text{-}C_4)$alkyl-aryl are unsubstituted or are substituted with from 1 to 4 substituents selected from —F, —Cl, —OH, (=O), —$NH_2$, $NH(C_1\text{-}C_4)$alkyl, —$N((C_1\text{-}C_4)\text{alkyl})_2$, aryl, unsubstituted —$(C_1\text{-}C_2)$alkyl, or unsubstituted —O—$(C_1\text{-}C_2)$alkyl;

$R^2$ is selected from —H, —F, —$CF_3$, —Cl, or —O—$(C_1\text{-}C_6)$alkyl;

$R^3$ is —H, —F, —Cl, —OH, —$(C_1\text{-}C_4)$alkyl, —O—$(C_1\text{-}C_3)$alkyl, or —S—$(C_1\text{-}C_2)$alkyl;

$R^{12a}$, $R^{12b}$, and $R^{12c}$ are independently selected from —H, —F, —Cl, —$(C_1\text{-}C_4)$alkyl, or —$O(C_1\text{-}C_4)$alkyl; and $R^{13}$ is selected from —H, —F, —$(C_1\text{-}C_4)$alkyl, and —O—$(C_1\text{-}C_4)$alkyl, and the ～ through the bond indicates the point of attachment to $L^1$ if present or X if $L^1$ is absent.

In some such embodiments, $R^2$ is selected from —H, —F, —$CF_3$, or —O—$(C_1\text{-}C_6)$alkyl. Therefore, in some embodiments, $R^2$ is —F. In other embodiments, $R^2$ is —Cl.

In some embodiments, the compound of any of the embodiments is a salt.

In some embodiments, where two or more chiral centers are present, the compound is a mixture of diastereomers. In some such embodiments, the percentage of one diastereomer is greater than 75%, greater than 80%, greater than 85%, greater than 90%, greater than 95%, greater than 98%, or greater than 99% based on the total diastereomers present in the mixture. In other embodiments, the compound is one specific diastereomer. In some embodiments, the compound is a mixture of enantiomers. In some such embodiments, the mixture comprises both enantiomers where the percent of one enantiomer with respect to both enantiomers is greater than 75%, greater than 80%, greater than 85%, greater than 90%, greater than 95%, greater than 98%, or greater than 99%. In other embodiments, the compound is a pure single enantiomer. In some embodiments with a single chiral center, the compound comprises a stereomerically pure S-enantiomer. In other embodiments with a single chiral center, the compound comprises a stereomerically pure R-enantiomer. In yet other embodiments with a single chiral center, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, the invention provides methods for treating a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. Such methods include administering to a subject in need thereof, a therapeutically effective amount of a compound of any of the embodiments. In some such embodiments, the disease or condition is type II diabetes. In some embodiments, a compound of any of the embodiments is administered in combination with a second therapeutic agent. In some such embodiments, the second therapeutic agent is metformin, is a thiazolidinedione, is a DPP-IV inhibitor or is a GLP-1 analog. The second therapeutic agent may be administered before, during, or after administration of the compound of any of the embodiments.

In another aspect, the invention provides methods for treating a disease or condition responsive to the modulation of GPR40. Such methods include administering to a subject in need thereof, a therapeutically effective amount of a compound of any of the embodiments.

In another aspect, the invention provides methods for treating a disease or condition mediated, regulated, or influenced by pancreatic β cells. Such methods include administering to a subject in need thereof, a therapeutically effective amount of a compound of any of the embodiments.

In another aspect, the invention provides methods for modulating GPR40 function in a cell. Such methods include contacting a cell with a compound of any of the embodiments.

In another aspect, the invention provides methods for modulating GPR40 function. Such methods include contacting GPR40 with a compound of any of the embodiments.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin, a thiazolidinedione, or a DPP-IV inhibitor.

In another aspect, the invention provides the use of a compound of any of the embodiments for modulating GPR40 or for use in the preparation of a medicament for modulating GPR40.

In another aspect, the invention provides a therapeutic composition that includes a compound of any of the embodiments and a second therapeutic agent such as those described herein, for example, metformin a thiazolidinedione, or a DPP-IV inhibitor, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

In some embodiments, the invention provides a compound of any of the embodiments described herein for use as a medicament.

In other embodiments, the invention provides a compound of any of the embodiments described herein for use in modulating GPR40.

In still other embodiments, the invention provides a compound of any of the embodiments described herein for use in a method for treating a disease or condition selected from type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, or edema.

The compounds of the invention may stimulate GLP-secretion. Cells contacted with compounds of the invention may increase GLP-1 secretion. Therefore, in some embodiments, the invention provides a method of stimulating GLP-1 secretion by cells. Such methods typically include contacting a cell capable of producing GLP-1 with a compound of any of the embodiments set forth herein. Administration of the compounds of the invention to subjects may provide increased levels of GLP-1 in the blood plasma of such subjects. Therefore, in some embodiments, a compound of any of the embodiments described herein may be used to stimulate GLP-1 secretion and increase the blood plasma level of GLP-1 in a subject. In some such embodiments, the compounds of the invention both stimulate GLP-1 secretion and activate GPR40. Therefore, in some embodiments, the compounds of the invention both stimulate GLP-1 secretion and display incretin effect by activating GPR40.

In some embodiments, the invention further provides a method for increasing GLP-1 levels in the blood plasma of a subject. Such methods typically include administering a compound of any of the embodiments to a subject. In some such embodiments, the subject is a diabetic patient. In other such embodiments, the subject is an obese patient. In some embodiments, the invention provides a method for stimulating weight loss in a subject. In such embodiments, a compound of any of the embodiments is administered to a subject in an effective amount to stimulate weight loss in the subject. The compounds of the invention may be administered in the fasted or non-fasted state. Therefore, in some embodiments, a compound of any of the embodiments is administered to a subject prior to a meal. In some such embodiments, the compound is administered 2 hours, 1, hour, 30 minutes, or 15 minutes before a meal. In other embodiments, a compound of any embodiments set forth herein is administered to a subject during a meal. In other embodiments, a compound of any of the embodiments described herein is administered to a subject within 2 hours, within 1 hour, within 30 minutes, or within 15 minutes of a meal.

Other objects, features and advantages of the invention will become apparent to those skilled in the art from the following description and claims.

5. DETAILED DESCRIPTION OF THE INVENTION

5.1 Abbreviations and Definitions

The terms "treat", "treating" and "treatment", as used herein, are meant to include alleviating or abrogating a condition or disease and/or its attendant symptoms. In some instances treating may also involve prevention of symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., $C_1$-$C_{10}$ means one to ten carbons). Examples of alkyl groups include, but are not limited to, methyl, ethyl, n-propyl, isopropyl, n-butyl, t-butyl, isobutyl, sec-butyl, pentyl, cyclohexyl, (cyclohexyl)methyl, methylcyclohexyl, dimethylcyclohexyl, cyclopropyl, cyclopropylmethyl, methylcyclopropyl, cyclobutyl, cyclobutylmethyl, methylcyclobutyl, cyclopentyl, methylcyclopentyl, cyclopentylmethyl, dimethylcyclopentyl, and homologs and isomers thereof, for example, n-pentyl, n-hexyl, n-heptyl, n-octyl, and the like. Alkyl groups may be substituted or unsubstituted.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include, but are not limited to, vinyl, 2-propenyl, crotyl, 2-isopentenyl, 2-(butadienyl), 2,4-pentadienyl, 3-(1,4-pentadienyl), cyclopentenyl, cyclohexenyl, 5,5-dimethylcycopentenyl, 6,6-dimethylcyclohexenyl, cycloheptenyl, cycloheptadienyl, and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include, but are not limited to, ethynyl, 1- and 3-propynyl, 3-butynyl, and higher homologs and isomers thereof.

The term "alkoxy" refers to a group of formula —O-alkyl where alkyl has the definition provided above. An alkoxy group can have a specified number of carbon atoms. For example, a methoxy group (—OCH$_3$) is a $C_1$ alkoxy group. Alkoxy groups typically have from 1 to 10 carbon atoms. Examples of alkoxy group include, but are not limited to, methoxy, ethoxy, propoxy, butoxy, pentoxy, hexoxy, heptoxy, and the like.

The term "cycloalkyl" by itself, or in combination with other terms, represents, unless otherwise stated, a cyclic type of "alkyl" in which 3 or more carbon atoms form a ring. Thus, the term "cycloalkyl" is meant to be included in the term "alkyl". Examples of cycloalkyl include cyclopropyl, cyclobutyl, cyclopentyl, cyclohexyl, cycloheptyl, and the like. Cycloalkyl groups typically include from 3 to 14 or 3 to 10 ring members. Cycloalkyl groups may be monocyclic, bicyclic, or multicyclic. Therefore, in addition to the groups described above, cycloalkyl groups include norbornyl and adamantyl groups.

The term "cycloalkenyl" by itself, or in combination with other terms, represents, unless otherwise stated, a cyclic type of "alkenyl" in which 3 or more carbon atoms form a ring that includes at least one carbon-carbon double bond. Thus, the term "cycloalkenyl" is meant to be included in the term "alkenyl". Examples of cycloalkenyl include cyclopropenyl, cyclobutenyl, cyclopentenyl, cyclohexenyl, cycloheptenyl, and the like. Cycloalkenyl groups typically include from 3 to 14 or 3 to 10 ring members. Cycloalkenyl groups may be monocyclic, bicyclic, or multicyclic.

The term "heterocyclyl" by itself or in combination with other terms, represents, unless otherwise stated, a ring system in which one or more ring members is a heteroatom selected from N, O, or S. The heteroatom can occupy the position at which the heterocycle is attached to the remainder of the molecule. A heterocyclyl group can also be attached to the remainder of the molecule through a carbon atom of the ring. Heterocyclyl groups typically include from 3 to 10 ring members of which 1, 2, or 3 are heteroatoms. Heterocyclyl groups can be saturated or may include some unsaturation. Heterocyclyl groups may also be substituted or unsubstituted. Examples of heterocyclyl groups include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any position of the heteroalkyl group. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, and —CH$_2$—CH=N—OCH$_3$. Up to two heteroatoms may be consecutive, such as, for example, —CH$_2$—NH—OCH$_3$. When a prefix such as (C$_2$-C$_8$) is used to refer to a heteroalkyl group, the number of carbons (2 to 8, in this example) is meant to include the heteroatoms as well. For example, a C$_2$-heteroalkyl group is meant to include, for example, —CH$_2$OH (one carbon atom and one heteroatom replacing a carbon atom) and —CH$_2$SH.

To further illustrate the definition of a heteroalkyl group, where the heteroatom is oxygen, a heteroalkyl group is a oxyalkyl group. For instance, (C$_2$-C$_5$)oxyalkyl is meant to include, for example —CH$_2$—O—CH$_3$ (a C$_3$-oxyalkyl group with two carbon atoms and one oxygen replacing a carbon atom), —CH$_2$CH$_2$CH$_2$CH$_2$OH, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo(C$_1$-C$_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2 m'+1) halogen atoms). The term "perhaloalkyl" means, unless otherwise stated, alkyl substituted with (2 m'+1) halogen atoms, where m' is the total number of carbon atoms in the alkyl group. For example, the term "perhalo(C$_1$-C$_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, aromatic, hydrocarbon substituent which can be a single ring or multiple rings (up to three rings) which are fused together or linked covalently. The term "heteroaryl" refers to aryl groups (or rings) that contain from one to four heteroatom ring members selected from the group consisting of N, O and S, wherein the nitrogen and sulfur atoms are optionally oxidized, and the nitrogen atom(s) are optionally quaternized. Heteroaryl groups can be unsubstituted or substituted. In some embodiments, a heteroaryl group includes 1 or 2 heteroatoms. A heteroaryl group can be attached to the remainder of the molecule through a heteroatom or through a carbon atom of the ring. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, dibenzofuryl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl. Typically an aryl group refers to an aromatic group that includes from 6-10 ring members such that it is a (C$_6$-C$_{10}$)aryl group. Typically, heteroaryl groups include 5 to 10 ring members of which 1 or 2 is selected from O, N, or S.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, pyrimidyl, benzothiazolyl, purinyl, benzimidazolyl, indolyl, isoquinolyl, triazolyl, tetrazolyl, quinoxalinyl. or quinolyl group which is unsubstituted or substituted.

For brevity, the term "aryl" when used in combination with other terms (e.g., aryloxy, arylalkoxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). As another example, the term "aryl(C$_1$-C$_4$)alkoxy" is mean to include radicals in which an aryl group is attached to an alkyl group having 1 to 4 carbon atoms that is bonded to an O which is attached to the rest of the molecule. Examples include substituted and unsubstituted phenylmethoxy, phenylethoxy, phenylpropoxy, pyridylmethoxy, and the like.

Each of the above terms (e.g., "alkyl," "alkenyl," "aryl," "heterocyclyl" and "heteroaryl") is meant to include both substituted and unsubstituted forms of the indicated radical, unless otherwise indicated. Preferred substituents for each type of radical are provided below.

Substituents for the alkyl radicals (as well as those groups referred to as alkenyl, alkynyl, cycloalkyl, and heterocyclyl) can be a variety of groups selected from: —OR', =O, =NR', =N—OR', —NR'R", R', —SR', halogen, —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —SiR'R"R'", —S(O)R', —SO$_2$R', —SO$_2$NR'R", —NR"SO$_2$R, —CN, —(C$_2$-C$_5$) alkynyl, —(C$_2$-C$_5$) alkenyl, and —NO$_2$, in a number ranging from zero to three, with those groups having zero, one or two substituents being particularly preferred. R', R" and R'" each independently refer to hydrogen; unsubstituted (C$_1$-C$_8$)alkyl, (C$_2$-C$_8$)alkenyl, and heteroalkyl; unsubstituted aryl; unsubstituted heterocyclyl; heterocyclyl substituted with up to three unsubstituted (C$_1$-C$_2$)alkyl groups; aryl substituted with one to three halogens, unsubstituted (C$_1$-C$_2$)alkyl, —O—(C$_1$-C$_4$)alkyl, and —S—(C$_1$-C$_4$)alkyl groups; unsubstituted halo(C$_1$-C$_4$)alkyl; unsubstituted —(C$_1$-C$_4$)alkyl-O—(C$_1$-C$_4$) alkyl; unsubstituted —(C$_1$-C$_4$)alkyl-aryl; or unsubstituted aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl group will have from zero to three substituents, with those groups having two or fewer substituents being preferred in the present invention. More preferably, an alkyl radical will be unsubstituted or monosubstituted. Most preferably, an alkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl radicals are selected from: —OR', =O, —NR'R", —SR', halogen, —OC(O)R', —C(O)R', —CO$_2$R', —CONR'R", —OC(O)NR'R", —NR"C(O)R', —NR"CO$_2$R', —NR'—SO$_2$NR"R'", —S(O) R', —SO$_2$R', —SO$_2$NR'R", —NR"SO$_2$R, —CN, —(C$_2$-C$_5$) alkynyl, —(C$_2$-C$_5$) alkenyl, R', and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO₂R', —NR'—SO₂NR"R''', —SO₂R', —SO₂NR'R", —NR"SO₂R, —CN, —(C₂-C₅) alkynyl, —(C₂-C₅) alkenyl, and —NO₂.

Similarly, substituents for the aryl and heteroaryl groups are varied and are selected from: -halogen, —OR', —OC(O)R', —NR'R", —SR', —R', —CN, —NO₂, —CO₂R', —CONR'R", —C(O)R', —OC(O)NR'R", —NR"C(O)R', —NR"C(O)₂R', —NR'—C(O)NR"R''', —NH—C(NH₂)=NH, —NR'C(NH₂)=NH, —NH—C(NH₂)=NR', —S(O)R', —S(O)₂R', —S(O)₂NR'R", —N₃, —CH(Ph)₂, perfluoro (C₁-C₄)alkoxy, and perfluoro(C₁-C₄)alkyl, in a number ranging from zero to the total number of open valences on the aromatic ring system; and where R', R" and R''' are independently selected from hydrogen, unsubstituted (C₁-C₈)alkyl and heteroalkyl; unsubstituted aryl and heteroaryl; unsubstituted aryl-(C₁-C₄)alkyl; unsubstituted aryl-O—(C₁-C₄)alkyl; unsubstituted —(C₂-C₅) alkynyl; and unsubstituted —(C₂-C₅) alkenyl.

Two of the substituents on adjacent atoms of the aryl or heteroaryl ring may optionally be replaced with a substituent of the formula -T-C(O)—(CH₂)$_q$—U—, wherein T and U are independently —NH—, —O—, —CH₂—, or a single bond, and q is an integer of from 0 to 2. Alternatively, two of the substituents on adjacent atoms of the aryl or heteroaryl ring may optionally be replaced with a substituent of the formula -A-(CH₂)$_r$—B—, wherein A and B are independently —CH₂—, —O—, —NH—, —S—, —S(O)—, —S(O)₂—, —S(O)₂NR'—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)$_s$—X—(CH₂)$_t$—, where s and t are independently integers of from 0 to 3, and X is —O—, —S—, —S(O)—, —S(O)₂—, or —S(O)₂NR'—. The substituent R' in —NR'— and —S(O)₂NR'— is selected from hydrogen or unsubstituted (C₁-C₆)alkyl. Otherwise, R' is as defined above.

As used herein, the term "heteroatom" is meant to include oxygen (O), nitrogen (N), and sulfur (S).

As used herein, the term "benzo-fused cycloalkyl" is meant to include bicyclic structures in which benzene is fused with a cycloalkane (or cycloheteroalkane). To illustrate, in some embodiments, a "benzo-fused cycloalkyl ring" includes the following structures:

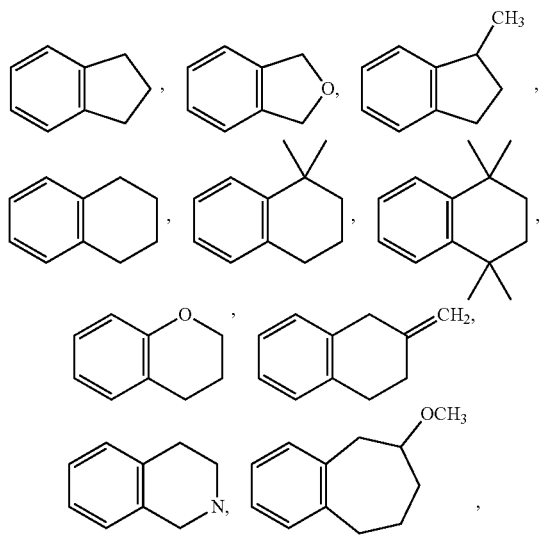

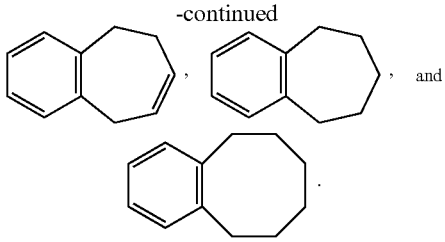

As used herein, the term "heteroaryl-fused (C₅-C₈)cycloalkane ring" has the same meaning as "benzo-fused (C₅-C₈) cycloalkane ring" except the benzene of the benzo-fused (C₅-C₈)cycloalkane ring is replaced with a six-membered heteroaryl ring comprising 1 or 2 nitrogen (N) atoms. As indicated in the structures shown above, the (C₅-C₈)cycloalkane of benzo-fused (C₅-C₈)cycloalkane rings and heteroaryl-fused (C₅-C₈)cycloalkane ring may include only carbon atoms, but may also include one or more heteroatoms. Such heteroatoms typically are selected from O, N, or S. In benzo-fused cycloalkyl and heteroaryl-fused cycloalkyl groups, the cycloalkyl group may be bonded to either the L¹, if present, or X variable or may be bonded to the L², if present, or Q variable. The same is true with respect to the aromatic or heteroaromatic part of the benzo-fused cycloalkyl and heteroaryl-fused cycloalkyl groups.

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate. In some embodiments, the compounds, salts of the compounds, tautomers of the compound, and salts of the tautomers may include a solvent or water such that the compound or salt is a solvate or hydrate.

Certain compounds of the invention may exist in multiple crystalline or amorphous forms. In general, all physical forms are equivalent for the uses contemplated by the invention and are intended to be within the scope of the invention.

As known by those skilled in the art, certain compounds of the invention may exist in one or more tautomeric forms. Because one chemical structure may only be used to represent one tautomeric form, it will be understood that convenience, referral to a compound of a given structural formula includes tautomers of the structure represented by the structural formula.

Certain compounds of the invention possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

5.2 Embodiments of the Invention

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

5.2.1 Compounds

In one aspect, the present invention provides a compound having the formula I'A or I'B or a pharmaceutically acceptable salt, stereoisomer, or mixture thereof. Compounds of formula I'A or I'B have the following structures:

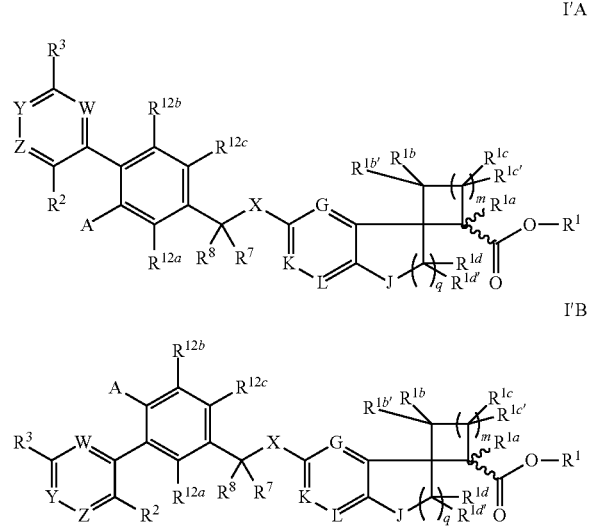

I'A

I'B where

G is selected from N or $CR^{11a}$;

K is selected from N or $CR^{11b}$;

L is selected from N or $CR^{11c}$;

wherein 0 or 1 of G, L, and K is N;

X is O, S, or $NR^a$ wherein $R^a$ is selected from —H or —($C_1$-$C_6$) alkyl groups;

J is selected from O, S, $NR^b$, $CR^cR^d$, C(=O), or —C(=O)—$NR^b$—; wherein $R^b$ is selected from H and ($C_1$-$C_4$)alkyl, and further wherein $R^c$ and $R^d$ are independently selected from H, F, and ($C_1$-$C_4$)alkyl;

W, Y, and Z are selected from N or $CR^{13}$; wherein 0, 1, or 2 of W, Y, and Z is N; and further wherein Z is not N if $R^2$ is —F; and A and W, when W is C, may join together to form a ring having 5 to 7 ring members of which 0 or 1 is a heteroatom selected from N, O, or S, and further wherein the ring having 5 to 7 ring members is optionally substituted with —($C_1$-$C_8$)alkyl, —($C_1$-$C_8$)alkenyl, —OH, —O—($C_1$-$C_8$) alkyl, —O—($C_1$-$C_8$)alkenyl, or halo;

A is selected from —H, —($C_1$-$C_{12}$)alkyl; —($C_2$-$C_{12}$)alkenyl; —($C_1$-$C_{12}$)alkyl-O—($C_1$-$C_4$)alkyl; —($C_1$-$C_{12}$)alkyl-OH; —($C_1$-$C_{12}$)alkyl-O—($C_2$-$C_4$)alkenyl; —($C_2$-$C_{12}$)alkenyl-O—($C_1$-$C_4$)alkyl; —($C_2$-$C_{12}$)alkenyl-OH; —($C_2$-$C_{12}$)alkenyl-O—($C_2$-$C_4$)alkenyl; —O—($C_1$-$C_{12}$)alkyl; —O—($C_2$-$C_{12}$)alkenyl; —O—($C_1$-$C_4$)alkyl-aryl; —S—($C_1$-$C_{12}$)alkyl; —S—($C_2$-$C_{12}$)alkenyl; —S(O)—($C_1$-$C_{12}$)alkyl; —S(O)—($C_2$-$C_{12}$)alkenyl; —S(O)$_2$—($C_1$-$C_{12}$)alkyl; —S(O)$_2$—($C_2$-$C_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; a —($C_1$-$C_4$)alkyl-heterocyclyl wherein the heterocyclyl of the —($C_1$-$C_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 ($C_1$-$C_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$) alkyl groups; further wherein the alkyl and alkenyl groups of —($C_1$-$C_{12}$)alkyl, —($C_2$-$C_{12}$)alkenyl, —($C_1$-$C_{12}$)alkyl-O—($C_1$-$C_4$)alkyl, —($C_1$-$C_{12}$)alkyl-O—H, —($C_1$-$C_{12}$)alkyl-O—($C_2$-$C_4$)alkenyl, —($C_2$-$C_{12}$)alkenyl-O—($C_1$-$C_4$)alkyl, —($C_2$-$C_{12}$)alkenyl-OH, —($C_2$-$C_{12}$)alkenyl-O—($C_2$-$C_4$)alkenyl, —O—($C_1$-$C_{12}$)alkyl, —O—($C_2$-$C_{12}$)alkenyl, and —O—($C_1$-$C_4$)alkyl-aryl are unsubstituted or are substituted with from 1 to 4 substituents selected from —F, —Cl, —OH, (=O), —NH$_2$, NH($C_1$-$C_4$)alkyl, —N(($C_1$-$C_4$)alkyl)$_2$, aryl, unsubstituted —($C_1$-$C_2$)alkyl, or unsubstituted —O—($C_1$-$C_2$)alkyl;

$R^1$ is H or —($C_1$-$C_6$)alkyl;

$R^{1a}$ is selected from —H and —($C_1$-$C_4$)alkyl;

$R^{1b}$ is selected from —H and —($C_1$-$C_4$)alkyl;

$R^{1b'}$ is selected from —H and —($C_1$-$C_4$)alkyl;

$R^{1c}$ is selected from —H and —($C_1$-$C_4$)alkyl;

$R^{1c'}$ is selected from —H and —($C_1$-$C_4$)alkyl;

$R^{1d}$ is in each instance independently selected from —H, —F, and —($C_1$-$C_4$)alkyl;

$R^{1d'}$ is in each instance independently selected from —H, —F, and —($C_1$-$C_4$)alkyl;

$R^2$ is selected from —H, —F, —CF$_3$, —Cl, or —O—($C_1$-$C_6$)alkyl;

$R^3$ is —H, —F, —Cl, —OH, —($C_1$-$C_4$)alkyl, —O—($C_1$-$C_3$)alkyl, or —S—($C_1$-$C_2$)alkyl;

$R^7$ and $R^8$ are independently selected from —H and —($C_1$-$C_4$)alkyl;

$R^{11a}$, $R^{11b}$, and $R^{11c}$ are independently selected from —H, —F, —Cl, —($C_1$-$C_4$)alkyl, or —O($C_1$-$C_4$)alkyl;

$R^{12a}$, $R^{12b}$, and $R^{12c}$ are independently selected from —H, —F, —Cl, —($C_1$-$C_4$)alkyl, or —O($C_1$-$C_4$)alkyl;

$R^{13}$ is selected from —H, —F, —($C_1$-$C_4$)alkyl, and —O—($C_1$-$C_4$)alkyl;

m is 0 or 1; and q is selected from 0, 1, 2, or 3, wherein the ～ indicates that the $R^{1a}$ and —C(=O)—O—$R^1$ may be attached to either side of the ring to which the ～ is attached and either R or S stereochemistry is allowed.

In some embodiments of the compound of formula I'A or I'B, A is A is selected from —($C_1$-$C_{12}$)alkyl; —($C_2$-$C_{12}$)alkenyl; —($C_1$-$C_{12}$)alkyl-O—($C_1$-$C_4$)alkyl; —($C_1$-$C_{12}$)alkyl-OH; —($C_1$-$C_{12}$)alkyl-O—($C_2$-$C_4$)alkenyl; —($C_2$-$C_{12}$)alkenyl-O—($C_1$-$C_4$)alkyl; —($C_2$-$C_{12}$)alkenyl-OH; —($C_2$-$C_{12}$)alkenyl-O—($C_2$-$C_4$)alkenyl; —O—($C_1$-$C_{12}$)alkyl; —O—($C_2$-$C_{12}$)alkenyl; —O—($C_1$-$C_4$)alkyl-aryl; —S—($C_1$-$C_{12}$)alkyl; —S—($C_2$-$C_{12}$)alkenyl; —S(O)—($C_1$-$C_{12}$)alkyl; —S(O)—($C_2$-$C_{12}$)alkenyl; —S(O)$_2$—($C_1$-$C_{12}$)alkyl; —S(O)$_2$—($C_2$-$C_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; a —($C_1$-$C_4$)alkyl-heterocyclyl wherein the heterocyclyl of the —($C_1$-$C_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 ($C_1$-$C_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$) alkyl groups; further wherein the alkyl and alkenyl groups of —($C_1$-$C_{12}$)alkyl, —($C_2$-$C_{12}$)alkenyl, —($C_1$-$C_{12}$)alkyl-O—($C_1$-$C_4$)alkyl, —($C_1$-$C_{12}$)alkyl-O—H, —($C_1$-$C_{12}$)alkyl-O—($C_2$-$C_4$)alkenyl, —($C_2$-$C_{12}$)alkenyl-O—($C_1$-$C_4$)alkyl, —($C_2$-$C_{12}$)alkenyl-OH, —($C_2$-$C_{12}$)alkenyl-O—($C_2$-$C_4$)alkenyl, —O—($C_1$-$C_{12}$)alkyl, —O—($C_2$-$C_{12}$)alkenyl, and —O—($C_1$-$C_4$)alkyl-aryl are unsubstituted or are substituted with from 1 to 4 substituents selected from —F, —Cl, —OH, (=O), —$NH_2$, NH($C_1$-$C_4$)alkyl, —N(($C_1$-$C_4$)alkyl)$_2$, aryl, unsubstituted —($C_1$-$C_2$)alkyl, or unsubstituted —O—($C_1$-$C_2$)alkyl.

In some embodiments, A is selected from —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, —($C_3$-$C_{12}$)alkenyl-OH, —O—($C_4$-$C_{12}$)alkyl, —O—($C_4$-$C_{12}$)alkenyl, a heterocycle comprising 4 to 7 ring members of which 1 or 2 are heteroatoms selected from N or O, wherein the heterocycle has 0 or 1 double bond between ring members and is unsubstituted or is substituted with from 1 to 4 ($C_1$-$C_2$) alkyl groups, a —($C_1$-$C_{12}$)alkyl-heterocyclyl wherein the heterocyclyl of the —($C_1$-$C_4$)alkyl-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 ($C_1$-$C_2$)alkyl groups, or a —O-heterocyclyl wherein the heterocyclyl of the —O-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 ($C_1$-$C_2$)alkyl groups, further wherein the alkyl and alkenyl groups of —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-O—H, —($C_3$-$C_{12}$)alkenyl-O—($C_1$-$C_4$)alkyl, —($C_3$-$C_{12}$)alkenyl-OH, —O—($C_4$-$C_{12}$)alkyl, or —O—($C_4$-$C_{12}$)alkenyl are unsubstituted or are substituted with from 1 to 4 substituents selected from —F, —Cl, —OH, (=O), —$NH_2$, NH($C_1$-$C_4$)alkyl, —N(($C_1$-$C_4$)alkyl)$_2$, aryl, unsubstituted —O—($C_1$-$C_2$)alkyl, or unsubstituted —($C_1$-$C_2$)alkyl. In some such embodiments, A is selected from —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, —($C_3$-$C_{12}$)alkenyl-OH, —O—($C_4$-$C_{12}$)alkyl, or —O—($C_4$-$C_{12}$)alkenyl, wherein the alkyl and alkenyl groups of —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-O—H, —($C_3$-$C_{12}$)alkenyl-O—($C_1$-$C_4$)alkyl, —($C_3$-$C_{12}$)alkenyl-OH, —O—($C_4$-$C_{12}$)alkyl, or —O—($C_4$-$C_{12}$)alkenyl are unsubstituted or are substituted with from 1 to 4 substituents selected from —F, —Cl, —OH, (=O), —$NH_2$, NH($C_1$-$C_4$)alkyl, -or N(($C_1$-$C_4$)alkyl)$_2$, unsubstituted —O—($C_1$-$C_2$)alkyl, or unsubstituted —($C_1$-$C_2$)alkyl. In some such embodiments, A is selected from —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, —($C_3$-$C_{12}$)alkenyl-OH, wherein the alkyl and alkenyl groups of —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-O—H, —($C_3$-$C_{12}$)alkenyl-O—($C_1$-$C_4$)alkyl, or —($C_3$-$C_{12}$)alkenyl-OH, are unsubstituted or are substituted with from 1 to 4 substituents selected from —F, —OH, unsubstituted —O—($C_1$-$C_2$)alkyl, or unsubstituted —($C_1$-$C_2$)alkyl. In some such embodiments, A is selected from —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, —($C_3$-$C_{12}$)alkenyl-OH, wherein the alkyl and alkenyl groups of —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-O—H, —($C_3$-$C_{12}$)alkenyl-O—($C_1$-$C_4$)alkyl, or —($C_3$-$C_{12}$)alkenyl-OH, are unsubstituted or are substituted with 1 to 4 substituent selected from —F, —OH, unsubstituted —O—($C_1$-$C_2$)alkyl, or unsubstituted —($C_1$-$C_2$)alkyl. In some such embodiments, A is a 5 to 7 membered cycloalkyl or cycloalkenyl group comprising from 1 to 4 methyl groups. In other embodiments, A is a —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, or —($C_3$-$C_{12}$)alkenyl-OH. In some embodiments, each of the alkyl and alkenyl groups of the —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, or —($C_3$-$C_{12}$)alkenyl-OH are unsubstituted whereas in other embodiments, each is substituted with 1 to 4 substituents selected from —OH, unsubstituted —O—($C_1$-$C_2$)alkyl, or unsubstituted —($C_1$-$C_2$)alkyl. In some embodiments, A is a —($C_4$-$C_8$)alkyl-O—($C_1$-$C_2$)alkyl, —($C_4$-$C_8$)alkyl-OH, —($C_4$-$C_8$)alkenyl-O—($C_1$-$C_2$)alkyl, or —($C_4$-$C_8$)alkenyl-OH and each of the alkyl and alkenyl groups of —($C_4$-$C_8$)alkyl-O—($C_1$-$C_2$)alkyl, —($C_4$-$C_8$)alkyl-OH, —($C_4$-$C_8$)alkenyl-O—($C_1$-$C_2$)alkyl, or —($C_4$-$C_8$)alkenyl-OH are unsubstituted or are substituted with 1 substituent selected from —OH, unsubstituted —O—($C_1$-$C_2$)alkyl, or unsubstituted —($C_1$-$C_2$)alkyl. In some such embodiments, at least one of the alkyl or alkenyl groups is branched or comprises a $C_3$-$C_7$ cycloalkyl ring. Therefore, in some embodiments, A is selected from

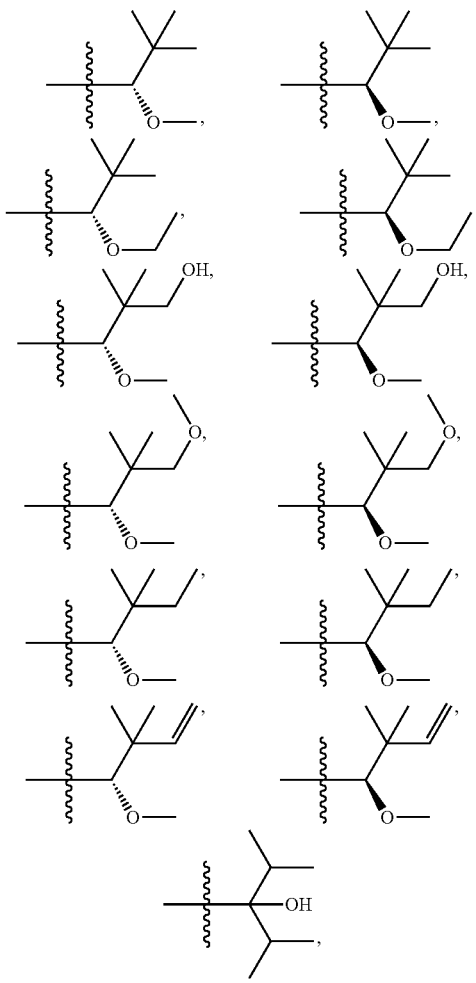

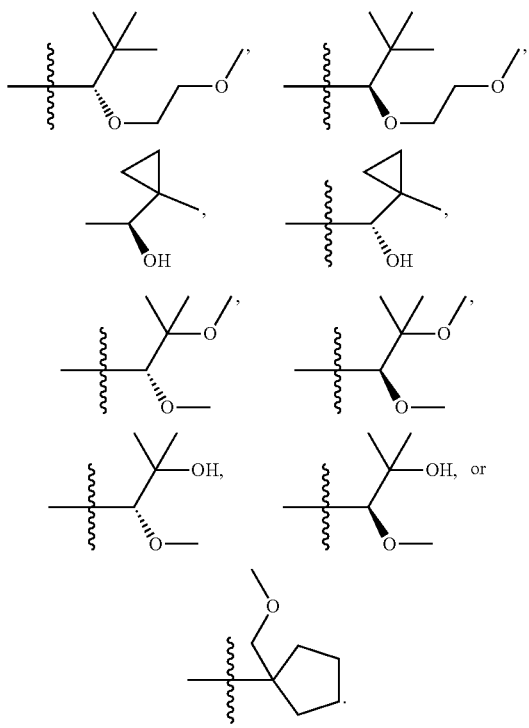

In some embodiments, A is selected from $(C_1-C_{12})$alkyl, $(C_2-C_{12})$alkenyl, —O—$(C_1-C_{12})$alkyl, —O—$(C_2-C_{12})$alkenyl, or —O—$(C_1-C_4)$alkyl-aryl.

In some embodiments, A is selected from a branched $(C_4-C_{10})$alkyl group, a $(C_4-C_{10})$alkenyl group, a bicyclic $(C_7-C_{12})$ alkyl group, an unsubstituted or a substituted $(C_5-C_7)$cycloalkyl group, or an unsubstituted or a substituted $(C_5-C_7)$ cycloalkenyl group. In some embodiments, A is a an unsubstituted $(C_5-C_7)$cycloalkyl group, a $(C_5-C_7)$cycloalkyl group substituted with 1, 2, 3, or 4 methyl groups, an unsubstituted $(C_5-C_7)$cycloalkenyl group, or a $(C_5-C_7)$cycloalkenyl group substituted with 1, 2, 3, or 4 methyl groups. In some such embodiments, $R^3$ is methoxy. In some such embodiments, $R^2$ is H whereas in other such embodiments, $R^2$ is F. In some such embodiments, A is selected from

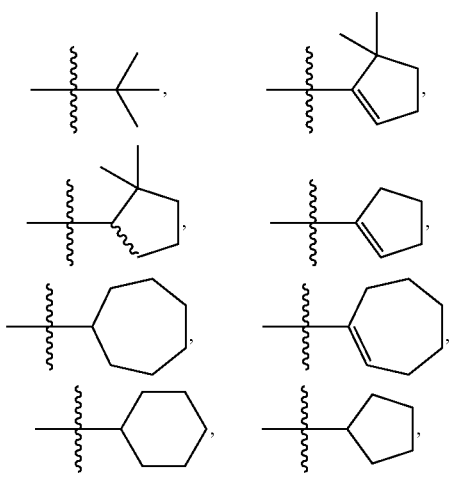

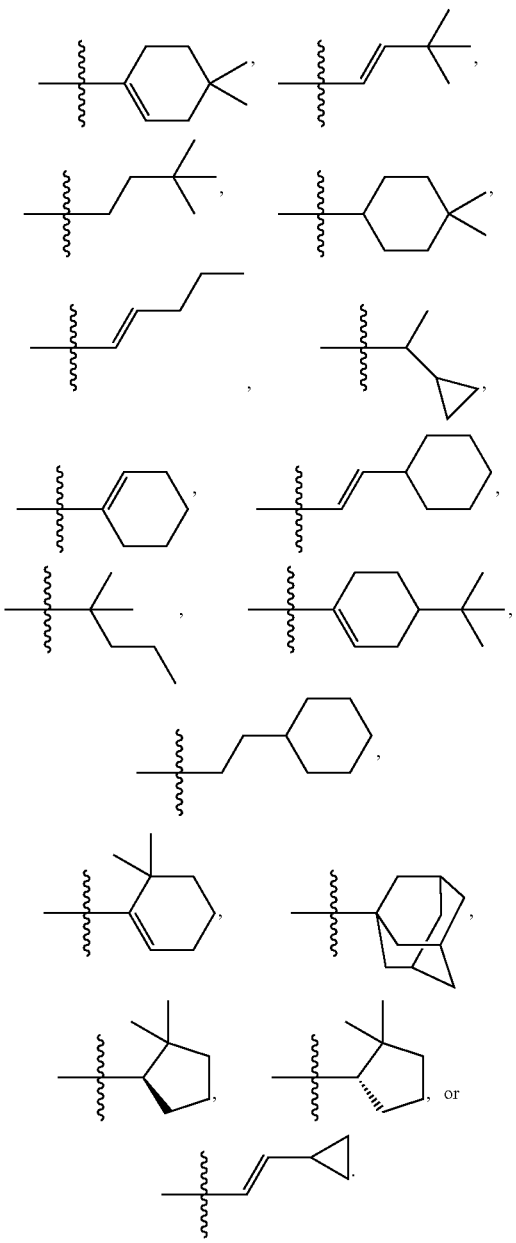

In some such embodiments, A is selected from

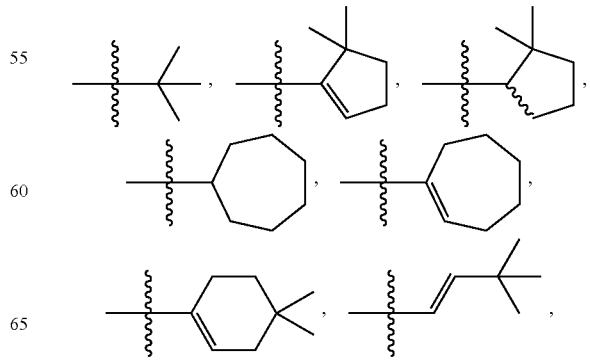

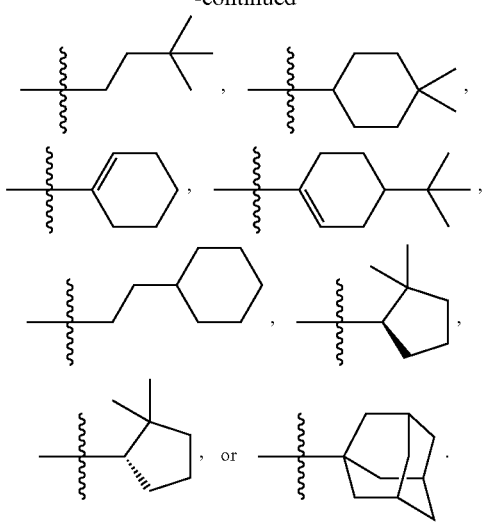

In some embodiments, A is selected from $(C_3-C_{10})$alkyl or $(C_4-C_{10})$alkenyl. In some such embodiments, A is t-butyl. In other such embodiments, A is an unsubstituted or optionally substituted cyclopentyl, cyclohexyl, or cycloheptyl group. In some such embodiments, A is an unsubstituted cyclopentyl, cyclohexyl, or cycloheptyl group. In some such embodiments, A is a cyclopentyl, cyclohexyl, or cycloheptyl group optionally substituted with 1, 2, 3, or 4 $(C_1-C_4)$alkyl groups. In some such embodiments, A is a cyclopentyl, cyclohexyl, or cycloheptyl group substituted with a t-butyl group. In other such embodiments A is a cyclopentyl, cyclohexyl, or cycloheptyl group substituted with 1 or 2 methyl groups. In some such embodiments, A is an unsubstituted or optionally substituted cyclopentenyl, cyclohexenyl, or cycloheptenyl group. In some such embodiments, A is an unsubstituted cyclopentenyl, cyclohexenyl, or cycloheptenyl group. In some such embodiments, A is a cyclopentenyl, cyclohexenyl, or cycloheptenyl group optionally substituted with 1, 2, 3, or 4 $(C_1-C_4)$alkyl groups. In some such embodiments, A is a cyclopentenyl, cyclohexenyl, or cycloheptenyl group substituted with a t-butyl group. In other such embodiments A is a cyclopentenyl, cyclohexenyl, or cycloheptenyl group substituted with 1 or 2 methyl groups.

In some embodiments, A is selected from

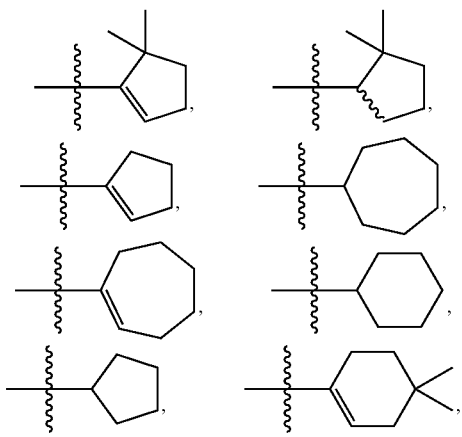

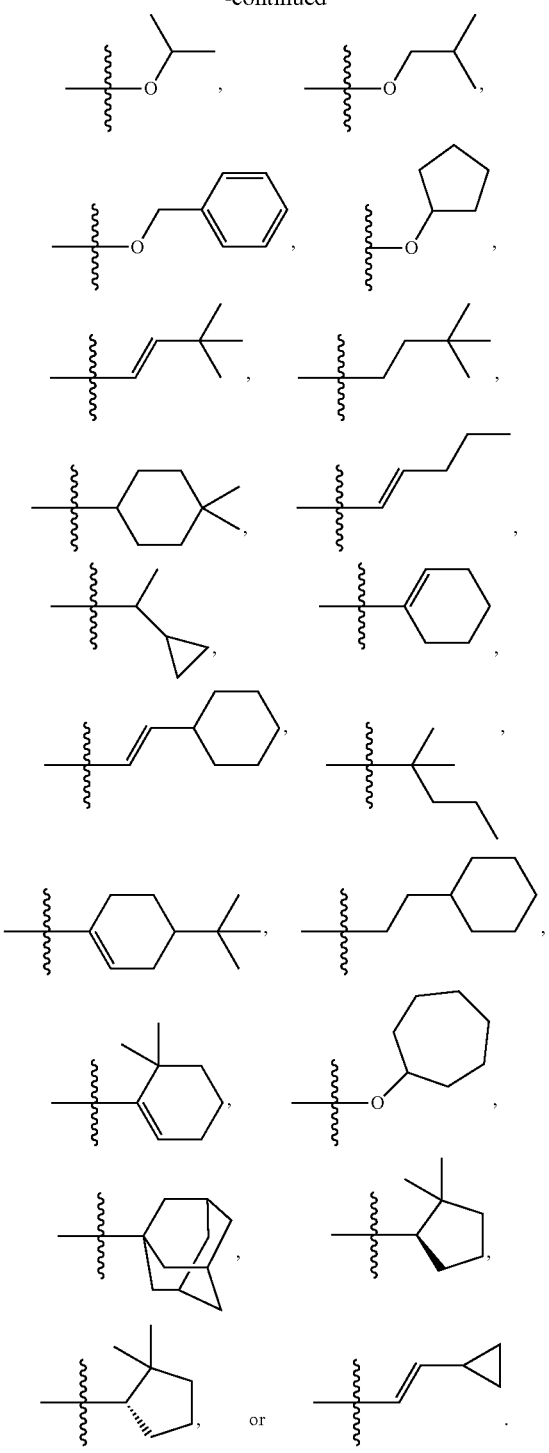

In some embodiments, A is selected from any one or more of

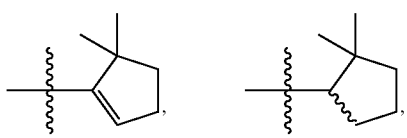

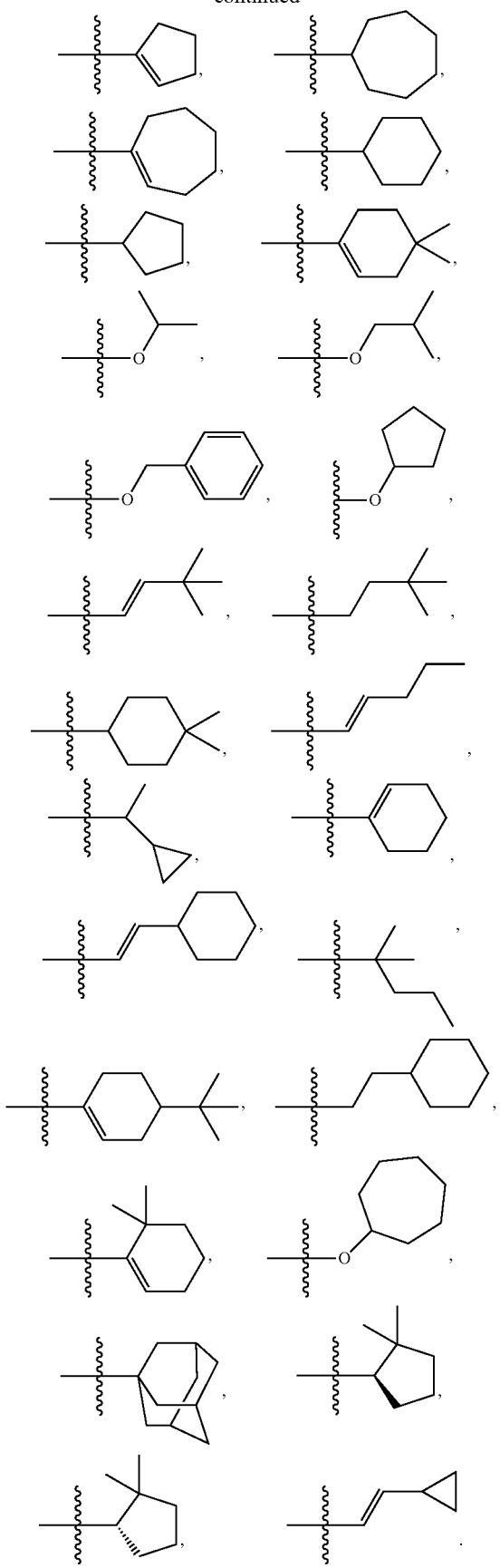
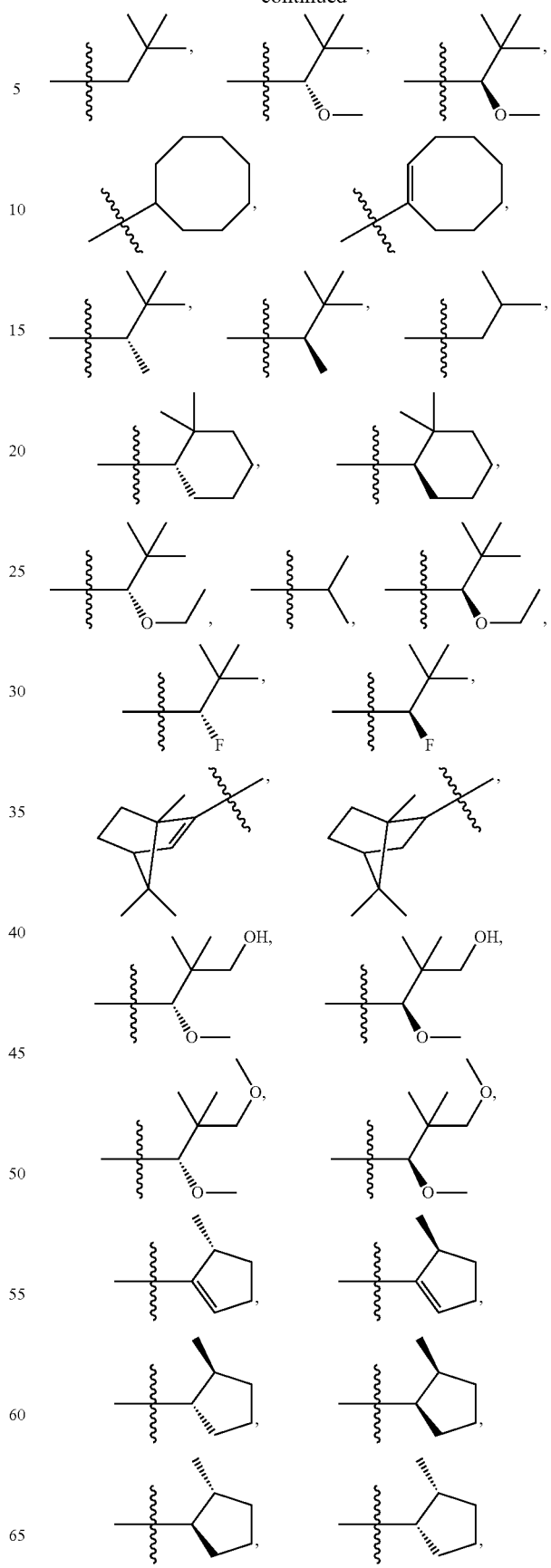

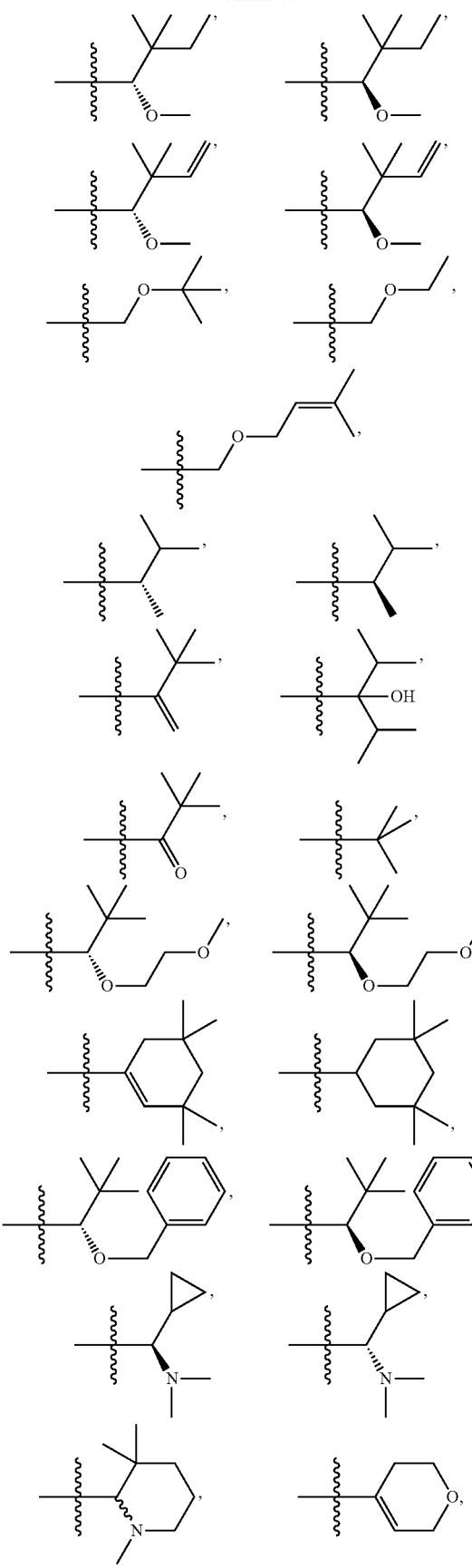
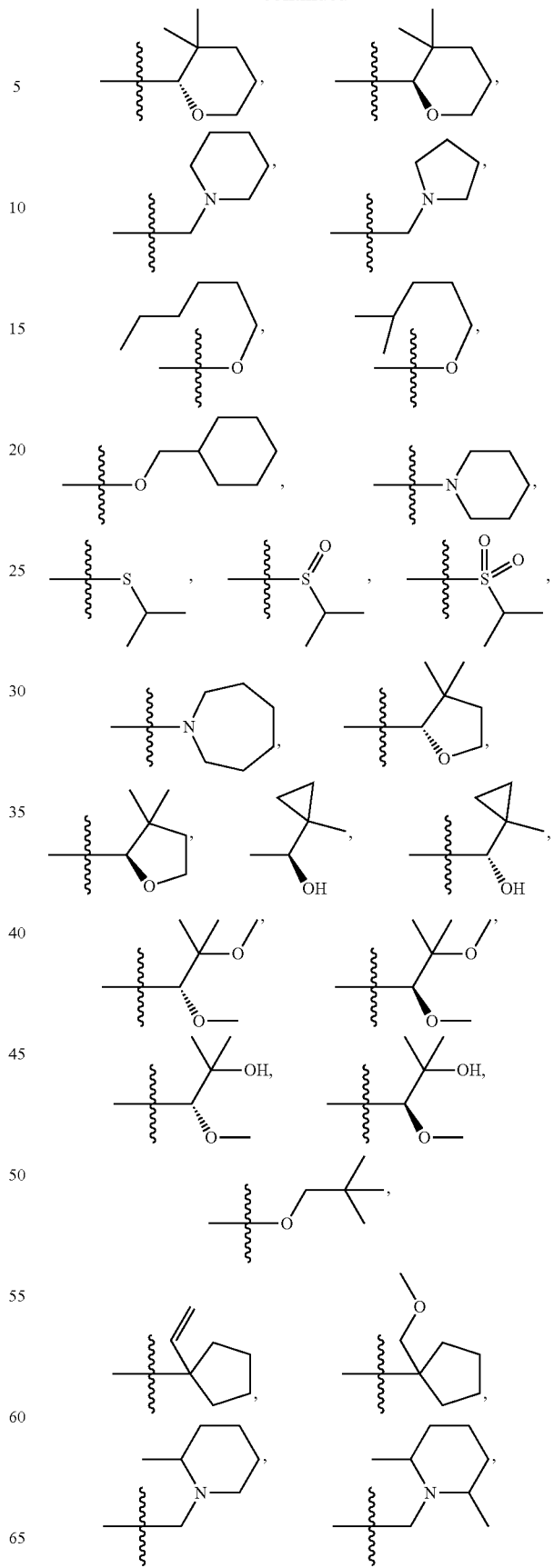

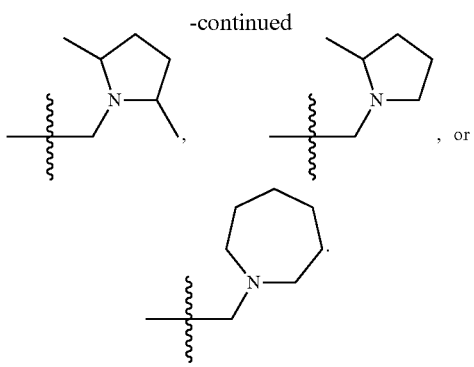

In some embodiments, A is a group of formula A'.

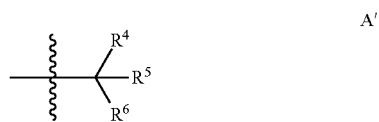

where the wavy line indicates the point of attachment and $R^4$, $R^5$, and $R^6$ are independently selected from H, F, $(C_1-C_4)$ alkyl, and two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring. In some such embodiments, $R^4$, $R^5$, and $R^6$ are independently selected from H and $(C_1-C_4)$ alkyl groups and at least two of $R^4$, $R^5$, and $R^6$ are $(C_1-C_4)$ alkyl groups. In some such embodiments, all three of $R^4$, $R^5$, and $R^6$ are independently selected from $(C_1-C_4)$alkyl groups. In some embodiments, two of $R^4$, $R^5$, and $R^6$ are methyl groups. In some embodiments, each of $R^4$, $R^5$, and $R^6$ is a methyl group. In other embodiments, $R^4$, $R^5$, and $R^6$ are independently selected from H, $(C_1-C_4)$alkyl groups, or a substituted $(C_1-C_4)$alkyl group selected from $(C_1-C_4)$haloalkyl groups, $(C_1-C_4)$perhaloalkyl groups, or $(C_1-C_4)$ alkoxy$(C_1-C_4)$alkyl groups. In some embodiments, at least one of $R^4$, $R^5$, and $R^6$ is a $CF_3$ group. In other embodiments at least one of $R^4$, $R^5$, and $R^6$ is a methoxymethyl group.

In some embodiments, A is a group of formula A' where the wavy line indicates the point of attachment and $R^4$, $R^5$, and $R^6$ are independently selected from H, F, OH, —O—$(C_1-C_3)$alkyl, $(C_1-C_6)$alkyl and $(C_2-C_6)$alkenyl, and two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring. In some such embodiments, $R^4$, $R^5$, and $R^6$ are independently selected from H, OH, OMe, OEt, $(C_1-C_6)$ alkyl, and $(C_2-C_6)$alkenyl groups and at least two of $R^4$, $R^5$, and $R^6$ are $(C_1-C_4)$alkyl groups. In some embodiments, all three of $R^4$, $R^5$, and $R^6$ are independently selected from $(C_1-C_4)$alkyl groups. In some embodiments, two of $R^4$, $R^5$, and $R^6$ are methyl groups. In some embodiments, each of $R^4$, $R^5$, and $R^6$ is a methyl group. In other embodiments, $R^4$, $R^5$, and $R^6$ are independently selected from H, $(C_1-C_4)$alkyl groups, or a substituted $(C_1-C_4)$alkyl group selected from $(C_1-C_4)$haloalkyl groups, $(C_1-C_4)$perhaloalkyl groups, or $(C_1-C_4)$alkoxy$(C_1-C_4)$alkyl groups. In some such embodiments, at least one of $R^4$, $R^5$, and $R^6$ is a $CF_3$ group. In other embodiments at least one of $R^4$, $R^5$, and $R^6$ is a methoxymethyl group. In other embodiments, at least one of $R^4$, $R^5$, and $R^6$ is selected from OH, methoxy, or is ethoxy. In some such embodiments one of $R^4$, $R^5$, and $R^6$ is a methoxy. In other such embodiments one of $R^4$, $R^5$, and $R^6$ is OH. In other such embodiments one of $R^4$, $R^5$, and $R^6$ is ethoxy.

In some embodiments where A is a group of formula A', two of $R^4$, $R^5$, and $R^6$, together with the C atom to which they are attached, join to form a 3-8 or 3-7 membered ring, and the other of $R^4$, $R^5$, and $R^6$ is selected from H, an unsubstituted $(C_1-C_4)$alkyl, or a substituted $(C_1-C_4)$alkyl. In some embodiments the ring is a carbocyclic ring which may be a fully saturated cycloalkyl ring. In some such embodiments, the 3-8 membered ring is a 5-7 membered ring, a 3-6 membered ring, or a 3-5 membered ring. Examples of such rings include cyclopropyl, cyclobutyl, cyclopentyl, cyclohexyl, and cycloheptyl rings. In some such embodiments, two of $R^4$, $R^5$, and $R^6$ join to form a cyclopropyl ring. In some such embodiments, the other of $R^4$, $R^5$, and $R^6$ is H. In some embodiments two of $R^4$, $R^5$, and $R^6$, together with the C atom to which they are attached, join to form an optionally substituted saturated or partially unsaturated 3-8 or 3-7 membered ring which may be monocyclic or bicyclic, and the other of $R^4$, $R^5$, and $R^6$ is selected from H, an unsubstituted $(C_1-C_4)$alkyl, or a substituted $(C_1-C_4)$alkyl. In some embodiments the ring only includes carbon ring members. In some such embodiments, the ring includes 0 or 1 double bonds between ring members. In some such embodiments, the 3-7 membered ring is a 3-6, or a 3-5 membered ring. Examples of such rings include cyclopropyl, cyclobutyl, cyclobutenyl, cyclopentyl, cyclopentenyl, cyclohexyl, cyclohexenyl, cycloheptyl, and cycloheptenyl rings. In some such embodiments, two of $R^4$, $R^5$, and $R^6$ join to form an optionally substituted cyclopropyl ring. In some such embodiments, the other of $R^4$, $R^5$, and $R^6$ is H. In some such embodiments, two of $R^4$, $R^5$, and $R^6$ join to form an optionally substituted cyclopentenyl, cyclohexenyl, or cycloheptenyl ring. In some such embodiments, the other of $R^4$, $R^5$, and $R^6$ is H. In some embodiments all three of $R^4$, $R^5$, and $R^6$, together with the C atom to which they are attached, join to form an optionally substituted saturated or partially unsaturated 3-8 membered ring bicyclic ring system. For example, in some embodiments, A may comprise an adamantyl or another bicyclic ring system such as, but not limited to bicyclo[3.2.1] octane, bicyclo[2.2.1]heptane, and the like. In some such embodiments the ring only includes carbon ring members. In some such embodiments, the ring includes 0 or 1 double bonds between ring members. In some embodiments, A is a branched chain $(C_4-C_8)$alkyl group such as a t-butyl group. In other such embodiments, A is an optionally substituted $(C_5-C_7)$cycloalkyl group or an optionally substituted $(C_5-C_7)$cycloalkenyl group. In some embodiments, the $(C_5-C_7)$ cycloalkyl group or the $(C_5-C_7)$cycloalkenyl group are substituted with 1, 2, 3, or 4 methyl groups. In some other such embodiments, A has the formula

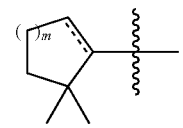

wherein m is 1, 2, or 3, and the dashed line indicates a single or double bond. In some such embodiments, A has the formula

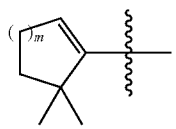

wherein m is 1, 2, or 3. In other such embodiments, A has the formula

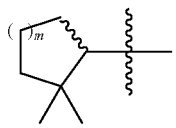

wherein m is 1, 2, or 3 and the wavy line indicates that the compound has the R stereochemistry, the S stereochemistry, or a mixture of the R and S stereochemistry with respect to the carbon attached to the rest of the molecule. In some such embodiments, A has the formula

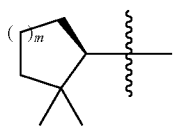

wherein m is 1, 2, or 3. In other embodiments, A has the formula

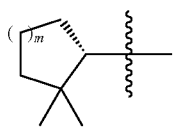

wherein m is 1, 2, or 3. In some embodiments, A is an —OR$^{4a}$ group, In some such embodiments, R$^{4a}$ is selected from a methyl, ethyl, propyl, butyl, pentyl, hexyl, isopropyl, t-butyl, or an isomer thereof. In some embodiments, R$^{4a}$ is selected from such an alkyl group that is substituted. For example, in some embodiments, R$^{4a}$ may a trihaloalkyl group such as a CF$_3$ group or another perhaloalkyl group.

In some embodiments, A is

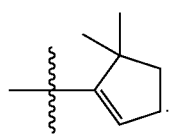

In some embodiments, A is selected from

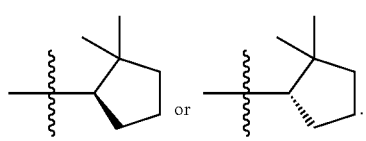

In some embodiments, A is

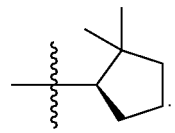

In some embodiments, A is

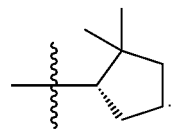

In some embodiments, A is a (C$_1$-C$_{12}$)alkyl or is a (C$_2$-C$_{12}$) alkenyl group and the (C$_1$-C$_{12}$)alkyl or the (C$_2$-C$_{12}$)alkenyl group is substituted with at least one A" group where A" is selected from —F, —OH, —O—(C$_1$-C$_4$)alkyl, —O(C$_1$-C$_4$) alkyl-aryl, —O(C$_2$-C$_8$)alkenyl, or —O—(C$_1$-C$_4$)alkyl-O—(C$_1$-C$_4$)alkyl. Therefore, in some embodiments A is selected from any one or all of:

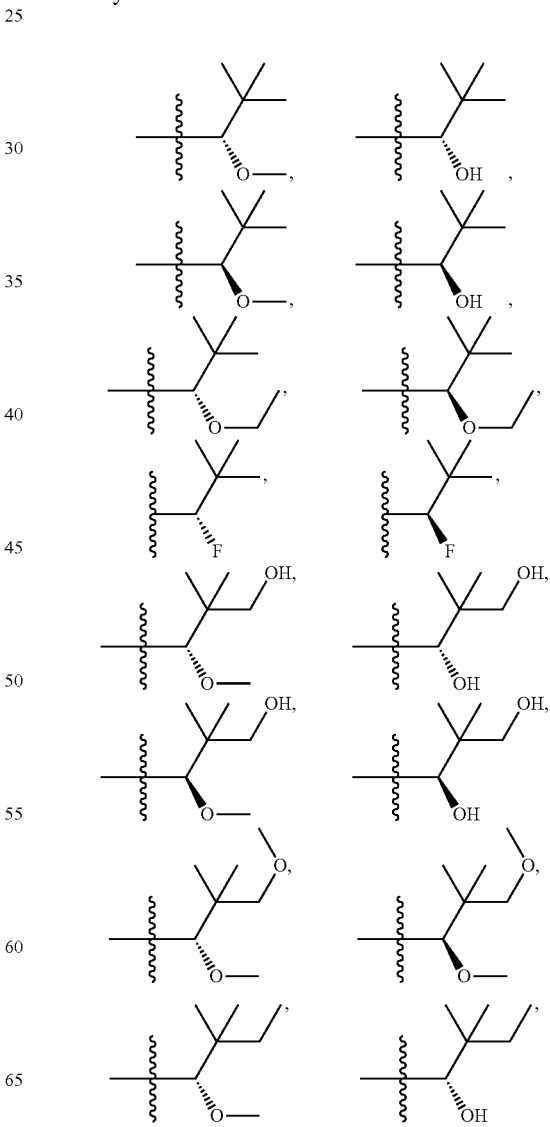

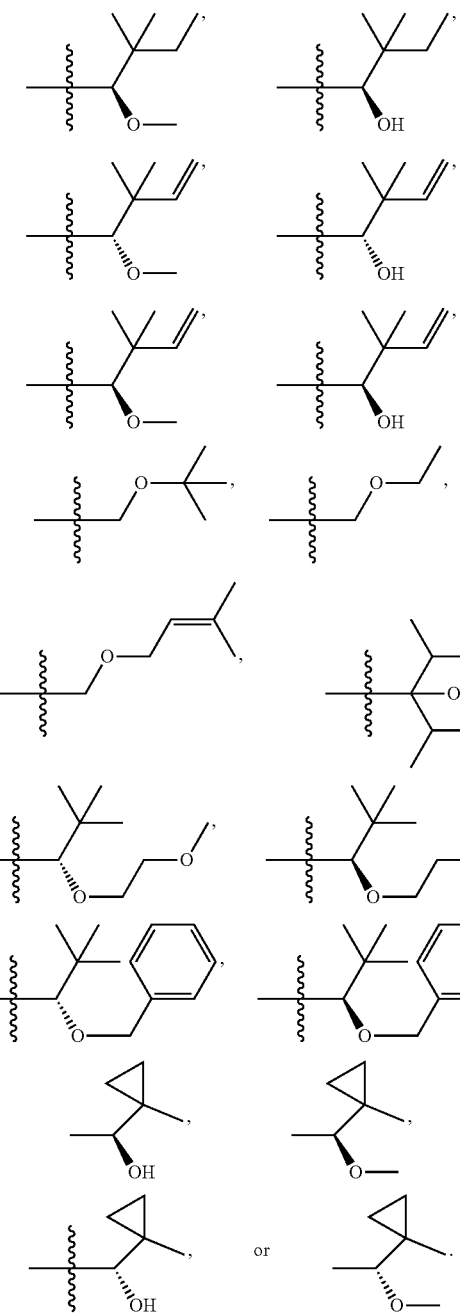

In some embodiments, A is selected from

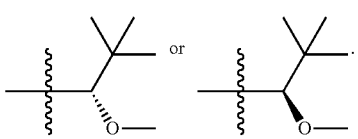

In some embodiments, A is

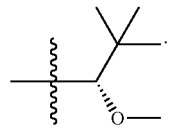

In some embodiments, A is

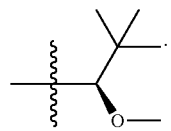 [SMILES: *[C@H](OC)C(C)(C)C]

In some embodiments, A is selected from

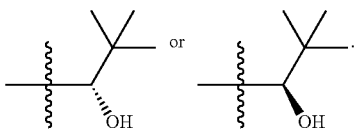

In some embodiments, A is

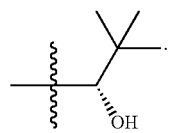

In some embodiments, A is

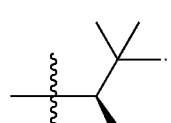

In some embodiments, X is O. In other embodiments, X is S. In still further embodiments X is $NR^a$. In some embodiments X is $NR^a$ and $R^a$ is selected from H or methyl. In still other embodiments, X is $NR^a$ and $R^a$ is H.

In some embodiments, $R^3$ is —H, —F, —Cl, —OH, —S($C_1$-$C_2$)alkyl, unsubstituted —($C_1$-$C_4$)alkyl, unsubstituted —O($C_1$-$C_3$)alkyl, —($C_1$-$C_4$)alkyl substituted with from 1 to 5 substituents selected from —F, —OH, (=O), or —O($C_1$-$C_2$)alkyl, or substituted —O($C_1$-$C_3$)alkyl, wherein the alkyl group of the substituted —O($C_1$-$C_3$)alkyl is substi In some embodiments, A is selected from

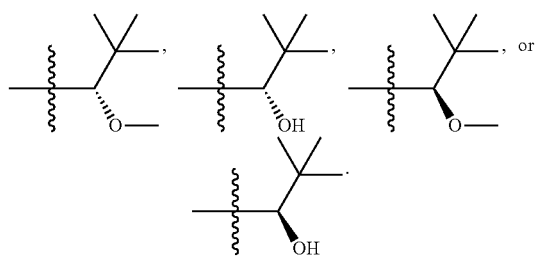

tuted with from 1 to 5 substituents selected from —F, —OH, or —O($C_1$-$C_2$)alkyl. In some embodiments, $R^3$ is selected from —OH, —O($C_1$-$C_2$)alkyl, or —S($C_1$-$C_2$)alkyl. In some embodiments, $R^3$ is selected from —O-Me or —S-Me. In some such embodiments, $R^3$ is —S-Me. In other such embodiments, $R^3$ is ethoxy (—O—$CH_2CH_3$). In still other such embodiments, $R^3$ is a —O—($C_1$-$C_2$)haloalkyl. Examples of some such groups include —$OCF_3$ and —$OCH_2CF_3$. In some embodiments, $R^3$ is selected from methoxy or ethoxy. In other embodiments, $R^3$ is a substituted ($C_1$-$C_2$)alkyl group such as a —$CHF_2$ or —$CF_3$ group. In other embodiments, $R^3$ is a ($C_1$-$C_3$)alkyl group that is substituted with a group such as —OH or with an oxo group. Examples of such groups include, but are not limited to, —$C(CH_3)_2OH$ and —$C(=O)$—$CH_3$. In some embodiments, $R^3$ is selected from —F, —Cl, —OH, —$OCH_3$, —$SCH_3$, —$OCH_2CH_3$, —$OCHF_2$, —$OCF_3$, —$OCH_2CF_3$, —O-cyclopropyl, —$CHF_2$, —$CF_3$, —$C(=O)$—$CH_3$, —$CH(CH_3)_2OH$, or —$CH_2CH_3$. In some such embodiments, $R^3$ is selected from —$OCH_3$, —$OCH_2CH_3$, —$OCHF_2$, —$OCF_3$, —$OCH_2CF_3$, —O-cyclopropyl, —$CHF_2$, or —$CF_3$. In some embodiments, $R^3$ is selected from —F, —Cl, —$OCHF_2$, —$OCH_2CF_3$, —$OCF_3$, —O-cyclopropyl, —$CF_3$, or —$CHF_2$. In some embodiments, $R^3$ is selected from —$OCHF_2$, —$OCH_2CF_3$, —$OCF_3$, —O-cyclopropyl, —$CF_3$, or —$CHF_2$.

In some embodiments, W, Y, and Z are all C—H. In other embodiments W and Z are C—H and Y is N.

In some embodiments, $R^7$ and $R^8$ are independently selected from H and unsubstituted —($C_1$-$C_4$)alkyl In some such embodiments, $R^7$ and $R^8$ are independently selected from H and —$CH_3$. In some such embodiments, $R^7$ and $R^8$ are both H. In some such embodiments, X is O.

In some embodiments, $R^{1a}$ is H or —$CH_3$. In some such embodiments, $R^{1a}$ is H.

In some embodiments, $R^{1b}$ is H or —$CH_3$. In some such embodiments, $R^{1b}$ is H.

In some embodiments, $R^{1b'}$ is H or —$CH_3$. In some such embodiments, $R^{1b'}$ is H.

In some embodiments, $R^{1c}$, if present, is H or —$CH_3$. In some such embodiments, $R^{1c}$, if present is H. In some embodiments, m is 0 and $R^{1c}$ is absent.

In some embodiments, $R^{1c'}$, if present, is H or —$CH_3$. In some such embodiments, $R^{1c'}$, if present, is H. In some embodiments, m is 0 and $R^{1c'}$ is absent.

In some embodiments, $R^{1d}$, if present, is H or —$CH_3$. In some such embodiments, $R^{1d}$, if present, is H. In some embodiments, q is 0 and $R^{1d}$ is absent.

In some embodiments, $R^{1d'}$, if present, is H or —$CH_3$. In some such embodiments, $R^{1d'}$, if present, is H. In some embodiments, q is 0 and $R^{1d'}$ is absent.

In some embodiments q is 0, 1, or 2. In some such embodiments, q is 0. In other such embodiments, q is 1. In still other such embodiments, q is 2.

In some embodiments of the compounds of formula I'A or I'B, m is 0 such that the compound of formula I'A or I'B is a compound of formula II'A or II'B or a pharmaceutically acceptable salt, stereoisomer, or mixture thereof. The compounds of formula II'A or II'B have the following structures where each of the variables have any of the definitions provided for any of the embodiments:

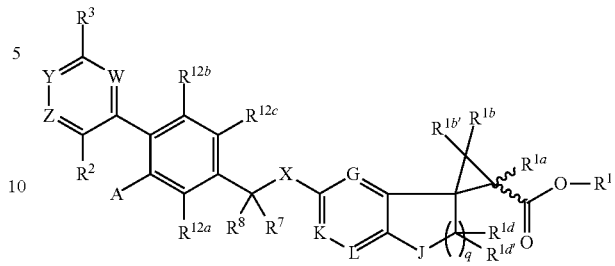

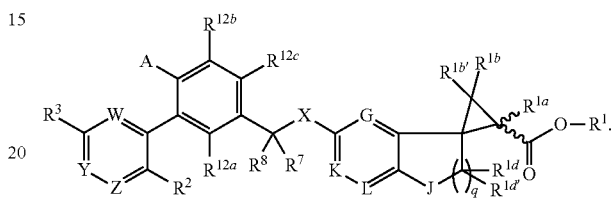

In some embodiments, J is selected from O, S, $NR^b$, or $CR^cR^d$; where $R^b$ is selected from H and ($C_1$-$C_4$)alkyl, and $R^c$ and $R^d$ are independently selected from H, F, and ($C_1$-$C_4$) alkyl.

In some embodiments, J is O, $NR^b$, or S. In some such embodiments, J is O. In other such embodiments, J is S. In still other such embodiments, J is $NR^b$. In some such embodiments J is $NR^b$ and $R^b$ is selected from H and —$CH_3$. In some such embodiments J is $NR^b$ and $R^b$ is H.

In other embodiments, J is $CR^cR^d$. In some such embodiments, $R^c$ and $R^d$ are independently selected from H or —$CH_3$. In some such embodiments, $R^c$ and $R^d$ are both H. In some such embodiments, q is 0, 1, or 2. In some such embodiments, q is 0. In other such embodiments, q is 1. In still other such embodiments, q is 2. In still other embodiments, J is $CR^cR^d$; $R^c$ and $R^d$ are both H; and q is 3. In some embodiments, J is $CR^cR^d$ and $R^c$ and $R^d$ are independently selected from H, F, or —$CH_3$.

In still other embodiments, J is selected from C(=O) or —C(=O)—$NR^b$— where $R^b$ is selected from H and ($C_1$-$C_4$) alkyl.

In some embodiments, $R^2$ is selected from —H, —F, —$CF_3$, or —O—($C_1$-$C_6$)alkyl. In some embodiments, $R^2$ is selected from F, $CF_3$, or ($C_1$-$C_6$)alkoxy. In some such embodiments, $R^2$ is selected from F, $CF_3$, or ($C_4$-$C_6$)alkoxy. In some embodiments, $R^2$ is H or F. In other embodiments, $R^2$ is F. In still other embodiments, $R^2$ is H. In other embodiments, $R^2$ is propoxy, butoxy, or pentoxy. In some such embodiments, $R^2$ is butoxy. In still further embodiments, $R^2$ is selected from F or ($C_3$-$C_4$) alkoxy. In some such embodiments, $R^2$ is a —$OCF_3$. In other embodiments, $R^2$ is a —$CF_3$ group. In still other embodiments, $R^2$ is —Cl.

In some embodiments, the compound has the formula I'A.
In some embodiments, the compound has the formula I'B.
In some embodiments, $R^{12c}$ is H or F. In some such embodiments, $R^{12c}$ is H whereas in other such embodiments, $R^{12c}$ is F. In some such embodiments, $R^{12a}$ and $R^{12b}$ are both H.

In some embodiments, each of $R^{12a}$, $R^{12b}$, and $R^{12c}$ is independently selected from —H, —F, —Cl, unsubstituted —($C_1$-$C_4$)alkyl, $CF_3$, or —O($C_1$-$C_4$)alkyl.

In some embodiments, G is $CR^{11a}$, K is $CR^{11b}$, and L is $CR^{11b}$. In other embodiments, G is N, K is $CR^{11b}$, and L is CR$^{11b}$. In still other embodiments, G is CR$^{11a}$, K is N, and L is CR$^{11b}$. In still further embodiments, G is CR$^{11a}$, K is CR$^{11b}$, and L is N.

In some embodiments, G is CR$^{11a}$ and R$^{11a}$ is H. In other embodiments, G is CR$^{11a}$ and R$^{11a}$ is F.

In some embodiments, K is CR$^{11b}$, L is CR$^{11c}$, and both R$^{11b}$ and R$^{11c}$ are H.

In some embodiments, G is CR$^{11a}$; K is CR$^{11b}$; L is CR$^{11c}$; R$^{11b}$, R$^{11c}$, R$^{12a}$, and R$^{12b}$ are all H; J is CR$^c$R$^d$; R$^c$ is H; R$^d$ is H; R$^{1a}$ is H; R$^{1b}$ is H; R$^{1b'}$ is H; R$^{1d}$, if present, is H; R$^{1d'}$, if present, is H; W is C—H; Y is C—H or N; Z is C—H; R$^2$ is F; R$^3$ is methoxy; R$^7$ is H; R$^8$ is H; X is O; m is 0; and q is 0, 1, or 2. In some such embodiments, Y is C—H. In other such embodiments, Y is N. In some such embodiments, q is 0. In other such embodiments, q is 1. In still other such embodiments, q is 2. In some embodiments where q is 1 or 2, R$^{1d}$ and R$^{1e}$ are both H in every instance. In some such embodiments, R$^{12c}$ is H whereas in other such embodiments, R$^{12c}$ is F. In still other such embodiments, R$^{11a}$ is H whereas in other such embodiments, R$^{11a}$ is F.

In some embodiments, R$^{13}$ is selected from —H, —F, —(C$_1$-C$_4$)alkyl, and —O—(C$_1$-C$_4$)alkyl. In some such embodiments R$^{13}$ is H.

In some embodiments where W is C (a carbon atom), W and A join together to form a ring having 5 to 7 ring members of which 0 or 1 is a heteroatom selected from N, O, or S, and further wherein the ring having 5 to 7 ring members is optionally substituted with —(C$_1$-C$_8$)alkyl, —(C$_1$-C$_8$)alkenyl, —OH, —O—(C$_1$-C$_8$)alkyl, —O—(C$_1$-C$_8$)alkenyl, or halo. In some such embodiments, W and A join together to form a 5 or 6 membered ring with 0 heteroatoms. In some such embodiments, the ring is unsubstituted. In other such embodiments, the ring is substituted.

In some embodiments, the compound of formula I'A or I'B is a compound of formula III'A or III'B or a pharmaceutically acceptable salt, stereoisomer, or mixture thereof. The compounds of formula III'A and III'B have the following structures where each of the variables has any of the values of any of the embodiments described herein:

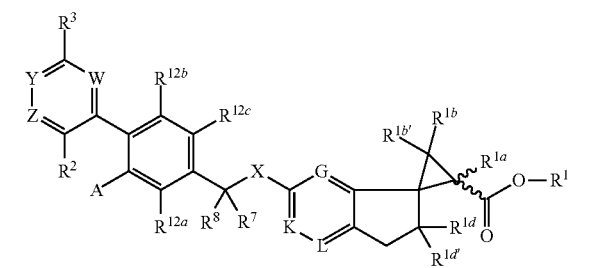

III'A

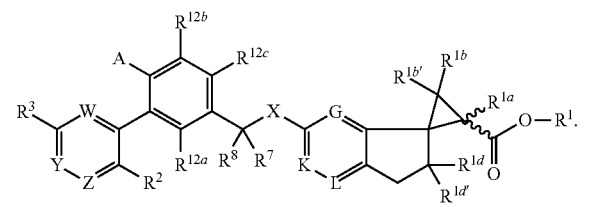

III'B

In some such embodiments, R$^{1a}$, R$^{1b}$, R$^{1b'}$, R$^{1d}$, and R$^{1d'}$ are H.

In some embodiments, the compound of formula I'A or I'B is a compound of formula IV'A or IV'B or a pharmaceutically acceptable salt, stereoisomer, or mixture thereof. The compounds of formula IV'A and IV'B have the following structures where each of the variables has any of the values of any of the embodiments described herein:

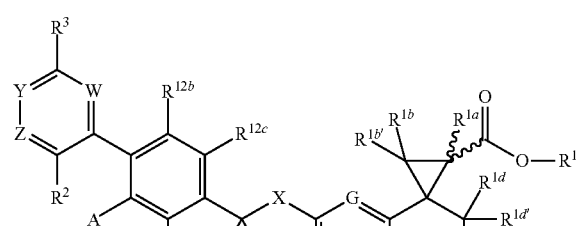

IV'A

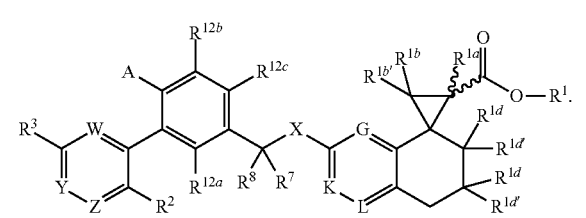

IV'B

In some such embodiments, R$^{1a}$, R$^{1b}$, R$^{1b'}$, and each instance of R$^{1d}$ and R$^{1d'}$ are H.

In some embodiments, the compound of formula I'A or I'B is a compound of formula V'A or V'B or a pharmaceutically acceptable salt, stereoisomer, or mixture thereof. The compounds of formula V'A and V'B have the following structures where each of the variables has any of the values of any of the embodiments described herein:

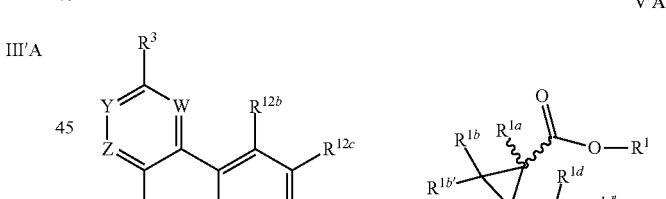

V'A

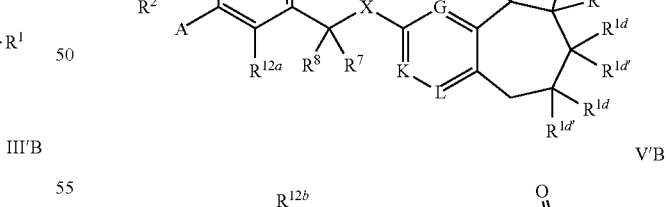

V'B

In some such embodiments, R$^{1a}$, R$^{1b}$, R$^{1b'}$, and each instance of R$^{1d}$ and R$^{1d'}$ are H.

In some embodiments, the compound of formula I'A or I'B is a compound of formula VI'A or VI'B or a pharmaceutically acceptable salt, stereoisomer, or mixture thereof. The compounds of formula VI'A and VI'B have the following structures where each of the variables has any of the values of any of the embodiments described herein:

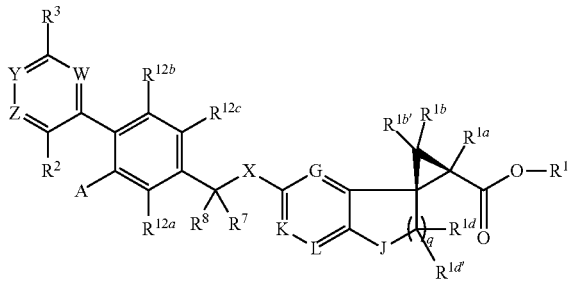

VI'A

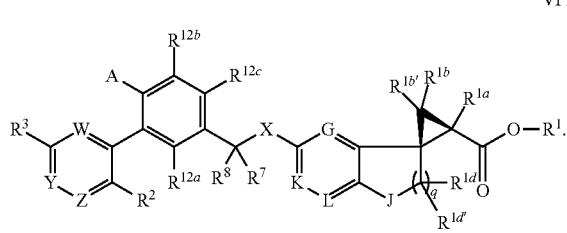

VI'B

In some such embodiments, $R^{1a}$, $R^{1b}$, $R^{1b'}$, and each instance of $R^{1d}$ and $R^{1d'}$ are H.

In some embodiments, the compound of formula I'A or I'B is a compound of formula VII'A or VII'B or a pharmaceutically acceptable salt, stereoisomer, or mixture thereof. The compounds of formula VII'A and VII'B have the following structures where each of the variables has any of the values of any of the embodiments described herein:

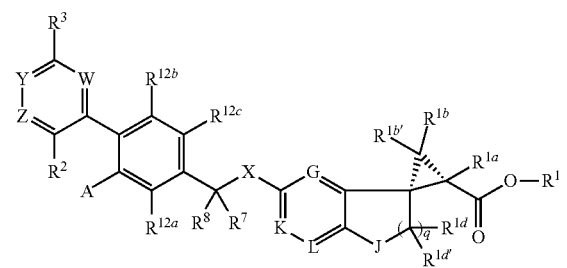

VII'A

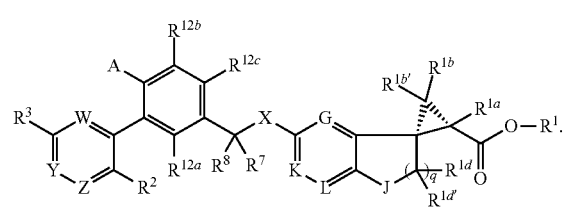

VII'B

In some such embodiments, $R^{1a}$, $R^{1b}$, $R^{1b'}$, and each instance of $R^{1d}$ and $R^{1d'}$ are H.

In some embodiments, the compound of formula I'A or I'B is a compound of formula VIII'A or VIII'B or a pharmaceutically acceptable salt, stereoisomer, or mixture thereof. The compounds of formula VIII'A and VIII'B have the following structures where each of the variables has any of the values of any of the embodiments described herein:

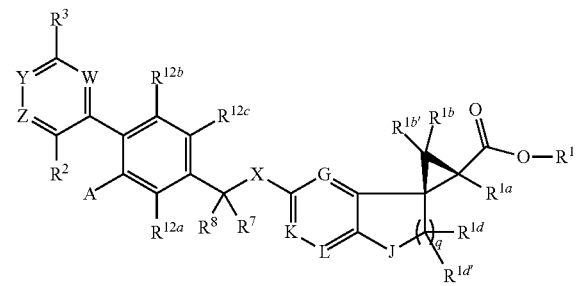

VIII'A

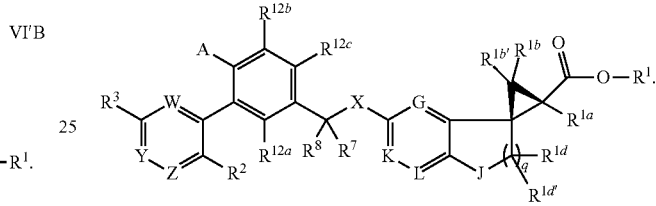

VIII'B

In some such embodiments, $R^{1a}$, $R^{1b}$, $R^{1b'}$, and each instance of $R^{1d}$ and $R^{1d'}$ are H.

In some embodiments, the compound of formula I'A or I'B is a compound of formula IX'A or IX'B or a pharmaceutically acceptable salt, stereoisomer, or mixture thereof. The compounds of formula IX'A and IX'B have the following structures where each of the variables has any of the values of any of the embodiments described herein:

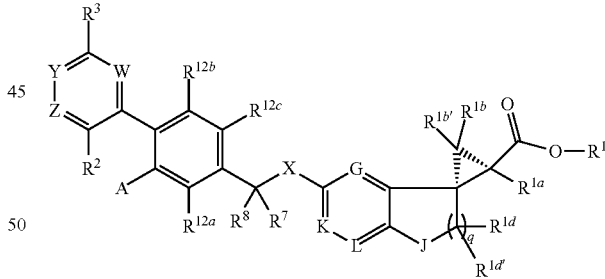

IX'A

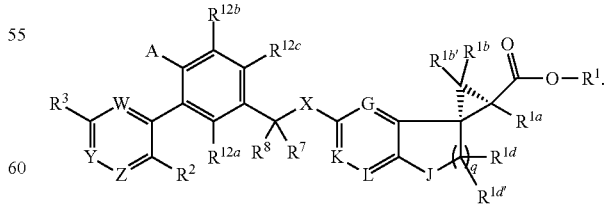

IX'B

In some such embodiments, $R^{1a}$, $R^{1b}$, $R^{1b'}$, and each instance of $R^{1d}$ and $R^{1d'}$ are H.

In another aspect, the invention provides a compound having the formula IA or IB or a pharmaceutically acceptable salt, stereoisomer, or mixture thereof. Compounds of formula IA and IB have the following structures:

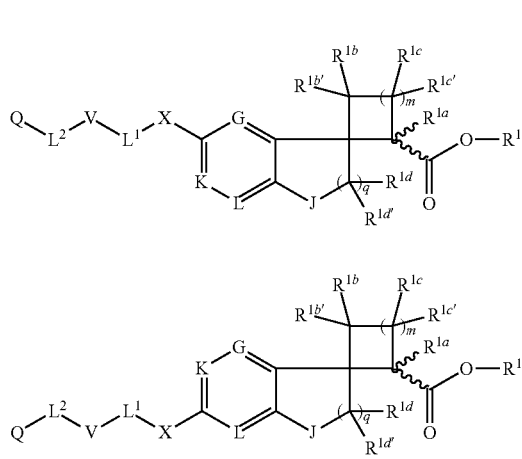

or a pharmaceutically acceptable salt, stereoisomer, or a mixture thereof,
wherein
G is selected from N or $CR^{11a}$;
K is selected from N or $CR^{11b}$;
L is selected from N or $CR^{11c}$;
wherein 0 or 1 of G, L, and K is N;
X is O, S, or $NR^a$ wherein $R^a$ is selected from —H or —$(C_1$-$C_6)$ alkyl groups;
J is selected from O, S, $NR^b$, $CR^cR^d$, C(=O), or —C(=O)—$NR^b$—; wherein $R^b$ is selected from H and $(C_1$-$C_4)$alkyl, and further wherein $R^c$ and $R^d$ are independently selected from H, F, and $(C_1$-$C_4)$alkyl;
$L^1$ is absent or is a $(C_1$-$C_4)$alkyl;
V is selected from a $(C_4$-$C_8)$cycloalkyl; a $(C_6$-$C_{10})$aryl; a heteroaryl comprising from 5 to 10 ring members of which from 1 to 3 are heteroatoms selected from N, O, and S; a benzo-fused $(C_5$-$C_8)$cycloalkyl wherein the cycloalkyl group of the benzo-fused cycloalkyl is bonded to $L^1$, if present, or is bonded to X if $L^1$ is absent; a benzo-fused $(C_5$-$C_8)$cycloalkyl wherein the aromatic group of the benzo-fused cycloalkyl is bonded to $L^1$, if present, or is bonded to X if $L^1$ is absent; a heteroaryl-fused $(C_5$-$C_8)$cycloalkyl wherein the cycloalkyl group of the heteroaryl-fused cycloalkyl is bonded to $L^1$, if present, or is bonded to X if $L^1$ is absent; or a heteroaryl-fused $(C_5$-$C_8)$cycloalkyl wherein the heteroaryl group of the heteroaryl-fused cycloalkyl is bonded to $L^1$, if present, or is bonded to X if $L^1$ is absent; wherein the $(C_6$-$C_{10})$aryl, heteroaryl, benzo-fused $(C_5$-$C_8)$cycloalkyl, and heteroaryl-fused $(C_5$-$C_8)$cycloalkyl group are optionally substituted with from 1 to 4 substituents independently selected from F, Cl, Br, OH, —$O(C_1$-$C_6)$alkyl groups, —$S(C_1$-$C_6)$alkyl groups $(C_1$-$C_6)$alkyl groups, —$CF_3$, or a group of formula A wherein A is selected from —$(C_1$-$C_{12})$alkyl; —$(C_2$-$C_{12})$alkenyl; —$(C_1$-$C_{12})$alkyl-O—$(C_1$-$C_4)$alkyl; —$(C_1$-$C_{12})$alkyl-OH; —$(C_1$-$C_{12})$alkyl-O—$(C_2$-$C_4)$alkenyl; —$(C_2$-$C_{12})$alkenyl-O—$(C_1$-$C_4)$alkyl; —$(C_2$-$C_{12})$alkenyl-OH; —$(C_2$-$C_{12})$alkenyl-O—$(C_2$-$C_4)$alkenyl; —O—$(C_1$-$C_{12})$alkyl; —O—$(C_2$-$C_{12})$alkenyl; —O—$(C_1$-$C_4)$alkyl-aryl; —S—$(C_1$-$C_{12})$alkyl; —S—$(C_2$-$C_{12})$alkenyl; —S(O)—$(C_1$-$C_{12})$alkyl; —S(O)—$(C_2$-$C_{12})$alkenyl; —$S(O)_2$—$(C_1$-$C_{12})$alkyl; —$S(O)_2$—$(C_2$-$C_{12})$alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 $(C_1$-$C_2)$alkyl groups; a —$(C_1$-$C_{12})$alkyl-heterocyclyl wherein the heterocyclyl of the —$(C_1$-$C_4)$alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 $(C_1$-$C_2)$alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 $(C_1$-$C_2)$ alkyl groups; further wherein the alkyl and alkenyl groups of —$(C_1$-$C_{12})$alkyl, —$(C_2$-$C_{12})$alkenyl, —$(C_1$-$C_{12})$alkyl-O—$(C_1$-$C_4)$alkyl, —$(C_1$-$C_{12})$alkyl-O—H, —$(C_1$-$C_{12})$alkyl-O—$(C_2$-$C_4)$alkenyl, —$(C_2$-$C_{12})$alkenyl-O—$(C_1$-$C_4)$alkyl, —$(C_2$-$C_{12})$alkenyl-OH, —$(C_2$-$C_{12})$alkenyl-O—$(C_2$-$C_4)$alkenyl, —O—$(C_1$-$C_{12})$alkyl, —O—$(C_2$-$C_{12})$alkenyl, and —O—$(C_1$-$C_4)$alkyl-aryl are unsubstituted or are substituted with from 1 to 4 substituents selected from —F, —Cl, —OH, (=O), —$NH_2$, NH$(C_1$-$C_4)$alkyl, —N$((C_1$-$C_4)$alkyl$)_2$, aryl, unsubstituted —$(C_1$-$C_2)$alkyl, or unsubstituted —O—$(C_1$-$C_2)$alkyl;
$L^2$ is absent or is selected from O, S, SO, $SO_2$, C(=O), $(C_1$-$C_2)$alkyl, or $NR^x$ wherein $R^x$ is selected from —H or —$(C_1$-$C_6)$ alkyl groups;
Q is selected from H, a $(C_4$-$C_8)$cycloalkyl; a $(C_6$-$C_{10})$aryl; or a heteroaryl comprising from 5 to 10 ring members of which from 1 to 3 are heteroatoms selected from N, O, and S; wherein the $(C_4$-$C_8)$cycloalkyl, $(C_6$-$C_{10})$aryl, and heteroaryl groups are optionally substituted with from 1 to 5 substituents independently selected from F, Cl, Br, OH, —$O(C_1$-$C_6)$alkyl groups, —$S(C_1$-$C_6)$alkyl groups $(C_1$-$C_6)$alkyl groups, or —$CF_3$.
$R^1$ is H or —$(C_1$-$C_6)$alkyl;
$R^{1a}$ is selected from —H and —$(C_1$-$C_4)$alkyl;
$R^{1b}$ is selected from —H and —$(C_1$-$C_4)$alkyl;
$R^{1b'}$ is selected from —H and —$(C_1$-$C_4)$alkyl;
$R^{1c}$ is selected from —H and —$(C_1$-$C_4)$alkyl;
$R^{1c'}$ is selected from —H and —$(C_1$-$C_4)$alkyl;
$R^{1d}$ is in each instance independently selected from —H, —F, and —$(C_1$-$C_4)$alkyl;
$R^{1d'}$ is in each instance independently selected from —H, —F and —$(C_1$-$C_4)$alkyl;
$R^{11a}$, $R^{11b}$, and $R^{11c}$ are independently selected from —H, —F, —Cl, —$(C_1$-$C_4)$alkyl, or —$O(C_1$-$C_4)$alkyl;
m is 0 or 1; and
q is selected from 0, 1, 2, or 3,
wherein the ⌇⌇⌇ indicates that the $R^{1a}$ and —C(=O)—O—$R^1$ may be attached to either side of the ring to which the ⌇⌇⌇ is attached and either R or S stereochemistry is allowed.

In some embodiments of the compound of formula IA or IB, $L^1$ is absent. In some such embodiments, X is O. In other embodiments $L^1$ is a $(C_1$-$C_4)$ alkyl. In some such embodiments, X is O. In some embodiments $L^1$ is —$CH_2$—. In some embodiments $L^1$ is —$CH_2$— and X is O. In other embodiments, $L^1$ is —$CH_2CH_2$—. In still other embodiments, $L^1$ is —$CH_2CH_2CH_2$—.

In some embodiments of the compound of formula IA or IB, $L^2$ is absent or O. In some such embodiments, $L^2$ is absent. In other embodiments, $L^2$ is O.

In some embodiments of the compound of formula IA or IB, Q is H. In other embodiments, Q is an optionally substituted $(C_6$-$C_{10})$aryl. In some such embodiments, Q is an optionally substituted benzene. In still other embodiments, Q is an optionally substituted heteroaryl comprising from 5 to 10 ring members of which from 1 to 3 are heteroatoms selected from N, O, and S. In some such embodiments Q is an optionally substituted pyridine.

In some embodiments of the compound of formula IA or IB, V is an optionally substituted $(C_4$-$C_8)$cycloalkyl such as a cyclopentyl, cyclohexyl, or cycloheptyl group. In other embodiments, V is an optionally substituted $(C_6$-$C_{10})$aryl such as an optionally substituted benzene. In some such embodiments, V is a benzene that is substituted with an A group as described in any of the embodiments described herein. In yet other embodiments, V is an optionally substituted heteroaryl comprising from 5 to 10 ring members of which from 1 to 3 are heteroatoms selected from N, O, and S. For example, in some such embodiments, V is a methyl substituted thiazole group. In still other embodiments, V is an optionally substituted benzo-fused $(C_5$-$C_8)$cycloalkyl wherein the cycloalkyl group of the benzo-fused cycloalkyl is bonded to $L^1$, if present, or is bonded to X if $L^1$ is absent. For example, in some such embodiments, V is a tetrahydronaphthalene or an indane in which the cycloalkyl group is bonded to the $L^1$ if present or to the X if $L^1$ is absent. In still other embodiments, V is an optionally substituted benzo-fused $(C_5$-$C_8)$cycloalkyl and the aromatic group of the benzo-fused cycloalkyl is bonded to $L^1$, if present, or is bonded to X if $L^1$ is absent. For example, ins some embodiments, V is an optionally substituted 1,2,3,4-tetrahydronaphthalene group. In some such embodiments, the cycloalkyl group of the tetrahydronaphthalene is substituted with 1 to 4 $(C_1$-$C_4)$alkyl groups. In other embodiments, V is an optionally substituted heteroaryl-fused $(C_5$-$C_8)$cycloalkyl and the cycloalkyl group of the heteroaryl-fused cycloalkyl is bonded to $L^1$, if present, or is bonded to X if $L^1$ is absent. In still other embodiments, V is an optionally substituted heteroaryl-fused $(C_5$-$C_8)$cycloalkyl and the heteroaryl group of the heteroaryl-fused cycloalkyl is bonded to $L^1$, if present, or is bonded to X if $L^1$ is absent.

In some embodiments of the compound of formula IA or IB, G is $CR^{11a}$ and $R^{11a}$ is H.

In some embodiments of the compound of formula IA or IB, G is $CR^{11a}$ and $R^{11a}$ is F.

In some embodiments of the compound of formula IA or IB, K is $CR^{11b}$, L is $CR^{11c}$, and both $R^{11b}$ and $R^{11c}$ are H.

In some embodiments of the compound of formula IA or IB, $R^{1a}$ is H or —$CH_3$. In some such embodiments, $R^{1a}$ is H.

In some embodiments of the compound of formula IA or IB, $R^{1b}$ is H or —$CH_3$. In some such embodiments $R^{1b}$ is H.

In some embodiments of the compound of formula IA or IB, $R^{1b'}$ is H or —$CH_3$. In some such embodiments $R^{1b'}$ is H.

In some embodiments of the compound of formula IA or IB, $R^{1c}$ is H or —$CH_3$. In some such embodiments $R^{1c}$ is H.

In some embodiments of the compound of formula IA or IB, $R^{1c'}$ is H or —$CH_3$. In some such embodiments $R^{1c'}$ is H.

In some embodiments of the compound of formula IA or IB, $R^{1d}$ is H or —$CH_3$. In some such embodiments $R^{1d}$ is H.

In some embodiments of the compound of formula IA or IB, $R^{1d'}$ is H or —$CH_3$. In some such embodiments $R^{1d'}$ is H.

In some embodiments of the compound of formula IA or IB, q is 0, 1, or 2. In some such embodiments, q is 0. In other such embodiments, q is 1. In still other embodiments, q is 2.

In some embodiments of the compound of formula IA or IB, m is 0.

In some embodiments of the compound of formula IA or IB, J is O, $NR^b$, or S. In other embodiments, J is $CR^cR^d$. In some such embodiments, $R^c$ and $R^d$ are independently selected from H or —$CH_3$ and in some such embodiments $R^c$ and $R^d$ are both H.

In some embodiments of the compound of formula IA or IB, the compound has the formula IA.

In some embodiments of the compound of formula IA or IB, the compound has the formula IB.

In some embodiments of the compound of formula IA or IB, X is O.

In some embodiments of the compound of formula IA or IB,

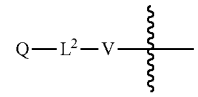

has the formula

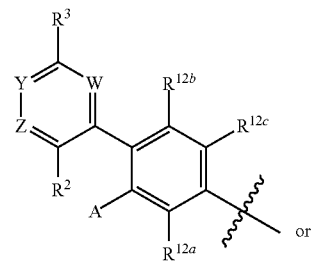 or

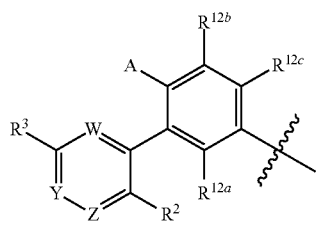

wherein

W, Y, and Z are selected from N or $CR^{13}$; wherein 0, 1, or 2 of W, Y, and Z is N; and further wherein Z is not N if $R^2$ is —F;

A is selected from —$(C_1$-$C_{12})$alkyl; —$(C_2$-$C_{12})$alkenyl; —$(C_1$-$C_{12})$alkyl-O—$(C_1$-$C_4)$alkyl; —$(C_1$-$C_{12})$alkyl-OH; —$(C_1$-$C_{12})$alkyl-O—$(C_2$-$C_4)$alkenyl; —$(C_2$-$C_{12})$alkenyl-O—$(C_1$-$C_4)$alkyl; —$(C_2$-$C_{12})$alkenyl-OH; —$(C_2$-$C_{12})$alkenyl-O—$(C_2$-$C_4)$alkenyl; —O—$(C_1$-$C_{12})$alkyl; —O—$(C_2$-$C_{12})$alkenyl; —O—$(C_1$-$C_4)$alkyl-aryl; —S—$(C_1$-$C_{12})$alkyl; —S—$(C_2$-$C_{12})$alkenyl; —S(O)—$(C_1$-$C_{12})$alkyl; —S(O)—$(C_2$-$C_{12})$alkenyl; —S(O)$_2$—$(C_1$-$C_{12})$alkyl; —S(O)$_2$—$(C_2$-$C_{12})$alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 $(C_1$-$C_2)$alkyl groups; a —$(C_1$-$C_4)$alkyl-heterocyclyl wherein the heterocyclyl of the —$(C_1$-$C_4)$alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 $(C_1$-$C_2)$alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 $(C_1-C_2)$alkyl groups; further wherein the alkyl and alkenyl groups of —$(C_1-C_{12})$alkyl, —$(C_2-C_{12})$alkenyl, —$(C_1-C_{12})$alkyl-O—$(C_1-C_4)$alkyl, —$(C_1-C_{12})$alkyl-O—H, —$(C_1-C_{12})$alkyl-O—$(C_2-C_4)$alkenyl, —$(C_2-C_{12})$alkenyl-O—$(C_1-C_4)$alkyl, —$(C_2-C_{12})$alkenyl-OH, —$(C_2-C_{12})$alkenyl-O—$(C_2-C_4)$alkenyl, —O—$(C_1-C_{12})$alkyl, —O—$(C_2-C_{12})$alkenyl, and —O—$(C_1-C_4)$alkyl-aryl are unsubstituted or are substituted with from 1 to 4 substituents selected from —F, —Cl, —OH, (=O), —$NH_2$, $NH(C_1-C_4)$alkyl, —$N((C_1-C_4)$alkyl$)_2$, aryl, unsubstituted —$(C_1-C_2)$alkyl, or unsubstituted —O—$(C_1-C_2)$alkyl;

$R^2$ is selected from —H, —F, —$CF_3$, —Cl, or —O—$(C_1-C_6)$alkyl;

$R^3$ is —H, —F, —Cl, —OH, —$(C_1-C_4)$alkyl, —O—$(C_1-C_3)$alkyl, or —S—$(C_1-C_2)$alkyl;

$R^{12a}$, $R^{12b}$, and $R^{12c}$ are independently selected from —H, —F, —Cl, —$(C_1-C_4)$alkyl, or —$O(C_1-C_4)$alkyl; and $R^{13}$ is selected from —H, —F, —$(C_1-C_4)$alkyl, and —O—$(C_1-C_4)$alkyl, and the ⌇ through the bond indicates the point of attachment to $L^1$ if present or X if $L^1$ is absent. In some such embodiments, X is O. In other embodiments, $R^3$ is selected from —OH, —$O(C_1-C_2)$alkyl, or —$S(C_1-C_2)$alkyl. In some such embodiments, $R^3$ is methoxy. In some embodiments, W, Y, and Z are all C—H whereas in other embodiments W and Z are C—H and Y is N. In some embodiments, $R^{12c}$ is H whereas in other embodiments, $R^{12c}$ is F. In some embodiments, $R^{12a}$ and $R^{12b}$ are both H. In some embodiments, G is $CR^{11a}$ and $R^{11a}$ is H. In other embodiments, G is $CR^{11a}$ and $R^{11a}$ is F. In some embodiments, K is $CR^{11b}$, L is $CR^{11c}$, and both $R^{11b}$ and $R^{11c}$ are H. In some embodiments, $R^2$ is selected from —H, —F, —$CF_3$, or —O—$(C_1-C_6)$alkyl. In some embodiments, $R^2$ is selected from F, $CF_3$, or $(C_1-C_6)$alkoxy. In some such embodiments, $R^2$ is selected from F, $CF_3$, or $(C_4-C_6)$alkoxy. Therefore, in some embodiments, $R^2$ is F. In some embodiments, $R^2$ is propoxy, butoxy, or pentoxy. In other embodiments, $R^2$ is —Cl. In some embodiments, G is $CR^{11a}$; K is $CR^{11b}$; L is $CR^{11c}$; $R^{11b}$, $R^{11c}$, $R^{12a}$ and $R^{12b}$ are all H; J is $CR^cR^d$; $R^c$ is H; $R^d$ is H; $R^{1a}$ is H; $R^{1b}$ is H; $R^{1b'}$ is H; $R^{1d}$, if present, is H; $R^{1d'}$, if present, is H; W is C—H; Y is C—H or N; Z is C—H; $R^2$ is F; $R^3$ is methoxy; $R^7$ is H; $R^8$ is H; X is O; m is 0; and q is 0, 1, or 2. In some such embodiments Y is C—H whereas in other such embodiments, Y is N. In some such embodiments q is 0 whereas in other such embodiments q is 1 and in still other embodiments, q is 2. In some such embodiments, $R^{12c}$ is F whereas in other embodiments, $R^{12c}$ is H. In some such embodiments, $R^{11a}$ is F whereas in other embodiments, $R^{11a}$ is H. In some embodiments, A has the definitions of any of the embodiments described herein.

In some embodiments of the compound of formula IA or IB, $R^1$ is H

In some embodiments, the compound is selected from a group that includes each, all, or any one of the compounds in any of the tables or is a pharmaceutically acceptable salt thereof. In some such embodiments where the compound has a chiral center, the compound exists as a single enantiomer whereas in other embodiments, the compound is a mixture of enantiomers of the compounds shown above. In some such embodiments, the compound is one of the compounds in any of the tables or is a pharmaceutically acceptable salt thereof. In other embodiments, the compound is an enantiomer or diastereomer of one of the compounds in any of the tables or is a pharmaceutically acceptable salt, or mixture thereof.

In some embodiments, the compound is selected from any of those in any of the tables. Furthermore, in some embodiments, the compound has a variable corresponding to any of the groups in the compounds of any of the tables. For example, if a compound in any of the tables has a group corresponding to the A group, then in some embodiments of the compound, the A group will correspond to that set forth in the compound(s) in any of the tables.

In some embodiments, $R^1$ is H such that the compound is a carboxylic acid. In other embodiments, $R^1$ is an unsubstituted —$(C_1-C_6)$ alkyl group such as a methyl, ethyl, propyl, butyl, pentyl, hexyl, or isopropyl group. Therefore, in some embodiments, $R^1$ is a —$CH_3$ or a —$CH_2CH_3$ group.

In some embodiments of the compound of formula IA or IB, the compound of formula IA or IB is a compound of formula IIA or IIB. The compounds of formula IIA and IIB have the following structures where each of the variables has any of the values of any of the embodiments described herein:

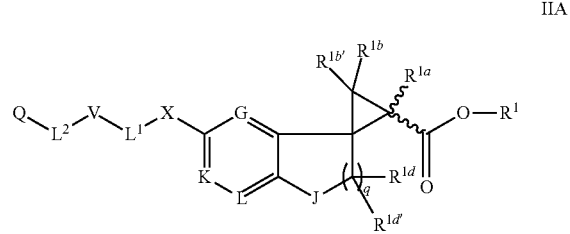

IIA

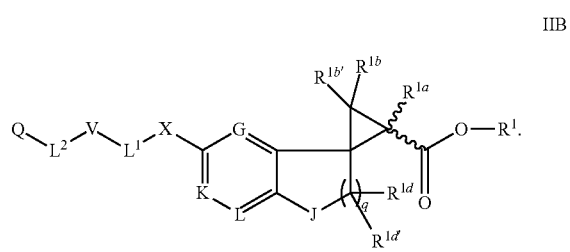

IIB

In some such embodiments, the compound has the formula IIA whereas in other embodiments, the compound has the formula IIB.

In some embodiments, the compound of any of the embodiments is a salt.

In some embodiments, the compound comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, a compound of any of the embodiments described herein is used to prepare a medicament.

In yet another aspect, the invention provides a therapeutic composition that includes a compound of any of the embodiments and a second therapeutic agent as a combined preparation for simultaneous, separate, or sequential use in the treatment of a disease or condition mediated by GPR40. In some such embodiments, the disease or condition is type II diabetes. In some embodiments, the second therapeutic agent is selected from metformin, a thiazolidinedione, or a DPP-IV inhibitor. In some embodiments, the compound of any of the embodiments described herein and the second therapeutic agent are provided as single composition. In other embodiments, the compound of any of the embodiments described herein and the second therapeutic agent are provided separately as parts of a kit.

In some embodiments, the invention provides a compound of any of the embodiments described herein for use as a medicament.

In some embodiments, the invention provides a compound of any of the embodiments described herein for use in modulating GPR40.

In some embodiments, the invention provides a compound of any of the embodiments described herein for use in treating a disease or condition selected from type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, or edema. In some such embodiments, the compound is used for treating type II diabetes.

The compounds of the invention may stimulate GLP-secretion. Cells contacted with compounds of the invention may increase GLP-1 secretion. Therefore, in some embodiments, the invention provides a method of stimulating GLP-1 secretion by cells. Such methods typically include contacting a cell capable of producing GLP-1 with a compound of any of the embodiments set forth herein. Administration of the compounds of the invention to subjects may provide increased levels of GLP-1 in the blood plasma of such subjects. Therefore, in some embodiments, a compound of any of the embodiments described herein may be used to stimulate GLP-1 secretion and increase the blood plasma level of GLP-1 in a subject. In some such embodiments, the compounds of the invention both stimulate GLP-1 secretion and activate GPR40. Therefore, in some embodiments, the compounds of the invention both stimulate GLP-1 secretion and display incretin effect by activating GPR40.

In some embodiments, the invention further provides a method for increasing GLP-1 levels in the blood plasma of a subject. Such methods typically include administering a compound of any of the embodiments to a subject. In some such embodiments, the subject is a diabetic patient. In other such embodiments, the subject is an obese patient. In some embodiments, the invention provides a method for stimulating weight loss in a subject. In such embodiments, a compound of any of the embodiments is administered to a subject in an effective amount to stimulate weight loss in the subject. The compounds of the invention may be administered in the fasted or non-fasted state. Therefore, in some embodiments, a compound of any of the embodiments is administered to a subject prior to a meal. In some such embodiments, the compound is administered 2 hours, 1, hour, 30 minutes, or 15 minutes before a meal. In other embodiments, a compound of any embodiments set forth herein is administered to a subject during a meal. In other embodiments, a compound of any of the embodiments described herein is administered to a subject within 2 hours, within 1 hour, within 30 minutes, or within 15 minutes of a meal.

The compounds of the invention can be prepared by a variety of synthetic or semisynthetic techniques. Scheme 1 provides a general synthetic scheme for exemplary compounds of the invention of formula I'A utilizing ester A where the variables in Scheme 1 have any of the values described above with respect to any of the embodiments, V is a OH or a halogen such as, but not limited to a Cl, Br, or I, or sulfonate ester such as, but not limited to OTs (tosylate) or OTf (triflate); and Alk is a straight or branched chain alkyl group having from 1-8 carbon atoms. It will be understood that the phenolic OH group of A can be replaced with an SH and reacted with a compound where V is a halogen to produce the analogous S-containing derivative (X=S) to the compounds shown. The synthesis of various chloromethyl, bromomethyl, and hydroxymethyl biphenyl tail group compounds and phenol carboxylic acid head group compounds is described herein. Appropriate starting materials can be prepared by techniques known or apparent to those of skill in the art or the starting materials may be commercially available. One of skill in the art will understand that the synthetic routes can be modified to use different starting materials or alternative reagents and that suitable adjustments in conditions (e.g., temperatures, solvents, etc.) can be made to accomplish the desired transformations. One of skill in the art will recognize that protecting groups may be necessary for the preparation of certain compounds and will be aware of those conditions compatible with a selected protecting group. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof. One of skill in the art will recognize that compounds of formula I'B may be prepared using a similar scheme using the appropriately substituted tail group in place of that shown in Scheme 1. The same is true for compounds with tail groups different from that of the compounds of formula I'A and I'B.

Scheme 1

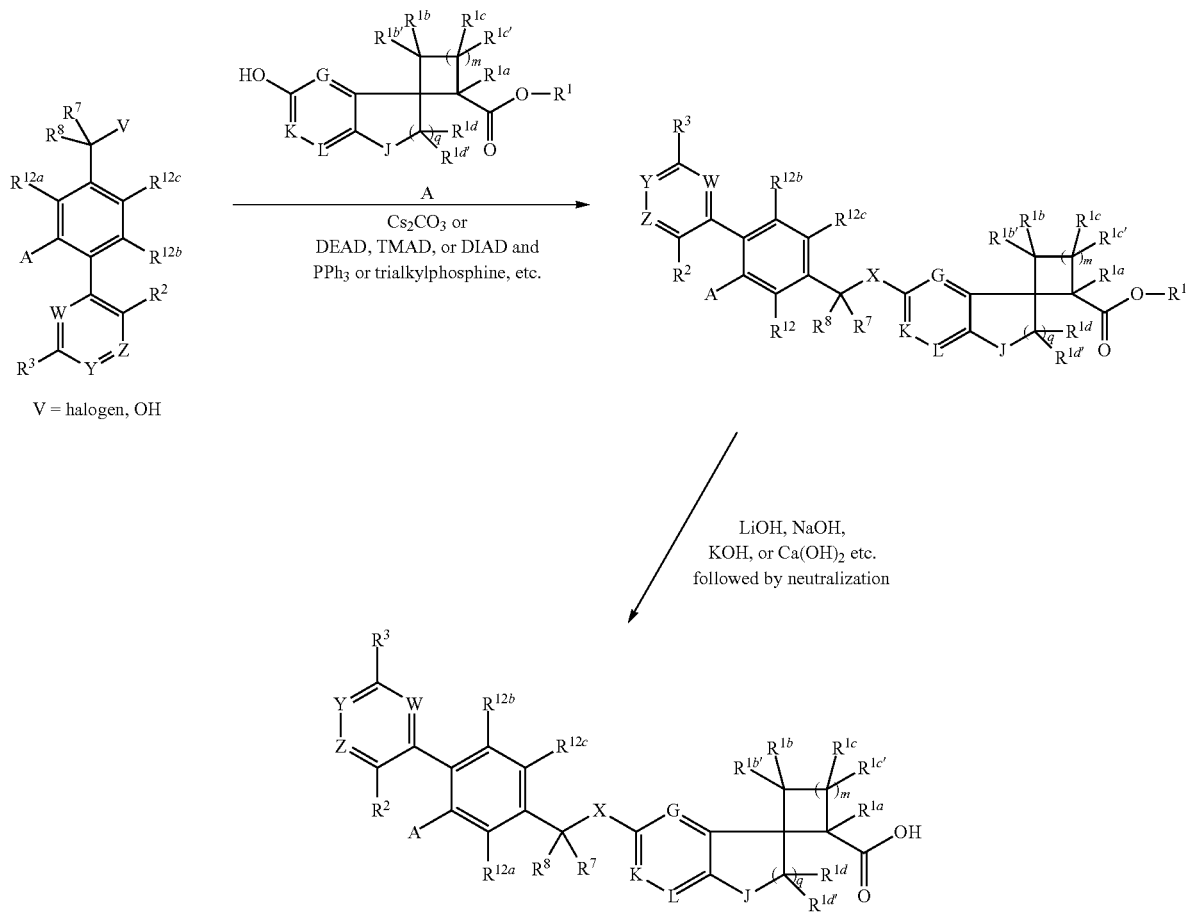

V = halogen, OH

5.2.2 Compositions

In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

5.2.3 Methods of Use

In another aspect, the invention provides methods of treating a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. The methods comprise administering to a subject in need thereof, a therapeutically effective amount of a compound or composition of any of the embodiments of the invention.

In one embodiment, the disease or condition is type II diabetes.

In another aspect, the present invention provides a method for treating a disease or condition responsive to the modulation of GPR40. Such methods comprise administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hypertension.

In some embodiments of administering the compounds or compositions of the invention, the compound or composition is administered orally, parenterally, or topically. In some embodiments, the compound or composition is administered orally. In other embodiments, the compound or composition is administered parenterally. In other embodiments, the compound or composition is administered topically.

The compounds of the invention may be administered alone or in combination with one or more other therapeutic agents. Therefore, in some embodiments, the compound or composition of any of the embodiments is administered in combination with a second therapeutic agent. In some such embodiments, the second therapeutic agent is an insulin sensitizing agent, such as metformin or a thiazolidinedione, for example. In some embodiments, the second therapeutic agent is a GLP-1 analog. In some embodiments, the second therapeutic agent is an inhibitor of DPP-IV such as, but not limited to, sitagliptin.

In another aspect, the invention provides methods of treating a disease or disorder responsive to modulation of GPR40 comprising administering to a subject having such a disease or disorder, a therapeutically effective amount of one or more of the subject compounds or compositions.

In yet another aspect, the invention provides methods of treating a GPR40-mediated condition, disease or disorder comprising administering to a subject having such a condition, disease or disorder, a therapeutically effective amount of one or more of the subject compounds or compositions.

In yet another aspect, the invention provides methods of modulating GPR40 comprising contacting a cell with one or more of the subject compounds or compositions.

For example, in some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day. For oral administration, the compositions are preferably provided in the form of tablets containing from 1.0 to 1000 milligrams of the active ingredient, particularly 1.0, 3.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. In some embodiments, therapeutic compositions are provided that include a compound of the invention and a second therapeutic agent as a combined preparation for simultaneous, separate or sequential use in the prophylactic treatment of a subject at risk for a disease or condition mediated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enalopriIat); and (c) antidiabetic agents such as insulin and insulin mimetics, sulfonylureas (e.g., glyburide, meglinatide), biguanides, e.g., metformin (GLUCOPHAGE®), α-glucosidase inhibitors (acarbose), insulin sensitizers, e.g., thiazolidinone compounds, rosiglitazone (AVANDIA®), troglitazone (REZULIN®), ciglitazone, pioglitazone (ACTOS®) and englitazone, DPP-IV inhibitors, e.g., vildagliptin (Galvus®), sitagliptin (Januvia™), and GLP-I analogs, e.g., exenatide (Byetta®). In some embodiments, a compound of the invention may be administered along with a DPP-IV inhibitor or a GLP-I analog. In some embodiments, a compound of the invention is administered with any of the DPP-IV inhibitors set forth in U.S. Patent Publication No. 2006/0270701 which is hereby incorporated by reference in its entirety and for all purposes as if specifically set forth herein.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

In some embodiments, the insulin concentration is increased after the compound is administered to the subject.

In other embodiments, the insulin concentration is decreased after the compound is administered to the subject.

The compounds and compositions described herein may be used to treat a variety of disease states and conditions. Therefore, in some embodiments, a compound of composition of any of the described embodiments is used for treating a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes.

The compounds of the invention may also be used to modulate GPR40. Therefore, in some embodiments, a compound or composition of any of the embodiments is used for modulating GPR40.

The compounds of any of the embodiments described herein may be used to prepare medicaments for treating the diseases or conditions described herein such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and/or edema. In some embodiment, the disease or condition is type II diabetes. The compounds of any of the embodiments may also be used to prepare medicaments for modulating GPR40 in a subject such as in a mammalian subject with type II diabetes.

The following examples are offered by way of illustration and are not intended to limit the scope of the invention. Those of skill in the art will readily recognize a variety of noncritical parameters that could be modified to yield essentially similar results.

6. EXAMPLES

Unless otherwise stated, all compounds were obtained from commercial sources or were prepared using the methods and experimental procedures described herein. Various procedures are also set forth in published U.S. Patent Application No. 2006/0004012 which is hereby incorporated by reference in its entirety and for all purposes as if set forth herein. The following abbreviations are used to refer to various reagents, solvents, experimental procedures, or analytical techniques that are described in the examples:

ACN Acetonitrile
AcOH Acetic acid
DCM Dichloromethane
DMF N,N'-Dimethyl Formamide
DMAP Dimethylaminopyridine
DME Dimethoxyethane
DMSO Dimethylsulfoxide
ESI Electrospray Ionization
EtOAc Ethyl acetate
EtOH Ethanol
HMPA Hexamethylphosphoramide
HPLC High Performance Liquid Chromatography
HSA Human Serum Albumin
IPA Isopropanol
LAH Lithium Aluminum Hydride
LDA Lithium Diisopropylamide
MeOH Methanol
MS Mass Spectrometry
NMP N-Methyl-2-pyrrolidone
NMR Nuclear Magnetic Resonance
PPTS Pyridinium p-Toluenesulfonate
TBAF Tetrabutylammonium fluoride
TBDPS t-Butyldiphenylsilane
TEA Triethylamine
TFA Trifluoroacetic acid
THF Tetrahydrofuran
THP Tetrahydropyran
SPA Scintilliation Proximity Assay

Synthesis of Spiro Carboxylic Acid Intermediates

Intermediates H1A, H1B, H1C and H1D

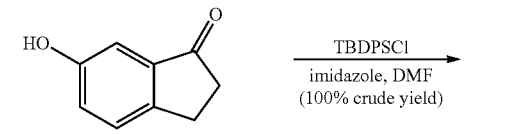

6-hydroxy-1-indanone (Aldrich)

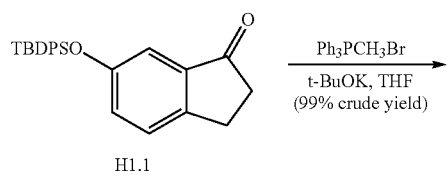

H1.1

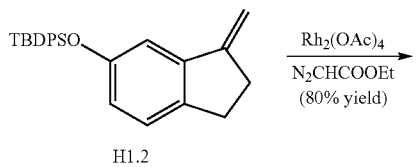

H1.2

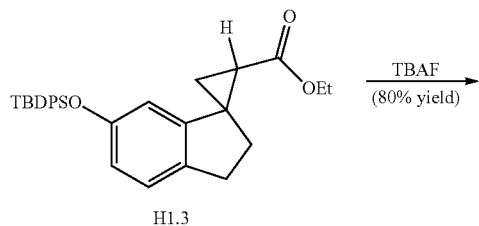

H1.3

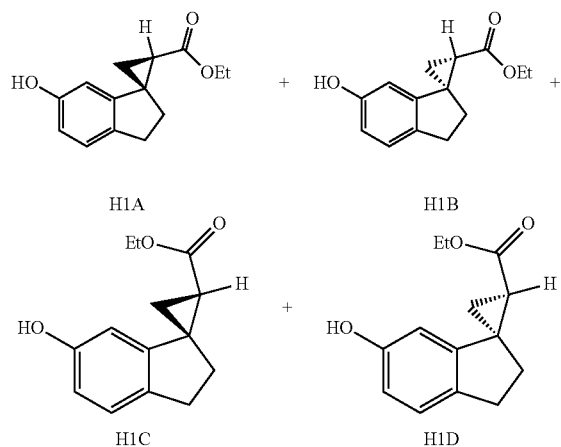

6-(tert-Butyldiphenylsilyloxy)-2,3-dihydroinden-1-one (H1.1)

A mixture of 6-hydroxy-1-indanone (250 g, 1687 mmol) (634549, commercially available from Sigma-Aldrich, St. Louis, Mo., USA), t-butyldiphenylchlorosilane (487 g, 1772 mmol) and imidazole (138 g, 2025 mmol) in degassed DMF (900 mL) was heated at 60° C. for 16 hours. The mixture was then concentrated to remove most of DMF, diluted with ether (3000 mL), filtered, and concentrated to give the initial product H1.1 (674 g, 100% yield) which was used in the next step reaction without further purification. MS ESI (pos.) M/E: 409 (M+Na).

tert-Butyl(3-methylene-2,3-dihydro-1H-inden-5-yloxy)diphenylsilane (H1.2)

To a solution of H1.1 (607 g, 1570 mmol) and triphenylmethylphosphonium bromide (673 g, 1884 mmol) in THF (1000 mL) was added potassium tert-butoxide 1.0 M solution in THF (1884 mL, 1884 mmol) via an addition funnel over 2 hours. The resulting mixture was stirred at room temperature for 16 hour and distilled to remove most of THF. The resulting mixture was suspended in hexanes, passed through a pad of silica gel (1 kg), rinsed with hexanes (total 8 L), and then with 10% EtOAc in hexanes (4 L). The resulting mixture was concentrated to give H1.2 (600 g, 99% yield). MS ESI (pos.) M/E: 385 (M+H).

Synthesis of H1.3

To a solution of tert-butyl(3-methylene-2,3-dihydro-1H-inden-5-yloxy)diphenylsilane H1.2 (599.6 g, 1559 mmol) and rhodium (ii) acetate, dimer (2.8 g, 6.3 mmol) in refluxing DCM (1400 mL) was added ethyl diazoacetate (227 mL, 2191 mmol) in DCM via addition funnel over 2 hours. The resulting mixture was stirred at 45° C. for 1 hour and then at room temperature for 2 hours. The reaction mixture was concentrated and passed through a short pad of silica gel (1 kg) with 5% EtOAc in hexanes (8 L) to give H1.3 (588 g, 80% yield) after removal of solvent.

Synthesis of H1A, H1B, H1C and H1D

To a solution of H1.3 (119 g, 253 mmol) in THF (500 mL) was added TBAF (303 mL, 303 mmol) in THF. The resulting mixture was stirred at room temperature for 1 hour. The mixture was then concentrated, redissolved in EtOAc, washed with saturated aqueous NH$_4$Cl, and concentrated with silica gel (300 g) to give a yellow solid after high vacuum. The solid was loaded into an empty solid load cartridge and purified by column chromatography (20% EtOAc in hexanes). The collected products were combined and separated by chiral column (ChiralPak® AD, 4% IPA/hexanes) to give H1A (8.3 g, 14% yield, 98% ee, retention time 34.5 min on AD-H with 5% IPA/hex, $\alpha_D$=−346°, CDCl$_3$), H1B (8.3 g, 14% yield, 99% ee, retention time 23.9 min on AD-H with 5% IPA/hex, $\alpha_D$=370°, CDCl$_3$), H1C (10.0 g, 17% yield, 98% ee, retention time 17.6 min on AD-H with 5% IPA/hex, $\alpha_D$=−0.5°, CDCl$_3$), H1D (10.0 g, 17% yield, 99% ee, retention time 13.2 min on AD-H with 5% IPA/hex, $\alpha_D$=−5°, CDCl$_3$). MS ESI (pos.) M/E: 233 (M+H). The absolute stereochemistries were assigned based on the agreement of experimental values of optical rotations and vibrational circular dichroisms with theoretical calculations. The structure of H1B was further confirmed by X-ray analysis of a crystal derivatized from H1B (dibromination followed by hydrolysis).

Intermediates H2A and H2B

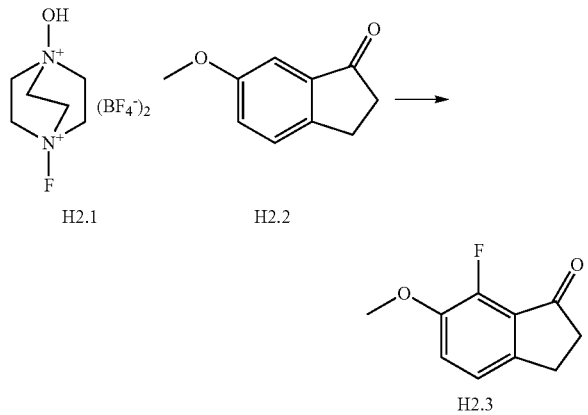

H2.1   H2.2

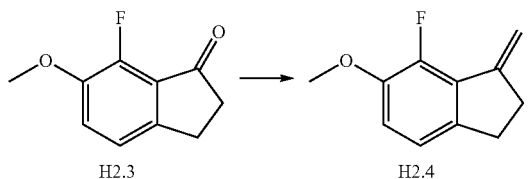

H2.3

7-Fluoro-6-methoxy-2,3-dihydroinden-1-one (H2.3)

To a solution of H2.2 (17.99 g, 111 mmol)(commercially available from Sigma-Aldrich, St. Louis, Mo., USA) in ACN (600 mL) was added H2.1 (37.5 g, 116 mmol)(commercially available from Alfa)(NFTh, 100 g on alumina), and the suspension was heated under reflux for 2 hours. The solvent was removed and the resulting mixture was redissolved in DCM (600 mL). The mixture was filtered and the filtrate was concentrated to give a residue which was purified by CombiFlash® chromatography to give a yellow solid (5.22 g, 26%). $^1$H NMR (400 MHz, CDCl$_3$) δ ppm 7.25 (d, J=8 Hz, 1H), 7.17 (m, 1H), 3.94 (s, 3H), 3.10 (m, 2H), 2.75 (m, 2H).

7-Fluoro-6-methoxy-1-methylene-2,3-dihydro-1H-indene (H2.4)

To a solution of H2.3 (5.22 g, 29.0 mmol) and triphenylmethylphosphonium bromide (12.4 g, 34.8 mmol) in THF (100 mL) was added potassium tert-butoxide (1.0 M solution in THF)(34.8 mL, 34.8 mmol) via addition funnel over 15 minutes. The resulting mixture was stirred at room temperature for 30 minutes. The resulting mixture was then filtered, and the filtrate was concentrated to give a residue which was purified by CombiFlash® chromatography to give the product as a solid (3.85 g, 74.6%). $^1$H NMR (400 MHz, CDCl$_3$) δ ppm 6.94 (d, J=8 Hz, 1H), 6.87 (d, J=8 Hz, 1H), 5.74 (s, 1H), 5.27 (s, 1H), 3.90 (s, 3H), 2.94 (m, 2H), 2.85 (m, 2H).

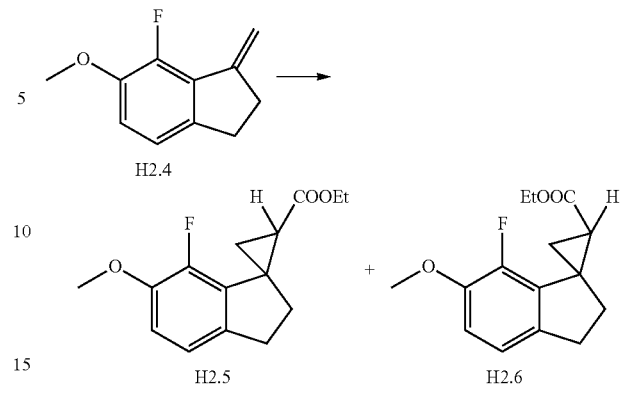

Synthesis of H2.5 and H2.6

To a solution of H2.4 (3.90 g, 21.9 mmol) and rhodium (ii) acetate, dimer (0.145 g, 0.328 mmol) in refluxing DCM (200 mL) was added ethyl diazoacetate (3.41 mL, 32.8 mmol) (commercially available from Sigma-Aldrich, St. Louis, Mo., USA) in DCM via syringe pump over 40 minutes. The resulting mixture was stirred at 45° C. for 1 hour and filtered. The filtrate was concentrated to give a residue which was purified by CombiFlash® chromatography to give two products: trans H2.5 and cis H2.6 (the structures of these compounds was confirmed by NMR analysis). H2.5 $^1$H NMR (400 MHz, CDCl$_3$) δ ppm 6.89 (d, J=8 Hz, 1H), 6.77 (m, 1H), 4.14 (q, J=8 Hz, 2H), 3.85 (s, 3H), 2.96 (m, 2H), 2.57 (m 1H), 2.27 (m, 2H), 1.89 (dd, J=8 Hz, J=4 Hz, 1H), 1.56 (m, 1H), 1.29 (t, J=8 Hz, 3H). H2.6 $^1$H NMR (400 MHz, CDCl$_3$) δ ppm 6.89 (d, J=8 Hz, 1H), 6.76 (m, 1H), 4.01 (m, 2H), 3.84 (s, 3H), 3.05 (m, 1H), 2.78 (dd, J=16 Hz, J=8 Hz, 1H), 2.45 (m, 2H), 2.01 (m, 1H), 1.71 (m, 1H), 1.42 (m, 1H) 1.14 (t, J=8 Hz, 3H).

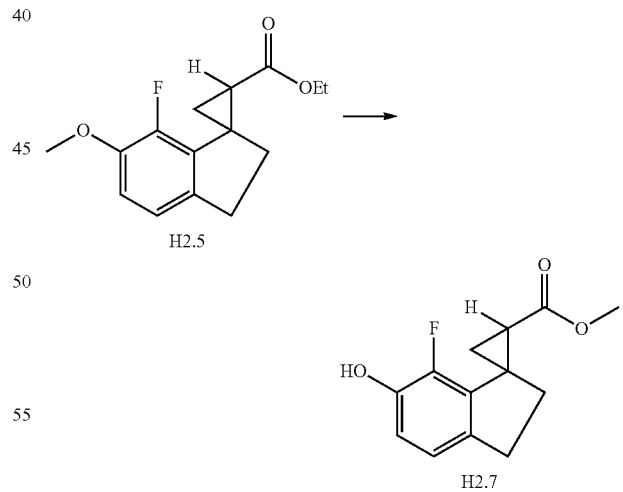

Synthesis of H2.7

To a solution of H2.5 (2.50 g, 9.46 mmol) in 20 mL of NMP, was added NaOH (1.70 g, 42.6 mmol) and 1-dodecanethiol (7.94 mL, 33.1 mmol). The mixture was stirred at 125° C. for 16 hours, cooled to room temperature, and diluted with 1 N HCl and ether. The organic layer was washed with water and brine, dried (MgSO$_4$) and concentrated to give a residue which was purified by CombiFlash® chromatography to give the desired acid (1.40 g). The solution of acid in 40 mL of benzene and 10 mL of MeOH was treated with (trimethylsilyl)diazomethane, 2.0 M in diethyl ether (9.46 mL, 18.9 mmol) at room temperature for 1 hour. Solvent was then removed to give H2.7 (1.40 g, 63%). MS ESI m/e: 237.10 (M+1)$^+$.

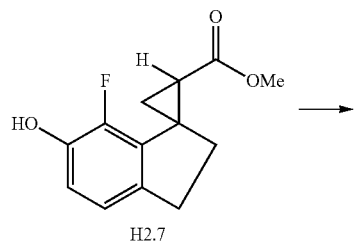

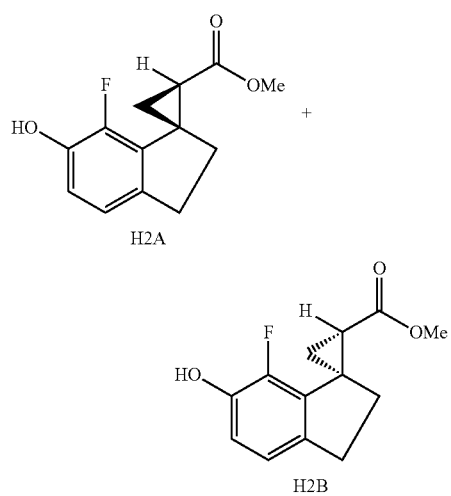

Synthesis of H2A and H2B

Chiral separation of H2.7 was accomplished on a CHIRALCEL® OD column (3% IPA in hexane) to provide H2A and H2B. The stereochemistry of H2A and H2B was determined based on a comparison of their chiral HPLC retention times with those of H1A and H1B. However, absolute configurations are not known with certainty. Therefore, when H2A was used to synthesize a compound, both enantiomers are shown.

Intermediates H3A, H3B, H3C and H3D

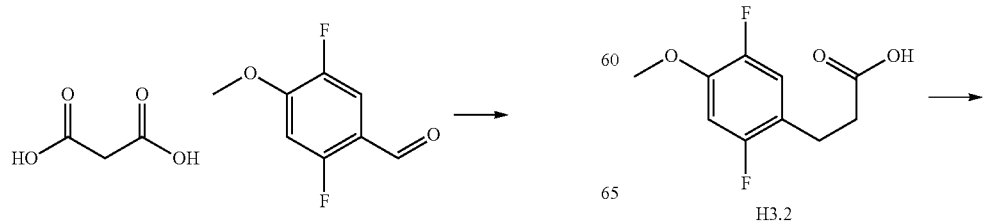

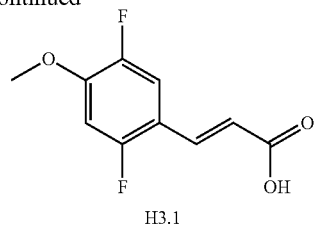

(2E)-3-(2,5-Difluoro-4-(methyloxy)phenyl)-2-propenoic acid (H3.1)

A 250 mL round bottom flask was charged with 2,5-difluoro-4-methyoxybenzaldehyde (commercially available from Manchester Organics Ltd., UK) (18.45 g, 107.2 mmol), malonic acid (commercially available from Sigma-Aldrich, St. Louis, Mo., USA) (12.27 g, 117.9 mmol), and 10:1 EtOH/pyridine (27 mL). The mixture was stirred overnight at 70° C. under a reflux condenser and cooled to 0° C. for 2 hours. The precipitated solid was filtered, rinsed with ether, and dried in vacuo to afford H3.1 (16.96 g, 74% yield) as a white powder.

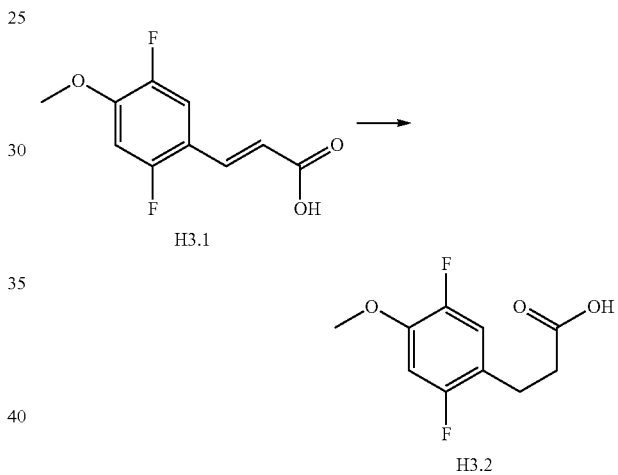

3-(2,5-Difluoro-4-methoxyphenyl)propanoic acid (H3.2)

To a homogeneous solution of H3.1 (6.78 g, 32 mmol) in 1:1 EtOH/EtOAc (384 mL) was added wet palladium on carbon (10 wt. % (dry basis), water ca. 50%) (commercially available from Sigma-Aldrich, St. Louis, Mo., USA) (0.67 g, 0.32 mmol). The mixture was subjected to 3 cycles of evacuation/back-filling with H$_2$ and stirred for 2 hours under a H$_2$ balloon. The mixture was filtered through Celite® filter aid (EtOAc) and concentrated to afford H3.2 (6.81 g, 100% yield) as a white solid.

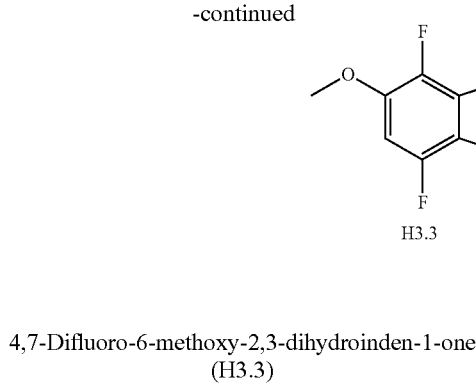

4,7-Difluoro-6-methoxy-2,3-dihydroinden-1-one (H3.3)

A 200 mL round bottom flask was charged with H3.2 (6.75 g, 31.2 mmol), DCM (62 mL), oxalyl chloride (5.45 mL, 62.4 mmol), and a catalytic amount of DMF (0.0242 mL, 0.312 mmol) (vigorous gas evolution occurred). The solution was stirred for 30 minutes at room temperature and concentrated to afford the desired acid chloride as a yellow oil. A 500 mL round bottom flask was charged with aluminum(III) chloride (5.00 g, 37.5 mmol) and DCM (62 mL) and cooled to 0° C. under $N_2$. To the cold slurry was added a solution of the above acid chloride in DCM (62 mL) dropwise. The resulting solution was stirred for 6 hours at 45° C. (reflux). The mixture was carefully poured into ice-cold water (600 mL) with stirring and after 1 hour, was extracted with DCM (2×300 mL). The combined organic layers were washed with 1 N NaOH (1×300 mL) and brine (1×300 mL), dried ($MgSO_4$), and concentrated. The initially obtained product was purified by recrystallization from hot toluene to afford H3.3 (0.968 g, 16% yield) as a flaky, light brown solid.

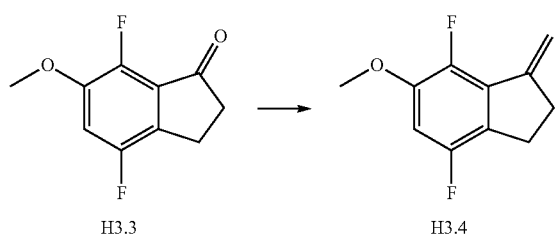

4,7-Difluoro-6-methoxy-1-methylene-2,3-dihydro-1H-indene (H3.4)

A screw-cap vial was charged with H3.3 (0.962 g, 4.85 mmol), methyltriphenylphosphonium bromide (commercially available from Sigma-Aldrich, St. Louis, Mo., USA) (2.08 g, 5.83 mmol), and THF (20 mL). To the white slurry was added potassium tert-butoxide (1.0 M in THF) (commercially available from Sigma-Aldrich, St. Louis, Mo., USA) (5.83 mL, 5.83 mmol) dropwise under $N_2$. The resulting brown mixture was stirred for 30 minutes at room temperature, quenched with acetone (1 mL) and saturated aqueous $NH_4Cl$, and diluted with EtOAc. The organic layer was washed with water and brine, dried ($MgSO_4$), and concentrated. The residue was suspended in hexanes, filtered, and concentrated, and the initially obtained product was purified by silica gel flash chromatography (0-5% EtOAc/hexane) to afford H3.4 (0.835 g, 88% yield) as a colorless oil.

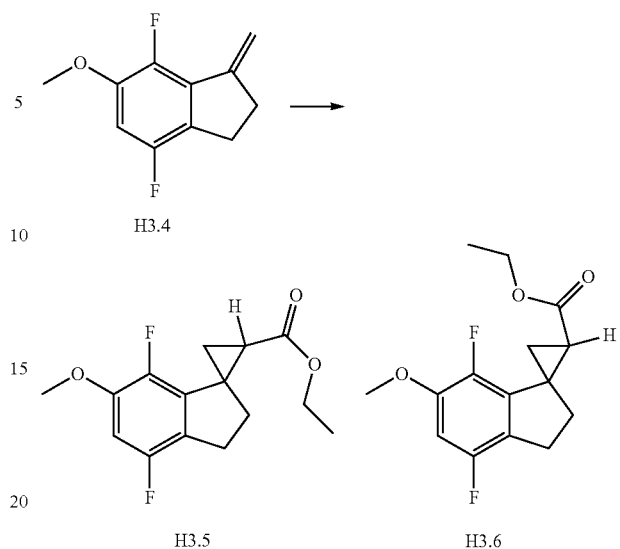

Synthesis of H3.5 and H3.6

A 250 mL 3-neck round bottom flask was charged with H3.4 (0.835 g, 4.26 mmol), DCM (43 mL), and rhodium(II) acetate dimer (commercially available from Sigma-Aldrich, St. Louis, Mo., USA) (0.0188 g, 0.0426 mmol) and fitted with two septa and a reflux condenser. The green suspension was heated to reflux (45° C. bath temperature) under a flaccid balloon, and to it was added a solution of ethyl diazoacetate (commercially available from Sigma-Aldrich, St. Louis, Mo., USA) (0.662 mL, 6.38 mmol) in DCM (6 mL) dropwise over 2 hours (syringe pump). The mixture was stirred for an additional 15 minutes, cooled to room temperature, filtered through Celite® filter aid (EtOAc), and concentrated. The initially obtained product was purified by silica gel flash chromatography (0-25% EtOAc/hexane) to afford (in order of elution) H3.5 (0.351 g, 29% yield) and H3.6 (0.413 g, 34% yield). The cis and trans stereochemistries were determined by NMR.

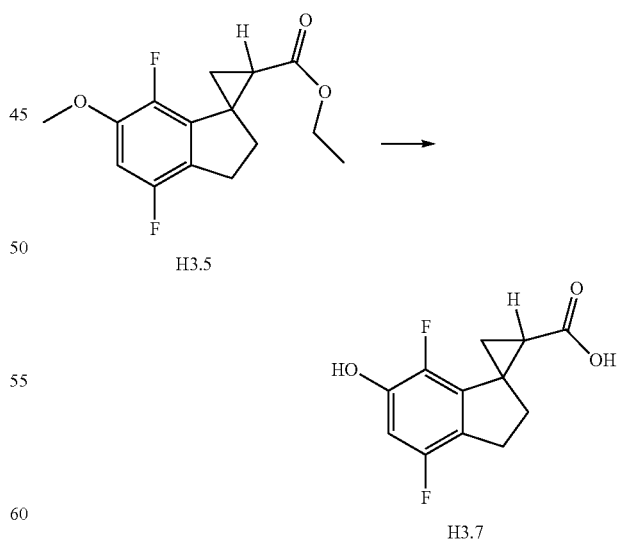

Synthesis of H3.7

A screw-cap vial was charged with H3.5 (0.347 g, 1.23 mmol), N-methylpyrrolidone (NMP)(1.2 mL), NaOH (0.221 g, 5.53 mmol), and 1-dodecanethiol (commercially available from Sigma-Aldrich, St. Louis, Mo., USA) (1.03 mL, 4.30 mmol). The mixture was stirred overnight at 125° C. (sealed vial) and cooled to room temperature. The solidified mixture was fractured with a spatula, quenched with 1 N HCl, and diluted with EtOAc. The organic layer was washed with water and brine, dried (MgSO₄), and concentrated. The initially obtained product was purified by silica gel flash chromatography (0-40% EtOAc/hexane) to afford H3.7 (0.245 g, 83% yield) as a white solid.

Synthesis of H3.8

A 100 mL round bottom flask was charged with H3.7 (0.242 g, 1.01 mmol) and 10:1 DCM/MeOH (10 mL). To the colorless solution was added (trimethylsilyl)diazomethane (2.0 M in ether) (commercially available from Sigma-Aldrich, St. Louis, Mo., USA) (0.604 mL, 1.21 mmol) dropwise (vigorous gas evolution occurred). The pale yellow solution was stirred for 15 minutes at room temperature, quenched with AcOH (0.0577 mL, 1.01 mmol), and concentrated. The initially obtained product was purified by silica gel flash chromatography (0-15% EtOAc/hexane) to afford H3.8 (0.207 g, 81% yield) as a crystalline, white solid.

Synthesis of H3B and H3A

Racemic H3.8 (0.207 g, 0.81 mmol) was resolved by chiral HPLC (CHIRALCEL® OJ column, 4% IPA/hexane, detection at 220 nm) to afford (in order of elution) H3B (0.083 g, 80% yield, 99% e.e.) and H3A (0.089 g, 86% yield, 95% e.e.) as white solids. H3B was the first eluting enantiomer; H3A was the second eluting enantiomer.

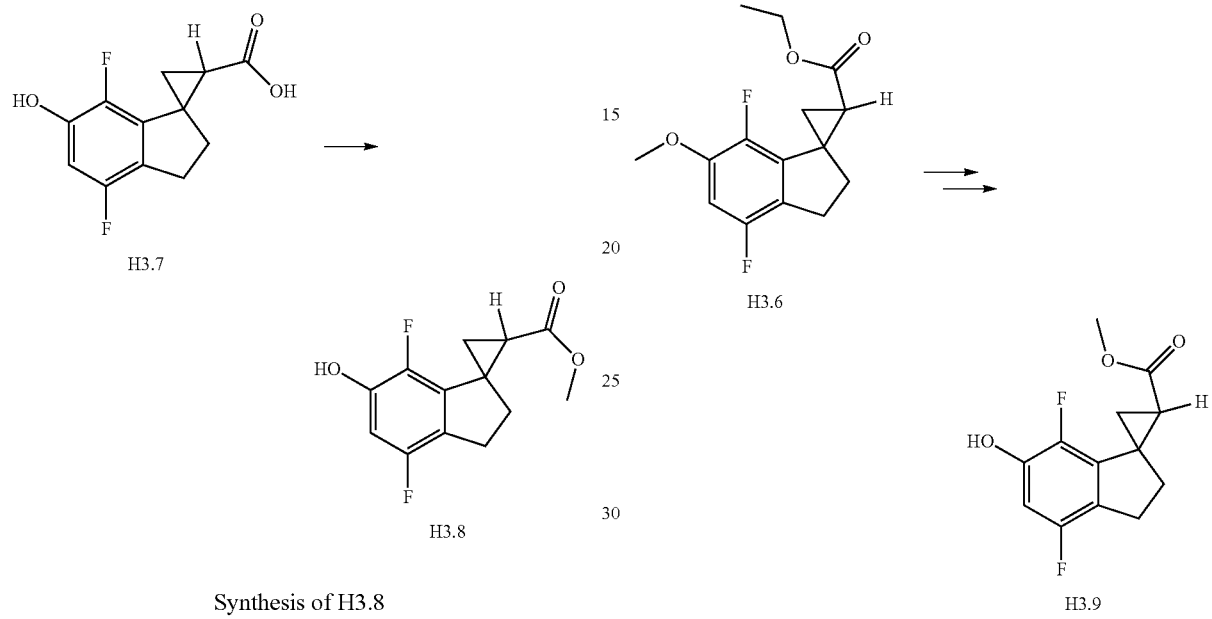

Synthesis of H3.9

H3.9 was prepared from H3.6 according to the analogous methods described for the synthesis of H3.8.

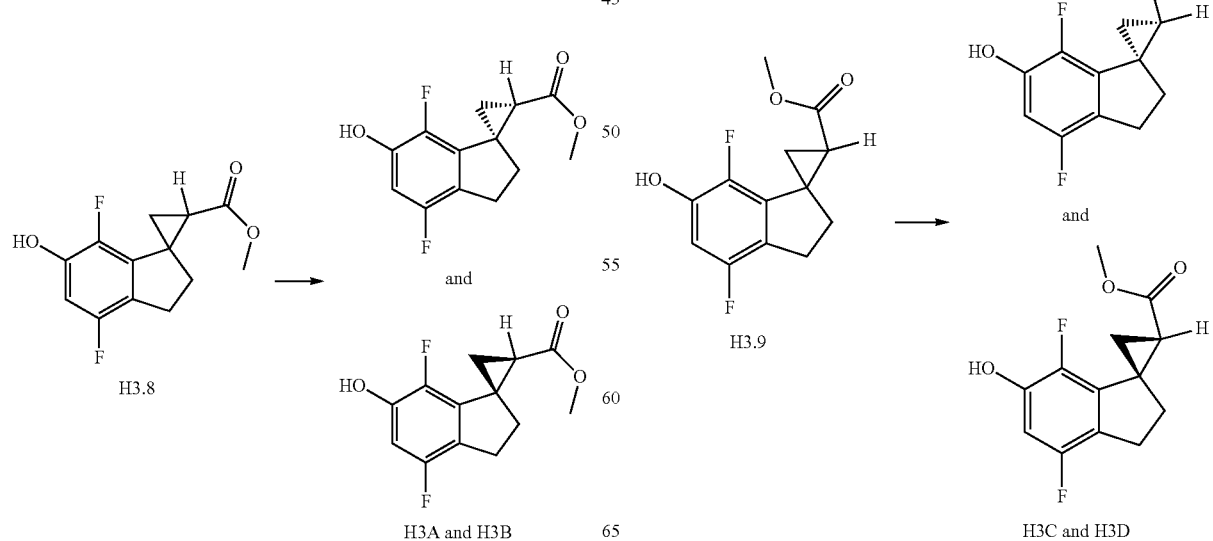

Synthesis of H3D and H3C

Racemic H3.9 (0.156 g, 0.61 mmol) was resolved by chiral HPLC (CHIRALCEL® OJ column, 6% then 20% IPA/hexane, detection at 220 nm) to afford (in order of elution) H3D (0.069 g, 88% yield, 99% e.e.) and H3C (0.070 g, 90% yield, 99% e.e.) as white solids. H3D was the first eluting enantiomer; H3C was the second eluting enantiomer.

Intermediates H4A and H4B

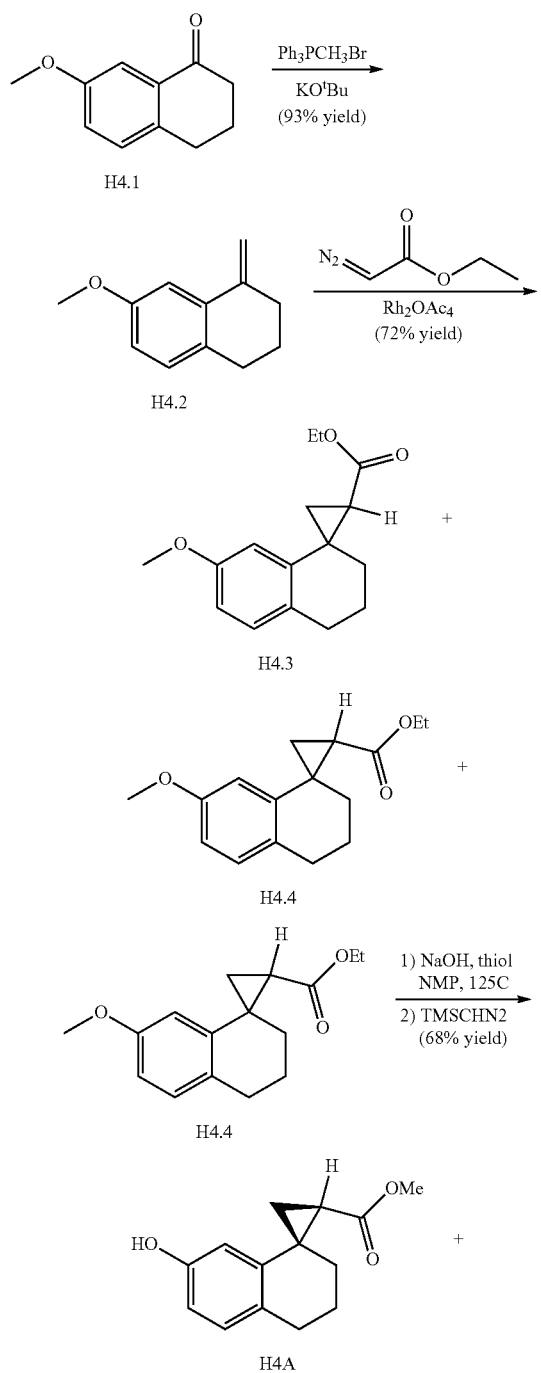

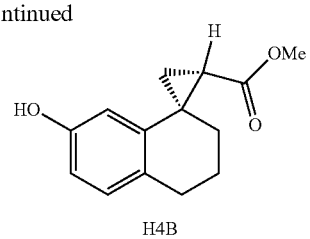

7-Methoxy-1-methylene-1,2,3,4-tetrahydronaphthalene (H4.2)

To a solution of 7-methoxy-1-tetralone H4.1 (26.9 g, 153 mmol) (commercially available from Sigma-Aldrich, St. Louis, Mo., USA) and triphenylmethylphosphonium bromide (65.4 g, 183 mmol) in THF (550 mL) was added potassium tert-butoxide (1.0 M solution in THF)(183 mL, 183 mmol) via addition funnel over 1 hour. The resulting mixture was stirred at room temperature for 60 minutes after addition. The reaction was then concentrated and resuspended in hexanes (250 mL). The mixture was passed through a silica gel plug (25 g silica) and rinsed with 250 mL of hexanes. Removal of solvent gave H4.2 (24.5 g, 92% yield). MS ESI (pos.) M/E: 175 (M+H).

Ethyl 7'-methoxy-3',4'-dihydro-2'H-spiro[cyclopropane-1,1'-naphthalene]-2-carboxylate (H4.3 and H4.4)

To a solution of H4.2 (5.23 g, 30.0 mmol) and rhodium (ii) acetate, dimer (0.133 g, 0.30 mmol) in refluxing DCM (200 mL) was added ethyl diazoacetate (4.67 mL, 45.0 mmol) in DCM via syringe pump over 60 minutes. The resulting mixture was stirred at 45° C. for 1 hour and then at room temperature for 2 hours. The reaction was concentrated and column purification (20% EtOAc in hexane) gave two products with the desired mass (H4.3 and H4.4). H4.3 (2.88 g) was obtained as oil which became a white solid after a few days, and NOE using $^1$H NMR showed this to be the cis product. H4.4 (3.04 g) was obtained as a colorless oil, and NOE using $^1$H NMR showed this to be the trans product. MS ESI (pos.) M/E: 261 (M+H).

Synthesis of H4A and H4B

A 100 mL flask was charged with H4.4 (2.56 g, 9.8 mmol), NMP (22 mL), NaOH (1.77 g, 44.3 mmol), and 1-dodecanethiol (8.25 mL, 34.4 mmol). The mixture was stirred for 24 hours at 125° C., cooled to room temperature, and diluted with 1 N HCl (200 mL) and ether (300 mL). The organic layer was washed with water and brine, dried (MgSO$_4$), and concentrated. Column chromatography purification (10-40% EtOAc/hex) gave the desired acid (1.45 g, 68% yield), which was dissolved in 40 mL of benzene and 10 mL of MeOH, treated with (trimethylsilyl)diazomethane (2.0 M in diethyl ether)(8.3 mL, 16.6 mmol) at 0° C. for 1 hour. The reaction mixture was concentrated to give methyl 7'-hydroxy-3',4'-dihydro-2'H-spiro[cyclopropane-1,1'-naphthalene]-2-carboxylate (1.55 g, 100% yield), which was separated from CHIRALCEL® OJ column (15% IPA/hex) to give H4A (>99% ee, peak 2, 765 mg) and H4B (>99% ee, peak 1, 773 mg). MS ESI (pos.) M/E: 233 (M+H).

Intermediates H5A and H5B

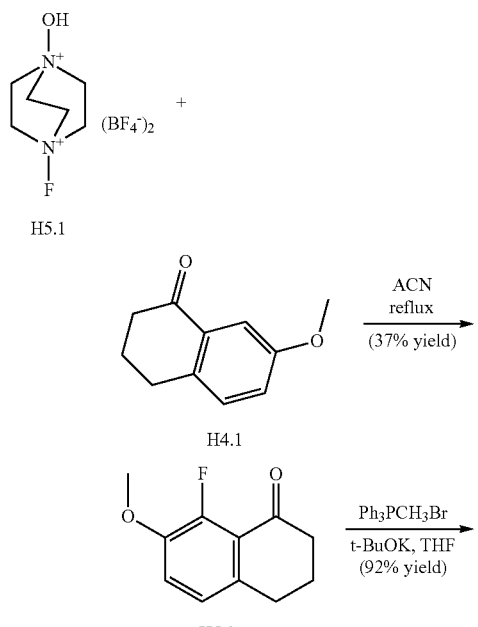

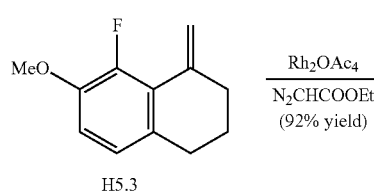

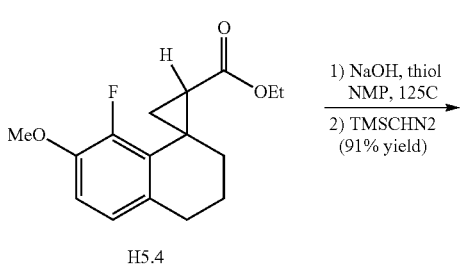

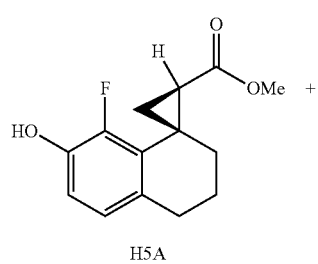

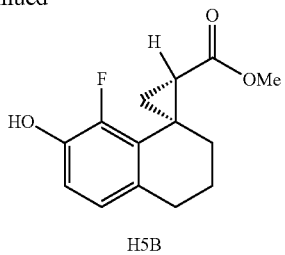

8-Fluoro-7-methoxy-3,4-dihydronaphthalen-1(2H)-one (H5.2)

To a solution of 7-methoxy-1-tetralone H4.1 (199 g, 1130 mmol) (commercially available from Sigma-Aldrich, St. Louis, Mo., USA) in ACN (1200 mL) was added H5.1 (200.0 g, 622 mmol) (NFTh, 400 g on alumina), and the suspension was heated under reflux for 1.5 hours. The solvent was removed and the residue was redissolved in DCM (1500 mL). The resulting mixture was filtered, concentrated, and purified by column chromatography (0% to 20% then 40% EtOAc in Hexanes) to give 8-fluoro-7-methoxy-3,4-dihydronaphthalen-1(2H)-one H5.2 (43 g). (Reference: Stojan Stavber, Chemical Communication 2000, 1323). MS ESI (pos.) M/E: 195 (M+H).

8-Fluoro-7-methoxy-1-methylene-1,2,3,4-tetrahydronaphthalene (H5.3)

To a solution of H5.2 (44.0 g, 227 mmol) and triphenylmethylphosphonium bromide (97.1 g, 272 mmol) in THF (1000 mL) was added potassium tert-butoxide (1.0 M solution in THF)(272 mL, 272 mmol) via addition funnel over 3 hours. The resulting mixture was stirred at room temperature for 30 minutes after addition. The solvent was removed and the residue was resuspended in hexanes (1 L). The resulting mixture was passed through a silica gel plug (50 g silica) and rinsed with 1 L of hexanes. Removal of solvent gave H5.3 (40.1 g, 92.1% yield). MS ESI (pos.) M/E: 193 (M+H).

Ethyl 8'-fluoro-7'-methoxy-3',4'-dihydro-2'H-spiro[cyclopropane-1,1'-naphthalene]-2-carboxylate (H5.4)

To a solution of H5.3 (4.18 g, 21.7 mmol) and rhodium (ii) acetate, dimer (0.0961 g, 0.217 mmol) in refluxing DCM (200 mL) was added ethyl diazoacetate (3.38 mL, 32.6 mmol) in DCM via syringe pump over 40 minutes. The resulting mixture was stirred at 45° C. for 1 hour and then at room temperature for 2 hours. Solvent was removed and the residue was purified by column chromatography (20% EtOAc in hexane) giving two products with the desired mass. The cis product (2.31 g) was obtained as an oil that became a white solid after a few days. A NOESY[1] established this as the cis product. The trans product H5.4 (2.31 g), was obtained as a colorless oil, and a NOESY[1]. MS ESI (pos.) M/E: 279 (M+H).

Synthesis of H5A and H5B

A 100 mL flask was charged with H5.4 (2.30 g, 8.26 mmol), NMP (20 mL), sodium hydroxide (1487 mg, 37.2 mmol), and 1-dodecanethiol (6936 µL, 28.9 mmol). The mixture was stirred for 16 hours at 125° C., cooled to room temperature, and diluted with 1 N HCl (200 mL) and ether (300 mL). The organic layer was washed with water and brine, dried (MgSO₄), and concentrated. Column purification (10-40% EtOAc/hex) gave desired the acid (1.77 g, 91% yield). The acid was then dissolved in 40 mL of benzene and 10 mL of MeOH, treated with (trimethylsilyl)diazomethane (2.0 M in diethyl ether) (8.3 mL, 16.6 mmol) at 0° C. for 1 hour. Solvent was removed from the resulting mixture to give methyl 8'-fluoro-7'-hydroxy-3',4'-dihydro-2'H-spiro[cyclopropane-1,1'-naphthalene]-2-carboxylate (1.88 g, 99% yield), which was separated using a CHIRALCEL® OJ column (15% IPA/hex) to give H5A (>99% ee, peak 2, 796 mg) and H5B (>99% ee, peak 1, 780 mg). MS ESI (pos.) M/E: 251 (M+H).

Intermediates H6A and H6B

Methyl 2-(benzyloxy)-5-(3-methoxy-3-oxoprop-1-enyl)isonicotinate (H6.2)

To NMP (1 mL) was added methyl acrylate (commercially available from Sigma-Aldrich, St. Louis, Mo., USA), tri-o-tolylphosphine (8.5 mg, 28 μmol) (commercially available from Sigma-Aldrich, St. Louis, Mo., USA) and palladium diacetate (2.5 mg, 11 μmol) (commercially available from Sigma-Aldrich, St. Louis, Mo., USA). The solution was degassed three time with nitrogen. To this solution was then added a 1 mL NMP solution of methyl 2-(benzyloxy)-5-bromoisonicotinate (120 mg, 372 μmol). The reaction was stirred at 90° C. overnight and then purified by column chromatography (silica gel, 10% EtOAc/hexane) to give desired product H6.2 (50.2 mg, 41.4%). MS ESI (pos.) m/e: 328.1 (M+H)⁺.

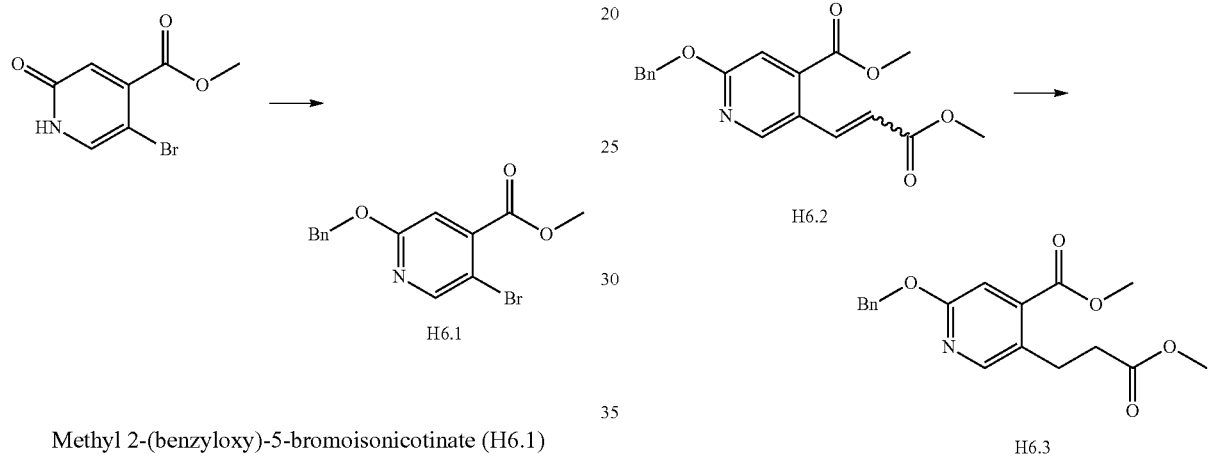

Methyl 2-(benzyloxy)-5-bromoisonicotinate (H6.1)

To 2 mL of methyl 5-bromo-2-oxo-1,2-dihydropyridine-4-carboxylate (232 mg, 1.00 mmol)(commercially available from Combi-Blocks) was added benzyl bromide (205 mg, 1.20 mmol) and silver carbonate (413 mg, 1.50 mmol) (commercially available from Sigma-Aldrich, St. Louis, Mo., USA). The resulting mixture was stirred at 50° C. overnight. After reaction completion, the mixture was loaded onto a solid silica gel cartridge and purified by chromatography with 10% EtOAc/hexane to afford the desired product H6.1 (293 mg, 91%). MS ESI (pos.) m/e: 322.1 (M+H)⁺.

Methyl 2-(benzyloxy)-5-(3-methoxy-3-oxopropyl) isonicotinate (H6.3)

To 1 mL EtOH was added compound H6.2 (50.0 mg, 152 μmol) and palladium on carbon (16.2 mg, 15.2 μmol). The resulting mixture was stirred under a balloon of H₂ for 4 hours. The catalyst was then filtered off, and the solvent was removed. The residue was redissolved in 1 mL toluene. To the resulting mixture was added silver carbonate (41.3 mg, 0.152 mmol) and benzyl bromide (20.5 mg, 0.120 mmol). The resulting mixture was stirred at 50° C. overnight. After the reaction was done, the mixture was loaded onto silica gel and purified by column chromatography with 10% EtOAc/hexane to give desired product F.3 (40.3 mg, 80.1%). MS ESI (pos.) m/e: 330.1 (M+H)⁺.

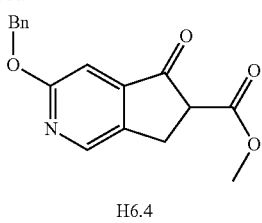

H6.4

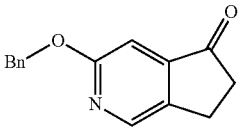

H6.5

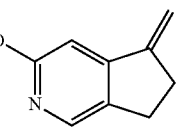

H6.6

Methyl 3-(benzyloxy)-5-oxo-6,7-dihydro-5H-cyclopenta[c]pyridine-6-carboxylate (H6.4)

To 75 mL dry THF was added methyl 2-(benzyloxy)-5-(3-methoxy-3-oxopropyl)isonicotinate (2.50 g, 7.59 mmol). The temperature of the solution was lowered to −78° C. To this solution was added 1N sodium bis(trimethylsilyl)amide (15.2 mL, 15.2 mmol) (commercially available from Sigma-Aldrich, St. Louis, Mo., USA) dropwise over 30 minutes. After completion, the reaction was stirred for an hour and then quenched by addition of 25 mL saturated $NH_4Cl$. The organic layer was extracted with EtOAc and washed with 150 mL water and 100 mL brine, and then dried over $MgSO_4$. The organic solvent was evaporated, and the residue was purified by column chromatography with 15% EtOAc/hexane to give desired product H6.4 (1.90 g, 84.1%). MS ESI (pos.) m/e: 298.1 $(M+H)^+$.

3-(Benzyloxy)-5-methylene-6,7-dihydro-5H-cyclopenta[c]pyridine (H6.6)

To a 100 mL round bottom flask were added compound H6.5 (1.70 g, 7.10 mmol) and 35 mL THF. To this solution was added triphenylmethyl phosphonium bromide (3.05 g, 8.53 mmol) (commercially available from Sigma-Aldrich, St. Louis, Mo., USA) and potassium tert-butoxide (8.53 mL, 8.53 mmol) (commercially available from Sigma-Aldrich, St. Louis, Mo., USA) dropwise. After completion, the reaction was stirred another hour and quenched with saturated $NH_4Cl$. The mixture was then extracted twice with EtOAc. The combined organic layers were washed with brine and then dried over $MgSO_4$. The solvent was removed and the residue was purified by column chromatography to give H6.6 (1.25 g, 73.9%). MS ESI (pos.) m/e: 238.1 $(M+H)^+$.

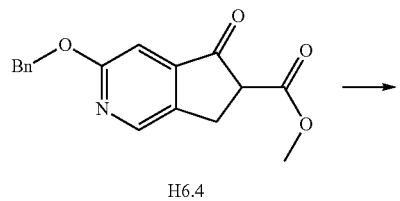

H6.4

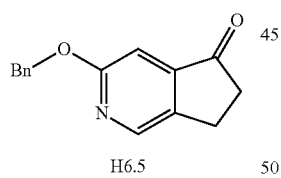

H6.5

3-(Benzyloxy)-6,7-dihydrocyclopenta[c]pyridin-5-one (H6.5)

Compound H6.4 (2.50 g, 8.41 mmol) was dissolved in 27 mL DMSO and 3 mL water. The resulting mixture was heated to 150° C. and stirred for 30 minutes. After the reaction was complete, the reaction was diluted with 120 mL water and extracted twice with 50 mL EtOAc. The combined organic layers were washed with brine, dried over $MgSO_4$, and concentrated onto silica gel. The resulting product was purified by column chromatography with 10% EtOAc/hexane to afford desired product H6.5 (1.76 g, 87.5%). MS ESI (pos.) m/e: 240.1 $(M+H)^+$.

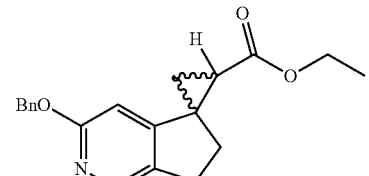

H6.6

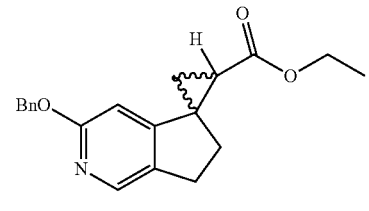

H6.7

Ethyl 3-(benzyloxy)-6,7-dihydrospiro[cyclopenta[c]pyridine-5,1'-cyclopropane]-2'-carboxylate (H6.7)

Compound H6.6 (50.0 mg, 211 μmol) and rhodium (ii) acetate, dimer (9.31 mg, 21.1 μmol) (commercially available from Sigma-Aldrich, St. Louis, Mo., USA) were mixed in 1.6 mL dry DCM. The resulting solution was refluxed at 45° C. for 10 minutes. Ethyl diazoacetate (26.2 μL, 253 μmol) (commercially available from Sigma-Aldrich, St. Louis, Mo., USA) was then added to the mixture very slowly. After 1 hour, the reaction was cooled to room temperature. The catalyst was then filtered off, and the solvent was concentrated down with silica gel. The product was purified by column chromatography to give H6.7 (25.1 mg, 36.9%). NMR confirmed that the product was the trans isomer. MS ESI (pos.) m/e: 324.2 $(M+H)^+$. $^1H$ NMR (500 MHz, DMSO-$d_6$) δ ppm 7.55-7.60 (3H, m), 7.37-7.47 (4H, m), 4.90 (2H, d, J=3.7 Hz), 4.12 (2H, q, J=7.1 Hz), 2.92 (2H, d, J=19.3 Hz), 2.82 (1H, dd, J=8.6, 6.4 Hz), 2.31 (1H, dd, J=8.4, 5.0 Hz), 2.19 (2H, ddd, J=8.7, 6.8, 2.8 Hz), 1.36 (1H, dd, J=6.0, 5.5 Hz), 1.21 (3H, t, J=7.1 Hz).

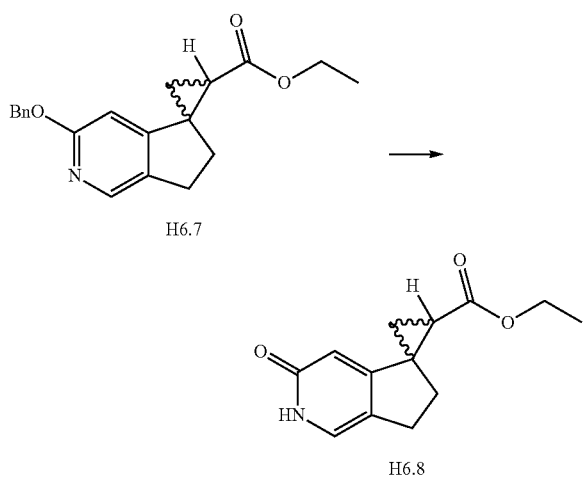

Ethyl 3-oxo-2,3,6,7-tetrahydrospiro[cyclopenta[c]pyridine-5,1'-cyclopropane]-2'-carboxylate (H6.8)

Compound H6.7 (200 mg, 618 μmol) was dissolved in 5 mL EtOH. To this solution was added palladium on carbon (65.8 mg, 618 μmol) and hydrogen was introduced by balloon. The reaction was stirred at room temperature for 1 hour. After the reaction was complete, the catalyst was filtered off and the solvent was removed to provide H6.8 (135 mg, 93.6%). MS ESI (pos.) m/e: 234.2 (M+H)$^+$.

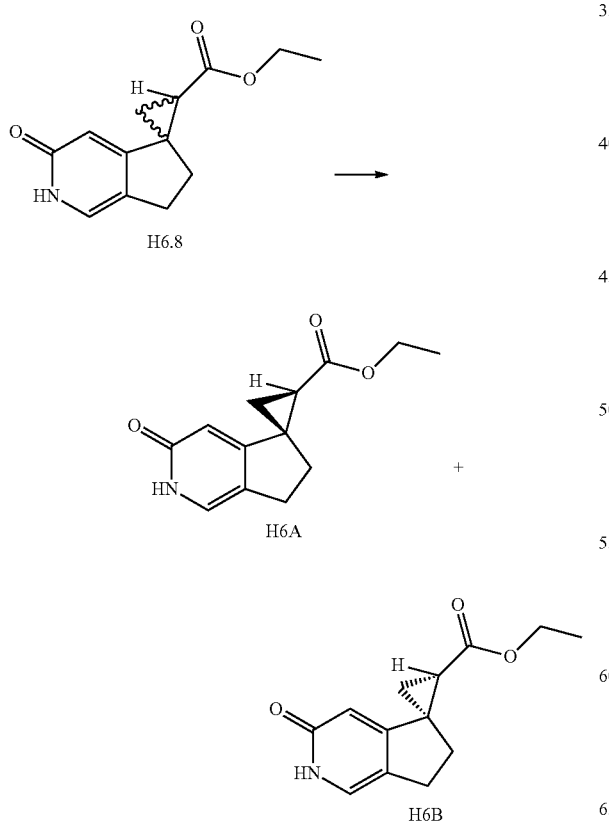

Ethyl (2'R,5R)-3-oxo-2,3,6,7-tetrahydrospiro[cyclopenta[c]pyridine-5,1'-cyclopropane]-2'-carboxylate (H6A) and Ethyl (2'S,5S)-3-oxo-2,3,6,7-tetrahydrospiro[cyclopenta[c]pyridine-5,1'-cyclopropane]-2'-carboxylate (H6B)

Racemate H6.8 (120 mg, 0.537 mmol) was resolved by ChiralPak® AS-H chromatography (15×0.46 cm, 30% MeOH (0.1% DEA)/CO$_2$, 100 bar, 3 mL/min, 220 nm) to afford the two enantiomers represented by two peaks. The first peak is the compound H6B (55.0 mg, 45.8%) and the second peak is H6A (53.0 mg, 44.1%). The stereochemistry of H6A and H6B was determined by their chiral HPLC retention times compared to those of H1A and H1B.

Intermediates H7A, H7B, H7C and H7D

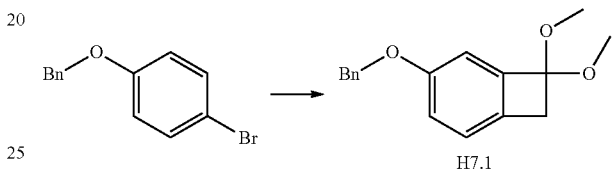

5-(Benzyloxy)-1,1-dimethoxy-1,2-dihydrocyclobutabenzene (H7.1)

To a 6 mL THF solution of 1-(benzyloxy)-4-bromobenzene (500 mg, 1900 μmol) (commercially available from Sigma-Aldrich, St. Louis, Mo., USA) and ketene dimethyl acetal (359 μL, 3800 μmol) (commercially available from Sigma-Aldrich, St. Louis, Mo., USA) was added neat sodium amide (107 μL, 3800 μmol) (commercially available from Sigma-Aldrich, St. Louis, Mo., USA). The resulting mixture was heated to 80° C. and stirred for 48 hours. After the reaction was complete, it was quenched by slow addition of water. The resulting mixture was then extracted with EtOAc. The organic layer was washed with brine and dried over MgSO$_4$. Solvent was removed in the presence of silica gel, and the residue was purified by column chromatography with 20% EtOAc/hexane to afford desired product H7.1 (274 mg, yield, 60%). MS ESI (pos.) m/e: 271.1 (M+H)$^+$.

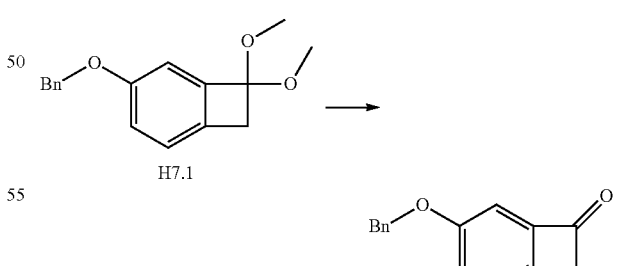

5-(Benzyloxy)cyclobutabenzen-1(2H)-one (H7.2)

H7.1 (270 mg, 1.00 mmol) was dissolved in 6 mL 5:1 THF and water. To this solution was added 0.5 mL 1N HCl, and the resulting mixture was stirred for 1 hour. The resulting mixture was then diluted with 20 mL EtOAc and washed with saturated NaHCO$_3$ and brine. The organic layer was dried over MgSO$_4$, filtered, and concentrated in the presence of silica gel. The residue was then purified by column chromatography with 10% EtOAc/hexane to afford H7.2 (204 mg, yield, 91.1%). MS ESI (pos.) m/e: 225.1 (M+H)$^+$.

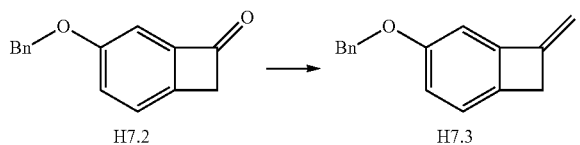 [SMILES: O=C1Cc2ccc(OCc3ccccc3)cc21 ; C=C1Cc2ccc(OCc3ccccc3)cc21]

5-(Benzyloxy)-1-methylene-1,2-dihydrocyclobutabenzene (H7.3)

H7.2 (13.0 g, 58.0 mmol) was dissolved in 300 mL THF. The resulting solution was cooled to 0° C. in an ice-water bath. Methyltriphenylphosphonium bromide (24.8 g, 69.6 mmol) (commercially available from Sigma-Aldrich, St. Louis, Mo., USA) was added and some yellow solid appeared. Potassium 2-methylpropan-2-olate (69.6 mL, 69.6 mmol) (commercially available from Sigma-Aldrich, St. Louis, Mo., USA) was then added dropwise over an hour. The reaction was stirred at 0° C. for another hour and then quenched by addition of 200 mL saturated NaHCO$_3$. The THF solvent was evaporated by vacuum and the residue was extracted twice with 200 mL EtOAc. The combined organic layers were washed with brine, dried over MgSO$_4$, filtered, and then concentrated in the presence of silica gel. The residue was purified by column chromatography with 10% EtOAc/hexane to afford H7.3 (4.1 g, 31.8%). MS ESI (pos.) m/e: 223.1 (M+H)$^+$.

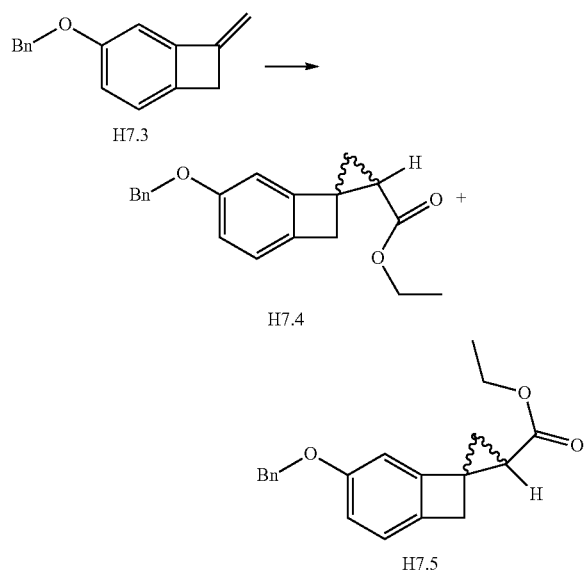

Ethyl 4-(benzyloxy)spiro[bicyclo[4.2.0]octane-7,1'-cyclopropane]-1,3,5-triene-2'-carboxylate (H7.4 and H7.5)

H7.3 (1.77 g, 7.96 mmol) was dissolved in 64 mL DCM. To this solution was added rhodium (ii) acetate dimer (0.176 g, 0.398 mmol) (commercially available from Sigma-Aldrich, St. Louis, Mo., USA). The resulting mixture was then refluxed at 45° C. for 30 minutes. Ethyl diazoacetate (1.36 g, 11.9 mmol) (commercially available from Sigma-Aldrich, St. Louis, Mo., USA) was added to the refluxed solution via syringe pump over 1 hour. After completion, the reaction was stirred for another hour. The solution was then filtered through Celite® filter aid, concentrated in the presence of silica gel and purified by column chromatography (5% EtOAc/hexane) to give compound H7.4 (0.85 g, 35%) and compound H7.5 (0.85 g, 35%). NMR confirmed that H7.4 was the trans isomer and H7.5 was the cis isomer. Compound H7.4: MS ESI (pos.) m/e: 309.1 (M+H)$^+$. $^1$H NMR (400 MHz, DMSO-d$_6$) δ ppm 7.28-7.44 (5H, m), 7.01 (1H, dd, J=8.0, 0.6 Hz), 6.84 (1H, dd, J=7.9, 2.2 Hz), 6.66 (1H, s), 5.02 (1H, d, J=3.9 Hz), 4.98-5.06 (1H, m), 4.05 (2H, qd, J=7.1, 3.4 Hz), 3.15-3.29 (2H, m), 2.30 (1H, dd, J=8.4, 6.1 Hz), 1.64 (1H, dd, J=8.5, 4.8 Hz), 1.55-1.60 (1H, m), 1.13-1.18 (3H, m). Compound H7.5: MS ESI (pos.) m/e: 309.1 (M+H)$^+$. $^1$H NMR (400 MHz, DMSO-d$_6$) δ ppm 7.30-7.46 (5H, m), 7.02 (1H, d, J=7.8 Hz), 6.83 (1H, dd, J=8.0, 2.2 Hz), 6.72 (1H, dd, J=1.9, 0.5 Hz), 5.03 (2H, s), 4.10 (2H, q, J=7.3 Hz), 3.20-3.26 (1H, m), 3.08-3.14 (1H, m), 2.25 (1H, dd, J=8.5, 6.0 Hz), 1.56-1.66 (2H, m), 1.15-1.27 (3H, m).

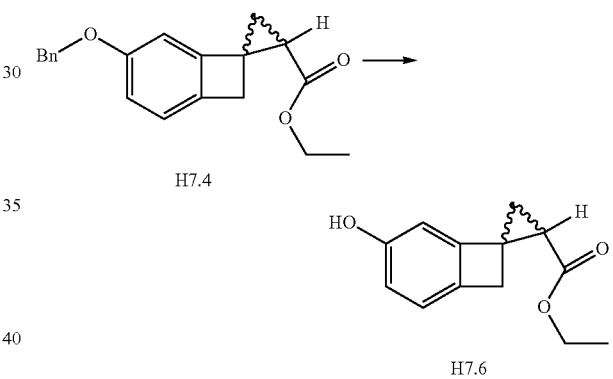

Ethyl 4-hydroxyspiro[bicyclo[4.2.0]octane-7,1'-cyclopropane]-1,3,5-triene-2'-carboxylate (H7.6)

H7.4 (700 mg, 2.27 mmol) was dissolved in 5 mL MeOH. To this solution was added 10% palladium on carbon (242 mg, 0.227 mmol) and a balloon of H$_2$ was placed over the reaction. The reaction mixture was stirred for 1 hour, and the catalyst was then removed by filtration. The filtrate was concentrated down in the presence of silica gel and purified by column chromatography with 30% EtOAc/hexane to give 250 mg compound H7.6 (yield, 50.1%). MS ESI (pos.) m/e: 218.2 (M+H)$^+$.

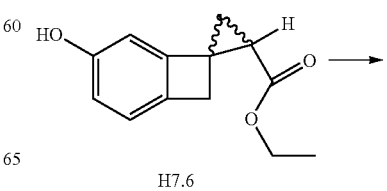

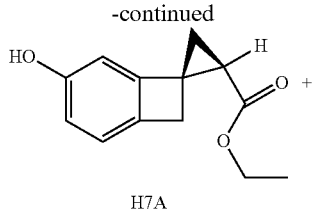

H7A

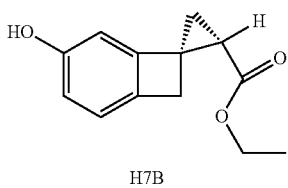

H7B

Ethyl (2'R,7S)-4-hydroxyspiro[bicyclo[4.2.0]octane-7,1'-cyclo propane]-1,3,5-triene-2'-carboxylate (H7A) and Ethyl (2'S,7R)-4-hydroxy spiro[bicycle [4.2.0]octane-7,1'-cyclopropane]-1,3,5-triene-2'-carboxylate (H7B)

Racemate H7.6 (350 mg, 1.60 mmol) was resolved by chiral HPLC (CHIRALCEL® OJ column, 10% IPA/hexane). The first peak corresponded to H7B (150 mg, 43%) and the second peak corresponded to H7A (152 mg, 43%). The stereochemistry of H7A and H7B was determined by their chiral HPLC retention times compared to those of H1.A and H1.B.

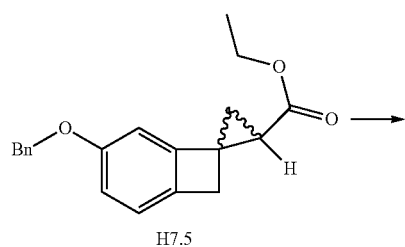

H7.5

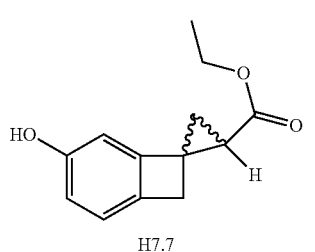

H7.7

Ethyl 4-hydroxyspiro[bicyclo[4.2.0]octane-7,1'-cyclopropane]-1,3,5-triene-2'-carboxylate (H7.7).

The hydrogenation of compound H7.5 (700 mg, 2.27 mmol) using the method reported for preparation of the compound H7.6 to afford H7.7 (302 mg, 60.1%). MS ESI (pos.) m/e: 218.2 (M+H)⁺

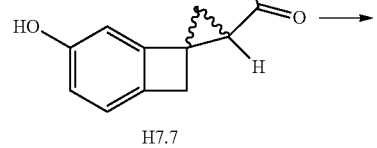

H7.7

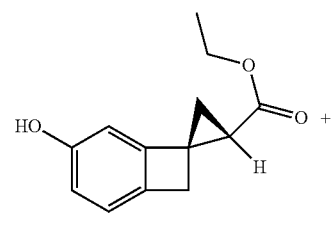

H7C

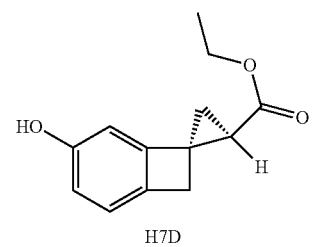

H7D

Ethyl (2'S,7S)-4-hydroxyspiro[bicyclo[4.2.0]octane-7,1'-cyclopropane]-1,3,5-triene-2'-carboxylate (H7C) and Ethyl (2'R,7R)-4-hydroxyspiro[bicyclo[4.2.0]octane-7,1'-cyclopropane]-1,3,5-triene-2'-carboxylate (H7D)

Racemate H7.7 (300 mg, 1.37 mmol) was resolved by chiral HPLC (CHIRALCEL® OJ column, 10% IPA/hexane). The first peak corresponds to H7C (132 mg, 44%) and the second peak corresponded to H7D (130 mg, 44%). The stereochemistry of H7C and H7D was determined by their chiral HPLC retention times compared to those of H1C and H1D.

Intermediates H9A, H9B, H9C, H9D, H9E, H9F, H9G and H9H

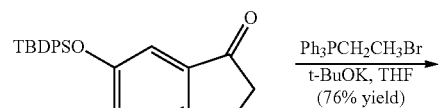

H1.1

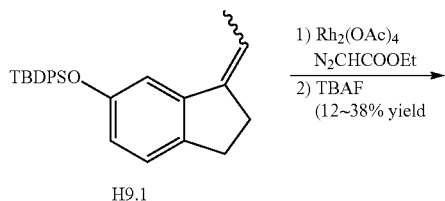

H9.1

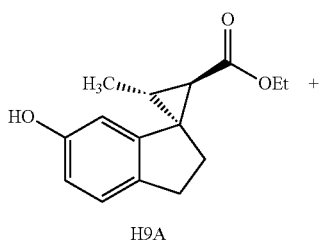

H9A

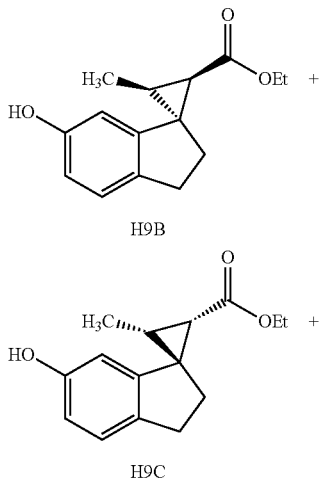

H9B

H9C

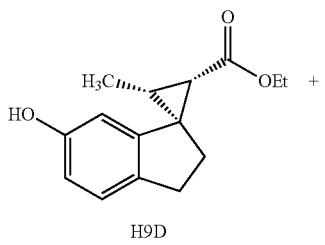

H9D

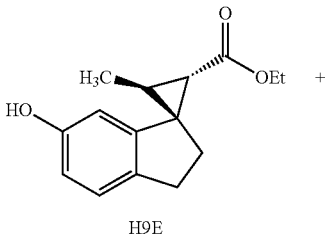

H9E

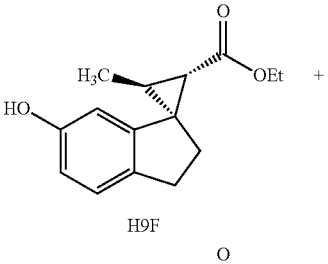

H9F

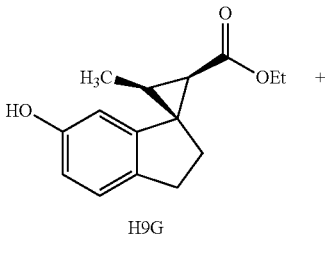

H9G

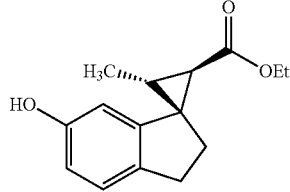

H9H tert-Butyl(3-ethylidene-2,3-dihydro-1H-inden-5-yloxy)diphenylsilane (H9.1)

To a solution of H1.1 (3.87 g, 10.0 mmol) and ethyltriphenylphosphonium bromide (4.46 g, 12.0 mmol) in THF (20 mL) was added potassium tert-butoxide, 1.0 M solution in THF (12.0 mL, 12.0 mmol). The resulting mixture was stirred at room temperature for 4 hours and concentrated to remove most of the THF. The resulting mixture was suspended in hexanes (50 mL), passed through a pad of silica gel (2027-U, 25 g), and rinsed with hexanes (250 mL) to give H9.1 (3.02 g, 76% yield) as a mixture of cis/trans isomers. MS ESI (pos.) M/E: 399 (M+H).

Synthesis of H9A, H9B, H9C, H9D, H9E, H9F, H9G and H9H

To a solution of H9.1 (2.61 g, 6548 µmol) and rhodium (II) acetate, dimer (29 mg, 65 µmol) in refluxing DCM (200 mL) was added ethyl diazoacetate (1019 µL, 9822 µmol) in refluxing DCM via syringe pump over 60 minutes. The resulting mixture was stirred at 45° C. for 1 hour and then at room temperature for 16 hours. The resulting mixture was concentrated and purified by flash chromatography (0-10% EtOAc/hexane) to give several fractions of mixtures. These fractions were treated individually with 1 equivalent of TBAF in THF at room temperature for 1 hour. The mixtures were diluted with DCM, washed with aqueous NH$_4$Cl, loaded onto a silica gel cartridge, and purified by flash chromatography (20% EtOAc/hexane) to give eight fractions. Most of the fractions were mixtures of two or three isomers. These eight fractions of mixtures were separated individually on an AD column (ChiralPak® AD, 4% IPA/hexanes) to give H9A (54 mg, 27% yield, 99% ee, retention time 11.7 minutes on AD-H with 4% IPA/hex,); H9B (34 mg, 17% yield, 99% ee, retention time 13.9 minutes on AD-H with 4% IPA/hex,); H9C (33 mg, 16% yield, 99% ee, retention time 20.2 minutes on AD-H with 4% IPA/hex,); H9D (61 mg, 30% yield, 99% ee, retention time 23.6 minutes on AD-H with 4% IPA/hex,); H9E (53 mg, 26% yield, 99% ee, retention time 28.6 minutes on AD-H with 4% IPA/hex,); H9F (28 mg, 14% yield, 95% ee, retention time 30.4 minutes on AD-H with 4% IPA/hex,); H9G (76 mg, 38% yield, 99% ee, retention time 31.9 minutes on AD-H with 4% IPA/hex,); and H9H (25 mg, 12% yield, 95% ee, retention time 35.4 minutes on AD-H with 4% IPA/hex,). MS ESI (pos.) M/E: 247 (M+H). Relative stereochemistry was assigned based on $^1$H NMR and NOE studies. Absolute configuration was assigned based on their chiral HPLC retention times compared to those of H1A, H1B, H1C, and H1D. However, absolute configurations are not known with certainty.

Therefore, when H9A, H9B, H9C, H9D, H9E, H9F, H9G, or H9H was used to synthesize an Example compound, all eight stereoisomers are shown.

Intermediate H10

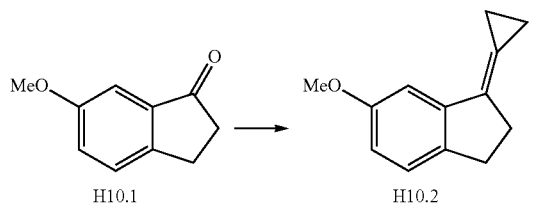 [SMILES: COc1ccc2c(c1)C(=O)CC2 ; COc1ccc2c(c1)C(=C1CC1)CC2]

1-Cyclopropylidene-6-methoxy-2,3-dihydro-1H-indene (H10.2)

NaH (1.5 g, 62 mmol) was added to a suspension of cyclopropyltriphenyl-phosphonium bromide (24 g, 62 mmol) (commercially available from Sigma-Aldrich, St. Louis, Mo., USA) in THF (100 mL), and the resulting mixture was stirred at room temperature for 2 hours. Then, 6-methoxy-1-indanone (H10.1) (Oakwood Products, Inc.) (5.00 g, 31 mmol) and tris(2-(2-methoxyethoxy)ethyl)amine (commercially available from Sigma-Aldrich, St. Louis, Mo., USA) (1.1 mL, 3.1 mmol) were added slowly. The resulting mixture was stirred at room temperature for 10 minutes and then at 62° C. for 4 hours. The reaction mixture was concentrated and purified by chromatography (silica gel, eluting with 1:9 EtOAc/hexane) to provide H10.2 (4.53 g, 79% yield) as a solid. MS ESI (pos.) M/E: 187.1 (M+H).

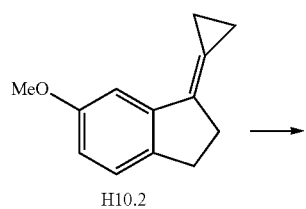

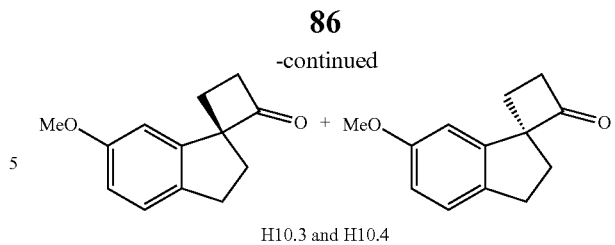

(S)-6'-Methoxy-2',3'-dihydrospiro[cyclobutane-1,1'-inden]-2-one and (R)-6'-methoxy-2',3'-dihydrospiro[cyclobutane-1,1'-inden]-2-one (H10.3 and H10.4)

At 0-5° C., 3-chloroperbenzoic acid (5.84 g, 33.8 mmol) (commercially available from Sigma-Aldrich, St. Louis, Mo., USA) was added portion by portion to a solution of 1-cyclopropylidene-6-methoxy-2,3-dihydro-1H-indene (10.2) (4.50 g, 24.2 mmol) in DCM (70 mL). The resulting mixture was stirred at 0-5° C. for 42 minutes and then at room temperature for 60 minutes. The mixture was then diluted with DCM (200 mL), washed with 10% NaOH solution and brine, and then dried over anhydrous sodium sulfate. Solvent was removed, and the residue was purified by chromatography (silica gel, eluting with 1:9 EtOAc/hexane) to give the product ketone (1.95 g, 40% yield) as a pale yellow oil. MS ESI (pos.) M/E: 203.1 (M+H). Chiral separation was conducted on an OD column, eluting with 1% IPA/hexane. Pure enantiomer H10.3 (0.896 g, oil) (first peak, retention time 8.4 minutes) and H10.4 (1.01 g, oil) (second peak, retention time 10.5 min) were obtained. The absolute stereochemistry was not determined for either peak.

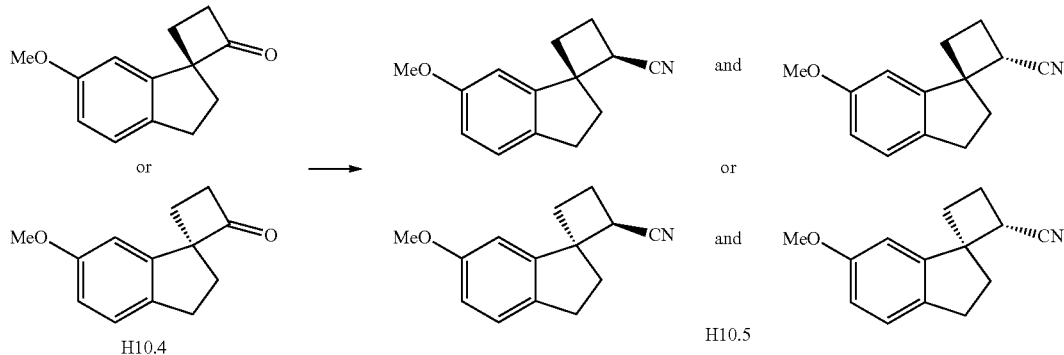

(1S,2R)-6'-Methoxy-2',3'-dihydrospiro[cyclobutane-1,1'-indene]-2-carbonitrile and (1S,2S)-6'-methoxy-2',3'-dihydrospiro[cyclobutane-1,1'-indene]-2-carbonitrile or (1R,2R)-6'-methoxy-2',3'-dihydrospiro[cyclobutane-1,1'-indene]-2-carbonitrile and (1R,2S)-6'-methoxy-2',3'-dihydrospiro[cyclobutane-1,1'-indene]-2-carbonitrile (H10.5)

At 0-5° C., potassium 2-methylpropan-2-olate (2.41 g, 21.5 mmol) was added in one portion to a solution of H10.4 (0.870 g, 4.30 mmol) and tosylmethyl isocyanide (1.68 g, 8.60 mmol) (commercially available from Sigma-Aldrich, St. Louis, Mo., USA) in dimethoxyethane (30 mL) and MeOH (1.4 mL). The resulting mixture was stirred at room temperature for 2.4 hours and then the reaction mixture was poured into water (20 mL) and neutralized with 1N HCl to pH 6-7. The mixture was then extracted with EtOAc (3×100 mL) and the combined organic phase was washed with brine and dried over anhydrous sodium sulfate. After filtration, the solvent was removed and the residue was purified by chromatography (silica gel, eluting with 1:9 EtOAc/hexane) to give H10.5, pale yellow oil, in 24% yield. MS ESI (pos.) M/E: 214.1 (M+H).

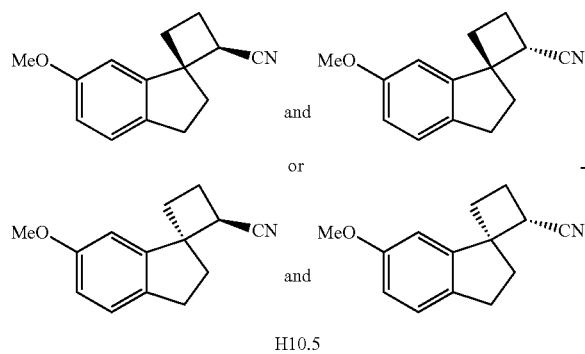

H10.5

(1S,2R)-6'-Hydroxy-2',3'-dihydrospiro[cyclobutane-1,1'-indene]-2-carbonitrile and (1S,2S)-6'-hydroxy-2',3'-dihydrospiro[cyclobutane-1,1'-indene]-2-carbonitrile or (1R,2R)-6'-hydroxy-2',3'-dihydrospiro[cyclobutane-1,1'-indene]-2-carbonitrile and (1R,2S)-6'-hydroxy-2',3'-dihydrospiro[cyclobutane-1,1'-indene]-2-carbonitrile (H10.6)

A mixture of H10.5 (0.220 g, 1.0 mmol) and sodium methanethiolate (0.506 g, 7.22 mmol) (commercially available from Sigma-Aldrich, St. Louis, Mo., USA) in DMF (27 mL) was stirred at 135° C. for 3 hours. The reaction mixture was poured into NH$_4$Cl solution (20 mL). The resulting mixture was extracted with EtOAc (230 mL). The organic phase was then washed with brine, dried over anhydrous sodium sulfate, and filtered. The solvent was removed and the residue was purified by chromatography (silica gel, eluting with 1:3 EtOAc/hexane) to give H10.6 as a colorless oil, in 77% yield. MS ESI (pos.) M/E: 200.2 (M+H).

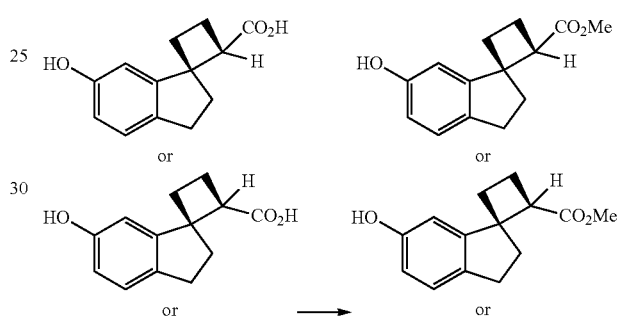

H10.6

(1S,2R)-6'-Hydroxy-2',3'-dihydrospiro[cyclobutane-1,1'-indene]-2-carboxylic acid and (1S,2S)-6'-hydroxy-2',3'-dihydrospiro[cyclobutane-1,1'-indene]-2-carboxylic acid or (1R,2R)-6'-hydroxy-2',3'-dihydrospiro[cyclobutane-1,1'-indene]-2-carboxylic acid and (1R,2S)-6'-hydroxy-2',3'-dihydrospiro[cyclobutane-1,1'-indene]-2-carboxylic acid (H10.7 and H10.8)

A mixture of H10.6 (0.154 g, 0.77 mmol) and NaOH (aq., 10%) (5 mL) in ethylene glycol (8 mL) was stirred at 135° C. for 2 hours. The resulting mixture was diluted with water (0.6 mL) and acidified with 1N HCl to pH 2-5. The resulting solution was purified by reverse phase HPLC to give H10.7 (shorter retention time), 48 mg, white solid and H10.8 (longer retention time), 18 mg. H10.7: MS ESI (pos.) M/E: 219.1 (M+H). H10.8: MS ESI (pos.) M/E: 219.1 (M+H).

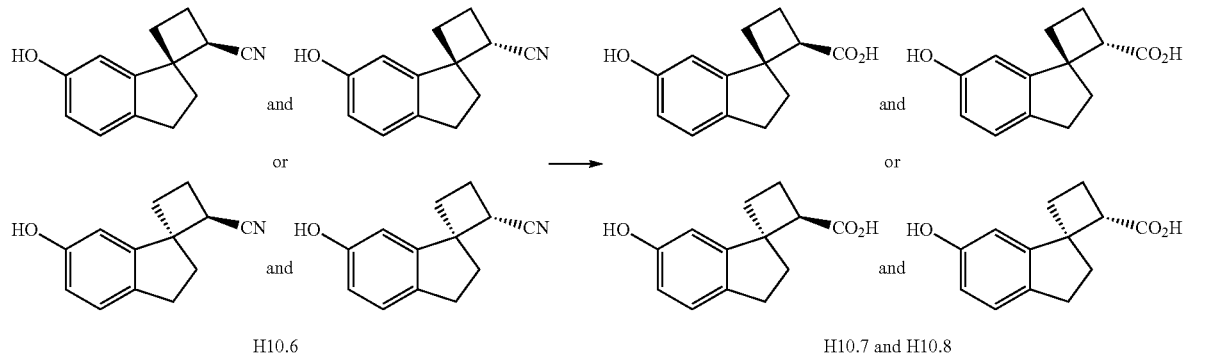

H10.7 and H10.8

-continued

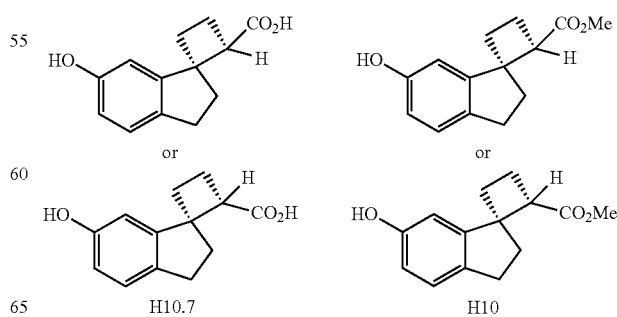

H10.7        H10

(1S,2R)-Methyl 6'-hydroxy-2',3'-dihydrospiro[cyclobutane-1,1'-indene]-2-carboxylate or (1S,2S)-methyl 6'-hydroxy-2',3'-dihydrospiro[cyclobutane-1,1'-indene]-2-carboxylate or (1R,2R)-methyl 6'-hydroxy-2',3'-dihydrospiro[cyclobutane-1,1'-indene]-2-carboxylate or (1R,2S)-methyl 6'-hydroxy-2',3'-dihydrospiro[cyclobutane-1,1'-indene]-2-carboxylate (H10)

A solution of H10.7 (0.028 g, 0.13 mmol) in MeOH (7 mL) (containing 2 drops of concentrated $H_2SO_4$) was refluxed for 16 hours. The mixture was then cooled to room temperature and neutralized with $NaHCO_3$ solution. The mixture was concentrated and extracted with EtOAc (120 mL). The organic phase was dried over anhydrous sodium sulfate. After removal of solvent, H10 (30 mg) was obtained. MS ESI (pos.) M/E: 250.1 (M+$H_2O$).

Intermediate H11

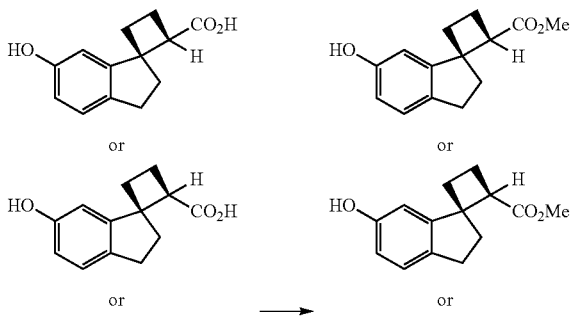

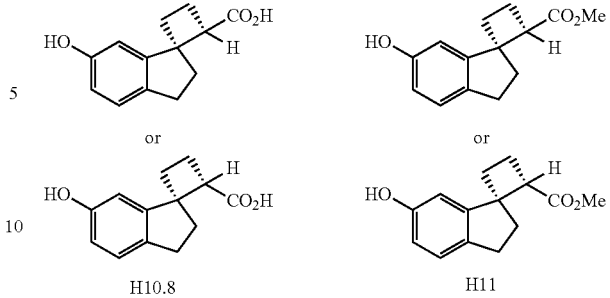

(1S,2R)-Methyl 6'-hydroxy-2',3'-dihydrospiro[cyclobutane-1,1'-indene]-2-carboxylate or (1S,2S)-methyl 6'-hydroxy-2',3'-dihydrospiro[cyclobutane-1,1'-indene]-2-carboxylate or (1R,2R)-methyl 6'-hydroxy-2',3'-dihydrospiro[cyclobutane-1,1'-indene]-2-carboxylate or (1R,2S)-methyl 6'-hydroxy-2',3'-dihydrospiro[cyclobutane-1,1'-indene]-2-carboxylate (H11)

H11 was synthesized from H10.8 using a procedure similar to that used to prepare H10 from H10.7.

Intermediate H12

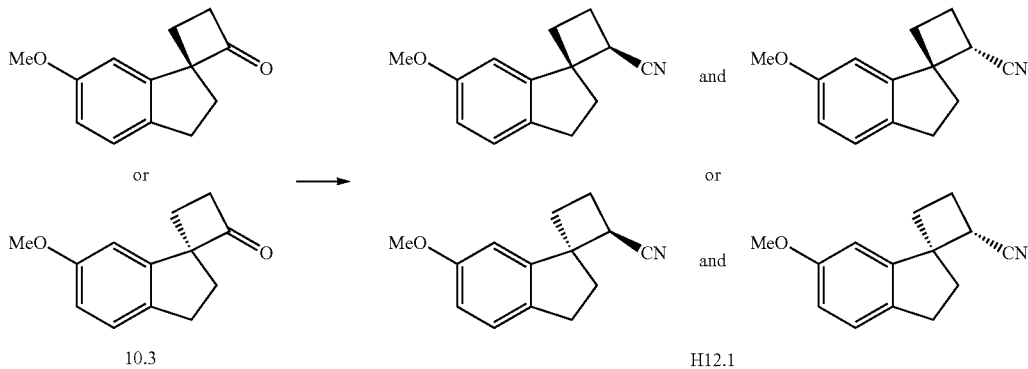

(1S,2R)-6'-Methoxy-2',3'-dihydrospiro[cyclobutane-1,1'-indene]-2-carbonitrile and (1S,2S)-6'-methoxy-2',3'-dihydrospiro[cyclobutane-1,1'-indene]-2-carbonitrile or (1R,2R)-6'-methoxy-2',3'-dihydrospiro[cyclobutane-1,1'-indene]-2-carbonitrile and (1R,2S)-6'-methoxy-2',3'-dihydrospiro[cyclobutane-1,1'-indene]-2-carbonitrile (H12.1)

H12.1 was synthesized from H10.3 using the same procedure used to prepare H10.5 from H10.4.

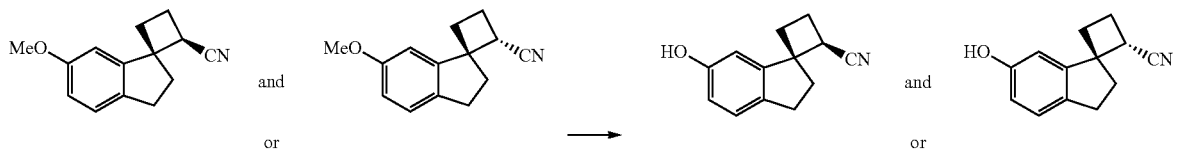

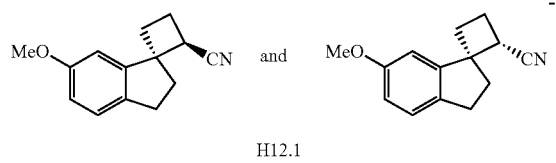

H12.1

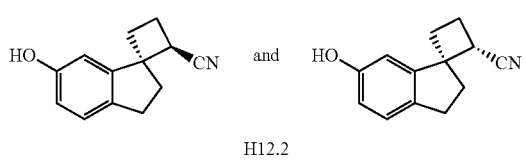

H12.2

(1S,2R)-6'-Hydroxy-2',3'-dihydrospiro[cyclobutane-1,1'-indene]-2-carbonitrile and (1S,2S)-6'-hydroxy-2',3'-dihydrospiro[cyclobutane-1,1'-indene]-2-carbonitrile or (1R,2R)-6'-hydroxy-2',3'-dihydrospiro[cyclobutane-1,1'-indene]-2-carbonitrile and (1R,2S)-6'-hydroxy-2',3'-dihydrospiro[cyclobutane-1,1'-indene]-2-carbonitrile (H12.2)

H12.2 was synthesized from H12.1 using the same procedure used to prepare H10.6 from H10.5.

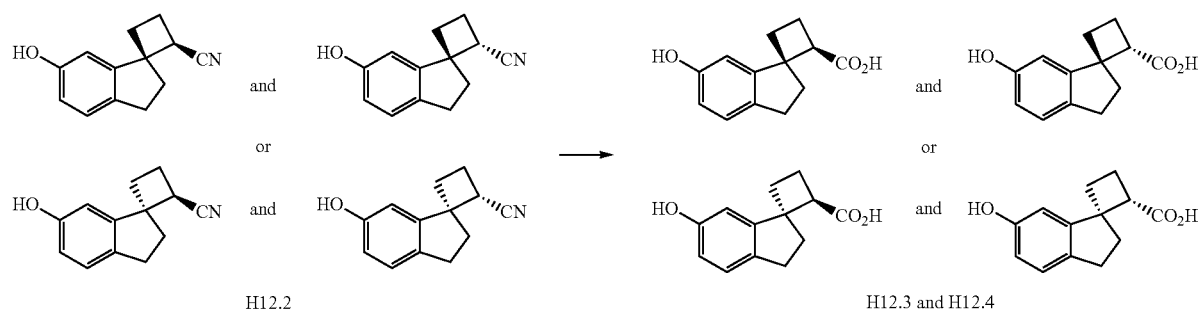

H12.2                    H12.3 and H12.4

(1S,2R)-6'-Hydroxy-2',3'-dihydrospiro[cyclobutane-1,1'-indene]-2-carboxylic acid and (1S,2S)-6'-hydroxy-2',3'-dihydrospiro[cyclobutane-1,1'-indene]-2-carboxylic acid or (1R,2R)-6'-hydroxy-2',3'-dihydrospiro[cyclobutane-1,1'-indene]-2-carboxylic acid and (1R,2S)-6'-hydroxy-2',3'-dihydrospiro[cyclobutane-1,1'-indene]-2-carboxylic acid (H12.3 and H12.4)

H12.3 (first peak from reverse phase HPLC) and H12.4 were synthesized from H12.2 using the same procedure used to convert H10.6 to H10.7 and H10.8. MS ESI (pos.) M/E: 219.1 (M+H).

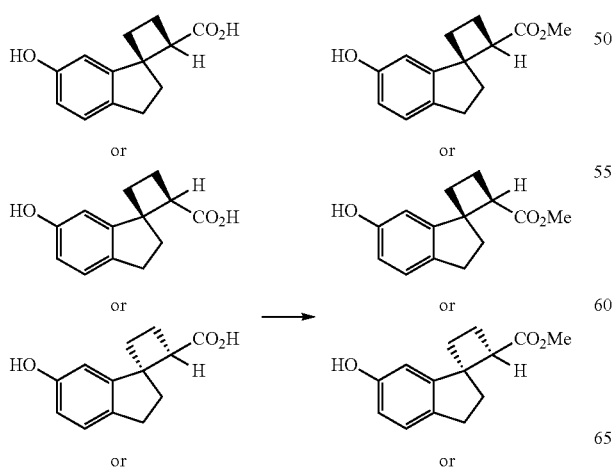

-continued

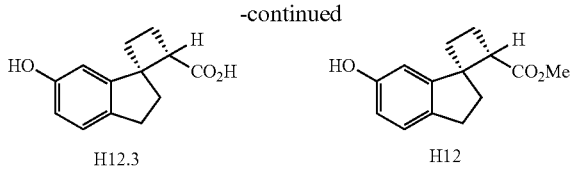

H12.3                    H12

(1S,2R)-Methyl 6'-hydroxy-2',3'-dihydrospiro[cyclobutane-1,1'-indene]-2-carboxylate or (1S,2S)-methyl 6'-hydroxy-2',3'-dihydrospiro[cyclobutane-1,1'-indene]-2-carboxylate or (1R,2R)-methyl 6'-hydroxy-2',3'-dihydrospiro[cyclobutane-1,1'-indene]-2-carboxylate or (1R,2S)-methyl 6'-hydroxy-2',3'-dihydrospiro[cyclobutane-1,1'-indene]-2-carboxylate (H12)

H12 was synthesized from H12.3 using the same procedure used to convert H10.7 to H10. M/E: 250.1 (M+H$_2$O).

Intermediate H13

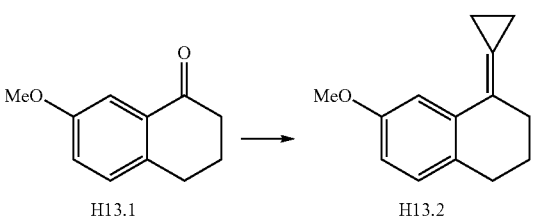 [SMILES: COc1ccc2c(c1)C(=O)CCC2 ; COc1ccc2c(c1)C(=C1CC1)CCC2]

H13.1                    H13.2

1-Cyclopropylidene-7-methoxy-1,2,3,4-tetrahydronaphthalene (H13.1)

H13.2 was synthesized from 7-methoxy-3,4-dihydro-1(2H)-naphthalenone (H13.1, commercially available from Sigma-Aldrich, St. Louis, Mo., USA) using the same procedure used to prepare H10.2 from H10.1.

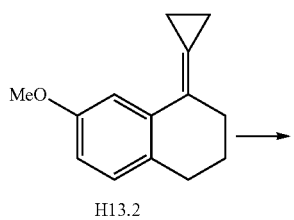

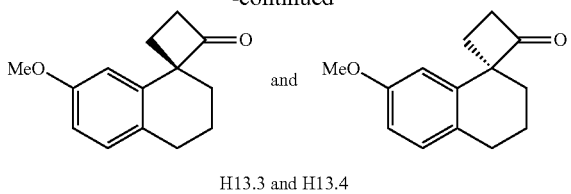

H13.3 and H13.4

(S)-7'-Methoxy-3',4'-dihydro-2'H-spiro[cyclobutane-1,1'-naphthalen]-2-one and (R)-7'-methoxy-3',4'-dihydro-2'H-spiro[cyclobutane-1,1'-naphthalen]-2-one (H13.3 and H13.4)

H13.3 and H13.4 were synthesized from H13.2 using the same procedure used to prepare H10.3 and H10.4 from H10.2. The racemic product gave MS ESI (pos.) M/E: 217.1 (M+H). Chiral separation was conducted on a chiral OD column, eluting with 1% IPA/hexane. Pure enantiomer H13.3 (1.35 g, white solid) (first peak, retention time 8.06 minutes) and H13.4 (1.37 g, white solid) (second peak, retention time 101.6 minutes) were obtained. The absolute stereochemistry of the products associated with either was not determined.

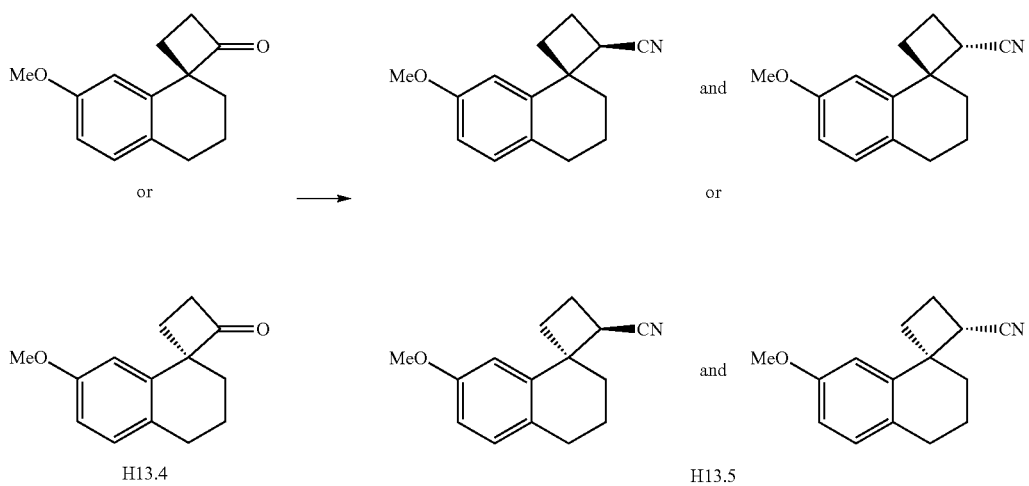

(1R,2S)-7'-Methoxy-3',4'-dihydro-2'H-spiro[cyclobutane-1,1'-naphthalene]-2-carbonitrile and (1R,2R)-7'-methoxy-3',4'-dihydro-2'H-spiro[cyclobutane-1,1'-naphthalene]-2-carbonitrile or (1S,2S)-7'-methoxy-3',4'-dihydro-2'H-spiro[cyclobutane-1,1'-naphthalene]-2-carbonitrile and (1S,2R)-7'-methoxy-3',4'-dihydro-2'H-spiro[cyclobutane-1,1'-naphthalene]-2-carbonitrile (H13.5)

H13.5 was synthesized from H13.4 using the same procedure used to prepare H10.5 from H10.4. MS ESI (pos.) M/E: 245.2 (M+H$_2$O).

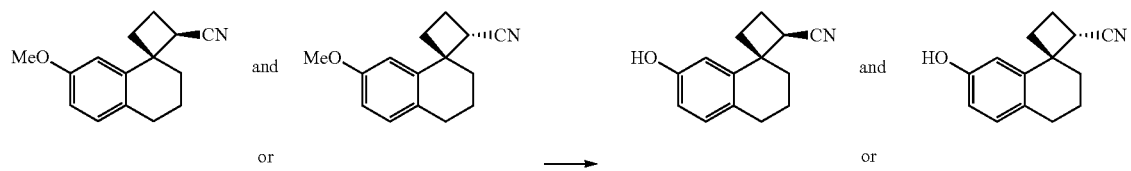

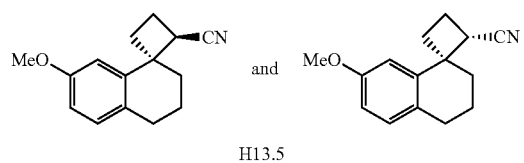

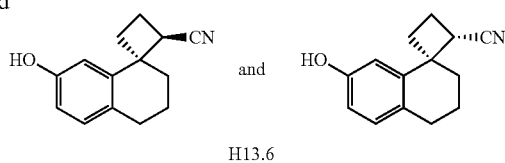

(1R,2S)-7'-Hydroxy-3',4'-dihydro-2'H-spiro[cyclobutane-1,1'-naphthalene]-2-carbonitrile and (1R,2R)-7'-hydroxy-3',4'-dihydro-2'H-spiro[cyclobutane-1,1'-naphthalene]-2-carbonitrile or (1S,2S)-7'-hydroxy-3',4'-dihydro-2'H-spiro[cyclobutane-1,1'-naphthalene]-2-carbonitrile and (1S,2R)-7'-hydroxy-3',4'-dihydro-2'H-spiro[cyclobutane-1,1'-naphthalene]-2-carbonitrile (H13.6)

H13.6 was synthesized from H13.5 using the same procedure used to prepare H10.6 from H10.5. MS ESI (pos.) M/E: 231.1 (M+H).

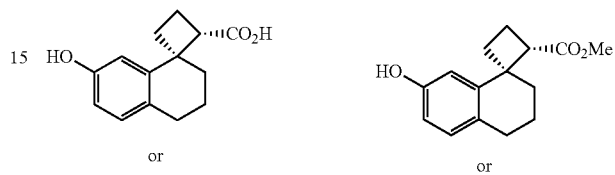

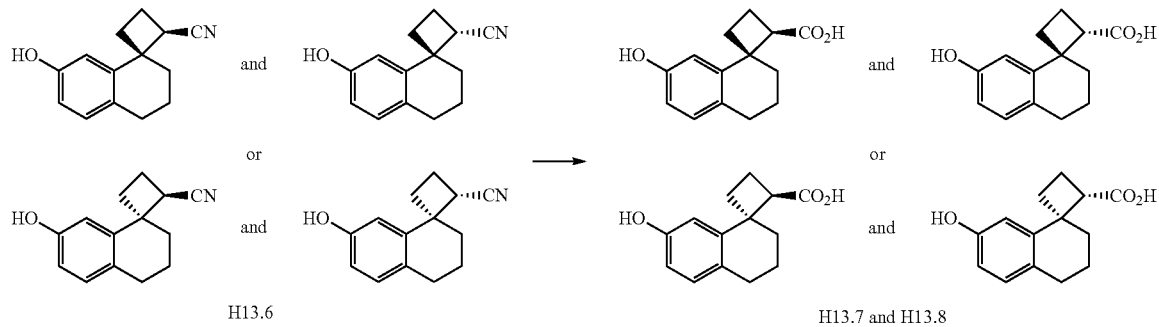

(1R,2S)-7'-Hydroxy-3',4'-dihydro-2'H-spiro[cyclobutane-1,1'-naphthalene]-2-carboxylic acid and (1R,2R)-7'-hydroxy-3',4'-dihydro-2'H-spiro[cyclobutane-1,1'-naphthalene]-2-carboxylic acid or (1S,2S)-7'-hydroxy-3',4'-dihydro-2'H-spiro[cyclobutane-1,1'-naphthalene]-2-carboxylic acid and (1S,2R)-7'-hydroxy-3',4'-dihydro-2'H-spiro[cyclobutane-1,1'-naphthalene]-2-carboxylic acid and (1R,2S)-7'-hydroxy-3',4'-dihydro-2'H-spiro[cyclobutane-1,1'-naphthalene]-2-carboxylic acid (H13.7 and H13.8)

H13.7 (first peak from reverse phase HPLC) and H13.8 (2nd' peak from reverse phase HPLC) were synthesized from H13.6 using the same procedure used to prepare H10.7 and H10.8 from H10.6. MS ESI (neg.) M/E: 231.1 (M−H).

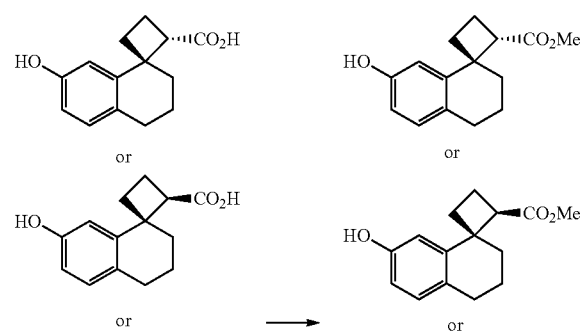

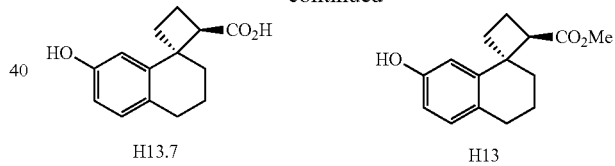

(1R,2S)-Methyl 7'-hydroxy-3',4'-dihydro-2'H-spiro[cyclobutane-1,1'-naphthalene]-2-carboxylate or (1R, 2R)-methyl 7'-hydroxy-3',4'-dihydro-2'H-spiro[cyclobutane-1,1'-naphthalene]-2-carboxylate or (1S, 2S)-methyl 7'-hydroxy-3',4'-dihydro-2'H-spiro[cyclobutane-1,1'-naphthalene]-2-carboxylate or (1S, 2R)-methyl 7'-hydroxy-3',4'-dihydro-2'H-spiro[cyclobutane-1,1'-naphthalene]-2-carboxylate (H13)

H13 was synthesized from H13.7 using the same procedure used to prepare H10 from H10.7. MS ESI (pos.) M/E: 247.2 (M+H).

Intermediate H14

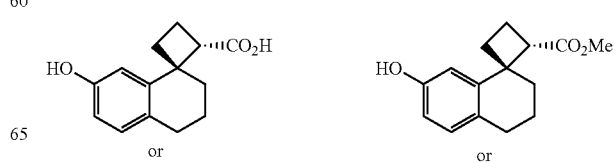

-continued

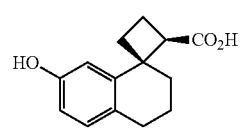

or

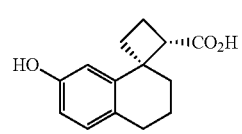

or

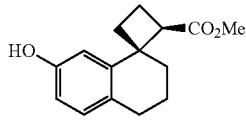

or

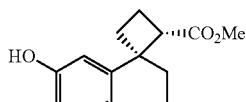

or

-continued

H13.8

H14

(1R,2S)-Methyl 7'-hydroxy-3',4'-dihydro-2'H-spiro[cyclobutane-1,1'-naphthalene]-2-carboxylate or (1R,2R)-methyl 7'-hydroxy-3',4'-dihydro-2'H-spiro[cyclobutane-1,1'-naphthalene]-2-carboxylate or (1S,2S)-methyl 7'-hydroxy-3',4'-dihydro-2'H-spiro[cyclobutane-1,1'-naphthalene]-2-carboxylate or (1S,2R)-methyl 7'-hydroxy-3',4'-dihydro-2'H-spiro[cyclobutane-1,1'-naphthalene]-2-carboxylate (H14)

H14 was synthesized from H13.8 using the same procedure used to prepare H10 from H10.7. MS ESI (pos.) M/E: 247.2 (M+H).

Intermediate H15

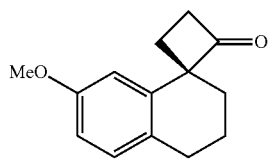

or

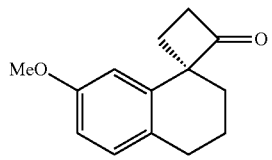

H13.3

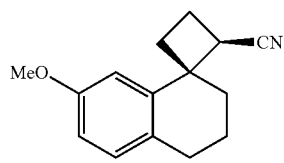

and

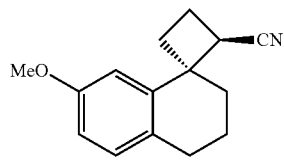

and

H15.1

(1R,2S)-7'-Methoxy-3',4'-dihydro-2'H-spiro[cyclobutane-1,1'-naphthalene]-2-carbonitrile and (1R,2R)-7'-methoxy-3',4'-dihydro-2'H-spiro[cyclobutane-1,1'-naphthalene]-2-carbonitrile or (1S,2S)-7'-methoxy-3',4'-dihydro-2'H-spiro[cyclobutane-1,1'-naphthalene]-2-carbonitrile and (1S,2R)-7'-methoxy-3',4'-dihydro-2'H-spiro[cyclobutane-1,1'-naphthalene]-2-carbonitrile (H15.2)

H15.2 was synthesized from H13.3 using the same procedure used to prepare H10.5 from H10.4. MS ESI (pos.) M/E: 245.2 (M+H$_2$O).

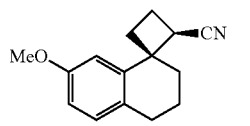 and 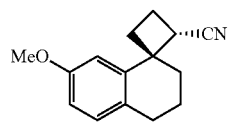

or

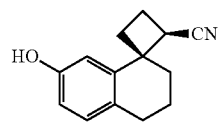 and 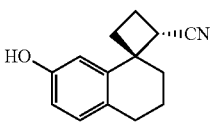

or

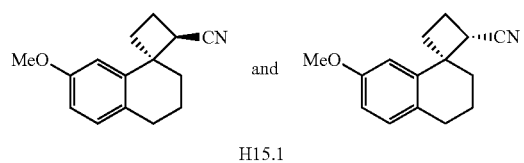

H15.1

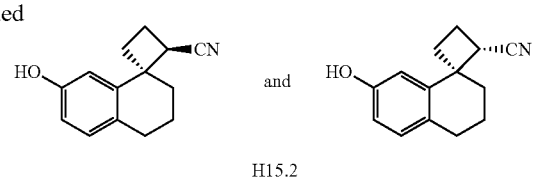

H15.2

(1R,2S)-7'-Hydroxy-3',4'-dihydro-2'H-spiro[cyclobutane-1,1'-naphthalene]-2-carbonitrile and (1R,2R)-7'-hydroxy-3',4'-dihydro-2'H-spiro[cyclobutane-1,1'-naphthalene]-2-carbonitrile or (1S,2S)-7'-hydroxy-3',4'-dihydro-2'H-spiro[cyclobutane-1,1'-naphthalene]-2-carbonitrile and (1S,2R)-7'-hydroxy-3',4'-dihydro-2'H-spiro[cyclobutane-1,1'-naphthalene]-2-carbonitrile (H15.2)

H15.2 was synthesized from H15.1 using the same procedure used to prepare H10.6 from H10.5. MS ESI (pos.) M/E: 231.1 (M+H).

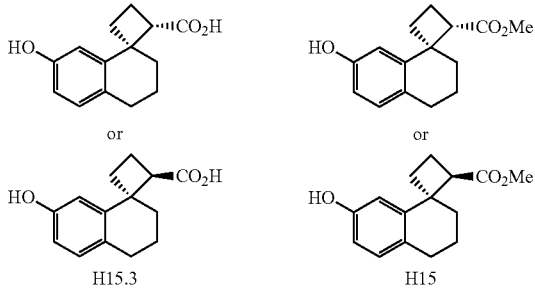

H15.3                H15

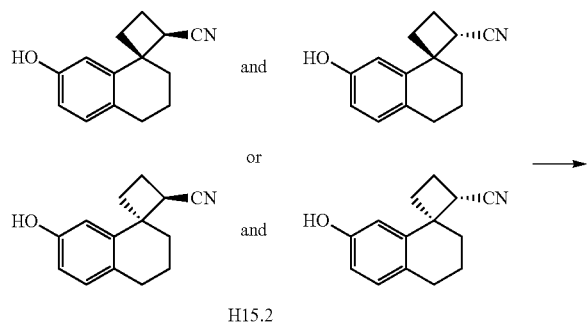

H15.2

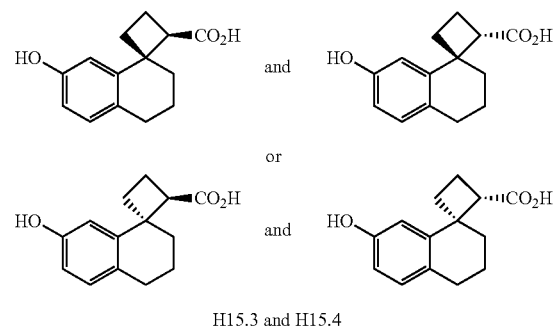

H15.3 and H15.4

(1R,2S)-7'-Hydroxy-3',4'-dihydro-2'H-spiro[cyclobutane-1,1'-naphthalene]-2-carboxylic acid and (1R,2R)-7'-hydroxy-3',4'-dihydro-2'H-spiro[cyclobutane-1,1'-naphthalene]-2-carboxylic acid or (1S,2S)-7'-hydroxy-3',4'-dihydro-2'H-spiro[cyclobutane-1,1'-naphthalene]-2-carboxylic acid and (1S,2R)-7'-hydroxy-3',4'-dihydro-2'H-spiro[cyclobutane-1,1'-naphthalene]-2-carboxylic acid and (1R,2S)-7'-hydroxy-3',4'-dihydro-2'H-spiro[cyclobutane-1,1'-naphthalene]-2-carboxylic acid (H15.3 and H15.4)

H15.3 (first peak from reverse phase HPLC) and H15.4 (2nd' peak from reverse phase HPLC) were synthesized from H15.2 using the same procedure used to prepare H10.7 and H10.8 from H10.6. MS ESI (neg.) M/E: 231.1 (M−H).

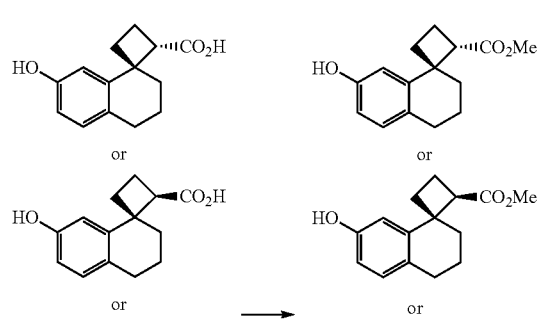

(1R,2S)-Methyl 7'-hydroxy-3',4'-dihydro-2'H-spiro[cyclobutane-1,1'-naphthalene]-2-carboxylate or (1R,2R)-methyl 7'-hydroxy-3',4'-dihydro-2'H-spiro[cyclobutane-1,1'-naphthalene]-2-carboxylate or (1S,2S)-methyl 7'-hydroxy-3',4'-dihydro-2'H-spiro[cyclobutane-1,1'-naphthalene]-2-carboxylate or (1S,2R)-methyl 7'-hydroxy-3',4'-dihydro-2'H-spiro[cyclobutane-1,1'-naphthalene]-2-carboxylate (H15)

H15 was synthesized from H15.3 using the same procedure used to prepare H10 from H10.7. MS ESI (pos.) M/E: 247.2 (M+H).

Synthesis of Biphenyl Intermediates

Intermediate T1

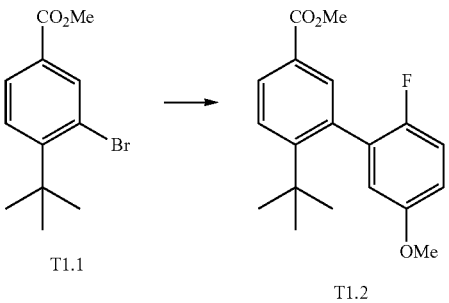 [SMILES: COC(=O)c1ccc(C(C)(C)C)c(Br)c1 ; COC(=O)c1ccc(C(C)(C)C)c(-c2cc(OC)ccc2F)c1]

T1.1          T1.2

Methyl 6-(1,1-dimethylethyl)-2'-fluoro-5'-(methyloxy)-1,1'-biphenyl-3-carboxylate (T1.2)

To a stirred solution of methyl 3-bromo-4-tert-butylbenzoate T1.2 (*Australian Journal of Chemistry* 1990, 43, 807-814) (1.00 g, 3.7 mmol) in toluene (4.00 mL, 4.0 mmol) and DMF (1.00 mL, 13.0 mmol) at 23° C. was added 2-fluoro-5-methoxyphenylboronic acid (2.50 g, 15 mmol) (commercially available from Sigma-Aldrich, St. Louis, Mo., USA) and potassium carbonate (1.50 g, 11 mmol), followed by tetrakis(triphenylphosphine)palladium (0.43 g, 0.37 mmol). The mixture was heated at 100° C. for 21 hours and then cooled to room temperature. Water (30 mL) was added to the mixture, and the mixture was extracted with EtOAc (3×50 mL). The combined organic layers were dried over MgSO$_4$ and concentrated in vacuo. The residue was then purified by flash chromatography (SiO$_2$ gel 60, eluted with 0%-10% EtOAc in hexanes) to give a clear oil (2.3 g, 99% yield). MS ESI (pos.) m/e: 339.1 (M+Na)$^+$, 334.1 (M+H$_2$O)$^+$, 317.2 (M+H)$^+$.

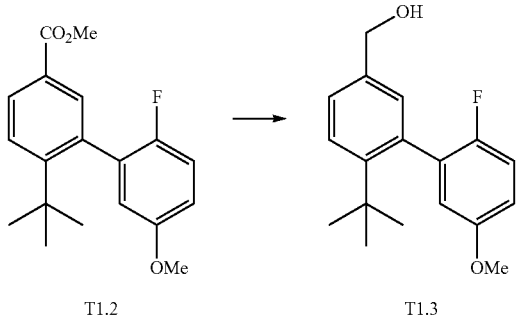 [SMILES: COC(=O)c1ccc(C(C)(C)C)c(-c2cc(OC)ccc2F)c1 ; COc1ccc(F)c(-c2cc(CO)ccc2C(C)(C)C)c1]

T1.2 → T1.3

(6-(1,1-Dimethylethyl)-2'-fluoro-5'-(methyloxy)-1,1'-biphenyl-3-yl)methanol (T1.3)

To a stirred solution of T1.2 (0.080 g, 0.3 mmol) in THF (10 mL, 3 mmol) at 0° C. was added LAH (1.0M solution in THF (0.5 mL, 0.5 mmol)). The mixture was stirred for 15 minutes. 1N NaOH (5 mL) was then added to quench the reaction, and the resulting solution was extracted with EtOAc (3×10 mL), dried over MgSO$_4$, filtered and concentrated in vacuo. The residue was then purified by flash chromatography (SiO$_2$ gel 60, eluted with 0-30% EtOAc in hexanes) to give a clear oil (0.07 g, 96% yield). $^1$H NMR (400 MHz, CDCl$_3$) δ ppm 7.57 (1H, d, J=8.2 Hz), 7.44-7.31 (1H, m), 7.04 (1H, d, J=4.0 Hz), 7.00 (1H, t, J=8.0 Hz), 6.86 (1H, m), 6.78 (1H, dd, J=5.9, 3.1 Hz), 4.68 (1H, d, J=5.9 Hz), 3.79 (3H, s), 1.63 (1H, t J=5.9 Hz), 1.23 (9H, s).

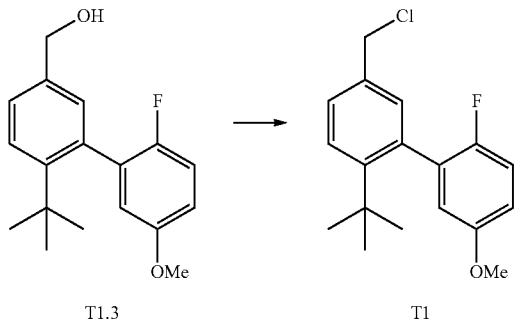 [SMILES: COc1ccc(F)c(-c2cc(CO)ccc2C(C)(C)C)c1 ; COc1ccc(F)c(-c2cc(CCl)ccc2C(C)(C)C)c1 ; "T1"]

T1.3 → T1

5-(Chloromethyl)-2-(1,1-dimethylethyl)-2'-fluoro-5'-(methyloxy)-1,1'-biphenyl (T1)

To a stirred solution of T1.3 (0.07 g, 0.2 mmol) in DCM (10 mL, 155 mmol) at 23° C. was added thionyl chloride (0.04 mL, 0.5 mmol). The resulting mixture was stirred for 16 hours and then concentrated in vacuo. The residue was purified by flash chromatography (SiO$_2$ gel 60, eluted with 0%-10% EtOAc in hexanes) to give a colorless oil (0.050 g, 67% yield). $^1$H NMR (400 MHz, CDCl$_3$) δ ppm 7.56 (1H, d, J=8.2 Hz), 7.37 (1H, dd, J=8.4, 2.2 Hz), 7.05 (1H, d, J=1.6 Hz), 7.01 (1H, t, J=9.2 Hz), 6.87 (1H, m), 6.79 (1H, dd, J=5.9, 3.1 Hz), 4.57 (2H, s), 3.80 (3H, s), 1.23 (9H, s).

Intermediate T2

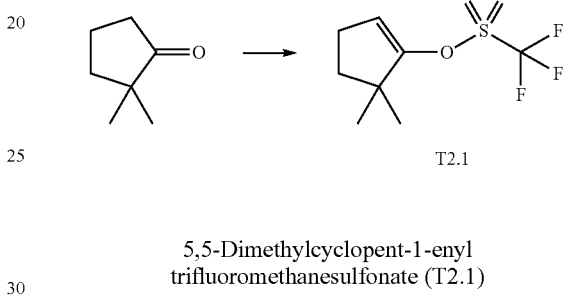

T2.1

5,5-Dimethylcyclopent-1-enyl trifluoromethanesulfonate (T2.1)

To a solution of 2,2-dimethylcyclopentanone (available from ChemSampCo)(3.00 g, 26.75 mmol) in THF (100 mL), was slowly added LDA (14.7 mL, 2.0 M, in heptane) at −78° C. The resulting mixture was stirred at −78° C. for 1 hour. A solution of N-phenyltriflimide (10.00 g, 28.00 mmol) was added to the mixture at −78° C., and the resulting mixture was stirred at 0° C. for 2 hours and then at room temperature overnight. The reaction mixture was extracted with hexane (80×2 mL). The combined organic layers were washed with saturated Na$_2$CO$_3$ (30 mL), brine (20 mL), dried with MgSO$_4$, and filtered. The solvent was removed, and the residue was purified by CombiFlash® chromatography (eluent was EtOAc and hexane) to give T2.1. $^1$H NMR (CDCl$_3$) δ 1.16 (s, 6H), 1.86 (t, J=7.1 Hz, 2H), 2.36 (t, J=7.1 Hz, 2H), 5.56 (m, 1H).

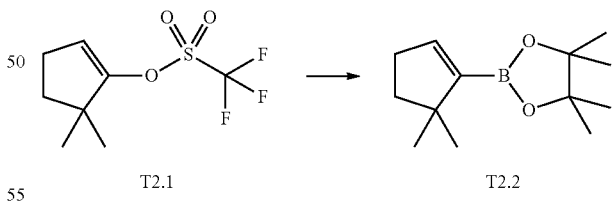

T2.1 → T2.2

2-(5,5-Dimethylcyclopent-1-enyl)-4,4,5,5-tetramethyl-1,3,2-dioxaborolane (T2.2)

PdCl$_2$(PPh$_3$)$_2$ (0.56 g, 0.80 mmol), PPh$_3$ (0.63 g, 2.40 mmol), bis(pinacolato)diboron (6.80 g, 26.75 mmol) and KOPh (fine powder, 5.30 g, 40.10 mmol) were added to a flask. The flask was flushed with nitrogen and charged with toluene (100 mL) and with T2.1 (6.53 g, 26.75 mmol). The mixture was stirred at 50° C. for 2 hours. The reaction mixture was treated with water at room temperature and extracted with benzene (60×2 mL). The organic layer was dried over MgSO$_4$. The product was then purified by CombiFlash® column chromatography to give intermediate T2.2. $^1$H NMR (CDCl$_3$) δ 1.04 (s, 6H), 1.18 (s, 12H), 1.57 (t, J=7.1 Hz, 2H), 2.29 (t, J=7.1 Hz, 2H), 6.29 (m, 1H).

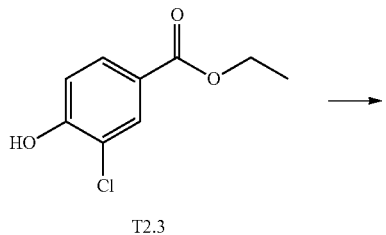

T2.3

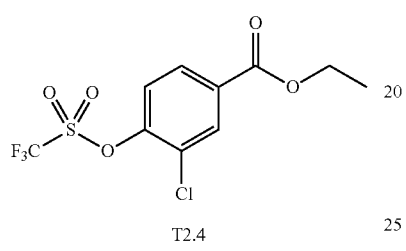

T2.4

Ethyl 3-chloro-4-(((trifluoromethyl)sulfonyl)oxy) benzoate (T2.4)

A mixture of ethyl 3-chloro-4-hydroxybenzoate (commercially available from Sigma-Aldrich, St. Louis, Mo., USA) (5.00 g, 25.0 mmol), N-phenyltriflimide (9.30 g, 26.0 mmol) and TEA (4.2 mL, 30.0 mmol) in DCM (40 mL) with a catalytic amount of DMAP, was stirred at ambient temperature overnight. DCM (150 mL) was added, and the reaction mixture was washed with brine (30×3 mL), dried over MgSO$_4$, and the solvent was removed under reduced pressure. The product T2.4 was used in the next step without further purification. MS ESI (pos.) m/e: 335.0 (M+Na)$^+$.

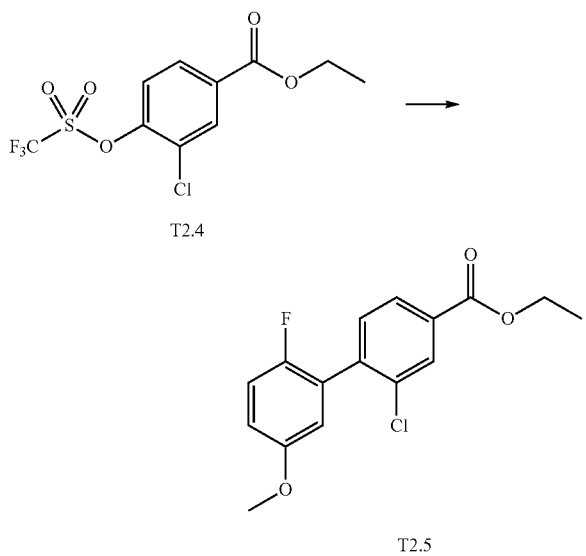

Ethyl 2-chloro-2'-fluoro-5'-(methyloxy)-1,1'-biphenyl-4-carboxylate (T2.5)

A mixture of ethyl 3-chloro-4-(trifluoromethylsulfonyloxy)benzoate T2.4 (3.00 g, 9.02 mmol), 2-fluoro-5-methoxyphenylboronic acid (commercially available from Sigma-Aldrich, St. Louis, Mo., USA) (1.84 g, 10.8 mmol), tetrakis(triphenylphosphine)palladium (0.521 g, 0.451 mmol) and potassium carbonate (2.49 g, 18.0 mmol) in DMF (20 mL), was purged with N$_2$ three times and then heated at 100° C. for 4 hours. The reaction was cooled to room temperature, and EtOAc (130 mL) was added. The mixture was then washed with brine (30×4 mL). The organic layer was dried over MgSO$_4$. The residue was purified by CombiFlash® silica gel column chromatography (eluent with hexane/EtOAc; 85/15) to give T2.5. $^1$H NMR (400 MHz, CDCl$_3$) δ ppm 8.08 (d, 1H), 7.90 (d, 1H), 7.33 (dd, 1H), 6.96-7.02 (m, 1H), 6.82-6.85 (m, 1H), 6.74 (d, 1H), 4.33 (q, 2H), 4.31 (s, 3H), 1.34 (t, 3H). MS ESI (pos.) m/e: 309.1 (M+H)$^+$.

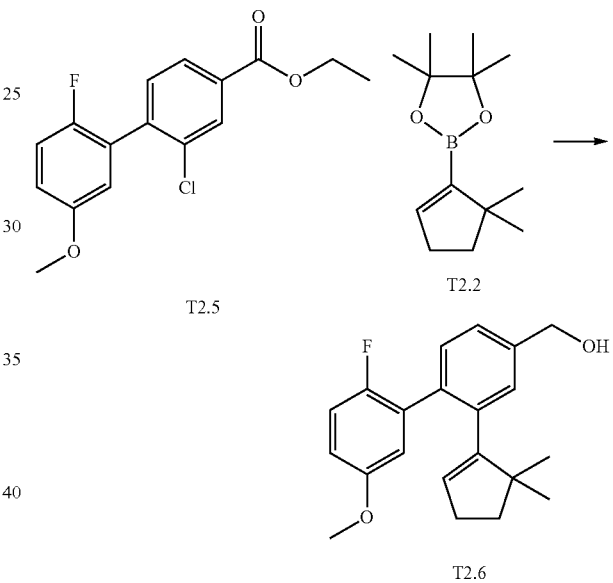

(2-(5,5-Dimethyl-1-cyclopenten-1-yl)-2'-fluoro-5'-(methyloxy)-1,1'-biphenyl-4-yl)methanol (T2.6)

A mixture of compound T2.5 (1.80 g, 5.80 mmol), 2-(5,5-dimethylcyclopent-1-enyl)-4,4,5,5-tetramethyl-1,3,2-dioxaborolane (T2.2)(1.40 g, 6.4 mmol), S-Phos (0.48 g, 1.20 mmol), tripotassium phosphate (3.10 g, 15.0 mmol) and palladium acetate (0.13 g, 0.58 mmol) in DMF (10.0 mL) and water (1.0 mL), was purged with N$_2$ three times. The resulting mixture was heated at 100° C. overnight. EtOAc (120 mL) was added, and the mixture was washed with brine (25×2 mL). The organic layer was dried with MgSO$_4$. The residue was purified by CombiFlash® silica gel column chromatography, eluting with hexane/EtOAc, 9/1 to give the Suzuki coupling product as an intermediate, ethyl 2-(5,5-dimethyl-1-cyclopenten-1-yl)-2'-fluoro-5'-(methyloxy)-1,1'-biphenyl-4-carboxylate. MS ESI (pos.) m/e: 369.1 (M+H)$^+$. To a solution of ethyl 2-(5,5-dimethyl-1-cyclopenten-1-yl)-2'-fluoro-5'-(methyloxy)-1,1'-biphenyl-4-carboxylate (1.00 g, 3.0 mmol) in THF (10.0 mL), was slowly added LAH, (1.0M solution in diethyl ether, 4.0 mL, 4.0 mmol) at 0° C. After the addition, the reaction mixture was stirred at 40° C. for 1.5 hours, and then at room temperature for 2 hours. A mixture of water (0.22 mL) in THF (2.0 mL) was slowly added and then 15% sodium hydroxide (0.22 mL) was added at 0° C. Finally, water (0.65 mL) was added at room temperature. The solid was removed by filtration, and the solvent was removed under reduced pressure. The residue was purified by CombiFlash® silica gel column chromatography, eluting with hexane/EtOAc, 90/10 to 70/30) to give the title compound T2.6. $^1$H NMR (400 MHz, CDCl$_3$) δ ppm. 7.24 (s, 2H), 7.09-7.21 (m, 1H), 6.84-6.96 (m, 1H), 6.68-6.72 (m, 2H), 5.43 (s, 1H), 4.65 (s, 2H), 3.66 (s, 3H), 2.17 (td, 2H), 1.77 (b, 1H), 1.58 (t, 2H), 0.78 (s, 6H). MS ESI (pos.) m/e: 309.1 (M−HO)$^+$, 345.2 (M+H$_3$O)$^+$.

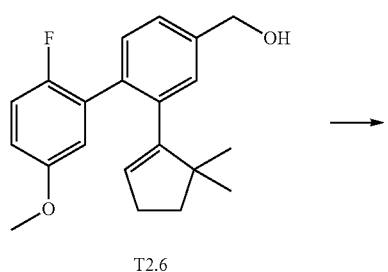

T2.6

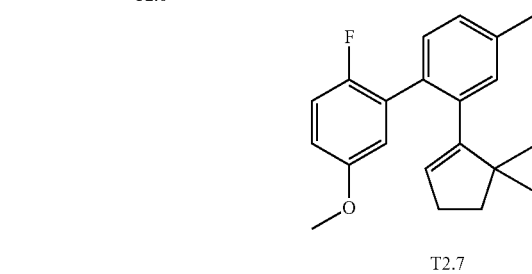

T2.7

4-(Bromomethyl)-2-(5,5-dimethyl-1-cyclopenten-1-yl)-2'-fluoro-5'-(methyloxy)-1,1'-biphenyl (T2.7)

To a solution of triphenylphosphine (0.13 g, 0.51 mmol) in DCM (1.0 mL), was slowly added bromine (0.081 g, 0.51 mmol, 0.25 mL, 2M in CCl$_4$) at 0° C. The resulting mixture was stirred at 0° C. for 15 minutes and then a mixture of compound T2.6 (0.15 g, 0.46 mmol) and anhydrous pyridine (0.041 mL, 0.51 mmol) in DCM (3.0 mL) was added to the mixture. The reaction mixture was stirred at room temperature for 2 hours. DCM (80 mL) was added, and the mixture was washed with water (20×2 mL), and dried over Na$_2$SO$_4$. The solvent was removed under reduced pressure to provide product T2.7. $^1$H NMR (400 MHz, CDCl$_3$) δ ppm. 7.16-7.29 (m, 3H), 6.88 (t, 1H), 6.72 (m, 2H), 5.45 (s, 1H), 4.46 (s, 2H), 3.68 (s, 3H), 2.16-2.19 (m, 2H), 1.59 (t, 2H), 0.78 (s, 6H).

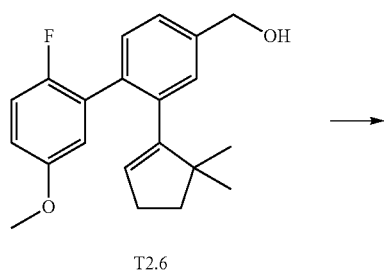

T2.6

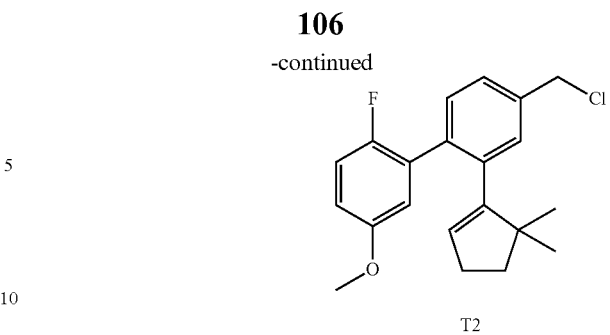

T2

4-(Chloromethyl)-2-(5,5-dimethyl-1-cyclopenten-1-yl)-2'-fluoro-5'-(methyloxy)-1,1'-biphenyl (T2)

To a solution of compound T2.6 (1.10 g, 3.37 mmol) and a catalytic amount of DMF (0.10 mL) in DCM (12.0 mL), was slowly added thionyl chloride (0.802 g, 6.74 mmol) at 0° C. After addition, the reaction mixture was stirred at room temperature for 1 hour. The solvent was removed under reduced pressure, and the resulting residue was purified by CombiFlash®® silica gel column chromatography eluting with hexane/EtOAc, 100/0 to 95/5) to give the title compound T2 (1.15 g). $^1$H NMR (400 MHz, CDCl$_3$) δ ppm. 7.32-7.39 (m, 2H), 7.28-7.29 (m. 1H), 6.88 (t, 1H), 6.80-6.82 (m, 2H), 5.56 (s, 1H), 4.66 (s, 2H), 3.78 (s, 3H), 2.27-2.29 (m, 2H), 1.69 (t, 2H), 0.89 (s, 6H).

Intermediate T3

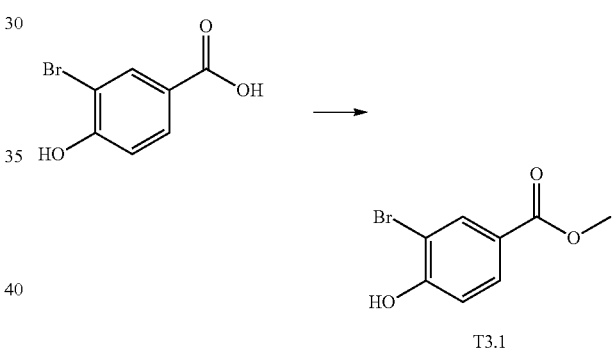

T3.1

Methyl 3-bromo-4-hydroxybenzoate (T3.1)

To a stirred solution of 3-bromo-4-hydroxybenzoic acid (available from Alfa Aesar, Avocado, Lancaster) (50.0 g, 231 mmol) in MeOH (300 mL) was added a cold solution of sulfuric acid (2.50 mL, 47 mmol). The mixture was heated to 80° C. and monitored by TLC. After 16.5 hours, the solvent was removed and the reaction mixture was diluted with EtOAc. The organic phase was washed carefully two times with saturated aqueous NaHCO$_3$, once with brine, and then dried over anhydrous sodium sulfate. After filtration, the organic solvent was removed in vacuo to yield T3.1 as a white solid (yield 100%) that was used without purification.

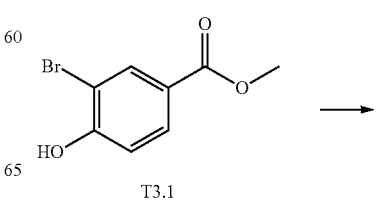

T3.1

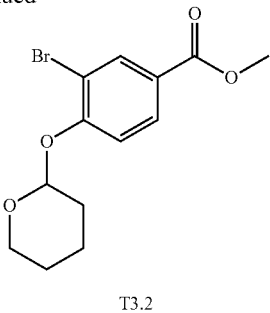

T3.2

Methyl 3-bromo-4-(tetrahydro-2H-pyran-2-yloxy) benzoate(T3.2)

To a stirred solution of T3.1 (38 g, 164 mmol) and 3,4-dihydro-2H-pyran (45 mL, 493 mmol) in DCM (355 mL,) was added 4-methylbenzenesulfonic acid hydrate (0.63 g, 3.30 mmol). The mixture was stirred at room temperature and monitored by TLC. After 2 hours, the solution was washed with a mixed aqueous solution of saturated aqueous sodium bicarbonate/brine/water (1:1:2). The aqueous layer was extracted three times with ether. After drying over anhydrous sodium sulfate and then filtering, the organic solvent was removed under reduced pressure. The residue was purified on silica gel (0-10% EtOAc in hexanes) to yield a white solid. The product was recrystallized from MeOH to provide T3.2 (yield 90%). $^1$H NMR (400 MHz, CDCl$_3$) δ 8.24 (1H, d, J=2.0 Hz), 7.93 (1H, dd, J=8.6, 2.0 Hz), 7.17 (1H, d, J=8.6 Hz), 5.62 (1H, t, J=2.5 Hz), 3.90 (3H, s), 3.83 (1H, td, J=11.1, 2.9 Hz), 3.66 (1H, m), 2.18 (1H, m), 2.04 (1H, m), 1.94 (1H, m), 1.79 (2H, m), 1.67 (1H, m).)

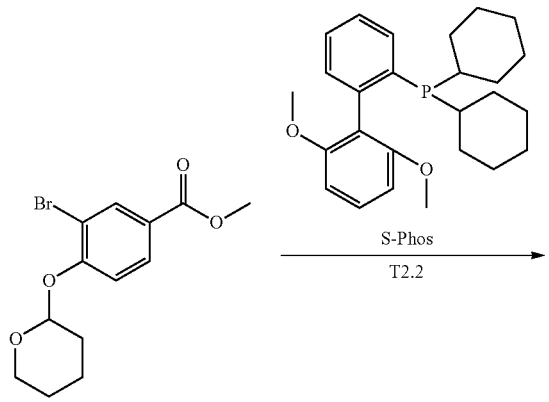

Methyl 3-(5,5-dimethylcyclopent-1-enyl)-4-(tetrahydro-2H-pyran-2-yloxy)benzoate (T3.3)

A stirred mixture of T3.2 (10.1 g, 31.9 mmol), ground S-Phos (2.62 g, 6.39 mmol), palladium acetate (0.72 g, 3.2 mmol), and potassium phosphate, tribasic (17.0 g, 80.2 mmol) in DMF (70 mL) and water (3.5 mL) was purged three times with argon and placed under vacuum three times. Before heating, 2-(5,5-dimethylcyclopent-1-enyl)-4,4,5,5-tetramethyl-1,3,2-dioxaborolane (T2.2)(8.50 g, 38.3 mmol) was added via syringe. The resulting mixture was then heated to 75° C. After 21 hours, the reaction was cooled to room temperature, diluted with water, and extracted three times with EtOAc. The organic layers were combined and washed twice with brine. After drying over anhydrous sodium sulfate and filtering, the organic solvent was removed under reduced pressure. The residue was purified on silica gel (0-20% EtOAc in hexanes) to yield T3.3 as a colorless oil that solidified (yield 80%). $^1$H NMR (400 MHz) (CDCl$_3$) δ 7.91 (1H, dd, J=8.6, 2.3 Hz), 7.74 (1H, d, J=2.3 Hz), 7.15 (1H, d, J=8.6 Hz), 5.55 (1H, t, J=2.3 Hz), 5.49 (1H, t, J=2.9 Hz), 3.88 (3H, s), 3.82 (1H, td, J=11.1, 2.9 Hz), 3.64 (1H, m), 2.43 (2H, td, J=7.0, 2.3 Hz), 1.92 (5H, m), 1.69 (1H, m), 1.61 (2H, m), 1.09 (6H, d, J=13.7 Hz).

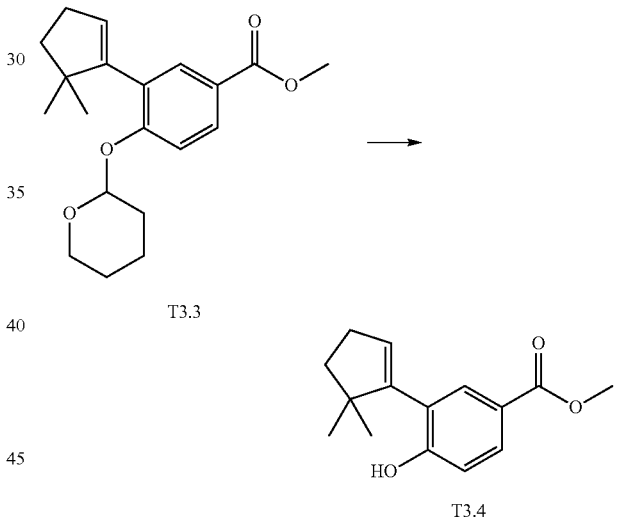

Methyl 3-(5,5-dimethylcyclopent-1-enyl)-4-hydroxybenzoate (T3.4)

To a stirred solution of T3.3 (19.0 g, 57.6 mmol) in MeOH (150 mL) was added pyridinium para-toluenesulfonate (PPTS) (1.46 g, 5.80 mmol). The mixture was heated to 50° C. and monitored with TLC. After 19 hours, the organic solvent was removed under reduced pressure and the product was then purified on silica gel (0-15% EtOAc in hexanes) to yield T3.4 as a white solid (yield 90%). $^1$H NMR (400 MHz) (CDCl$_3$) δ 7.89 (1H, dd, J=8.6, 2.0 Hz), 7.79 (1H, d, J=2.3 Hz), 6.97 (1H, d, J=8.6 Hz), 5.87 (1H, s), 5.81 (1H, t, J=2.3 Hz), 3.89 (3H, s), 2.51 (2H, td, J=7.1, 2.5 Hz), 1.94 (2H, t, J=7.0 Hz), 1.12 (6H, s).

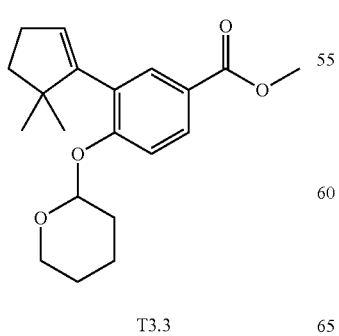

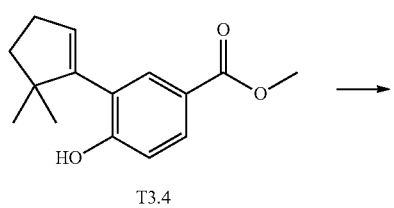

T3.4

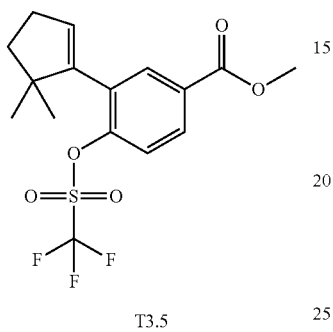

T3.5

Methyl 3-(5,5-dimethylcyclopent-1-enyl)-4-(trifluoromethylsulfonyloxy)benzoate (T3.5)

To a stirred solution of T3.4 (6.00 g, 24.4 mmol) in dry DCM (35 mL) was added TEA (6.80 mL, 48.9 mmol) and DMAP (0.30 g, 2.5 mmol). After about 20 minutes, N-phenyl bis-trifluoromethane sulfonimide (10.5 g, 29.3 mmol) was added in portion. Upon complete addition, the solution was stirred at room temperature and monitored with TLC. After 3 hours, the reaction was diluted with brine and extracted three times with DCM. After drying over anhydrous magnesium sulfate and filtering, the organic solvent was removed under reduced pressure and the product was then purified on silica gel (0-10% EtOAc in hexanes) to yield T3.5 as a colorless oil (yield 88%). $^1$H NMR (400 MHz, CDCl$_3$) δ 8.02 (1H, dd, J=8.6, 2.0 Hz), 7.94 (1H, d, J=2.0 Hz), 7.35 (1H, d, J=8.6 Hz), 5.80 (1H, t, J=2.5 Hz), 3.94 (3H, s), 2.48 (2H, td, J=7.0, 2.3 Hz), 1.91 (2H, t, J=7.0 Hz), 1.09 (6H, s).

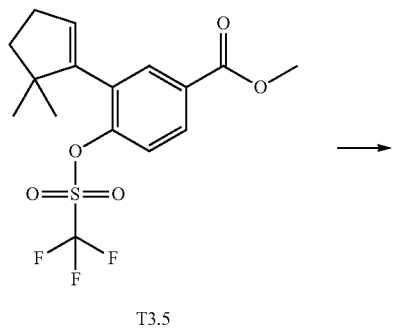

T3.5

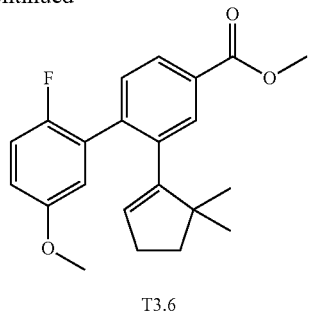

T3.6

Methyl 2-(5,5-dimethyl-1-cyclopenten-1-yl)-2'-fluoro-5'-(methyloxy)-1,1'-biphenyl-4-carboxylate (T3.6)

To a stirred solution of T3.5 (8.71 g, 23.0 mmol) in DMF (20 mL) at 23° C. was added 2-fluoro-5-methoxyphenylboronic acid (7.84 g, 46.1 mmol) (commercially available from Sigma-Aldrich, St. Louis, Mo., USA) and potassium carbonate (9.56 g, 69.1 mmol) followed by tetrakis(triphenylphosphine)palladium (0) (2.67 g, 2.31 mmol). The mixture was heated to 90° C. After 15 hours, LCMS-showed that the reaction was complete. The mixture was then cooled to room temperature and diluted with water. After extracting three times with EtOAc, the mixture was concentrated in vacuo and then purified on silica gel (0%-10% EtOAc/hexane) to give T3.6 as a clear oil that solidified (yield 91%). $^1$H NMR (400 MHz, CDCl$_3$) δ 7.98 (1H, dd, J=8.0, 1.8 Hz), 7.91 (1H, d, J=2.0 Hz), 7.40 (1H, d, J=7.8 Hz), 6.98 (1H, t, J=8.8 Hz), 6.85 (2H, m), 5.55 (1H, s), 3.95 (3H, s), 3.77 (3H, s), 2.27 (2H, td, J=7.0, 2.7 Hz), 1.68 (2H, t, J=7.0 Hz), 0.87 (6H, s).

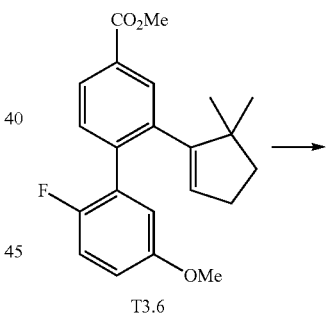

T3.6

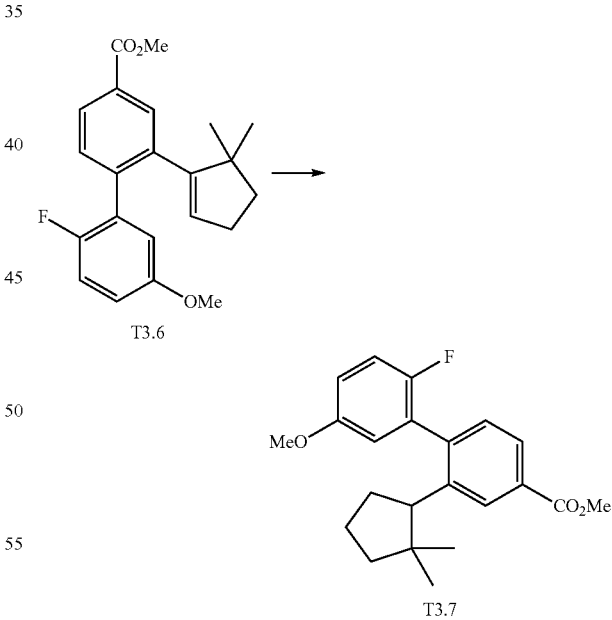

T3.7

Methyl 2-(2,2-dimethylcyclopentyl)-2'-fluoro-5'-(methyloxy)-1,1'-biphenyl-4-carboxylate (T3.7)

To a stirred solution of T3.6 (0.660 g, 1.86 mmol) in MeOH (20.00 mL, 1.86 mmol) at 23° C. was added Pd/C (0.0198 g, 0.186 mmol). The resulting mixture was stirred under an atmosphere of hydrogen (0.00375 g, 1.86 mmol) for 16 hours.

The reaction mixture was then filtered and concentrated in vacuo to give T3.7 as a clear oil (0.600 g, 90.4% yield).

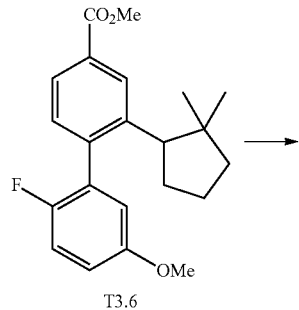

T3.6

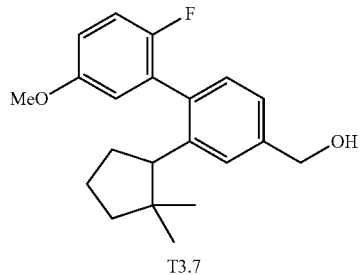

T3.7

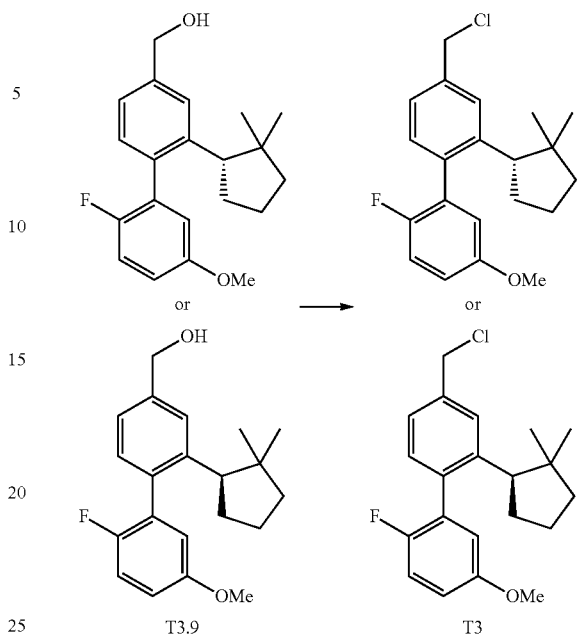

T3.9    T3

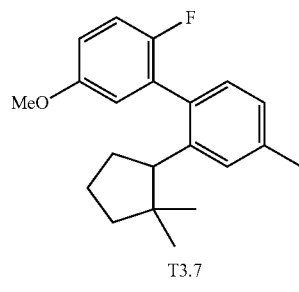

T3.7

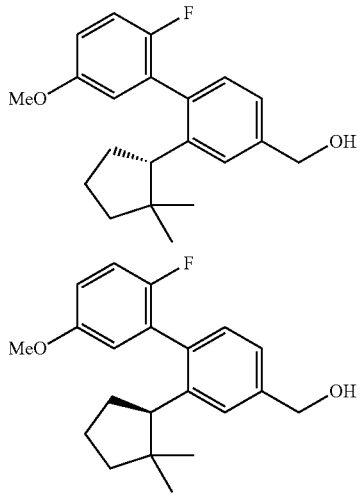

T3.8 and T3.9

(2-((1S)-2,2-Dimethylcyclopentyl)-2'-fluoro-5'-(methyloxy)-1,1'-biphenyl-4-yl)methanol and (2-((1R)-2,2-dimethylcyclopentyl)-2'-fluoro-5'-(methyloxy)-1,1'-biphenyl-4-yl)methanol (T3.8 and T3.9)

To a stirred solution of T3.6 (0.500 g, 1.4 mmol) in THF (7.0 mL, 1.4 mmol) at 0° C. was added LAH (1.4 mL, 1.4 mmol). After addition, the reaction was stirred for 1.5 hours. 1N NaOH (aq) was then added to quench the reaction, and the mixture was extracted with EtOAc. The organic layers were dried over magnesium sulfate, filtered, and concentrated in vacuo. The resulting product was then purified on silica gel (0%-20% EtOAc/hexane) to give T3.7 (0.442 g, 96% yield). Chiral separation of T3.7 was accomplished on a CHIRAL-CEL® OD column (3% IPA in hexane) to provide T3.8 and T3.9. Both enantiomers were used to synthesize example compounds, and both enantiomers gave active example compounds. However, the enantiomer corresponding to peak 2 provided the most active example compounds. Analytical column (CHIRALCEL® OD column (2% IPA in hexane, 45 min run) Peak 1-15.5 mins, Peak 2-38.0 mins).[1]

4-(Chloromethyl)-2-((1S)-2,2-dimethylcyclopentyl)-2'-fluoro-5'-(methyloxy)-1,1'-biphenyl or 4-(chloromethyl)-2-((1R)-2,2-dimethylcyclopentyl)-2'-fluoro-5'-(methyloxy)-1,1'-biphenyl T3

Thionyl chloride (1.5 mL, 20 mmol) was added to a stirred solution of T3.9 (3.280 g, 10.0 mmol) (derived from peak two from the chiral separation of T3.7) in DCM (100 mL, 10.0 mmol) and DMF (0.77 mL, 10.0 mmol) at 0° C. Stirring was continued at room temperature for 2 hours. The reaction mixture was then concentrated in vacuo and purified on silica gel (0-10% EtOAc in hexane) to give the desired product T3 (3.00 g, 87% yield) as a clear oil.

Intermediate T4

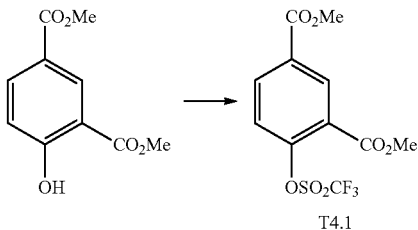

T4.1

Dimethyl 4-(trifluoromethylsulfonyloxy)isophthalate (T4.1)

To a stirred solution of dimethyl 4-hydroxyisophthalate (commercially available from Chem Service)(37.7 g, 179 mmol) in DCM (256 mL, 179 mmol) at 23° C. was added TEA (30 mL, 215 mmol), and a catalytic amount of DMAP. N-phenyltriflimide (70 g, 197 mmol) was then added to the mixture and the mixture was stirred at room temperature for 21 hours. The solvent was removed, and the residue was purified on silica gel (0-10% EtOAc in hexanes) to yield T4.1 dimethyl 4-(trifluoromethylsulfonyloxy)isophthalate as a colorless oil (59.00 g, 96% yield). MS ESI (pos.) m/e: 360.0 $(M+H_2O)^+$, 343.0 $(M+H)^+$.

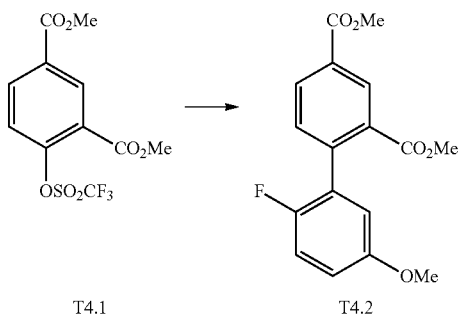

T4.1 → T4.2

Dimethyl 2'-fluoro-5'-(methyloxy)-1,1'-biphenyl-2,4-dicarboxylate (T4.2)

To a stirred solution of dimethyl 4-(trifluoromethylsulfonyloxy)isophthalate T4.1 (39.00 g, 114 mmol) in DMF (228 mL, 114 mmol) at 23° C. was added 2-fluoro-5-methoxyphenylboronic acid (29 g, 171 mmol) (commercially available from Sigma-Aldrich, St. Louis, Mo., USA), and potassium carbonate (47 g, 342 mmol), followed by tetrakis(triphenylphosphine)palladium (9.2 g, 8.0 mmol). The mixture was heated to 90° C. and stirred for 18 hours. The reaction was cooled to room temperature. Water was then added to the reaction, and the resulting mixture was extracted with EtOAc. The combined organic layers were dried over MgSO$_4$, and concentrated. The crude product was purified by silica gel flash chromatography (0-20% EtOAc/hexane) to afford dimethyl 2'-fluoro-5'-(methyloxy)-1,1'-biphenyl-2,4-dicarboxylate T4.2 as a clear oil (32.00 g, 88% yield). MS ESI (pos.) m/e: 319.1 $(M+H)^+$.

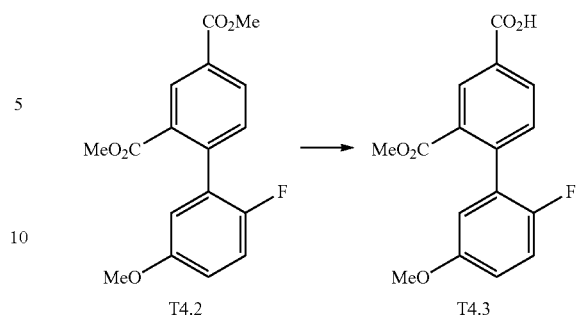

T4.2 → T4.3

2'-Fluoro-5'-(methyloxy)-2-((methyloxy)carbonyl)-1,1'-biphenyl-4-carboxylic acid (T4.3)

To a stirred solution of T4.2 (36.50 g, 115 mmol) in THF (70.0 mL, 854 mmol) and MeOH (70.0 mL, 1730 mmol) at 0° C. was added potassium hydroxide (63 mL, 126 mmol) slowly to maintain the temperature below 6° C. The reaction mixture was allowed to warm to room temperature and was stirred for 15 hours. The reaction mixture was concentrated in vacuo. 1N HCl was added to the aqueous phase, and the resulting mixture was extracted with EtOAc. The combined organic layers were dried over MgSO$_4$, and concentrated in vacuo to give 2'-fluoro-5'-(methyloxy)-2-((methyloxy)carbonyl)-1,1'-biphenyl-4-carboxylic acid T4.3 as a white solid (35.00 g, 100% yield). MS ESI (pos.) m/e: 322.1 $(M+H_2O)^+$, 305.0 $(M+H)^+$.

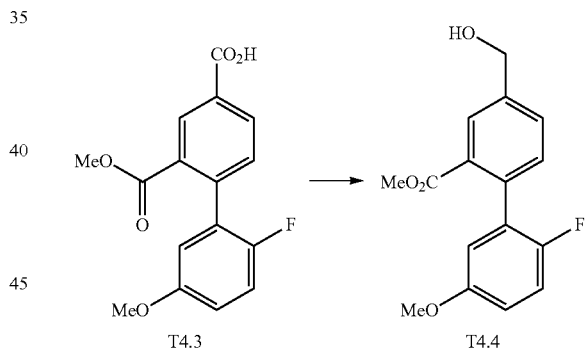

T4.3 → T4.4

Methyl 2'-fluoro-4-(hydroxymethyl)-5'-(methyloxy)-1,1'-biphenyl-2-carboxylate (T4.4)

To a stirred solution of 2'-fluoro-5'-(methyloxy)-2-((methyloxy)carbonyl)-1,1'-biphenyl-4-carboxylic acid T4.3 (35.60 g, 117 mmol) in THF (1170 mL, 117 mmol) at 0° C. was added borane-THF (234 mL, 234 mmol). The reaction was warmed to 23° C., and the mixture was stirred for 6 hours. The mixture was then concentrated in vacuo. 1 N HCl was added, and the mixture was extracted with EtOAc. The organic layers were combined, dried over MgSO$_4$, filtered, and concentrated in vacuo. The residue was purified on silica gel (0-40% EtOAc in hexane) to give methyl 2'-fluoro-4-(hydroxymethyl)-5'-(methyloxy)-1,1'-biphenyl-2-carboxylate T4.4 as a clear oil (30.00 g, 88% yield). MS ESI (pos.) m/e: 308.0 $(M+H_2O)^+$, 291.1 $(M+H)^+$.

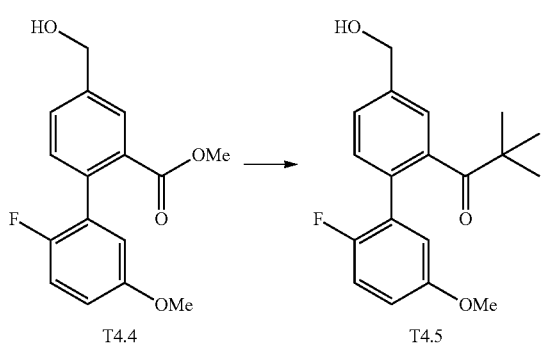 [SMILES: COC(=O)c1cc(CO)ccc1-c1cc(OC)ccc1F ; COc1ccc(F)c(-c2ccc(CO)cc2C(=O)C(C)(C)C)c1]

1-(2'-Fluoro-4-(hydroxymethyl)-5'-(methyloxy)-1,1'-biphenyl-2-yl)-2,2-dimethyl-1-propanone (T4.5)

To a stirred solution of methyl 2'-fluoro-4-(hydroxymethyl)-5'-(methyloxy)-1,1'-biphenyl-2-carboxylate T4.4 (2.00 g, 7 mmol) in THF (138 mL, 7 mmol) at −78° C. was added t-butyllithium (1.7M in pentane, 9 mL, 14 mmol). The resulting mixture was then stirred for 3 hours. A saturated solution of ammonium chloride was added, to quench the reaction, and the resulting mixture was extracted with EtOAc. The combined organic layers were dried over MgSO$_4$, filtered, and concentrated in vacuo. The residue was purified by silica gel flash chromatography (0-20% EtOAc/hexane) to afford 1-(2'-fluoro-4-(hydroxymethyl)-5'-(methyloxy)-1,1'-biphenyl-2-yl)-2,2-dimethyl-1-propanone T4.5 as a clear oil (2.00 g, 92% yield). MS ESI (pos.) m/e: 334.1 (M+H$_2$O)$^+$, 317.2 (M+H)$^+$.

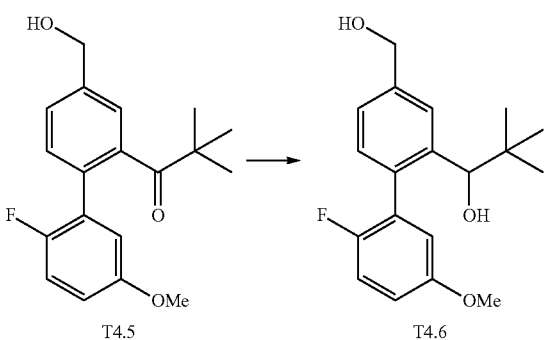

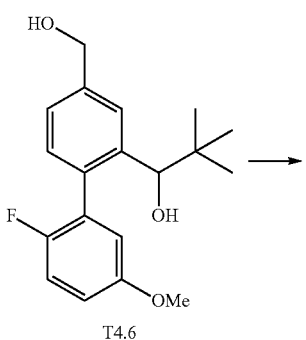

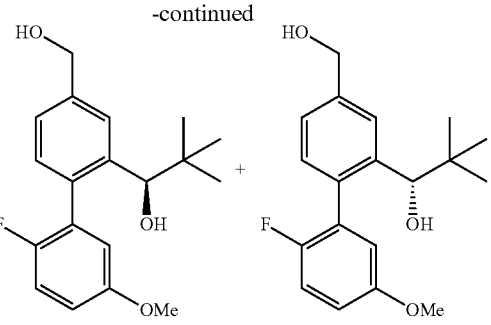

(1R)-1-(2'-Fluoro-4-(hydroxymethyl)-5'-(methyloxy)-1,1'-biphenyl-2-yl)-2,2-dimethyl-1-propanol and (1S)-1-(2'-fluoro-4-(hydroxymethyl)-5'-(methyloxy)-1,1'-biphenyl-2-yl)-2,2-dimethyl-1-propanol (T4.7 and T4.8)

To a stirred solution of 1-(2'-fluoro-4-(hydroxymethyl)-5'-(methyloxy)-1,1'-biphenyl-2-yl)-2,2-dimethyl-1-propanone T4.5 (2.00 g, 6.3 mmol) in THF (63 mL, 6.3 mmol) at 0° C. was added LAH (1.0 M in THF, 13 mL, 13 mmol). The reaction was then stirred for 2 hours. 1N NaOH (aq) was added to the mixture, and the resulting mixture was extracted with EtOAc. The organic layers were combined, dried over MgSO$_4$, filtered, and concentrated in vacuo. The residue was purified by silica gel flash chromatography (0-30% EtOAc/hexane) to afford 1-(2'-fluoro-4-(hydroxymethyl)-5'-(methyloxy)-1,1'-biphenyl-2-yl)-2,2-dimethyl-1-propanol T4.6 (1.50 g, 75% yield) as a white solid. MS ESI (pos.) m/e: 336.2 (M+H$_2$O)$^+$. Chiral separation of T.4.6 was accomplished on a CHIRALCEL® OD column (4% IPA in hexane) to provide T4.7 and T4.8. Both enantiomers were used to synthesize example compounds, and both enantiomers gave active example compounds. However, the enantiomer corresponding to peak 2 (T4.8) provided the most active example compounds. Analytical column (CHIRALCEL® OD column (4% IPA in hexane, 45 min run) Peak 1-18.5 mins, Peak 2-24.5 mins).[1]

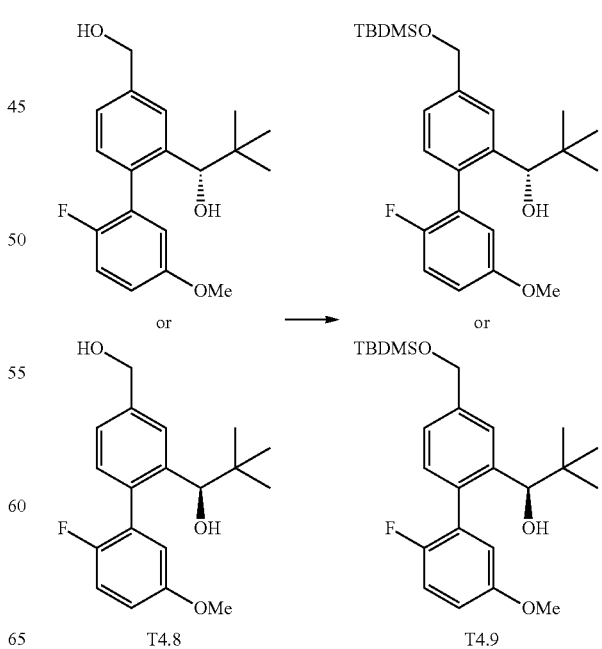

(1S)-1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanol or (1R)-1-(4-((((1,1-dimethylethyl)(dimethyl)silyl)oxy)methyl)-2'-fluoro-5'-(methyloxy)-1,1'-biphenyl-2-yl)-2,2-dimethyl-1-propanol (T4.9)

To a stirred solution of T4.9 (0.300 g, 0.9 mmol) (peak two from the chiral separation of T4.6) in DCM (10.00 mL, 155 mmol) at 23° C. was added tert-butyldimethylsilyl chloride (0.2 mL, 1 mmol), followed by TEA (0.2 mL, 1 mmol) and DMAP (0.01 g, 0.09 mmol). The resulting mixture was stirred for 16 hours. The mixture was then concentrated in vacuo to give a residue which was purified by silica gel flash chromatography (0-10% EtOAc/hexane) to afford T4.9 (0.375 g, 92% yield). MS ESI (pos.) m/e: 450.2 (M+H$_2$O)$^+$.

hours. Water was added to the mixture, and the resulting mixture was extracted with EtOAc, dried over MgSO$_4$, filtered, and concentrated in vacuo. The residue thus obtained was purified by silica gel flash chromatography (0-5% EtOAc/hexane) to afford T4.10 (0.051 g, 45% yield).

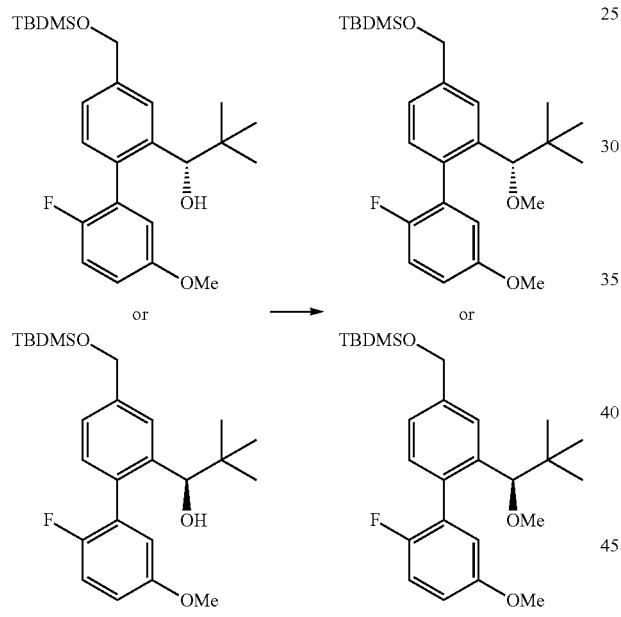

(1,1-Dimethylethyl)(((2-((1S)-2,2-dimethyl-1-(methyloxy)propyl)-2'-fluoro-5'-(methyloxy)-1,1'-biphenyl-4-yl)methyl)oxy)dimethylsilane or (1,1-dimethylethyl)(((2-((1R)-2,2-dimethyl-1-(methyloxy)propyl)-2'-fluoro-5'-(methyloxy)-1,1'-biphenyl-4-yl)methyl)oxy)dimethylsilane (T4.10)

To a stirred solution of T4.9 (0.110 g, 0.25 mmol) in DMF (2.00 mL, 26 mmol) at 23° C. was added iodomethane (0.069 g, 0.50 mmol), followed by sodium hydride (0.012 g, 0.50 mmol). The resulting mixture was stirred at 50° C. for 21

4-(Chloromethyl)-2-((1S)-2,2-dimethyl-1-(methyloxy)propyl)-2'-fluoro-5'-(methyloxy)-1,1'-biphenyl or 4-(chloromethyl)-2-((1R)-2,2-dimethyl-1-(methyloxy)propyl)-2'-fluoro-5'-(methyloxy)-1,1'-biphenyl (T4)

To a stirred solution of T4.10 (0.082 g, 0.18 mmol) in DCM (2.00 mL, 31 mmol) at 23° C. was added DMF (0.0014 mL, 0.018 mmol) followed by thionyl chloride (0.027 mL, 0.37 mmol). The resulting mixture was stirred for one hour and then concentrated in vacuo. The residue was purified by silica gel flash chromatography (0-5% EtOAc/hexane) to afford T4 (0.063 g, 98% yield).

Asymmetric Synthesis of T4.7 or T4.8

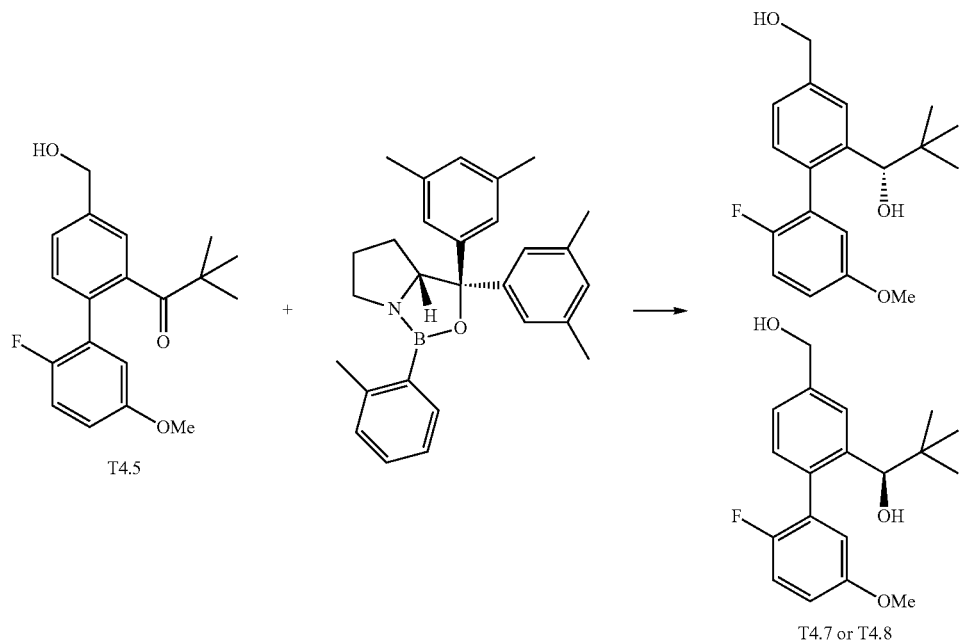

T4.5 → T4.7 or T4.8

(1R)-1-(2'-Fluoro-4-(hydroxymethyl)-5'-(methyloxy)-1,1'-biphenyl-2-yl)-2,2-dimethyl-1-propanol or (1S)-1-(2'-fluoro-4-(hydroxymethyl)-5'-(methyloxy)-1,1'-biphenyl-2-yl)-2,2-dimethyl-1-propanol (T4.7 or T4.8)

To a stirred solution of T4.5 (0.050 g, 0.2 mmol) in THF (2 mL, 0.2 mmol) at 0° C. was added (R)-3,3-bis(3,5-dimethylphenyl)-1-o-tolyl-hexahydropyrrolo[1,2-c][1,3,2]oxazaborole in toluene (0.02 mL, 0.02 mmol, 1.0 M, commercially available from Sigma-Aldrich, St. Louis, Mo., USA), followed by dropwise addition of borane in THF (0.2 mL, 0.2 mmol). The reaction was then stirred at 23° C. for 4 hours. The reaction was quenched with 1N HCl (aq) and extracted with EtOAc. The combined organic layers were dried over MgSO$_4$, filtered, and concentrated in vacuo. The residue was purified on silica gel (0%-20% EtOAc/hexane) to yield T4.7 or T4.8 (0.045 g, 89% yield). Chiral HPLC determined that the major product was the desired more potent enantiomer with an enantiomeric excess of 85%.

Intermediate T5

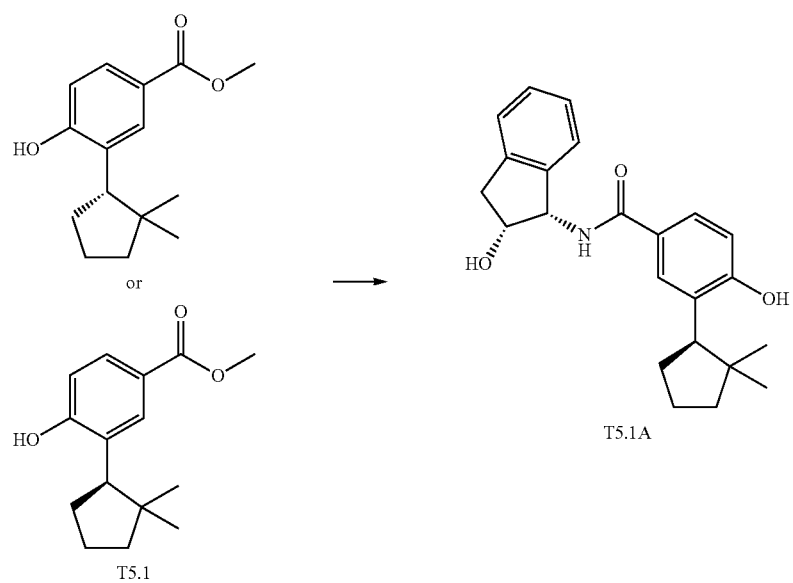 [SMILES: COC(=O)c1ccc(O)c([C@@H]2CCCC2(C)C)c1 ; COC(=O)c1ccc(O)c([C@H]2CCCC2(C)C)c1 ; CC1(C)CCC[C@H]1c1cc(C(=O)N[C@H]2c3ccccc3C[C@H]2O)ccc1O]

T5.1 → T5.1A

3-((R)-2,2-Dimethylcyclopentyl)-4-hydroxy-N-((1S,2R)-2-hydroxy-2,3-dihydro-1H-inden-1-yl)benzamide (T5.1A)

Intermediate T5.1 was synthesized by a method analogous to that described for compound T7.12. Since the absolute configuration of intermediate 5.1 was initially unknown, it was derivatized with (1S,2R)-1-amino-2-indanol (commercially available from Sigma-Aldrich, St. Louis, Mo.) to obtain the amide. A single crystal was obtained by slow recrystallization from a EtOAc/hexanes mixture and subjected to x-ray crystallographic structural determination. The crystal structure of intermediate T5.1A established that intermediate T5.1 is in the R configuration at the chiral center in the cyclopentyl ring.

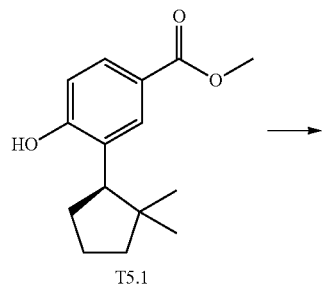

T5.1

(R)-Methyl 3-(2,2-dimethylcyclopentyl)-4-(trifluoromethylsulfonyloxy)benzoate (T5.2)

DMAP (220 mg, 1804 μmol) was added to a flask containing (R)-methyl 3-(2,2-dimethylcyclopentyl)-4-hydroxybenzoate (T5.1) (8960 mg, 36083 μmol). The flask was flushed with nitrogen and DCM (87 mL, 36083 μmol) was added, followed by addition of TEA (7.5 mL, 54124 μmol). After 15 minutes, PhN(Tf)2 (14180 mg, 39691 μmol) (commercially available from Sigma-Aldrich, St. Louis, Mo., USA) was added. The reaction was stirred overnight and concentrated. Silica gel chromatography with EtOAc and hexanes as eluent afforded 13.7 g of T5.2 (100%).

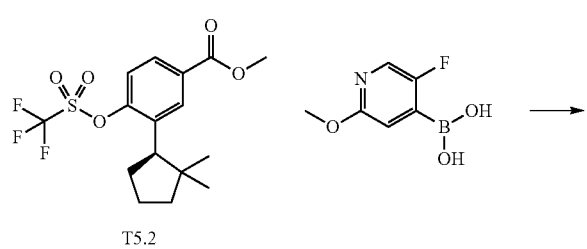

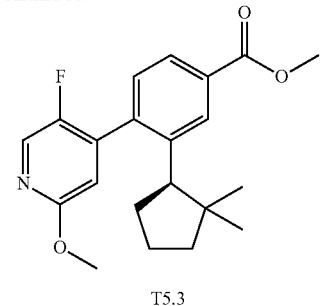

T5.3

Methyl 3-((R)-2,2-dimethylcyclopentyl)-4-(5-fluoro-2-methoxypyridin-4-yl)benzoate (T5.3)

To a flask with T5.2 (14.7 g, 38.6 mmol), was added 5-fluoro-2-methoxypyridin-4-ylboronic acid (12.7 g, 74.3 mmol, commercially available from Asymchem), potassium carbonate (15.6 g, 113 mmol), and Pd(PPh$_3$)$_4$ (4.36 g, 3.77 mmol). The flask was flushed with nitrogen. Degassed DMF (106 mL) was then added. The reaction was heated overnight and partitioned between EtOAc and water. Silica gel chromatography with EtOAc and hexanes as eluents afforded 13.75 g of T5.3 (100%). MS ESI (pos.) m/e: 358.1 (M+H)$^+$.

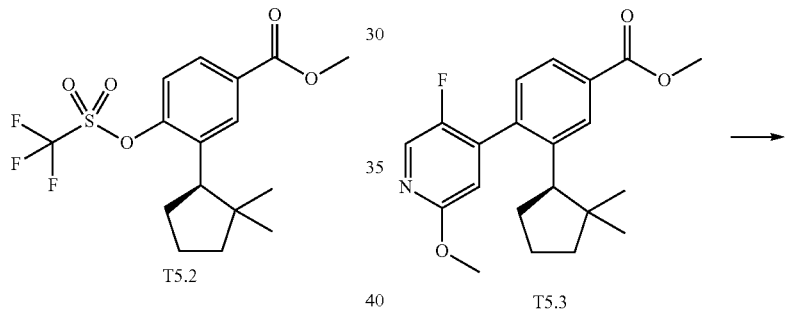

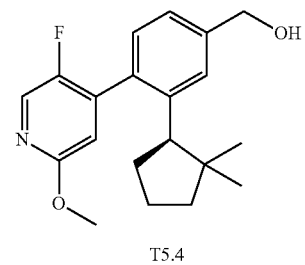

T5.4

(3-((R)-2,2-Dimethylcyclopentyl)-4-(5-fluoro-2-methoxypyridin-4-yl)phenyl)methanol (T5.4)

To a flask containing T5.3 (14290 mg, 40 mmol) was added 200 mL anhydrous THF. The reaction vessel was then immersed in an ice-bath. LAH (60 mL, 60 mmol, 1 M solution in THF) (commercially available from Sigma-Aldrich, St. Louis, Mo., USA) was added slowly. The flask was kept in the ice-bath and the temperature of the bath was allowed to rise on its own. After 1.5 hours, the reaction was quenched with 1N NaOH, and water was added. The reaction mixture was then extracted with EtOAc and purified by silica gel chromatography with EtOAc/hexanes gradient elution to afford 12 g of T5.4 (91%) as a colorless oil. MS ESI (pos.) m/e: 330.1 (M+H)$^+$.

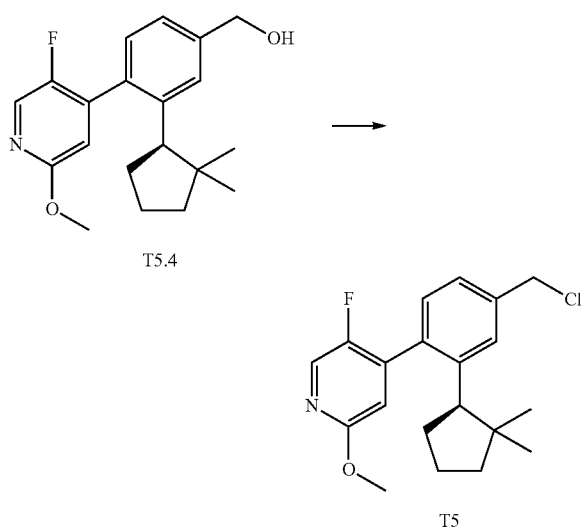

T5.4

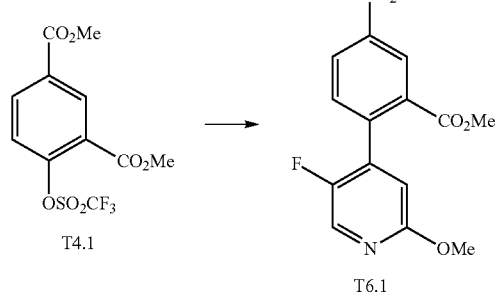

T5

4-(4-(Chloromethyl)-2-((R)-2,2-dimethylcyclopentyl)phenyl)-5-fluoro-2-methoxypyridine (T5)

To a flask containing T5.4 (10.7 g, 32 mmol) was added 160 mL of DCM. The resulting mixture was cooled in an ice-bath. Thionyl chloride (4.60 mL, 63 mmol) and DMF (0.5 mL, 6 mmol) were then added, and the mixture was stirred at room temperature for 1 hour. The reaction was concentrated and diluted with EtOAc. The resulting mixture was washed with NaHCO$_3$, brine, and the process repeated until the pH of the aqueous mixture was around 6. Silica gel chromatography with EtOAc/hexanes gradient elution afforded 9.44 g of the desired chloride T5 (84%). MS ESI (pos.) m/e: 348.1 (M+H)$^+$.

Intermediate T6

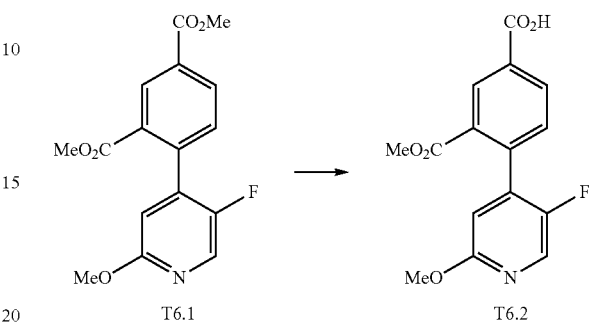

Dimethyl 4-(5-fluoro-2-(methyloxy)-4-pyridinyl)-1,3-benzenedicarboxylate (T6.1)

To a stirred solution of T4.1 (1.00 g, 2.9 mmol) in DMF (12 mL) at 23° C. was added 5-fluoro-2-methoxypyridin-4-ylboronic acid (0.75 g, 4.4 mmol, commercially available from Asymchem), potassium carbonate (1.2 g, 8.8 mmol), and tetrakis(triphenylphosphine)palladium (0.24 g, 0.20 mmol). The mixture was heated to 90° C. and stirred for 17 hours. The mixture was then cooled to room temperature, diluted with brine and extracted three times with EtOAc. The combined organic layers were dried over anhydrous magnesium sulfate, filtered, and the organic solvent was removed under reduced pressure. The resulting residue was purified on silica gel (0-30% EtOAc in hexanes) to yield T6.1 as a colorless solid (0.860 g, 92% yield).

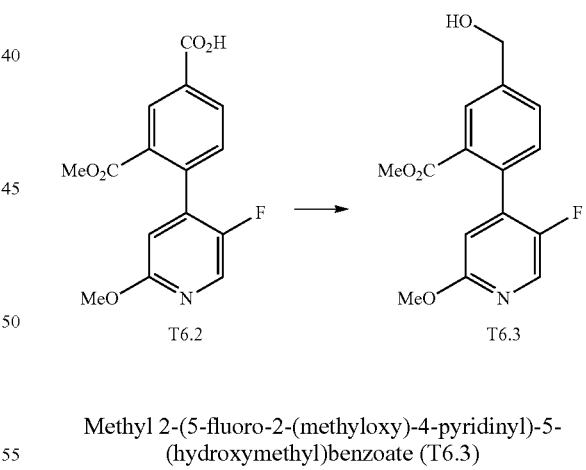

4-(5-Fluoro-2-(methyloxy)-4-pyridinyl)-3-((methyloxy)carbonyl)benzoic acid (T6.2)

To a stirred solution of T6.1 (0.860 g, 2.7 mmol) in THF (7.00 mL) and MeOH (7.00 mL) at 0° C. was added potassium hydroxide (1.5 mL, 3.0 mmol) slowly maintaining the temperature below 6° C. The reaction mixture was allowed to warm to room temperature and stirred for 17 hours. The reaction was next acidified with 1N HCl and extracted three times with EtOAc. The organic layers were combined, dried over anhydrous MgSO$_4$, and filtered. The organic solvent was then removed under reduced pressure to yield T6.2 as a colorless solid (0.82 g, 100% yield).

Methyl 2-(5-fluoro-2-(methyloxy)-4-pyridinyl)-5-(hydroxymethyl)benzoate (T6.3)

To a stirred solution of 4-(5-fluoro-2-methoxypyridin-4-yl)-3-(methoxycarbonyl)benzoic acid T6.2 (0.416 g, 1 mmol) in THF (14 mL) at 0° C. was added borane-THF (3 mL, 3 mmol, 1.0M). The reaction was warmed to 23° C. and stirred for 46 hours. The reaction was then concentrated in vacuo, diluted with 1N HCl and extracted three times with EtOAc. The organic layers were combined, dried over anhydrous MgSO$_4$, and filtered. The organic solvent was removed under reduced pressure, and the product was purified on silica gel (0-40% EtOAc in hexanes) to yield T6.3 as a colorless solid (0.307 g, 77% yield).

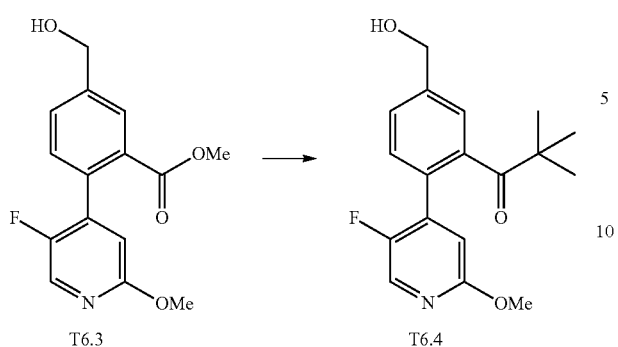
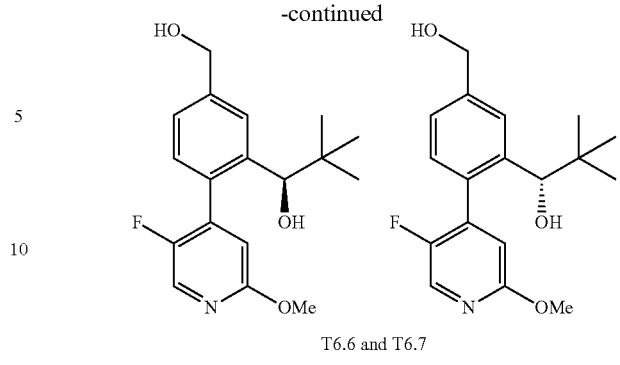

1-(2-(5-Fluoro-2-(methyloxy)-4-pyridinyl)-5-(hydroxymethyl)phenyl)-2,2-dimethyl-1-propanone (T6.4)

To a stirred solution of methyl 2-(5-fluoro-2-methoxypyridin-4-yl)-5-(hydroxymethyl)benzoate T6.3 (0.307 g, 1 mmol) in THF (11 mL) at −78° C. was added tert-butyl lithium (2 mL, 3 mmol). The resulting mixture was stirred for one hour. The reaction was then quenched with a saturated solution of ammonium chloride and extracted three times with EtOAc. The combined organic layers were dried over anhydrous magnesium sulfate, filtered, and the organic solvent was removed under reduced pressure. The residue was then purified on silica gel (0-40% EtOAc in hexanes) to yield T6.4 as a colorless solid (0.28 g, 84% yield).

(1R)-1-(2-(5-Fluoro-2-methoxypyridin-4-yl)-5-(hydroxymethyl)phenyl)-2,2-dimethylpropan-1-ol or (1S)-1-(2-(5-fluoro-2-methoxypyridin-4-yl)-5-(hydroxymethyl)phenyl)-2,2-dimethylpropan-1-ol (T6.6 and T6.7)

To a stirred solution of 1-(2-(5-fluoro-2-methoxypyridin-4-yl)-5-(hydroxymethyl)phenyl)-2,2-dimethylpropan-1-one T6.4 (0.130 g, 0.4 mmol) in THF (2 mL) at 0° C. was added LAH (0.6 mL, 0.6 mmol, 1.0M). The resulting mixture was stirred for 3 hours. Next, 1N NaOH(aq) was added to quench the reaction mixture. The reaction was extracted three times with EtOAc. The organic layers were combined, dried over MgSO$_4$, filtered, and the organic solvent was removed under reduced pressure. The residue was then purified on silica gel (0-20% EtOAc in hexanes) to yield T6.5 as a colorless solid (0.120 g, 92% yield). Chiral separation of T6.5 was accomplished on a CHIRALCEL® OD column (4% IPA in hexane) to provide T6.6 (peak one-23.87 mins) and T6.7 (peak two-29.04 mins). Both enantiomers were used to synthesize example compounds, and both enantiomers gave active example compounds. However, the enantiomer corresponding to peak 2 provided the most active example compounds.[1]

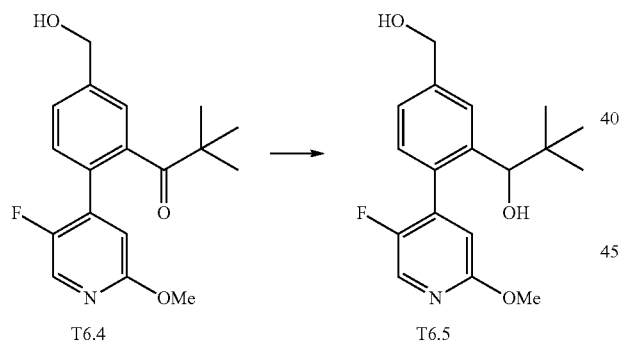
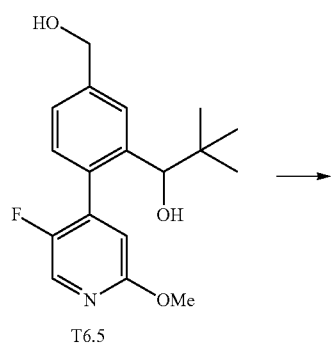
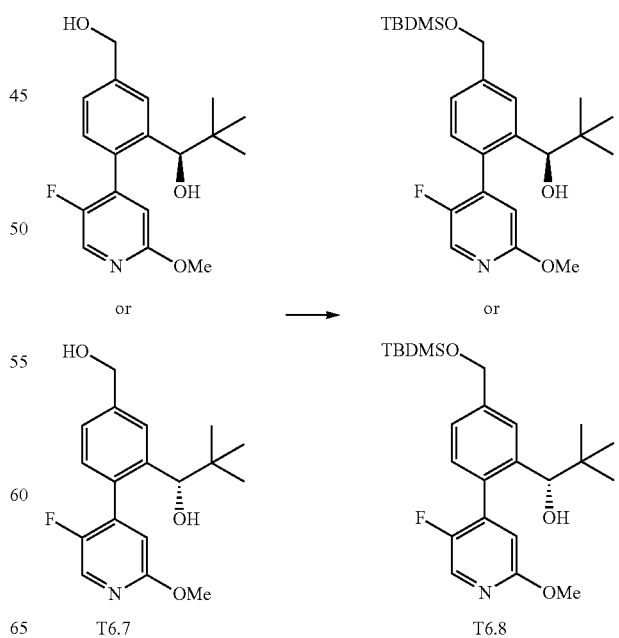

(1R)-1-(5-((((1,1-Dimethylethyl)(dimethyl)silyl)oxy)methyl)-2-(5-fluoro-2-(methyloxy)-4-pyridinyl)phenyl)-2,2-dimethyl-1-propanol or (1S)-1-(5-((((1,1-dimethylethyl)(dimethyl)silyl)oxy)methyl)-2-(5-fluoro-2-(methyloxy)-4-pyridinyl)phenyl)-2,2-dimethyl-1-propanol (T6.8)

To a stirred solution of T6.7 (0.050 g, 0.2 mmol) (from peak two from the chiral separation of T6.5) in DCM (2 mL) at 23° C. was added tert-butyldimethylsilyl chloride (0.03 mL, 0.2 mmol), followed by TEA (0.03 mL, 0.2 mmol) and DMAP (0.002 g, 0.02 mmol). The resulting mixture was stirred for 24 hours and then concentrated in vacuo. The reaction was extracted three times with EtOAc. The combined organic layers were dried over anhydrous MgSO$_4$ and filtered. The organic solvent was removed under reduced pressure and the product was then purified on silica gel (0-20% EtOAc in hexanes) to yield T6.8 as a colorless oil (0.062 g, 91% yield).

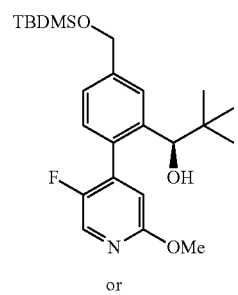
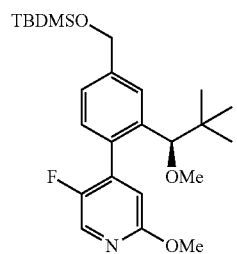

or

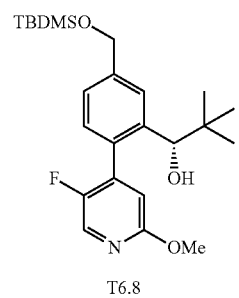
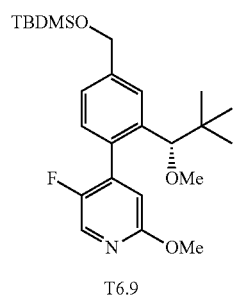

T6.8      T6.9

4-(4-((((1,1-Dimethylethyl)(dimethyl)silyl)oxy)methyl)-2-((1R)-2,2-dimethyl-1-(methyloxy)propyl)phenyl)-5-fluoro-2-(methyloxy)pyridine or 4-(4-((((1,1-dimethylethyl)(dimethyl)silyl)oxy)methyl)-2-((1S)-2,2-dimethyl-1-(methyloxy)propyl)phenyl)-5-fluoro-2-(methyloxy)pyridine (T6.9)

To a stirred solution of T6.8 (0.062 g, 0.14 mmol) in DMF (1.4 mL) at 23° C. was added iodomethane (0.018 mL, 0.29 mmol), followed by sodium hydride (0.0069 g, 0.29 mmol). The resulting mixture was stirred at 50° C. for 15 hours and was then diluted with water and extracted three times with EtOAc. The combined organic layers were dried over anhydrous MgSO$_4$, filtered, and the organic solvent was removed under reduced pressure. The residue was purified on silica gel (0-40% EtOAc in hexanes) to yield T6.9 as a colorless oil (0.047 g, 73% yield).

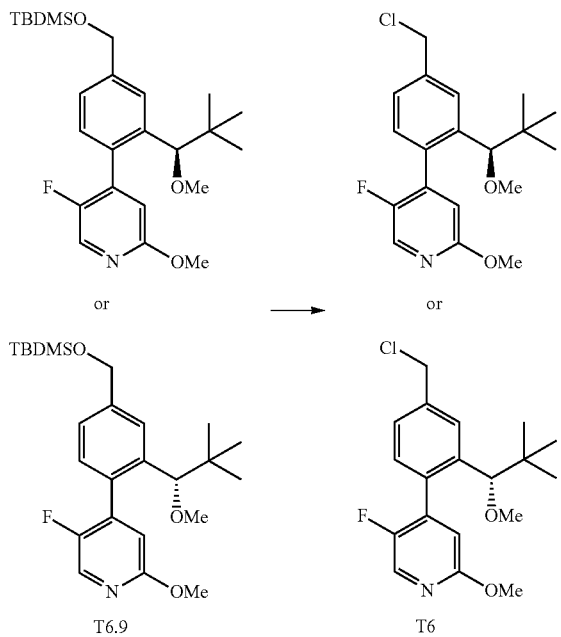

T6.9      T6

4-(4-(Chloromethyl)-2-((1R)-2,2-dimethyl-1-(methyloxy)propyl)phenyl)-5-fluoro-2-(methyloxy)pyridine or 4-(4-(chloromethyl)-2-((1S)-2,2-dimethyl-1-(methyloxy)propyl)phenyl)-5-fluoro-2-(methyloxy)pyridine (T6)

To a stirred solution of T6.9 (0.047 g, 0.10 mmol) in DCM (1.0 mL) and DMF (0.0081 mL) at 0° C. was added thionyl chloride (0.015 mL, 0.21 mmol). The mixture was stirred at room temperature for one hour and then the reaction mixture was concentrated in vacuo. The product thus obtained was purified on silica gel (0-10% EtOAc in hexanes) to yield T6 as a colorless solid (0.032 g, 87% yield).

Intermediate T7

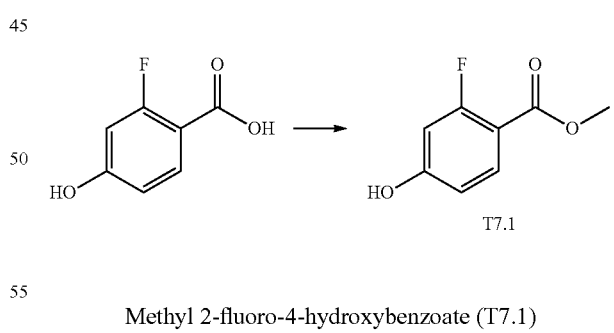

Methyl 2-fluoro-4-hydroxybenzoate (T7.1)

To a round bottom containing 2-fluoro-4-hydroxybenzoic acid (Commercially available from TCI America) (5.34 g, 34.19 mmol) was added a cold solution of MeOH (50 mL) and sulfuric acid (2.0 mL). The mixture was heated to 80° C. and monitored with TLC. After 20.5 hours, the solvent was removed and the residue was diluted with diethyl ether. The organic phase was washed carefully two times with saturated aqueous NaHCO$_3$, once with brine, and then dried over anhydrous sodium sulfate. After filtration, the organic solvent was removed in vacuo to yield T7.1 as a white solid (5.82, 85% yield). $^1$H NMR (400 MHz, DMSO-d$_6$) 10.79 (1H, s), 7.75 (1H, t, J=8.8 Hz), 6.69 (1H, dd, J=8.6, 2.3 Hz), 6.62 (1H, dd, J=13.1, 2.2 Hz), 3.78 (3H, s).

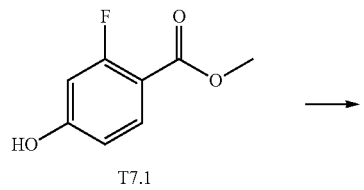

T7.1

Methyl 5-bromo-2-fluoro-4-hydroxybenzoate (T7.2)

To a solution of T7.1 (2.03 g, 11.9 mmol) in AcOH (65 mL) was added a pre-mixed solution of bromine (0.67 mL, 13.1 mmol) in AcOH (10 mL). The mixture was stirred at 45° C. and monitored with TLC and LC-MS. After 18 hours, the reaction mixture was concentrated under reduced pressure. Brine was added to the residue, and the mixture was extracted three times with EtOAc. The combined organic layers were dried over anhydrous magnesium sulfate, filtered, and then concentrated to provide T7.2 as a white solid (2.12 g, 71% yield). $^1$H NMR (400 MHz, CDCl$_3$) 8.13 (1H, d, J=7.4 Hz), 6.82 (1H, d, J=11.3 Hz), 6.04 (1H, s), 3.92 (3H, s).

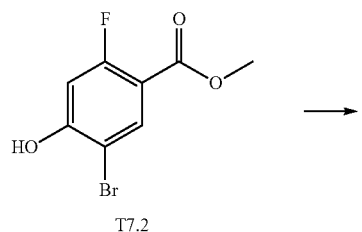

Methyl 5-bromo-2-fluoro-4-(tetrahydro-2H-pyran-2-yloxy)benzoate (T7.3)

To a round bottom containing T7.2 (13.15 g, 52.8 mmol) in dry DCM (90 mL) was added 3,4-dihydro-2H-pyran (10 mL, 110 mmol) followed by PPTS (0.13 g, 0.53 mmol). The reaction mixture was heated at a gentle reflux (50° C.) and monitored with TLC and LC-MS. After 24 hours, the reaction was concentrated under reduced pressure and then diluted with MeOH. After concentration, the residue was heated in a round bottom flask containing MeOH on a rotary evaporator (without vacuum) at 40° C. After about 30 minutes, the solution was concentrated to a volume of about 5 mL. After cooling to room temperature, the white solid was filtered and rinsed once with MeOH to yield T7.3 (13.35 g, 76% yield). $^1$H NMR (400 MHz, CDCl$_3$) δ ppm 8.25 (1H, m), 6.96 (1H, d, J=12.5 Hz), 5.56 (1H, m), 3.91 (3H, s), 3.79 (1H, td, J=11.1, 2.5 Hz), 3.65 (1H, d, J=10.6 Hz), 2.23 (2H, m), 1.96 (3H, m), 1.68 (1H, m).

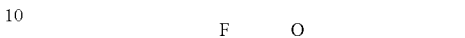

T7.3

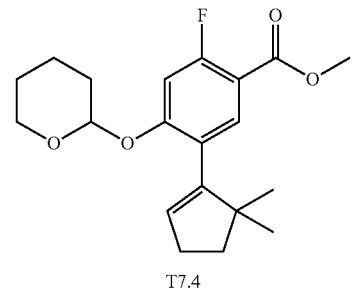

T7.4

Methyl 5-(5,5-dimethylcyclopent-1-enyl)-2-fluoro-4-(tetrahydro-2H-pyran-2-yloxy)benzoate (T7.4)

A stirred mixture of T7.3 (10.33 g, 31.0 mmol), ground S-Phos (2.55 g, 6.21 mmol), palladium acetate (0.70 g, 3.11 mmol), and potassium phosphate, tribasic (16.49 g, 77.7 mmol) in DMF (75 mL) and water (4 mL) was purged three times with argon and placed under vacuum three times. 2-(5,5-Dimethylcyclopent-1-enyl)-4,4,5,5-tetramethyl-1,3,2-dioxaborolane (T2.2) (8.96 g, 40.4 mmol) was added via syringe, and then the mixture was heated to 75° C. After 21 hours, the reaction was cooled to room temperature, diluted with water, and extracted three times with EtOAc. The combined organic layers were washed twice with brine. After drying over anhydrous sodium sulfate and filtration, the organic solvent was removed under reduced pressure. The residue was purified by silica gel flash chromatography (0-10% EtOAc/hexane) to yield T7.4 (5.65 g, 52% yield). $^1$H NMR (400 MHz, CDCl$_3$) δ ppm 7.63 (1H, d, J=8.6 Hz), 6.93 (1H, d, J=13.3 Hz), 5.55 (1H, t, J=2.3 Hz), 5.43 (1H, t, J=2.7 Hz), 3.90 (3H, s), 3.82 (1H, m), 3.67 (1H, m), 2.41 (2H, td, J=7.0, 2.3 Hz), 1.97 (5H, m), 1.79 (3H, m), 1.07 (6H, d, J=13.7 Hz).

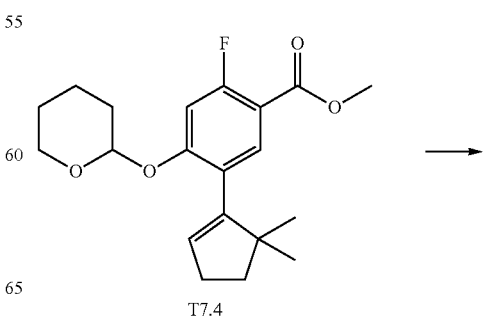

T7.4

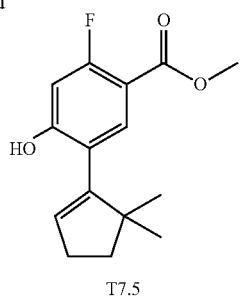

T7.5

Methyl 5-(5,5-dimethylcyclopent-1-enyl)-2-fluoro-4-hydroxybenzoate (T7.5)

To a stirred mixture of T7.4 (5.65 g, 16.2 mmol) in MeOH (60 mL) was added PPTS (0.42 g, 1.69 mmol). The mixture was heated to 50° C. and monitored with TLC and LCMS. After 19 hours, the organic solvent was removed under reduced pressure, and the residue was purified on silica gel (0-15% EtOAc in hexanes) to yield T7.5 as a white solid (3.47 g, 81% yield). $^1$H NMR (500 MHz, CDCl$_3$) δ ppm 7.69 (1H, d, J=8.3 Hz), 6.71 (1H, d, J=12.0 Hz), 5.93 (1H, d, J=1.7 Hz), 5.80 (1H, t, J=2.4 Hz), 3.90 (3H, s), 2.54 (2H, m), 1.93 (2H, t, J=7.1 Hz), 1.11 (6H, s).

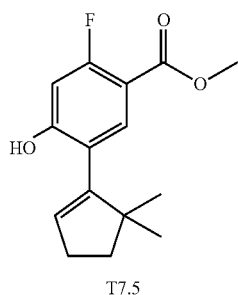

T7.5

→

F$_3$C—S—O

T7.6

Methyl 5-(5,5-dimethylcyclopent-1-enyl)-2-fluoro-4-(trifluoromethylsulfonyloxy)benzoate (T7.6)

To a stirred solution of T7.5 (0.80 g, 3.02 mmol) in dry DCM (15 mL) was added TEA (1.0 mL, 7.19 mmol) and DMAP (38.1 mg, 0.312 mmol). After about 20 minutes, N-phenyl-bis(trifluoromethanesulfonimide) (1.30 g, 3.64 mmol) was added in portions. Upon complete addition, the solution was stirred at room temperature and monitored with TLC and LC-MS. After 19 hours, the organic solvent was removed under reduced pressure, and the residue was then purified with silica gel chromatography using 0-10% EtOAc in hexanes to yield T7.6 as a colorless oil (1.05 g, 88% yield). $^1$H NMR (400 MHz, CDCl$_3$) δ ppm 7.84 (1H, d, J=7.8 Hz), 7.13 (1H, d, J=10.2 Hz), 5.79 (1H, t, J=2.3 Hz), 3.96 (3H, s), 2.47 (2H, td, J=7.0, 2.3 Hz), 1.91 (2H, t, J=7.0 Hz), 1.08 (6H, s).

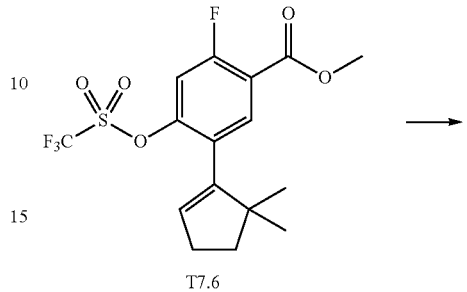

T7.6

→

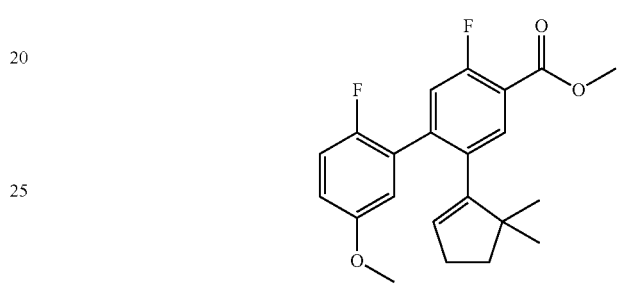

T7.7

Methyl 2-(5,5-dimethyl-1-cyclopenten-1-yl)-2',5-difluoro-5'-(methyloxy)-1,1'-biphenyl-4-carboxylate (T7.7)

To a stirred solution of T7.6 (1.05 g, 2.65 mmol) in DMF (5 mL) at 23° C. was added 2-fluoro-5-methoxyphenylboronic acid (0.90 g, 5.32 mmol) (commercially available from Sigma-Aldrich, St. Louis, Mo., USA) and potassium carbonate (1.10 g, 7.96 mmol) followed by tetrakis(triphenylphosphine)palladium (0.31 g, 0.27 mmol). The mixture was heated to 90° C. After 17 hours, the mixture was cooled to room temperature and then diluted with water. After extracting three times with EtOAc, the mixture was concentrated in vacuo and then purified on silica gel (0%-10% EtOAc/hexane) to give T7.7 as a clear oil that was used without further purification (0.92 g, 93% yield). $^1$H NMR (400 MHz, CDCl$_3$) δ ppm 7.79 (1H, d, J=7.4 Hz), 7.13 (1H, d, J=11.3 Hz), 6.99 (1H, t, J=9.0 Hz), 6.84 (1H, dt, J=8.7, 3.7 Hz), 6.78 (1H, dd, J=5.9, 3.1 Hz), 5.55 (1H, s), 3.96 (3H, s), 3.79 (3H, s), 2.27 (2H, td, J=7.1, 2.5 Hz), 1.67 (2H, t, J=7.0 Hz), 0.84 (6H, s).

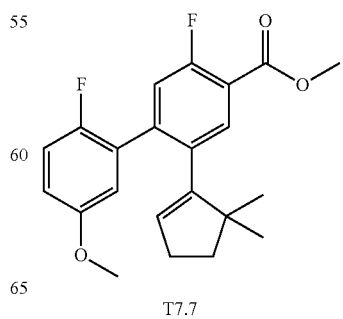

T7.7

→

-continued

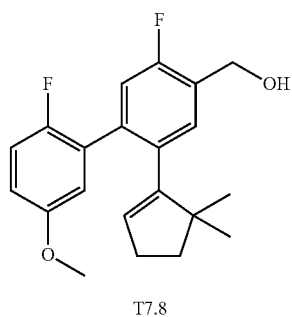
T7.8

(2-(5,5-Dimethyl-1-cyclopenten-1-yl)-2',5-difluoro-5'-(methyloxy)-1,1'-biphenyl-4-yl)methanol (T7.8)

To a cooled solution of T7.7 (0.92 g, 2.47 mmol) in dry THF (15 mL) at 0° C. was added LAH (1.0 M in THF)(5.0 mL, 5.0 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After combining the organic layers, drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to provide T7.8 as a colorless oil (0.70 g, 82% yield). $^1$H NMR (500 MHz, CDCl$_3$) δ ppm 7.30 (1H, m), 7.05 (1H, dd, J=10.6, 1.1 Hz), 6.97 (1H, t, J=8.9 Hz), 6.83 (2H, m), 5.52 (1H, td, J=2.4, 0.9 Hz), 4.81 (2H, s), 3.76 (3H, s), 2.25 (2H, td, J=7.1, 2.4 Hz), 1.76 (1H, br. s.), 1.69 (2H, m), 0.85 (6H, s).

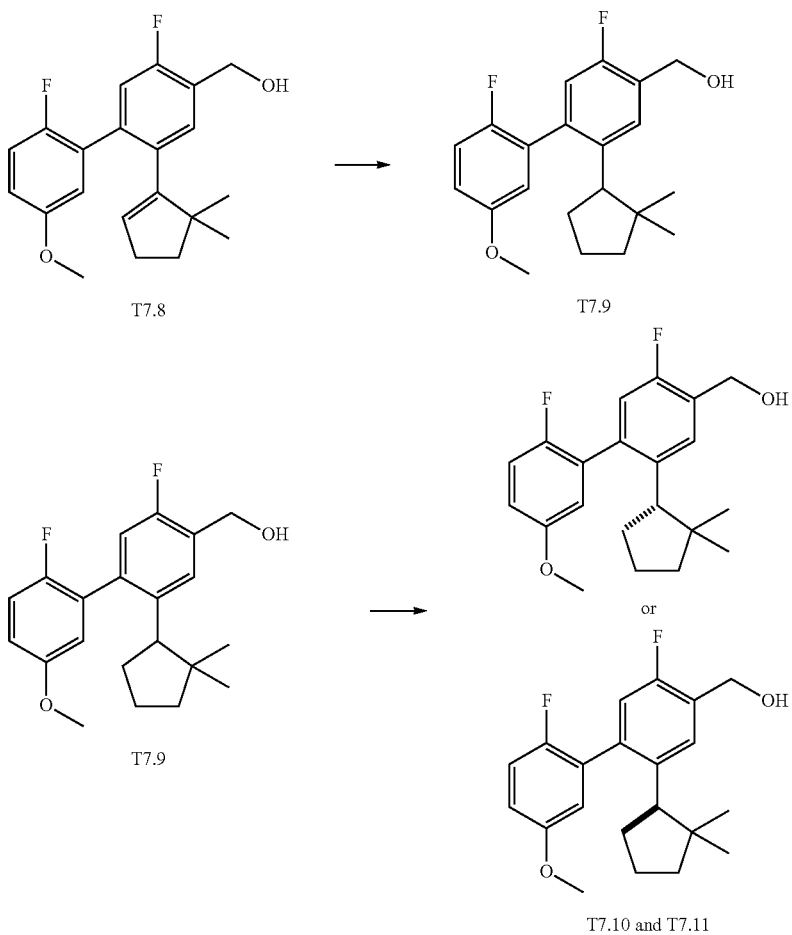

(2-(2,2-Dimethylcyclopentyl)-2',5-difluoro-5'-(methyloxy)-1,1'-biphenyl-4-yl)methanol (T7.9).

To a dry flask containing T7.8 (0.70 g, 2.03 mmol) in dry MeOH (5 mL) and EtOAc (3 mL) was added Pd, 10 wt. % on activated carbon (77.2 mg). After purging, the mixture was stirred under an atmosphere of hydrogen at room temperature. After 4.5 hours, the mixture was filtered through Celite® filter aid. After concentration, the residue was identified as T7.9 as a mixture of enantiomers and rotamers (0.31 g, 45% yield). Chiral separation of T7.9 was accomplished on a CHIRALCEL® OJ column (2% IPA in hexane) to provide T7.10 (peak 1) and T7.11 (peak 2). Both enantiomers were used to synthesize example compounds, and both enantiomers gave active compounds.

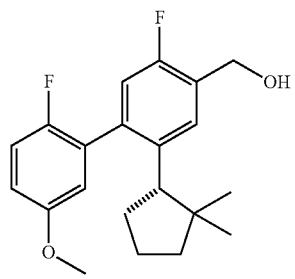

T7.10

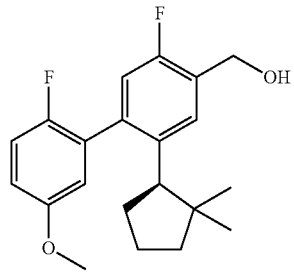

T7.10

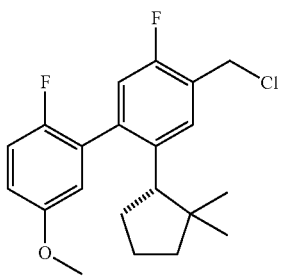

T7

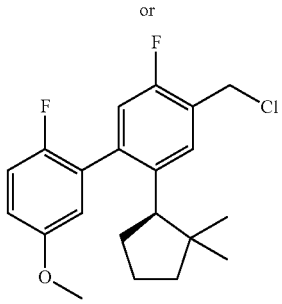

T7

4-(Chloromethyl)-2-((1S)-2,2-dimethylcyclopentyl)-2',5-difluoro-5'-(methyloxy)-1,1'-biphenyl or 4-(chloromethyl)-2-((1R)-2,2-dimethylcyclopentyl)-2',5-difluoro-5'-(methyloxy)-1,1'-biphenyl (T7)

To a solution of T7.10 (0.71 g, 2.05 mmol) (derived from peak one from the chiral separation of T7.9) in dry DCM (23 mL) and dry DMF (0.18 mL) was added thionyl chloride (0.3 mL, 4.1 mmol) dropwise at 0° C. The resulting solution was warmed to room temperature and monitored with TLC and LCMS. After 45 minutes, the reaction was concentrated and then purified by silica gel flash chromatography (0-5% EtOAc/hexane) to yield T7 as a colorless oil (0.73 g, 97% yield). $^1$H NMR (400 MHz, CDCl$_3$) δ ppm 7.46 (1H, m), 7.11 (3H, m), 6.75 (1H, m), 4.78 (2H, m), 3.80 (3H, s), 2.91 (1H, m), 2.20 (2H, m), 1.87 (2H, m), 1.59 (1H, m), 1.43 (1H, m), 0.77 (3H, m), 0.64 (3H, m).

Asymmetric Synthesis of T7

The following procedures were used to synthesize T7.10 using a highly enantioselective procedure to hydrogenate T7.5 to form T7.11.

(R)-Methyl 5-(2,2-dimethylcyclopentyl)-2-fluoro-4-hydroxybenzoate or (S)-methyl 5-(2,2-dimethylcyclopentyl)-2-fluoro-4-hydroxybenzoate (T7.12)

A mixture of Rh(COD)$_2$BF$_4$ (Stern Chemical, 35138-22-8, 36.95 mg, 0.091 mmol) and (R)-1-[(S)-2-(R)-(Ditertbutylphosphino)ferrocenyl]ethyl-bis-(3,5-bistrifluoromethylphenyl)phosphine (Solvias, SL-J210-1, 81.5 mg, 0.100 mmol) in THF (75 mL) was stirred under N$_2$ for 60 minutes and a dark red solution formed. To the resulting solution was added methyl 5-(5,5-dimethylcyclopent-1-enyl)-2-fluoro-4-hydroxybenzoate T7.5 (8.2 g, 45.4 mmol) and TEA (10 mol %, 0.63 mL, 4.54 mmol). The resulting mixture was flushed with H$_2$ (200 psi) three times and stirred at room temperature under 200 psi H$_2$ for 2 hours. The resulting mixture was passed through a short plug of silica gel, eluting with 1:1 hexane/EtOAc. The mixture was then concentrated affording the desired product T7.12 as a white solid (83% yield (6.8 g), 99.3% ee).

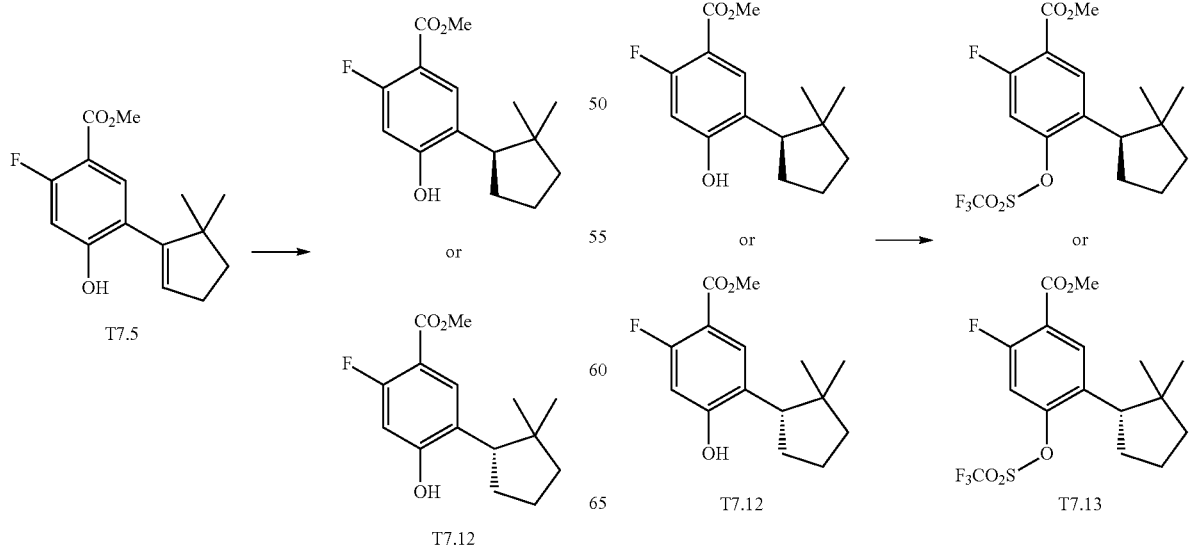

(R)-Methyl 5-(2,2-dimethylcyclopentyl)-2-fluoro-4-(trifluoromethylsulfonyloxy)benzoate or (S)-methyl 5-(2,2-dimethylcyclopentyl)-2-fluoro-4-(trifluoromethylsulfonyloxy)benzoate (T7.13)

To a stirred solution of T7.12 (4.02 g, 15.1 mmol) in dry DCM (50 mL) was added TEA (4.2 mL, 30.2 mmol) and DMAP (0.19 g, 1.52 mmol). After 20 minutes, N-phenyl-bis(trifluoromethanesulfonimide) (5.94 g, 16.6 mmol) was added in portions. Upon complete addition, the solution was stirred at room temperature and monitored with TLC and LC-MS. After 4 hours, the mixture was washed twice with brine and then dried over anhydrous $MgSO_4$. After filtration and concentration, the residue was purified with silica gel chromatography (0-10% EtOAc in hexanes) to yield T7.13 as a colorless oil (5.51, 92%). $^1H$ NMR (500 MHz, $CDCl_3$) δ ppm 7.97 (1H, d, J=7.8 Hz), 7.14 (1H, d, J=10.0 Hz), 3.96 (3H, s), 3.13 (1H, dd, J=10.1, 8.2 Hz), 2.14 (2H, m), 1.96 (2H, m), 1.70 (2H, m), 1.00 (3H, s), 0.69 (3H, s).

room temperature and then diluted with water. After extracting three times with EtOAc, the mixture was concentrated in vacuo and then purified on silica gel (0%-10% EtOAc/hexane) to yield T7.14 as an oil that solidified (5.11 g, 99%).

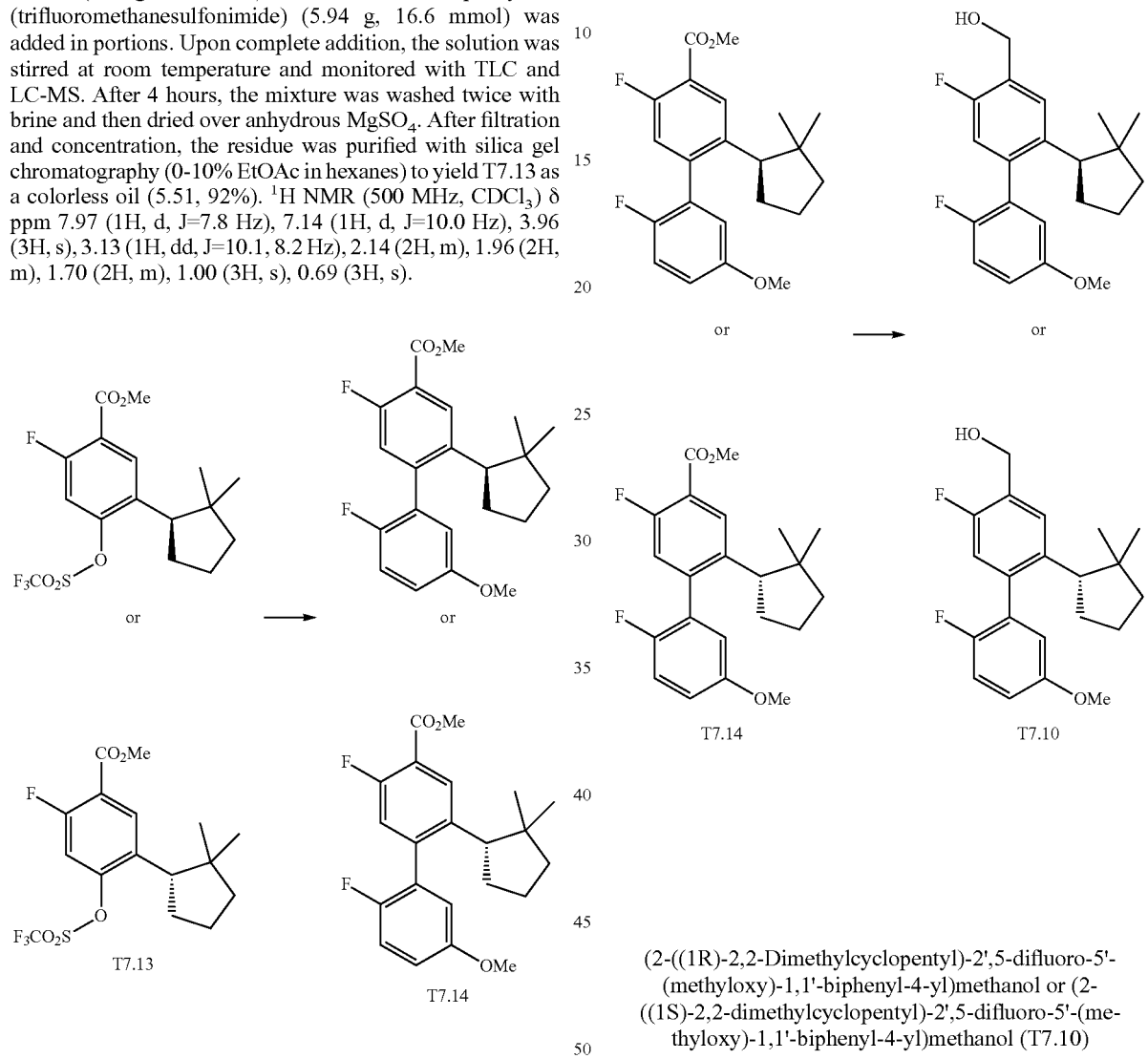

Methyl 2-((1R)-2,2-dimethylcyclopentyl)-2',5-difluoro-5'-(methyloxy)-1,1'-biphenyl-4-carboxylate or methyl 2-((1S)-2,2-dimethylcyclopentyl)-2',5-difluoro-5'-(methyloxy)-1,1'-biphenyl-4-carboxylate (T7.14)

To a stirred solution of T7.13 (5.51 g, 13.8 mmol) in DMF (25 mL) at 23° C. was added 2-fluoro-5-methoxyphenylboronic acid (4.71 g, 27.7 mmol) (commercially available from Sigma-Aldrich, St. Louis, Mo., USA) and potassium carbonate (5.74 g, 41.6 mmol) followed by tetrakis(triphenylphosphine)palladium (1.60 g, 1.39 mmol). The mixture was heated to 90° C. After 3.5 hours, the mixture was cooled to

(2-((1R)-2,2-Dimethylcyclopentyl)-2',5-difluoro-5'-(methyloxy)-1,1'-biphenyl-4-yl)methanol or (2-((1S)-2,2-dimethylcyclopentyl)-2',5-difluoro-5'-(methyloxy)-1,1'-biphenyl-4-yl)methanol (T7.10)

To a cooled solution of T7.14 (5.11 g, 13.6 mmol) in dry THF (40 mL) at 0° C. was added LAH (1.0 M in THF)(27.3 mL, 27.30 mmol) dropwise. Upon complete addition, the reaction was maintained at 0° C. and monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by silica gel chromatography (0-25% EtOAc in hexanes) to yield T7.10 as a colorless oil (3.94 g, 83%). $^1H$ NMR (400 MHz, $CDCl_3$) δ ppm 7.50 (1H, m), 7.11 (3H, m), 6.85 (1H, m), 4.81 (2H, s), 3.80 (3H, s), 2.92 (1H, m), 2.19 (2H, m), 1.83 (1H, m), 1.72 (1H, m), 1.59 (2H, m), 1.42 (1H, m), 0.82 (3H, m), 0.65 (3H, m).

Intermediate T8

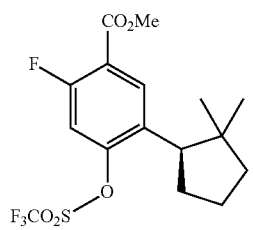

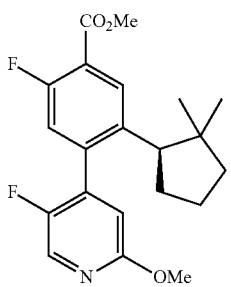

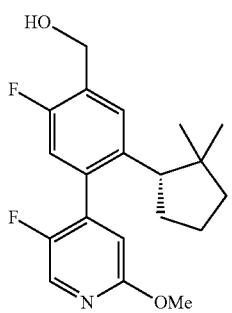

T8.1

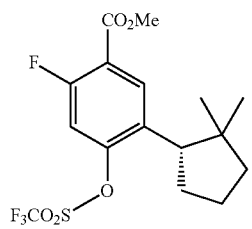

T7.13

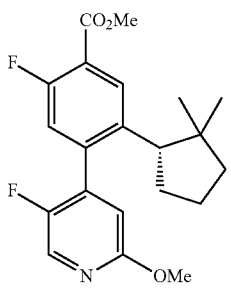

T8.1

Methyl 5-((1S)-2,2-dimethylcyclopentyl)-2-fluoro-4-(5-fluoro-2-(methyloxy)-4-pyridinyl)benzoate or methyl 5-((1R)-2,2-dimethylcyclopentyl)-2-fluoro-4-(5-fluoro-2-(methyloxy)-4-pyridinyl)benzoate (T8.1)

To a stirred solution of T7.13 (0.7937 g, 1.992 mmol) in DMF (4 mL) at 23° C. was added 5-fluoro-2-methoxypyridine boronic acid (commercially available from Asymchem) (0.5115 g, 2.992 mmol) and potassium carbonate (0.8279 g, 5.990 mmol) followed by tetrakis(triphenylphosphine)palladium (0.2374 g, 0.2054 mmol). The mixture was heated to 90° C. After 2 hours, LCMS-showed reaction was complete. The mixture was cooled to room temperature then diluted with water. After extracting three times with EtOAc, the mixture was concentrated in vacuo and then purified on silica gel (0%-20% EtOAc/hexane) to afford T8.1 (601.2 mg, 80% yield). MS ESI (pos.) m/e: 376.1 (M+H)⁺.

(5-((1S)-2,2-Dimethylcyclopentyl)-2-fluoro-4-(5-fluoro-2-(methyloxy)-4-pyridinyl)phenyl)methanol or (5-((1R)-2,2-dimethylcyclopentyl)-2-fluoro-4-(5-fluoro-2-(methyloxy)-4-pyridinyl)phenyl)methanol (T8.2)

To a cooled solution of T8.1 (0.6012 g, 1.601 mmol) in dry THF (15 mL) at 0° C. was added LAH (1.0M in THF)(3.2 mL, 3.2 mmol) dropwise. Upon complete addition, the reaction was maintained at 0° C. and monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified on silica gel (0%-20% EtOAc/hexane) to afford T8.2 (449.9 mg, 81% yield). MS ESI (pos.) m/e: 348.1 (M+H)⁺.

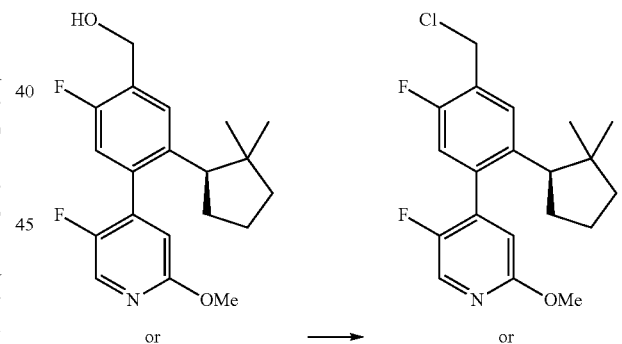

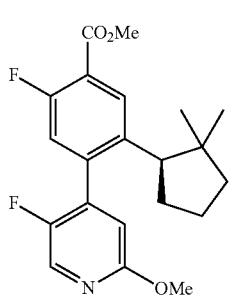

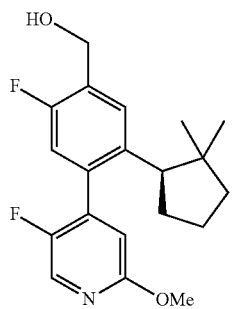

T8.2

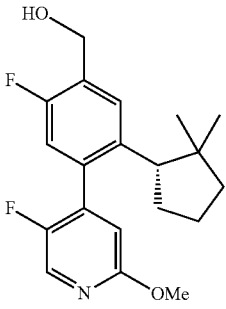

T8

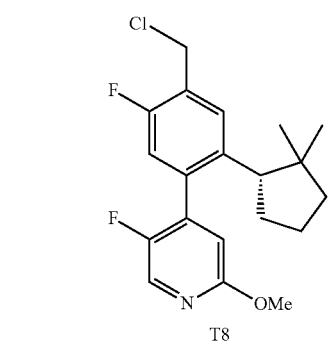

4-(4-(Chloromethyl)-2-((1S)-2,2-dimethylcyclopentyl)-5-fluorophenyl)-5-fluoro-2-(methyloxy)pyridine or 4-(4-(chloromethyl)-2-((1R)-2,2-dimethylcyclopentyl)-5-fluorophenyl)-5-fluoro-2-(methyloxy)pyridine (T8)

To a solution of T8.2 (0.4463 g, 1.285 mmol) in dry DCM (17 mL) and dry DMF (0.12 mL) was added thionyl chloride (0.19 mL, 2.605 mmol) at 0° C. The resulting solution was warmed to room temperature and monitored with TLC and LCMS. After 1.5 hours, the reaction was concentrated. The residue was diluted with EtOAc and washed once with saturated aqueous sodium bicarbonate solution and once with brine. The organic layer was subsequently dried over anhydrous sodium sulfate, filtered, concentrated, and purified by silica gel flash chromatography (0-15% EtOAc/hexane) to afford T8 (446.9 mg, 95% yield). MS ESI (pos.) m/e: 366.1 $(M+H)^+$.

Intermediate T9

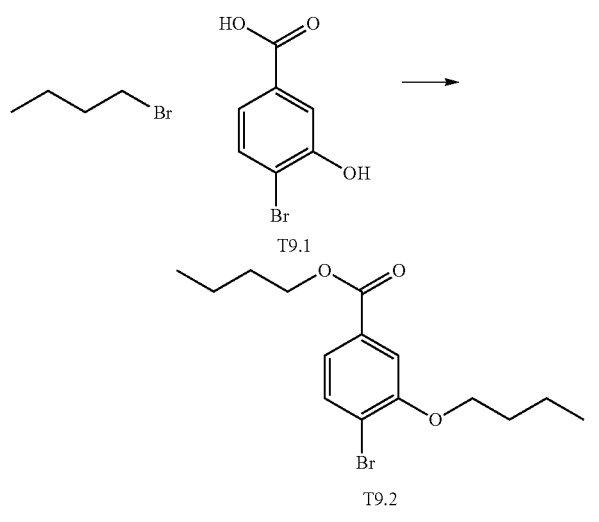

Butyl 4-bromo-3-(butyloxy)benzoate (T9.2)

To a flask containing 4-bromo-3-hydroxybenzoic acid (T9.1)(available from Combi-Blocks Inc.)(2.40 g, 11.06 mmol) and $Cs_2CO_3$ (8.287 g, 25.44 mmol) in DMF (40 mL), was added 1-bromobutane (2.494 mL, 23.22 mmol), and the mixture was stirred overnight. The reaction was diluted with water and extracted with EtOAc. The organic layers were washed with brine, dried over $Na_2SO_4$, filtered, concentrated, and then purified by CombiFlash® column chromatography (0 to 20% EtOAc/Hexanes) to provide T9.2 (2.4326 g, 66.81% yield).

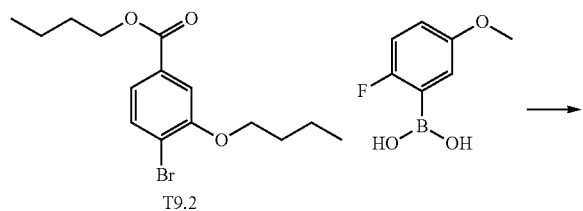

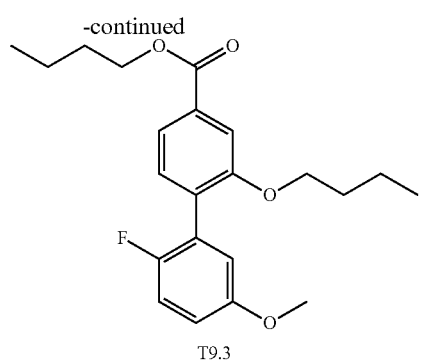

Butyl 2-(butyloxy)-2'-fluoro-5'-(methyloxy)-1,1'-biphenyl-4-carboxylate (T9.3)

To a 2 dram vial charged with 2-fluoro-5-methoxyphenylboronic acid (commercially available from Sigma-Aldrich, St. Louis, Mo., USA) (2.323 g, 13.67 mmol), tetrakis(triphenylphosphine) palladium(0) (0.7897 g, 0.6834 mmol), cesium fluoride (0.8409 mL, 22.78 mmol), and T9.2 (1.50 g, 4.556 mmol), was added DME (20 mL). The resulting mixture was heated at 90° C. overnight. The reaction was allowed to cool and then filtered and concentrated. The residue was purified by CombiFlash® column chromatography (0 to 10% EtOAc/hexanes) yielding T9.3 (1.1530 g, 67.58% yield).

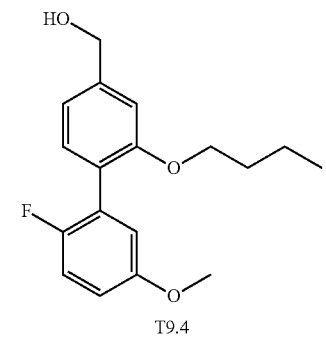

(2-(Butyloxy)-2'-fluoro-5'-(methyloxy)-1,1'-biphenyl-4-yl)methanol (T9.4)

To a mixture of T9.3 (1.1530 g, 3.079 mmol) and THF (10 mL) at 0° C. was added LAH (1.0 M solution in THF (4.619 mL, 4.619 mmol)). The reaction was stirred for one hour and then carefully diluted with water, extracted with EtOAc, washed with brine, dried over sodium sulfate, filtered, and concentrated to provide T9.4 (0.9050 g, 96.57% yield).

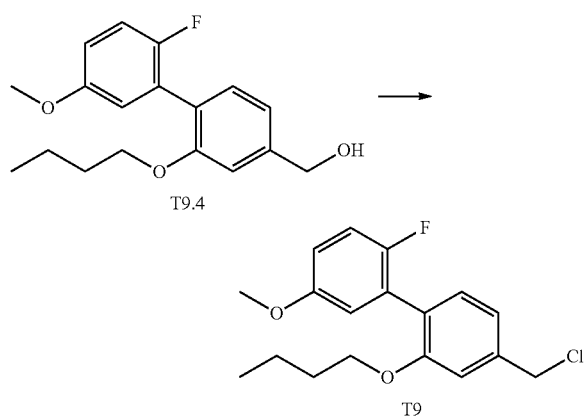

2-(Butyloxy)-4-(chloromethyl)-2'-fluoro-5'-(methyloxy)-1,1'-biphenyl (T9)

To a stirred solution of T9.4 (0.8800 g, 2.891 mmol) in DCM (15 mL) at 23° C. was added thionyl chloride (0.4218 mL, 5.783 mmol). The reaction mixture was stirred overnight and then concentrated and purified by CombiFlash® column chromatography (0 to 10% EtOAc/Hexanes) to provide T9 (0.7980 g, 85.50% yield).

Intermediate T10

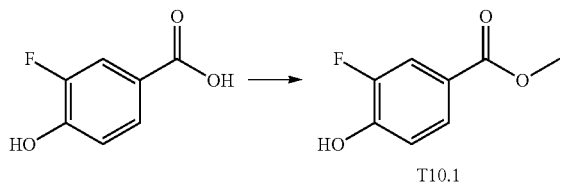

Methyl 3-fluoro-4-hydroxybenzoate (T10.1)

To a round bottom flask containing 3-fluoro-4-hydroxybenzoic acid (commercially available from Sigma-Aldrich, St. Louis, Mo., USA) (5.03 g, 32.22 mmol) was added a cold solution of MeOH (50.0 mL) and sulfuric acid (2.0 mL). The mixture was heated to 80° C. and monitored with TLC. After 20.5 hours, the solvent was removed and the resulting mixture was diluted with diethyl ether. The organic phase was washed carefully two times with saturated aqueous $NaHCO_3$, once with brine, and then dried over anhydrous sodium sulfate. After filtration, the organic solvent was removed in vacuo to afford T10.1 as a white solid (4.79 g, 87% yield). $^1$H NMR (400 MHz, $CDCl_3$) 7.81 (2H, m), 7.06 (1H, t, J=8.4 Hz), 5.62 (1H, d, J=4.3 Hz), 3.91 (3H, s).

Methyl 3-bromo-5-fluoro-4-hydroxybenzoate (T10.2)

Bromine (1.60 mL, 31.1 mmol) was added dropwise with stirring over 30 minutes to an ice-cooled solution of T10.1 (4.79 g, 28.1 mmol) in a 1:1 mixture of DCM (20 mL) and AcOH (20 mL). Upon complete addition, the reaction mixture was allowed to warm to room temperature and monitored with TLC and LC-MS. After stirring at room temperature for 40 hours, the mixture was diluted with EtOAc. The resulting solution was washed twice with aqueous saturated $Na_2SO_3$, once with water, and once with brine. After drying over anhydrous $MgSO_4$, filtration, and concentration, the white solid was identified as T10.2 (6.69 g, 95% yield). $^1$H NMR (400 MHz, $CDCl_3$) 8.05 (1H, m), 7.75 (1H, dd, J=10.6, 2.0 Hz), 6.12 (1H, s), 3.94 (3H, s).

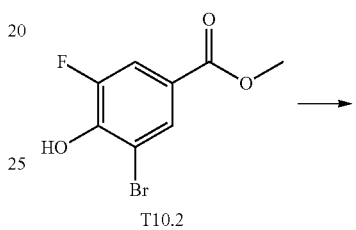

Methyl 3-bromo-5-fluoro-4-(((4-(methyloxy)phenyl)methyl)oxy)benzoate (T10.3)

To a vial containing T10.2 (0.64 g, 2.58 mmol) in 5.0 mL dry DMF was added $Cs_2CO_3$ (1.10 g, 3.36 mmol). The mixture was stirred at room temperature for 10 minutes and then 4-methoxybenzyl bromide (0.45 mL, 3.1 mmol) was added. After 4 hours, the reaction was diluted with water and then extracted five times with EtOAc. The combined organic layers were then washed once with brine and dried over anhydrous $MgSO_4$. The solid was filtered off, and the solvent was concentrated. The residue was purified by silica gel flash chromatography (0-40% EtOAc/hexane) to afford T10.3 as a white solid (679.1 mg, 71% yield). $^1$H NMR (400 MHz, $CDCl_3$) 8.02 (1H, t, J=2.0 Hz), 7.72 (1H, dd, J=11.5, 2.2 Hz), 7.42 (2H, m, J=8.6 Hz), 6.90 (2H, m), 5.20 (2H, s), 3.91 (3H, s), 3.82 (3H, s).

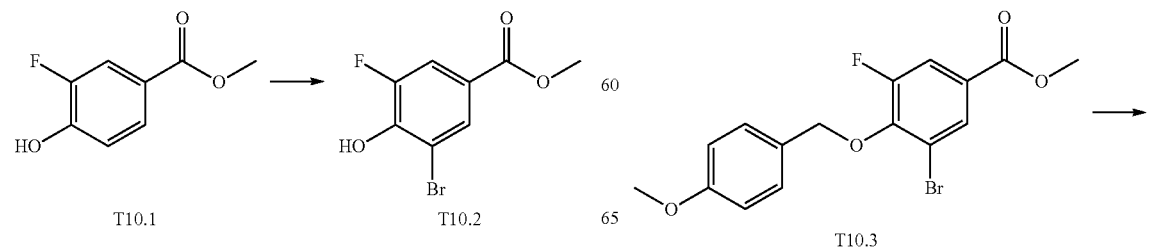

145
-continued

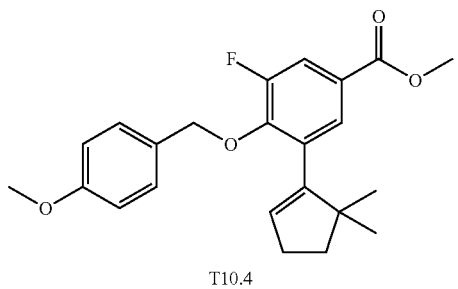

T10.4

Methyl 3-(5,5-dimethyl-1-cyclopenten-1-yl)-5-fluoro-4-(((4-(methyloxy)phenyl)methyl)oxy)benzoate (T10.4)

A stirred mixture of T10.3 (1.63 g, 4.420 mmol), ground S-Phos (0.36 g, 0.88 mmol), palladium acetate (0.10 g, 0.45 mmol), and potassium phosphate tribasic (2.35 g, 11.06 mmol) in DMF (13 mL) and water (0.4 mL) was purged three times with argon and placed under vacuum three times. 2-(5,5-Dimethylcyclopent-1-enyl)-4,4,5,5-tetramethyl-1,3,2-dioxaborolane (T2.2) (1.47 g, 6.63 mmol) was added to the mixture via syringe, and the resulting mixture was heated to 75° C. After 18 hours (black solution), the reaction was cooled to room temperature, diluted with water, and extracted three times with EtOAc. The combined organic layers were washed twice with brine. After drying over anhydrous sodium sulfate and filtration, the organic solvent was removed under reduced pressure. The residue was purified on a 40 g column of silica gel (0-10% EtOAc in hexanes) to afford T10.4 as a white solid (1.12 g, 66% yield). $^1$H NMR (400 MHz, CDCl$_3$) δ ppm 7.69 (1H, dd, J=11.7, 2.3 Hz), 7.57 (1H, dd, J=2.0, 1.2 Hz), 7.31 (2H, m), 6.88 (2H, m), 5.56 (1H, t, J=2.5 Hz), 5.01 (2H, s), 3.91 (3H, s), 3.82 (3H, s), 2.42 (2H, td, J=7.0, 2.7 Hz), 1.86 (2H, t, J=7.2 Hz), 1.06 (6H, s).

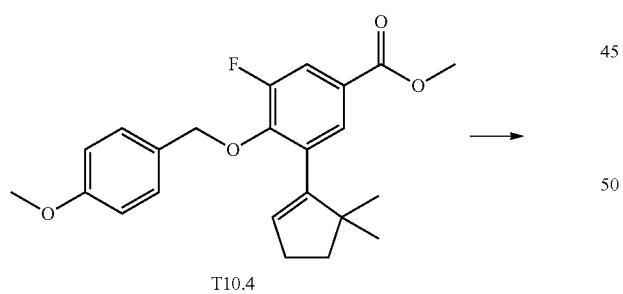

T10.4

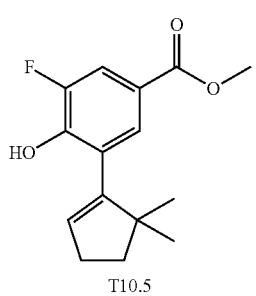

T10.5

146

Methyl 3-(5,5-dimethyl-1-cyclopenten-1-yl)-5-fluoro-4-hydroxybenzoate (T10.5)

To a flask containing T10.4 (1.12 g, 2.93 mmol) was added a premixed solution of DCM (14 mL) and TFA (1 mL). The mixture was stirred at room temperature and monitored with TLC and LC-MS. After 1 hour, the reaction was diluted with DCM and then washed once with a saturated aqueous sodium bicarbonate solution and brine. The organic layer was then dried over anhydrous sodium sulfate, filtered, and concentrated under vacuum. The residue was purified by flash chromatography (SiO$_2$ gel 60, eluted with 0%-50% EtOAc in hexanes). Fractions containing the desired product were combined and concentrated to provide a colorless oil that solidified as T10.5 and was used without further purification (732.6 mg, 95% yield).

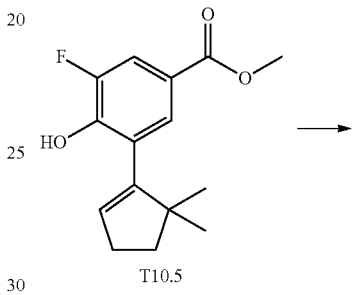

T10.5

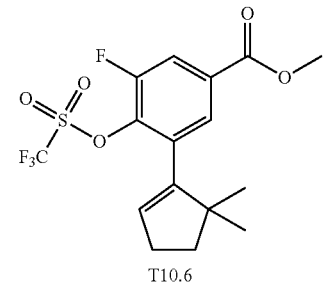

T10.6

Methyl 3-(5,5-dimethyl-1-cyclopenten-1-yl)-5-fluoro-4-(((trifluoromethyl)sulfonyl)oxy)benzoate (T10.6)

To a stirred solution of T10.5 (0.7326 g, 2.77 mmol) in dry DCM (15 mL) was added TEA (0.78 mL, 5.60 mmol) and DMAP (0.0354 g, 0.29 mmol). After about 20 minutes, N-phenyl-bis(trifluoromethanesulfonimide) (1.20 g, 3.36 mmol) was added in portions. Upon complete addition, the solution was stirred at room temperature and monitored with TLC and LC-MS. After 19 hours, the organic solvent was removed under reduced pressure and the residue was purified with silica gel chromatography using 0-10% EtOAc in hexanes to afford T10.6 as a colorless oil (946.4 mg, 86% yield). $^1$H NMR (400 MHz, CDCl$_3$) δ ppm 7.82 (1H, dd, J=9.9, 2.1 Hz), 7.75 (1H, m), 5.87 (1H, t, J=2.4 Hz), 3.95 (3H, s), 2.49 (2H, td, J=7.1, 2.4 Hz), 1.92 (2H, t, J=7.0 Hz), 1.11 (6H, s).

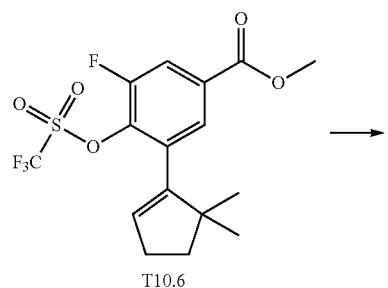

T10.6

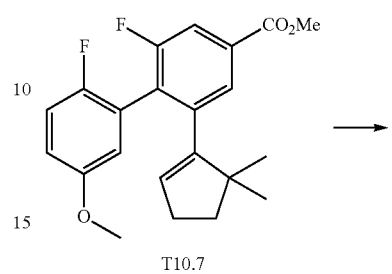

T10.7 removed under reduced pressure. The residue was purified on an 80 g column of silica gel (0-20% EtOAc in hexanes) to afford T10.7 as a colorless oil that was used as is without further purification (850.5 mg, 95% yield). MS ESI (pos.) m/e: 373.0 (M+H)$^+$.

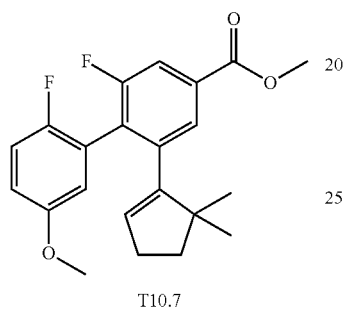

T10.7

Methyl 2-(5,5-dimethyl-1-cyclopenten-1-yl)-2',6-difluoro-5'-(methyloxy)-1,1'-biphenyl-4-carboxylate (T10.7)

A stirred mixture of T10.6 (0.9464 g, 2.39 mmol), ground S-Phos (0.1977 g, 0.482 mmol), palladium acetate (0.0555 g, 0.247 mmol), 2-fluoro-5-methoxyphenylboronic acid (0.8114 g, 4.77 mmol) (commercially available from Sigma-Aldrich, St. Louis, Mo., USA), and potassium phosphate tribasic (1.2888 g, 6.072 mmol) in dry DMF (7.000 mL) was purged three times with argon and placed under vacuum three times. The mixture was heated to 75° C. After 21 hours, the reaction was cooled to room temperature, diluted with water and extracted three times with EtOAc. The combined organic layers were washed twice with brine. After drying over anhydrous sodium sulfate and filtering, the organic solvent was

Methyl 2-(2,2-dimethylcyclopentyl)-2',6-difluoro-5'-(methyloxy)-1,1'-biphenyl-4-carboxylate (T10.8)

To a flask containing T10.7 (0.7168 g, 1.925 mmol) in dry MeOH (8 mL) and EtOAc (5 mL) was added palladium (10 wt % on activated carbon, (0.2103 g, 0.1976 mmol)). After purging, the mixture was stirred under an atmosphere of hydrogen at room temperature. After 18.5 hours, the mixture was filtered through Celite® filter aid. After concentration, the residue was identified T10.8 (703.6 mg, 98% yield). $^1$H NMR (400 MHz, CDCl$_3$) δ ppm 7.88 (1H, s), 7.65 (1H, dd, J=9.4, 1.6 Hz), 7.13 (2H, m), 6.96 (2H, m), 6.77 (1H, dd, J=5.5, 3.1 Hz), 3.95 (3H, s), 3.80 (3H, s), 2.76 (1H, ddd, J=10.3, 8.3, 1.8 Hz), 2.19 (1H, m), 2.08 (1H, m), 1.91 (1H, m), 1.75 (2H, m), 1.45 (1H, m), 0.78 (3H, s), 0.64 (3H, s).

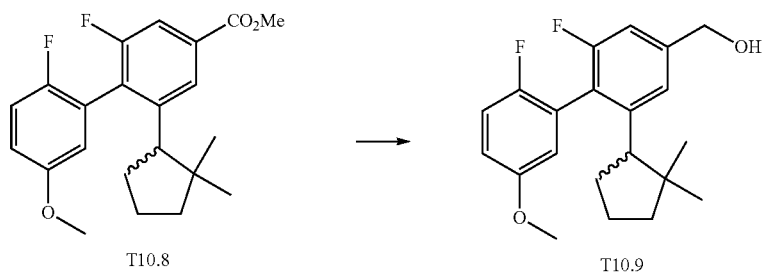

T10.8     T10.9

-continued

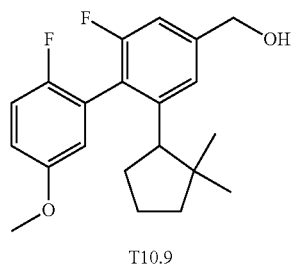

T10.9

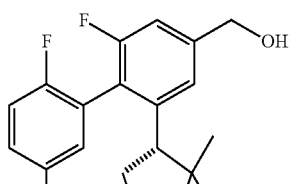

or

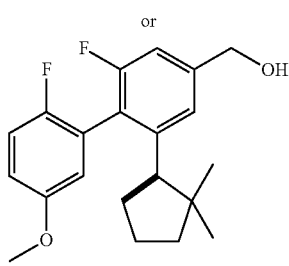

T10.10 and T10.11

(2-((1S)-2,2-Dimethylcyclopentyl)-2',6-difluoro-5'-(methyloxy)-1,1'-biphenyl-4-yl)methanol and (2-((1R)-2,2-dimethylcyclopentyl)-2',6-difluoro-5'-(methyloxy)-1,1'-biphenyl-4-yl)methanol (T10.10 and T10.11)

To a cooled solution of T10.8 (0.7036 g, 1.879 mmol) in dry THF (15 mL) at 0° C. was added LAH (1.0 M in THF (4 mL, 4.0 mmol)) dropwise. Upon complete addition, the reaction was maintained at 0° C. and monitored by TLC and LCMS. After 45 minutes, 1N NaOH was added to quench the reaction (gas evolution occurred). The resulting mixture was extracted three times with EtOAc. The combined organic layers were dried over anhydrous MgSO$_4$, filtered, and concentrated. The residue was purified by flash chromatography (SiO$_2$ gel 60, eluted with 0%-50% EtOAc in hexanes). Fractions containing the desired product were combined and concentrated to provide a colorless oil that solidified as T10.9 (300.5 mg, 46% yield). $^1$H NMR (400 MHz, CDCl$_3$) δ ppm 7.16 (1H, s), 7.10 (2H, m), 6.92 (1H, m), 6.77 (1H, dd, J=5.9, 3.1 Hz), 4.74 (2H, s), 3.81 (3H, m), 2.73 (1H, ddd, J=10.3, 8.3, 1.8 Hz), 2.17 (1H, m), 2.04 (1H, m), 1.87 (1H, m), 1.73 (3H, m), 1.42 (1H, m), 0.78 (3H, s), 0.64 (3H, s). Chiral separation of T10.9 was accomplished on a CHIRALCEL®® OJ column (2% IPA in hexane) to provide T10.10 (peak 1) and T10.11 (peak 2). Both enantiomers were used to synthesize example compounds, and both enantiomers gave active compounds.

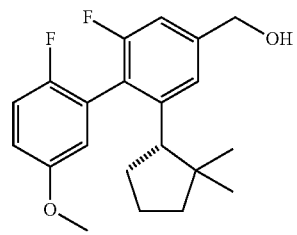

or

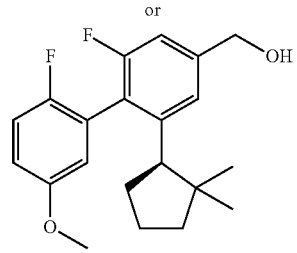

T10.10

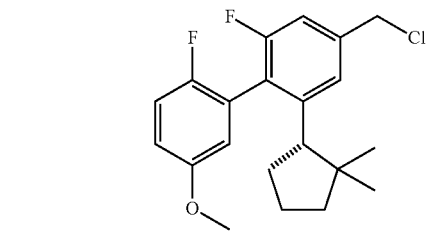

or

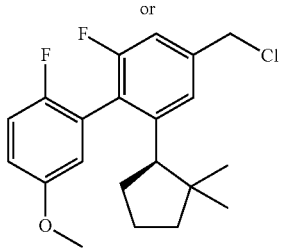

T10.12

4-(Chloromethyl)-2-((1S)-2,2-dimethylcyclopentyl)-2',6-difluoro-5'-(methyloxy)-1,1'-biphenyl or 4-(chloromethyl)-2-((1R)-2,2-dimethylcyclopentyl)-2',6-difluoro-5'-(methyloxy)-1,1'-biphenyl (T10.12)

To a solution of T10.10 (0.1171 g, 0.338 mmol) (derived from peak one of the chiral separation of T10.9) in dry DCM (4.5 mL) and dry DMF (0.03 mL) was added thionyl chloride (0.05 mL, 0.685 mmol) at 0° C. The resulting solution was warmed to room temperature and monitored with TLC and LCMS. After 19 hours, the reaction was concentrated and then purified by silica gel flash chromatography (0-5% EtOAc/hexane) to afford T10.12 (99.7 mg, 81% yield). $^1$H NMR (400 MHz, CDCl$_3$) δ ppm 7.18 (1H, d, J=1.6 Hz), 7.13 (2H, m), 6.95 (1H, m), 6.77 (1H, dd, J=5.9, 3.1 Hz), 4.68 (2H, m), 3.84 (3H, m), 2.73 (1H, ddd, J=10.3, 8.3, 1.8 Hz), 2.18 (1H, m), 2.01 (1H, m), 1.88 (1H, m), 1.73 (3H, m), 1.44 (1H, m), 0.78 (3H, s), 0.64 (3H, s).

Intermediate T11

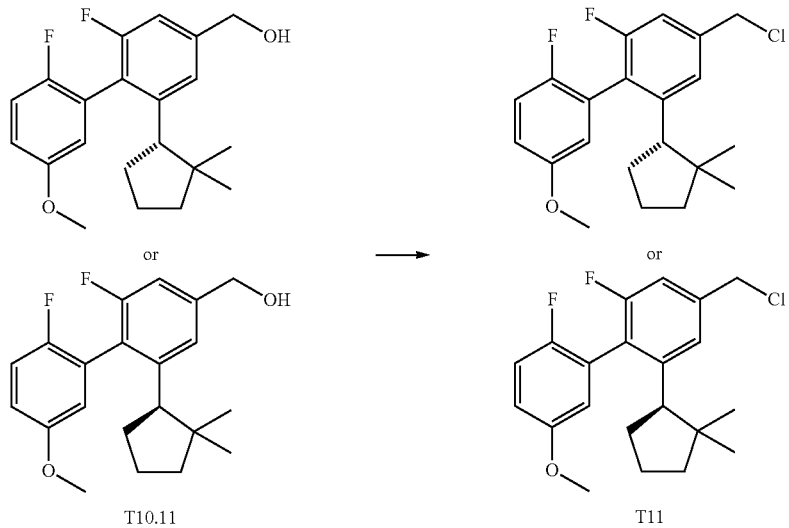

4-(Chloromethyl)-2-((1R)-2,2-dimethylcyclopentyl)-2',6-difluoro-5'-(methyloxy)-1,1'-biphenyl or 4-(chloromethyl)-2-((1S)-2,2-dimethylcyclopentyl)-2',6-difluoro-5'-(methyloxy)-1,1'-biphenyl (T11)

To a solution of T10.11 (0.1492 g, 0.431 mmol) (derived from peak two of the chiral separation of T10.9) in dry DCM (4.5 mL) and dry DMF (0.035 mL) was added thionyl chloride (0.063 mL, 0.864 mmol) at 0° C. The resulting solution was warmed to room temperature and monitored with TLC and LCMS. After 20 hours, the reaction was concentrated then purified by silica gel flash chromatography (0-5% EtOAc/hexane) to afford T11 that was used as is without further purification (117.1 mg, 74% yield). $^1$H NMR (400 MHz, CDCl$_3$) δ ppm 7.18 (1H, d, J=1.6 Hz), 7.13 (2H, m), 6.95 (1H, m), 6.81 (1H, m), 4.68 (2H, m), 3.85 (3H, m), 2.73 (1H, ddd, J=10.3, 8.3, 1.8 Hz), 2.18 (1H, m), 2.01 (1H, m), 1.80 (1H, d, J=4.3 Hz), 1.72 (3H, m), 1.46 (1H, m), 0.78 (3H, s), 0.64 (3H, s).

Intermediate T12

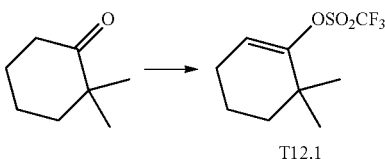

6,6-Dimethyl-1-cyclohexen-1-yl trifluoromethanesulfonate (T12.1)

To a solution of 2,2-dimethylcyclohexanone (2.00 g, 16 mmol, commercially available from Sigma-Aldrich, St. Louis, Mo., USA) in THF (35 mL) at −78° C. was added dropwise LDA (9 mL, 18 mmol, 2.0 M). The resulting solution was stirred at −78° C. for 20 minutes. A solution of N-phenyl-bis(trifluoromethane sulfonimide) (6 g, 17 mmol) in THF (15 mL) was then slowly added at −78° C. The reaction mixture was then allowed to warm to 23° C. over 3 hours. And then was concentrated in vacuo. The reaction was diluted with brine and extracted three times with EtOAc. The combined organic layers were dried over anhydrous MgSO$_4$ and filtered. The organic solvent was removed under reduced pressure, and the product was purified on silica gel (0-10% EtOAc in hexanes) to provide T12.1 as a clear oil (4.1 g, 100%).

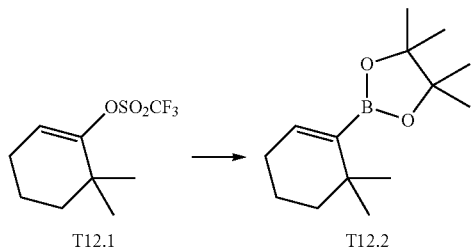

2-(6,6-Dimethyl-1-cyclohexen-1-yl)-4,4,5,5-tetramethyl-1,3,2-dioxaborolane (T12.2)

A mixture of triphenylphosphine (0.4 g, 2 mmol), potassium phenolate (3 g, 22 mmol), 4,4,5,5-tetramethyl-2-(4,4,5,5-tetramethyl-1,3,2-dioxaborolan-2-yl)-1,3,2-dioxaborolane (4 g, 16 mmol) and T12.1 (4.1 g, 16 mmol) in toluene (79 mL, 16 mmol) was degassed using N$_2$. Dichlorobis(triphenylphosphine)palladium(II) (0.6 g, 0.8 mmol) was then added, and the reaction mixture was further degassed with N$_2$. The reaction was then stirred at 50° C. for 3.5 hours. The reaction was then diluted with brine and extracted three times with EtOAc. The combined organic layers were dried over anhydrous MgSO₄, filtered, and the organic solvent was removed under reduced pressure. The product was then purified on silica gel (0-10% EtOAc in hexanes) to yield T12.2 as a colorless oil (3.00 g, 80% yield).

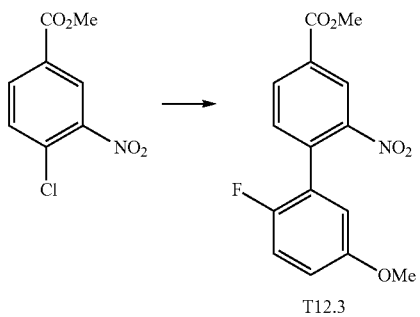 [SMILES: COC(=O)c1ccc(Cl)c([N+](=O)[O-])c1 ; COC(=O)c1ccc(-c2cc(OC)ccc2F)c([N+](=O)[O-])c1]

T12.3

Methyl 2'-fluoro-5'-(methyloxy)-2-nitro-1,1'-biphenyl-4-carboxylate (T12.3)

To a stirred solution of methyl 4-chloro-3-nitrobenzoate (10.00 g, 46 mmol, commercially available from TCI) in DMF (15.00 mL, 194 mmol) at 23° C. was added 2-fluoro-5-methoxyphenylboronic acid (12 g, 70 mmol) (commercially available from Sigma-Aldrich, St. Louis, Mo., USA), potassium carbonate (19 g, 139 mmol), and then tetrakis(triphenylphosphine)palladium (2.1 g, 1.9 mmol). The mixture was heated at 90° C. for 18 hours and then cooled to room temperature. The reaction was diluted with brine and extracted three times with EtOAc. The organic layers were combined, dried over anhydrous MgSO₄, and filtered. The organic solvent was removed under reduced pressure and the residue was purified on silica gel (0-40% EtOAc in hexanes) to yield T12.3 as a colorless oil (14.00 g, 99% yield).

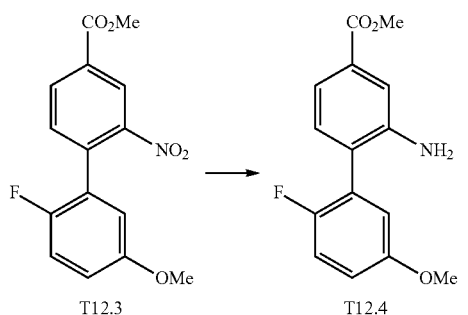 [SMILES: COC(=O)c1ccc(-c2cc(OC)ccc2F)c([N+](=O)[O-])c1 ; COC(=O)c1ccc(-c2cc(OC)ccc2F)c(N)c1]

T12.3    T12.4

Methyl 2-amino-2'-fluoro-5'-(methyloxy)-1,1'-biphenyl-4-carboxylate (T12.4)

To a stirred solution of T12.3 (1.00 g, 3.3 mmol) in AcOH (2.00 mL, 35 mmol) at 23° C. was added DME (15.00 mL, 144 mmol), EtOH (10.00 mL), and then tin(II) chloride (4.7 g, 25 mmol). The mixture was heated at 60° C. for 17 hours and then was cooled to room temperature. The reaction was diluted with water and extracted three times with EtOAc. The organic layers were combined, dried over anhydrous magnesium sulfate, and filtered. The organic solvent was removed under reduced pressure to give the T12.4 (0.90 g, 100% yield).

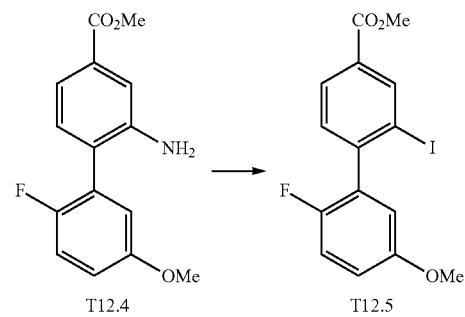 [SMILES: COC(=O)c1ccc(-c2cc(OC)ccc2F)c(N)c1 ; COC(=O)c1ccc(-c2cc(OC)ccc2F)c(I)c1]

T12.4    T12.5

Methyl 2'-fluoro-2-iodo-5'-(methyloxy)-1,1'-biphenyl-4-carboxylate (T12.5)

To a stirred solution of T12.4 (1.00 g, 3.6 mmol) in DME (10.00 mL, 96 mmol) at 23° C. was added sulfuric acid (0.19 mL, 3.6 mmol) in water (8 mL), followed by dropwise addition of a solution of sodium nitrite (0.38 g, 5.4 mmol) in water (2 mL) at 0° C. over 30 minutes. The resulting mixture was stirred for 20 minutes and then a solution of sodium iodide (3.0 g, 20 mmol) in water (7 mL) was added at 0° C. The resulting mixture was stirred for 1 hour and then quenched with sodium thiosulfate and extracted three times with diethyl ether. The organic layers were combined, dried over anhydrous magnesium sulfate and filtered. The organic solvent was removed under reduced pressure, and the product was purified on silica gel (0-40% EtOAc in hexanes) to yield a colorless solid T12.5 (0.820 g, 58% yield).

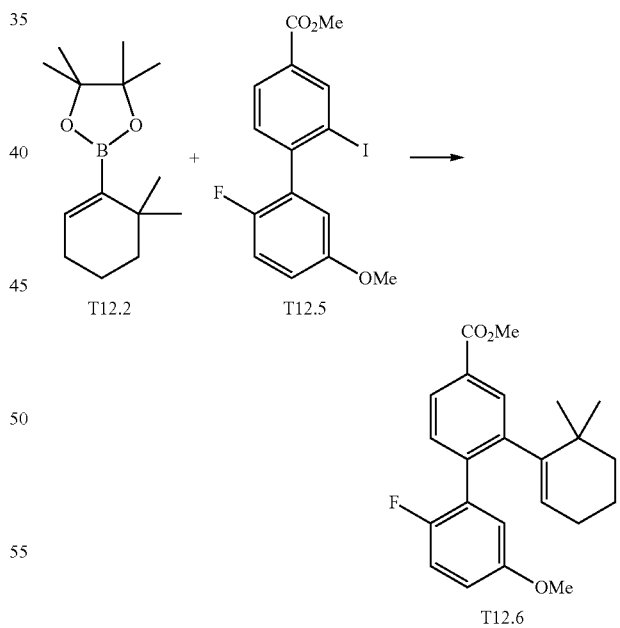

T12.2    T12.5

T12.6

Methyl 2-(6,6-dimethyl-1-cyclohexen-1-yl)-2'-fluoro-5'-(methyloxy)-1,1'-biphenyl-4-carboxylate (T12.6)

To a stirred solution of T12.5 (0.750 g, 1.9 mmol) in DMF (4.00 mL, 52 mmol) at 23° C. was added T12.2 (0.92 g, 3.9 mmol), potassium carbonate (0.81 g, 5.8 mmol), and then tetrakis(triphenylphosphine)palladium (0.22 g, 0.19 mmol). The mixture was heated to 90° C., stirred for 24 hours, and then cooled to room temperature. The reaction was diluted with brine and extracted three times with EtOAc. The organic layers were combined, dried over anhydrous magnesium sulfate and filtered. The organic solvent was removed under reduced pressure, and the residue was purified on silica gel (0-10% EtOAc in hexanes) to yield T12.6 as a colorless oil (0.34 g, 48% yield).

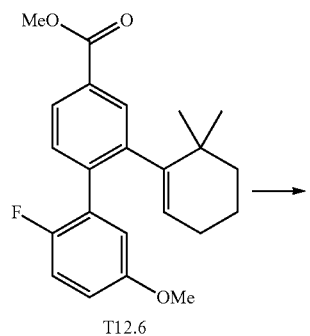

T12.6

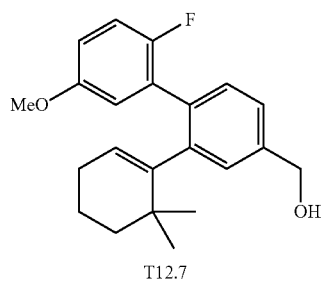

T12.7

(2-(6,6-Dimethyl-1-cyclohexen-1-yl)-2'-fluoro-5'-(methyloxy)-1,1'-biphenyl-4-yl)methanol (T12.7)

To a stirred solution of T12.6 (0.300 g, 0.814 mmol) in THF (0.0587 g, 0.814 mmol) at 0° C. was added LAH (1.63 mL, 1.63 mmol, 1.0M). The resulting mixture was stirred for 4.5 hours. Next, 1N NaOH(aq) was added to quench the mixture. The reaction was extracted three times with EtOAc. The combined organic layers were dried over anhydrous magnesium sulfate and filtered. The organic solvent was removed under reduced pressure, and the product was purified on silica gel (0-20% EtOAc in hexanes) to yield T12.7 as a colorless oil (0.250 g, 90.2% yield).

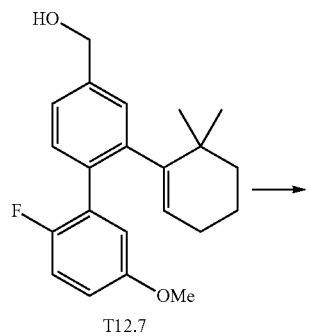

T12.7

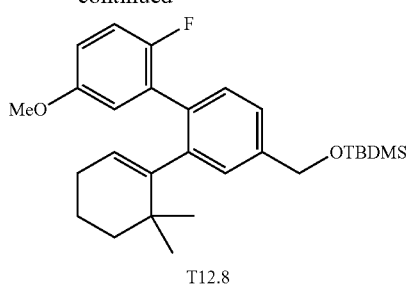

T12.8

(((2-(6,6-Dimethyl-1-cyclohexen-1-yl)-2'-fluoro-5'-(methyloxy)-1,1'-biphenyl-4-yl)methyl)oxy)(1,1-dimethylethyl)dimethylsilane (T12.8)

To a stirred solution of T12.7 (0.160 g, 0.5 mmol) in DCM (10.00 mL, 155 mmol) at 23° C. was added tert-butyldimethylsilyl chloride (0.09 mL, 0.6 mmol), followed by TEA (0.08 mL, 0.6 mmol) and DMAP (0.006 g, 0.05 mmol). The mixture was stirred for one hour and then was concentrated in vacuo. The residue was purified on silica gel (0-5% EtOAc in hexanes) to yield T12.8 as a colorless oil (0.198 g, 93% yield).

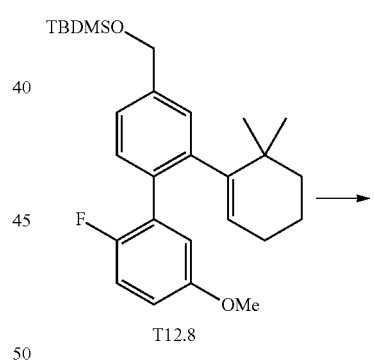

T12.8

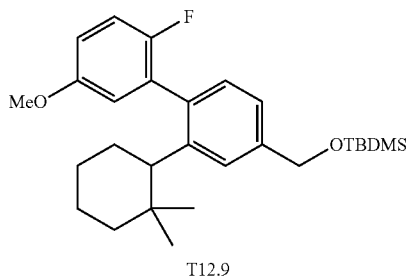

T12.9

(((2-(2,2-Dimethylcyclohexyl)-2'-fluoro-5'-(methyloxy)-1,1'-biphenyl-4-yl)methyl)oxy)(1,1-dimethylethyl)dimethylsilane (T12.9)

To a stirred solution of T12.8 (0.090 g, 0.20 mmol) in EtOAc (2.00 mL, 20 mmol) at 23° C. was added palladium on carbon (0.0021 g, 0.020 mmol). The mixture was stirred under an atmosphere of hydrogen (0.00040 g, 0.20 mmol) for 4 days. The reaction mixture was then filtered and the filtrate was concentrated in vacuo to yield T12.9 as a colorless oil (0.090 g, 100% yield)

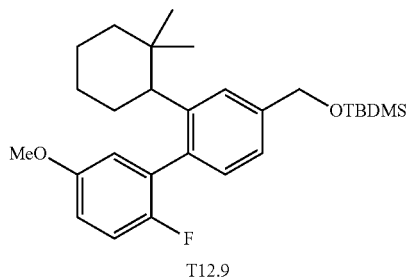

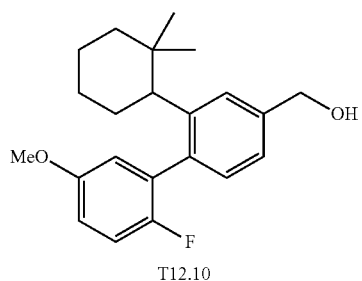

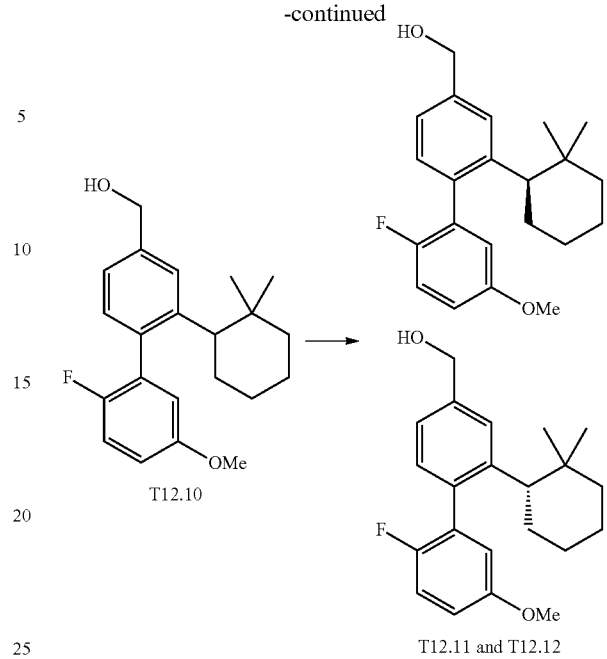

(2-((1R)-2,2-Dimethylcyclohexyl)-2'-fluoro-5'-(methyloxy)-1,1'-biphenyl-4-yl)methanol and (2-((1S)-2,2-dimethylcyclohexyl)-2'-fluoro-5'-(methyloxy)-1,1'-biphenyl-4-yl)methanol (T12.11 and T12.12)

To a stirred mixture of T12.9 (0.090 g, 0.20 mmol) in MeOH (0.99 mL, 0.20 mmol) was added PPTS (0.0050 g, 0.020 mmol). The mixture was stirred for 4.5 hours and then was concentrated in vacuo. The residue was purified on silica gel (0-15% EtOAc in hexanes) to yield T12.10 as a colorless oil (0.067 g, 99% yield). Chiral separation of T12.10 was accomplished on CHIRALCEL® OD (3% IPA in hexane) to provide T12.11 (peak one) and T12.12 (peak two). Both enantiomers were used to synthesize example compounds, and both enantiomers gave active example compounds. However, the enantiomer corresponding to peak 2 provided the most active example compounds.[1]

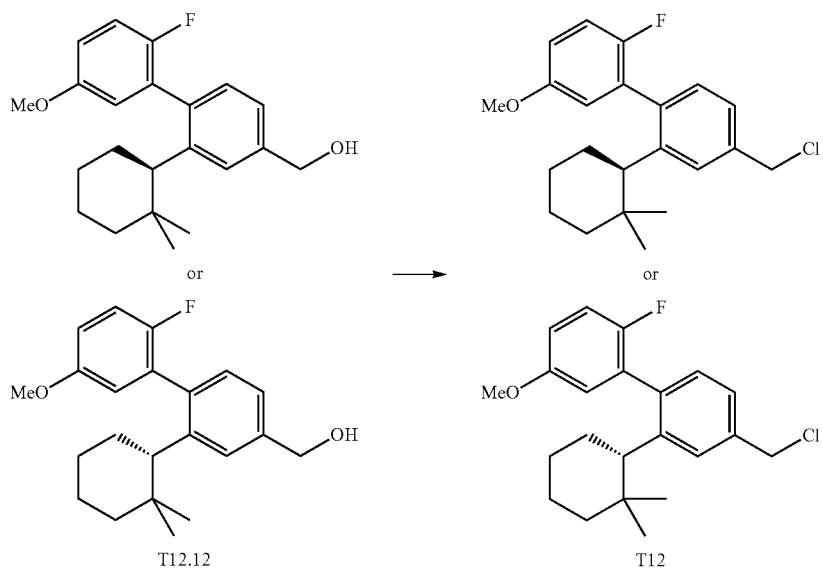

4-(Chloromethyl)-2-((1R)-2,2-dimethylcyclohexyl)-2'-fluoro-5'-(methyloxy)-1,1'-biphenyl or 4-(chloromethyl)-2-((1S)-2,2-dimethylcyclohexyl)-2'-fluoro-5'-(methyloxy)-1,1'-biphenyl (T12).

To a stirred solution of T12.12 (0.035 g, 0.10 mmol) (from peak two from the chiral separation of T12.10) in DCM (2.00 mL, 31 mmol) at 23° C. was added DMF (0.00079 mL, 0.010 mmol) followed by thionyl chloride (0.015 mL, 0.20 mmol). The mixture was stirred for one hour and then concentrated in vacuo. The residue was purified on silica gel (0-10% EtOAc in hexanes) to yield T12 as a colorless oil (0.025 g, 68% yield).

Intermediate T13

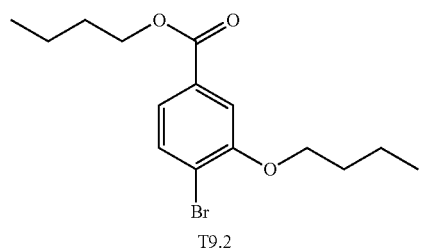

T9.2

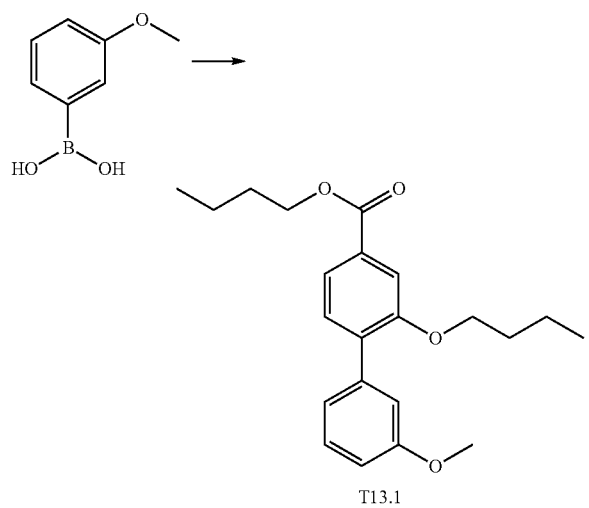

T13.1

Propyl 2-(butyloxy)-3'-(methyloxy)-1,1'-biphenyl-4-carboxylate (T13.1)

To a flask charged with 3-methoxyphenylboronic acid (1.02 g, 6.69 mmol, commercially available from Sigma-Aldrich, St. Louis, Mo., USA), tetrakis(triphenylphosphine) palladium (0) (0.258 g, 0.223 mmol), cesium fluoride (0.411 mL, 11.1 mmol), and T9.2 (0.734 g, 2.23 mmol), was added DME (20 mL). The resulting mixture was then heated at 90° C. overnight. The reaction was allowed to cool and was then filtered and concentrated. The residue was purified by silica gel column chromatography (0 to 10% EtOAc/hexanes) yielding T13.1 (795 mg, 99% yield).

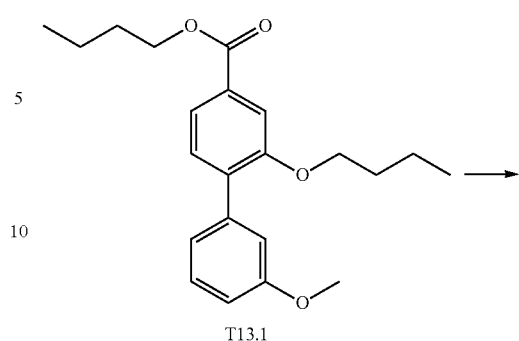

T13.1

T13.2

(2-(Butyloxy)-3'-(methyloxy)-1,1'-biphenyl-4-yl)methanol (T13.2)

To a mixture of T13.1 (795 mg, 2230 μmol) and THF (10 mL) at 0° C. was added LAH (1.0 M solution in THF (3345 μL, 3345 μmol)). The reaction was stirred for one hour and then carefully diluted with water and extracted with EtOAc. The combined organic layers were washed with brine and then dried over sodium sulfate, filtered, and concentrated to provide T13.2 (530 mg, 83.0% yield).

T13.2

T13

2-(Butyloxy)-4-(chloromethyl)-3'-(methyloxy)-1,1'-biphenyl (T13)

To a stirred solution of T13.2 (530 mg, 1851 μmol) in DCM (15 mL) at 23° C. was added thionyl chloride (270 μL, 3702 μmol). The resulting mixture was stirred overnight and was then concentrated and then purified by silica gel chromatography (0 to 10% EtOAc/hexanes) to provide T13.

Intermediate T14

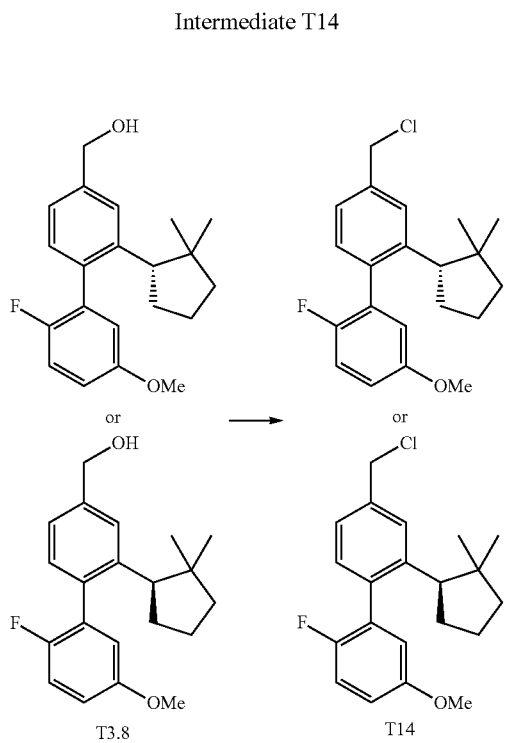

4-(Chloromethyl)-2-((1S)-2,2-dimethylcyclopentyl)-2'-fluoro-5'-(methyloxy)-1,1'-biphenyl or 4-(chloromethyl)-2-((1R)-2,2-dimethylcyclopentyl)-2'-fluoro-5'-(methyloxy)-1,1'-biphenyl (T14)

Thionyl chloride (1.5 mL, 20 mmol) was added to a stirred solution of T3.8 (3.280 g, 10.0 mmol) (derived from peak one from the chiral separation of T3.7) in DCM (100 mL, 10.0 mmol) and DMF (0.77 mL, 10.0 mmol) at 0° C. The resulting mixture was stirred at room temperature for 2 hours. The reaction mixture was then concentrated in vacuo and purified on silica gel (0-10% EtOAc in hexane) to give the desired product T14 (3.00 g, 87% yield) as a clear oil.

Intermediate T15

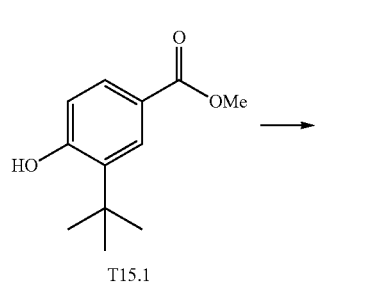

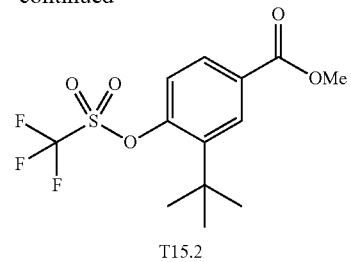

Methyl 3-tert-butyl-4-(trifluoromethylsulfonyloxy) benzoate (T15.2)

To a stirred solution of methyl 3-tert-butyl-4-hydroxybenzoate (T15.1)(available from Apin Chemical Ltd, United Kingdom)(0.100 g, 0.48 mmol) in DCM (10 mL, 155 mmol) at 23° C., was added TEA (0.080 mL, 0.58 mmol) and DMAP (0.0059 g, 0.048 mmol), followed by triflic anhydride (0.097 mL, 0.58 mmol). The dark solution was stirred at room temperature and monitored by TLC and LC-MS. After 19 hours, the reaction was concentrated in vacuo. The residue was then purified by flash chromatography (SiO$_2$ gel 60, eluted with 0%-10% EtOAc in hexanes). Fractions containing the desired product were combined and concentrated to provide T15.2 as a colorless oil (0.16 g, 98%). MS ESI (pos.) m/e: 341.0 (M+H)$^+$.

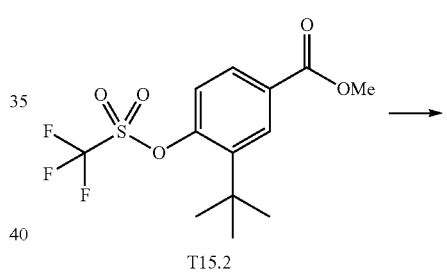

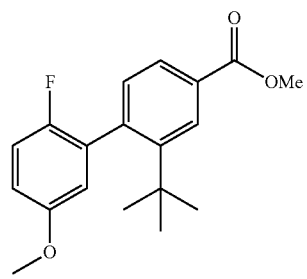

Methyl 2-(1,1-dimethylethyl)-2'-fluoro-5'-(methyloxy)-1,1'-biphenyl-4-carboxylate (T15.3)

To a stirred solution of T15.2 (0.100 g, 0.29 mmol) in DMF (2.00 mL, 26 mmol) at 23° C., was added 2-fluoro-5-methoxyphenylboronic acid (commercially available from Sigma-Aldrich, St. Louis, Mo., USA) (0.100 g, 0.59 mmol), potassium carbonate (0.12 g, 0.88 mmol), followed by tetrakis(triphenylphosphine)palladium (0.034 g, 0.029 mmol). The mixture was heated to 100° C. After 2 hours, the reaction was cooled to room temperature and diluted with water. The mixture was extracted with EtOAc (3×50 mL) and concentrated in vacuo. The residue was then purified by flash chromatography (SiO$_2$ gel 60, eluted with 0%-15% EtOAc in hexanes). Fractions containing the desired product were combined and concentrated to provide T15.3 as a colorless oil (0.85 g, 71%). MS ESI (pos.) m/e: 317.2 (M+H)$^+$.

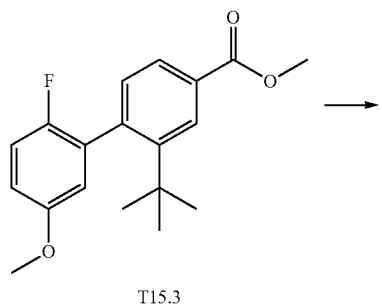

T15.3

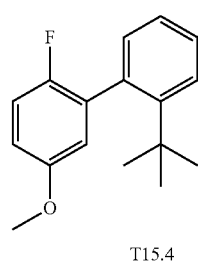

T15.4

(2-(1,1-Dimethylethyl)-2'-fluoro-5'-(methyloxy)-1,1'-biphenyl-4-yl)methanol (T15.4)

To a cooled solution of T15.3 (0.85 g, 2.69 mmol) in dry THF (10.0 mL, 2.69 mmol) at 0° C., was added LAH (1.0 M solution in THF (6.0 mL, 6.0 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL). The combined organic layers were dried over MgSO$_4$, filtered, and concentrated in vacuo. The residue was then purified by flash chromatography (SiO$_2$ gel 60, eluted with 0%-40% EtOAc in hexanes). Fractions containing the desired product were combined and concentrated to provide T15.4 as a colorless oil (0.56 g, 72%). MS ESI (pos.) m/e: 311.2 (M+Na)$^+$.

T.15.4

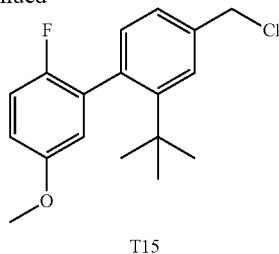

T15

4-(Chloromethyl)-2-(1,1-dimethylethyl)-2'-fluoro-5'-(methyloxy)-1,1'-biphenyl (T15)

To a cooled solution of T15.4 (0.56 g, 1.93 mmol) in dry DCM (3.60 mL, 1.93 mmol) at 0° C., was added thionyl chloride (0.40 mL, 5.48 mmol) dropwise. Upon complete addition of thionyl chloride, the mixture was allowed to warm to room temperature. After 18 hours, the reaction was concentrated in vacuo. The residue was then purified by flash chromatography (SiO$_2$ gel 60, eluted with 0%-15% EtOAc in hexanes). Fractions containing the desired product were combined and concentrated to provide T15 as a colorless solid (0.44 g, 74%). $^1$H NMR (500 MHz, CDCl$_3$) δ ppm 7.56 (1H, s), 7.25 (5H, dd, J=7.7, 1.6 Hz), 7.01 (2H, m), 6.86 (1H, dd, J=9.0, 3.2 Hz), 6.77 (1H, dd, J=5.9, 3.2 Hz), 4.65 (3H, s), 3.79 (3H, s), 1.24 (9H, s).

Intermediate T16

T15.2

T16.1

Methyl 2-(1,1-dimethylethyl)-3'-(methyloxy)-1,1'-biphenyl-4-carboxylate (T16.1)

A dry round bottom flask containing T15.2 (1.40 g, 4.1 mmol), 3-methoxyphenylboronic acid (commercially available from Sigma-Aldrich, St. Louis, Mo., USA) (1.27 g, 8.34 mmol), tetrakis(triphenylphosphine)palladium (0.49 g, 0.42 mmol), and potassium carbonate (1.71 g, 12.36 mmol) was evacuated and backfilled three times with argon. Dry DMF (12.0 mL) was added via syringe under argon, and the mixture was then heated to 100° C. and monitored by TLC. After 2 hours, the reaction was cooled to room temperature and diluted with water. The mixture was extracted three times with EtOAc and then concentrated under reduced pressure. The residue was then purified by flash chromatography (SiO₂ gel 60, eluted with 0%-15% EtOAc in hexanes). Fractions containing the desired product were combined and concentrated to provide T16.1 as a colorless oil (1.01, 82%). MS ESI (pos.) m/e: 299.2 (M+H)⁺.

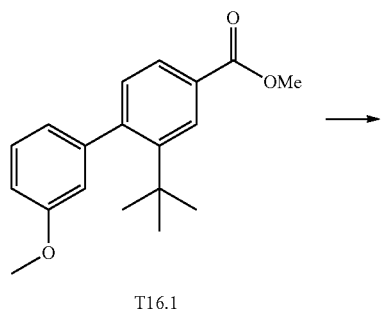

T16.1

(2-(1,1-Dimethylethyl)-3'-(methyloxy)-1,1'-biphenyl-4-yl)methanol (T16.2)

To a cooled solution of T16.1 (1.01 g, 3.38 mmol) in dry THF (10.0 mL) at 0° C., was added LAH (1.0 M solution in THF (6.7 mL, 6.7 mmol)). Upon complete addition, the reaction was allowed to warm to room temperature and monitored by TLC and LCMS. Upon completion, 1N NaOH (5 mL) was carefully added to quench the reaction.

The resulting solution was extracted with EtOAc (3×10 mL), dried over MgSO₄, filtered and concentrated in vacuo. The residue was then purified by flash chromatography (SiO₂ gel 60, eluted with 0%-40% EtOAc in hexanes). Fractions containing the desired product were combined and concentrated to provide T16.2 as a colorless oil (0.82, 90%). ¹H NMR (500 MHz, CDCl₃) δ ppm 7.56 (1H, s), 7.29 (1H, t, J=3.8 Hz), 7.24 (1H, m), 7.07 (1H, d, J=7.6 Hz), 6.93 (2H, m), 6.86 (1H, d, J=1.5 Hz), 4.77 (2H, s), 3.85 (3H, s), 1.72 (1H, s), 1.26 (9H, s).

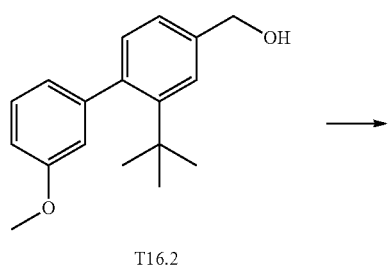

T16.2

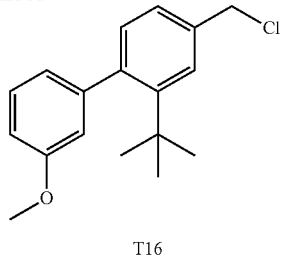

T16

4-(Chloromethyl)-2-(1,1-dimethylethyl)-3'-(methyloxy)-1,1'-biphenyl (T16)

A dry, round bottom flask containing T16.2 (0.82 g, 3.04 mmol) and DCM (8.5 mL) was cooled to 0° C. After 15 minutes, thionyl chloride (1.50 mL, 20.56 mmol) was carefully added dropwise at 0° C. Upon complete addition of thionyl chloride, the mixture was allowed to warm to room temperature and stirred overnight. After 25 hours, the reaction was concentrated under reduced pressure. The residue was then purified by flash chromatography (SiO₂ gel 60, eluted with 0%-15% EtOAc in hexanes). Fractions containing the desired product were combined and concentrated to provide T16 as a colorless oil (0.82, 93%). ¹H NMR (500 MHz, CDCl₃) δ ppm 7.53 (1H, d, J=1.7 Hz), 7.28 (3H, m), 7.03 (1H, d, J=7.8 Hz), 6.90 (3H, m), 4.65 (2H, s), 3.82 (3H, s), 1.23 (9H, s).

Intermediates T17A and T17B

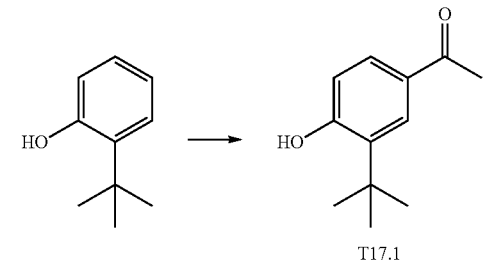

T17.1

1-(3-(1,1-Dimethylethyl)-4-hydroxyphenyl)ethanone (T17.1)

To a dry, round bottom flask was added aluminum chloride (4.402 g, 33.0 mmol). The flask was then cooled to −45° C. After 10 minutes, dry toluene (80 mL) was added followed by dropwise addition of 2-tert-butylphenol (5.00 mL, 32.7 mmol) (commercially available from Sigma-Aldrich, St. Louis, Mo., USA). The mixture was stirred and maintained at −4° C. After 1.5 hours, acetyl chloride (2.40 mL, 33.8 mmol) was carefully added dropwise. The mixture was allowed to warm to room temperature and monitored with TLC and LC-MS. After 18 hours, the mixture was slowly poured onto crushed ice. This mixture was stirred at room temperature and the crystals were collected by filtration. The light yellow solid was identified as T17.1 (4.2589 g, 68%). MS ESI (pos.) m/e: 193.1 (M+H)⁺.

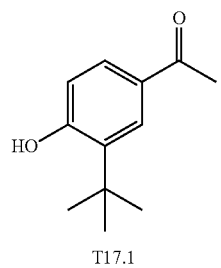

T17.1

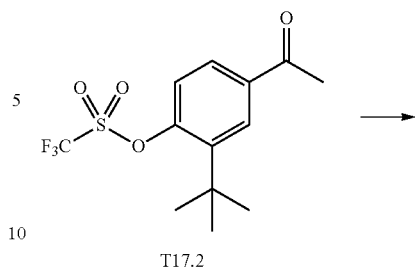

T17.2

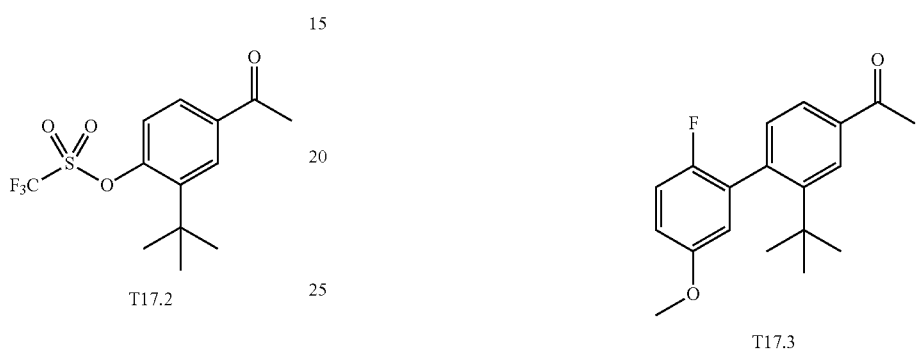

T17.2

T17.3

4-Acetyl-2-(1,1-dimethylethyl)phenyl trifluoromethanesulfonate (T17.2)

To a stirred solution of T17.1 (2.0006 g, 10.41 mmol) in dry DCM (37 mL) was added TEA (3.0 mL, 21.57 mmol) and DMAP (0.1309 g, 1.071 mmol). After 20 minutes, N-phenyl-trifluoromethanesulfonimide (5.5846 g, 15.63 mmol) was added in portions. Upon complete addition, the solution was stirred at room temperature and monitored with TLC and LC-MS. After 4.5 hours, the reaction was diluted with brine and extracted three times with DCM. After drying over anhydrous magnesium sulfate and filtration, the solvent was removed under reduced pressure. The residue was purified by silica gel flash chromatography (0-20% EtOAc/hexane) to yield T17.2 (3.0227 g, 90% yield). MS ESI (pos.) m/e: 325.1 (M+H)$^+$.

1-(2-(1,1-Dimethylethyl)-2'-fluoro-5'-(methyloxy)-1,1'-biphenyl-4-yl)ethanone (T17.3)

A dry round bottom containing T17.2 (3.0227 g, 9.3202 mmol), 2-fluoro-5-methoxyphenylboronic acid (2.4005 g, 14.125 mmol) (commercially available from Sigma-Aldrich, St. Louis, Mo., USA), tetrakis(triphenylphosphine)palladium (1.0853 g, 0.93920 mmol), and potassium carbonate (3.9996 g, 28.940 mmol) was evacuated and backfilled three times with argon. Dry DMF (25 mL) was added via syringe under argon, then the mixture was heated to 100° C. and monitored with TLC. After 3 hours, the reaction was cooled to room temperature, then diluted with water. The mixture was extracted three times with EtOAc then concentrated under reduced pressure. The residue was purified by silica gel flash chromatography (0-15% EtOAc/hexane) to yield T17.3 (2.6053 g, 93% yield). MS ESI (pos.) m/e: 301.1 (M+H)$^+$.

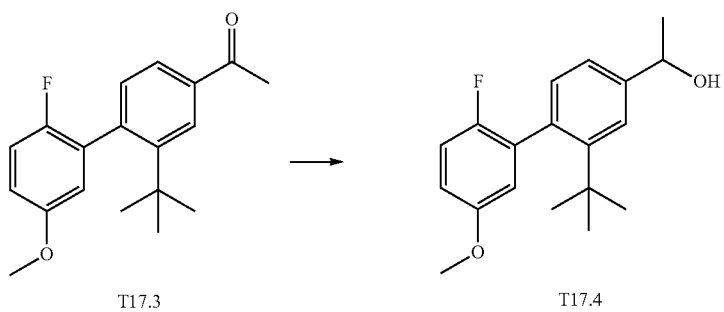

T17.3

T17.4

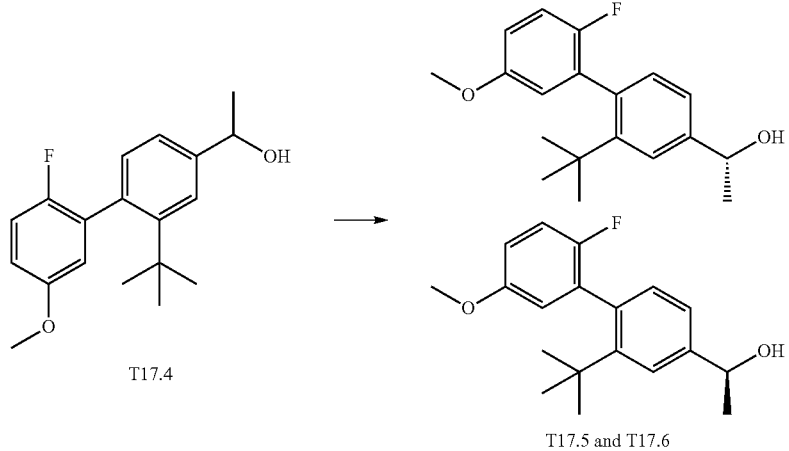

1-(2-(1,1-Dimethylethyl)-2'-fluoro-5'-(methyloxy)-1,1'-biphenyl-4-yl)ethanol (T17.4)

To a dry round bottom flask containing T17.3 (2.5921 g, 8.630 mmol) was added a premixed solution of dry MeOH (10 mL) and dry DCM (10 mL). After stirring at 0° C. for about 15 minutes, sodium borohydride (0.6632 g, 17.53 mmol) was carefully added at 0° C. Upon complete addition, the reaction was allowed to warm to room temperature. After 2 hours, the reaction was cooled in an ice bath, then carefully quenched with water and extracted three times with DCM. After drying over anhydrous magnesium sulfate and filtration, the organic solvent was removed under reduced pressure. The residue was purified by silica gel flash chromatography (0-15% EtOAc/hexane) to yield T17.4 (2.5329 g, 97% yield). MS ESI (pos.) m/e: 285.1 (M–H$_2$O)$^+$. Chiral separation of T17.4 was accomplished using SFC with 9 g/min MeOH (0.6% DEA)+81 g/min CO$_2$ on a 250×30 mm OD-H column. The outlet pressure of the system was set to 140 bar, temperature at 25° C. and detector wavelength was 220 nm. Sample was dissolved to 54 mg/mL in MeOH and separations on 13.5 mg injections were performed at a rate of one injection per 1.65 minutes to provide T7.5 (peak 1) and T17.6 (peak 2).

4-((1S)-1-Chloroethyl)-2-(1,1-dimethylethyl)-2'-fluoro-5'-(methyloxy)-1,1'-biphenyl or 4-((1R)-1-chloroethyl)-2-(1,1-dimethylethyl)-2'-fluoro-5'-(methyloxy)-1,1'-biphenyl (T17A)

A dry, round bottom flask containing T17.6 (1.0221 g, 3.380 mmol) was evacuated and backfilled with argon. Dry DCM (14 mL) was added under argon, and the homogeneous solution was cooled to 0° C. After 15 minutes, thionyl chloride (1.0 mL, 13.71 mmol) was carefully added dropwise at 0° C. Upon complete addition of thionyl chloride, the mixture was allowed to warm to room temperature and stirred overnight. After 2.5 hours, the reaction was concentrated under reduced pressure. The residue was purified by silica gel flash chromatography (0-15% EtOAc/hexane) to yield T17A (744.7 mg, 69% yield). MS ESI (pos.) m/e: 338.2 (M+H$_2$O)$^+$.

4-((1S)-1-Chloroethyl)-2-(1,1-dimethylethyl)-2'-fluoro-5'-(methyloxy)-1,1'-biphenyl or 4-((1R)-1-chloroethyl)-2-(1,1-dimethylethyl)-2'-fluoro-5'-(methyloxy)-1,1'-biphenyl (T17B)

This compound is prepared from T17.5 using the same procedure described above with respect to T17A.

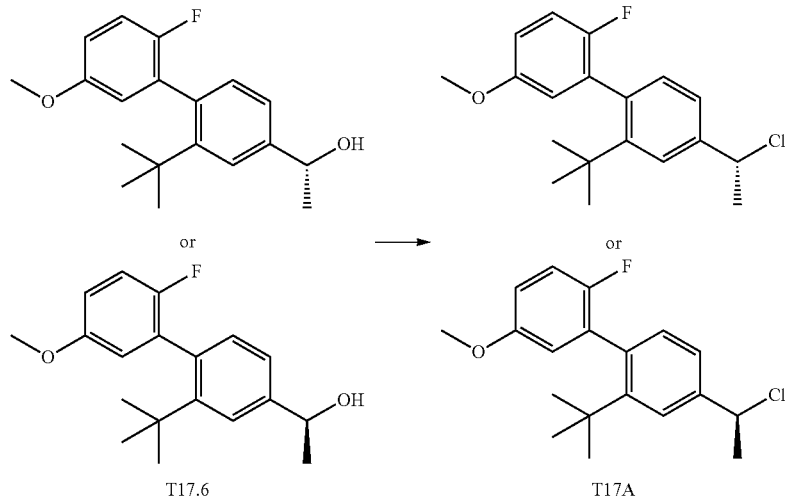

Intermediates T18A and T18B

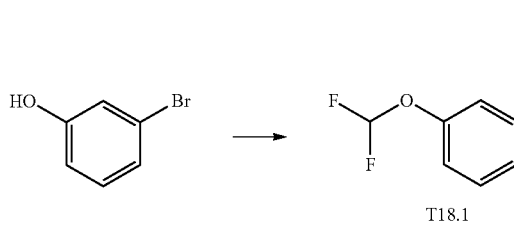

T18.1

1-Bromo-3-(difluoromethoxy)benzene (T18.1)

To a solution of 3-bromophenol (commercially available from Sigma-Aldrich, St. Louis, Mo., USA) (1.28 g, 7.39 mmol) in DMF (12.0 mL) was added sodium 2-chloro-2,2-difluoroacetate (commercially available from Sigma-Aldrich, St. Louis, Mo., USA) (2.82 g, 18.49 mmol) and $Cs_2CO_3$ (4.82 g, 14.79 mmol). The reaction mixture was heated at 100° C. Gas was released from the reaction so care should be taken. After 2 hours, the reaction was cooled to room temperature then diluted with EtOAc, washed with water and then brine and re-extracted three times with EtOAc. The combined organic layers were dried over magnesium sulfate and then filtered, concentrated, and purified with silica gel chromatography (0-5% EtOAc in hexanes) to yield T18.1 as an oil that was used without further purification (yield 61%).

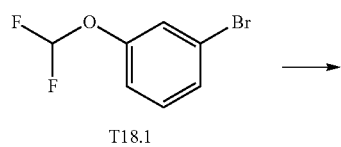

T18.1

2-(3-(Difluoromethoxy)phenyl)-4,4,5,5-tetramethyl-1,3,2-dioxaborolane (T18.2)

A stirred mixture of T18.1 (1.00 g, 4.50 mmol), bis(pinacolato)diboron (1.26 g, 4.95 mmol), potassium acetate (1.34 g, 13.70 mmol), and dichloro[1,1'-bis(diphenylphosphino)ferrocene]dichloride palladium(II) DCM adduct (0.17 g, 0.23 mmol) in dry 1,4-dioxane (10.0 mL) was purged three times with argon and placed under vacuum three times. The mixture was heated to 100° C. and monitored with LC-MS and TLC. After 21 hours, the reaction was cooled to room temperature and then filtered through Celite® filter aid. The organic solvent was removed under reduced pressure, and the residue was purified on silica gel (0-10% EtOAc in hexanes) to yield T18.2 as a colorless oil (0.41 g, 34%). $^1$H NMR (400 MHz, $CDCl_3$) δ ppm 7.67 (1H, d, J=7.4 Hz), 7.56 (1H, d, J=2.3 Hz), 7.41 (1H, m), 7.22 (1H, dd, J=7.8, 2.3 Hz), 6.73 (1H, t, J=74 Hz), 1.36 (12H, s).

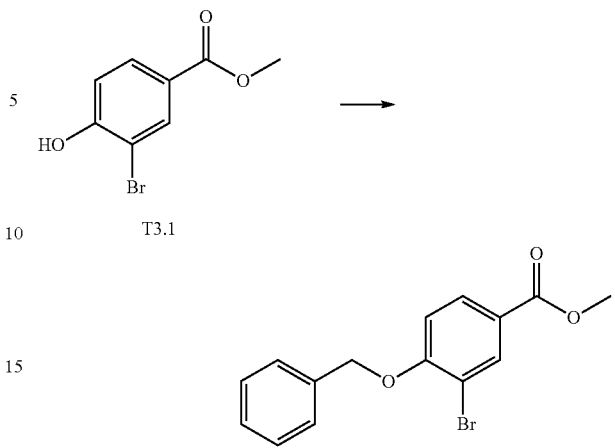

Methyl 4-(benzyloxy)-3-bromobenzoate (T18.3)

To a solution of T3.1 (53.2 g, 230 mmol) in DMSO (45.0 mL) was added 1-(bromomethyl)benzene (35.6 mL, 299 mmol). After cooling in an ice water bath, $Cs_2CO_3$ (128 g, 391 mmol) was carefully added to the mixture, and the mixture was allowed to warm to room temperature. After overnight stirring, the mixture was diluted with water and extracted three times with EtOAc. The organic layers were combined and then washed with brine. After drying over anhydrous magnesium sulfate and filtration, the organic solvent was removed under reduced pressure to yield T18.3 as a white solid.

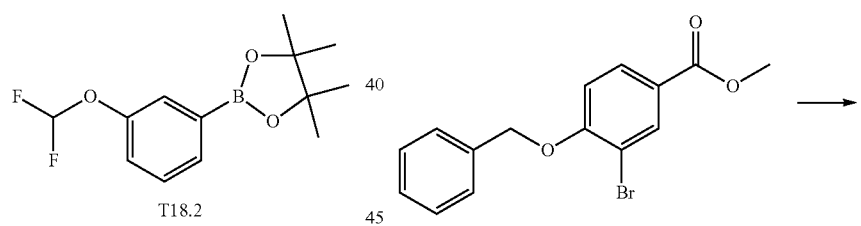

Methyl 4-(benzyloxy)-3-(5,5-dimethylcyclopent-1-enyl)benzoate (T18.4)

A stirred mixture of T18.3 (3.75 g, 11.66 mmol), ground S-Phos (0.96 g, 2.33 mmol), palladium acetate (0.26 g, 1.17 mmol), and potassium phosphate, tribasic (6.19 g, 29.17 mmol) in DMF (28.0 mL) and water (1.50 mL) was purged three times with argon and placed under vacuum three times.

Before heating, 2-(5,5-dimethylcyclopent-1-enyl)-4,4,5,5-tetramethyl-1,3,2-dioxaborolane (T2.2) (3.11 g, 13.99 mmol) was added via syringe, then the mixture was heated to 75° C. After 21 hours (black solution), the reaction was cooled to room temperature, diluted with water, and extracted three times with EtOAc. The combined organic layers were washed twice with brine. After drying over anhydrous sodium sulfate and filtration, the organic solvent was removed under reduced pressure. The residue was purified on silica gel (0-10% EtOAc in hexanes) to yield T18.4 as a colorless oil (3.03 g, 77%). MS ESI (pos.) m/e: 337.0 (M+H)$^+$.

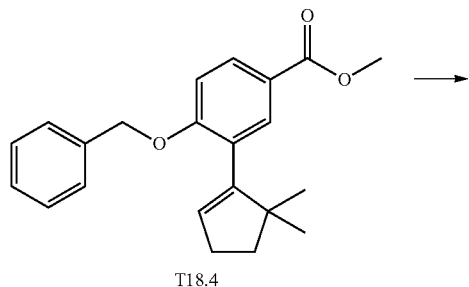

T18.4

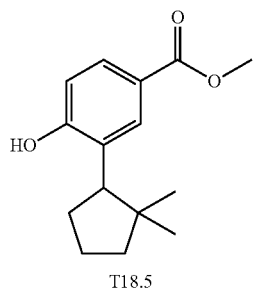

T18.5

Methyl 3-(2,2-dimethylcyclopentyl)-4-hydroxybenzoate (T18.5)

To a flask containing T18.4 (3.03 g, 9.0 mmol) in MeOH (25.0 mL) was added palladium, 10% wt. on activated carbon (0.48 g, 0.45 mmol). After purging, the mixture was stirred under an atmosphere of hydrogen at room temperature. The reaction was monitored with TLC and LC-MS. After 27.5 hours, the reaction was filtered through Celite® filter aid. After concentration, the residue was purified on silica gel using 0-50% EtOAc in hexanes to yield T18.5 as a colorless oil that solidified (1.99 g, 89%). $^1$H NMR (400 MHz, CDCl$_3$) δ ppm 7.91 (1H, d, J=2.3 Hz), 7.79 (1H, dd, J=8.4, 2.2 Hz), 6.82 (1H, d, J=8.2 Hz), 5.54 (1H, s), 3.90 (3H, s), 3.17 (1H, dd, J=10.4, 8.0 Hz), 2.17 (1H, m), 2.04 (1H, m), 1.92 (1H, m), 1.81 (1H, m), 1.68 (2H, m), 1.06 (3H, s), 0.72 (3H, s).

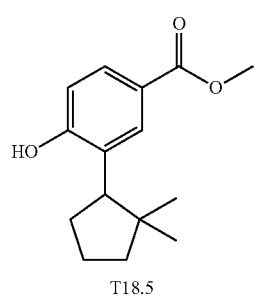

T18.5

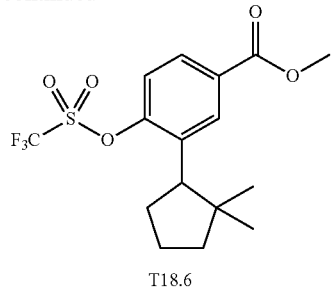

T18.6

Methyl 3-(2,2-dimethylcyclopentyl)-4-(trifluoromethylsulfonyloxy)benzoate (T18.6)

To a stirred solution of T18.5 (0.93 g, 3.74 mmol) in dry DCM (10.0 mL) was added TEA (1.1 mL, 7.89 mmol) and 4-(dimethylamino)pyridine (46.2 mg, 0.378 mmol). After about 20 minutes, N-phenyl-bis(trifluoromethanesulfonimide) (1.61 g, 4.51 mmol) was added in portions. Upon complete addition, the solution was stirred at room temperature and monitored with TLC and LC-MS. After 3.5 hours, the reaction was diluted with brine and extracted three times with DCM. After drying over anhydrous magnesium sulfate and filtration, the organic solvent was removed under reduced pressure and the residue was purified with silica gel chromatography using 0-10% EtOAc in hexanes to yield T18.6 as a colorless oil (1.21 g, 85%). $^1$H NMR (400 MHz, CDCl$_3$) δ ppm 8.08 (1H, d, J=2.2 Hz), 7.95 (1H, dd, J=8.6, 2.2 Hz), 7.35 (1H, d, J=8.6 Hz), 3.95 (3H, s), 3.21 (1H, dd, J=9.8, 8.4 Hz), 2.14 (2H, m), 1.95 (1H, m), 1.86 (1H, m), 1.69 (2H, m), 1.02 (3H, s), 0.70 (3H, s).

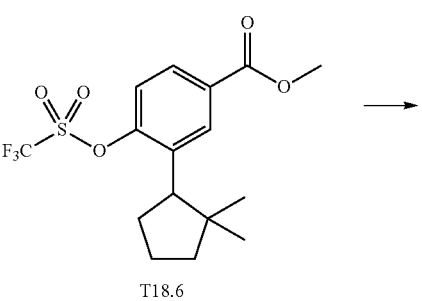

T18.6

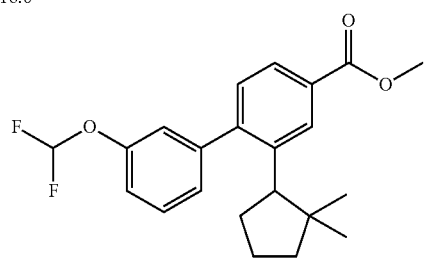

T18.7

Methyl 3'-((difluoromethyl)oxy)-2-(2,2-dimethylcyclopentyl)-1,1'-biphenyl-4-carboxylate (T18.7)

A stirred mixture of T18.6 (0.48 g, 1.26 mmol), ground S-Phos (104.8 mg, 0.255 mmol), palladium acetate (29.1 mg, 0.130 mmol), and potassium phosphate tribasic (0.6727 g, 3.17 mmol) in dry DMF (5.0 mL) was purged with argon and placed under vacuum (repeated three times). Before heating, T18.2 (0.512 g, 1.89 mmol) was added via syringe, and then the mixture was heated to 75° C. After 16 hours, the reaction was cooled to room temperature, diluted with water and extracted three times with EtOAc. The combined organic layers were washed twice with brine. After drying over anhydrous sodium sulfate and filtration, the organic solvent was removed under reduced pressure. The residue was purified on silica gel (0-20% EtOAc in hexanes) to yield T18.7 as a colorless oil (308.9 mg, 65%). $^1$H NMR (500 MHz, CDCl$_3$) δ ppm 8.11 (1H, d, J=1.7 Hz), 7.90 (1H, dd, J=7.9, 1.8 Hz), 7.44 (1H, m), 7.28 (1H, m), 7.16 (2H, m), 7.07 (1H, s), 6.57 (1H, t, J=75 Hz), 3.97 (3H, s), 3.10 (1H, t, J=9.4 Hz), 2.13 (2H, m), 1.90 (1H, m), 1.73 (1H, m), 1.61 (1H, m), 1.38 (1H, ddd, J=12.6, 9.4, 7.6 Hz), 0.75 (3H, s), 0.58 (3H, s).

mL, 1.70 mmol) dropwise. Upon complete addition, the reaction was maintained at 0° C. and was monitored by TLC and LCMS. After 45 minutes, 1N NaOH was added to quench the reaction. The resulting solution was extracted three times with EtOAc. After drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to yield T18.8 as a colorless oil (261.6 mg, 92%). $^1$H NMR (500 MHz, CDCl$_3$) δ ppm 7.41 (2H, m), 7.26 (1H, m), 7.21 (1H, m), 7.14 (2H, m), 7.05 (1H, s), 6.55 (1H, t, J=75 Hz), 4.76 (2H, m), 3.07 (1H, dd, J=10.3, 8.6 Hz),

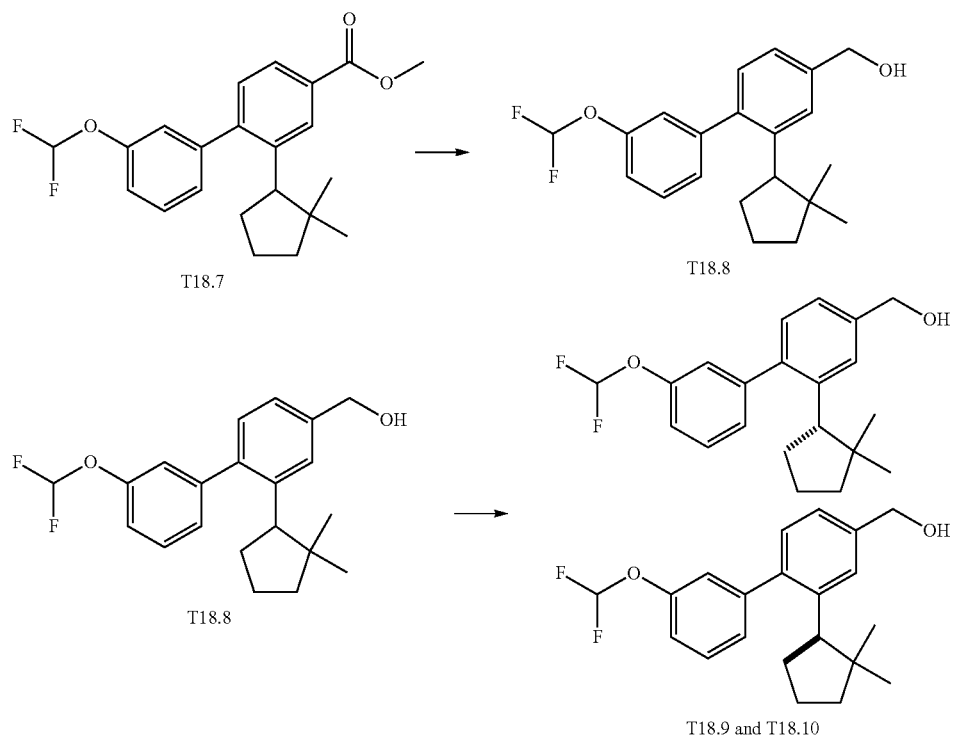

(3'-((Difluoromethyl)oxy)-2-(2,2-dimethylcyclopentyl)-1,1'-biphenyl-4-yl)methanol (T18.8)

To a cooled solution of T18.7 (308.9 mg, 0.82 mmol) in dry THF (8.0 mL) at 0° C. was added LAH, 1.0 M in THF (1.70

2.10 (2H, m), 1.86 (1H, m), 1.71 (1H, m), 1.55 (1H, ddd, J=12.7, 8.1, 4.9 Hz), 1.37 (1H, ddd, J=12.5, 9.5, 7.6 Hz), 0.75 (3H, s), 0.60 (3H, s). Chiral separation of T18.8 was accomplished on a CHIRALCEL® OD column (3% IPA in hexane) to provide T18.9 (peak 1) and T18.10 (peak 2).

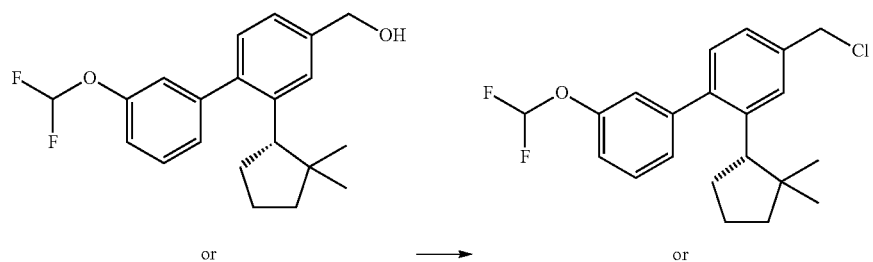

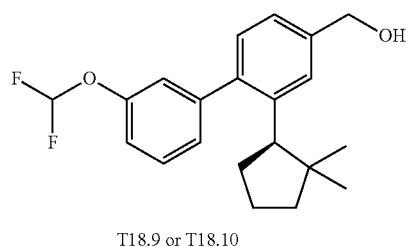

T18.9 or T18.10

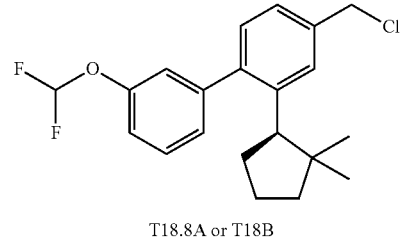

T18.8A or T18B

4-(Chloromethyl)-3'-((difluoromethyl)oxy)-2-((1S)-2,2-dimethylcyclopentyl)-1,1'-biphenyl or 4-(chloromethyl)-3'-((difluoromethyl)oxy)-2-((1R)-2,2-dimethylcyclopentyl)-1,1'-biphenyl (T18A or T18B)

To a solution of T18.9 or T18.10 (112.7 mg, 0.325 mmol) in dry DCM (4.0 mL) and dry DMF (0.03 mL) was added thionyl chloride (0.06 mL, 0.823 mmol) at 0° C. The resulting solution was warmed to room temperature and monitored with TLC and LCMS. After 45 minutes, the reaction was concentrated then purified by silica gel flash chromatography (0-5% EtOAc/hexane) to yield T18A or T18B (99.5 mg, 84%). $^1$H NMR (400 MHz, CDCl$_3$) δ ppm 7.42 (2H, m), 7.25 (1H, d, J=2.0 Hz), 7.19 (1H, m), 7.11 (2H, dd, J=7.8, 2.0 Hz), 7.03 (1H, s), 6.54 (1H, t, J=74 Hz), 4.66 (2H, m), 3.04 (1H, dd, J=10.4, 8.4 Hz), 2.14 (2H, m), 1.88 (1H, m), 1.73 (1H, m), 1.54 (2H, ddd, J=12.7, 8.2, 4.9 Hz), 1.41 (1H, m), 0.73 (3H, s), 0.56 (3H, s).

Intermediate T19

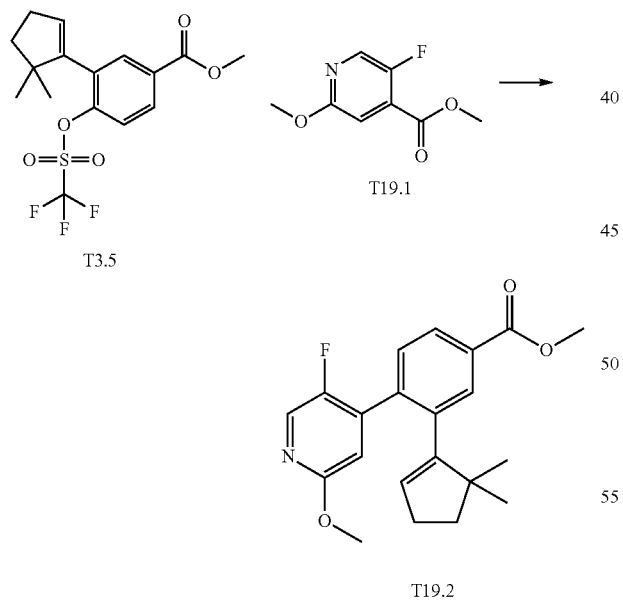

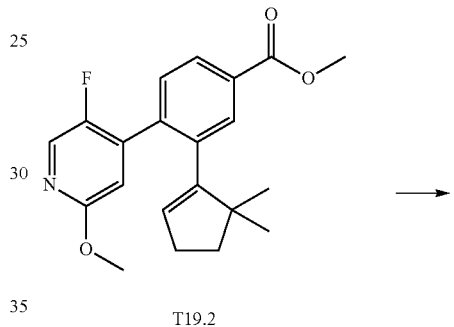

T19.2

Methyl 3-(5,5-dimethylcyclopent-1-enyl)-4-(5-fluoro-2-methoxypyridin-4-yl)benzoate (T19.2)

To a flask with methyl 3-(5,5-dimethylcyclopent-1-enyl)-4-(trifluoromethylsulfonyloxy)benzoate T3.5 (404 mg, 1068 μmol) was added Pd(PPh$_3$)$_4$ (123 mg, 107 μmol), potassium carbonate (443 mg, 3203 μmol), 5-fluoro-2-methoxypyridin-4-ylboronic acid T19.1 (456 mg, 2669 μmol, commercially available from Asymchem). The mixture was then degassed, and DMF (3 mL) was added. The reaction was stirred overnight at 87° C. and worked up with EtOAc and water. Silica gel chromatography (0-50% EtOAc/Hexanes) afforded methyl 3-(5,5-dimethylcyclopent-1-enyl)-4-(5-fluoro-2-methoxypyridin-4-yl)benzoate T19.2 (295 mg. 78%).

(3-(5,5-Dimethylcyclopent-1-enyl)-4-(5-fluoro-2-methoxypyridin-4-yl)phenyl)methanol (T19.3)

To methyl 3-(5,5-dimethylcyclopent-1-enyl)-4-(5-fluoro-2-methoxypyridin-4-yl)benzoate T19.2 (295 mg, 830 μmol) was added THF. The mixture was cooled to 0° C., and LAH (1660 μL, 1660 μmol) was added dropwise. The reaction was stirred at room temperature for 1 hour, and was quenched with water and a small amount of Rochelle's salt solution. Purification with silica gel chromatography afforded (3-(5,5-dimethylcyclopent-1-enyl)-4-(5-fluoro-2-methoxypyridin-4-yl)phenyl)methanol T19.3 (201 mg) as an oil (74%).

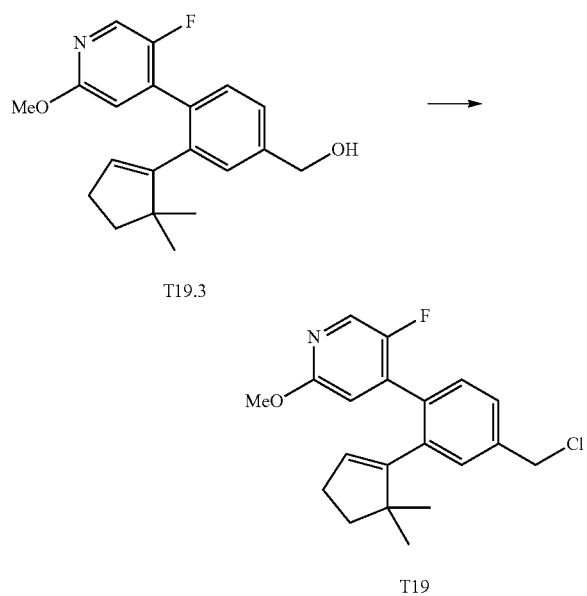

T19.3

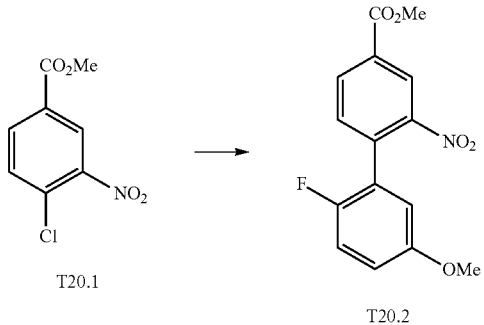 [SMILES: COC(=O)c1ccc(Cl)c([N+](=O)[O-])c1 ; COC(=O)c1ccc(-c2cc(OC)ccc2F)c([N+](=O)[O-])c1]

T19

4-(4-(Chloromethyl)-2-(5,5-dimethylcyclopent-1-enyl)phenyl)-5-fluoro-2-methoxypyridine (T19)

To (3-(5,5-dimethylcyclopent-1-enyl)-4-(5-fluoro-2-methoxypyridin-4-yl)phenyl)methanol T19.3 (34.5 mg, 105 μmol) was added DCM (1.1 mL) and DMF (8.2 μL, 105 μmol) followed by thionyl chloride (15 μL, 211 μmol) in an ice bath. The reaction was then stirred at room temperature for 1 hour. The reaction was concentrated and directly purified on silica gel to afford 4-(4-(chloromethyl)-2-(5,5-dimethylcyclopent-1-enyl)phenyl)-5-fluoro-2-methoxypyridine T19 (36 mg) as an oil (99%).

Intermediate T20

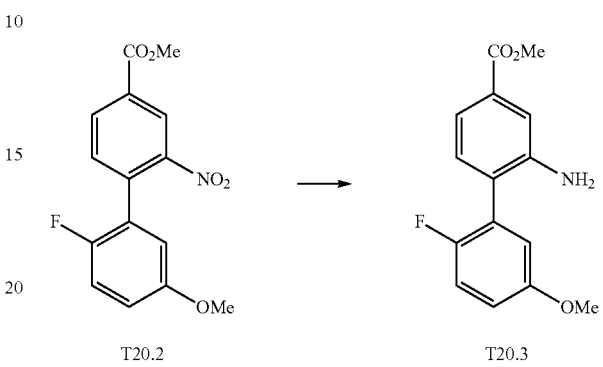

T20.1   T20.2

Methyl 2'-fluoro-5'-(methyloxy)-2-nitro-1,1'-biphenyl-4-carboxylate (T20.2)

To a stirred solution of methyl 4-chloro-3-nitrobenzoate T20.1 (10.00 g, 46 mmol) (commercially available from Sigma-Aldrich, St. Louis, Mo., USA) in DMF (15.00 mL, 194 mmol) at 23° C. was added 2-fluoro-5-methoxyphenylboronic acid (12 g, 70 mmol) (commercially available from Sigma-Aldrich, St. Louis, Mo., USA), and potassium carbonate (19 g, 139 mmol). Tetrakis(triphenylphosphine)palladium (2.1 g, 1.9 mmol) was then added to the mixture, and the mixture was heated at 90° C. for 18 hours. The mixture was then cooled to room temperature, diluted with brine and extracted three times with EtOAc. After drying over anhydrous magnesium sulfate and filtering, the organic solvent was removed under reduced pressure and the product was purified on silica gel (0-40% EtOAc in hexanes) to yield T20.2 as a colorless oil (14.00 g, 99% yield).

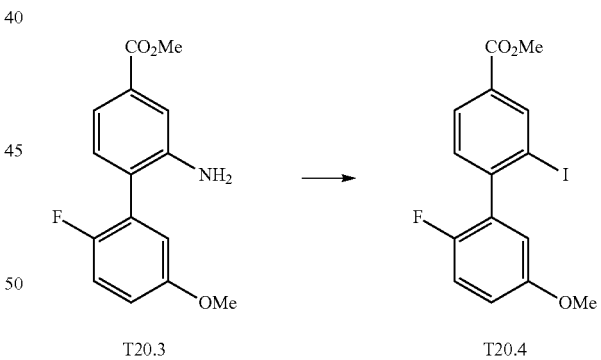

T20.2   T20.3

Methyl 2-amino-2'-fluoro-5'-(methyloxy)-1,1'-biphenyl-4-carboxylate (T20.3)

To a stirred solution of T20.2 (1.00 g, 3.3 mmol) in acetic acid (2.00 mL, 35 mmol) at 23° C. was added DME (15.00 mL, 144 mmol), EtOH (10.00 mL), followed by tin(II) chloride (4.7 g, 25 mmol). The mixture was heated at 60° C. for 17 hours. After which, the reaction was cooled to room temperature. The reaction was diluted with water and extracted three times with EtOAc. After drying over anhydrous magnesium sulfate and filtering, the organic solvent was removed under reduced pressure to give the product T20.3 (0.90 g, 100% yield).

T20.3   T20.4

Methyl 2'-fluoro-2-iodo-5'-(methyloxy)-1,1'-biphenyl-4-carboxylate (T20.4)

To a stirred solution of T20.3 (1.00 g, 3.6 mmol) in DME (10.00 mL, 96 mmol) at 23° C. was added sulfuric acid (0.19 mL, 3.6 mmol) in water (8 mL), followed by dropwise addition of a solution of sodium nitrite (0.38 g, 5.4 mmol) in water (2 mL) at 0° C. over 30 minutes. The reaction was then stirred for 20 minutes. To the mixture was added a solution of sodium iodide (3.0 g, 20 mmol) in water (7 mL) at 0° C. The resulting mixture was then stirred for 1 hour. The reaction was quenched with sodium thiosulfate and extracted three times with diethyl ether. After drying over anhydrous magnesium sulfate and filtering, the organic solvent was removed under reduced pressure and the product was purified on silica gel (0-40% EtOAc in hexanes) to yield a colorless solid T20.4 (0.820 g, 58% yield).

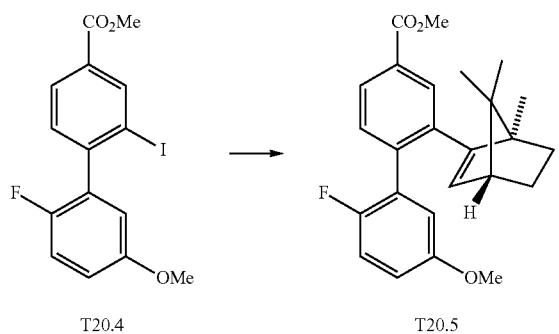 [SMILES: COC(=O)c1ccc(-c2cc(OC)ccc2F)c(I)c1 ; COC(=O)c1ccc(-c2cc(OC)ccc2F)c(C2=C[C@H]3CC[C@]2(C)C3(C)C)c1]

Methyl 2'-fluoro-5'-(methyloxy)-2-((1R,4R)-1,7,7-trimethylbicyclo[2.2.1]hept-2-en-2-yl)-1,1'-biphenyl-4-carboxylate (T20.5)

To a stirred solution of T20.4 (0.200 g, 0.52 mmol) in DMF (4.00 mL, 52 mmol) at 23° C. was added (1S,4R)-1,7,7-trimethylbicyclo[2.2.1]hept-2-en-2-ylboronic acid (0.19 g, 1.0 mmol, commercially available from Combi-Blocks, Cat. No. BB-2567), potassium carbonate (0.21 g, 1.6 mmol), and then tetrakis(triphenylphosphine)palladium (0.060 g, 0.052 mmol). The mixture was heated at 90° C. for 19 hours and then cooled to room temperature. The reaction was diluted with brine and extracted three times with EtOAc. After drying over anhydrous magnesium sulfate and filtering, the organic solvent was removed under reduced pressure and the product was purified on silica gel (0-10% EtOAc in hexanes) to yield T20.5 as a colorless oil (0.165 g, 81% yield).

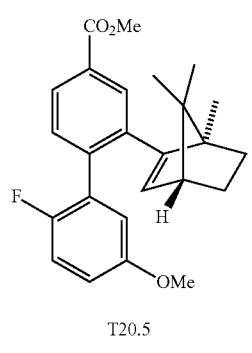

T20.5

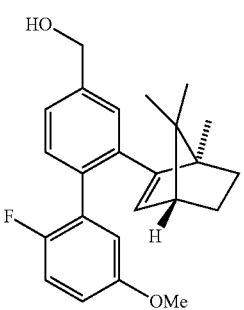

T20.6

(2'-Fluoro-5'-(methyloxy)-2-((1R,4R)-1,7,7-trimethylbicyclo[2.2.1]hept-2-en-2-yl)-1,1'-biphenyl-4-yl)methanol (T20.6)

To a stirred solution of T20.5 (0.050 g, 0.1 mmol) in THF (4 mL) at 0° C. was added LAH in THF (0.3 mL, 0.3 mmol, 1.0M). The resulting mixture was stirred for 2 hours. 1N NaOH(aq) was added to the mixture to quench it. The reaction was then extracted three times with EtOAc. After drying over anhydrous magnesium sulfate and filtering, the organic solvent was removed under reduced pressure and the product was purified on silica gel (0-20% EtOAc in hexanes) to yield T20.6 as a colorless oil (0.035 g, 75% yield).

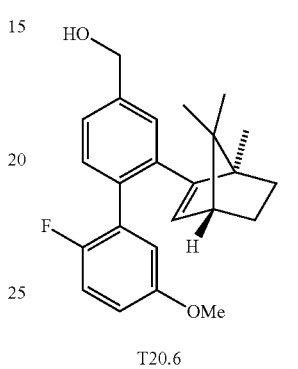

T20.6

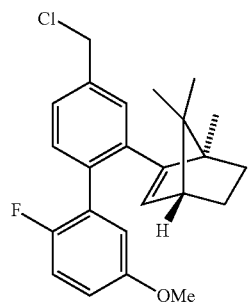

T20

4'-(Chloromethyl)-6-fluoro-2'-((1R,4R)-1,7,7-trimethylbicyclo[2.2.1]hept-2-en-2-yl)-1,1'-biphenyl-3-yl methyl ether (T20)

To a stirred solution of T20.6 (0.035 g, 0.10 mmol) in DCM (2.00 mL) and DMF (0.01 mL) at 0° C. was added thionyl chloride (0.01 g, 0.10 mmol). The reaction was then stirred at room temperature for 2 hours and was then concentrated in vacuo. The resulting product was then purified on silica gel (0-10% EtOAc in hexanes) to yield T20 as a colorless oil (0.035 g, 95% yield).

Intermediate T21

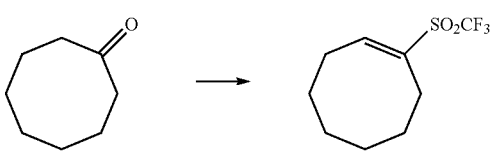

T21.1    T21.2

1-Cycloocten-1-yl trifluoromethyl sulfone (T21.2)

To a stirred solution of cyclooctanone (T21.1) (5.00 g, 40 mmol) (commercially available from Sigma-Aldrich, St. Louis, Mo., USA) in THF (35 mL) at −78° C. was added LDA (22 mL, 44 mmol, 2.0M). The resulting solution was stirred at −78° C. for 20 minutes. Then, a solution of N-phenyl-bis (trifluoromethane sulfonimide) (16 g, 44 mmol) in THF (15 mL) was added slowly at −78° C. The reaction mixture was allowed to warm to 23° C. over 3 hours and then was concentrated in vacuo. The residue was diluted with water and extracted three times with hexanes. After drying over anhydrous magnesium sulfate and filtering, the organic solvent was removed under reduced pressure and the product was then purified on silica gel (0-5% EtOAc in hexanes) to yield T21.2 as a colorless oil (10.00 g, 98% yield).

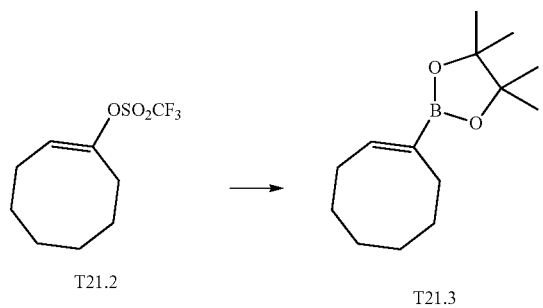

2-(1-Cycloocten-1-yl)-4,4,5,5-tetramethyl-1,3,2-dioxaborolane (T21.3)

A mixture of triphenylphosphine (1 g, 4 mmol), potassium phenolate (7 g, 54 mmol), 4,4,5,5-tetramethyl-2-(4,4,5,5-tetramethyl-1,3,2-dioxaborolan-2-yl)-1,3,2-dioxaborolane (10 g, 39 mmol) and T21.2 (10.00 g, 39 mmol) in toluene (194 mL) was degassed with nitrogen. Then, dichlorobis(triphenylphosphine)palladium(II) (1 g, 2 mmol) was added and the mixture was further degassed with nitrogen. The reaction mixture was stirred at 50° C. for 3.5 hours. The reaction mixture was diluted with water and extracted three times with EtOAc. After drying over anhydrous magnesium sulfate and filtering, the organic solvent was removed under reduced pressure and the product was then purified on silica gel (0-5% EtOAc in hexanes) to yield T21.3 as a colorless oil (7.00 g, 77% yield).

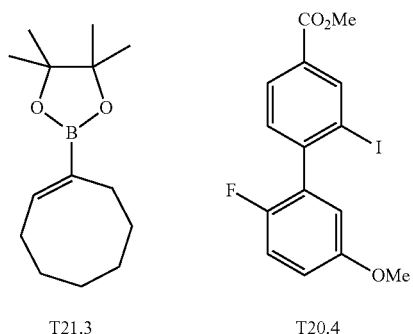

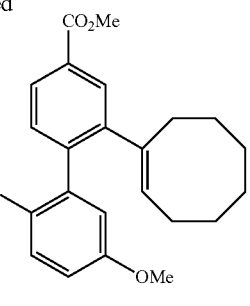

T21.4

Methyl 2-(1-cycloocten-1-yl)-2'-fluoro-5'-(methyloxy)-1,1'-biphenyl-4-carboxylate (T21.4)

To a stirred solution of T20.4 (0.750 g, 1.9 mmol) in DMF (4.00 mL, 52 mmol) at 23° C. was added (Z)-2-cyclooctenyl-4,4,5,5-tetramethyl-1,3,2-dioxaborolane T21.3 (0.92 g, 3.9 mmol), potassium carbonate (0.81 g, 5.8 mmol), and then tetrakis(triphenylphosphine)palladium (0.22 g, 0.19 mmol). The mixture was heated at 90° C. for 19 hours and then cooled to room temperature. The reaction was diluted with brine and extracted three times with EtOAc. After drying over anhydrous magnesium sulfate and filtering, the organic solvent was removed under reduced pressure and the product was purified on silica gel (0-10% EtOAc in hexanes) to yield T21.4 as a colorless oil (0.35 g, 49% yield).

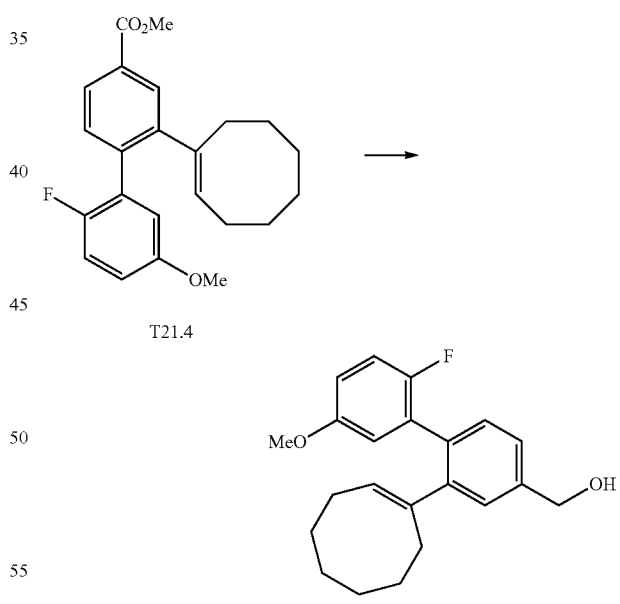

(2-(1-Cycloocten-1-yl)-2'-fluoro-5'-(methyloxy)-1,1'-biphenyl-4-yl)methanol (T21.5)

To a stirred solution of T21.4 (0.350 g, 0.9 mmol) in THF (9 mL, 0.9 mmol) at 0° C. was added LAH in THF (2 mL, 2 mmol, 1.0M). The reaction was stirred for 1 hour. 1N NaOH (aq) was then added to quench the reaction. The reaction was extracted three times with EtOAc. After drying over anhydrous magnesium sulfate and filtering, the organic solvent was removed under reduced pressure and the product was then purified on silica gel (0-20% EtOAc in hexanes) to yield T21.5 as a colorless oil (0.387 g, 120% yield).

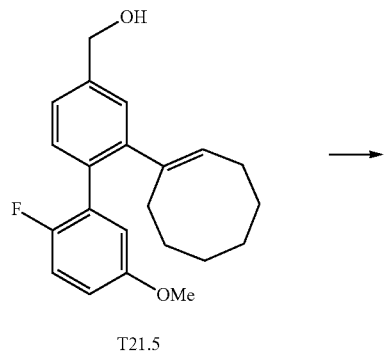

T21.5

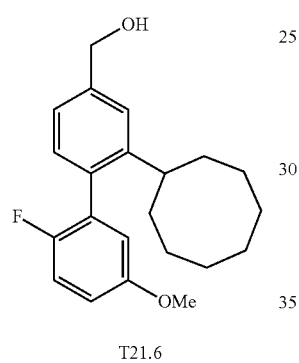

T21.6

(2-Cyclooctyl-2'-fluoro-5'-(methyloxy)-1,1'-biphenyl-4-yl)methanol (T21.6)

To a stirred solution of T21.5 (0.387 g, 1 mmol) in EtOAc (11 mL) at 23° C. was added palladium on carbon (0.1 g, 1 mmol). The reaction was placed under an atmosphere of hydrogen and stirred for 2 hours. The reaction mixture was then filtered and concentrated in vacuo. The residue was purified on silica gel (0-20% EtOAc in hexanes) to yield T21.6 as a colorless oil (0.13 g, 33% yield).

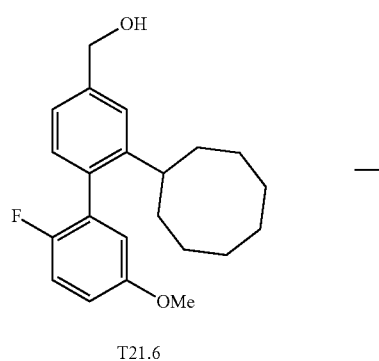

T21.6

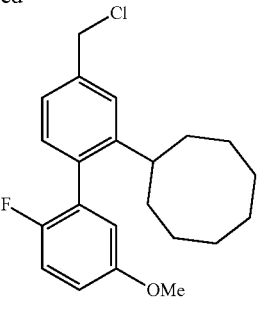

T21

4-(Chloromethyl)-2'-fluoro-5'-(methyloxy)-2-cyclooctyl-1,1'-biphenyl (T21)

To a stirred solution of T21.6 (0.130 g, 0.4 mmol) in DCM (2.00 mL) and DMF (0.03 mL) at 0° C. was added thionyl chloride (0.06 mL, 0.8 mmol). The reaction was stirred at room temperature for 2 hours. After which, the reaction was concentrated in vacuo and the product was then purified on silica gel (0-10% EtOAc in hexanes) to yield T21 as a colorless oil (0.130 g, 95% yield).

Intermediates T22A and T22B

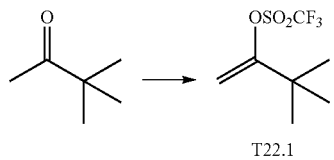

T22.1

Synthesis of T22.1

To a solution of 3,3-dimethylbutan-2-one (5.00 g, 50 mmol, commercially available from Sigma-Aldrich, St. Louis, Mo., USA) in THF (71 mL) at −78° C. was added dropwise a solution of LDA (28 mL, 56 mmol). The resulting solution was stirred at −78° C. for 20 minutes. A solution of N-phenyl-bis(trifluoromethane sulfonimide) (20 g, 55 mmol) in THF (15 mL) was then added slowly at −78° C. The reaction mixture was allowed to room temperature over 3 hours. The reaction was concentrated in vacuo. The reaction was then diluted with water and extracted three times with EtOAc. After drying over anhydrous magnesium sulfate and filtering, the organic solvent was removed under reduced pressure and the product was purified on silica gel (0-5% EtOAc in hexanes) to yield T22.1 as a colorless oil (10.00 g, 86% yield)

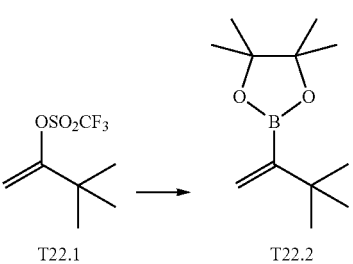

T22.1    T22.2

Synthesis of T22.2

A mixture of triphenylphosphine (0.90 g, 3.4 mmol), potassium phenolate (6.4 g, 48 mmol), 4,4,5,5-tetramethyl-2-(4,4,5,5-tetramethyl-1,3,2-dioxaborolan-2-yl)-1,3,2-dioxaborolane (8.7 g, 34 mmol) and T22.1 (8.00 g, 34 mmol) in toluene (172 mL) was degassed by $N_2$. Then dichlorobis(triphenylphosphine)palladium(II) (1.2 g, 1.7 mmol) was added, and the reaction mixture was further degassed with $N_2$. The reaction was then stirred at 50° C. for 3.5 hours. The reaction was then filtered and concentrated in vacuo. The product was purified on silica gel (0-5% EtOAc in hexanes) to yield T22.2 as a colorless oil (5.0 g, 69% yield).

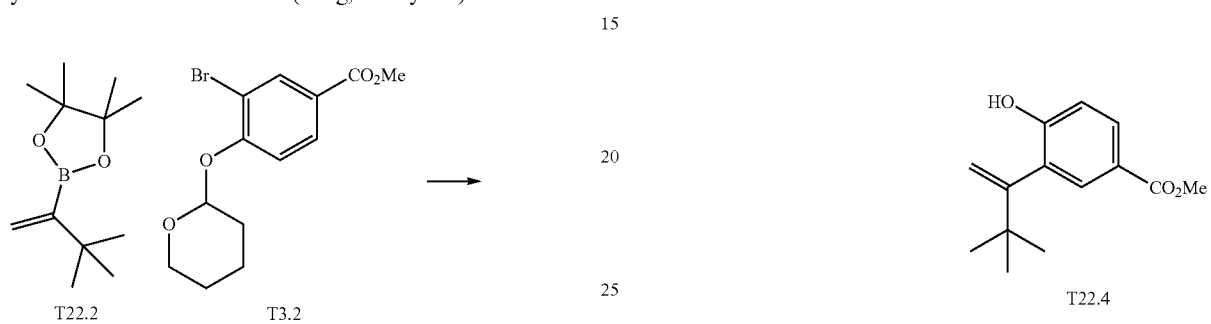

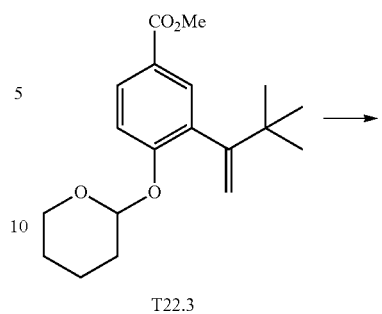

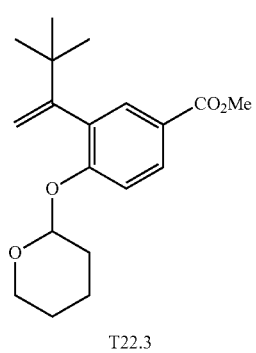

Methyl 3-(1-(1,1-dimethylethyl)ethenyl)-4-(tetrahydro-2H-pyran-2-yloxy)benzoate (T22.3)

A stirred solution of methyl 3-bromo-4-(tetrahydro-2H-pyran-2-yloxy)benzoate T3.2 (2.50 g, 7.9 mmol), palladium acetate (0.18 g, 0.79 mmol), S-Phos (0.65 g, 1.6 mmol), tripotassium phosphate (1.6 mL, 20 mmol) in DMF (15.00 mL, 194 mmol) and water (0.600 mL, 33 mmol) was purged 3 times with nitrogen and placed under vacuum and the process repeated three times. Before heating, T22.2 (2.0 g, 9.5 mmol) was added, and the mixture was heated to 70° C. and stirred for 19 hours. The resulting mixture was then cooled to room temperature, diluted with water and extracted three times with EtOAc. After drying over anhydrous magnesium sulfate and filtering, the organic solvent was removed under reduced pressure and the product was then purified on silica gel (0-20% EtOAc in hexanes) to yield T22.3 as a colorless oil (2.50 g, 99% yield).

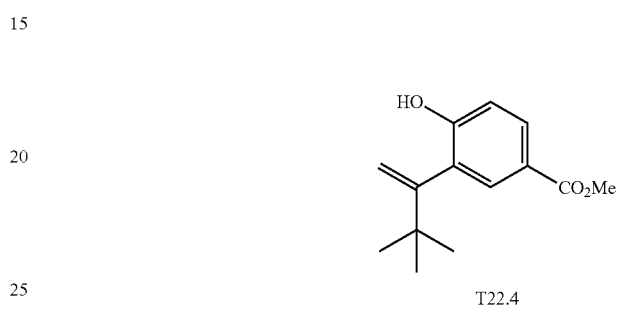

Methyl 3-(1-(1,1-dimethylethyl)ethenyl)-4-hydroxybenzoate (T22.4)

To a stirred solution of T22.3 (2.500 g, 7.85 mmol) in MeOH (10.00 mL, 7.85 mmol) at 23° C. was added PPTS (0.197 g, 0.785 mmol). The reaction was heated to 60° C. and stirred for 19 hours. The reaction was then concentrated in vacuo to give a clear oil. The product was then purified on silica gel (0-20% EtOAc in hexanes) to yield T22.4 as a colorless oil (1.50 g, 81.5% yield).

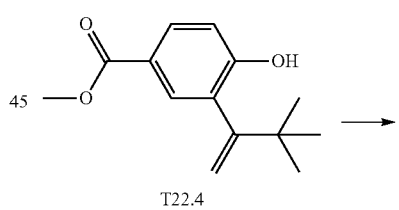

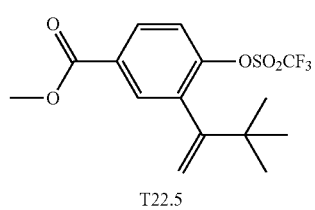

Methyl 3-(1-(1,1-dimethylethyl)ethenyl)-4-(((trifluoromethyl)sulfonyl)oxy)benzoate (T22.5)

To a stirred solution of T22.4 (0.500 g, 2 mmol) in DCM (11 mL) at 23° C. was added TEA (0.4 mL, 3 mmol), DMAP (catalytic), and then N-phenyltriflimide (0.8 g, 2 mmol). The reaction was further stirred for 19 hours and then concentrated in vacuo. The product was purified on silica gel (0-10% EtOAc in hexanes) to yield T22.5 as a colorless oil (0.1 g, 13% yield).

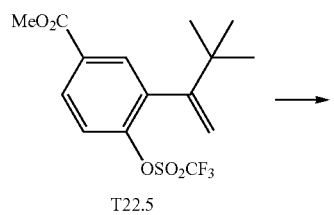

T22.5

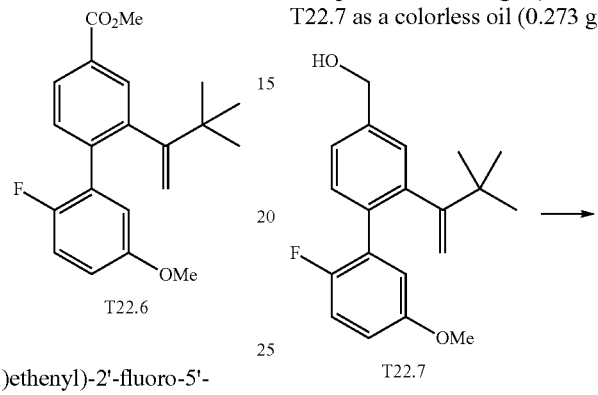

Methyl 2-(1-(1,1-dimethylethyl)ethenyl)-2'-fluoro-5'-(methyloxy)-1,1'-biphenyl-4-carboxylate (T22.6)

To a stirred solution of T22.5 (0.550 g, 1.5 mmol) in DMF (3.0 mL, 1.5 mmol) at 23° C. was added 2-fluoro-5-methoxyphenylboronic acid (0.38 g, 2.3 mmol) (commercially available from Sigma-Aldrich, St. Louis, Mo., USA), potassium carbonate (0.62 g, 4.5 mmol) and then tetrakis(triphenylphosphine)palladium (0.12 g, 0.11 mmol). The mixture was heated to 90° C. and stirred for 17 hours. The resulting mixture was then cooled to room temperature, diluted with water and extracted three times with EtOAc. After drying over anhydrous magnesium sulfate and filtering, the organic solvent was removed under reduced pressure and the product was then purified on silica gel (0-10% EtOAc in hexanes) to yield T22.6 as a colorless oil (0.100 g, 19% yield).

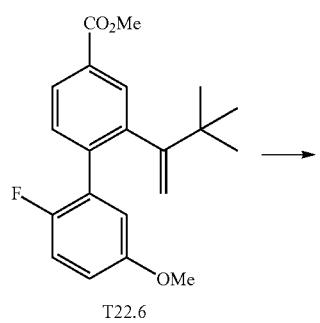

T22.6

(2-(1-(1,1-Dimethylethyl)ethenyl)-2'-fluoro-5'-(methyloxy)-1,1'-biphenyl-4-yl)methanol (T22.7)

To a stirred solution of T22.6 (0.400 g, 1 mmol) in THF (6 mL) at 0° C. was added LAH in THF (2 mL, 2 mmol, 1.0M). The resulting mixture was stirred for 2 hours. 1N NaOH(aq) was then added to the mixture, and the resulting mixture was extracted three times with EtOAc. After drying over anhydrous magnesium sulfate and filtering, the organic solvent was removed under reduced pressure and the product was then purified on silica gel (0-20% EtOAc in hexanes) to yield T22.7 as a colorless oil (0.273 g, 74% yield).

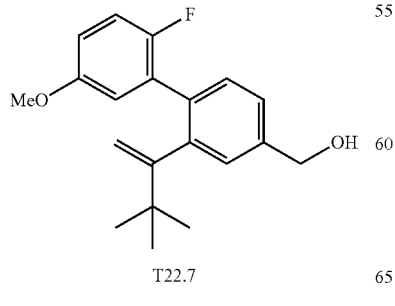

T22.7

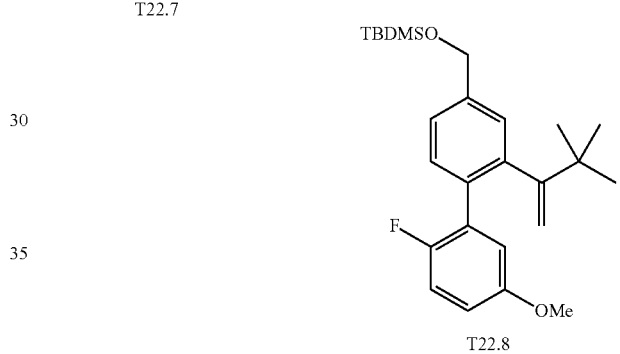

T22.8

(1,1-Dimethylethyl)(((2-(1-(1,1-dimethylethyl)ethenyl)-2'-fluoro-5'-(methyloxy)-1,1'-biphenyl-4-yl)methyl)oxy)dimethylsilane (T22.8)

To a stirred solution of T22.7 (0.273 g, 0.9 mmol) in DCM (2.00 mL) at 23° C. was added tert-butyldimethylsilyl chloride (0.2 mL, 1 mmol), followed by TEA (0.1 mL, 1 mmol) and DMAP (0.01 g, 0.09 mmol). The resulting mixture was then stirred for 16 hours and then was concentrated in vacuo to give the product. The product was purified on silica gel (0-5% EtOAc in hexanes) to yield T22.8 as a colorless oil (0.374 g, 100% yield).

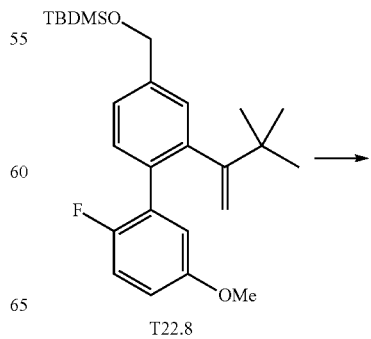

T22.8

(1,1-Dimethylethyl)(((2'-fluoro-5'-(methyloxy)-2-(1,2,2-trimethylpropyl)-1,1'-biphenyl-4-yl)methyl)oxy)dimethylsilane (T22.9)

To a stirred solution of T22.8 (0.400 g, 0.93 mmol) in EtOAc (2.00 mL) at 23° C. was added palladium on carbon (0.0099 g, 0.093 mmol). The resulting mixture was stirred under an atmosphere of hydrogen for 21 hours and then was filtered and concentrated in vacuo. The product was purified on silica gel (0-5% EtOAc in hexanes) to yield T22.9 as a colorless oil (0.400 g, 100% yield).

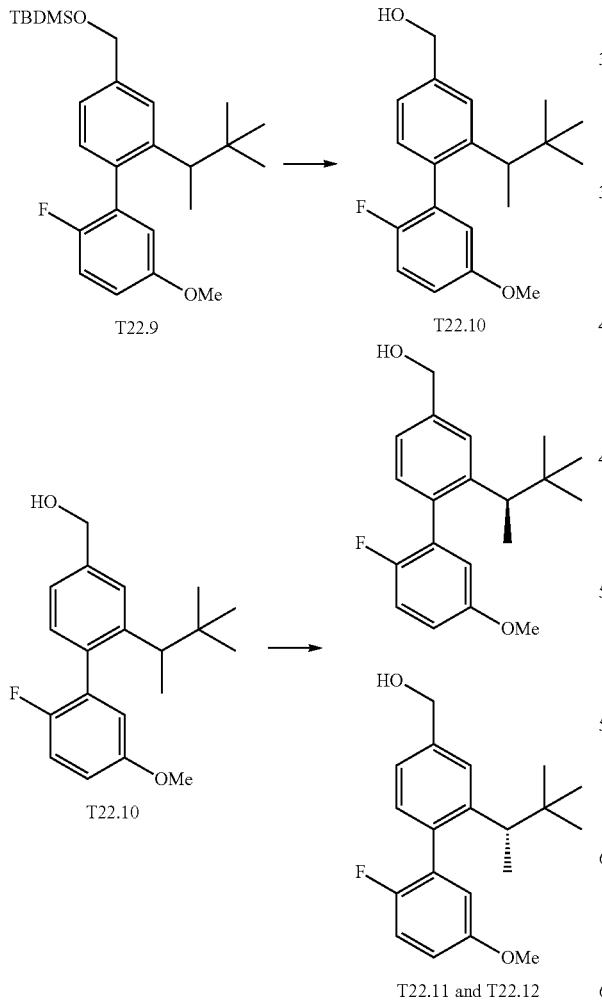

(2'-Fluoro-5'-(methyloxy)-2-((1R)-1,2,2-trimethylpropyl)-1,1'-biphenyl-4-yl)methanol and (2'-fluoro-5'-(methyloxy)-2-((1S)-1,2,2-trimethylpropyl)-1,1'-biphenyl-4-yl)methanol (T22.11 and T22.12)

To a stirred solution of T22.9 (0.400 g, 0.929 mmol) in MeOH (10.00 mL, 0.929 mmol) at 23° C. was added PPTS (0.0233 g, 0.0929 mmol). The mixture was stirred for 19 hours and then was concentrated in vacuo to give a clear oil. The product was then purified on silica gel (0-20% EtOAc in hexanes) to yield T22.10 as a colorless oil (0.250 g, 85% yield). Chiral separation of T22.10 was accomplished on a CHIRALCEL® OD column (3% IPA in hexane) to provide T22.11 (peak one) and T22.12 (peak two).[1]

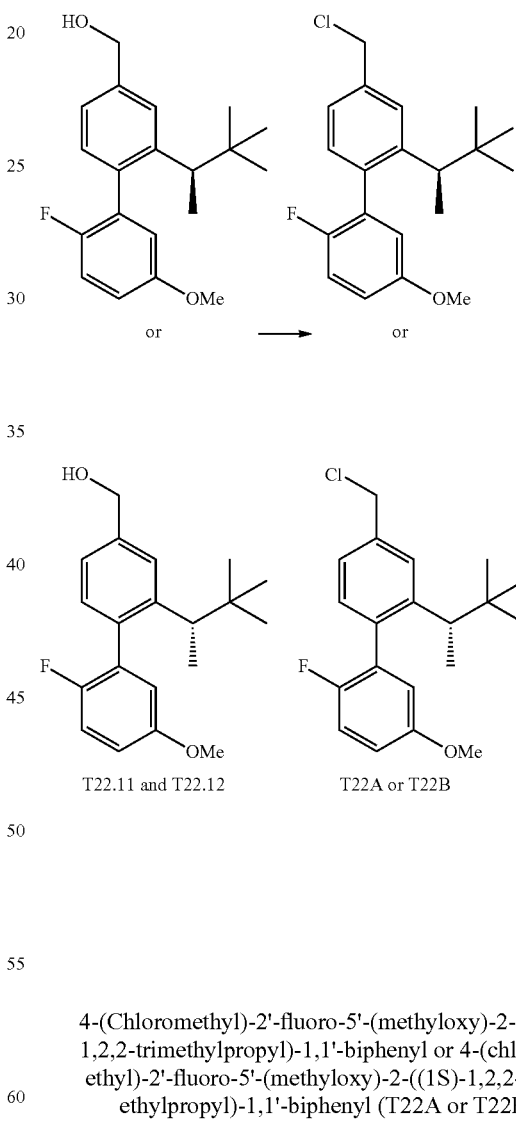

4-(Chloromethyl)-2'-fluoro-5'-(methyloxy)-2-((1R)-1,2,2-trimethylpropyl)-1,1'-biphenyl or 4-(chloromethyl)-2'-fluoro-5'-(methyloxy)-2-((1S)-1,2,2-trimethylpropyl)-1,1'-biphenyl (T22A or T22B)

To a stirred solution of T22.11 or T22.12 (0.050 g, 0.16 mmol) in DCM (2.00 mL) at 23° C. was added DMF (0.0012 mL) followed by thionyl chloride (0.023 mL, 0.32 mmol). The mixture was stirred for one hour and then was concentrated in vacuo. The resulting product was purified on silica gel (0-10% EtOAc in hexanes) to yield T22A or T22B as a colorless oil (0.050 g, 94% yield).

Intermediate T23

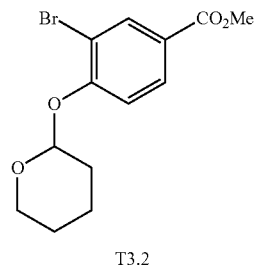

T3.2

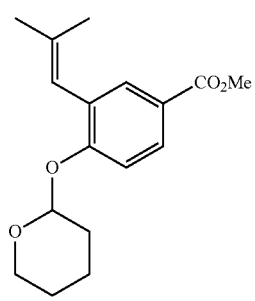

T23.1

Methyl 3-(2-methyl-1-propenyl)-4-(tetrahydro-2H-pyran-2-yloxy)benzoate (T23.1)

A mixture of methyl 3-bromo-4-(tetrahydro-2H-pyran-2-yloxy)benzoate T3.2 (0.500 g, 1.6 mmol), palladium acetate (0.036 g, 0.16 mmol), S-Phos (0.13 g, 0.32 mmol) and tripotassium phosphate (0.32 mL, 4.0 mmol) in DMF (10.00 mL, 129 mmol) and water (0.40 mL, 22 mmol) was stirred. The mixture was purged with nitrogen and placed under vacuum and the process repeated three times. Before heating, 2-methylprop-1-enylboronic acid (0.24 g, 2.4 mmol, commercially available from Synthonix, Cat. No. D3007G1) was added, and the mixture was heated to 70° C. and stirred for 23 hours. The mixture was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield T23.1 as a colorless oil (0.460 g, 100% yield).

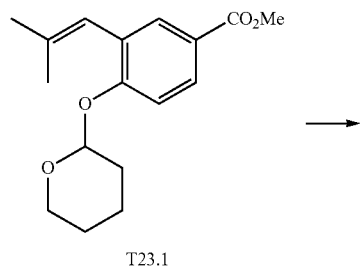

T23.1

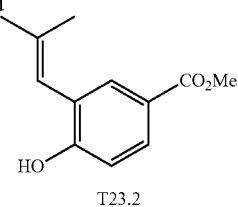

T23.2

Methyl 4-hydroxy-3-(2-methyl-1-propenyl)benzoate (T23.2)

To a stirred mixture of T23.1 (0.460 g, 2 mmol) in MeOH (8 mL) was added PPTS (0.04 g, 0.2 mmol). The reaction mixture was then stirred for 24 hours and then concentrated in vacuo. The residue was purified on silica gel (0-20% EtOAc in hexanes) to yield T23.2 as a colorless oil (0.320 g, 98% yield).

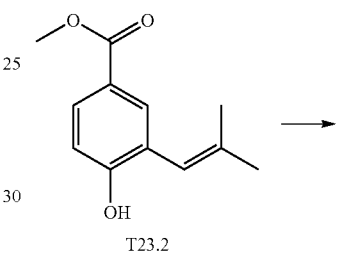

T23.2

T23.3

Methyl 4-hydroxy-3-(2-methylpropyl)benzoate (T23.3)

To a stirred solution of methyl 4-hydroxy-3-(2-methyl-prop-1-enyl)benzoate T23.2 (0.320 g, 1.6 mmol) in EtOAc (2.00 mL, 20 mmol) at 23° C. was added palladium on carbon (0.017 g, 0.16 mmol). The reaction was stirred under an atmosphere of hydrogen (0.0031 g, 1.6 mmol) for 16 hours. The reaction mixture was then filtered and concentrated in vacuo to give a clear oil. The residue was purified on silica gel (0-20% EtOAc in hexanes) to yield T23.3 as a colorless oil (0.256 g, 79% yield)

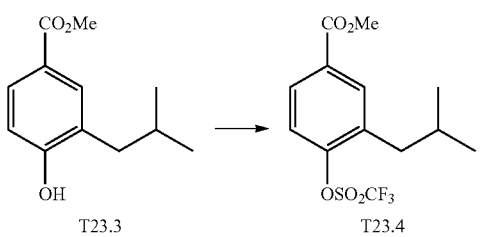

T23.3        T23.4

Methyl 3-(2-methylpropyl)-4-(((trifluoromethyl)sulfonyl)oxy)benzoate (T23.4)

To a stirred solution of T23.3 (0.256 g, 1 mmol) in DCM (12 mL, 1 mmol) at 0° C. was added TEA (0.2 mL, 1 mmol), and a catalytic amount of DMAP. N-phenyltriflimide (0.5 g, 1 mmol) was then added and the mixture was stirred at room temperature for 20 hours. The reaction was concentrated in vacuo, and the residue was purified on silica gel (0-10% EtOAc in hexanes) to yield T23.4 as a colorless oil (0.400 g, 96% yield).

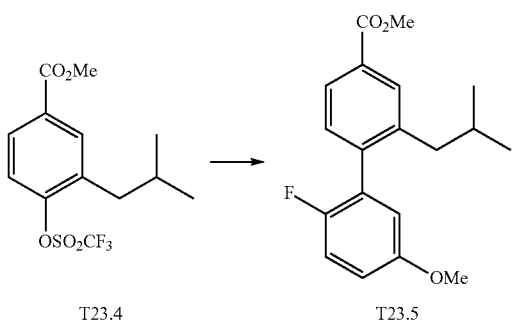

Methyl 2'-fluoro-5'-(methyloxy)-2-(2-methylpropyl)-1,1'-biphenyl-4-carboxylate (T23.5)

To a stirred solution of T23.4 (0.400 g, 1.2 mmol) in DMF (4.00 mL, 52 mmol) at 23° C. was added 2-fluoro-5-methoxyphenylboronic acid (0.40 g, 2.4 mmol) (commercially available from Sigma-Aldrich, St. Louis, Mo., USA), potassium carbonate (0.49 g, 3.5 mmol), and then tetrakis(triphenylphosphine)palladium (0.14 g, 0.12 mmol). The mixture was heated to 90° C. and stirred for 22 hours. The mixture was cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield T23.5 as a colorless oil (0.293 g, 79% yield).

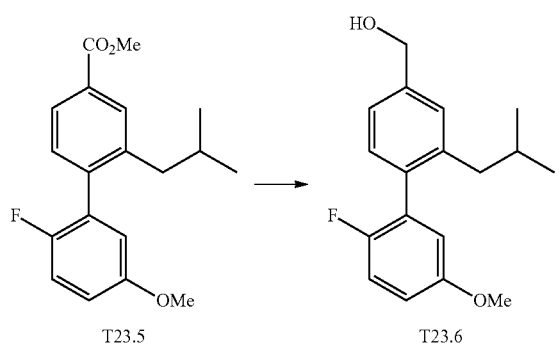 [SMILES: COC(=O)c1ccc(-c2cc(OC)ccc2F)c(CC(C)C)c1 ; COc1ccc(F)c(-c2ccc(CO)cc2CC(C)C)c1]

(2'-Fluoro-5'-(methyloxy)-2-(2-methylpropyl)-1,1'-biphenyl-4-yl) methanol (T23.6)

To a stirred solution of T23.5 (0.293 g, 0.9 mmol) in THF (5 mL, 0.9 mmol) at 0° C. was added LAH in THF (2 mL, 2 mmol, 1.0M). The reaction was stirred for one hour and then 1N NaOH(aq) was added to quench the mixture. The reaction was extracted three times with EtOAc. After drying over anhydrous magnesium sulfate and filtering, the organic solvent was removed under reduced pressure and the product was then purified on silica gel (0-20% EtOAc in hexanes) to yield T23.6 as a colorless oil (0.260 g, 97% yield).

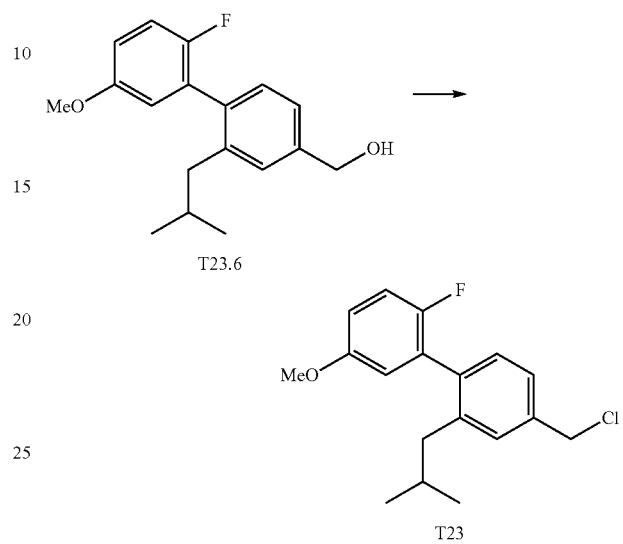

4-(Chloromethyl)-2'-fluoro-5'-(methyloxy)-2-(2-methylpropyl)-1,1'-biphenyl (T23)

To a stirred solution of T23.6 (0.260 g, 0.90 mmol) in DCM (2.00 mL, 31 mmol) at 23° C. was added DMF (0.0070 mL, 0.090 mmol) followed by thionyl chloride (0.13 mL, 1.8 mmol). The reaction was stirred for one hour and then the reaction was concentrated in vacuo. The residue was then purified on silica gel (0-10% EtOAc in hexanes) to yield T23 as a colorless oil (0.252 g, 91% yield).

Intermediate T24

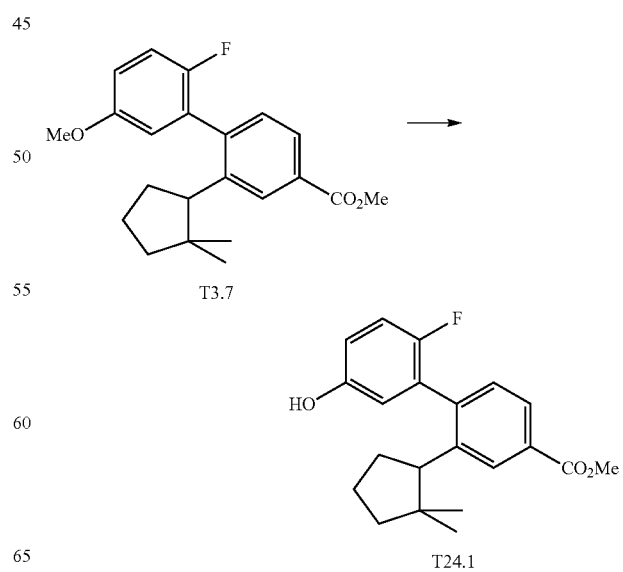

Methyl 2-(2,2-dimethylcyclopentyl)-2'-fluoro-5'-hydroxy-1,1'-biphenyl-4-carboxylate (T24.1)

To a stirred solution of T3.7 (0.400 g, 1.12 mmol) in DCM (10.00 mL) at 0° C. was added boron tribromide (1.0M in DCM)(4.49 mL, 4.49 mmol). The reaction was stirred for one hour at 0° C. Water was then added, and the mixture was extracted three times with EtOAc. After drying over anhydrous magnesium sulfate and filtering, the organic solvent was removed under reduced pressure and the desired product was isolated. The initial product was dissolved in a 1/1 mixture of THF/EtOH and to this was added 1N NaOH (aq), the resulting solution was stirred for 16 hours, after which it was concentrated in vacuo. The reaction was acidified with 1N HCl and the resulting solution was extracted three times with EtOAc. After drying over anhydrous magnesium sulfate and filtering, the organic solvent was removed under reduced pressure. The resulting product was dissolved in MeOH and a drop of sulfuric acid was added. The mixture was heated at 70° C. for 16 hours. The reaction mixture was then concentrated in vacuo. The product was then purified on silica gel (0-20% EtOAc in hexanes) to yield T24.1 as a colorless oil (0.250 g, 65% yield).

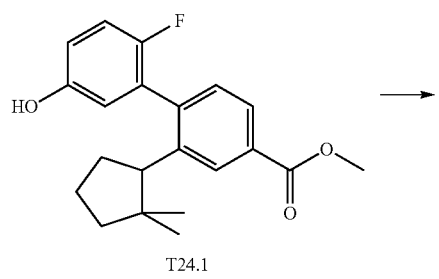

T24.1

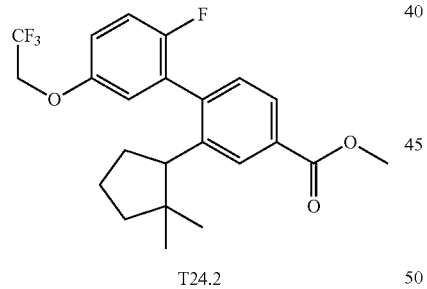

T24.2

Methyl 2-(2,2-dimethylcyclopentyl)-2'-fluoro-5'-((2,2,2-trifluoroethyl)oxy)-1,1'-biphenyl-4-carboxylate (T24.2)

To a flask containing T24.1 (0.100 g, 0.29 mmol) and Cs₂CO₃ (0.29 g, 0.88 mmol) in DMF (2 mL) was added 1,1,1-trifluoro-2-iodoethane (0.12 g, 0.58 mmol) (commercially available from Sigma-Aldrich, St. Louis, Mo., USA), and stirring was continued for 5 hours. The reaction was diluted with water and extracted three times with EtOAc. After drying over anhydrous magnesium sulfate and filtering, the organic solvent was removed under reduced pressure and the product was then purified on silica gel (0-10% EtOAc in hexanes) to yield T24.2 as a colorless oil (0.113 g, 91% yield).

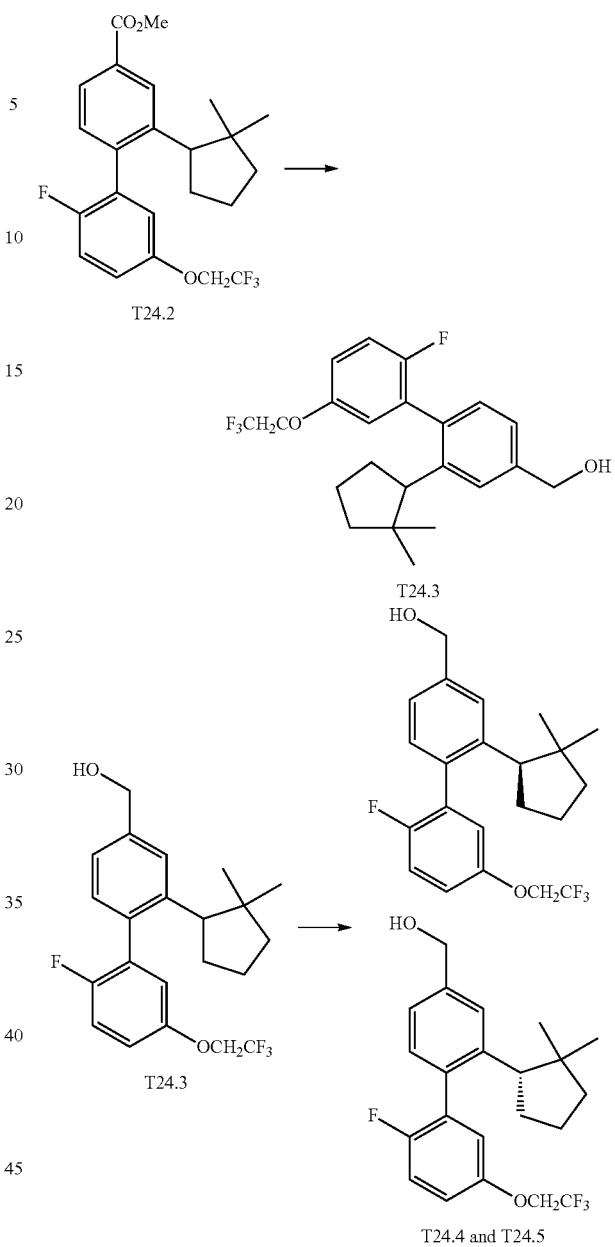

(2-((1R)-2,2-Dimethylcyclopentyl)-2'-fluoro-5'-((2,2,2-trifluoroethyl)oxy)-1,1'-biphenyl-4-yl)methanol and (2-((1S)-2,2-dimethylcyclopentyl)-2'-fluoro-5'-((2,2,2-trifluoroethyl)oxy)-1,1'-biphenyl-4-yl)methanol (T24.4 and T24.5)

To a stirred solution of T24.2 (0.113 g, 0.3 mmol) in THF (5 mL) at 0° C. was added LAH in THF (0.5 mL, 0.5 mmol, 1.0M). The mixture was stirred for one hour and then 1N NaOH(aq) was added to quench the reaction. The reaction mixture was extracted three times with EtOAc. After drying over anhydrous magnesium sulfate and filtering, the organic solvent was removed under reduced pressure and the product was then purified on silica gel (0-20% EtOAc in hexanes) to yield T24.3 as a colorless oil (0.075 g, 71% yield). Chiral separation of T24.3 was accomplished on CHIRALCEL® OD (3% IPA in hexane) to provide T24.4 (peak one) and T24.5 (peak two).[1]

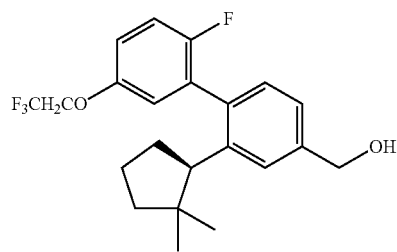
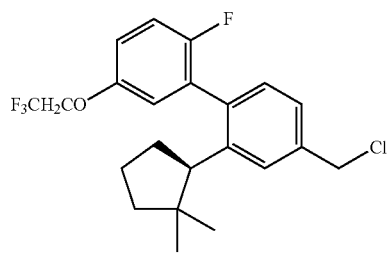

or

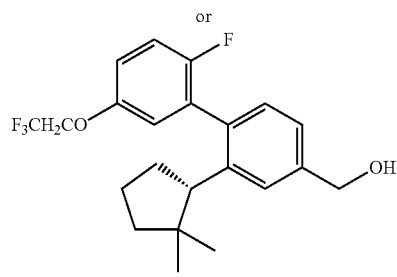
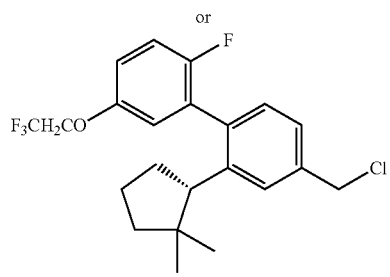

T24.4 or T24.5 → T24A or T24B 4-(Chloromethyl)-2-((1R)-2,2-dimethylcyclopentyl)-2'-fluoro-5'-((2,2,2-trifluoroethyl)oxy)-1,1'-biphenyl or 4-(chloromethyl)-2-((1S)-2,2-dimethylcyclopentyl)-2'-fluoro-5'-((2,2,2-trifluoroethyl)oxy)-1,1'-biphenyl (T24A or T24B)

To a stirred solution of T24.4 or T24.5 (0.022 g, 0.055 mmol) in DCM (2.00 mL) at 23° C. was added DMF (0.00043 mL) followed by thionyl chloride (0.0081 mL, 0.11 mmol). The reaction was stirred for two hours and then the reaction mixture was concentrated in vacuo. The product was then purified on silica gel (0-10% EtOAc in hexanes) to yield T24A or T24B as a colorless oil (0.019 g, 83% yield).

Intermediates T25A and T25B

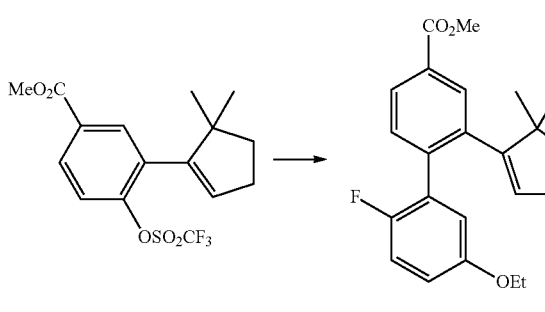

T3.5 → T16.1

Methyl 2-(5,5-dimethyl-1-cyclopenten-1-yl)-5'-(ethyloxy)-2'-fluoro-1,1'-biphenyl-4-carboxylate (T25.1)

To a stirred solution of methyl 3-(5,5-dimethylcyclopent-1-enyl)-4-(trifluoromethylsulfonyloxy)benzoate T3.5 (0.400 g, 1.1 mmol) in DMF (4.00 mL) at 23° C. was added 5-ethoxy-2-fluorophenylboronic acid (0.29 g, 1.6 mmol, commercially available from Sigma-Aldrich, St. Louis, Mo., USA), potassium carbonate (0.44 g, 3.2 mmol), and then tetrakis(triphenylphosphine)palladium (0.12 g, 0.11 mmol). The mixture was heated to 90° C. and stirred for 21 hours. The mixture was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield T25.1 as a colorless oil (0.350 g, 90% yield).

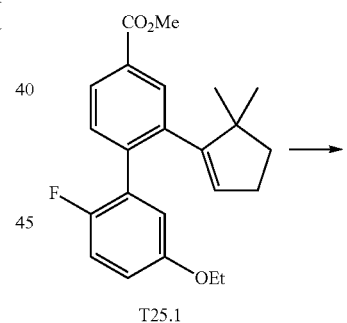

T25.1

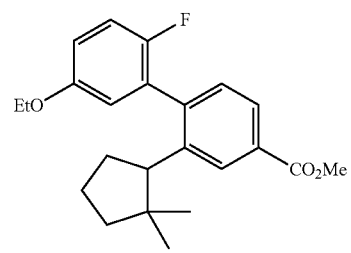

T25.2

Methyl 2-(2,2-dimethylcyclopentyl)-5'-(ethyloxy)-2'-fluoro-1,1'-biphenyl-4-carboxylate (T25.2)

To a stirred solution of T25.1 (0.400 g, 1.09 mmol) in MeOH (10.00 mL, 1.09 mmol) at 23° C. was added palladium on carbon (0.116 g, 1.09 mmol). The reaction was placed under an atmosphere of hydrogen and stirred for 23 hours. The mixture was then filtered and concentrated in vacuo. The initial product was then purified on silica gel (0-20% EtOAc in hexanes) to yield T25.2 as a colorless oil (0.400 g, 99.5% yield).

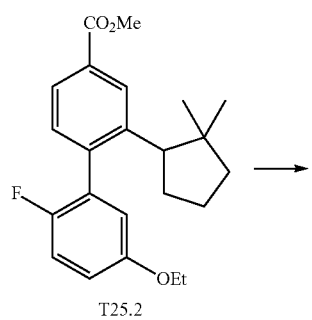

T25.2

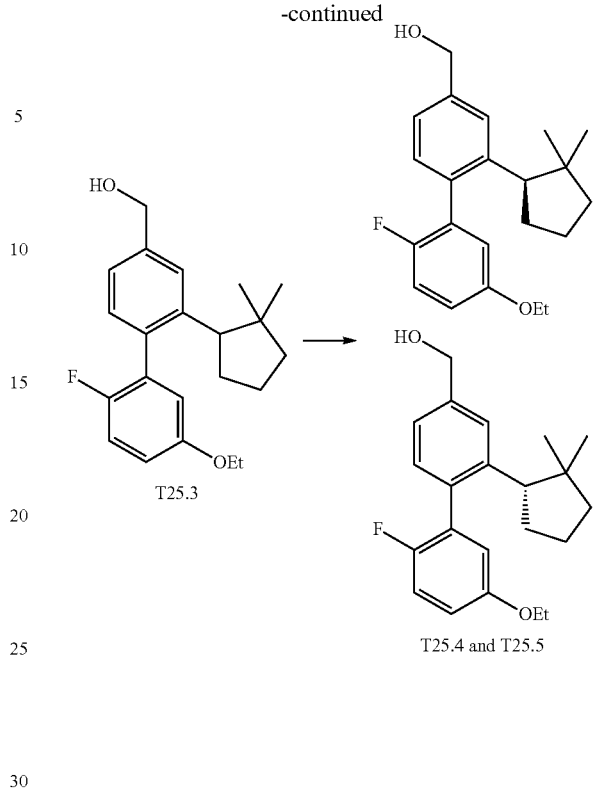

(2-((1R)-2,2-Dimethylcyclopentyl)-5'-(ethyloxy)-2'-fluoro-1,1'-biphenyl-4-yl)methanol and (2-((1S)-2,2-dimethylcyclopentyl)-5'-(ethyloxy)-2'-fluoro-1,1'-biphenyl-4-yl)methanol (T25.4 and T25.5)

To a stirred solution of T25.2 (0.400 g, 1.1 mmol) in THF (15.00 mL, 183 mmol) at 0° C. was added LAH in THF (2.2 mL, 2.2 mmol, 1.0M). The mixture was stirred for one hour and then 1N NaOH(aq) was added to quench the reaction. The reaction mixture was extracted three times with EtOAc. After drying over anhydrous magnesium sulfate and filtering, the organic solvent was removed under reduced pressure and the product was then purified on silica gel (0-20% EtOAc in hexanes) to yield T25.3 as a colorless oil (0.320 g, 87% yield). Chiral separation of T25.3 was accomplished on a CHIRALCEL® OD column (3% IPA in hexane) to provide T25.4 (peak one) and T25.5 (peak two).[1]

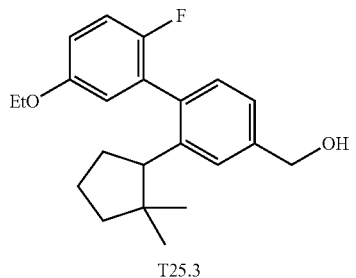

T25.3

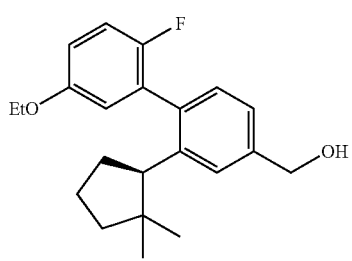

or

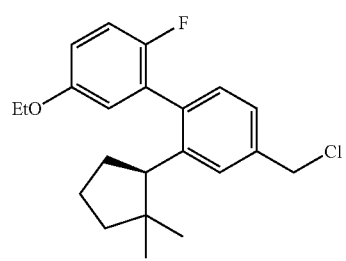

or

-continued

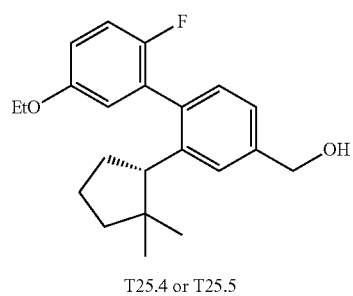

T25.4 or T25.5

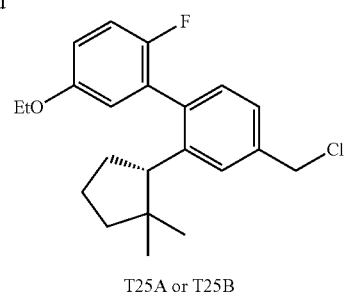

T25A or T25B 4-(Chloromethyl)-2-(((1R)-2,2-dimethylcyclopentyl)-5'-(ethyloxy)-2'-fluoro-1,1'-biphenyl or 4-(chloromethyl)-2-((1S)-2,2-dimethylcyclopentyl)-5'-(ethyloxy)-2'-fluoro-1,1'-biphenyl (T25A or T25B)

To a stirred solution of T25.4 or T25.5 (0.147 g, 0.43 mmol) in DCM (2.00 mL) at 23° C. was added DMF (0.0033 mL) followed by thionyl chloride (0.063 mL, 0.86 mmol). The reaction was then stirred for 4 hours and then concentrated in vacuo. The initial product was then purified on silica gel (0-10% EtOAc in hexanes) to yield T25A or T25B as a colorless oil (0.120 g, 77% yield).

Intermediates T26A and T26B

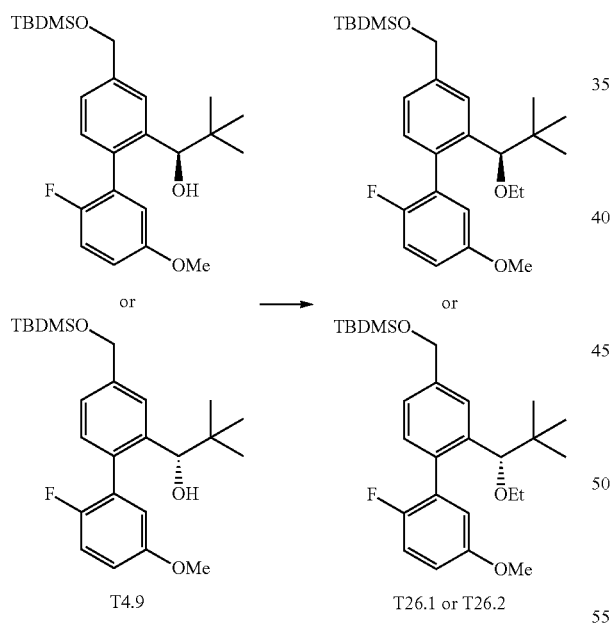

(1,1-Dimethylethyl)(((2-((1R)-1-(ethyloxy)-2,2-dimethylpropyl)-2'-fluoro-5'-(methyloxy)-1,1'-biphenyl-4-yl)methyl)oxy)dimethylsilane or (1,1-dimethylethyl)(((2-((1S)-1-(ethyloxy)-2,2-dimethylpropyl)-2'-fluoro-5'-(methyloxy)-1,1'-biphenyl-4-yl)methyl)oxy)dimethylsilane (T26.1 or T26.2)

To a stirred solution of T4.9 (derived from peak two from chiral separation of T4.6) (0.110 g, 0.25 mmol) in DMF (2.00 mL) at 23° C. was added iodoethane (0.048 g, 0.31 mmol), followed by sodium hydride (0.0073 g, 0.31 mmol). The mixture was stirred at 60° C. for 21 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-10% EtOAc in hexanes) to yield T26.1 or T26.2 as a colorless oil (0.065 g, 55% yield).

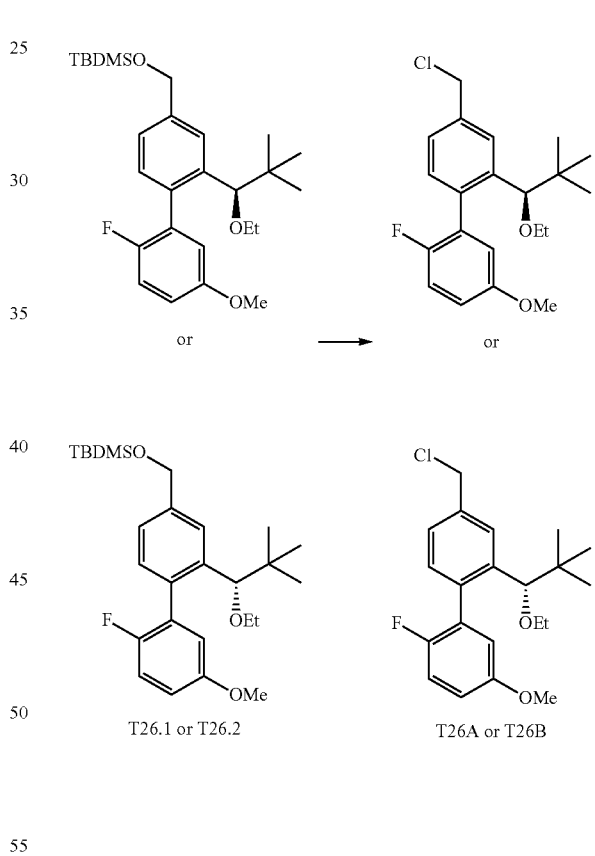

4-(Chloromethyl)-2-((1R)-1-(ethyloxy)-2,2-dimethylpropyl)-2'-fluoro-5'-(methyloxy)-1,1'-biphenyl or 4-(chloromethyl)-2-((1S)-1-(ethyloxy)-2,2-dimethylpropyl)-2'-fluoro-5'-(methyloxy)-1,1'-biphenyl (T26A or T26B)

To a stirred solution of T26.1 or T26.2 (0.065 g, 0.1 mmol) in DCM (2.00 mL) at 23° C. was added DMF (0.001 mL) followed by thionyl chloride (0.02 mL, 0.3 mmol). The mixture was stirred for 2 hours and then concentrated in vacuo.

The product was then purified on silica gel (0-10% EtOAc in hexanes) to yield T26A or T26B as a colorless oil (0.04 g, 78% yield).

Intermediates T27A and T27B

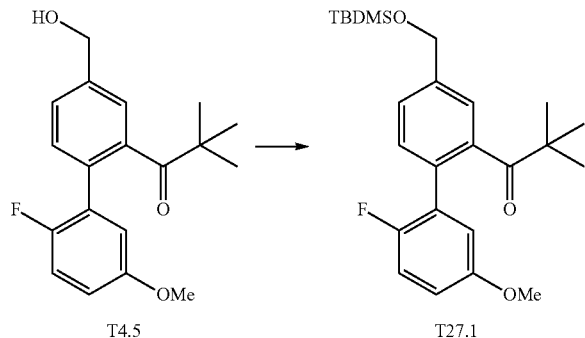 [SMILES: COc1ccc(F)c(-c2ccc(CO)cc2C(=O)C(C)(C)C)c1 ; COc1ccc(F)c(-c2ccc(CO[Si](C)(C)C(C)(C)C)cc2C(=O)C(C)(C)C)c1]

1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanone (T27.1)

To a stirred solution of T4.5 (1.00 g, 3 mmol) in DCM (10.00 mL) at 23° C. was added tert-butyldimethylsilyl chloride (0.6 mL, 4 mmol), followed by TEA (0.5 mL, 4 mmol) and DMAP (0.04 g, 0.3 mmol). The reaction was stirred for 16 hours and then the reaction was concentrated in vacuo. The product was purified on silica gel (0-10% EtOAc in hexanes) to yield T27.1 as a colorless oil (1.30 g, 96% yield).

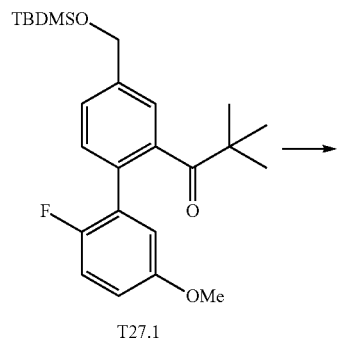

1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanol (T27.2)

To a stirred solution of T27.1 (0.500 g, 1.2 mmol) in THF (15.00 mL, 183 mmol) at 0° C. was added LAH in THF (2.3 mL, 2.3 mmol, 1.0M). The reaction was stirred for two hours. 1N NaOH(aq) was added to quench the reaction mixture, and the reaction was then extracted three times with EtOAc. After drying over anhydrous magnesium sulfate and filtering, the organic solvent was removed under reduced pressure and the product was then purified on silica gel (0-10% EtOAc in hexanes) to yield T27.2 as a colorless oil (0.400 g, 80% yield).

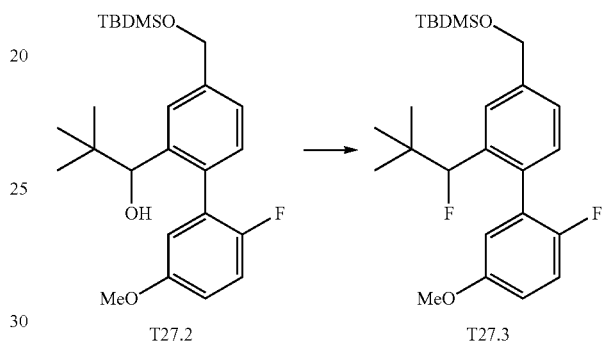

(1,1-Dimethylethyl)(((2'-fluoro-2-(1-fluoro-2,2-dimethylpropyl)-5'-(methyloxy)-1,1'-biphenyl-4-yl)methyl)oxy)dimethylsilane (T27.3)

To a solution of T27.2 (0.400 g, 0.925 mmol) in toluene (10 mL) at −78° C. was added DAST (0.209 g, 1.29 mmol) dropwise. The reaction was stirred at −78° C. for 30 minutes and then warmed to 23° C. and stirred for an additional 2 hours. Water was added to quench the reaction mixture. The reaction was then extracted three times with EtOAc. After drying over anhydrous magnesium sulfate and filtering, the organic solvent was removed under reduced pressure and the product was then purified on silica gel (0-10% EtOAc in hexanes) to yield T27.3 as a colorless oil (0.400 g, 99% yield).

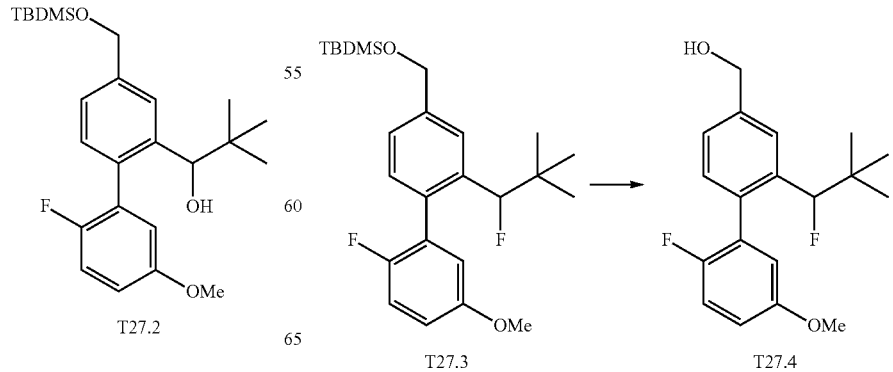

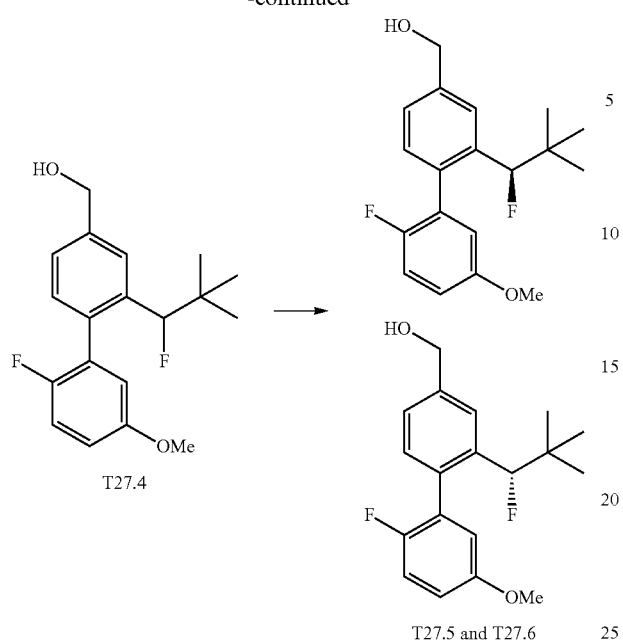

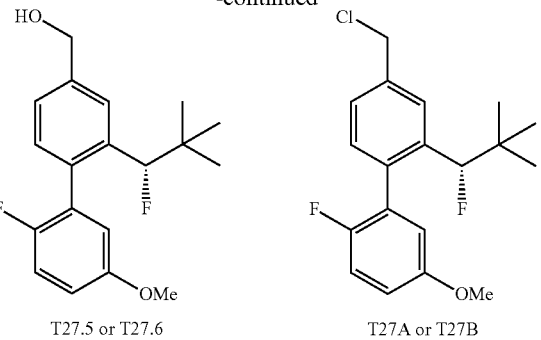

T27.5 or T27.6

T27A or T27B 4-(Chloromethyl)-2'-fluoro-2-((1R)-1-fluoro-2,2-dimethylpropyl)-5'-(methyloxy)-1,1'-biphenyl or 4-(chloromethyl)-2'-fluoro-2-((1R)-1-fluoro-2,2-dimethylpropyl)-5'-(methyloxy)-1,1'-biphenyl (T27A or T27B).

To a stirred solution of T27.5 or T27.6 (0.102 g, 0.3 mmol) in DCM (2.00 mL) at 23° C. was added DMF (0.002 mL) followed by thionyl chloride (0.05 mL, 0.6 mmol). The reaction was stirred for 1.5 hours. The reaction was concentrated in vacuo. The product was then purified on silica gel (0-10% EtOAc in hexanes) to yield T27A or T27B as a colorless oil (0.09 g, 83% yield).

Intermediates T28A and T28B

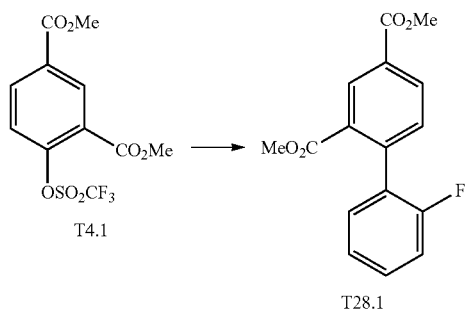

(2'-Fluoro-2-((1R)-1-fluoro-2,2-dimethylpropyl)-5'-(methyloxy)-1,1'-biphenyl-4-yl)methanol and (2'-fluoro-2-((1S)-1-fluoro-2,2-dimethylpropyl)-5'-(methyloxy)-1,1'-biphenyl-4-yl)methanol (T27.5 and T27.6)

To a stirred solution of T27.3 (0.400 g, 0.920 mmol) in MeOH (10.00 mL) at 23° C. was added PPTS (0.0231 g, 0.0920 mmol). The reaction was stirred for 19 hours and then concentrated in vacuo to give a clear oil. The product was then purified on silica gel (0-20% EtOAc in hexanes) to yield T27.4 as a colorless oil (0.272 g, 92% yield). Chiral separation of T27.4 was accomplished on a CHIRALCEL® OD column (3% IPA in hexane) to provide T27.5 and T27.6.

Dimethyl 2'-fluoro-1,1'-biphenyl-2,4-dicarboxylate (T28.1)

To a stirred solution of dimethyl 4-(trifluoromethylsulfonyloxy)isophthalate T4.1 (1.60 g, 4.7 mmol) in DMF (9.4 mL, 4.7 mmol) at 23° C. was added 2-fluorophenylboronic acid (0.98 g, 7.0 mmol, commercially available from Sigma-Aldrich, St. Louis, Mo., USA), potassium carbonate (1.9 g, 14 mmol), and then tetrakis(triphenylphosphine)palladium (0.54 g, 0.47 mmol). The reaction mixture was heated to 90° C. and the reaction was stirred for 22 hours. The reaction was then cooled to room temperature, diluted with water, and extracted three times with EtOAc. After drying over anhydrous magnesium sulfate and filtering, the organic solvent was removed under reduced pressure and the product was then purified on silica gel (0-10% EtOAc in hexanes) to yield T28.1 as a colorless oil (1.10 g, 82% yield).

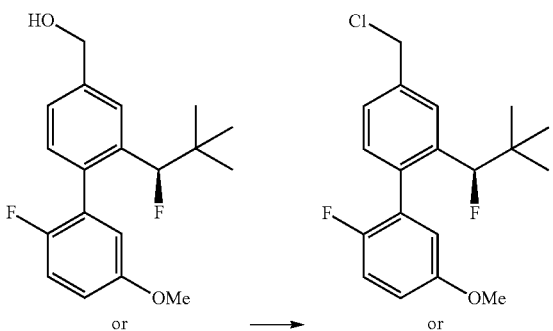

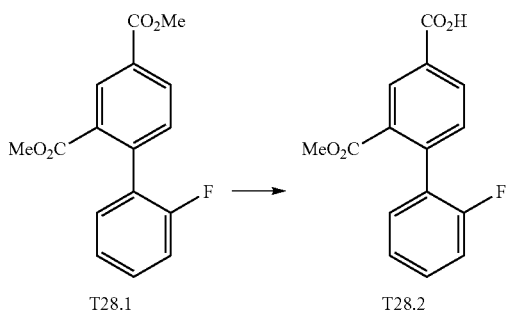 [SMILES: COC(=O)c1ccc(-c2ccccc2F)c(C(=O)OC)c1 ; COC(=O)c1cc(C(=O)O)ccc1-c1ccccc1F]

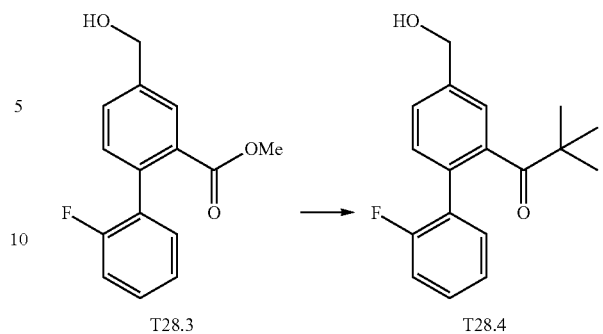

1-(2'-Fluoro-4-(hydroxymethyl)-1,1'-biphenyl-2-yl)-
2,2-dimethyl-1-propanone (T28.4)

2'-Fluoro-2-((methyloxy)carbonyl)-1,1'-biphenyl-4-
carboxylic acid (T28.2)

To a stirred solution of T28.1 (1.00 g, 3.5 mmol) in THF (70.0 mL) and MeOH (70.0 mL) at 0° C. was slowly added potassium hydroxide (1.9 mL, 3.8 mmol) to maintain the temperature below 6° C. The reaction mixture was allowed to warm to room temperature and stirred for 48 hours. The reaction mixture was then concentrated in vacuo, acidified with 1N HCl, and extracted three times with EtOAc. After drying over anhydrous magnesium sulfate and filtering, the organic solvent was removed under reduced pressure and to give a white solid T28.2 (0.90 g, 95% yield).

To a stirred solution of T28.3 (0.850 g, 3 mmol) in THF (33 mL) at −78° C. was added tert-butyllithium (6 mL, 10 mmol, 1.7M). The reaction was stirred for 5 hours and then a saturated solution of ammonium chloride was added and the mixture was extracted three times with EtOAc. After drying over anhydrous magnesium sulfate and filtering, the organic solvent was removed under reduced pressure and the product was then purified on silica gel (0-40% EtOAc in hexanes) to yield T28.4 as a colorless oil (0.670 g, 72% yield).

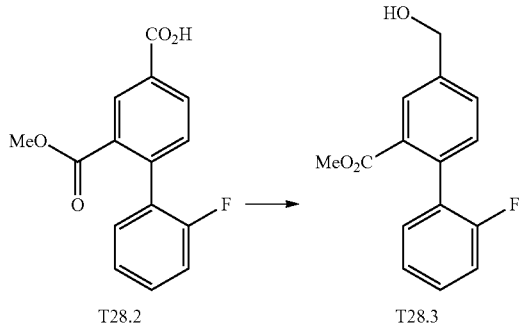 [SMILES: COC(=O)c1cc(C(=O)O)ccc1-c1ccccc1F ; COC(=O)c1cc(CO)ccc1-c1ccccc1F]

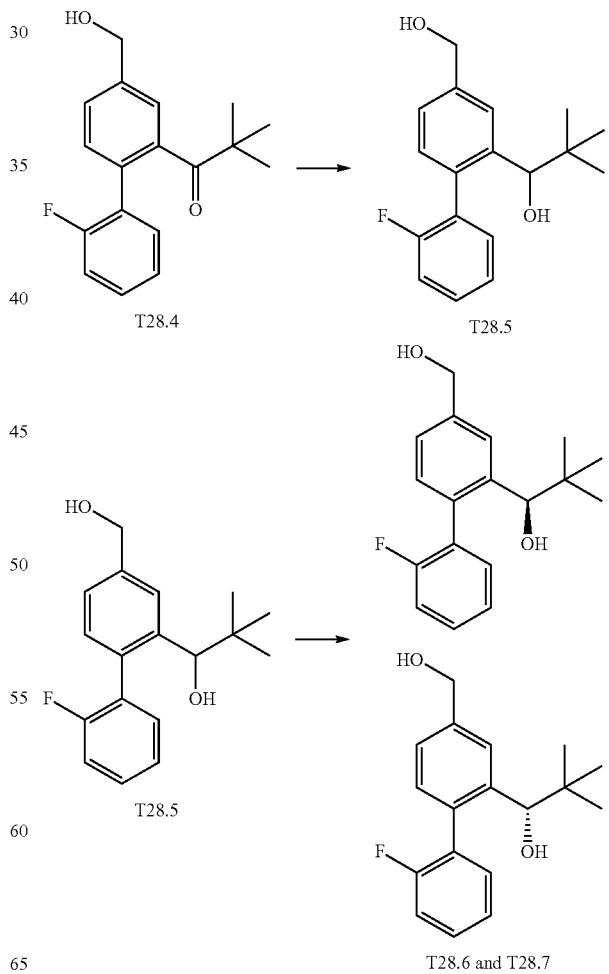

Methyl 2'-fluoro-4-(hydroxymethyl)-1,1'-biphenyl-2-
carboxylate (T28.3)

To a stirred solution of T28.2 (0.90 g, 3 mmol) in THF (33 mL) at 0° C. was added borane-THF complex (7 mL, 7 mmol, 1.0M). The reaction was allowed to warm to 23° C. and stirred for 7 hours. The reaction mixture was then concentrated in vacuo. The reaction was diluted with 1N HCl and extracted three times with EtOAc. After drying over anhydrous magnesium sulfate and filtering, the organic solvent was removed under reduced pressure and the product was then purified on silica gel (0-40% EtOAc in hexanes) to yield T28.3 as a colorless solid (0.850 g, 100% yield).

(1R)-1-(2'-Fluoro-4-(hydroxymethyl)-1,1'-biphenyl-2-yl)-2,2-dimethyl-1-propanol and (1S)-1-(2'-fluoro-4-(hydroxymethyl)-1,1'-biphenyl-2-yl)-2,2-dimethyl-1-propanol (T28.6 and T28.7)

To a stirred solution of T28.4 (0.670 g, 2 mmol) in THF (6 mL) at 0° C. was added LAH in THF (5 mL, 5 mmol, 1.0M). The reaction was stirred for 1.5 hours and then 1N NaOH(aq) was added to quench the reaction mixture. The reaction was then extracted three times with EtOAc. After drying over anhydrous magnesium sulfate and filtering, the organic solvent was removed under reduced pressure and the product was purified on silica gel (0-20% EtOAc in hexanes) to yield T28.5 as a colorless oil (0.450 g, 67% yield). Chiral separation of T28.5 was accomplished on a CHIRALCEL® OD column (3% IPA in hexane) to provide T28.6 and T28.7.

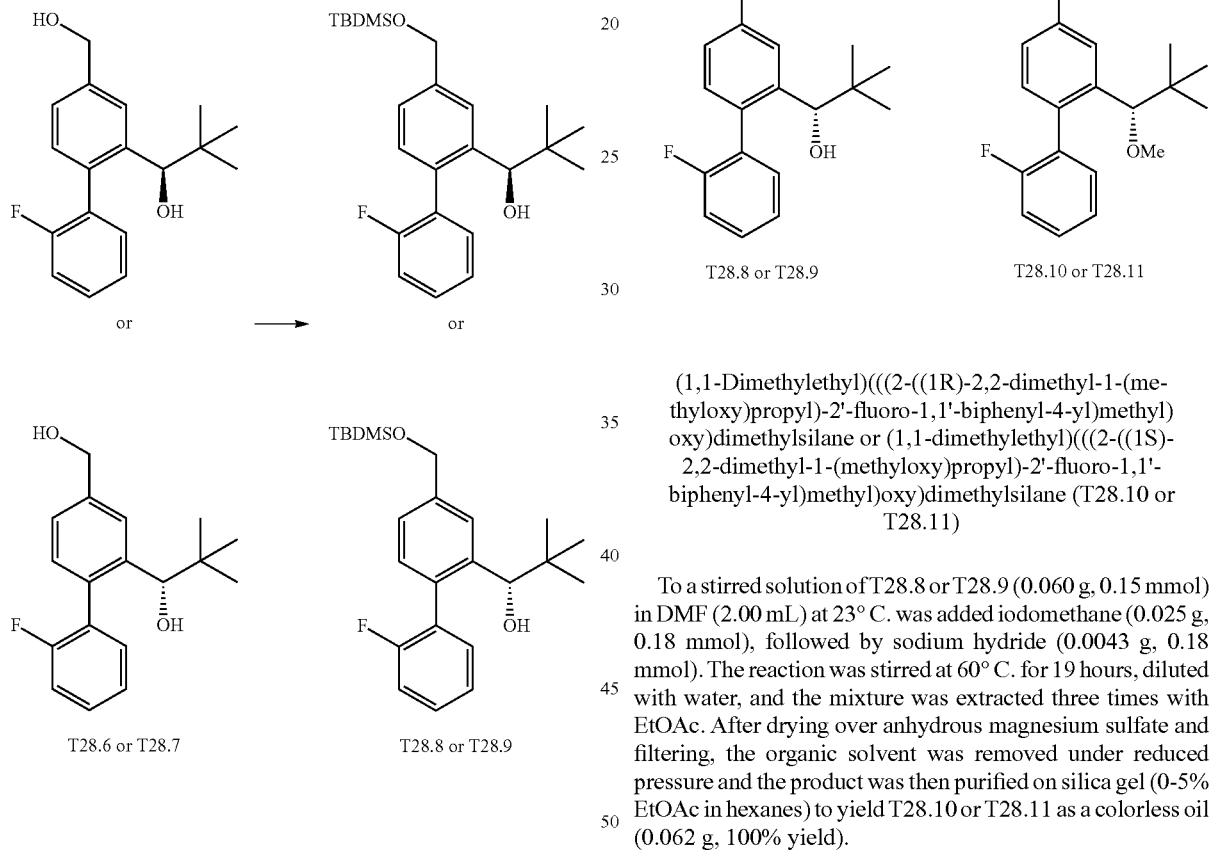

(1R)-1-(4-(((((1,1-Dimethylethyl)(dimethyl)silyl)oxy)methyl)-2'-fluoro-1,1'-biphenyl-2-yl)-2,2-dimethyl-1-propanol or (1S)-1-(4-(((((1,1-dimethylethyl)(dimethyl)silyl)oxy)methyl)-2'-fluoro-1,1'-biphenyl-2-yl)-2,2-dimethyl-1-propanol (T28.8 or T28.9)

To a stirred solution of T28.6 or T28.7 (0.200 g, 0.7 mmol) in DCM (10.00 mL) at 23° C. was added tert-butyldimethylsilyl chloride (0.1 mL, 0.8 mmol), followed by TEA (0.1 mL, 0.8 mmol) and DMAP (0.008 g, 0.07 mmol). The reaction was stirred for 14 hours and then concentrated in vacuo. The product was then purified on silica gel (0-10% EtOAc in hexanes) to yield T28.8 or T28.9 as a colorless oil (0.250 g, 90% yield).

(1,1-Dimethylethyl)(((2-((1R)-2,2-dimethyl-1-(methyloxy)propyl)-2'-fluoro-1,1'-biphenyl-4-yl)methyl)oxy)dimethylsilane or (1,1-dimethylethyl)(((2-((1S)-2,2-dimethyl-1-(methyloxy)propyl)-2'-fluoro-1,1'-biphenyl-4-yl)methyl)oxy)dimethylsilane (T28.10 or T28.11)

To a stirred solution of T28.8 or T28.9 (0.060 g, 0.15 mmol) in DMF (2.00 mL) at 23° C. was added iodomethane (0.025 g, 0.18 mmol), followed by sodium hydride (0.0043 g, 0.18 mmol). The reaction was stirred at 60° C. for 19 hours, diluted with water, and the mixture was extracted three times with EtOAc. After drying over anhydrous magnesium sulfate and filtering, the organic solvent was removed under reduced pressure and the product was then purified on silica gel (0-5% EtOAc in hexanes) to yield T28.10 or T28.11 as a colorless oil (0.062 g, 100% yield).

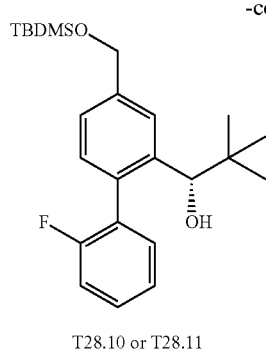

T28.10 or T28.11

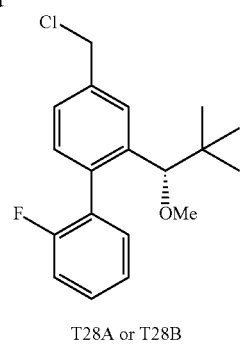

T28A or T28B

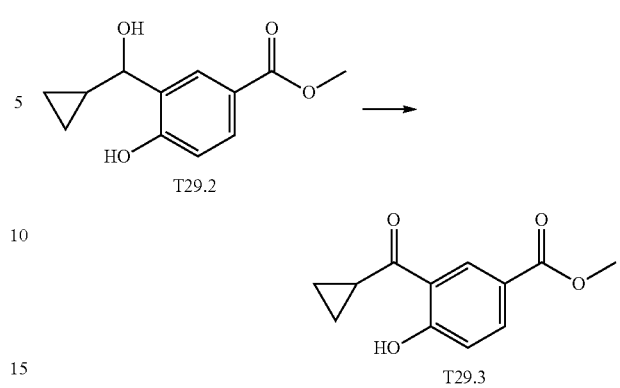

4-(Chloromethyl)-2-((1R)-2,2-dimethyl-1-(methyloxy)propyl)-2'-fluoro-1,1'-biphenyl or 4-(chloromethyl)-2-((1S)-2,2-dimethyl-1-(methyloxy)propyl)-2'-fluoro-1,1'-biphenyl (T28A or T28B)

To a stirred solution of T28.10 or T28.11 (0.071 g, 0.17 mmol) in DCM (1.7 mL) and DMF (0.013 mL) at 0° C. was added thionyl chloride (0.025 mL, 0.34 mmol). The reaction was stirred at room temperature for 1.5 hours and then concentrated in vacuo. The product was then purified on silica gel (0-5% EtOAc in hexanes) to yield T28A or T28B as a colorless oil (0.036 g, 66% yield).

Intermediate T29

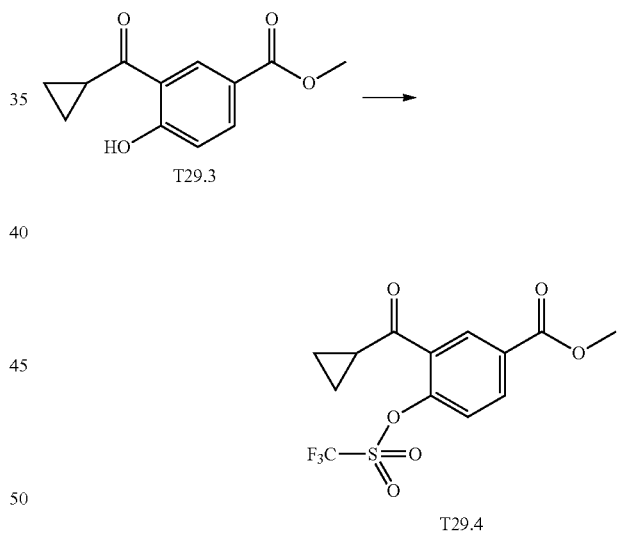

Methyl 3-(cyclopropyl(hydroxy)methyl)-4-hydroxybenzoate (T29.2)

In an ice-bath, methyl 3-formyl-4-hydroxybenzoate T29.1 (900 mg, 5 mmol) (commercially available from Sigma-Aldrich, St. Louis, Mo., USA) was dissolved in 5 mL THF. Then cyclopropylmagnesium bromide, 0.5 m in THF (22000 µL, 11 mmol) (commercially available from Sigma-Aldrich, St. Louis, Mo., USA) was added slowly. The reaction was raised to room temperature immediately and stirred at room temperature for 2 hours. After quenching with 1N HCl 11 mL, the reaction was extracted with EtOAc and dried. Silica gel chromatography afforded 950 mg of the product T29.2 (85%).

Methyl 3-(cyclopropanecarbonyl)-4-hydroxybenzoate (T29.3)

To a flask with methyl 3-(cyclopropyl(hydroxy)methyl)-4-hydroxybenzoate (T29.2) (845 mg, 0.38 mmol) was added manganese (IV) oxide (1.65 g, 1.9 mmol). Then dioxane 3.5 mL was added and the reaction was heated at reflux for 4 hours. The reaction was filtered and concentrated and silica gel chromatography afforded 693 mg of T29.3 (83%).

Methyl 3-(cyclopropanecarbonyl)-4-(trifluoromethylsulfonyloxy)benzoate (T29.4)

To a flask with methyl 3-(cyclopropanecarbonyl)-4-hydroxybenzoate T29.3 (693 mg, 3.1 mmol) was added DMAP (38 mg, 0.31 mmol), and the mixture was flushed with nitrogen. DCM was then added followed by TEA (0.88 mL, 6.3 mmol). After stirring at room temperature for 20 minutes, PhN(Tf)2 (1.2 g, 3.5 mmol) was added. The reaction gradually turned red and was stirred for another hour. The mixture was concentrated and purified by silica gel chromatography to afford 1.077 g of T29.4 as a colorless oil (97%).

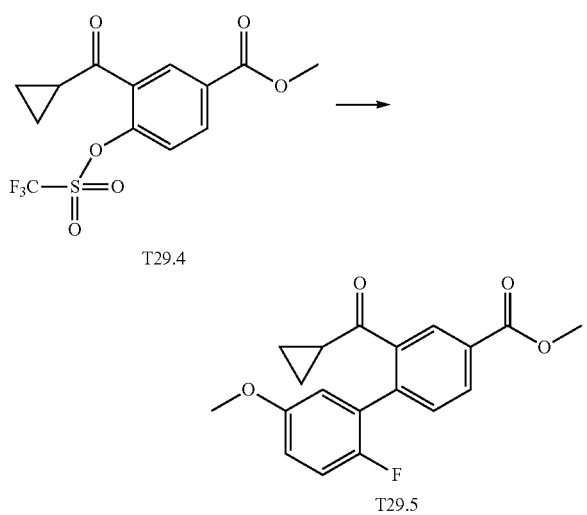

T29.4

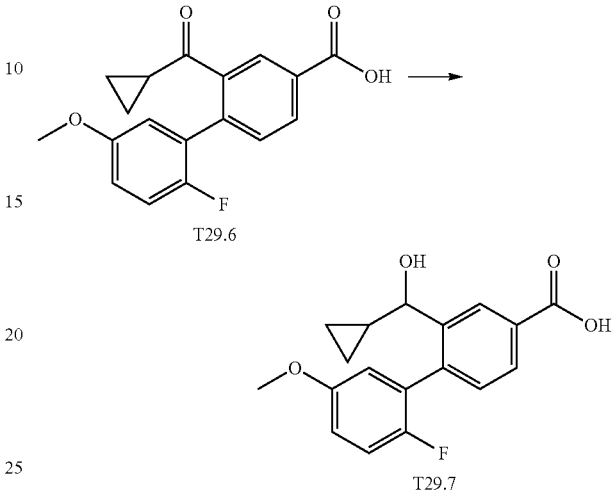

μmol) was added 9.6 mL of MeOH and 1N NaOH (3186 μL, 3186 μmol). The reaction was heated to 55 C for 2 hours. The mixture was then acidified with 1N HCl, concentrated, and extracted with EtOAc. Removal of the solvent afforded 500 mg of T29.6 (100%).

T29.5

Methyl 3-(cyclopropanecarbonyl)-4-(2-fluoro-5-methoxyphenyl))benzoate (T29.5)

Methyl 3-(cyclopropanecarbonyl)-4-(trifluoromethylsulfonyloxy)benzoate (T29.4) (1.077 g, 3.1 mmol) was dried under vacuum. To a second flask was added 2-fluoro-5-methoxyphenylboronic acid (1.5 g, 8.9 mmol) (commercially available from Sigma-Aldrich, St. Louis, Mo., USA), $Cs_2CO_3$ (3.5 g, 11 mmol), and tetrakis(triphenylphosphine) Palladium (0) (0.35 g, 0.31 mmol). Both flasks were flushed with nitrogen followed by vacuum. Degassed DME was then added to the flask with T29.4 (3 mL). Another 17 mL DME was added to the flask with the palladium catalyst followed by the DME solution of T29.4. The resulting slurry was stirred overnight in a 95° C. oil-bath. The reaction was filtered, concentrated, and purified by silica gel chromatography to afford 0.94 g of the desired product T29.5 (94%).

T29.6

T29.7

3-(Cyclopropyl(hydroxy)methyl)-4-(2-fluoro-5-methoxyphenyl))benzoic acid (T29.7)

To a flask with 3-(cyclopropanecarbonyl)-4-(2-fluoro-5-methoxyphenyl))benzoic acid (T29.6) (500 mg, 1591 μmol) was added anhydrous EtOH 10 mL, followed by addition of sodium borohydride (361 mg, 0.95 mmol). The reaction mixture was stirred overnight, quenched with water, and extracted with EtOAc. Removal of solvent gave 503 mg of T29.7 in racemic form.

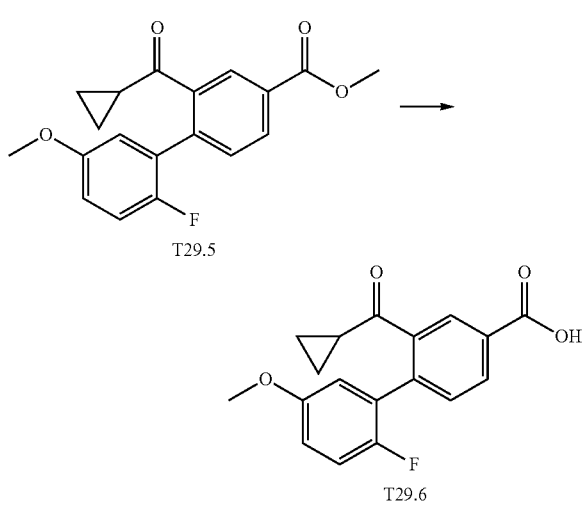

T29.5

T29.6

3-(Cyclopropanecarbonyl)-4-(2-fluoro-5-methoxyphenyl))benzoic acid (T29.6)

To a flask with methyl 3-(cyclopropanecarbonyl)-4-(2-fluoro-5-methoxyphenyl))benzoate (T29.5) (523 mg, 1593

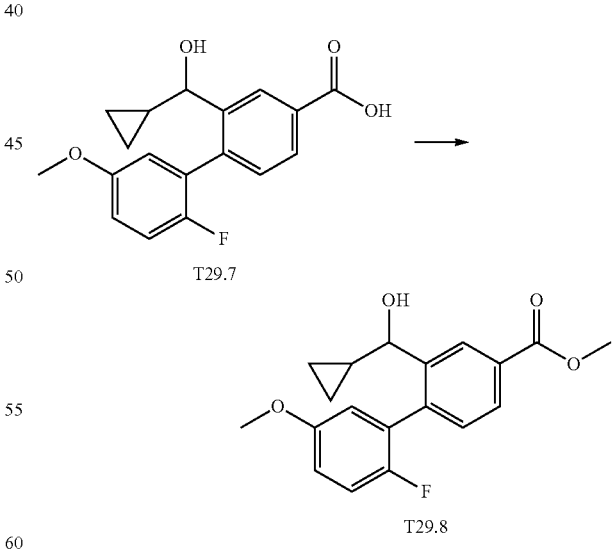

T29.7

T29.8

Methyl 3-(cyclopropyl(hydroxy)methyl)-4-(2-fluoro-5-methoxyphenyl))benzoate (T29.8)

To a flask with 3-(cyclopropyl(hydroxy)methyl)-4-(2-fluoro-5-methoxyphenyl))benzoic acid (T29.7), (503 mg, 1.6 mmol) was added 10 mL DCM and 2 mL MeOH. TMSdiazomethane (795 µL, 1590 µmol) in ether was then added, and the reaction was stirred at room temperature for 1 hour, and then quenched with a acetic acid. Water was added, and the reaction was extracted with EtOAc. Purification by silica gel chromatography afforded 484 mg of T29.8 (92%) in racemic form.

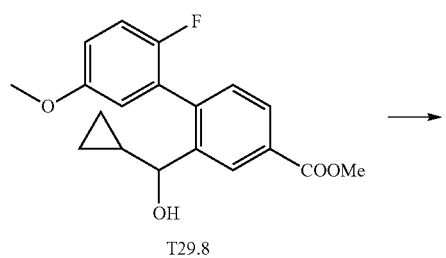

T29.8

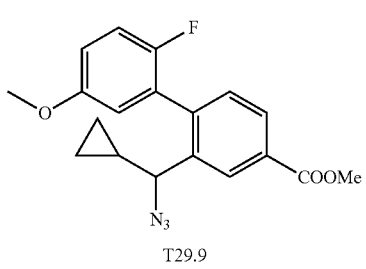

T29.9

Methyl 3-(azido(cyclopropyl)methyl)-4-(2-fluoro-5-methoxyphenyl))benzoate (T29.9)

To methyl 3-(cyclopropyl(hydroxy)methyl)-4-(2-fluoro-5-methoxyphenyl))benzoate (T29.8) (235 mg, 711 µmol) was added DMF 4 mL, then 1,8-diazabicyclo[5.4.0]undec-7-ene (160 µL, 1067 µmol), and diphenylphosphoryl azide (231 µL, 1067 µmol). The mixture was heated to 80° C. After 3 hours, 1.5 equivalents more of each of the 1,8-diazabicyclo[5.4.0]undec-7-ene and diphenylphosphoryl azide were added. The reaction was heated for two more hours and water was then added followed by EtOAc extraction. Purification by silica gel chromatography afforded 260 mg of T29.9 mixed with a non-polar side product. The product thus obtained was carried to the next step without further purification.

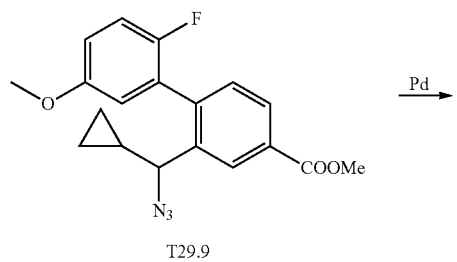

T29.9

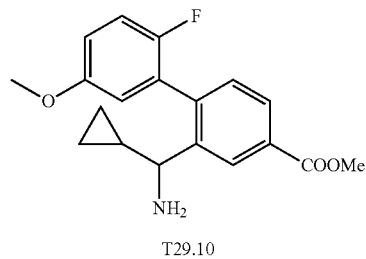

T29.10

Methyl 3-(amino(cyclopropyl)methyl)-4-(2-fluoro-5-methoxyphenyl))benzoate (T29.10)

To a flask with methyl 3-(azido(cyclopropyl)methyl)-4-(2-fluoro-5-methoxyphenyl))benzoate (T29.9) (260 mg, 732 µmol) was added 10% Pd/C (78 mg, 732 µmol), and then 6 mL of MeOH was added. The reaction was purged with hydrogen and stirred under a hydrogen balloon for about 6 hours. The reaction was filtered through a pad of Celite® filter aid, concentrated, and purified by silica gel chromatography to afford 76 mg of the desired product T29.10 (32% for 2 steps).

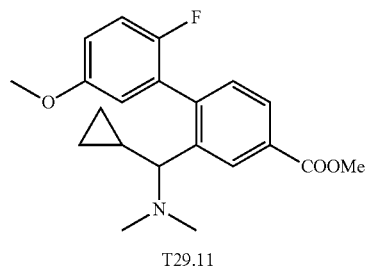

T29.10

T29.11

Methyl 3-(cyclopropyl)dimethylamino)methyl)-4-(2-fluoro-5-methoxyphenyl)benzoate (T29.11)

To a flask with methyl 3-(amino(cyclopropyl)methyl)-4-(2-fluoro-5-methoxyphenyl))benzoate (T29.10) (76 mg, 231 µmol) were added 2 mL DCM, formaldehyde (70 µL, 923 µmol), and acetic acid (26 µL, 461 µmol). Sodium triacetoxyborohydride (245 mg, 1154 µmol) was then added to the reaction mixture. The reaction was stirred for 1.5 hours and worked up with water and EtOAc. Silica gel chromatography afforded 35 mg of T29.11 (43%).

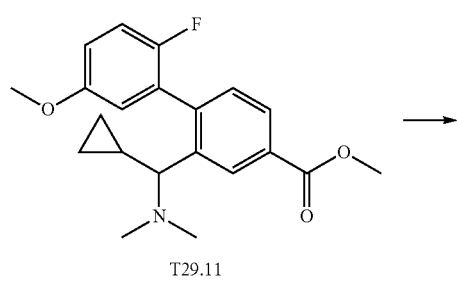

T29.11

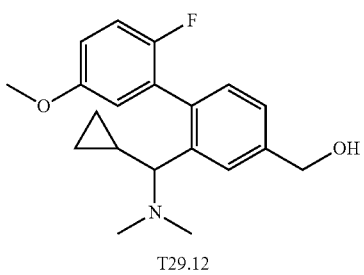

T29.12

(3-(Cyclopropyl(dimethylamino)methyl))-4-(2-fluoro-5-methoxyphenyl)phenyl)methanol (T29.12)

To a flask with methyl 3-(amino(cyclopropyl)methyl)-4-(2-fluoro-5-methoxyphenyl))benzoate (T29.11) (35 mg, 98 µmol) was added THF (1.5 mL). The mixture was cooled to 0° C. and then 1M LAH (196 µL, 196 µmol, 1M solution in THF) was added. The temperature was slowly raised to room temperature over 1 hour. Water and a small amount of Rochelle's salt solution were added to quench the reaction and it was then extracted with EtOAc. Silica gel chromatography afforded 26 mg of T29.12 (81%).

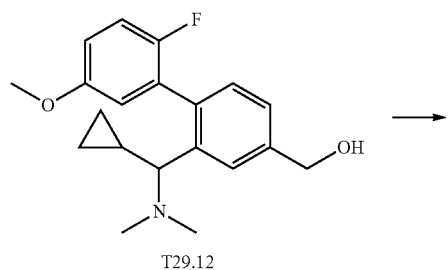

T29.12

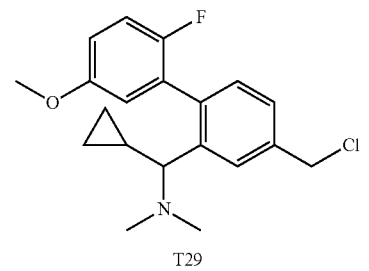

T29

(5-(Chloromethyl)-2-(2-fluoro-5-methoxyphenyl)phenyl)(cyclopropyl)-N,N-dimethylmethanamine (T29)

To a flask with (3-(cyclopropyl(dimethylamino)methyl))-4-(2-fluoro-5-methoxyphenyl)phenyl)methanol (T29.12) (26 mg, 79 µmol) was added DCM. The mixture was cooled in an ice-bath and then thionyl chloride (12 µL, 158 µmol) and DMF (6 µL, 79 µmol) were added. The reaction was stirred at room temperature for 1 hour, and then it was concentrated and purified by silica gel chromatography to afford 28 mg of T29 (102%).

Intermediate T30

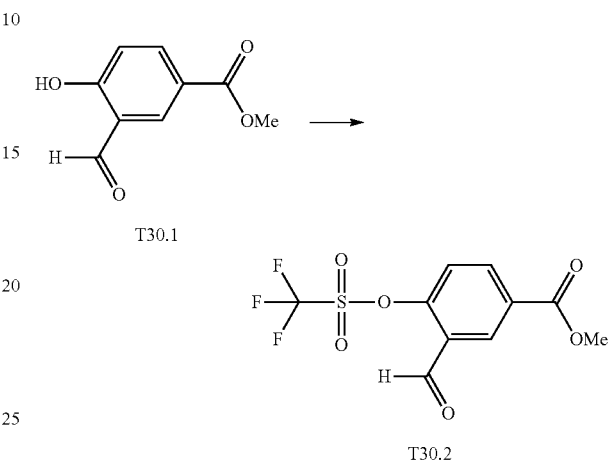

T30.1

T30.2

Methyl 3-formyl-4-(trifluoromethylsulfonyloxy)benzoate (T30.2)

Compound T30.2 was synthesized from methyl 3-formyl-4-hydroxybenzoate T30.1 (commercially available from Sigma-Aldrich, St. Louis, Mo., USA) using a method analogous to the method used to prepare compound T3.5 from T3.4. MS ESI m/e: 313.2 (M+H)+.

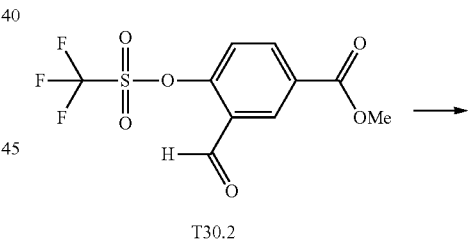

T30.2

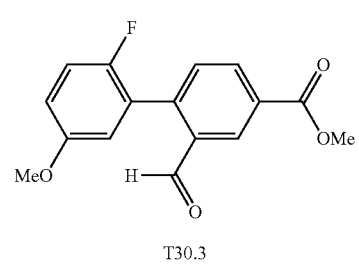

T30.3

2'-Fluoro-2-formyl-5'-methoxy-biphenyl-4-carboxylic acid methyl ester (T30.3)

To a round bottle flask, was added methyl 3-formyl-4-(trifluoromethylsulfonyloxy)benzoate (6300 mg, 20 mmol), 2-fluoro-5-methoxyphenylboronic acid (10 g, 61 mmol) (commercially available from Sigma-Aldrich, St. Louis, Mo., USA), potassium phosphate tribasic (6.6 mL, 81 mmol) (granular) and tetrakis(triphenylphosphine)palladium (2.3 g, 2.0 mmol). The flask was flushed with nitrogen, DME was added, and the mixture was heated at 90° C. for 6 hours. The reaction mixture was diluted with EtOAc and water. The organic phase was washed with water and brine and then dried over anhydrous sodium sulfate. After filtration, the organic solvent was removed in vacuo to give a residue which was purified by chromatography to give the product as a yellow solid (5.80 g, 100%). MS ESI m/e: 289.2 (M+H)$^+$.

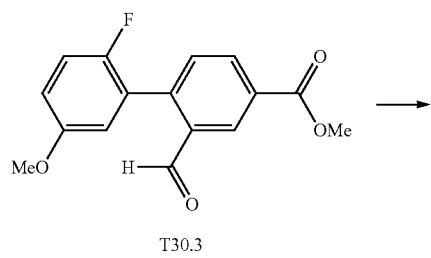

T30.3

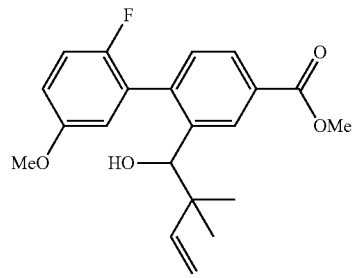

T30.4

2'-Fluoro-2-(1-hydroxy-2,2-dimethyl-but-3-enyl)-5'-methoxy-biphenyl-4-carboxylic acid methyl ester (T30.4)

To a mixed solution of sodium iodide (2080 mg, 13876 μmol), indium (2000 mg, 6938 μmol) and 1-bromo-3-methylbut-2-ene (1616 μL, 13876 μmol) in DMF (30 mL), was added T30.3 (1593 mg, 13876 μmol). The mixture was stirred at room temperature for 1 hour, and then was diluted with EtOAc and water. The organic phase was washed with water and brine and then dried over anhydrous sodium sulfate. After filtration, the organic solvent was removed in vacuo to give a residue which was purified by chromatography to give the product as an oil (2.30 g, 92%). MS ESI m/e: 376.1 (M+18)$^+$.

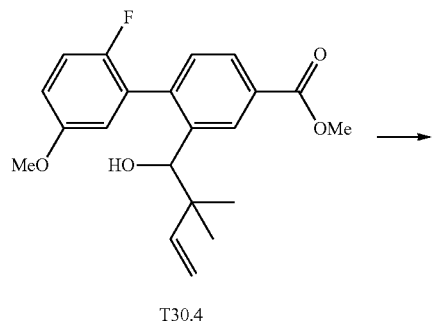

T30.4

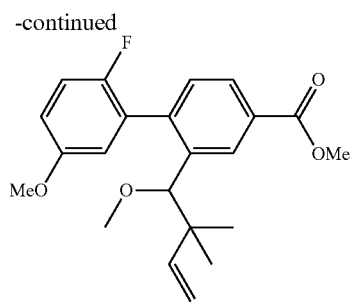

T30.5

2'-Fluoro-5'-methoxy-2-(1-methoxy-2,2-dimethyl-but-3-enyl)-biphenyl-4-carboxylic acid methyl ester (T30.5)

To a solution of T30.4 (1530 mg, 4269 μmol) in DMF (40 mL), was added sodium hydride (60% in oil)(213 μL, 8538 μmol). The mixture was stirred at room temperature for 10 minutes and then methyl iodide (530 μL, 8538 μmol) was added in one portion and the mixture was stirred at room temperature for 30 minutes. Water was added and the mixture was, extracted with EtOAc. The organic phase was washed with water and brine and then dried over anhydrous sodium sulfate. After filtration, the organic solvent was removed in vacuo to give the product as a residue which was purified by chromatography to give the product as an oil (0.75 g, 47%). MS ESI m/e: 373.2 (M+18)$^+$.

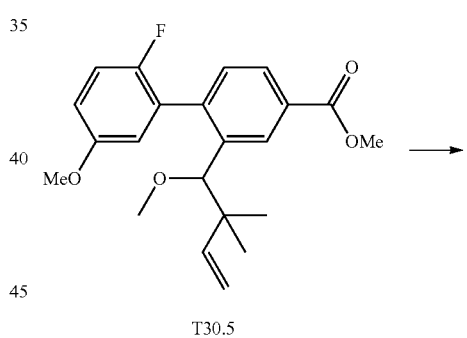

T30.5

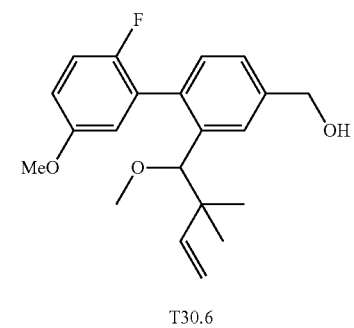

T30.6

[2'-Fluoro-5'-methoxy-2-(1-methoxy-2,2-dimethyl-but-3-enyl)-biphenyl-4-yl]-methanol (T30.6)

Compound T30.6 was synthesized from T30.5 by a method analogous to that used to prepare compound T15.4 from T15.3. MS ESI m/e: 345.2 (M+H)$^+$.

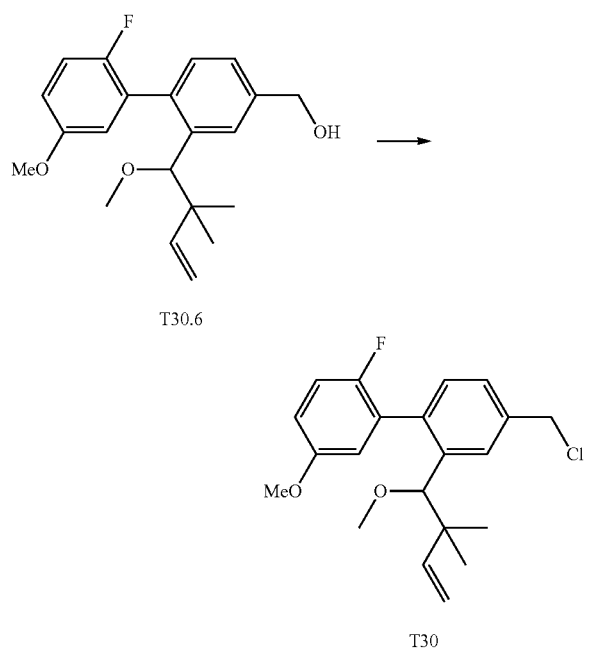

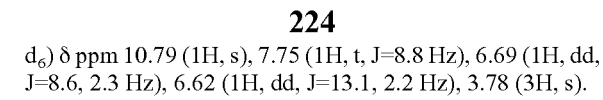

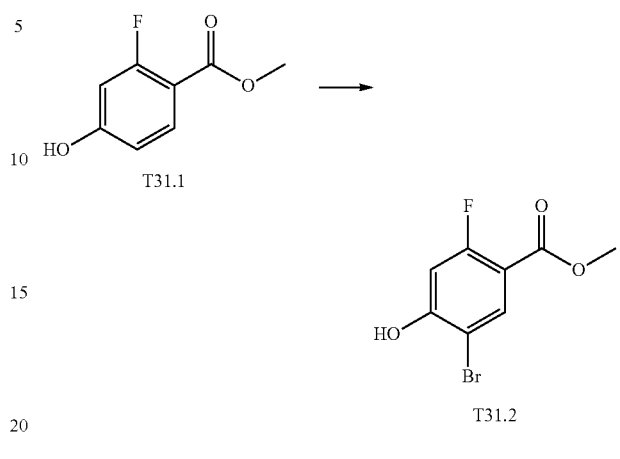

4-Chloromethyl-2'-fluoro-5'-methoxy-2-(1-methoxy-2,2-dimethyl-but-3-enyl)-biphenyl (T30)

Compound T30 was synthesized from T30.6 by a method analogous to the method used to prepare compound T15 from T15.4. MS ESI m/e: 363.2 (M+H)$^+$.

Intermediate T31

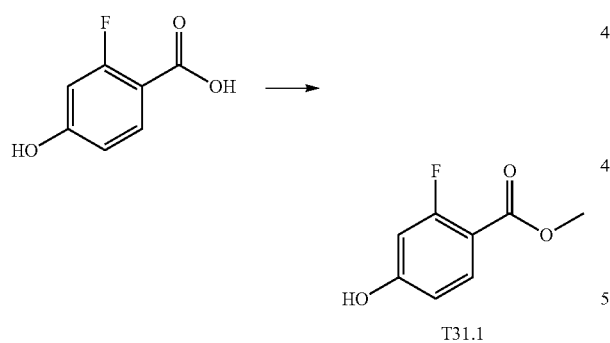

Methyl 2-fluoro-4-hydroxybenzoate (T31.1)

To a round bottom containing 2-fluoro-4-hydroxybenzoic acid (5.34 g, 34.19 mmol) (commercially available from Matrix Scientific and TCI America) was added a cold solution of MeOH (50 mL) and sulfuric acid (2.0 mL). The mixture was heated to 80° C. and monitored with TLC. After 20.5 hours, the solvent was removed, and the mixture was diluted with diethyl ether. The organic phase was washed carefully two times with saturated. aqueous NaHCO$_3$, once with brine, and then dried over anhydrous sodium sulfate. After filtration, the organic solvent was removed in vacuo to yield T31.1 as a white solid (5.82, 85% yield). $^1$H NMR (400 MHz, DMSO-d$_6$) δ ppm 10.79 (1H, s), 7.75 (1H, t, J=8.8 Hz), 6.69 (1H, dd, J=8.6, 2.3 Hz), 6.62 (1H, dd, J=13.1, 2.2 Hz), 3.78 (3H, s).

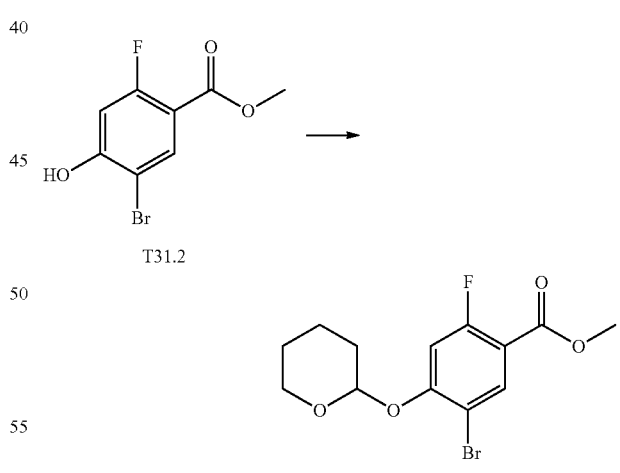

Methyl 5-bromo-2-fluoro-4-hydroxybenzoate (T31.2)

To a solution of T31.1 (2.03 g, 11.9 mmol) in acetic acid (65 mL) was added a pre-mixed solution of bromine (0.67 mL, 13.1 mmol) in acetic acid (10 mL). The mixture was stirred at 45° C. and monitored with TLC and LC-MS. After 18 hours, the reaction mixture was concentrated under reduced pressure. Brine was added to the residue, and the mixture was extracted three times with EtOAc. The combined organic layers were dried over anhydrous magnesium sulfate, filtered and concentrated to provide T31.2 as a white solid (2.12 g, 71% yield). $^1$H NMR (400 MHz, CDCl$_3$) δ ppm 8.13 (1H, d, J=7.4 Hz), 6.82 (1H, d, J=11.3 Hz), 6.04 (1H, s), 3.92 (3H, s).

Methyl 5-bromo-2-fluoro-4-(tetrahydro-2H-pyran-2-yloxy)benzoate (T31.3)

To a round bottom containing T31.2 (13.15 g, 52.8 mmol) in dry DCM (90 mL) was added 3,4-dihydro-2H-pyran (10 mL, 110 mmol) followed by PPTS (0.13 g, 0.53 mmol). The reaction mixture was heated to a gentle reflux (50° C.) and monitored with TLC and LC-MS. After 24 hours, the reaction was concentrated under reduced pressure and then diluted with MeOH. After concentration, the residue was heated in a round bottom flask containing MeOH on the rotary evaporator (without vacuum.) at 40° C. After about 30 minutes, the solution was concentrated to a volume of about 5 mL. After cooling to room temperature, the white solid was filtered and rinsed once with MeOH to yield T31.3 (13.35 g, 76% yield). $^1$H NMR (400 MHz, CDCl$_3$) δ ppm 8.25 (1H, m), 6.96 (1H, d, J=12.5 Hz), 5.56 (1H, m), 3.91 (3H, s), 3.79 (1H, td, J=11.1, 2.5 Hz), 3.65 (1H, d, J=10.6 Hz), 2.23 (2H, m), 1.96 (3H, m), 1.68 (1H, m).

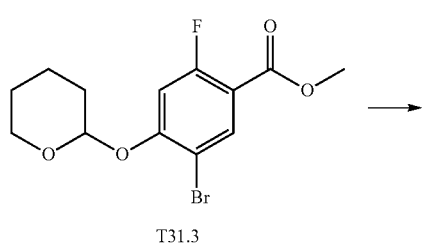

T31.3

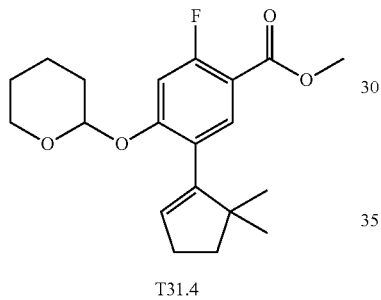

T31.4

Methyl 5-(5,5-dimethylcyclopent-1-enyl)-2-fluoro-4-(tetrahydro-2H-pyran-2-yloxy)benzoate (T31.4)

A stirred mixture of T31.3 (10.33 g, 31.0 mmol), ground S-Phos (2.55 g, 6.21 mmol), palladium acetate (0.70 g, 3.11 mmol), and potassium phosphate, tribasic (16.49 g, 77.7 mmol) in DMF (75 mL) and water (4 mL) was purged with argon and placed under vacuum and the process repeated three times. Before heating, 2-(5,5-dimethylcyclopent-1-enyl)-4,4,5,5-tetramethyl-1,3,2-dioxaborolane (T2.2) (8.96 g, 40.4 mmol) was added via syringe. The mixture was then heated at 75° C. After 21 hours, the reaction was cooled to room temperature, diluted with water, and extracted three times with EtOAc. The organic layers were combined and washed twice with brine. After drying over anhydrous sodium sulfate and filtration, the organic solvent was removed under reduced pressure. The residue was purified by silica gel flash chromatography (0-10% EtOAc/hexane) to yield T31.4 (5.65 g, 52% yield). $^1$H NMR (400 MHz, CDCl$_3$) δ ppm 7.63 (1H, d, J=8.6 Hz), 6.93 (1H, d, J=13.3 Hz), 5.55 (1H, t, J=2.3 Hz), 5.43 (1H, t, J=2.7 Hz), 3.90 (3H, s), 3.82 (1H, m), 3.67 (1H, m), 2.41 (2H, td, J=7.0, 2.3 Hz), 1.97 (5H, m), 1.79 (3H, m), 1.07 (6H, d, J=13.7 Hz).

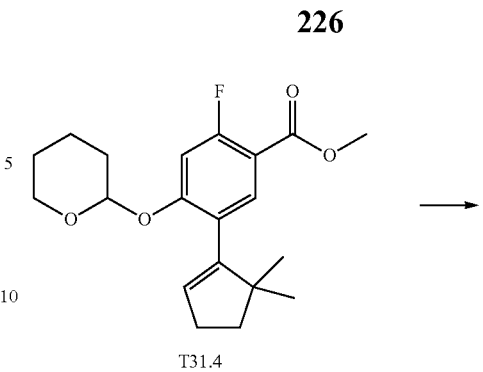

Methyl 5-(5,5-dimethylcyclopent-1-enyl)-2-fluoro-4-hydroxybenzoate (T31.5).

To a stirred mixture of T31.4 (5.65 g, 16.2 mmol) in MeOH (60 mL) was added PPTS (0.42 g, 1.69 mmol). The mixture was heated to 50° C. and monitored with TLC and LCMS. After 19 hours, the organic solvent was removed under reduced pressure, and the residue was then purified on silica gel (0-15% EtOAc in hexanes) to yield T31.5 as a white solid (3.47 g, 81% yield). $^1$H NMR (500 MHz, CDCl$_3$) δ ppm 7.69 (1H, d, J=8.3 Hz), 6.71 (1H, d, J=12.0 Hz), 5.93 (1H, d, J=1.7 Hz), 5.80 (1H, t, J=2.4 Hz), 3.90 (3H, s), 2.54 (2H, m), 1.93 (2H, t, J=7.1 Hz), 1.11 (6H, s).

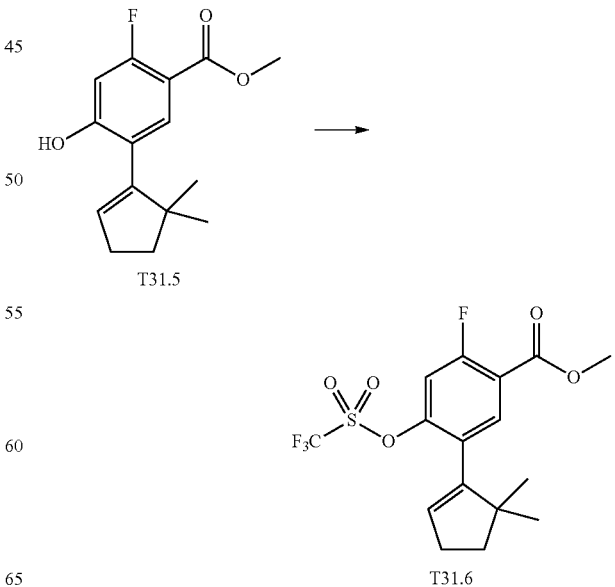

Methyl 5-(5,5-dimethylcyclopent-1-enyl)-2-fluoro-4-(trifluoromethylsulfonyloxy)benzoate (T31.6)

To a stirred solution of T31.5 (0.80 g, 3.02 mmol) in dry DCM (15 mL) was added TEA (1.0 mL, 7.19 mmol) and 4-dimethylaminopyridine (38.1 mg, 0.312 mmol). After about 20 minutes, N-phenyl-bis(trifluoromethanesulfonimide) (1.30 g, 3.64 mmol) was added in portions. Upon complete addition, the solution was stirred at room temperature and monitored with TLC and LC-MS. After 19 hours, the organic solvent was removed under reduced pressure and the resulting residue was purified with silica gel chromatography using 0-10% EtOAc in hexanes to yield T31.6 as a colorless oil (1.05 g, 88% yield). $^1$H NMR (400 MHz, CDCl$_3$) δ ppm 7.84 (1H, d, J=7.8 Hz), 7.13 (1H, d, J=10.2 Hz), 5.79 (1H, t, J=2.3 Hz), 3.96 (3H, s), 2.47 (2H, td, J=7.0, 2.3 Hz), 1.91 (2H, t, J=7.0 Hz), 1.08 (6H, s).

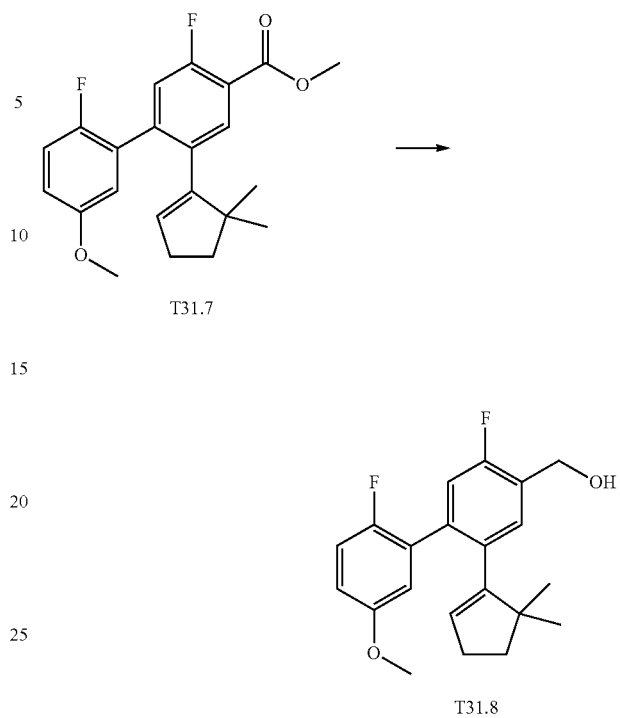

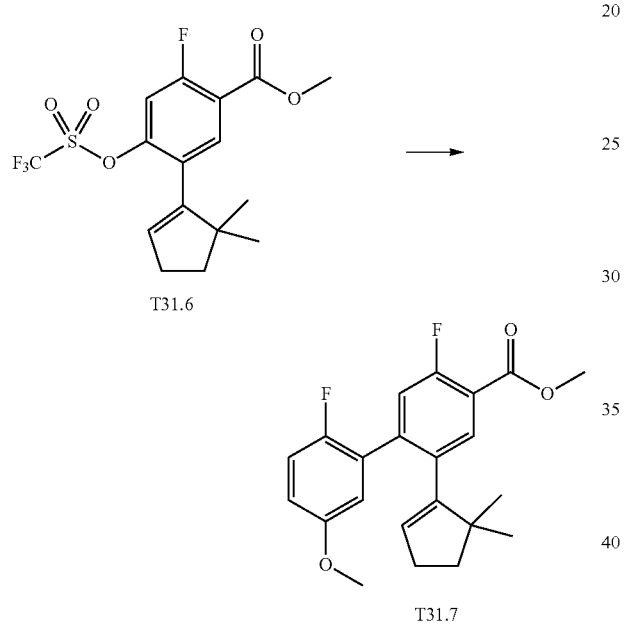

Methyl 2-(5,5-dimethyl-1-cyclopenten-1-yl)-2',5-difluoro-5'-(methyloxy)-1,1'-biphenyl-4-carboxylate (T31.7)

To a stirred solution of T31.6 (1.05 g, 2.65 mmol) in DMF (5 mL) at 23° C. was added 2-fluoro-5-methoxyphenylboronic acid (0.90 g, 5.32 mmol) (commercially available from Sigma-Aldrich, St. Louis, Mo., USA) and potassium carbonate (1.10 g, 7.96 mmol) followed by tetrakis(triphenylphosphine)palladium (0.31 g, 0.27 mmol). The mixture was heated to 90° C. After 17 hours, the mixture was cooled to room temperature and then diluted with water. After extracting three times with EtOAc, the mixture was concentrated in vacuo and then purified on silica gel (0%-10% EtOAc/hexane) to give T31.7 as a clear oil that was used without further purification (0.92 g, 93% yield). $^1$H NMR (400 MHz, CDCl$_3$) δ ppm 7.79 (1H, d, J=7.4 Hz), 7.13 (1H, d, J=11.3 Hz), 6.99 (1H, t, J=9.0 Hz), 6.84 (1H, dt, J=8.7, 3.7 Hz), 6.78 (1H, dd, J=5.9, 3.1 Hz), 5.55 (1H, s), 3.96 (3H, s), 3.79 (3H, s), 2.27 (2H, td, J=7.1, 2.5 Hz), 1.67 (2H, t, J=7.0 Hz), 0.84 (6H, s).

(2-(5,5-Dimethyl-1-cyclopenten-1-yl)-2',5-difluoro-5'-(methyloxy)-1,1'-biphenyl-4-yl)methanol (T31.8)

To a cooled solution of T31.7 (0.92 g, 2.47 mmol) in dry THF (15 mL) at 0° C. was added LAH (1.0 M in THF)(5.0 mL, 5.0 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography (silica gel 60, eluted with 0%-50% EtOAc in hexanes). Fractions containing the desired product were combined and concentrated to provide T31.8 as a colorless oil (0.70 g, 82% yield). $^1$H NMR (500 MHz, CDCl$_3$) δ ppm 7.30 (1H, m), 7.05 (1H, dd, J=10.6, 1.1 Hz), 6.97 (1H, t, J=8.9 Hz), 6.83 (2H, m), 5.52 (1H, td, J=2.4, 0.9 Hz), 4.81 (2H, s), 3.76 (3H, s), 2.25 (2H, td, J=7.1, 2.4 Hz), 1.76 (1H, br. s.), 1.69 (2H, m), 0.85 (6H, s).

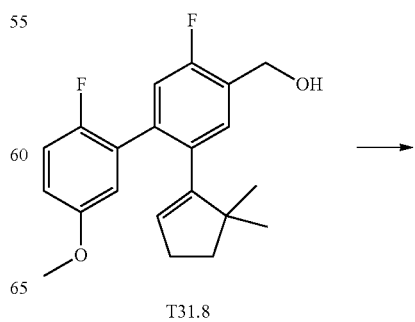

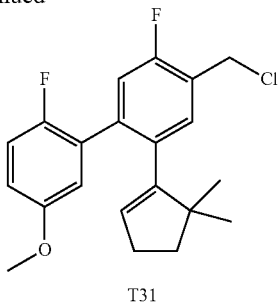

T31

4-(Chloromethyl)-2-(5,5-dimethyl-1-cyclopenten-1-yl)-2',5-difluoro-5'-(methyloxy)-1,1'-biphenyl (T31)

To a solution of T31.8 (0.17 g, 0.48 mmol) in dry DCM (2.0 mL) and dry DMF (0.020 mL) was added thionyl chloride (0.080 mL, 1.1 mmol) dropwise at 0° C. The resulting solution was warmed to room temperature and monitored with TLC and LCMS. After 45 minutes, the reaction was concentrated and then purified by silica gel flash chromatography (0-5% EtOAc/hexane) to afford T31 as a colorless oil (0.16 g, 93% yield). $^1$H NMR (400 MHz, CDCl$_3$) δ ppm 7.29 (1H, d, J=7.8 Hz), 7.08 (1H, d, J=10.2 Hz), 6.98 (1H, t, J=9.0 Hz), 6.85 (2H, m), 5.56 (1H, s), 4.69 (2H, s), 3.77 (3H, s), 2.27 (2H, td, J=7.0, 2.7 Hz), 1.68 (2H, t, J=7.0 Hz), 0.86 (6H, s).

Intermediate T32

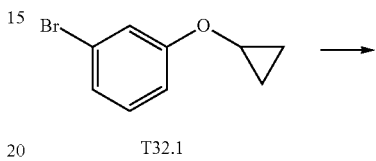

3-Bromophenyl cyclopropyl ether (T32.1)

To a solution of 3-bromophenol (0.57 g, 3.29 mmol) (commercially available from Sigma-Aldrich, St. Louis, Mo., USA) in dry DMF (5.0 mL) was added cyclopropyl bromide (0.53 mL, 6.62 mmol) (commercially available from Sigma-Aldrich, St. Louis, Mo., USA), sodium iodide (50.1 mg, 0.334 mmol), and Cs$_2$CO$_3$ (3.2 g, 9.86 mmol). The reaction mixture was heated in a pressure tube to 150° C. After 19 hours, the reaction was cooled to room temperature then diluted with EtOAc, washed with water, and extracted three times with EtOAc. The combined organic layers were dried over sodium sulfate, filtered, and concentrated. The residue was purified by silica gel flash chromatography (0-5% EtOAc/hexane) to afford T32.1 as a colorless oil (144 mg, 21% yield). $^1$H NMR (400 MHz, CDCl$_3$) δ ppm 7.29 (1H, m), 7.19 (2H, m), 6.99 (1H, d, J=7.8 Hz), 3.74 (1H, ddd, J=8.9, 5.8, 3.3 Hz), 0.81 (4H, ddd, J=11.2, 9.0, 8.8 Hz.).

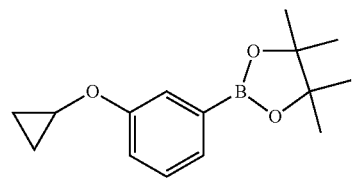

2-(3-(Cyclopropyloxy)phenyl)-4,4,5,5-tetramethyl-1,3,2-dioxaborolane (T32.2)

A stirred mixture of T32.1 (0.144 g, 0.676 mmol), bis(pinacolato)diboron (0.189 g, 0.745 mmol), potassium acetate (0.2007 g, 2.04 mmol), and dichloro[1,1'-bis(diphenylphosphino)ferrocene]palladium (II) DCM adduct (25.3 mg, 0.0346 mmol) in dry 1,4-dioxane (3.0 mL) was purged three times with argon and placed under vacuum three times. The mixture was heated to 100° C., and monitored with LC-MS and TLC. After 21 hours, the reaction was cooled to room temperature and filtered through Celite® filter aid. The organic solvent was removed under reduced pressure. The residue was purified by silica gel flash chromatography (0-10% EtOAc/hexane) to afford T32.2 as a colorless oil (72 mg, 41% yield). $^1$H NMR (400 MHz, CDCl$_3$) δ ppm 7.51 (1H, d, J=2.7 Hz), 7.44 (1H, d, J=7.0 Hz), 7.34 (1H, m), 7.14 (1H, dd, J=7.6, 2.2 Hz), 3.80 (1H, ddd, J=8.8, 5.9, 3.3 Hz), 1.36 (12H, s), 0.82 (4H, m).

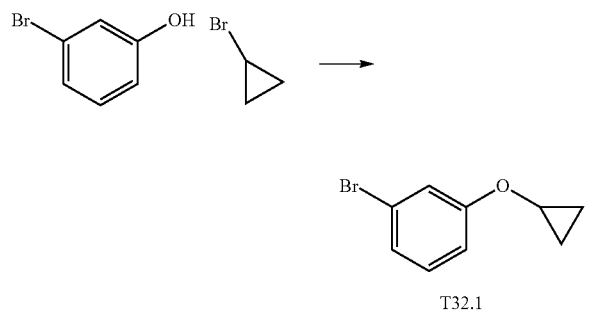

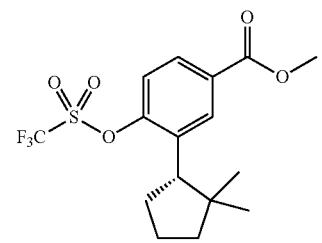

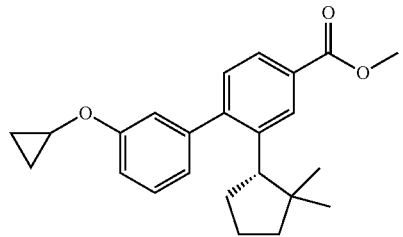

-continued

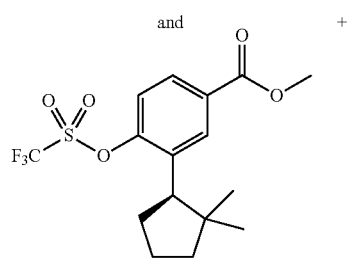

T18.6 and +

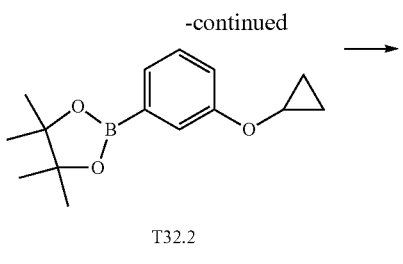

T32.2

→ and

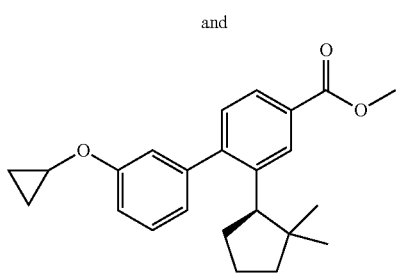

T32.3

Methyl 3'-(cyclopropyloxy)-2-(2,2-dimethylcyclopentyl)-1,1'-biphenyl-4-carboxylate (T32.3)

To a stirred solution of T18.6 (438.2 mg, 1.15 mmol) in dry DMF (5.0 mL) at 23° C. was added potassium carbonate (480.3 mg, 3.47 mmol) followed by tetrakis(triphenylphosphine)palladium (140.2 mg, 0.121 mmol). The mixture was purged three times with argon and placed under vacuum three times. Before heating, T32.2 (523.1 mg, 2.01 mmol) was added via syringe and then the mixture was heated to 90° C. After 19 hours, LCMS showed that the reaction was complete. The mixture was cooled to room temperature and then diluted with water. After extracting three times with EtOAc, the mixture was concentrated in vacuo and then purified on silica gel (0%-10% EtOAc/hexane) to afford T32.3 as a colorless oil that was used without further purification (411.5 mg, 98% yield). MS ESI (pos.) m/e: 365.0 (M+H)$^+$.

(S)-(3'-Cyclopropoxy-2-(2,2-dimethylcyclopentyl) biphenyl-4-yl)methanol and (R)-(3'-cyclopropoxy-2-(2,2-dimethylcyclopentyl)biphenyl-4-yl)methanol (T32.4 and T32.5)

To a cooled solution of T32.3 (0.4115 g, 1.129 mmol) in dry THF (10 mL) at 0° C. was added LAH (1.0 M in THF) (2.30 mL, 2.3 mmol) dropwise. Upon complete addition, the reaction was maintained at 0° C. and was monitored by TLC and LCMS. After 45 minutes, 1N NaOH was added to quench the reaction. The resulting mixture was extracted three times with EtOAc. After drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to provide a colorless oil (317.1 mg, 83% yield, MS ESI (pos.) m/e: 319.0 (M–H$_2$O)$^+$). The mixture of enantiomers was then separated by chiral chromatography on a CHIRALCEL® OD chromatography column (3% IPA in hexane) to provide T32.4 (first peak) and T32.5 (second peak).

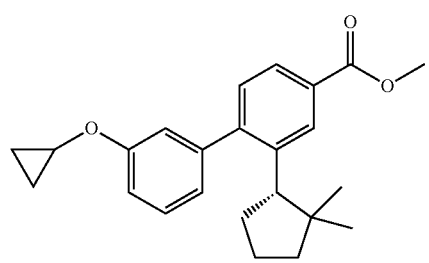

and

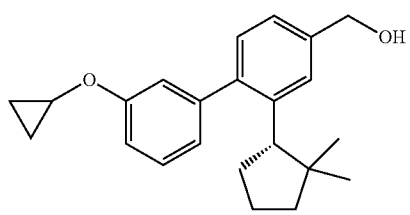

→ and

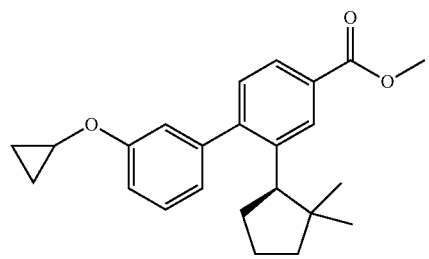

T32.3

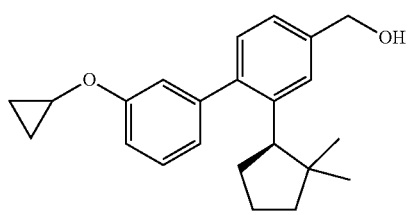

T32.4 and T32.5

233

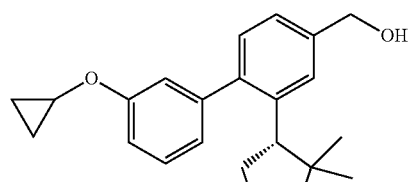

or

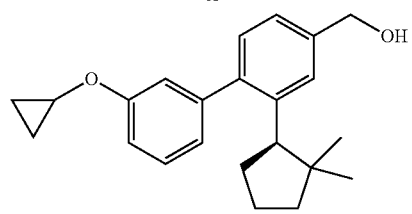

T32.5

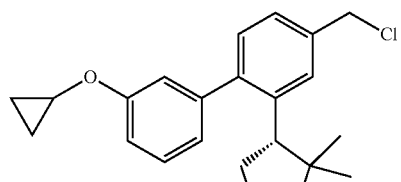

or

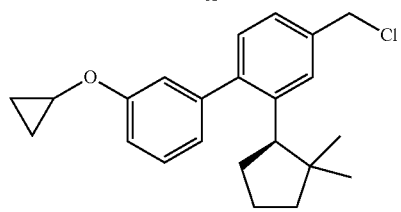

T32

4-(Chloromethyl)-3'-(cyclopropyloxy)-2-((1S)-2,2-dimethylcyclopentyl)-1,1'-biphenyl or 4-(chloromethyl)-3'-(cyclopropyloxy)-2-((1R)-2,2-dimethylcyclopentyl)-1,1'-biphenyl (T32)

To a solution of T32.5 (0.1335 g, 0.397 mmol) in dry DCM (4 mL) and dry DMF (0.03 mL) was added thionyl chloride (0.07 mL, 0.96 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T32 as a colorless oil (118.3 mg, 84% yield). $^1$H NMR (400 MHz, CDCl$_3$) δ ppm 7.39 (1H, d, J=1.6 Hz), 7.34 ( ), 3.78 (1H, m), 3.15 (1H, dd, J=10.4, 3 H, m), 7.01 (1H, dd, J=7.8, 3.1 Hz), 6.98 (1H, m), 6.85 (1H, d, J=7.4 Hz), 4.69 (2H, m 8.4 Hz), 2.13 (2H, m), 1.88 (1H, m), 1.72 (1H, m), 1.59 (1H, m), 1.41 (1H, m), 0.82 (6H, m), 0.58 (3H, s).

Intermediate T33

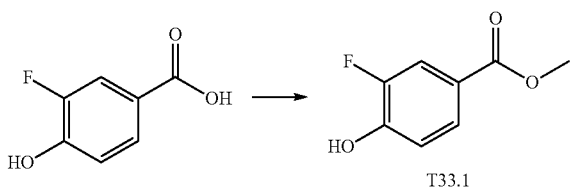

Methyl 3-fluoro-4-hydroxybenzoate (T33.1)

To a round bottom flask containing 3-fluoro-4-hydroxybenzoic acid (5.03 g, 32.22 mmol) (commercially available from Sigma-Aldrich, St. Louis, Mo., USA) was added a cold solution of MeOH (50.0 mL) and sulfuric acid (2.0 mL). The mixture was heated to 80° C. and monitored with TLC. After 20.5 hours, the solvent was removed and the mixture was diluted with diethyl ether. The organic phase was washed carefully twice with saturated aqueous NaHCO$_3$ and once with brine. The organic phase was then dried over anhydrous sodium sulfate. After filtration, the organic solvent was removed in vacuo to afford T33.1 as a white solid (4.79 g, 87% yield). $^1$H NMR (400 MHz, CDCl$_3$) δ ppm 7.81 (2H, m), 7.06 (1H, t, J=8.4 Hz), 5.62 (1H, d, J=4.3 Hz), 3.91 (3H, s).

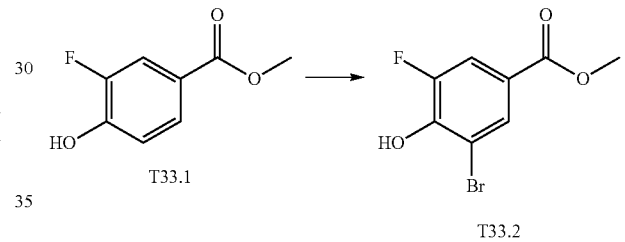

Methyl 3-bromo-5-fluoro-4-hydroxybenzoate (T33.2)

Bromine (1.60 mL, 31.1 mmol) was added dropwise with stirring over 30 minutes to an ice-cooled solution of T33.1 (4.79 g, 28.1 mmol) in a 1:1 mixture of DCM (20 mL) and acetic acid (20 mL). Upon complete addition, the reaction mixture was allowed to warm to room temperature and monitored with TLC and LC-MS. After stirring at room temperature for 40 hours, the mixture was diluted with EtOAc, and then the resulting solution was washed twice with aqueous saturated Na$_2$SO$_3$, once with water, and once with brine. After drying over anhydrous magnesium sulfate, filtration, and concentration, the white solid T33.2 was obtained 6.69 g, 95% yield). $^1$H NMR (400 MHz, CDCl$_3$) δ ppm 8.05 (1H, m), 7.75 (1H, dd, J=10.6, 2.0 Hz), 6.12 (1H, s), 3.94 (3H, s).

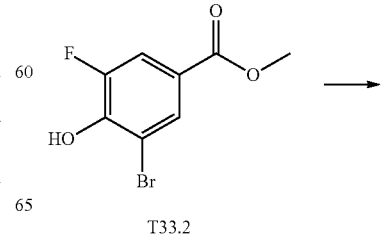

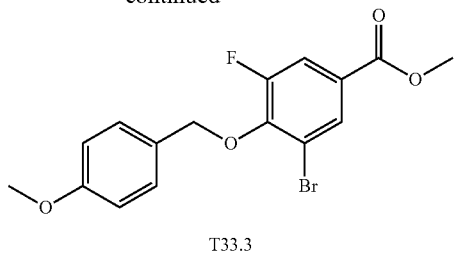

T33.3

Methyl 3-bromo-5-fluoro-4-(((4-(methyloxy)phenyl)-methyl)oxy)benzoate (T33.3)

To a vial containing T33.2 (0.64 g, 2.58 mmol) in 5.0 mL dry DMF was added $Cs_2CO_3$ (1.10 g, 3.36 mmol) The mixture was stirred at room temperature for 10 minutes and then 4-methoxybenzyl bromide (0.45 mL, 3.1 mmol) was added. After 4 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-40% EtOAc/hexane) to afford T33.3 as a white solid (679.1 mg, 71% yield). $^1$H NMR (400 MHz, $CDCl_3$) δ ppm 8.02 (1H, t, J=2.0 Hz), 7.72 (1H, dd, J=11.5, 2.2 Hz), 7.42 (2H, m, J=8.6 Hz), 6.90 (2H, m), 5.20 (2H, s), 3.91 (3H, s), 3.82 (3H, s).

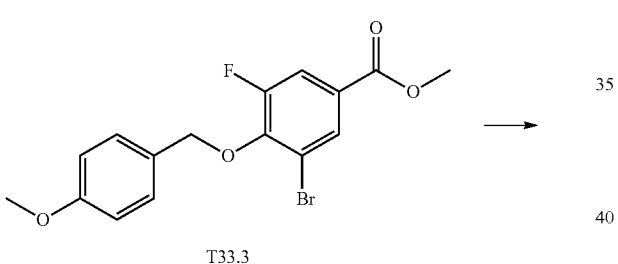

T33.3

T33.4

Methyl 3-(5,5-dimethyl-1-cyclopenten-1-yl)-5-fluoro-4-(((4-(methyloxy)phenyl)methyl)oxy)benzoate (T33.4)

A stirred mixture of T33.3 (1.63 g, 4.420 mmol), ground S-Phos (0.36 g, 0.88 mmol), palladium acetate (0.10 g, 0.45 mmol), and potassium phosphate tribasic (2.35 g, 11.06 mmol) in DMF (13 mL) and water (0.4 mL) was purged with argon and placed under vacuum and the process repeated three times. Before heating, 2-(5,5-dimethylcyclopent-1-enyl)-4,4,5,5-tetramethyl-1,3,2-dioxaborolane (T2.2) (1.47 g, 6.63 mmol) was added via syringe and then the mixture was heated to 75° C. After 18 hours, the reaction was cooled to room temperature, diluted with water, and extracted three times with EtOAc. The organic layers were combined and washed twice with brine. After drying over anhydrous sodium sulfate and filtration, the organic solvent was removed under reduced pressure. The residue was purified on a 40 g column of silica gel (0-10% EtOAc in hexanes) to afford T33.4 as a white solid (1.12 g, 66% yield). $^1$H NMR (400 MHz, $CDCl_3$) δ ppm 7.69 (1H, dd, J=11.7, 2.3 Hz), 7.57 (1H, dd, J=2.0, 1.2 Hz), 7.31 (2H, m), 6.88 (2H, m), 5.56 (1H, t, J=2.5 Hz), 5.01 (2H, s), 3.91 (3H, s), 3.82 (3H, s), 2.42 (2H, td, J=7.0, 2.7 Hz), 1.86 (2H, t, J=7.2 Hz), 1.06 (6H, s).

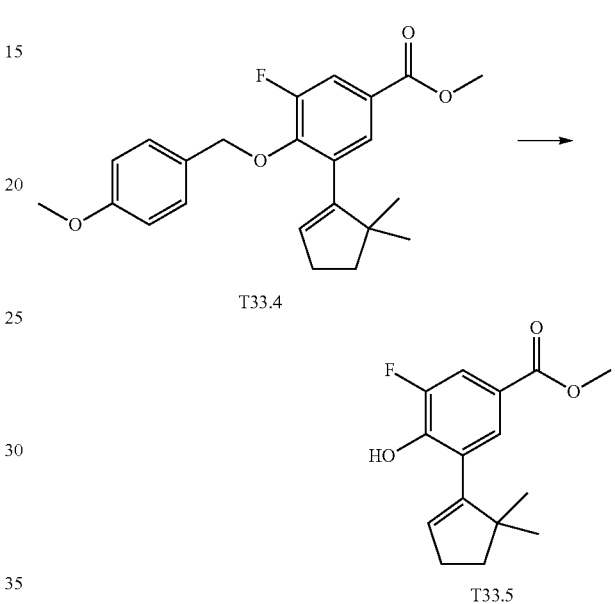

T33.4

T33.5

Methyl 3-(5,5-dimethyl-1-cyclopenten-1-yl)-5-fluoro-4-hydroxybenzoate (T33.5)

To a flask containing T33.4 (1.12 g, 2.93 mmol) was added a premixed solution of DCM (14 mL) and TFA (1 mL). The mixture was stirred at room temperature and monitored with TLC and LC-MS. After 1 hour, the reaction was diluted with DCM and then washed once with saturated aqueous sodium bicarbonate solution and brine. After washing, the organic layer was dried over anhydrous sodium sulfate, filtered, and concentrated in vacuo. The residue was purified by flash chromatography ($SiO_2$ gel 60, eluted with 0%-50% EtOAc in hexanes). Fractions containing the desired product were combined and concentrated to provide a colorless oil that solidified as T33.5 and which was used without further purification (732.6 mg, 95% yield).

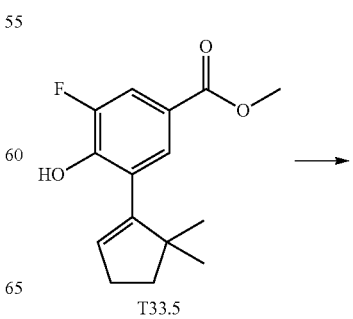

T33.5

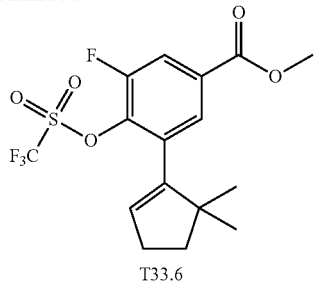

T33.6

Methyl 3-(5,5-dimethyl-1-cyclopenten-1-yl)-5-fluoro-4-(((trifluoromethyl)sulfonyl)oxy)benzoate (T33.6)

To a stirred solution of T33.5 (0.7326 g, 2.77 mmol) in dry DCM (15 mL) was added TEA (0.78 mL, 5.60 mmol) and 4-(dimethylamino)pyridine (0.0354 g, 0.29 mmol). After about 20 minutes, N-phenyl-bis(trifluoromethanesulfonimide) (1.20 g, 3.36 mmol) was added in portions. Upon complete addition, the solution was stirred at room temperature and monitored with TLC and LC-MS. After 19 hours, the organic solvent was removed under reduced pressure and the product thus obtained was then purified with silica gel chromatography using 0-10% EtOAc in hexanes to afford T33.6 as a colorless oil (946.4 mg, 86% yield). $^1$H NMR (400 MHz, CDCl$_3$) δ ppm 7.82 (1H, dd, J=9.9, 2.1 Hz), 7.75 (1H, m), 5.87 (1H, t, J=2.4 Hz), 3.95 (3H, s), 2.49 (2H, td, J=7.1, 2.4 Hz), 1.92 (2H, t, J=7.0 Hz), 1.11 (6H, s).

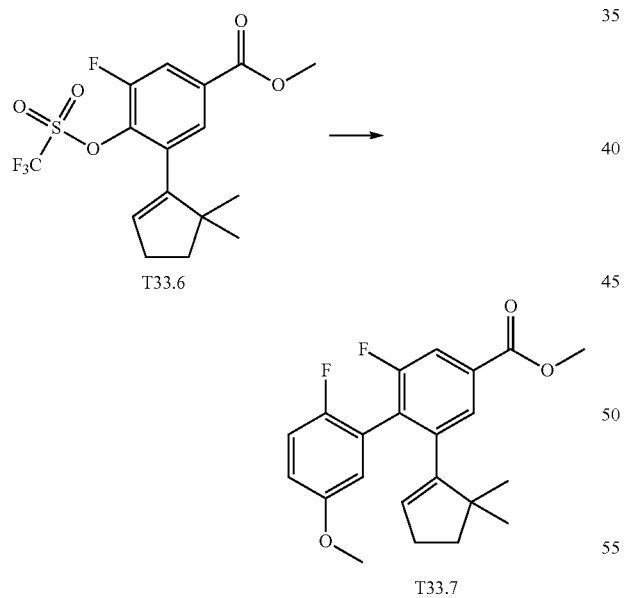

Methyl 2-(5,5-dimethyl-1-cyclopenten-1-yl)-2',6-difluoro-5'-(methyloxy)-1,1'-biphenyl-4-carboxylate (T33.7)

A stirred mixture of T33.6 (0.9464 g, 2.39 mmol), ground S-Phos (0.1977 g, 0.482 mmol), palladium acetate (0.0555 g, 0.247 mmol), 2-fluoro-5-methoxyphenylboronic acid (0.8114 g, 4.77 mmol) (commercially available from Sigma-Aldrich, St. Louis, Mo., USA), and potassium phosphate tribasic (1.2888 g, 6.072 mmol) in dry DMF (7.000 mL) was purged with argon and placed under vacuum and the process repeated three times. The mixture was then heated to 75° C. and the reaction was stirred for 21 hours. The reaction was then cooled to room temperature, diluted with water and extracted three times with EtOAc. The organic layers were combined and washed twice with brine. After drying over anhydrous sodium sulfate and filtration, the organic solvent was removed under reduced pressure. The residue was purified on an 80 g column of silica gel (0-20% EtOAc in hexanes) to afford T33.7 as a colorless oil that was used without further purification (850.5 mg, 95% yield). MS ESI (pos.) m/e: 373.0 (M+H)$^+$.

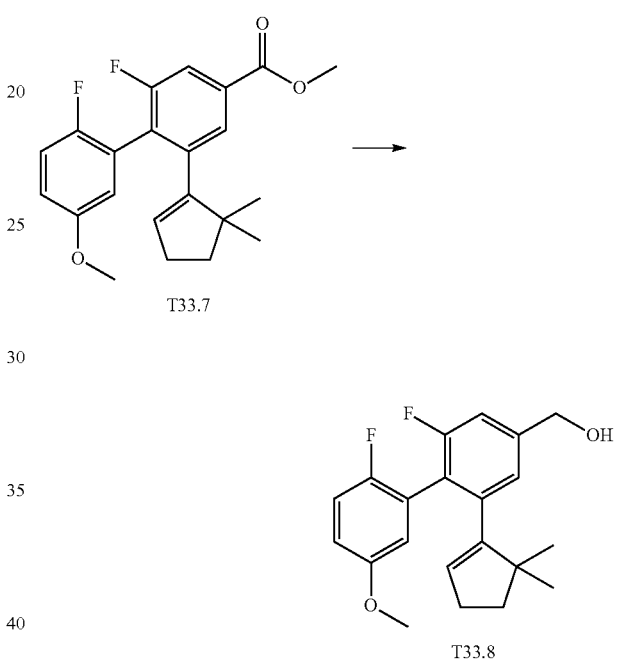

(2-(5,5-Dimethyl-1-cyclopenten-1-yl)-2',6-difluoro-5'-(methyloxy)-1,1'-biphenyl-4-yl)methanol (T33.8)

To a cooled solution of T33.7 (0.1435 g, 0.385 mmol) in dry THF (9 mL) at 0° C. was added LAH (1.0 M in THF)(0.8 mL, 0.80 mmol) dropwise. Upon complete addition, the reaction was maintained at 0° C. and was monitored by TLC and LCMS. After 45 minutes, 1N NaOH was added to quench the reaction (gas evolution occurred), and the resulting solution was extracted three times with EtOAc. After drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to provide T33.8 as a colorless oil (114.9 mg, 87% yield). $^1$H NMR (400 MHz, CDCl$_3$) δ ppm 7.12 (1H, dd, J=9.8, 1.6 Hz), 7.04 (2H, m), 6.84 (1H, dt, J=9.0, 3.5 Hz), 6.74 (1H, dd, J=5.5, 3.1 Hz), 5.50 (1H, t, J=2.3 Hz), 4.74 (2H, s), 3.76 (3H, s), 2.24 (2H, td, J=7.0, 2.3 Hz), 1.75 (5H, m), 0.97 (3H, s), 0.78 (3H, s).

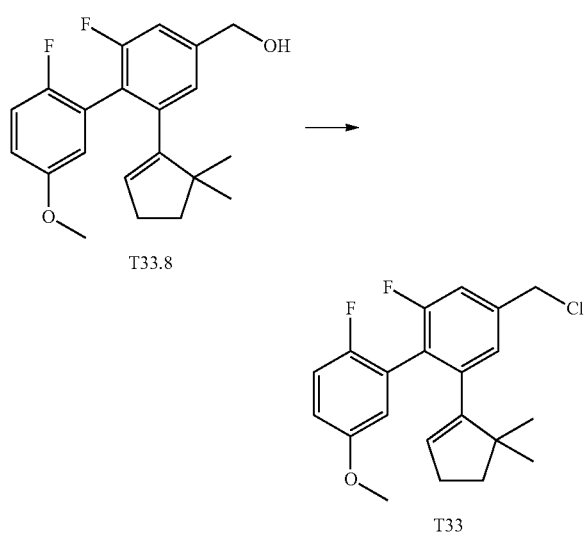

T33.8

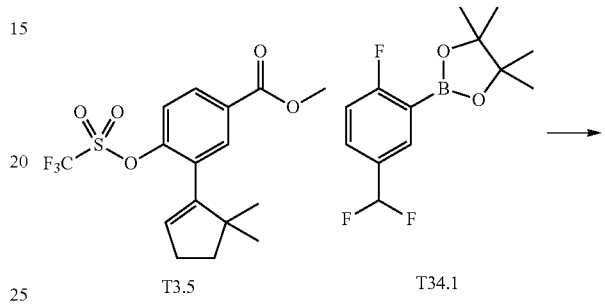

T33

4-(Chloromethyl)-2-(5,5-dimethyl-1-cyclopenten-1-yl)-2',6-difluoro-5'-(methyloxy)-1,1'-biphenyl (T33)

To a solution of T33.8 (0.1149 g, 0.334 mmol) in dry DCM (4 mL) and dry DMF (0.03 mL) was added thionyl chloride (0.05 mL, 0.685 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T33 as a colorless oil (35.6 mg, 29% yield). $^1$H NMR (400 MHz, CDCl$_3$) δ ppm 7.14 (1H, dd, J=9.4, 1.6 Hz), 7.06 (1H, s), 7.00 (1H, t, J=9.0 Hz), 6.85 (1H, dt, J=9.0, 3.7 Hz), 6.74 (1H, dd, J=5.5, 3.1 Hz), 5.53 (1H, t, J=2.3 Hz), 4.61 (2H, s), 3.76 (3H, s), 2.25 (2H, td, J=7.1, 2.5 Hz), 1.73 (2H, m), 0.97 (3H, s), 0.78 (3H, s).

Intermediate T34

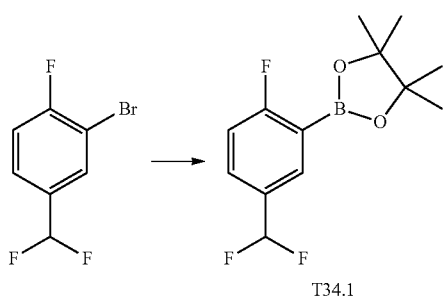 [SMILES: Fc1ccc(C(F)F)cc1Br ; CC1(C)OB(c2cc(C(F)F)ccc2F)OC1(C)C]

T34.1

2-(5-(Difluoromethyl)-2-fluorophenyl)-4,4,5,5-tetramethyl-1,3,2-dioxaborolane (T34.1)

A stirred mixture of 1-bromo-5-difluoromethyl-2-fluorobenzene (commercially available from Oakwood Products, Inc.) (2.0231 g, 8.991 mmol), bis(pinacolato)diboron (2.5123 g, 9.893 mmol), dichloro[1,1'-bis(diphenylphosphino)ferrocene]palladium (II) DCM adduct (0.3688 g, 0.4516 mmol), and potassium acetate (2.6504 g, 27.01 mmol) in dry 1,4-dioxane (35 mL) was purged with argon and placed under vacuum and the purging vacuum process repeated three times. The mixture was heated to 90° C. and monitored with LC-MS and TLC. After 18 hours, the reaction was cooled to room temperature and then filtered through Celite® filter aid. The organic solvent was removed under reduced pressure, and the residue was purified on a 40 g column of silica gel (0-10% EtOAc in hexanes) to afford T34.1 as a colorless oil that was used without further purification (1.6019 g, 65% yield). $^1$H NMR (400 MHz, CDCl$_3$) δ ppm 7.89 (1H, td, J=2.7, 1.2 Hz), 7.63 (1H, m), 7.09 (1H, t, J=8.6 Hz), 6.62 (1H, t), 1.35 (12H, s).

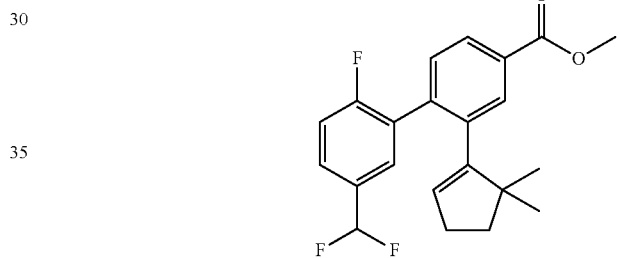

T3.5                                          T34.1

T34.2

Methyl 5'-(difluoromethyl)-2-(5,5-dimethyl-1-cyclopenten-1-yl)-2'-fluoro-1,1'-biphenyl-4-carboxylate (T34.2)

To a stirred solution of T3.5 (1.1209 g, 2.962 mmol) in dry DMF (10 mL) at 23° C. was added potassium carbonate (1.2262 g, 8.872 mmol) and then tetrakis(triphenylphosphine)palladium (0.3408 g, 0.2949 mmol). The mixture was purged with argon and placed under vacuum and the purging and vacuum process repeated three times. Before heating, T34.1 (1.6019 g, 5.888 mmol) was added via syringe and then the mixture was heated to 90° C. After 19 hours, LC-MS showed that the reaction was complete. The mixture was cooled to room temperature and then diluted with water. After extracting three times with EtOAc, the mixture was concentrated in vacuo and then purified on silica gel (0%-10% EtOAc/hexane) to afford T34.2 as a clear oil (994.4 mg, 90% yield). $^1$H NMR (400 MHz, CDCl$_3$) δ ppm 8.00 (1H, dd, J=8.0, 1.8 Hz), 7.94 (1H, d, J=1.6 Hz), 7.50 (3H, m), 7.16 (1H, t, J=9.0 Hz), 6.63 (1H, t), 5.53 (1H, s), 3.96 (3H, s), 2.25 (2H, td, J=7.0, 2.3 Hz), 1.65 (2H, t, J=7.0 Hz), 0.85 (6H, s).

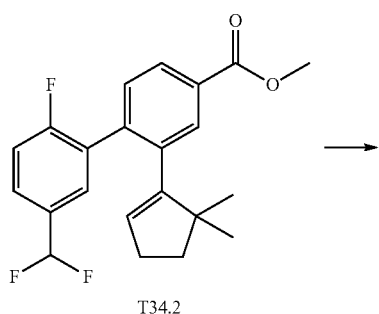

T34.2

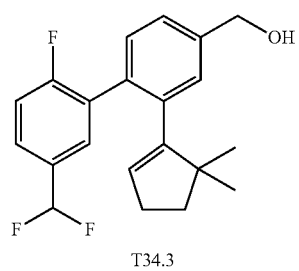

T34.3

(5'-(Difluoromethyl)-2-(5,5-dimethyl-1-cyclopenten-1-yl)-2'-fluoro-1,1'-biphenyl-4-yl)methanol (T34.3)

To a cooled solution of T34.2 (0.2349 g, 0.6274 mmol) in dry THF (5 mL) at 0° C. was added LAH (1.0 M in THF)(1.3 mL, 1.3 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was then purified by flash chromatography (SiO₂ gel 60, eluted with 0%-50% EtOAc in hexanes). Fractions containing the desired product were combined and concentrated to a colorless oil as T34.3 (166.6 mg, 77% yield). ¹H NMR (400 MHz, CDCl₃) δ ppm 7.47 (2H, m), 7.38 (2H, m), 7.14 (1H, t, J=9.0 Hz), 6.62 (1H, t), 5.50 (1H, td, J=2.4, 1.0 Hz), 4.76 (2H, s), 2.23 (2H, td, J=7.0, 2.3 Hz), 1.74 (3H, m), 0.85 (6H, s).

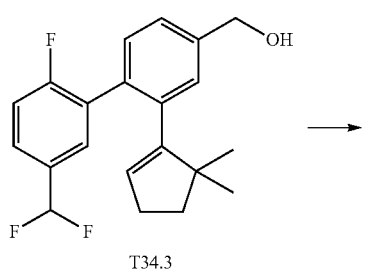

T34.3

-continued

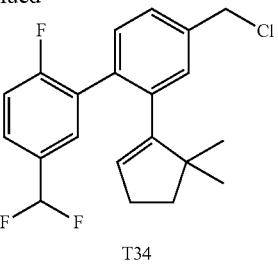

T34

4-(Chloromethyl)-5'-(difluoromethyl)-2-(5,5-dimethyl-1-cyclopenten-1-yl)-2'-fluoro-1,1'-biphenyl (T34)

To a solution of T34.3 (0.1666 g, 0.481 mmol) in dry DCM (3 mL) and dry DMF (0.06 mL) was added thionyl chloride (0.07 mL, 0.96 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T34 (172.1 mg, 98% yield). ¹H NMR (500 MHz, CDCl₃) δ ppm 7.46 (2H, m), 7.39 (1H, m), 7.33 (1H, m), 7.28 (1H, d, J=1.7 Hz), 7.17 (1H, m), 6.62 (1H, t), 5.51 (1H, td, J=2.3, 1.0 Hz), 4.64 (2H, s), 2.24 (2H, td, J=7.1, 2.4 Hz), 1.68 (2H, m), 0.85 (6H, s).

Intermediates T35A and T35B

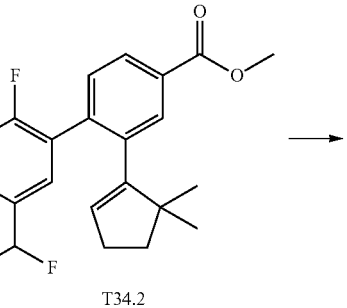

T34.2

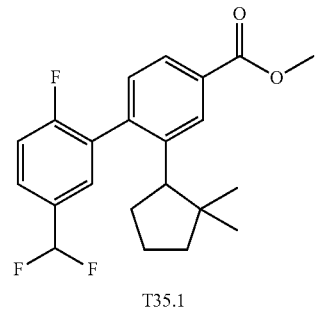

T35.1

Methyl 5'-(difluoromethyl)-2-(2,2-dimethylcyclopentyl)-2'-fluoro-1,1'-biphenyl-4-carboxylate (T35.1)

To a dry flask containing T34.2 (0.8621 g, 2.303 mmol) in dry MeOH (10 mL) and EtOAc (2 mL) was added palladium (10% wt. on activated carbon)(0.2455 g, 0.2307 mmol). After purging, the mixture was stirred under an atmosphere of hydrogen at room temperature. The reaction was monitored with TLC and LC-MS. After 22.5 hours, the reaction was filtered through Celite® filter aid. After concentration, the residue was identified as T35.1 and was used without purification (863 mg, 99% yield). MS ESI (pos.) m/e: 376.9 (M+H)⁺.

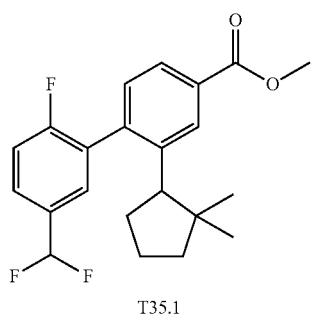

T35.1

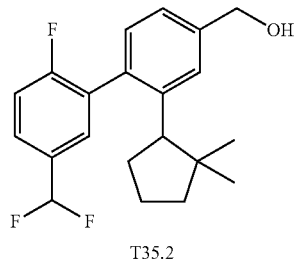

T35.2

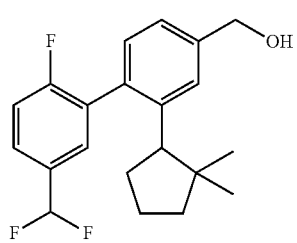

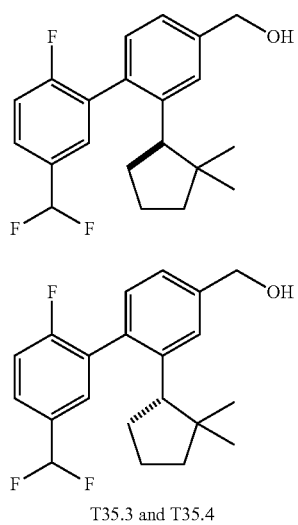

T35.3 and T35.4

(5'-(Difluoromethyl)-2-(2,2-dimethylcyclopentyl)-2'-fluoro-1,1'-biphenyl-4-yl)methanol (T35.2)

To a cooled solution of T35.1 (0.8631 g, 2.293 mmol) in dry THF (15.4 mL) at 0° C. was added LAH (1.0 M in THF)(4.6 mL, 4.6 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was then purified by flash chromatography (SiO₂ gel 60, eluted with 0%-100% EtOAc in hexanes). Fractions containing the desired product were combined and concentrated to a colorless oil as T35.2 (617.1 mg, 77% yield). MS ESI (pos.) m/e: 331.0 (M–H$_2$O)$^+$. Chiral separation of T35.2 was accomplished on a CHIRALCEL® OD column (4% IPA in hexane) to provide T35.3 (peak 1) and T35.4 (peak 2). Both enantiomers were used to synthesize example compounds, and both enantiomers gave active compounds.

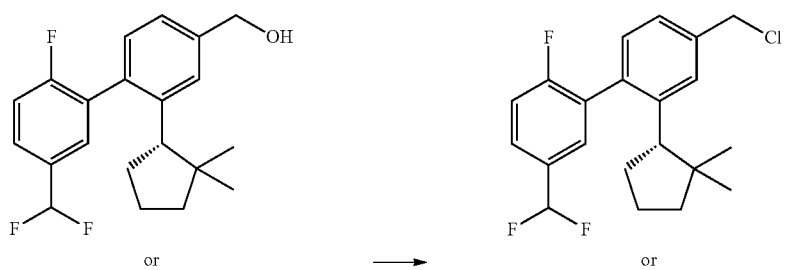

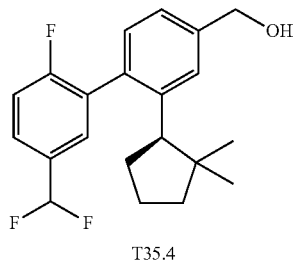

T35.4

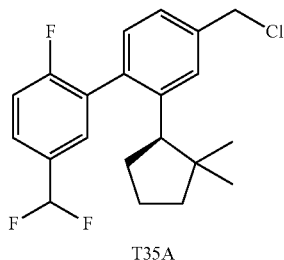

T35A

4-(Chloromethyl)-5'-(difluoromethyl)-2-((1S)-2,2-dimethylcyclopentyl)-2'-fluoro-1,1'-biphenyl or 4-(chloromethyl)-5'-(difluoromethyl)-2-((1R)-2,2-dimethylcyclopentyl)-2'-fluoro-1,1'-biphenyl (T35A)

To a solution of T35.4 (0.2882 g, 0.827 mmol) in dry DCM (10.5 mL) and dry DMF (0.08 mL) was added thionyl chloride (0.12 mL, 1.65 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T35A. (272.1 mg, 90% yield).

4-(Chloromethyl)-5'-(difluoromethyl)-2-((1S)-2,2-dimethylcyclopentyl)-2'-fluoro-1,1'-biphenyl or 4-(chloromethyl)-5'-(difluoromethyl)-2-((1R)-2,2-dimethylcyclopentyl)-2'-fluoro-1,1'-biphenyl (T35B)

To a solution of T35.3 (0.2798 g, 0.803 mmol) in dry DCM (10 mL) and dry DMF (0.076 mL) was added thionyl chloride (0.12 mL, 1.65 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T35B (282.5 mg, 96% yield).

Intermediate T36

Methyl 2-(5,5-dimethyl-1-cyclopenten-1-yl)-2'-fluoro-5'-(trifluoromethyl)-1,1'-biphenyl-4-carboxylate (T36.1)

To a stirred solution of T3.5 (0.7595 g, 2.007 mmol) in DMF (5 mL) at 23° C. was added 2-fluoro-5-(trifluoromethyl)phenylboronic acid (commercially available from Sigma-Aldrich, St. Louis, Mo., USA) (0.8352 g, 4.017 mmol) and potassium carbonate (0.8357 g, 6.047 mmol) followed by tetrakis(triphenylphosphine)palladium (0.2364 g, 0.2046 mmol). The mixture was heated to 90° C. After 17 hours, LCMS-showed that the reaction was complete. The mixture was cooled to room temperature and then diluted with water. After extracting three times with EtOAc, the mixture was concentrated in vacuo and then purified on silica gel (0%-10% EtOAc/hexane) to afford T36.1 as a clear oil that was used without further purification (414.2 mg, 53% yield).

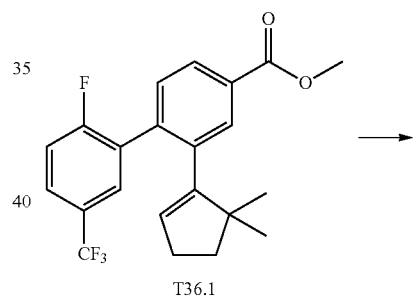

T36.1

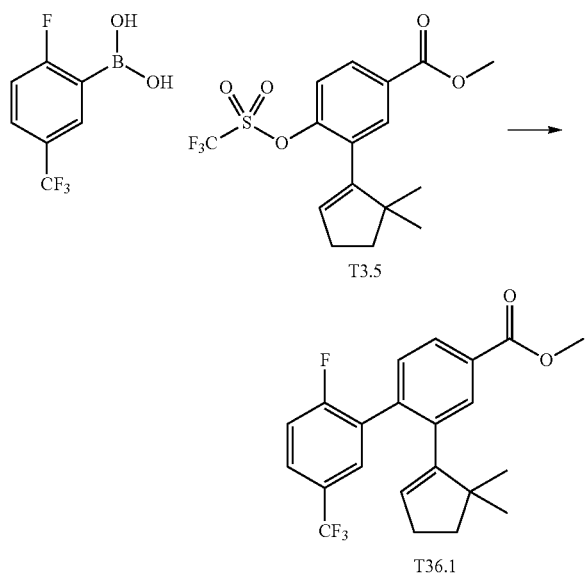

(2-(5,5-Dimethyl-1-cyclopenten-1-yl)-2'-fluoro-5'-(trifluoromethyl)-1,1'-biphenyl-4-yl)methanol (T36.2)

To a cooled solution of T36.1 (0.4142 g, 1.056 mmol) in dry THF (7.8 mL) at 0° C. was added LAH (1.0 M in THF) (2.2 mL, 2.200 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography (SiO₂ gel 60, eluted with 0%-100% EtOAc in hexanes). Fractions containing the desired product were combined and concentrated to afford T36.2 as a colorless oil (257.4 mg, 67% yield). $^1$H NMR (400 MHz, CDCl₃) δ ppm 7.61 (2H, m), 7.40 (2H, m), 7.17 (1H, t, J=8.8 Hz), 5.52 (1H, m), 4.77 (2H, s), 2.24 (2H, td, J=7.0, 2.3 Hz), 1.71 (3H, m), 0.84 (6H, s).

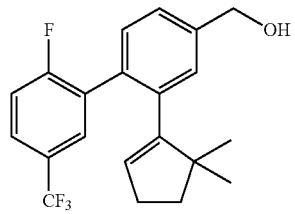

4-(Chloromethyl)-2-(5,5-dimethyl-1-cyclopenten-1-yl)-2'-fluoro-5'-(trifluoromethyl)-1,1'-biphenyl (T36)

To a solution of T36.2 (0.2574 g, 0.706 mmol) in dry DCM (10 mL) and dry DMF (0.07 mL) was added thionyl chloride (0.11 mL, 1.51 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T36 (242.8 mg, 90% yield). $^1$H NMR (400 MHz, CDCl₃) δ ppm 7.60 (2H, m), 7.40 (1H, m), 7.35 (2H, m), 7.21 (1H, m), 5.52 (1H, td, J=2.4, 0.9 Hz), 4.66 (2H, m), 2.24 (2H, td, J=7.0, 2.3 Hz), 1.68 (2H, m), 0.84 (6H, s).

Intermediate T37

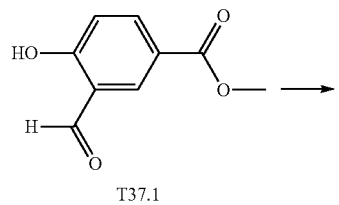

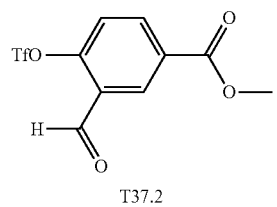

Methyl 3-formyl-4-(trifluoromethylsulfonyloxy)benzoate (T37.2)

TEA (6.81 mL, 48.8 mmol), and N,N-dimethylpyridin-4-amine (0.298 g, 2.44 mmol) were added to a solution of methyl 3-formyl-4-hydroxybenzoate (T37.1) (commercially available from Sigma-Aldrich, St. Louis, Mo., USA) (4.40 g, 24.4 mmol) in DCM (26 mL). The resulting mixture was stirred at room temperature for 20 minutes and then N-phenyltrifluoromethanesulfonimide (9.60 g, 26.9 mmol) was added in one portion. The mixture was then stirred at room temperature for 30 minutes. After removing solvent, the residue was purified by flash chromatography (silica gel, 1:1 EtOAc/hexane) and gave T37.2, a colorless oil, in 99% yield (7.57 g).

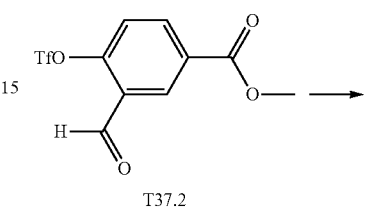

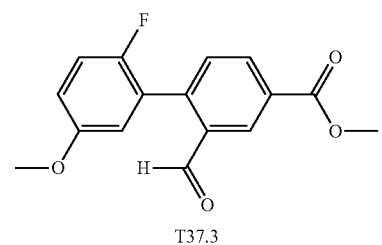

Methyl 2'-fluoro-2-formyl-5'-(methyloxy)-1,1'-biphenyl-4-carboxylate (T37.3)

A mixture of methyl 3-formyl-4-(trifluoromethyl-sulfonyloxy)benzoate (T37.2) (7.57 g, 24.2 mmol), 2-fluoro-5-methoxy-phenylboronic acid (commercially available from Sigma-Aldrich, St. Louis, Mo., USA) (12.4 g, 72.7 mmol), Cs₂CO₃ (27.6 g, 84.9 mmol), and tetrakis(triphenylphosphine) palladium (2.80 g, 2.42 mmol) in 1,2-dimethoxyethane (DME) (75 mL) was degassed with N₂ at room temperature The mixture was heated at 95° C. for 9 hours. After removing solvent, the residue was purified by flash chromatography (silica gel, 1:19 EtOAc/hexane) and gave T37.3, a white solid, in 56% yield (2.9 g). $^1$H NMR (400 MHz, DMSO-d6) δ ppm 9.88 (dd, J=4 Hz, 1H), 8.45 (s, 1H), 8.28 (m, 1H), 7.69 (d, j=8 Hz, 1H), 7.29 (t, J=9 HZ, 1H), 7.08 (m, 2H), 3.92 (s, 3H), 3.79 (s, 3H).

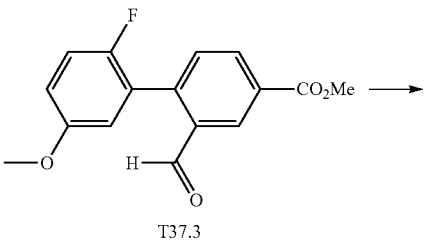

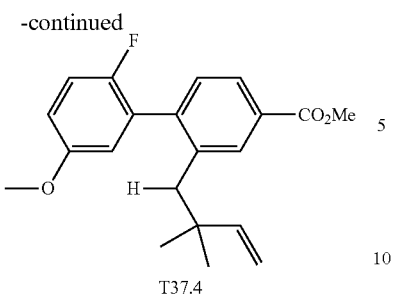

T37.4

Methyl 2'-fluoro-2-(1-hydroxy-2,2-dimethyl-3-butenyl)-5'-(methyloxy)-1,1'-biphenyl-4-carboxylate (T37.4)

To a mixture of T37.3 (0.38 g, 1.3 mmol), 1-bromo-3-methylbut-2-ene (commercially available from Sigma-Aldrich, St. Louis, Mo., USA) (0.31 mL, 2.6 mmol) and sodium iodide (0.40 g, 2.6 mmol) in DMF (8 mL), was added indium (0.30 g, 2.6 mmol). The resulting mixture was stirred at room temperature for 1 hour and then additional 1-bromo-3-methylbut-2-ene (100 mg) and indium (100 mg) were added and the mixture was stirred at room temperature for one more hour. The reaction was quenched with water (20 mL) and extracted with EtOAc (200 mL). The organic phase was washed with brine, dried over anhydrous sodium sulfate, and filtered. After removing solvent, the residue was purified by flash chromatography (silica gel, 1:4 EtOAc/hexane) and gave product (T37.4), in 94% yield.

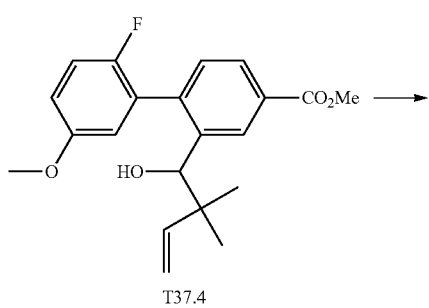

T37.4

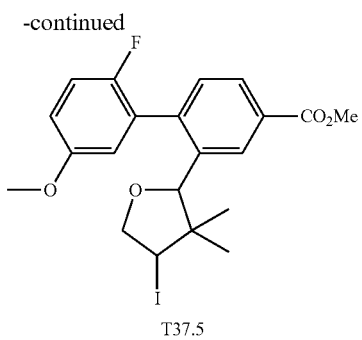

T37.5

Methyl 2'-fluoro-2-(3-iodo-2,2-dimethylcyclopentyl)-5'-(methyloxy)-1,1'-biphenyl-4-carboxylate (T37.5)

To a mixture of NaHCO$_3$ (0.035 g, 0.42 mmol) and T37.4 (0.050 g, 0.14 mmol) in ACN (2 mL), was added iodine (0.12 g, 0.49 mmol). The mixture was then stirred at room temperature for 16 hours. Next, the mixture was poured into a 0.2 M solution of Na$_2$S$_2$O$_3$ and extracted with EtOAc. The organic phase was dried over anhydrous Na$_2$SO$_4$ and filtered. After removing solvent, the residue was purified by flash chromatography (silica gel, 1:19 EtOAc/hexane) and gave product T37.5, a white solid, in 84% yield.

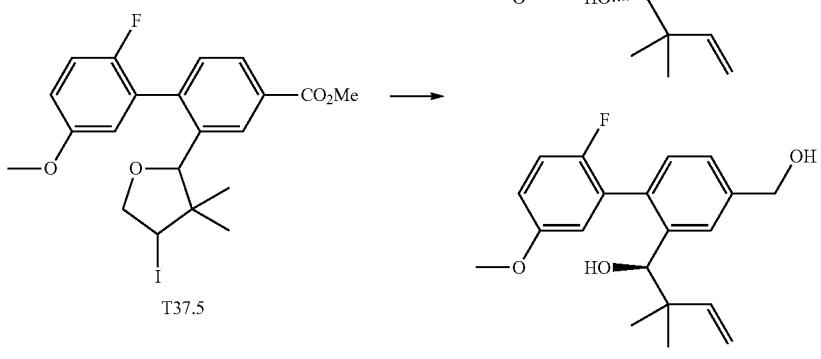

T37.5

T37.6 and T37.7

(1S)-1-(2'-Fluoro-4-(hydroxymethyl)-5'-(methyloxy)-1,1'-biphenyl-2-yl)-2,2-dimethyl-3-buten-1-ol and (1R)-1-(2'-fluoro-4-(hydroxymethyl)-5'-(methyloxy)-1,1'-biphenyl-2-yl)-2,2-dimethyl-3-buten-1-ol (T37.6 and T37.7)

To a mixture of T37.5 (0.460 g, 0.950 mmol) in THF (12 mL), was added LAH (0.108 g, 2.85 mmol), and the mixture was stirred at room temperature for 45 minutes. The reaction mixture was then poured into water and extracted with EtOAc. The organic phase was dried over anhydrous Na$_2$SO$_4$ and filtered. After removing solvent, the residue was purified by flash chromatography (silica gel, 1:2 EtOAc/hexane) and gave racemic product, which was separated by chiral chromatography (column: OD-H; solvent: 6% IPA/hexane) to yield T37.6 (72 mg) (retention time=12.9 min) and T37.7 (74 mg) (retention time=18.2 min).

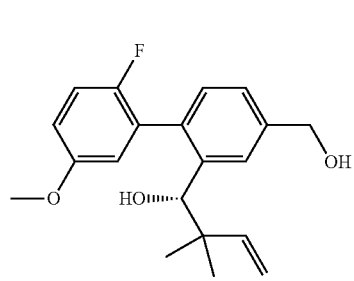

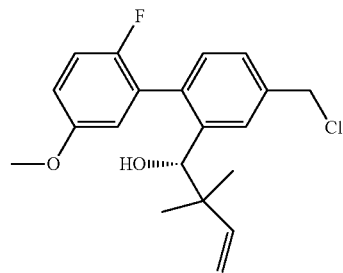

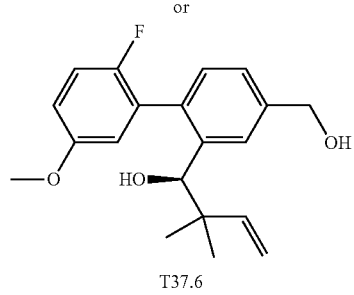

T37.6

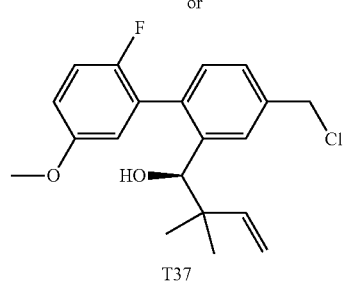

T37

(1S)-1-(4-(Chloromethyl)-2'-fluoro-5'-(methyloxy)-1,1'-biphenyl-2-yl)-2,2-dimethyl-3-buten-1-ol or (1R)-1-(4-(chloromethyl)-2'-fluoro-5'-(methyloxy)-1,1'-biphenyl-2-yl)-2,2-dimethyl-3-buten-1-ol (T37)

Thionyl chloride (0.27 g, 2.2 mmol) was added to a solution of T37.6 (0.074 g, 0.22 mmol) in DCM (2 mL), and the mixture was stirred at room temperature for 40 minutes. After removing solvent, T37 was obtained.

Intermediate T38

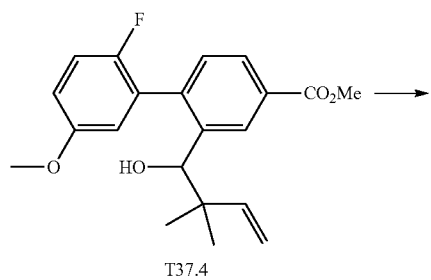

T37.4

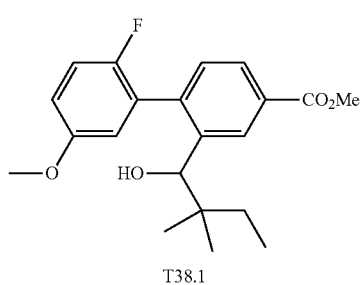

T38.1

Methyl 2'-fluoro-2-(1-hydroxy-2,2-dimethylbutyl)-5'-(methyloxy)-1,1'-biphenyl-4-carboxylate (T38.1)

To a solution of T37.4 (0.453 g, 1.26 mmol) in MeOH (10 mL)(degassed by $N_2$), was added palladium on carbon (0.135 g, 1.26 mmol). The resulting mixture was stirred at room temperature under $H_2$ for 18 hours. The reaction mixture was then filtered through silica gel. After removing solvent, T38.1 (394 mg) was obtained as a colorless oil.

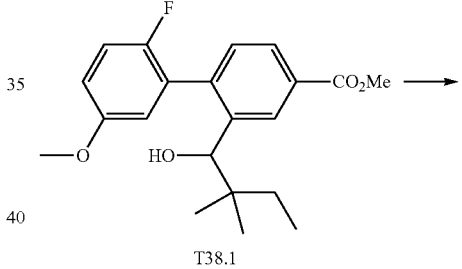

T38.1

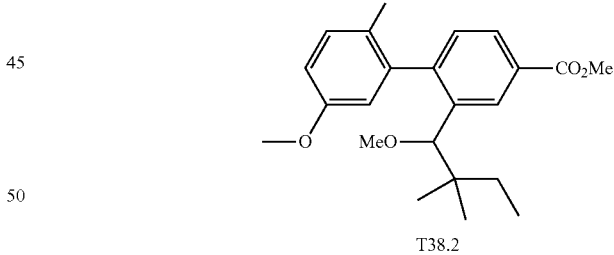

T38.2

Methyl 2-(2,2-dimethyl-1-(methyloxy)butyl)-2'-fluoro-5'-(methyloxy)-1,1'-biphenyl-4-carboxylate (T38.2)

To a solution of T38.1 (0.39 g, 1.1 mmol) in DMF (5 mL), was added NaH (0.034 g, 1.4 mmol). The mixture was stirred at room temperature for 10 minutes and then iodomethane (0.20 mL, 3.2 mmol) was added. The mixture was stirred at room temperature for 60 minutes and then it was diluted with EtOAc, washed with water and brine, and dried over anhydrous $Na_2SO_4$. After removing solvent, the residue was purified by flash chromatography (silica gel, 1:9 EtOAc/hexane) and gave T38.2, colorless oil, in 64% yield (260 mg).

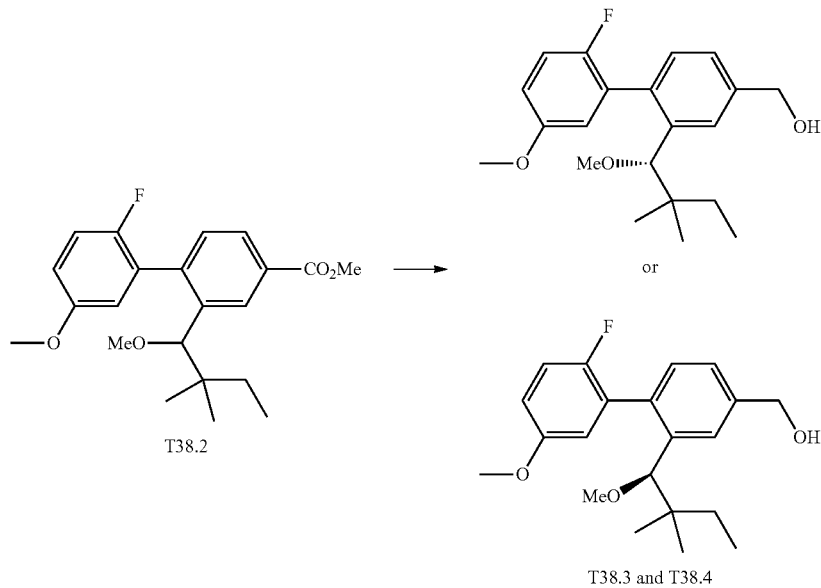 [SMILES: CCC(C)(C)C(OC)c1cc(C(=O)OC)ccc1-c1cc(OC)ccc1F ; CCC(C)(C)[C@@H](OC)c1cc(CO)ccc1-c1cc(OC)ccc1F ; CCC(C)(C)[C@H](OC)c1cc(CO)ccc1-c1cc(OC)ccc1F]

(2-((1S)-2,2-Dimethyl-1-(methyloxy)butyl)-2'-fluoro-5'-(methyloxy)-1,1'-biphenyl-4-yl)methanol and (2-((1R)-2,2-dimethyl-1-(methyloxy)butyl)-2'-fluoro-5'-(methyloxy)-1,1'-biphenyl-4-yl)methanol (T38.3 and T38.4)

To a solution of T38.2 (0.26 g, 0.69 mmol) in THF (4 mL), was added LAH (0.026 g, 0.69 mmol). The resulting mixture was stirred at room temperature for 10 minutes and then was poured into to water and extracted with EtOAc. The combined organic layers were dried over anhydrous Na₂SO₄. After removing solvent, the residue was purified by flash chromatography (silica gel, 1:6 EtOAc/hexane) and gave racemic product (157 mg) as a colorless oil, which was separated by chiral chromatography (column: OD; solvent: 6% IPA/hexane) to yield T38.3 (68 mg) (retention time=11.8 min) and T38.4 (70 mg) (retention time=15.1 min).

4-(Bromomethyl)-2-((1S)-2,2-dimethyl-1-(methyloxy)butyl)-2'-fluoro-5'-(methyloxy)-1,1'-biphenyl or 4-(bromomethyl)-2-((1R)-2,2-dimethyl-1-(methyloxy)butyl)-2'-fluoro-5'-(methyloxy)-1,1'-biphenyl (T38)

To a solution of T38.3 (0.070 g, 0.20 mmol) in THF (2 mL), was added triphenylphosphine (0.11 g, 0.40 mmol) and 1-bromopyrrolidine-2,5-dione (0.072 g, 0.40 mmol). The resulting mixture was stirred at room temperature for 10 minutes. After removing solvent, the residue was purified by flash chromatography (silica gel, 1:6 EtOAc/hexane) and gave T38 (73 mg).

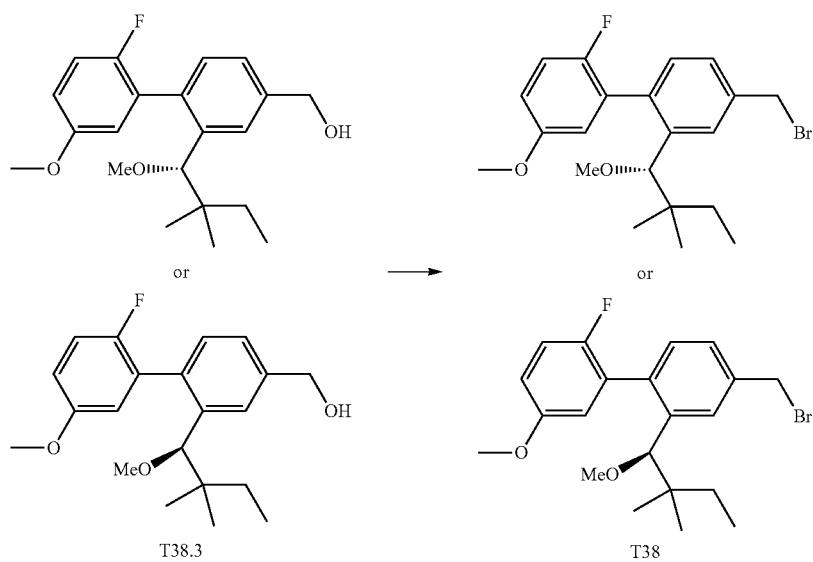

Intermediate T39

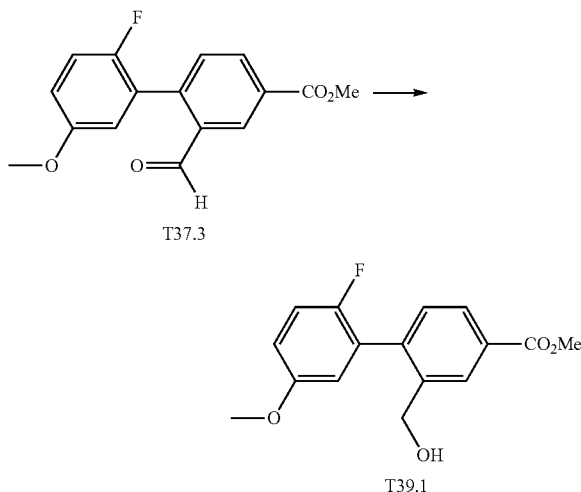

Methyl 2'-fluoro-2-(hydroxymethyl)-5'-(methyloxy)-1,1'-biphenyl-4-carboxylate (T39.1)

Sodium tetrahydroborate (commercially available from Sigma-Aldrich, St. Louis, Mo., USA) (0.656 g, 17.3 mmol) was added portion by portion slowly to T37.3 (1.00 g, 3.47 mmol) in MeOH (20 mL). The resulting mixture was stirred at room temperature for 25 minutes. After removing solvent, the residue was purified by flash chromatography (silica gel, 1:2 EtOAc/hexane) and gave T39.1 (725 mg) in 72% yield.

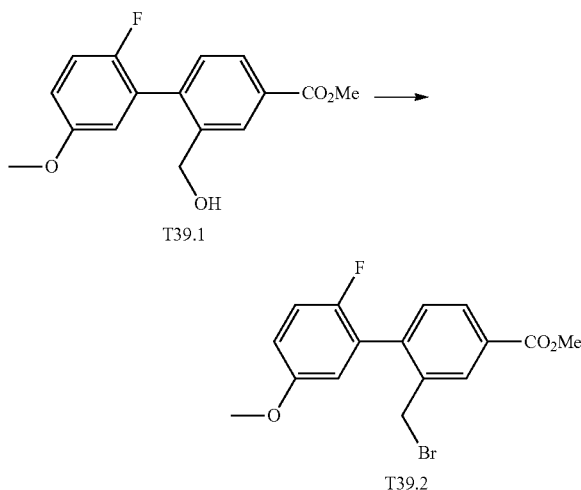

Methyl 2-(bromomethyl)-2'-fluoro-5'-(methyloxy)-1,1'-biphenyl-4-carboxylate (T39.2)

To a solution of T39.1 (0.725 g, 2.50 mmol) and triphenylphosphine (2.62 g, 9.99 mmol) in THF (20 mL) was added portion by portion 1-bromopyrrolidine-2,5-dione (commercially available from Sigma-Aldrich, St. Louis, Mo., USA) (1.78 g, 9.99 mmol). The resulting mixture was stirred at room temperature for 20 minutes. After removing solvent, the residue was purified by flash chromatography (silica gel, 1:9 EtOAc/hexane) and gave T39.2 (882 mg) in 100% yield.

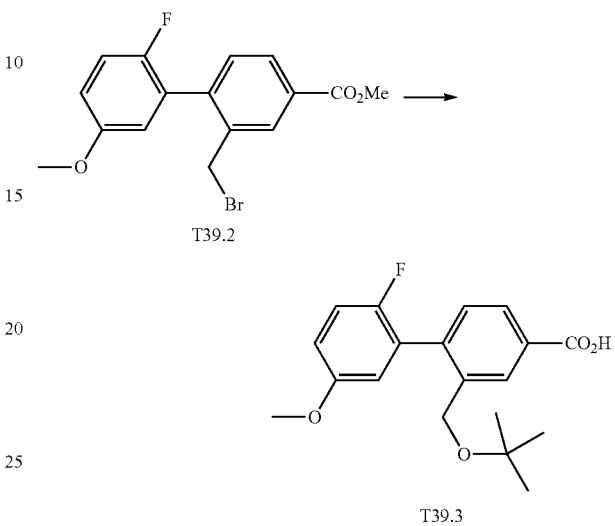

2-(((1,1-Dimethylethyl)oxy)methyl)-2'-fluoro-5'-(methyloxy)-1,1'-biphenyl-4-carboxylic acid (T39.3)

A mixture of T39.2 (0.245 g, 0.69 mmol) and sodium 2-methylpropan-2-olate (0.20 g, 2.1 mmol) in DMF (6 mL) was stirred at room temperature for 28 minutes. The mixture was acidified with 1N HCl to pH 3-4 and then was extracted with EtOAc (100 mL). The organic phase was washed with brine and dried over anhydrous $Na_2SO_4$. After removing solvent, the residue was purified by flash chromatography (silica gel, 1:4 EtOAc/hexane) and gave T39.3 (49 mg) in 20% yield.

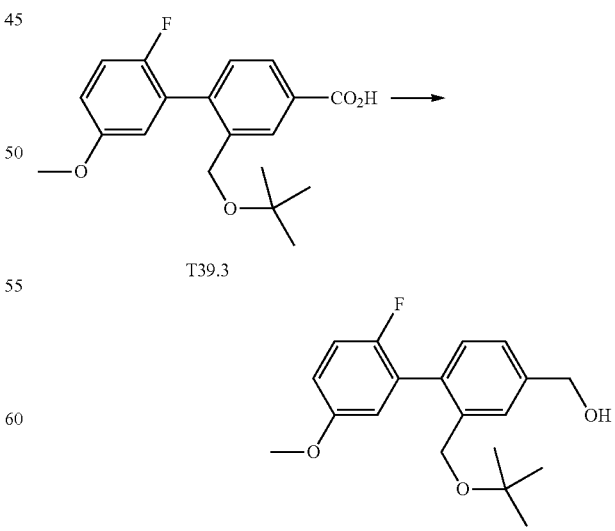

(2-(((1,1-Dimethylethyl)oxy)methyl)-2'-fluoro-5'-(methyloxy)-1,1'-biphenyl-4-yl)methanol (T39.4)

LAH (0.15 mL, 0.15 mmol) was added to a solution of T39.3 (0.049 g, 0.15 mmol) in THF (2 mL). The resulting mixture was stirred at room temperature for 10 minutes and then was poured slowly into brine (5 mL). The mixture was extracted with EtOAc (2×50 mL). The organic phase was dried over anhydrous sodium sulfate. After filtering and removing solvent, the residue was purified by flash chromatography (silica gel, 1:2 EtOAc/hexane) and gave T39.4 (6 mg).

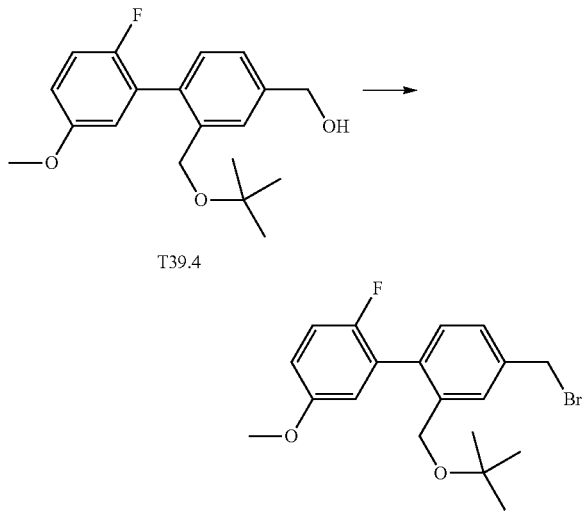

4-(Bromomethyl)-2-(((1,1-dimethylethyl)oxy)methyl)-2'-fluoro-5'-(methyloxy)-1,1'-biphenyl (T39)

Bromomethyl compound T39 was prepared using an analogous procedure to that set forth for the synthesis of T39.2.

Intermediate T40

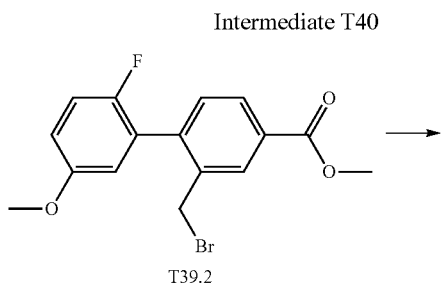

Methyl 2'-fluoro-5'-(methyloxy)-2-(1-piperidinylmethyl)-1,1'-biphenyl-4-carboxylate (T40.1)

Piperidine (commercially available from Sigma-Aldrich, St. Louis, Mo., USA) (0.038 g, 0.44 mmol) was added to a solution of T39.2 (0.13 g, 0.37 mmol) in DMSO (3 mL). Cs$_2$CO$_3$ (0.18 g, 0.55 mmol) was then added to the reaction and it was stirred at room temperature for 1 hour. EtOAc (100 mL) was added and the organic phase was washed with water and brine and dried over anhydrous sodium sulfate. After removing solvent, the residue was purified by flash chromatography (silica gel, 1:1 EtOAc/DCM) and gave T40.1 (100 mg) in 76% yield. MS ESI (pos.) m/e: 358 (M+H)$^+$.

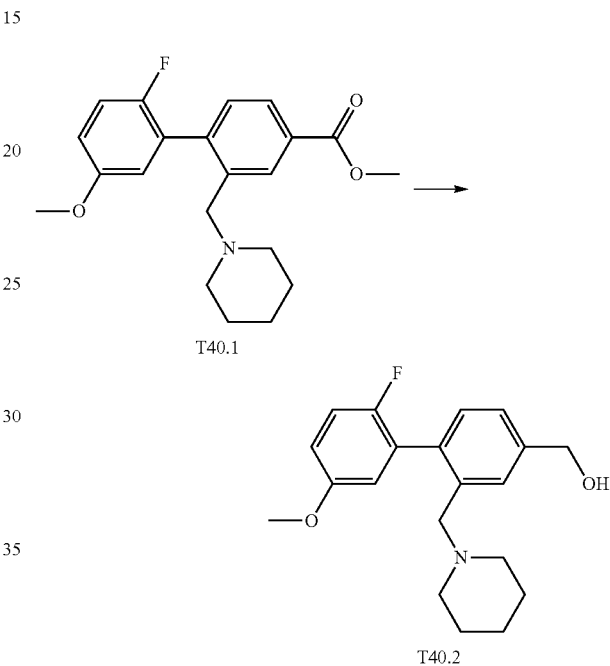

(2'-Fluoro-5'-(methyloxy)-2-(1-piperidinylmethyl)-1,1'-biphenyl-4-yl)methanol (T40.2)

LAH (1.0 M solution in THF) (0.55 mL, 0.55 mmol) was added to a solution of T40.1 (0.098 g, 0.27 mmol) in THF (5 mL). The resulting mixture was stirred at room temperature for 1 hour and then it was diluted with EtOAc, washed with water and brine, and dried over anhydrous Na$_2$SO$_4$. After removing solvent, T40.2 was obtained as a colorless oil in 100% yield.

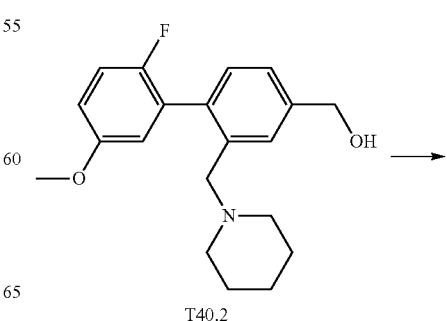

filtered and concentrated. The residue was purified by recrystallization from isopropanol to afford T41.1 as an off white solid (726.2 mg, 59% yield). $^1$H NMR (400 MHz, CDCl$_3$) δ ppm 8.78 (1H, s), 7.91 (1H, d, J=7.8 Hz), 7.36 (1H, d, J=7.8 Hz), 7.15 (1H, t, J=9.2 Hz), 7.08 (1H, s), 6.97 (1H, dt, J=9.0, 3.7 Hz), 6.81 (1H, dd, J=5.9, 3.1 Hz), 3.94 (3H, s), 3.83 (3H, s), 3.39 (2H, t, J=6.3 Hz), 2.28 (2H, t, J=7.0 Hz), 1.89 (2H, m), 1.82 (2H, m).

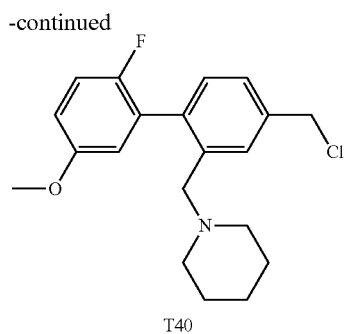

T40

1-((4-(Chloromethyl)-2'-fluoro-5'-(methyloxy)-1,1'-biphenyl-2-yl)methyl)piperidine (T40)

Thionyl chloride (0.066 g, 0.56 mmol) was added to a solution of T40.2 (0.023 g, 0.070 mmol) in DCM (1 mL). The resulting mixture was stirred at room temperature for 2 hours. After removing solvent, T40 was obtained in 100% yield.

Intermediate T41

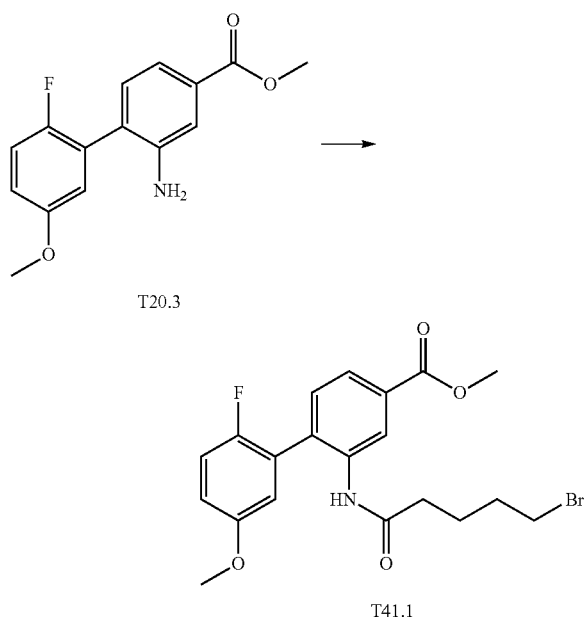 [SMILES: COC(=O)c1ccc(-c2cc(OC)ccc2F)c(N)c1 ; COC(=O)c1ccc(-c2cc(OC)ccc2F)c(NC(=O)CCCCBr)c1]

Methyl 2-((5-bromopentanoyl)amino)-2'-fluoro-5'-(methyloxy)-1,1'-biphenyl-4-carboxylate (T41.1)

To a dry round bottom flask containing T20.3 (0.7779 g, 2.83 mmol) was added dry chloroform (8 mL) at 0° C. After five minutes, 5-bromovaleryl chloride (0.5 mL, 3.73 mmol) (commercially available from Sigma-Aldrich, St. Louis, Mo., USA) was added followed by dropwise addition of dry pyridine (0.31 mL, 3.80 mmol). The reaction mixture was allowed to warm to room temperature and monitored with TLC and LC-MS. After 3 hours, the reaction was diluted with DCM and washed twice with saturated aqueous sodium bicarbonate solution, twice with water, and once with brine. The organic layer was dried over anhydrous sodium sulfate then

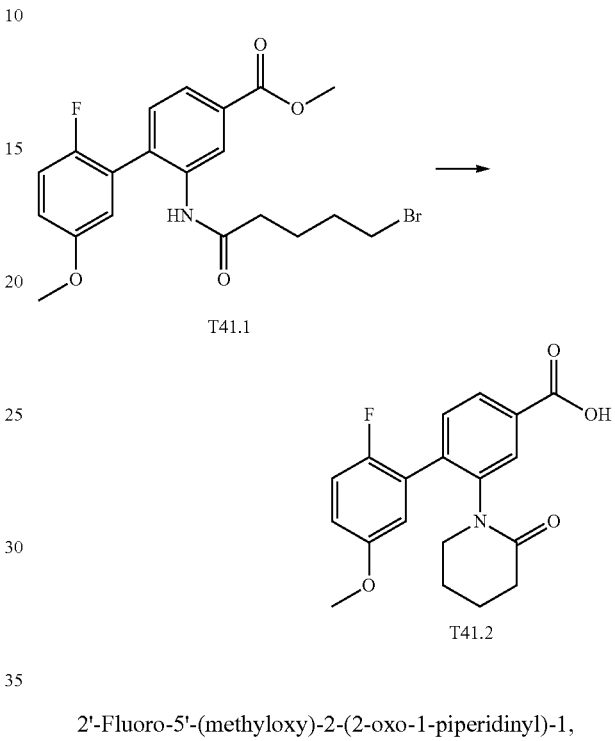

2'-Fluoro-5'-(methyloxy)-2-(2-oxo-1-piperidinyl)-1,1'-biphenyl-4-carboxylic acid (T41.2)

To a dry vial containing T41.1 (0.5858 g, 1.337 mmol) was added dry DMF (25 mL). The mixture was stirred at 0° C. for about 15 minutes, then potassium tert-butoxide (0.3766 g, 3.356 mmol) was carefully added in portions. The mixture was heated to 145° C. and monitored with TLC and LC-MS. After 2.5 hours, the reaction was cooled to room temperature and then carefully quenched with 2 M aqueous citric acid solution. After extracting three times with DCM, the organic layer was dried over anhydrous magnesium sulfate, filtered and concentrated. The residue was purified with silica gel flash chromatography (0-25% MeOH in DCM) to afford T41.2 as an oil (440.1 mg, 96% yield). MS ESI (neg.) m/e: 342.0 (M–H)$^+$.

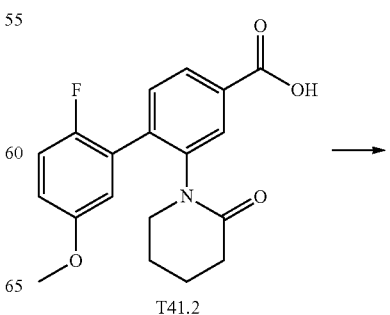

T41.2

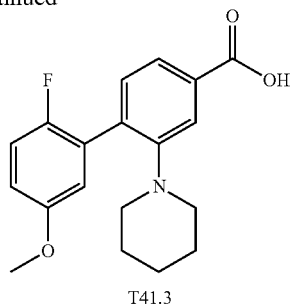

T41.3

2'-Fluoro-5'-(methyloxy)-2-(1-piperidinyl)-1,1'-biphenyl-4-carboxylic acid (T41.3)

To a cooled solution of T41.2 (0.4401 g, 1.282 mmol) in dry THF (8 mL) at 0° C. was added borane•THF complex, 1.0 M in THF (2.5 mL, 2.5 mmol) dropwise. Upon complete addition, the reaction was maintained at 0° C. and monitored by TLC and LCMS. After 3 hours, water was added to quench the reaction, and the resulting solution was extracted three times with EtOAc. The organic extractions were combined and washed successively with saturated aqueous sodium bicarbonate, water, and then brine. After drying over anhydrous magnesium sulfate, filtration, and concentration, the residue was purified with silica gel flash chromatography (0-25% MeOH in DCM) to afford T41.3 as an oil (292.9 mg, 69% yield). $^1$H NMR (400 MHz, CDCl$_3$) δ ppm 7.85 (2H, m), 7.36 (1H, d, J=7.8 Hz), 7.11 (2H, m), 6.86 (1H, dt, J=8.9, 3.6 Hz), 3.83 (3H, s), 2.85 (4H, m), 1.46 (6H, m).

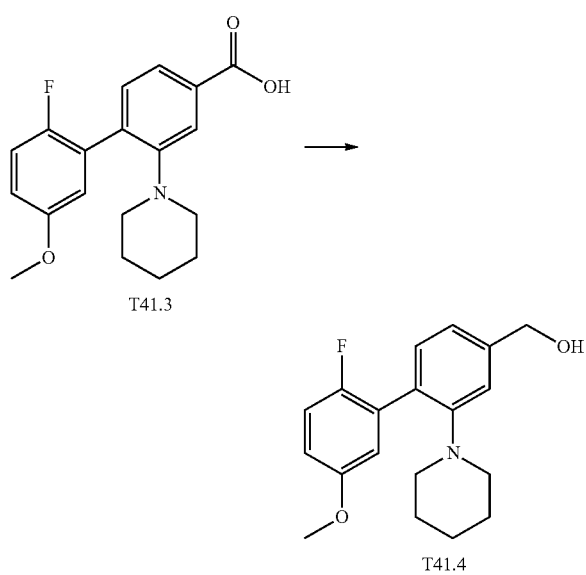

(2'-Fluoro-5'-(methyloxy)-2-(1-piperidinyl)-1,1'-biphenyl-4-yl)methanol (T41.4)

To a cooled solution of T41.3 (0.2929 g, 0.8893 mmol) in dry THF (10 mL) at 0° C. was added LAH (1M in THF) (1.8 mL, 1.8 mmol). Upon complete addition, the reaction was maintained at 0° C. and was monitored by TLC and LCMS. After 2 hours, 1N NaOH was added to quench the reaction (gas evolution occurred). The resulting solution was extracted three times with EtOAc. After drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to afford T41.4 as a colorless oil (231.8 mg, 83% yield). $^1$H NMR (400 MHz, CDCl$_3$) δ ppm 7.25 (1H, d, J=9.0 Hz), 7.11 (4H, m), 6.82 (1H, dt, J=9.0, 3.5 Hz), 4.71 (2H, d, J=5.5 Hz), 3.81 (3H, s), 2.81 (4H, m), 1.69 (1H, s), 1.43 (6H, m).

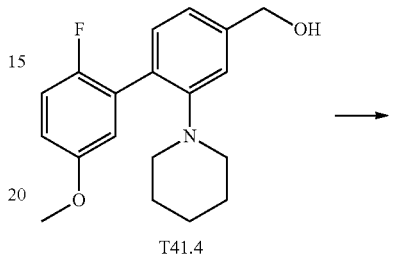

T41.4

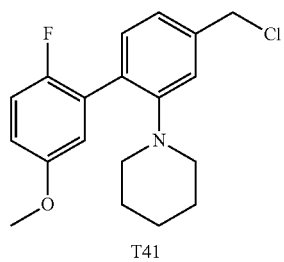

T41

1-(4-(Chloromethyl)-2'-fluoro-5'-(methyloxy)-1,1'-biphenyl-2-yl)piperidine (T41)

To a solution of T41.4 (0.2318 g, 0.73 mmol) in dry DMF (0.03 mL) and dry DCM (3 mL) was added thionyl chloride (0.13 mL, 1.8 mmol) at 0° C. The resulting solution was warmed to room temperature and monitored with TLC and LCMS. After 45 minutes, the reaction was diluted with DCM and then washed once with saturated aqueous sodium bicarbonate and once with brine. After drying over anhydrous magnesium sulfate, filtering, and removing the solvent under reduced pressure, the residue was purified by silica gel flash chromatography (0-5% EtOAc/hexane) to afford T41 (86.3 mg, 35% yield). $^1$H NMR (400 MHz, CDCl$_3$) δ ppm 7.16 (1H, m), 7.00 (4H, m), 6.72 (1H, dt, J=9.0, 3.5 Hz), 4.50 (2H, s), 3.71 (3H, s), 2.71 (4H, m), 1.34 (6H, m).

Intermediate T42

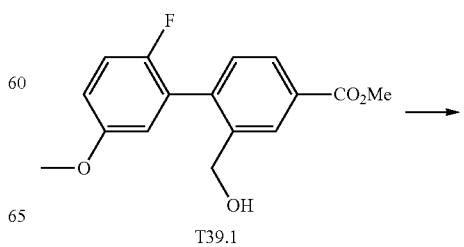

T39.1

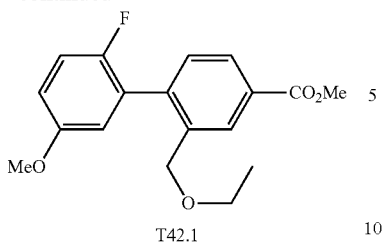

T42.1

Methyl 2-((ethyloxy)methyl)-2'-fluoro-5'-(methyloxy)-1,1'-biphenyl-4-carboxylate (T42.1)

To a solution of T39.1 (0.200 g, 0.689 mmol) in DMF (5 mL), was added NaH (0.0198 g, 0.827 mmol). The reaction was stirred at room temperature for 10 minutes. Ethyl iodide was then added and the reaction was stirred at room temperatures for 1 hour. The mixture was diluted with EtOAc, washed with water and brine, and dried over anhydrous $Na_2SO_4$. After removing solvent, the residue was purified by flash chromatography (silica gel, 1:1 EtOAc/hexane) and gave T42.1 in 79% yield. MS ESI (pos.) m/e: 336 (M+18)$^+$.

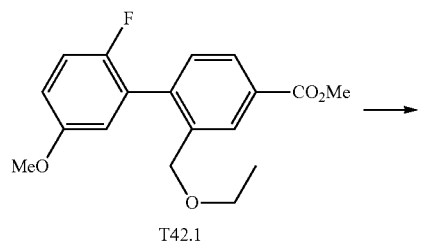

T42.1

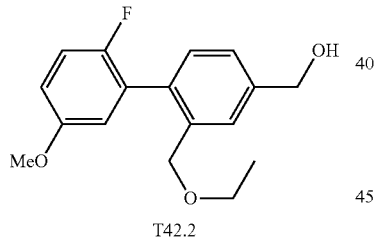

T42.2

(2-((Ethyloxy)methyl)-2'-fluoro-5'-(methyloxy)-1,1'-biphenyl-4-yl)methanol (T42.2)

Example T42.1 was reduced using LAH using a procedure similar to those described herein to yield T42.2.

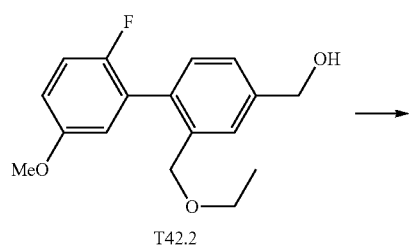

T42.2

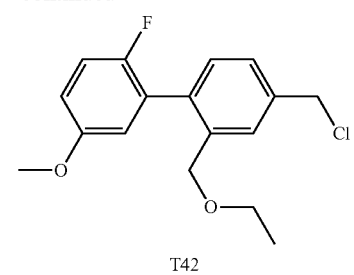

T42

4-(Chloromethyl)-2-((ethyloxy)methyl)-2'-fluoro-5'-(methyloxy)-1,1'-biphenyl (T42)

Compound T42.2 was converted to the chloromethyl compound T42 using a procedure analogous to those described herein.

Intermediate T43

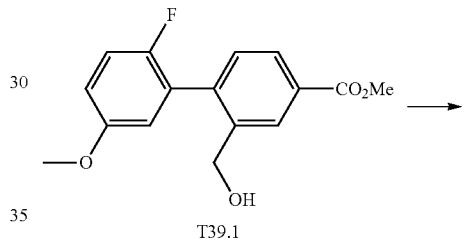

T39.1

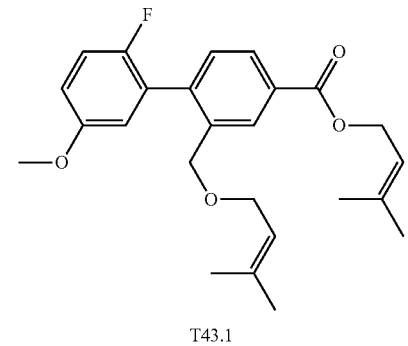

T43.1

3-Methyl-2-butenyl 2'-fluoro-2-(((3-methyl-2-butenyl)oxy)methyl)-5'-(methyloxy)-1,1'-biphenyl-4-carboxylate (T43.1)

To a solution of T39.1 (0.322 mmol) in DMF (4 mL), was added NaH (0.0100 g, 0.419 mmol). The resulting mixture was stirred at room temperature for 10 minutes. 1-Bromo-3-methylbut-2-ene (0.240 g, 1.61 mmol) (commercially available from Sigma-Aldrich, St. Louis, Mo., USA) was added and the mixture was stirred at room temperature for 2 hours. After removing solvent, the residue was purified by flash chromatography (silica gel, 1:6 EtOAc/hexane) and gave T43.1 as a colorless oil, in 77% yield. MS ESI (pos.) m/e: 430 (M+18)$^+$.

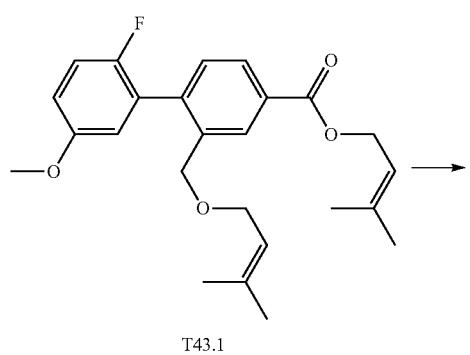

T43.1

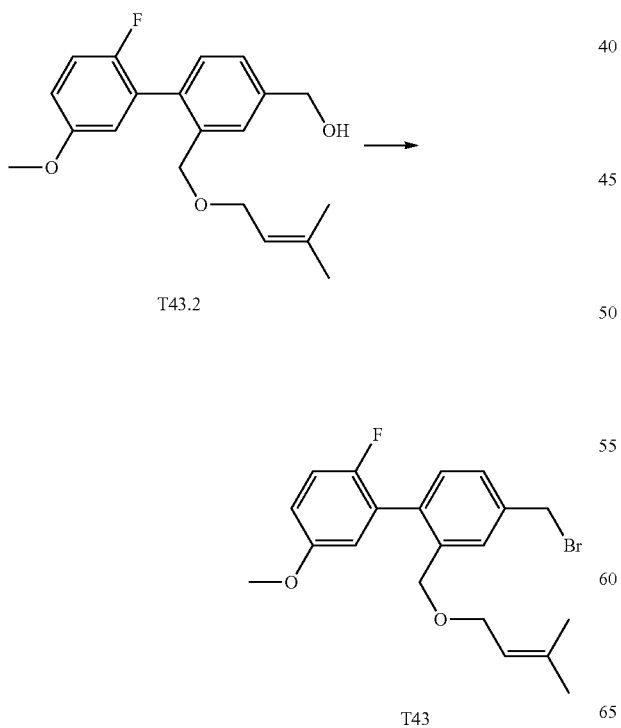

(2'-Fluoro-2-(((3-methyl-2-butenyl)oxy)methyl)-5'-(methyloxy)-1,1'-biphenyl-4-yl)methanol (T43.2)

The conversion of ester T43.1 to hydroxymethyl compound T35.2 was conducted using a procedure analogous to that described in Example T39.4.

4-(Bromomethyl)-2'-fluoro-2-(((3-methyl-2-butenyl)oxy)methyl)-5'-(methyloxy)-1,1'-biphenyl (T43)

Hydroxymethyl compound T43.2 was converted to bromomethyl T43 using a procedure analogous to that of Example T38.

Intermediate T44

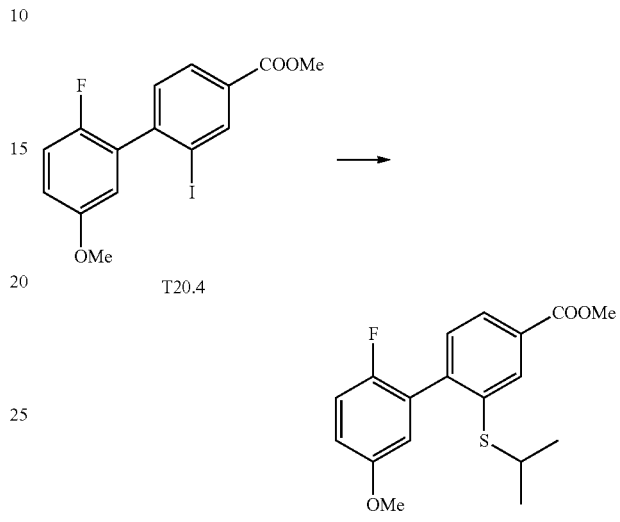

2'-Fluoro-2-isopropylsulfanyl-5'-methoxy-biphenyl-4-carboxylic acid methyl ester (T44.1)

A tube was charged with T20.4 (213 mg, 552 µmol), N-ethyl-N-isopropylpropan-2-amine (143 mg, 1103 µmol) and toluene, evacuated and back-filled with nitrogen three times. Pd$_2$(dba)$_3$, 4,5-bis(diphenylphosphino)-9,9-dimethyl-9H-xanthene (31.9 mg, 55.2 µmol) and propane-2-thiol (63.0 mg, 827 µmol) were added to the mixture and then the mixture was degassed three times. The suspension was refluxed overnight, filtered, and concentrated to give a residue which was purified by silica gel chromatography to give T44.1 as a pale yellow solid (164 mg, 89%). MS ESI m/e: 335.2 (M+1)$^+$.

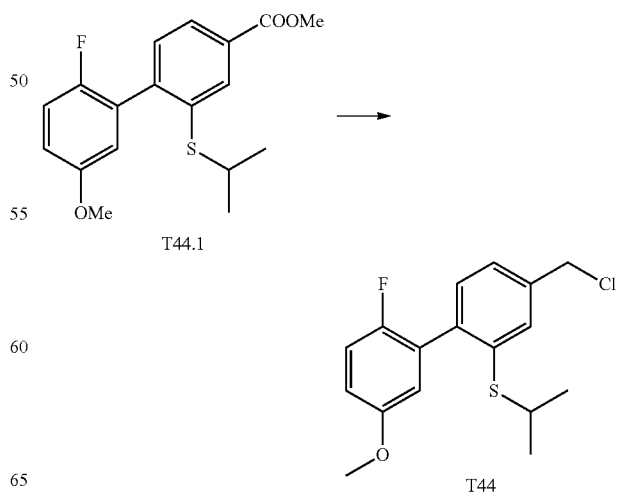

4-Chloromethyl-2'-fluoro-2-isopropylsulfanyl-5'-methoxy-biphenyl (T44)

The reduction and chlorination of T44.1 was conducted in an analogous manner to that described herein. MS ESI m/e: 325.10 (M+H)$^+$.

Intermediate T45

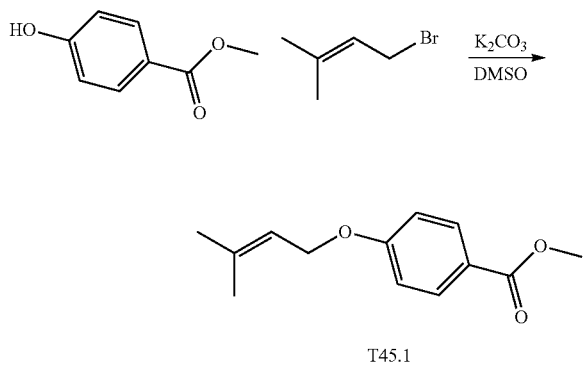

T45.1

Methyl 4-(3-methylbut-2-enyloxy)benzoate (T45.1)

A mixture of 4-hydroxybenzoic acid, methyl ester (17.0 mL, 66 mmol) (commercially available from Sigma-Aldrich, St. Louis, Mo., USA), 1-bromo-3-methylbut-2-ene (12.0 g, 79 mmol) (commercially available from Sigma-Aldrich, St. Louis, Mo., USA) and potassium carbonate (23.0 g, 164 mmol) in DMSO (25 mL) was stirred at room temperature for 24 hours. EtOAc (150 mL) was added, and the mixture was washed with water (25×3 mL) and brine (25×2 mL) and dried over MgSO$_4$. The solvent was removed, and the product was purified by CombiFlash® silica gel column chromatography, eluent with hexane/EtOAc, 90/10 to give T45.1 (12.0 g, yield 83%). $^1$H NMR (500 MHz, CDCl$_3$) δ ppm 7.99 (2H, d, J=8.8 Hz), 6.92 (2H, d, J=8.8 Hz), 5.42-5.58 (1H, m), 4.57 (2H, d, J=6.8 Hz), 3.89 (3H, s), 1.81 (3H, s), 1.76 (3H, s).

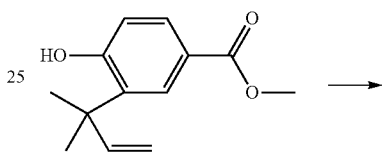

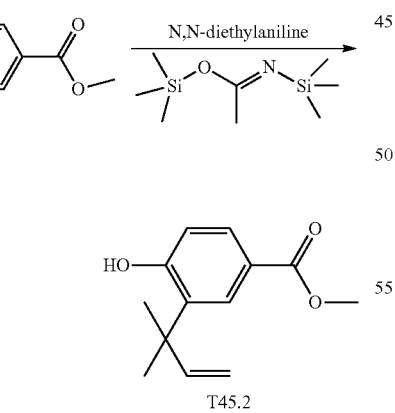

Methyl 4-hydroxy-3-(2-methylbut-3-en-2-yl)benzoate (T45.2)

The reaction mixture of T45.1 (1.2 g, 5.0 mmol), N,N-diethylaniline (3.0 mL, 16 mmol) and N,O-bis(trimethylsilyl) acetamide (2.0 mL, 8 mmol) in a 15 mL sealed tube was heated at 210° C. for 48 hours. Ether (60 mL) was added, and the mixture was washed over HCl (3N in water, 20 mL). The organic layer was separated, and the solvent was removed. The residue was dissolved in MeOH (10 mL) and HCl (3N in water, 2 mL) and was stirred at room temperature for 30 minutes. Ether (80 mL) was added, and the mixture was washed with NaHCO$_3$ (30 mL) and brine (15 mL). The organic layer was then dried over MgSO$_4$. The solvent was removed, and the residue was purified by CombiFlash® silica gel column chromatography, eluent with hexane/EtOAc, 95/5 to give T45.2 (0.30 g, 25% yield). MS ESI (pos.) m/e: 221.2 (M+H)$^+$. $^1$H NMR (500 MHz, CDCl$_3$) δ ppm 8.01 (1H, d, J=2.0 Hz), 7.87 (1H, dd, J=8.4, 2.0 Hz), 6.87 (1H, d, J=8.4 Hz), 6.32 (1H, s), 6.21 (1H, dd, J=17.9, 10.5 Hz), 5.24-5.45 (2H, m), 3.90 (3H, s), 1.48 (6H, s).

T45.2

T45.3

Methyl 3-(2-methylbut-3-en-2-yl)-4-(trifluoromethyl-sulfonyloxy)benzoate (T45.3)

The reaction mixture of T45.2 (0.28 g, 1.3 mmol), pyridine (0.23 mL, 2.8 mmol), and trifluoromethanesulfonic anhydride (0.28 mL, 1.7 mmol) with a catalytic amount of DMAP was stirred at ambient temperature overnight. EtOAc (70 mL) was added, and the mixture was washed with citric acid (15 mL), brine (20 mL), and then dried with MgSO$_4$. The solvent was removed. The product T45.3 was used without further purification in the next step, (0.45 g, 99% yield). $^1$H NMR (500 MHz, CDCl$_3$) δ ppm 8.20 (1H, d, J=2.2 Hz), 7.99 (1H, dd, J=8.8, 2.2 Hz), 7.42 (1H, d, J=8.8 Hz), 6.08 (1H, dd, J=17.4, 10.6 Hz), 5.10 (1H, d, J=10.6 Hz), 4.97 (1H, d, J=17.4 Hz), 3.91 (3H, s), 1.53 (6H, s).

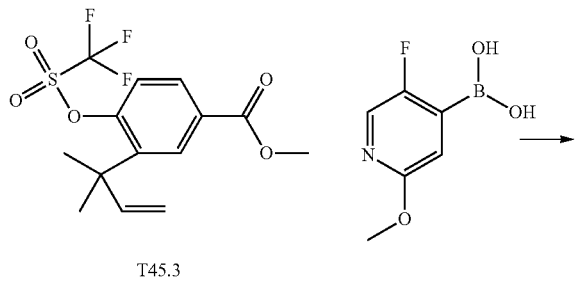

T45.3

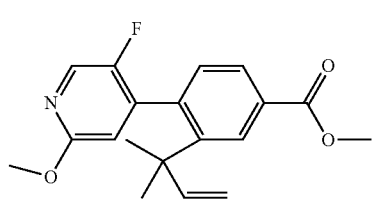

T45.4

Methyl 4-(5-fluoro-2-methoxypyridin-4-yl)-3-(2-methylbut-3-en-2-yl)benzoate (T45.4)

The reaction mixture of T45.3 (0.45 g, 1.3 mmol), 5-fluoro-2-methoxypyridin-4-ylboronic acid (0.55 g, 3.2 mmol), potassium phosphate (0.81 g, 3.8 mmol), S-phos (0.11 g, 0.26 mmol) and palladium acetate (0.03 g, 0.13 mmol) in DMF (1.5 mL) was purged with nitrogen three times. The resulting mixture was heated at 90° C. for 2 hours. The mixture was then purified by CombiFlash® silica gel chromatography, eluent with hexane/EtOAc, 9/1 to give T45.4. MS ESI (pos.) m/e: 330.2 (M+H)$^+$. $^1$H NMR (400 MHz, CDCl$_3$) δ ppm 8.26 (1H, d, J=1.8 Hz), 7.95 (1H, s), 7.90 (1H, dd, J=7.8, 1.8 Hz), 7.06 (1H, d, J=7.8 Hz), 6.59 (1H, d, J=4.9 Hz), 5.88-6.02 (1H, m), 4.75-4.85 (2H, m), 3.95 (3H, s), 3.94 (3H, s), 1.38 (3H, s), 1.36 (3H, s)

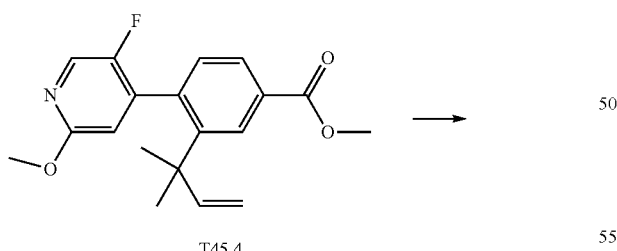

T45.4

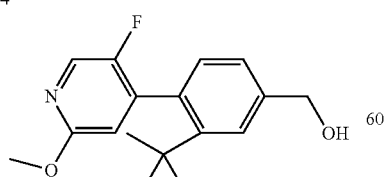

T45.5

(4-(5-Fluoro-2-methoxypyridin-4-yl)-3-(2-methylbut-3-en-2-yl)phenyl)methanol (T45.5)

To a solution of T45.4 (68.0 mg, 0.21 mmol) in THF (3.0 mL) was slowly added lithium aluminum hydride (17.3 μL, 1.0 M solution in diethyl ether, 0.41 mmol) at room temperature. The resulting mixture was stirred at 45° C. for 5 hours. Water (0.07 mL) was added at 0° C. and then 0.07 mL of NaOH (15% in water) was added. The reaction mixture was stirred for 10 minutes and then 0.21 mL of water was added, and the mixture was stirred at room temperature for 10 minutes. The precipitate was filtered away and washed with THF (10×3 mL). The organic layer was dried over Na$_2$SO$_4$ and then the solvent was removed. T45.5 was used in the next step without further purification. MS ESI (pos.) m/e: 302.2 (M+H)$^+$.

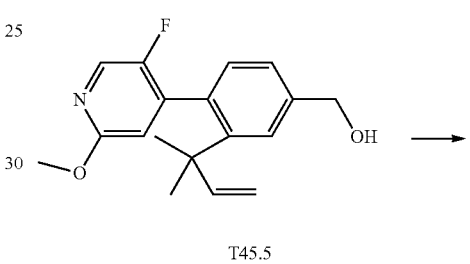

T45.5

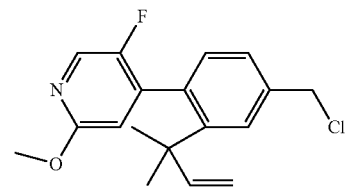

T45

4-(4-(Chloromethyl)-2-(2-methylbut-3-en-2-yl)phenyl)-5-fluoro-2-methoxypyridine (T45)

To a solution of T45.5 (57.0 mg, 0.19 mmol) in DCM (4.0 mL) and DMF (10 μL) was slowly added thionyl chloride (13.8 μL, 0.19 mmol) at 0° C. After addition, the resulting mixture was stirred at room temperature for 1 hour. The solvent was removed to provide T45 which was used to provide compounds as described herein. MS ESI (pos.) m/e: 320.2 (M+H)$^+$.

Intermediate T46

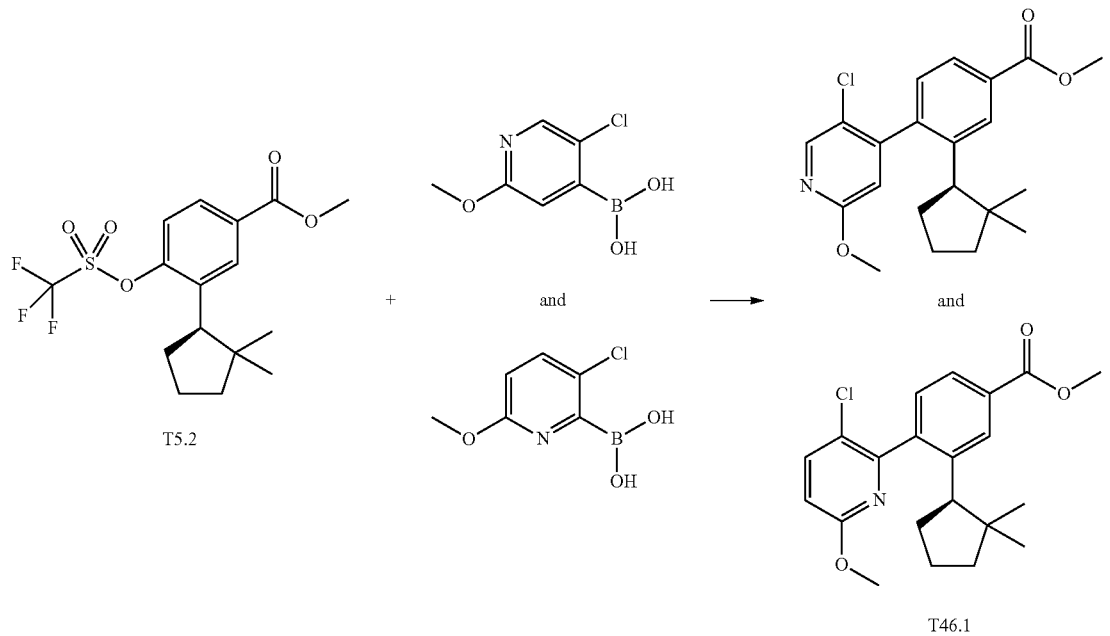 [SMILES: COC(=O)c1ccc(OS(=O)(=O)C(F)(F)F)c([C@@H]2CCCC2(C)C)c1 ; COc1cc(B(O)O)c(Cl)cn1 ; COc1ccc(Cl)c(B(O)O)n1 ; COC(=O)c1ccc(-c2nc(OC)ccc2Cl)c([C@@H]2CCCC2(C)C)c1 ; COC(=O)c1ccc(-c2cc(OC)ncc2Cl)c([C@@H]2CCCC2(C)C)c1]

Methyl 4-(5-chloro-2-methoxypyridin-4-yl)-3-(R)-2,2-dimethylcyclopentyl)benzoate and methyl 4-(3-chloro-6-methoxypyridin-2-yl)-3-((R)-2,2-dimethyl-cyclopentyl)benzoate (T46.1)

To a flask with T5.2 (401 mg, 1.05 mmol) was added 5-chloro-2-methoxypyridin-4-ylboronic acid (494 mg, 2.64 mmol, commercially from Chem-IMPEX Lot #JI-02-031, also containing 30% 3-chloro-6-methoxypyridin-2-ylboronic acid), potassium carbonate (437 mg, 3.16 mmol), and trans-dichlorobis(triphenylphosphine)palladium (II) (74 mg, 0.11 mmol, commercially available from Alfa Aesar). The flask was flushed with nitrogen. Degassed DMF (8 mL) was then added. The resulting mixture was heated at 90° C. for 3.0 hours, cooled to room temperature, treated with water, and extracted with EtOAc. After removal of organic solvents under reduced pressure, purification of the residue through silica gel chromatography with 0-20% EtOAc in hexanes as eluents afforded T46.1, a mixture of two compounds that showed two peaks on LCMS with identical mass (498 mg, 92%). MS ESI (pos.) m/e: 374.0 (M+H)$^+$.

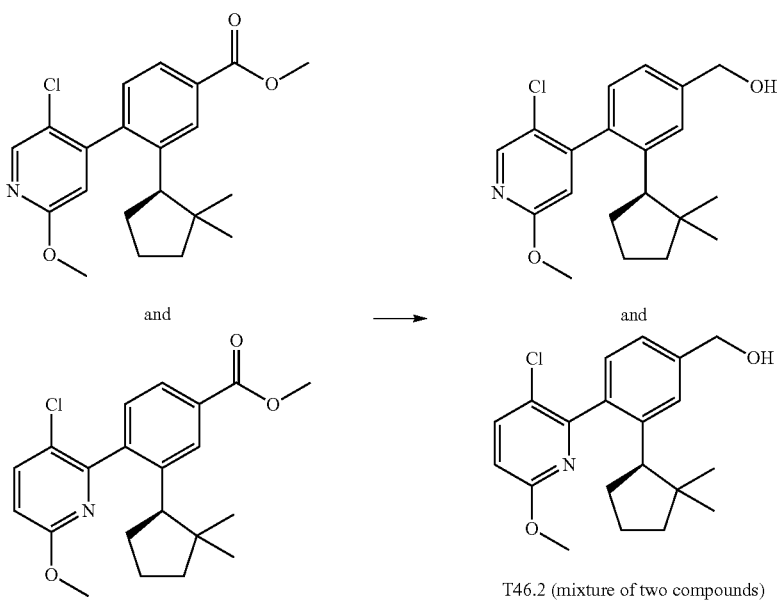

T46.2 (mixture of two compounds)

(4-(5-Chloro-2-methoxypyridin-4-yl)-3-(R)-2,2-dimethylcyclopentyl)phenyl)methanol and (4-(3-chloro-6-methoxypyridin-2-yl)-3-(R)-2,2-dimethylcyclopentyl)phenyl)methanol (T46.2)

To a flask containing T46.1 (195 mg, 1.37 mmol) was added 4 mL anhydrous THF. The reaction vessel was cooled to −78° C. and diisobutylaluminum hydride (244 μL, 1369 μmol, 1.0 M in toluene, commercially available from Sigma-Aldrich, St. Louis, Mo., USA) was added slowly. The resulting solution was allowed to warm to room temperature with an ice bath and left overnight. To the mixture was added MeOH (2.0 mL). After removal of organic solvents, the resulting mixture was treated with 1.0 N HCl (1.0 mL) and water (3.0 mL), and then was extracted with EtOAc. After removal of organic solvents under reduced pressure, purification of the residue through silica gel chromatography with 0-50% EtOAc in hexanes as eluents afforded T46.2 (77 mg, 65%), a mixture of two compounds that showed two peaks on LCMS but were of identical mass. MS ESI (pos.) m/e: 346.2 (M+H)$^+$.

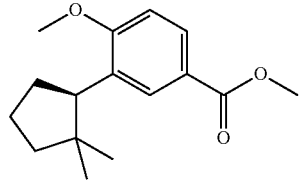

T47.1

(R)-Methyl 3-(2,2-dimethylcyclopentyl)-4-methoxybenzoate (T47.1)

To a flask containing T5.1 (75.0 mg, 302 μmol) and Cs$_2$CO$_3$ (226 mg, 695 μmol) in DMF (1 mL) was added MeI

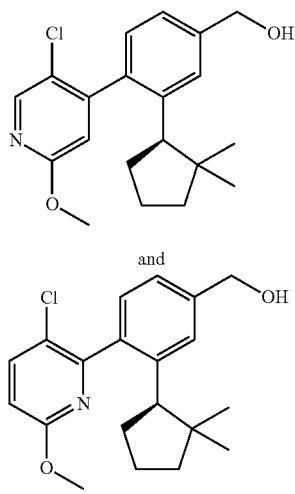

T46.2

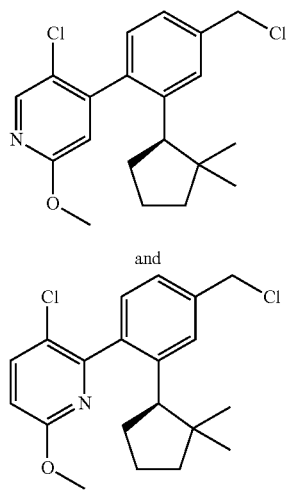

T46

5-Chloro-4-(4-(chloromethyl)-2-((R)-2,2-dimethylcyclopentyl)phenyl)-2-methoxypyridine AND 3-chloro-2-(4-(chloromethyl)-2-(R)-2,2-dimethylcyclopentyl)phenyl)-6-methoxypyridine (T46)

The title mixture of compounds was synthesized from T46.2 using a procedure analogous to that described for synthesizing T5 from T5.4. The final product T46 was isolated as a mixture of two compounds that showed two peaks on HPLC which had an identical mass on LCMS. MS ESI (pos.) M/E: 364.1 (M+1).

(37.8 μL, 604 μmol) (commercially available from Sigma-Aldrich, St. Louis, Mo., USA), and the resulting mixture was stirred overnight. The reaction was diluted with water and extracted with EtOAc. The combined organic layers were washed with brine, dried over Na$_2$SO$_4$, filtered, concentrated, and then purified by CombiFlash® chromatography (0 to 20% EtOAc/hexanes) to provide T47.1 (73.9 mg, 93.3% yield). MS ESI (pos.) m/e: 263.0 (M+H)$^+$.

Intermediate T47

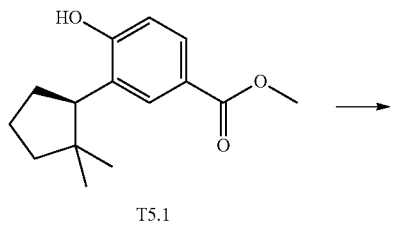

T5.1  T47.1

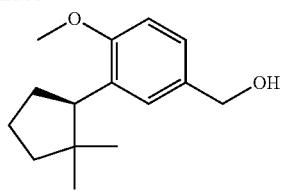

T47

(R)-Methyl 3-(2,2-dimethylcyclopentyl)-4-methoxybenzoate (T47)

To T47.1 (62.1 mg, 237 μmol) in THF (2 mL) at 0° C. was added a 1.0 M THF solution of lithium aluminum hydride (355 μL, 355 μmol). The resulting mixture was stirred for one hour and was then carefully diluted with water, extracted with EtOAc, washed with brine, dried over sodium sulfate, filtered, and concentrated to provide T47 (57.6 mg, 104% yield). MS ESI (pos.) m/e: 217.1 (M−OH)+.

Intermediate T48

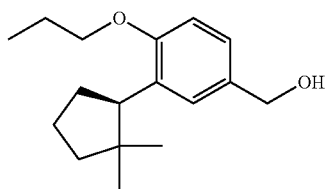

T48

((R)-(3-(2,2-Dimethylcyclopentyl)-4-propoxyphenyl)methanol (T48)

T48 was synthesized analogously to T47 from T5.1 and 1-bromopropane (commercially available from Sigma-Aldrich, St. Louis, Mo., USA). MS ESI (pos.) m/e: 245.2 (M−OH)+.

Intermediate T49

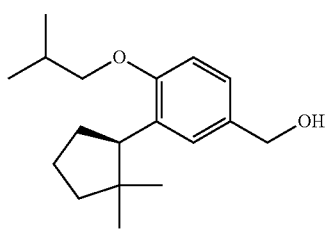

T49

(R)-(3-(2,2-Dimethylcyclopentyl)-4-isobutoxyphenyl)methanol (T49)

T49 was synthesized analogously to T47 from T5.1 and 1-bromo-2-methylpropane (commercially available from Sigma-Aldrich, St. Louis, Mo., USA). MS ESI (pos.) m/e: 259.1 (M−OH)+.

Intermediate T50

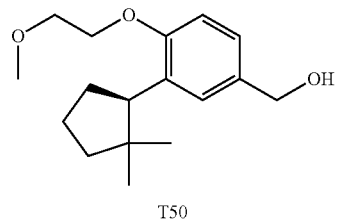

T50

(R)-(3-(2,2-Dimethylcyclopentyl)-4-(2-methoxyethoxy)phenyl)methanol (T50)

T50 was synthesized analogously to T47 from T5.1 and 1-bromo-2-methoxyethane (commercially available from Sigma-Aldrich, St. Louis, Mo., USA). MS ESI (pos.) m/e: 261.1 (M−OH)+.

SYNTHESIS OF EXAMPLE COMPOUNDS

Example 1

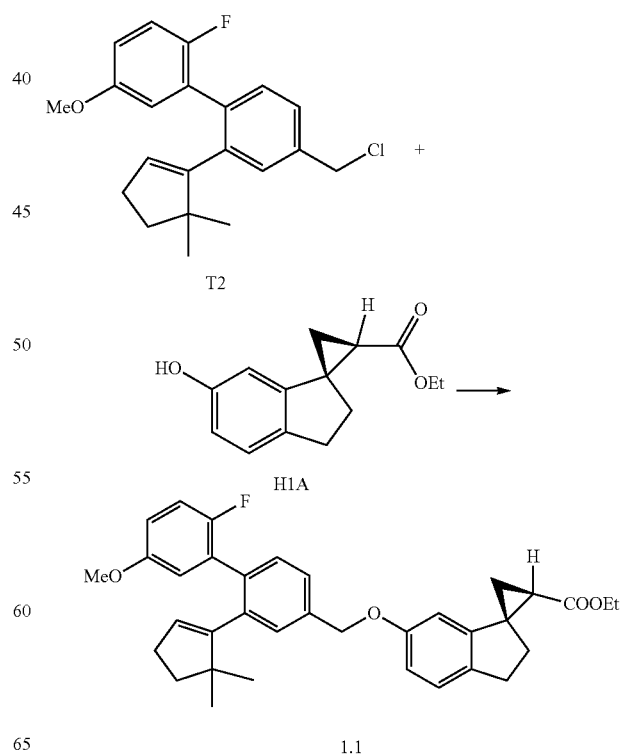

Compound 1.1

A mixture of compound T2 (0.038 g, 0.11 mmol), compound H1A (0.023 g, 0.10 mmol) and Cs$_2$CO$_3$ (0.065 g, 0.20 mmol) in DMF (1 mL) were stirred at 50° C. for 3 hours. The reaction mixture was loaded directly onto a silica gel cartridge and purified using column chromatography (1:7 EtOAc:hexanes) to obtain product 1.1.

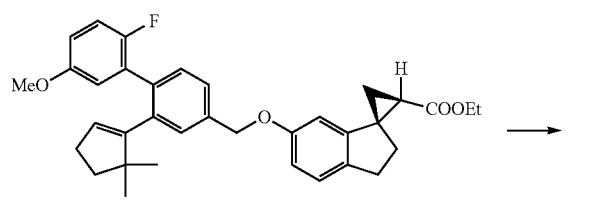

1.1

Example 1

A mixture of 1.1, LiOH (2.0 M, 1 mL), MeOH (1 mL) and THF (2 mL) was stirred at 50° C. for 15 hours. The mixture was concentrated by removing EtOH and water (2 mL) was added. The mixture was then acidified with 1 N HCl to a pH of 3-5. The product was purified by HPLC (reverse phase, C18, 0.1% TFA in water/0.1% TFA in ACN, 10-95%) to give Example 1 (24 mg, 47% yield over two steps). MS ESI (pos.) M/E: 535 (M+Na). $^1$HNMR (CDCl$_3$-d$_3$) δ ppm 7.32-7.40 (2H, m), 7.14 (1H, d, J=8.2 Hz), 6.97 (1H, t, J=9.4 Hz), 6.77-6.87 (3H, m), 6.36 (1H, d, J=2.7 Hz), 5.53 (1H, t, J=2.7 Hz), 5.06 (2H, s), 3.76 (3H, s), 2.99 (2H, dt, J=15.1, 2.0 Hz), 2.22-2.44 (4H, m), 2.01-2.07 (2H, m), 1.65-1.71 (3H, m), 1.50 (1H, dd, J=8.6, 4.7 Hz), 0.86 (6H, s)

Example 2

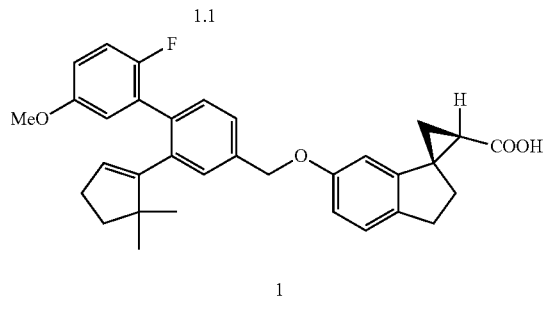

1

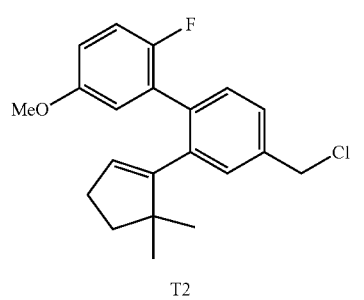

T2

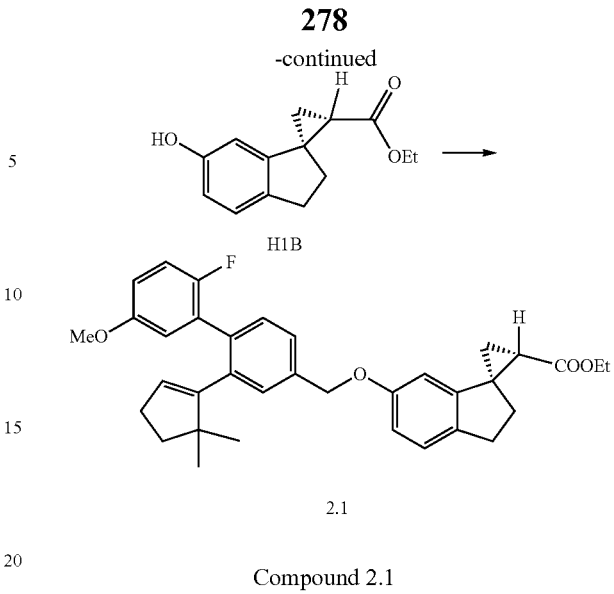

H1B 2.1

Compound 2.1

The title compound was synthesized from compound T2 and compound H1B using a procedure analogous to that described for synthesizing 1.1.

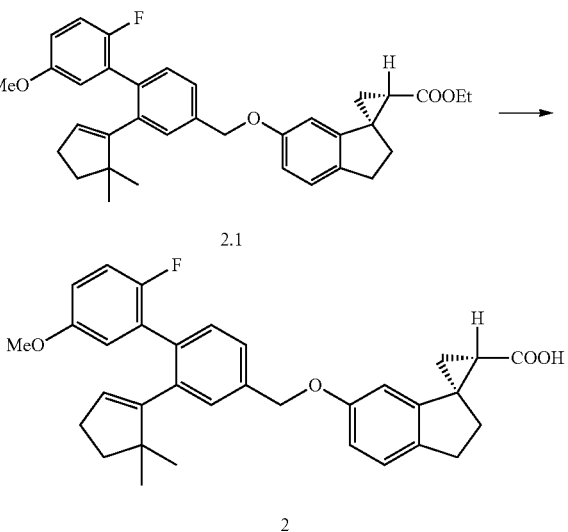

2.1

2

Example 2

The title compound was synthesized from 2.1 using a procedure analogous to that described for synthesizing 1 from 1.1. MS ESI (pos.) M/E: 535 (M+Na).

Example 3

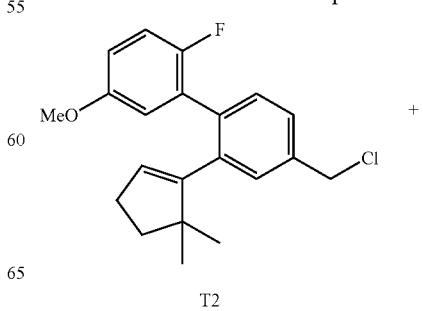

T2

-continued

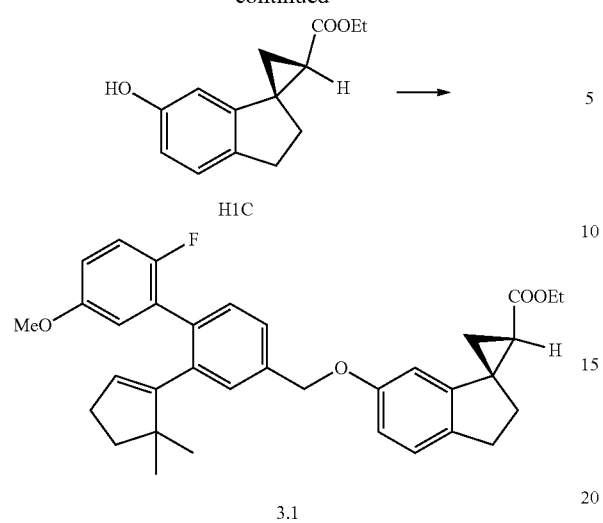

3.1

Compound 3.1

The title compound was synthesized from compound T2 and compound H1C using a procedure analogous to that described for synthesizing 1.1.

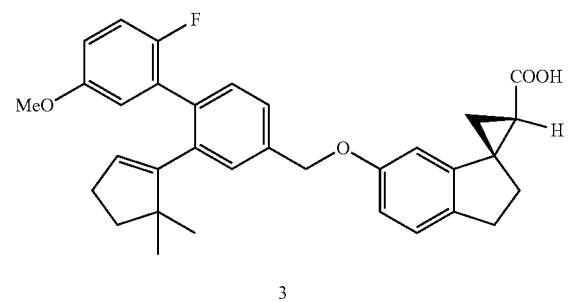

3.1

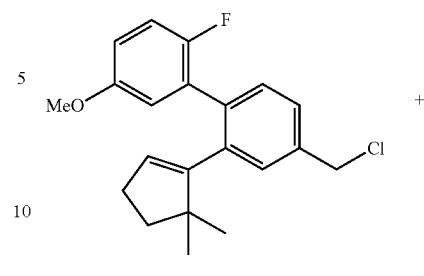

3

Example 3

The title compound was synthesized from 3.1 using a procedure analogous to that described for synthesizing 1 from 1.1. MS ESI (pos.) M/E: 535 (M+Na).

Example 4

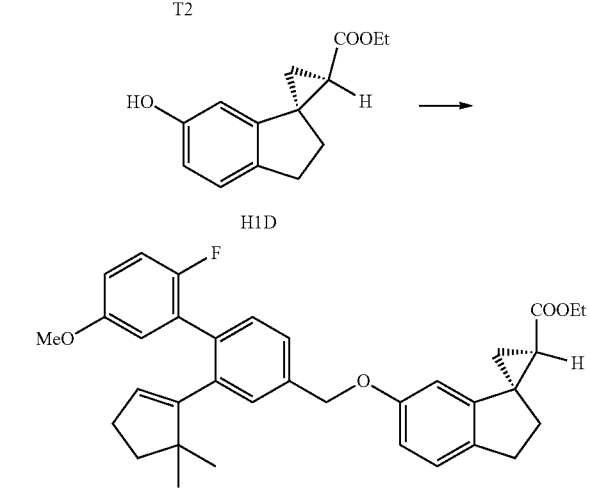

T2

H1D 4.1

Compound 4.1

The title compound was synthesized from compound T2 and compound H1D using a procedure analogous to that described for synthesizing 1.1.

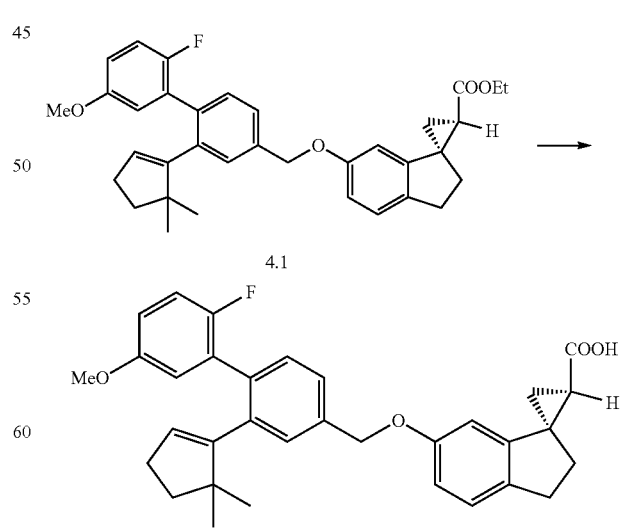

4.1

4

Example 4

The title compound was synthesized from 4.1 using a procedure analogous to that described for synthesizing 1 from 1.1. MS ESI (pos.) M/E: 535 (M+Na).

Example 5

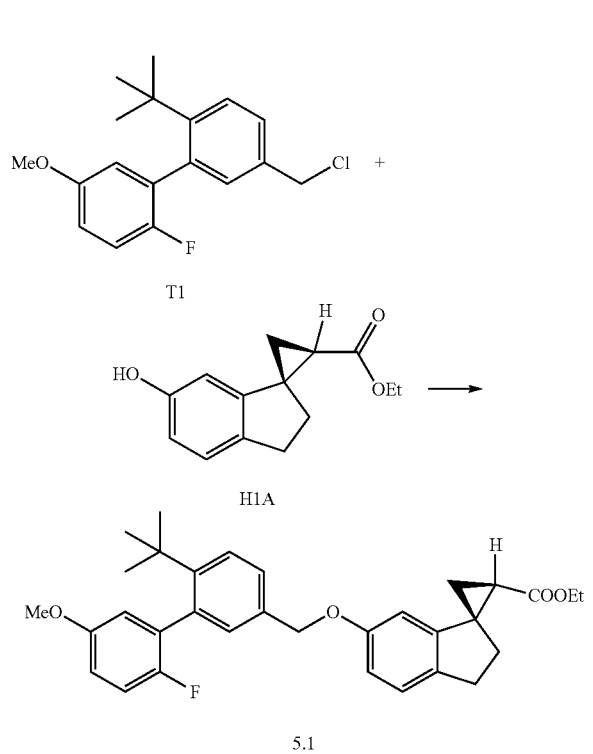

Compound 5.1

The title compound was synthesized from compound T1 and compound H1A using a procedure analogous to that described for synthesizing 1.1

Example 5

The title compound was synthesized from 5.1 using a procedure analogous to that described for synthesizing 1 from 1.1. MS ESI (pos.) M/E: 497 (M+Na).

Example 6

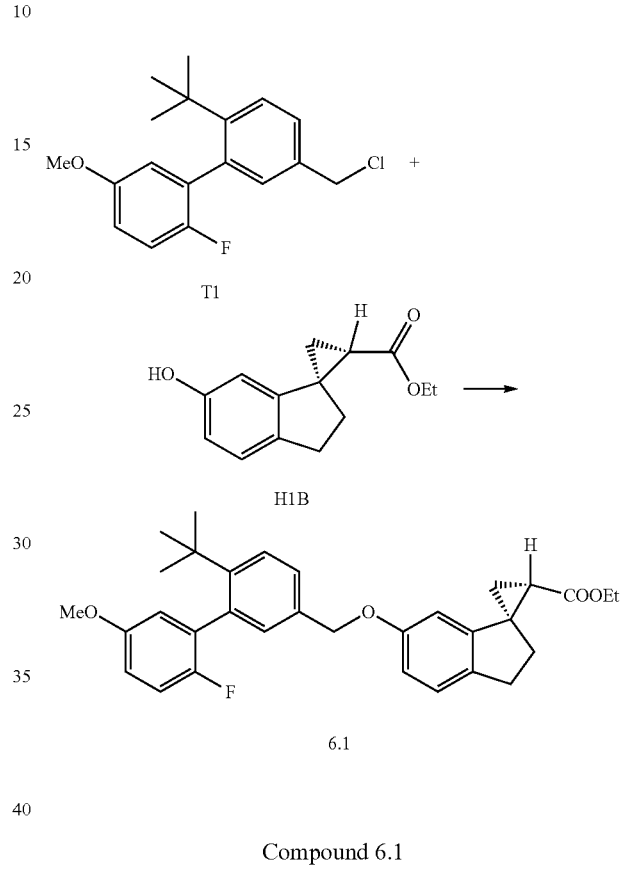

Compound 6.1

The title compound was synthesized from compound T1 and compound H1B using a procedure analogous to that described for synthesizing 1.1.

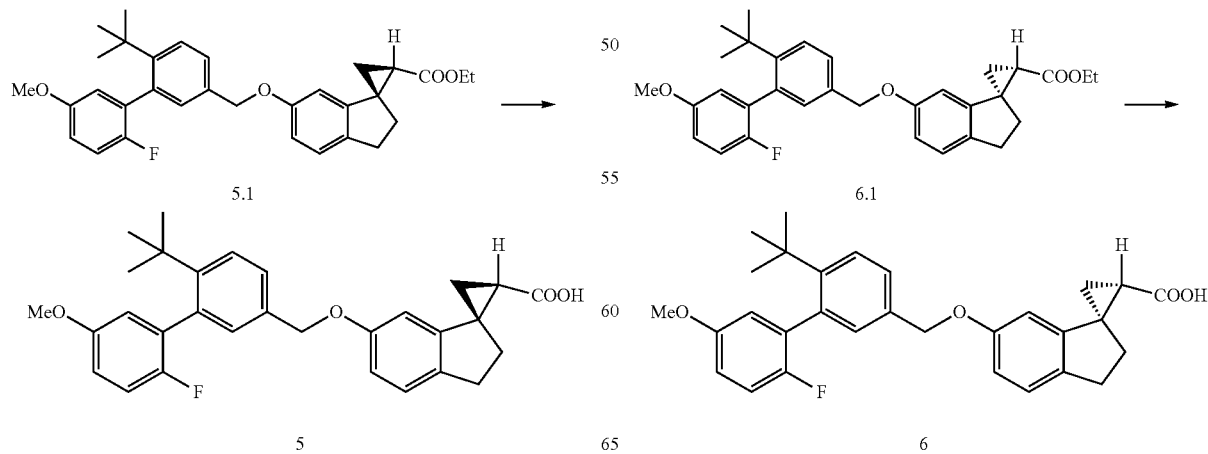

Example 6

The title compound was synthesized from 6.1 using a procedure analogous to that described for synthesizing 1 from 1.1. MS ESI (pos.) M/E: 497 (M+Na).

Example 7

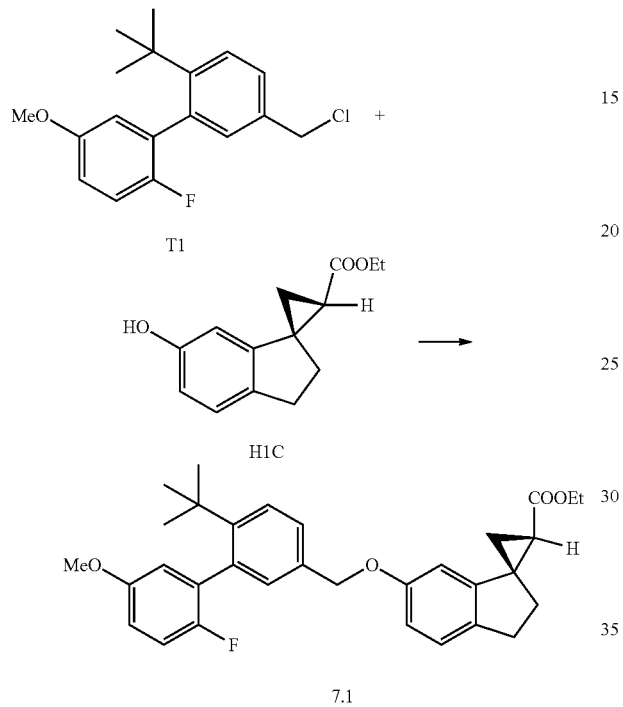

Compound 7.1

The title compound was synthesized from compound T1 and compound H1C using a procedure analogous to that described for synthesizing 1.1.

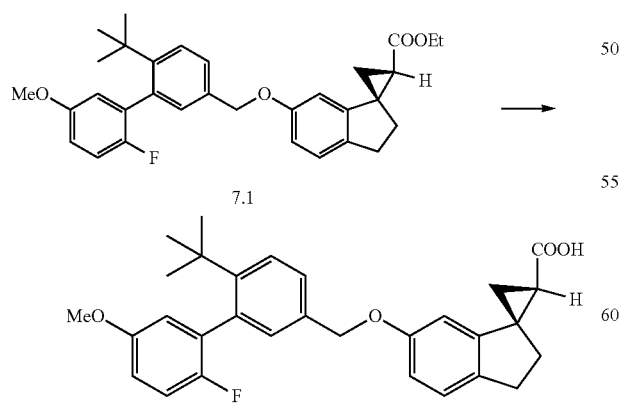

7

Example 7

The title compound was synthesized from 7.1 using a procedure analogous to that described for synthesizing 1 from 1.1. MS ESI (pos.) M/E: 497 (M+Na).

Example 8

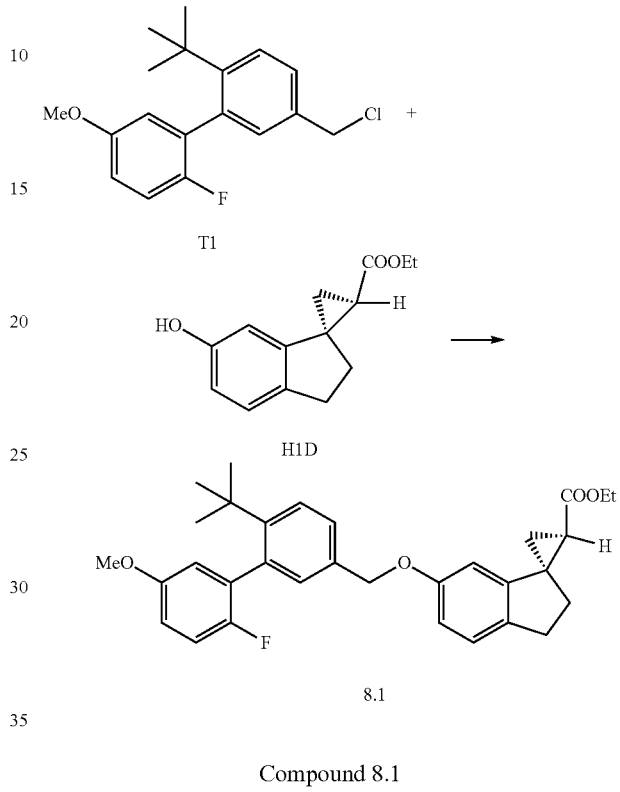

Compound 8.1

The title compound was synthesized from compound T1 and compound H1D using a procedure analogous to that described for synthesizing 1.1.

Example 8

The title compound was synthesized from 8.1 using a procedure analogous to that described for synthesizing 1 from 1.1. MS ESI (pos.) M/E: 497 (M+Na).

Example 9

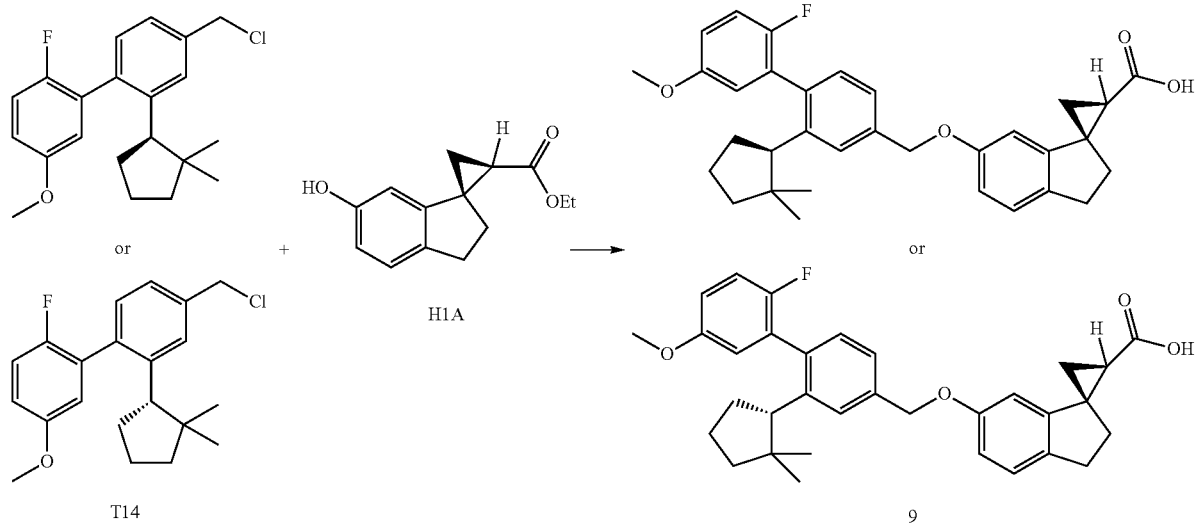

Example 9

To a stirred solution of T14 (10.0 mg, 28.8 µmol) and H1A (6.57 mg, 28.3 µmol) in DMSO (1 mL) was added Cs$_2$CO$_3$ (12.0 mg, 36.7 µmol). The resulting mixture was stirred at 23° C. for 16 hours and then 2N LiOH (0.5 mL) and MeOH (1 mL) were added, and the mixture was stirred for 15 hours at 50° C. The mixture was acidified with 2N HCl (0.6 mL), diluted with ACN, and purified by HPLC (reverse phase, C18, 0.1% TFA in water/0.1% TFA in ACN, 10-95%) to give 9 (10.5 mg, 72% yield) as white solid. MS ESI (pos.) M/E: 537 (M+Na).

Example 10

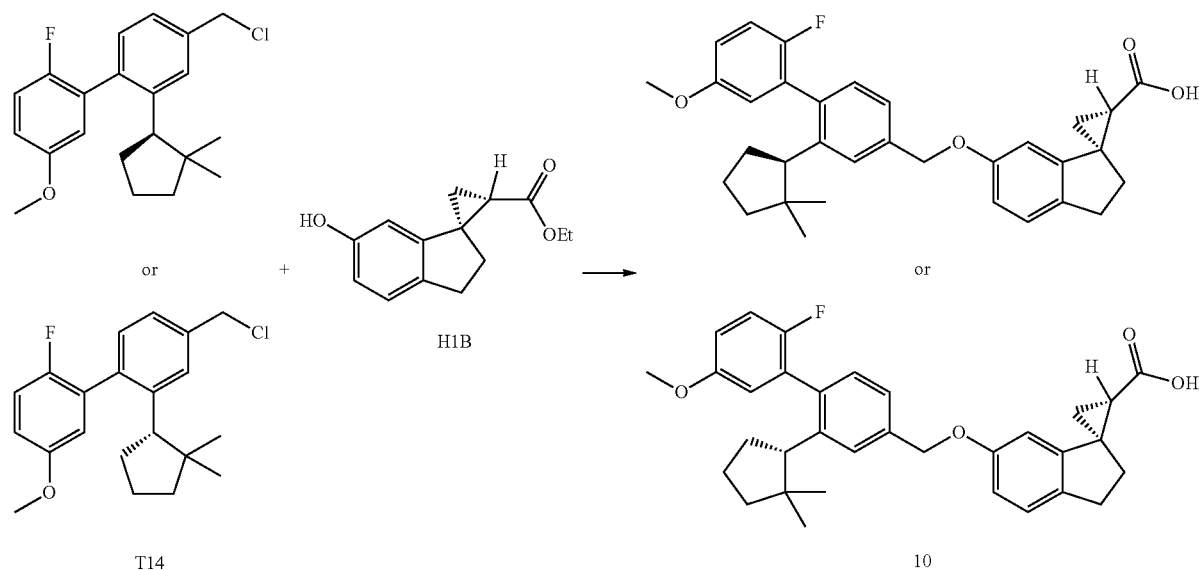

Example 10
The title compound was synthesized from T14 and H1B using a procedure analogous to that described for synthesizing 9. MS ESI (pos.) M/E: 537 (M+Na).
Example 11
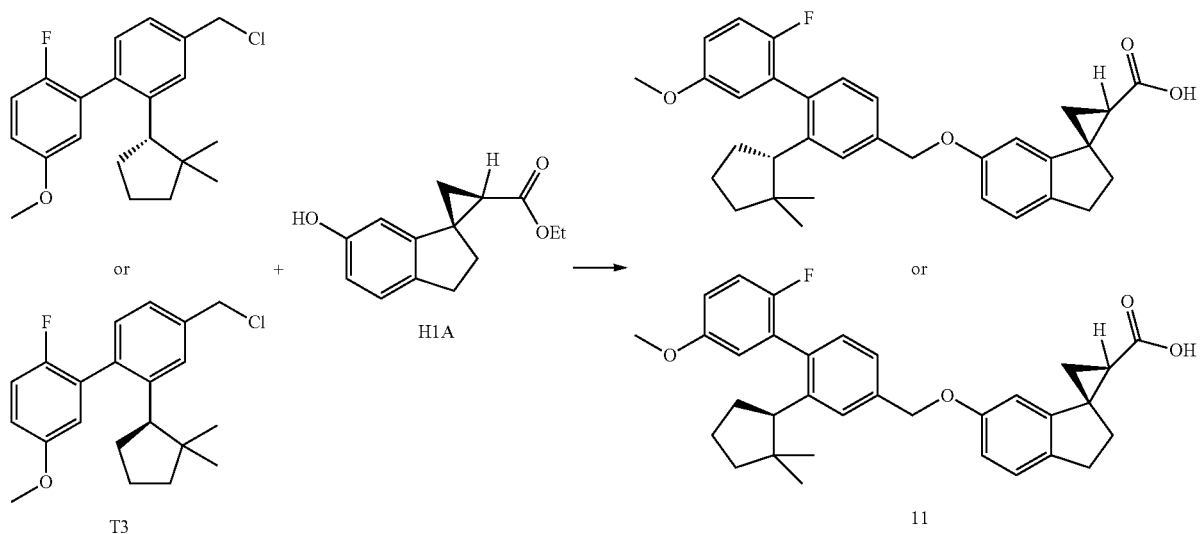
Example 11
The title compound was synthesized from T3 and H1A using a procedure analogous to that described for synthesizing 9. MS ESI (pos.) M/E: 537 (M+Na).
Example 12
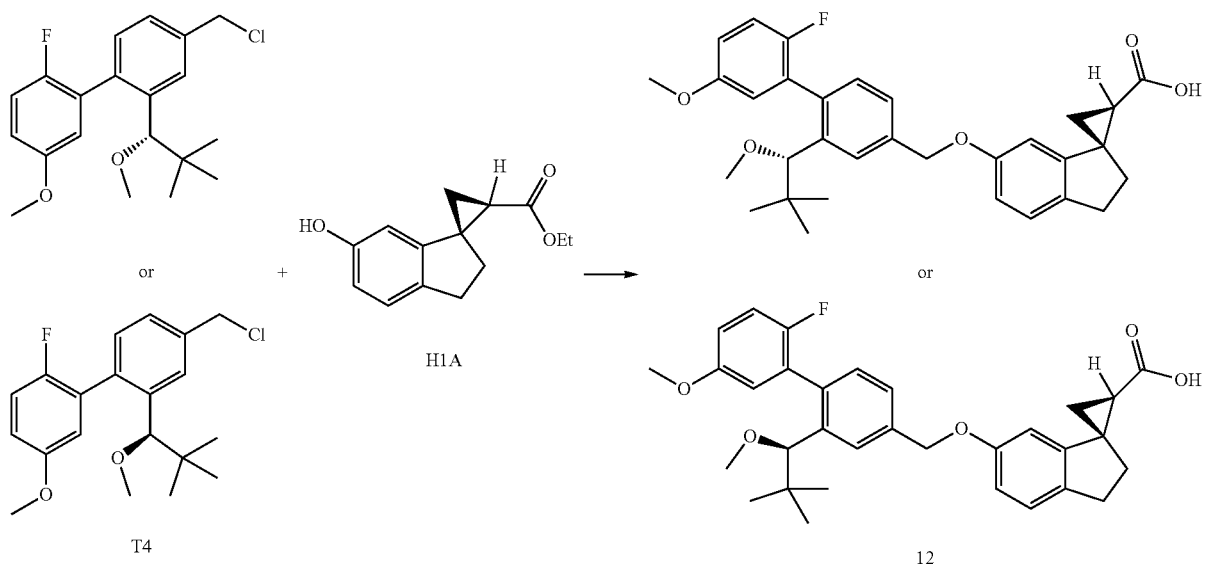

Example 12

The title compound was synthesized from T4 and H1A using a procedure analogous to that described for synthesizing 9. MS ESI (pos.) M/E: 541 (M+Na).

Example 13

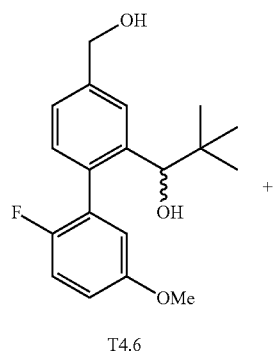

T4.6

+

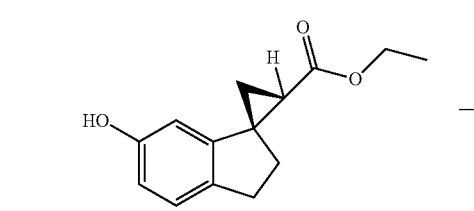

H1A

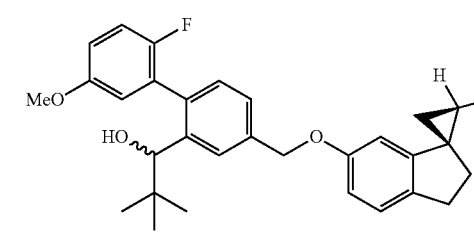

13.1

Compound 13.1

To a stirred solution of H1A (81 mg, 349 μmol) in THF (1.20 mL, 14645 μmol) at 23° C. was added T4.6 (122 mg, 384 μmol) and triphenylphosphine (137 mg, 523 μmol), followed by dropwise addition of DEAD (0.083 mL, 523 μmol) over 3 hours. The product was loaded onto a column and purified (10% EtOAc in hexanes) to give 13.1 (186 mg, 100% yield). MS ESI (pos.) M/E: 555 (M+Na).

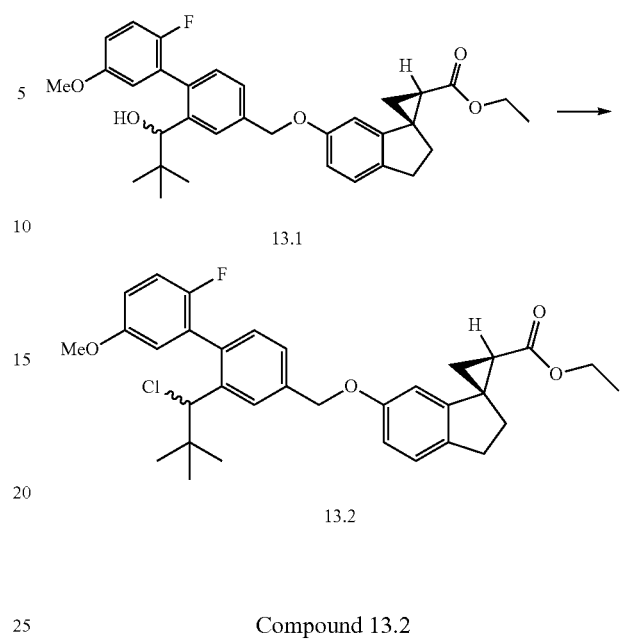

Compound 13.2

To a stirred solution of 13.1 (186 mg, 0.349 mmol) in DCM (5.00 mL, 78 mmol) at 23° C. was added DMF (2.69 μL, 0.0349 mmol) followed by thionyl chloride (50.9 μL, 0.698 mmol). The resulting mixture was stirred for 1.5 hours at 23° C. The reaction was then concentrated in vacuo and the residue was purified on silica gel (0-20% EtOAc/hexane) to give 13.2 (109 mg, 57% yield). MS ESI (pos.) M/E: 573 (M+Na).

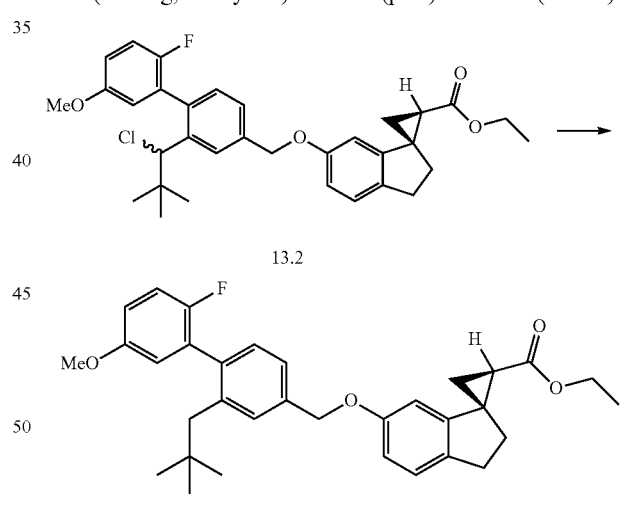

Compound 13.3

To a stirred solution of 13.3 (109 mg, 197.5 μmol) in toluene (3 mL) at 23° C. was added 2,2'-azobis(2-methylpropanenitrile) (3.24 mg, 19.75 μmol) followed by tri-n-butyltin hydride (157.0 μL, 592.4 μmol). The resulting mixture was stirred at 100° C. for 1.5 hours and then was cooled to room temperature and purified on HPLC (reverse phase, C18, 0.1% TFA in water/0.1% TFA in ACN, 10-95%) to give 13.3. MS ESI (pos.) M/E: 539 (M+Na).

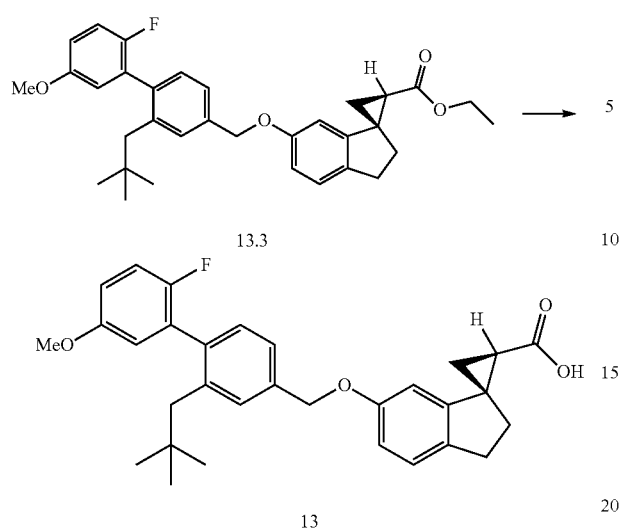

Example 13

To a stirred solution of 13.3 in MeOH (2 mL) at 23° C. was added THF (4 mL) and 2N LiOH (2 mL). The resulting mixture was stirred at 50° C. for 3 hours and then was acidified with 2N HCl (3 mL). The resulting mixture was extracted with water and EtOAc. The solvent was removed and the residue was purified on HPLC (reverse phase, C18, 0.1% TFA in water/0.1% TFA in ACN, 10-95%) to give 13 (42.4 mg, 44% yield over two steps). MS ESI (pos.) M/E: 511 (M+Na).

Example 14

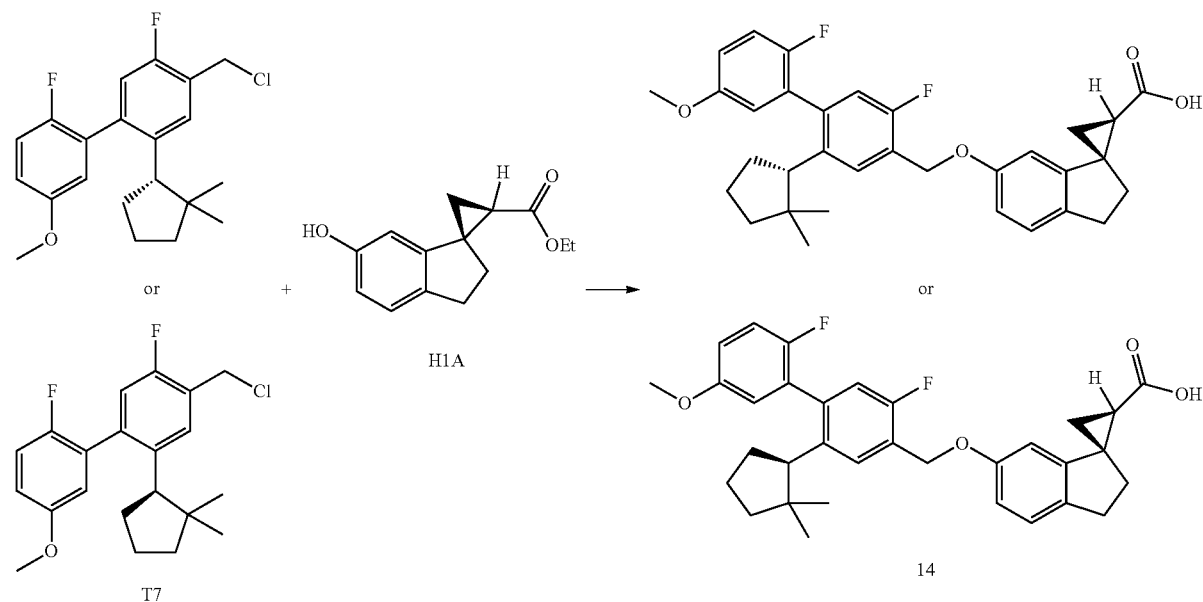

Example 14

The title compound was synthesized from H1A and T7 using a procedure analogous to that described for synthesizing 9. MS ESI (pos.) M/E: 555 (M+Na).

Example 15

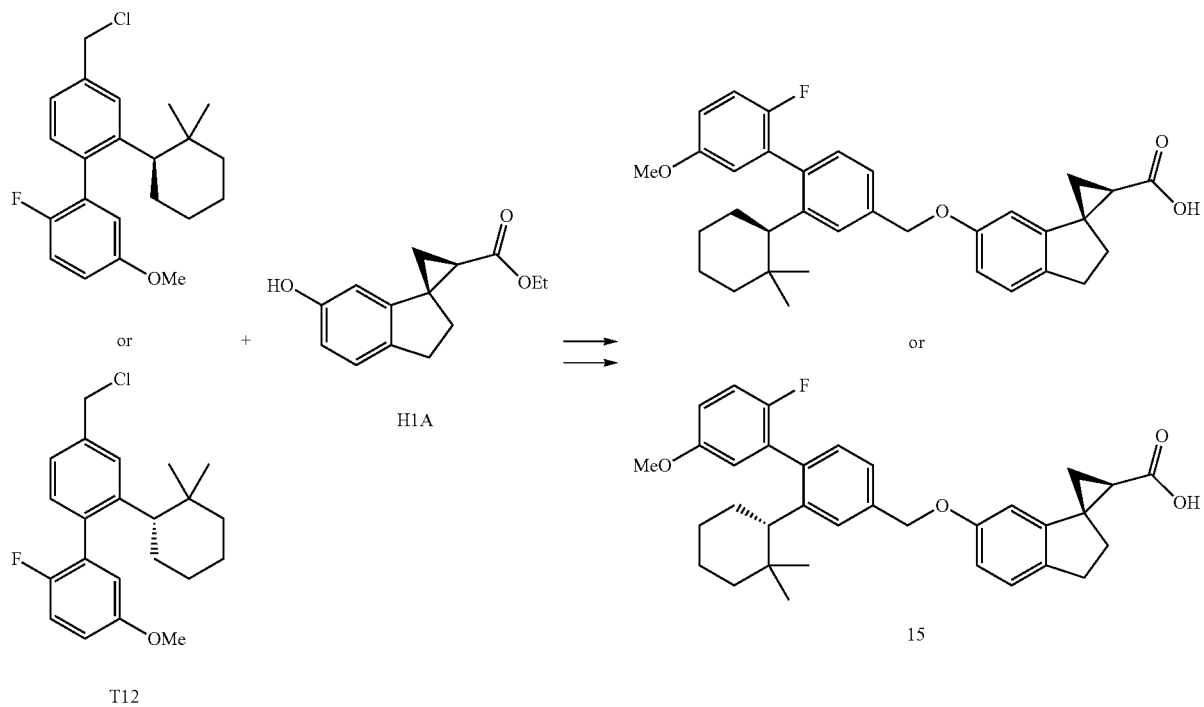

Example 15

To a stirred solution of H1A (0.0234 g, 0.1 mmol) in DMF (2.00 mL) at 23° C. was added T12 (0.036 g, 0.1 mmol) followed by $Cs_2CO_3$ (0.066 g, 0.2 mmol). The resulting mixture was stirred for 20 hours. Water was then added to the reaction, and the resulting mixture was extracted with EtOAc. The combined organic layers were dried over magnesium sulfate, filtered, and concentrated in vacuo. The residue was purified on silica gel (0%-20% EtOAc/hexane) to give the ester (0.045 g, 80.0% yield). To a stirred solution of the ester (0.045 g, 0.081 mmol) in THF (2.00 mL) and EtOH (2.00 mL) at 23° C. was added LiOH (1.0 mL, 1.0M). The mixture was stirred at 23° C. for 16 hours. The reaction mixture was then concentrated in vacuo. 1N HCl was then added, and the resulting mixture was extracted with EtOAc. The combined organic layers were dried over magnesium sulfate, filtered and concentrated in vacuo. The residue was purified on silica gel (0%-30% EtOAc/hexane) to give 15 (0.0375 g, 88% yield). MS ESI (neg.) m/e: 527.2 $(M-H)^+$.

Example 16

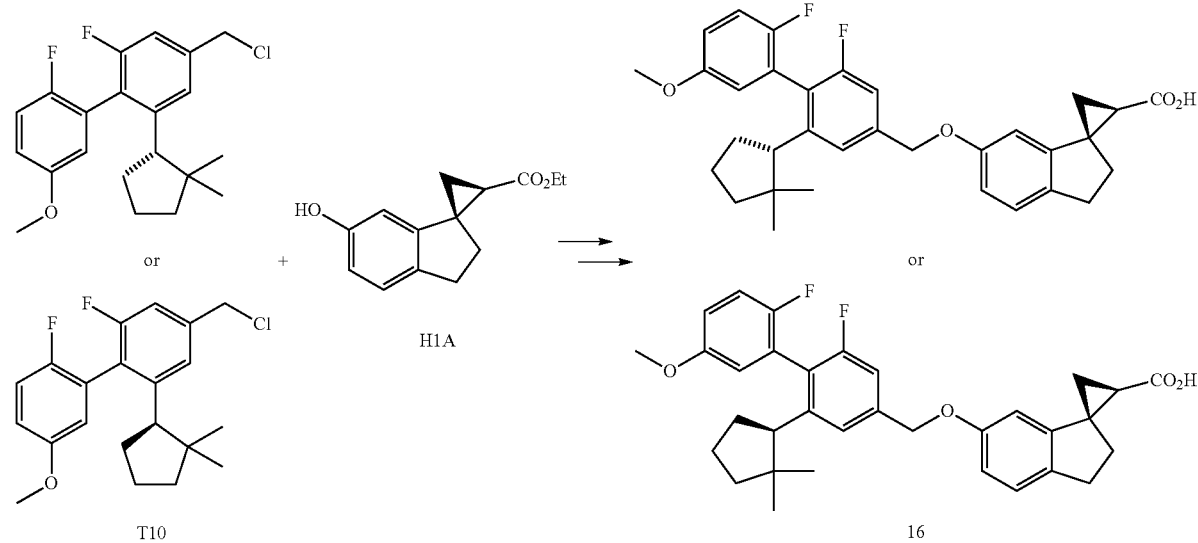

Example 16

The alkylation and hydrolysis were conducted in an analogous manner to Example 15 using T10 and H1A to yield 16 (38.1 mg). $^1$H NMR (500 MHz, CDCl$_3$) δ ppm 7.19 (1H, d, J=1.0 Hz), 7.17 (3H, m), 6.90 (1H, dt, J=9.0, 3.5 Hz), 6.83 (1H, dd, J=8.2, 2.3 Hz), 6.78 (1H, dd, J=5.6, 3.2 Hz), 6.34 (1H, d, J=2.2 Hz), 5.06 (2H, s), 3.80 (3H, s), 3.06 (2H, m), 2.73 (1H, ddd, J=10.1, 8.3, 1.7 Hz), 2.46 (1H, m), 2.35 (1H, m), 2.18 (1H, m), 2.03 (1H, dd, J=8.3, 6.1 Hz), 1.99 (1H, m), 1.85 (1H, m), 1.74 (2H, m), 1.57 (2H, m), 1.42 (1H, m), 0.75 (3H, s), 0.64 (3H, s). MS ESI (neg.) m/e: 531.1 (M−H)$^+$.

Example 17

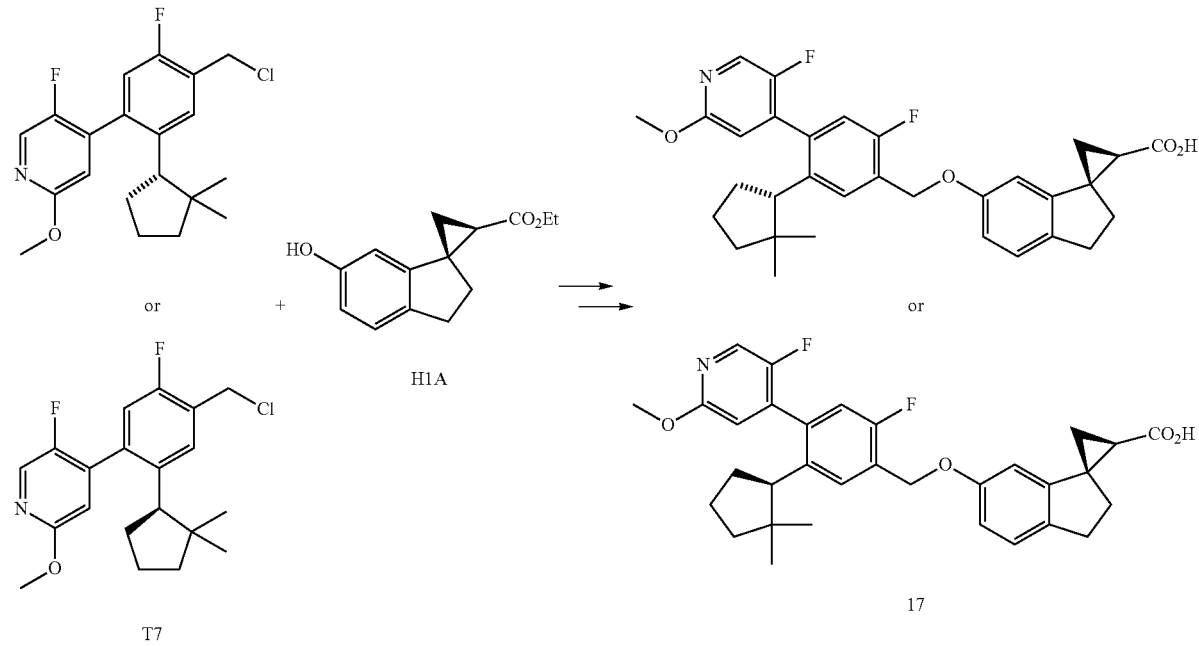

Example 17

The alkylation and hydrolysis were conducted in an analogous manner to Example 15 using T7 and H1A to yield 17 (34.3 mg). MS ESI (pos.) m/e: 534.2 (M+H)$^+$. MS ESI (neg.) m/e: 532.1 (M−H)$^+$.

Example 18

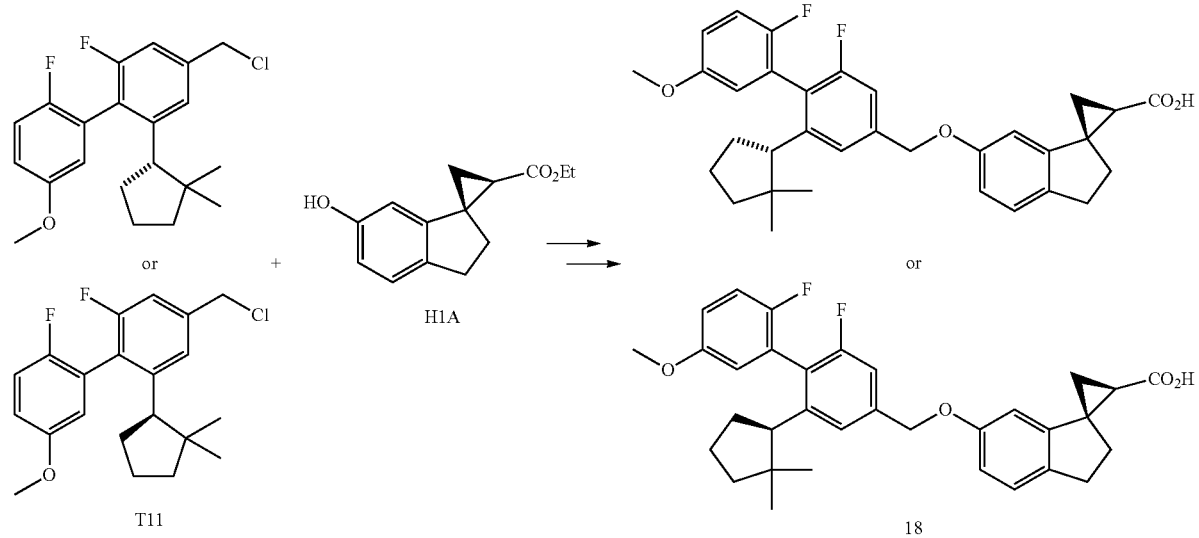

Example 18

The alkylation and hydrolysis were conducted in an analogous manner to Example 15 using T11 and H1A to yield 18 (46.4 mg). $^1$H NMR (500 MHz, CDCl$_3$) δ ppm 7.19 (1H, s), 7.17 (3H, m), 6.90 (1H, dt, J=9.0, 3.5 Hz), 6.84 (1H, dd, J=8.1, 2.4 Hz), 6.78 (1H, dd, J=5.6, 3.2 Hz), 6.34 (1H, d, J=2.4 Hz), 5.06 (2H, s), 3.84 (3H, m), 3.06 (2H, m), 2.74 (1H, ddd, J=10.1, 8.2, 1.7 Hz), 2.47 (1H, m), 2.35 (1H, m), 2.20 (1H, m), 2.07 (2H, m), 1.88 (1H, m), 1.75 (2H, m), 1.59 (2H, m), 1.44 (1H, m), 0.79 (3H, m), 0.65 (3H, s). MS ESI (neg.) m/e: 531.1 (M−H)$^+$.

Example 19

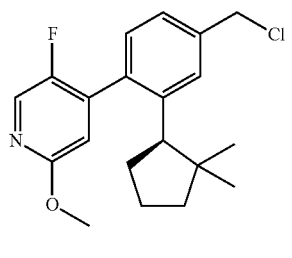

T5

+

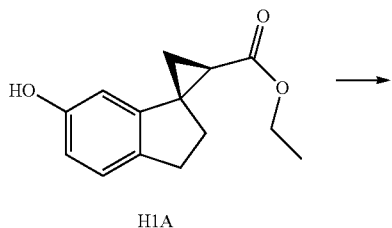

H1A

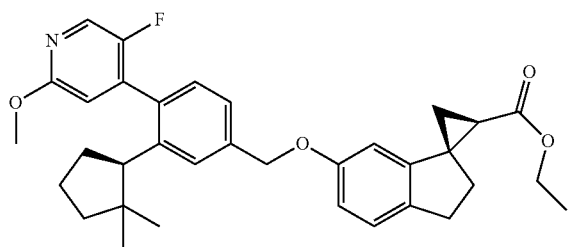

19.1

Compound 19.1

To a flask containing T5 (39 mg, 112 μmol) was added H1A (29 mg, 123 μmol), Cs$_2$CO$_3$ (55 mg, 168 μmol), and then DMF (1.5 mL). The reaction mixture was stirred at 40° C. for about 6 hours and was then partitioned between water and EtOAc. Silica gel chromatography afforded 60 mg of 19.1 (98%). MS ESI (pos.) m/e: 544.3 (M+H)$^+$.

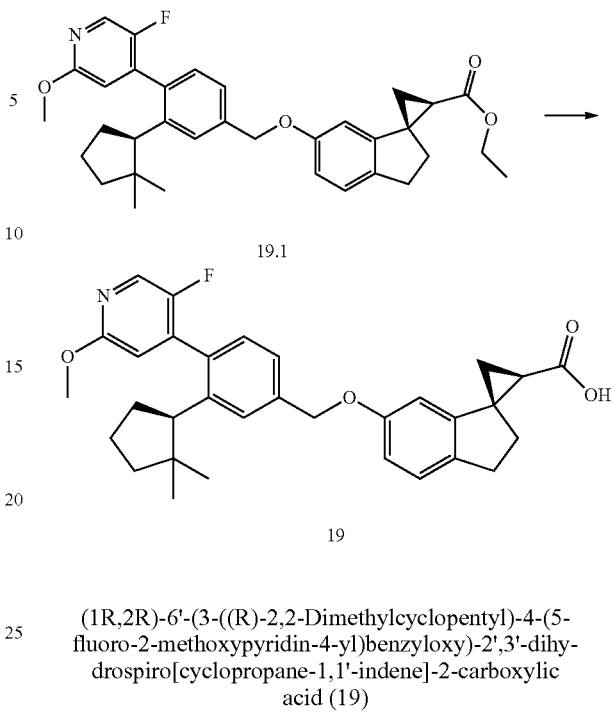

19.1

19

(1R,2R)-6'-(3-((R)-2,2-Dimethylcyclopentyl)-4-(5-fluoro-2-methoxypyridin-4-yl)benzyloxy)-2',3'-dihydrospiro[cyclopropane-1,1'-indene]-2-carboxylic acid (19)

To a flask containing 19.1 (60 mg, 0.11 mmol) was added 0.5 mL THF, 0.5 mL MeOH and 1 mL 1N LiOH. The reaction was heated at 40° C. overnight and partitioned between water and EtOAc. Silica gel chromatography afforded 45 mg of 19 (79%) as a white solid. MS ESI (pos.) m/e: 516.3 (M+H)$^+$. $^1$H NMR (400 MHz, CDCl$_3$) δ ppm 7.97-8.13 (m, 1H) 7.39-7.49 (m, 1H) 7.31-7.38 (m, 1H) 7.10-7.21 (m, 2H) 6.84 (dd, J=8.22, 2.35 Hz, 1H) 6.53-6.71 (m, 1H) 6.34 (d, J=1.96 Hz, 1H) 5.07 (s, 2H) 3.97 (s, 3H) 2.63-3.03 (m, 3H) 2.35-2.44 (m, 1H) 2.25-2.34 (m, 1H) 1.96-2.21 (m, 3H) 1.62-1.87 (m, 3H) 1.46-1.58 (m, 2H) 1.33-1.44 (m, 1H) 0.66-0.74 (m, 3H) 0.55-0.65 (m, 3H).

Example 20

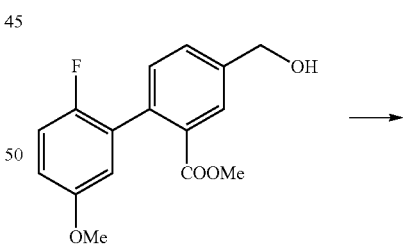

T4.5

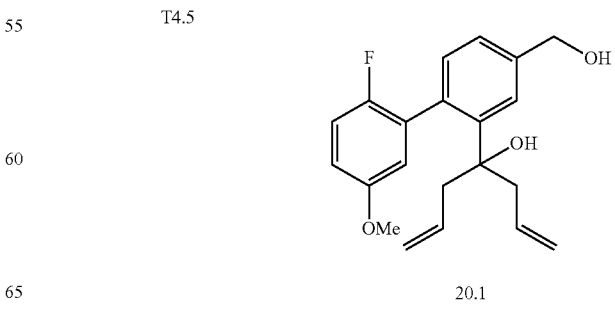

20.1

4-(2'-Fluoro-4-hydroxymethyl-5'-methoxy-biphenyl-2-yl)-hepta-1,6-dien-4-ol (20.1)

To a solution of T4.5 (712 mg, 2453 μmol) in benzene, was added allylmagnesium bromide (24528 μL, 24528 μmol) in ether (10 mL). The mixture was stirred at room temperature for 1 hour and then quenched with saturated NH₄Cl. EtOAc was added, and the organic layer was washed with water and brine, dried, and concentrated to give a residue which was purified by flash column to give the title compound as an oil (670 mg, 80%).

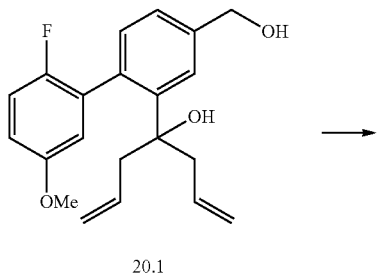

20.1

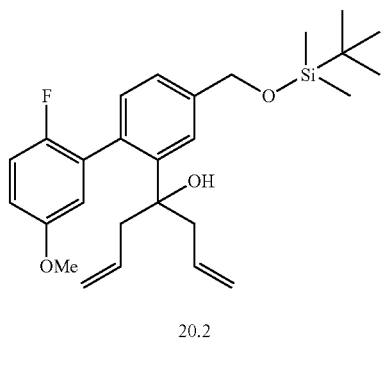

20.2

4-[4-(tert-Butyl-dimethyl-silanyloxymethyl)-2'-fluoro-5'-methoxy-biphenyl-2-yl]-hepta-1,6-dien-4-ol (20.2)

Compound 20.2 was synthesized by a method analogous to the method used to prepare compound 21.6 from 21.5. MS ESI m/e: 457.3 (M+1)⁺.

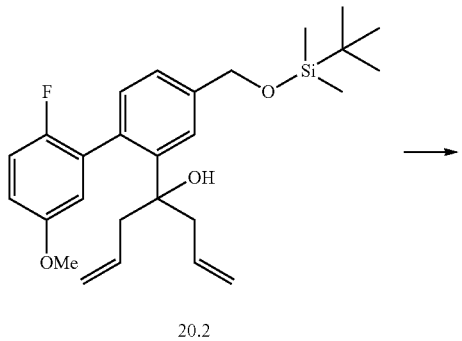

20.2

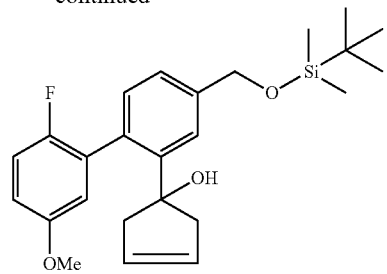

20.3

1-[4-(tert-Butyl-dimethyl-silanyloxymethyl)-2'-fluoro-5'-methoxy-biphenyl-2-yl]-cyclopent-3-enol (20.3)

Under nitrogen atmosphere, to a solution of 20.2 (259 mg, 567 μmol) in 20 mL of DCM, was added Grubbs reagent (53 mg, 85 μmol) (commercially available from Sigma-Aldrich, St. Louis, Mo., USA) in 20 mL of DCM by syringe. The mixture was stirred at room temperature for 2 hours and then the solvent was removed in vacuo to give a residue which was purified by CombiFlash® chromatography to give an oil (110 mg, 45%). MS ESI m/e: 429.3 (M+H)⁺.

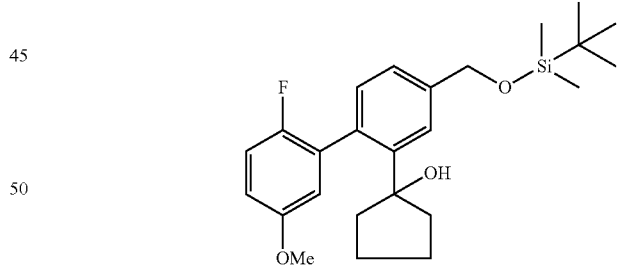

20.3                              20.4

1-[4-(tert-Butyl-dimethyl-silanyloxymethyl)-2'-fluoro-5'-methoxy-biphenyl-2-yl]-cyclopentanol (20.4)

To a solution of 20.3 (100 mg, 212 μmol) in 2 mL of EtOAc, was added 10% PtO₂/C (50 mg). The resulting mixture was stirred under a hydrogen atmosphere for 0.5 hours and then filtered. The filtrate was concentrated to give an oil which was used in the next step.

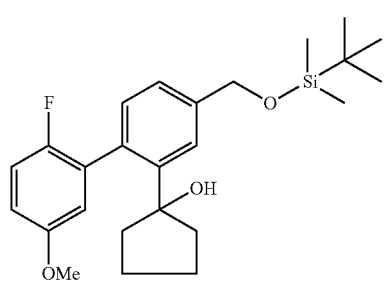

20.4

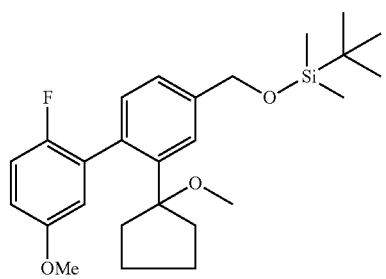

20.5 tert-Butyl-[2'-fluoro-5'-methoxy-2-(1-methoxy-cyclopentyl)-biphenyl-4-ylmethoxy]-dimethyl-silane (20.5)

To a solution of 20.4 (54 mg, 125 μmol) in DMF (3 mL), was added sodium hydride, 60% in oil (15 mg, 376 μmol). The mixture was stirred at room temperature for 10 minutes and then methyl iodide (36 mg, 251 μmol) was added in one portion. The resulting mixture was stirred at room temperature for 30 minutes. The reaction was then quenched with water and extracted with EtOAc. The organic phase was washed with water and brine and then dried over anhydrous sodium sulfate. After filtration, the organic solvent was removed in vacuo to give a residue which was purified by CombiFlash® chromatography to give the product as an oil (50 mg, 89%). MS ESI m/e: 445.3 (M+H)$^+$.

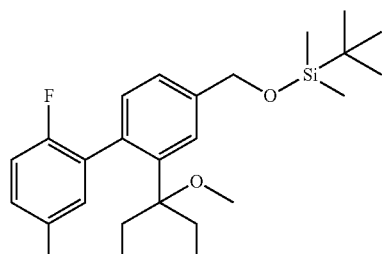

20.5

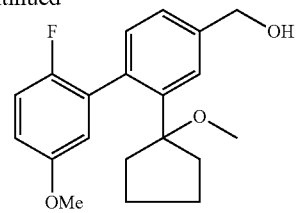

20.6

[2'-Fluoro-5'-methoxy-2-(1-methoxy-cyclopentyl)-biphenyl-4-yl]-methanol (20.6)

To a solution of 20.5 (66 mg, 168 μmol) in MeOH (3 mL), was added PPTS (11 mg, 45 μmol). The resulting mixture was stirred overnight. Solvent was removed in vacuo to give a residue which was purified by CombiFlash® chromatography to give an oil (30 mg, 61%). MS ESI m/e: 331.2 (M+H)$^+$.

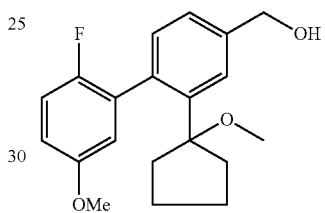

20.6

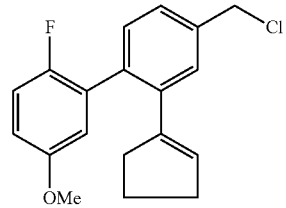

20.7

4-Chloromethyl-2-cyclopent-1-enyl-2'-fluoro-5'-methoxy-biphenyl (20.7)

Compound 20.6 was synthesized by a method analogous to the method used to prepare compound 21.9 from 21.8. MS ESI m/e: 317.1 (M+1)$^+$.

20.7

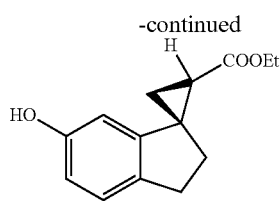

H1A

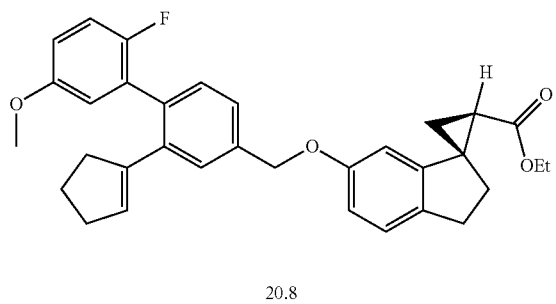

Compound 20.8

Compound 20.8 was synthesized from 20.7 and H1A by a method analogous to the method used to prepare compound 1.1. MS ESI m/e: 513.2 (M+H)⁺.

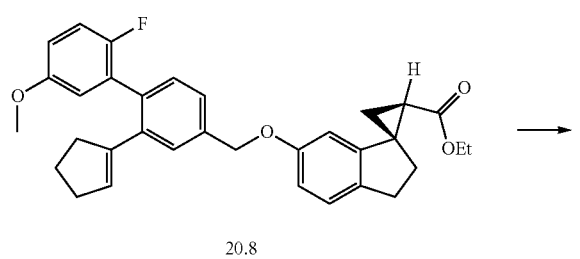

20.8

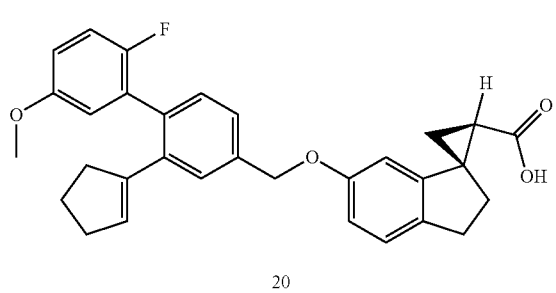

20

Example 20

Compound 20 was synthesized from 20.8 by a method analogous to the method used for Example 1. MS ESI m/e: 502.1 (M+18)⁺. ¹H NMR (400 MHz, CDCl₃) 7.42 (s, 1H,), 7.33 (m, 2H), 7.14 (d, J=8 Hz, 1H), 6.99 (m, 1H), 6.81 (m, 3H), 6.37 (s, 1H), 5.52 (m, 1H), 5.04 (s, 2H) 3.78 (s, 3H), 2.99 (m, 2H), 2.34 (m, 6H), 2.04 (m, 1H), 2.57 (m, 2H), 1.68 (m, 1H), 1.49 (m, 1H).

Example 21

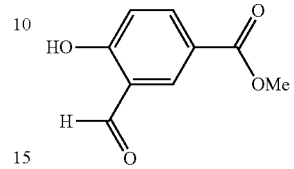

21.1

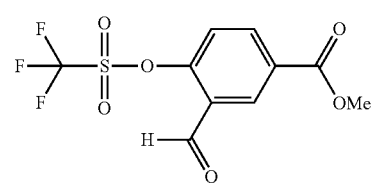

21.2

Methyl 3-formyl-4-(trifluoromethylsulfonyloxy)benzoate (21.2)

TEA (12.2 mL, 87.7 mmol) and N,N-dimethylpyridin-4-amine (0.536 g, 4.39 mmol) were added to a solution of methyl 3-formyl-4-hydroxybenzoate (7.90 g, 43.9 mmol) (commercially available from Sigma-Aldrich, St. Louis, Mo., USA) in 20 mL of DCM. The mixture was stirred at room temperature for 20 minutes and then N-phenyltrifluoromethanesulfonimide (18.8 g, 52.6 mmol) was added in one portion and the mixture was stirred at room temperature for another 32 minutes. The solvent was removed in vacuo to give a residue which was purified by CombiFlash® chromatography to give the product as an oil (10.0 g, 73%). MS ESI m/e: 313.2 (M+H)⁺.

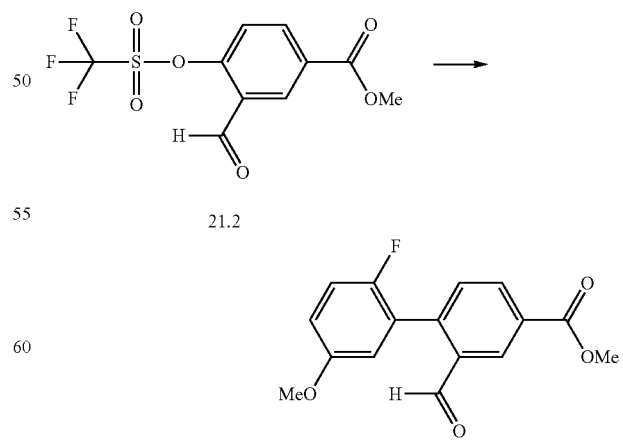

2'-Fluoro-2-formyl-5'-methoxy-biphenyl-4-carboxylic acid methyl ester (21.3)

To a round bottle flask, was added methyl 3-formyl-4-(trifluoromethylsulfonyloxy)benzoate (6300 mg, 20 mmol), 2-fluoro-5-methoxyphenylboronic acid (10 g, 61 mmol), potassium phosphate tribasic (6.6 mL, 81 mmol) (granular) and tetrakis(triphenylphosphine)palladium (2.3 g, 2.0 mmol). The flask was flushed with nitrogen and then 40 mL of DME was added. The resulting mixture was then heated at 90° C. for 6 hours. The reaction mixture was diluted with EtOAc and water. The organic phase was washed with water and brine and then dried over anhydrous sodium sulfate. After filtration, the organic solvent was removed in vacuo to give a residue which was purified by CombiFlash® chromatography to give a yellow solid (5.80 g, 100%). MS ESI m/e: 289.2 (M+H)$^+$.

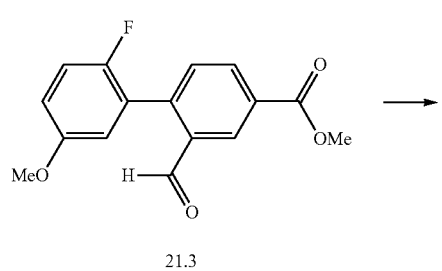

21.3

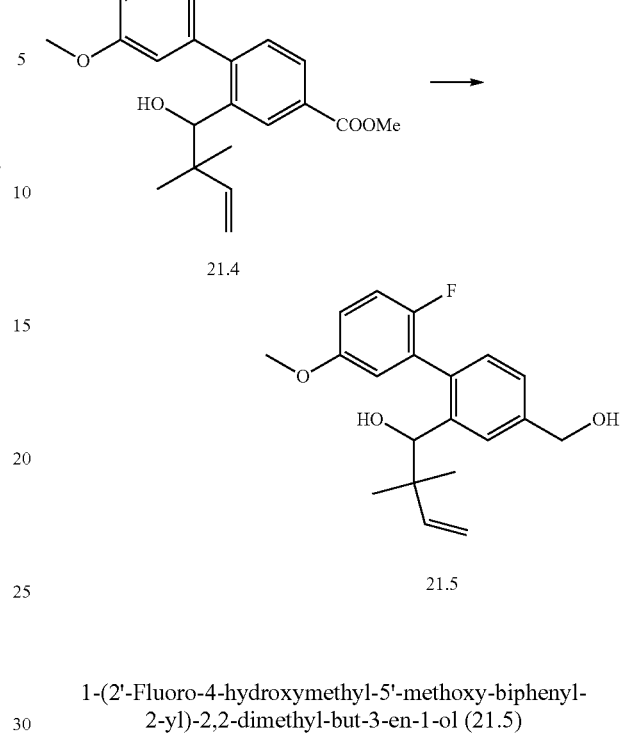

2'-Fluoro-2-(1-hydroxy-2,2-dimethyl-but-3-enyl)-5'-methoxy-biphenyl-4-carboxylic acid methyl ester (21.4)

To a mixed solution of sodium iodide (2080 mg, 13876 μmol), indium (2000 mg, 6938 μmol, commercially available from Sigma-Aldrich, St. Louis, Mo., USA) and 1-bromo-3-methylbut-2-ene (1616 μL, 13876 μmol, commercially available from Sigma-Aldrich, St. Louis, Mo., USA) in DMF (30 mL), was added 21.3 (1593 mg, 13876 μmol). The mixture was stirred at room temperature for 1 hour and then diluted with EtOAc and water. The organic phase was washed with water and brine and then dried over anhydrous sodium sulfate. After filtration, the organic solvent was removed in vacuo to give a residue which was purified by CombiFlash® chromatography to give the product as an oil (2.30 g, 92%). MS ESI m/e: 376.1 (M+18)$^+$.

1-(2'-Fluoro-4-hydroxymethyl-5'-methoxy-biphenyl-2-yl)-2,2-dimethyl-but-3-en-1-ol (21.5)

To a solution of 21.4 (530 mg, 1479 μmol) in THF (20 mL), was added LAH (168 mg, 4436 μmol). The resulting mixture was stirred at room temperature for 1 hour. The solvent was then removed, and the residue was diluted with EtOAc. The organic layer was washed with 1N NaOH, water, and brine. The organic layer was then dried over sodium sulfate, filtered, and the organic solvent was removed in vacuo to give an oil (442 mg, 90%) which was used without further purification. MS ESI m/e: 331.2 (M+H)$^+$.

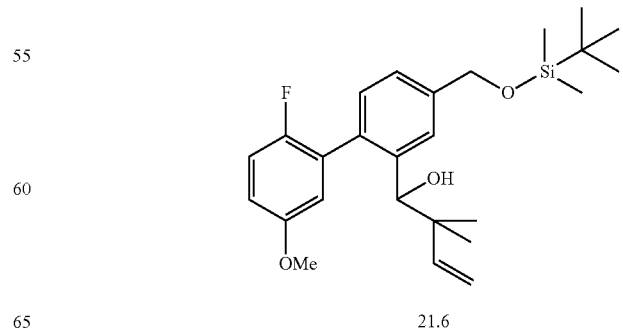

1-[4-(tert-Butyl-dimethyl-silanyloxymethyl)-2'-fluoro-5'-methoxy-biphenyl-2-yl]-2,2-dimethyl-but-3-en-1-ol (21.6)

To a solution of 21.5 (442 mg, 1338 μmol) and imidazole (221 μL, 3344 μmol) in DMF (5 mL), was added tert-butyl-chlorodimethylsilane (222 mg, 1472 μmol). The mixture was stirred overnight and diluted with EtOAc. The organic layer was washed with water and brine, dried over sodium sulfate, and filtered. The organic solvent was removed in vacuo to give a residue which was purified by CombiFlash® chromatography to give the product as an oil (520 mg, 87%). MS ESI m/e: 445.3 (M+1)$^+$.

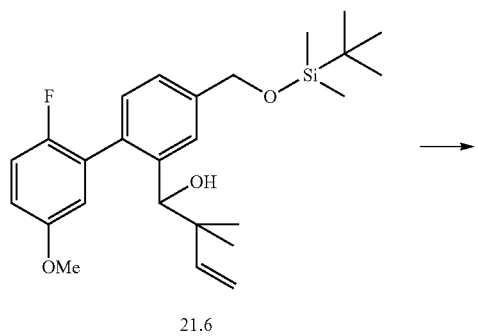

21.6

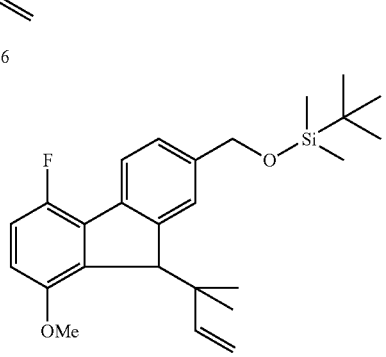

21.7 tert-Butyl-[9-(1,1-dimethyl-allyl)-5-fluoro-8-methoxy-9H-fluoren-2-ylmethoxy]-dimethyl-silane (21.7)

Allyltrimethylsilane (723 μL, 4552 μmol, commercially available from Sigma-Aldrich, St. Louis, Mo., USA) was added to a mixture of 21.6 (506 mg, 1138 μmol) and indium (iii) chloride (62.9 mg, 284 μmol, commercially available from Sigma-Aldrich, St. Louis, Mo., USA) in dichloroethane (7 mL) under a nitrogen atmosphere. The mixture was then refluxed for 3 hours. The organic solvent was removed in vacuo to give a residue which was purified by CombiFlash® chromatography to give the product as an oil (100 mg, 20%).

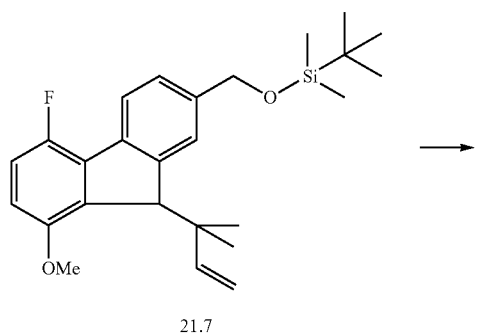

21.7

-continued

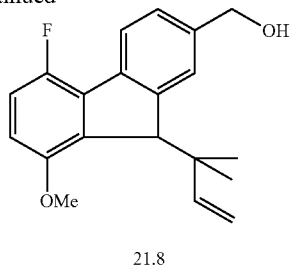

21.8

[9-(1,1-Dimethyl-allyl)-5-fluoro-8-methoxy-9H-fluoren-2-yl]-methanol (21.8)

To a solution of 21.7 (100 mg, 234 μmol) in MeOH, was added PPTS (12 mg, 47 μmol). The resulting mixture was stirred overnight. Solvent was then removed in vacuo to give a residue which was purified by CombiFlash® chromatography to give the product as an oil (70 mg, 96%). MS ESI m/e: 330.2 (M+18)$^+$.

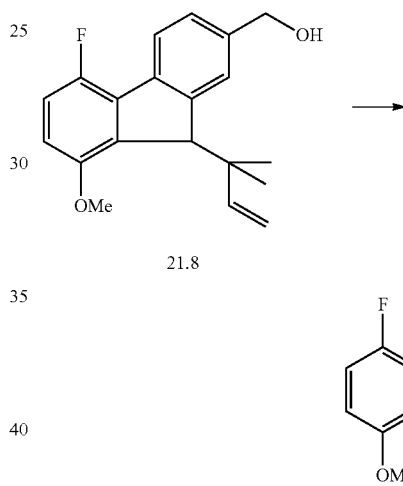

21.8

21.9

7-Chloromethyl-9-(1,1-dimethyl-allyl)-4-fluoro-1-methoxy-9H-fluorene (21.9)

To a solution of 21.8 (40 mg, 128 μmol) in DCM (0.8 mL), was added thionyl chloride (30 mg, 256 μmol). The resulting mixture was stirred at room temperature for 1 hour. Solvent was removed in vacuo to give a residue which was used without purification (40 mg, 94%).

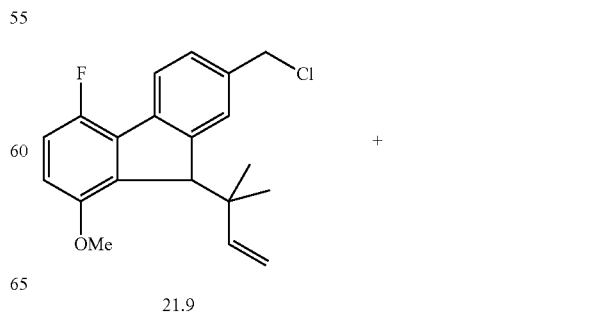

21.9

-continued

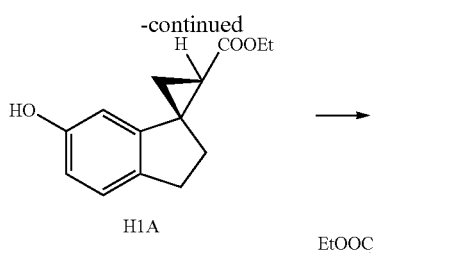

H1A

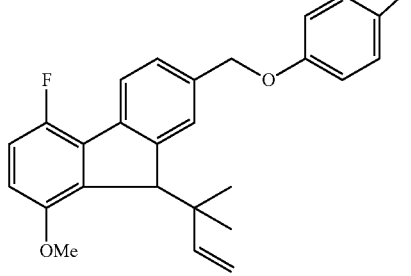

21.10

Compound 21.10

To a solution of 21.9 (100 mg, 234 µmol) and H1A in DMF (0.5 mL), was added Cs$_2$CO$_3$ (117 mg, 361 µmol). The mixture was stirred overnight and diluted with EtOAc. The organic layer was then washed with water and brine, dried over sodium sulfate, and filtered. The organic solvent was removed in vacuo to give a residue which was purified by CombiFlash® chromatography to give the product as an oil (40 mg, 63%). MS ESI m/e: 527.3 (M+1)$^+$.

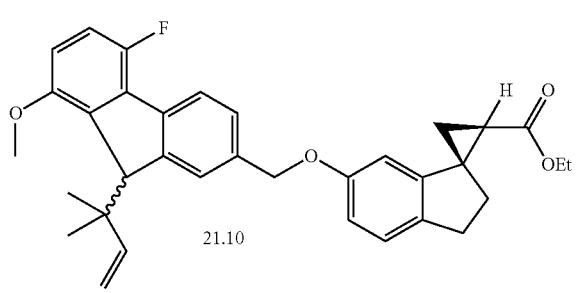

21.10

Example 21

To a solution of 21.10 (40 mg, 76 µmol) in a 1 mL of mixed solvent (THF/CH$_3$OH/H$_2$O=2/2/1), was added LiOH (9 mg, 380 µmol). The resulting mixture was stirred at 50° C. for 3 hours. The organic solvent was then removed in vacuo to give a residue which was purified by HPLC to give 21. MS ESI m/e: 516.3 (M+18)$^+$. $^1$H NMR (400 MHz, CDCl$_3$) 7.95 (dd, J=8 Hz, J=4 Hz, 1H), 7.34 (m, 1H), 7.25 (s, 1H), 7.14 (d, J=8 Hz, 1H), 7.01 (m, 1H) 6.83 (m, 2H), 6.37 (d, J=4 Hz, 1H), 5.75 (m, 1H), 5.08 (d, J=16 Hz, 1H) 5.03 (s, 2H), 4.95 (d, J=8 Hz, 1H), 3.81 (s, 3H), 3.01 (m, 3H), 2.35 (m, 2H), 2.04 (m, 1H), 1.70 (m, 1H), 1.51 (m, 1H), 1.40 (s, 3H), 1.12 (s, 3H).

Example 22

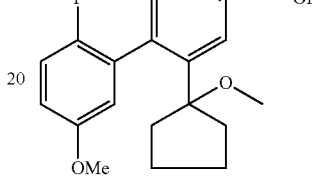

20.6

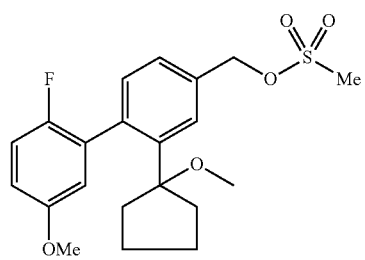

22.1

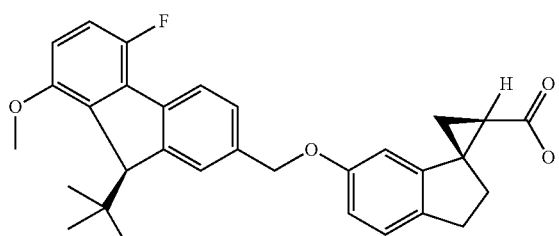

and

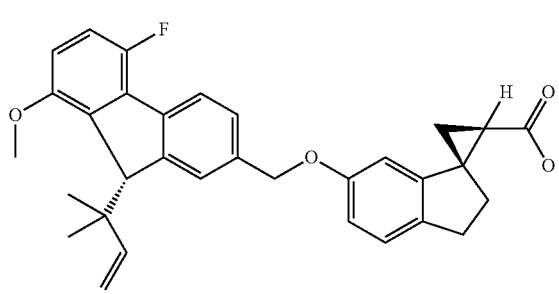

21

311

Methanesulfonic acid 2'-fluoro-5'-methoxy-2-(1-methoxy-cyclopentyl)-biphenyl-4-ylmethyl ester (22.1)

To a solution of 20.6 (30 mg, 91 mmol) in 1 mL of DCM at 0° C., was added TEA (11 mg, 109 μmol) followed by methanesulfonyl chloride (12 mg, 109 mmol). The mixture was stirred at room temperature for 30 minutes. The reaction was then quenched with water and extracted with EtOAc. The organic layers were combined, washed with water and brine and then dried over anhydrous sodium sulfate. After filtration, the organic solvent was removed in vacuo to give the product as a residue which was used without further purification. MS ESI m/e: 409.1 (M+H)$^+$.

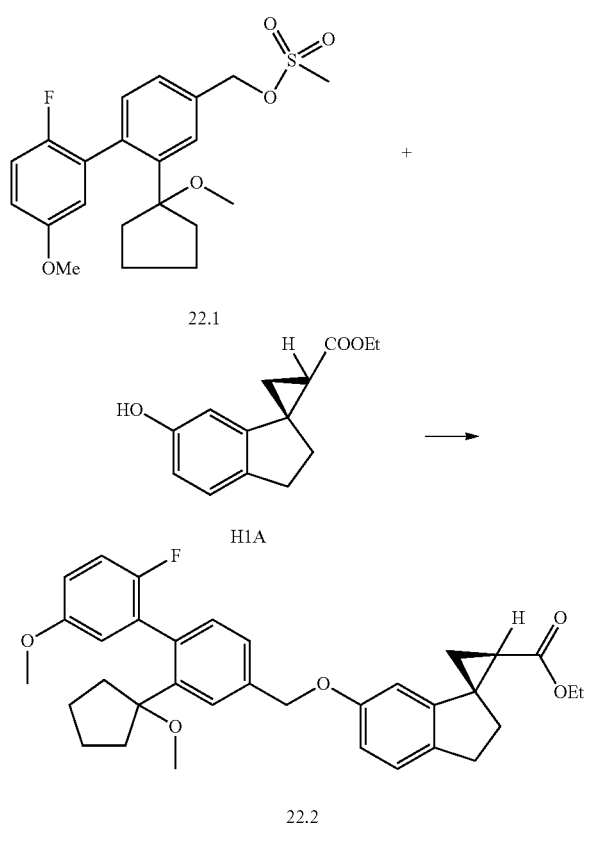

22.1

H1A

Compound 22.2

Compound 22.2 was synthesized form 22.1 and H1A by a method analogous to the method used for compound 1.1. MS ESI m/e: 545.3 (M+H)$^+$.

312

-continued

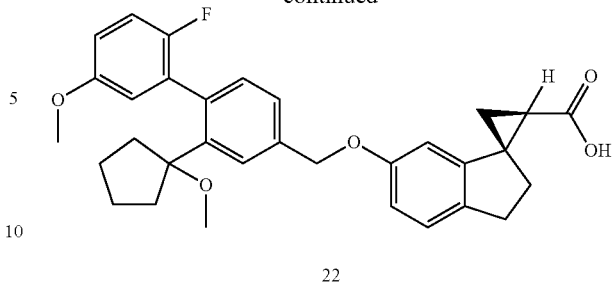

22

Example 22

Example 22 was synthesized from 22.2 by a method analogous to the method used for compound 1. $^1$H NMR (400 MHz, CDCl$_3$) 7.53 (s, 1H,), 7.37 (m, 1H), 7.17 (m, 2H), 6.99 (t, J=12 Hz, 1H), 6.85 (m, 2H), 6.75 (m 1H), 6.35 (s, 1H) 5.06 (s, 2H), 3.77 (s, 3H) 2.99 (m, 2H), 2.94 (s, 3H), 2.32 (m, 2H), 2.05 (m, 2H), 1.82 (m, 1H), 1.69 (m, 7H), 1.49 (m, 1H).

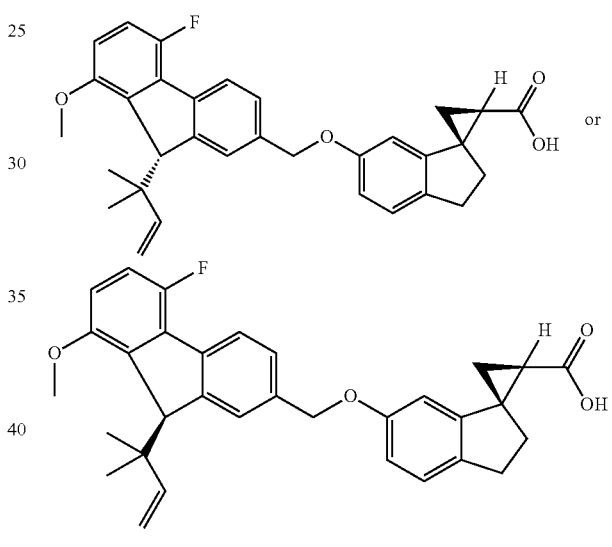

Example 23

Example 23 was separated from compound 21 (a mixture of two diastereomers) by HPLC. MS ESI m/e: 516.3 (M+18)$^+$.

Example 24

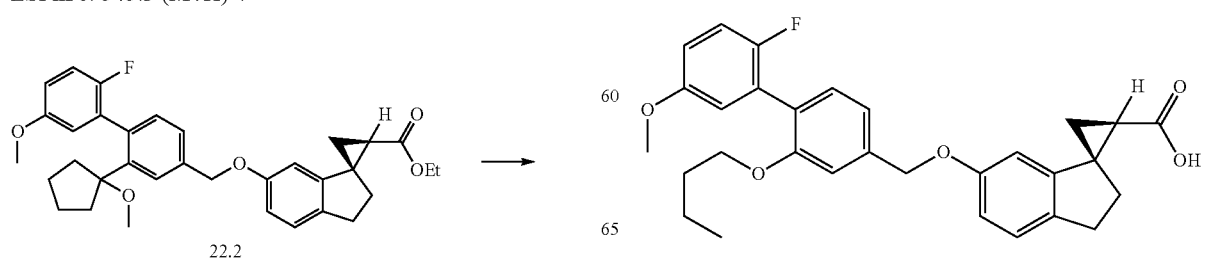

24

Example 24

The title compound was prepared from T9 and H1A according to the methods described for Example 15. MS ESI (neg.) m/e: 491.2 (M+H)⁺.

Example 25

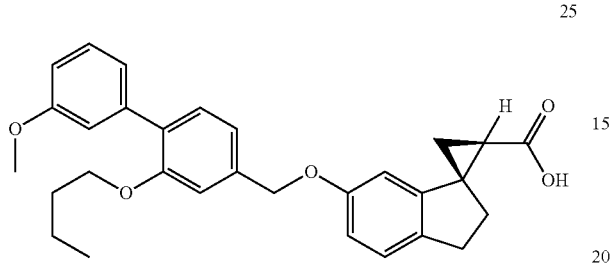

Example 25

The title compound was prepared from T13 and H1A according to the methods described in Example 15. MS ESI (neg.) m/e: 490.3 (M+H$_2$O)⁺.

Example 26

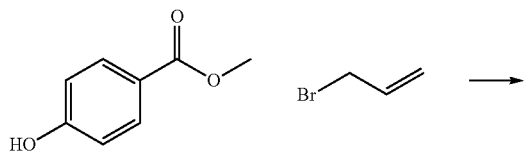

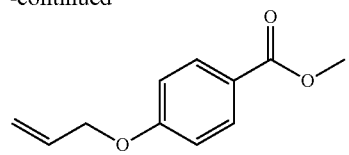

26.1

Methyl 4-(allyloxy)benzoate (26.1)

The reaction mixture of 4-hydroxybenzoic acid, methyl ester (20.0 g, 131.0 mmol) (commercially available from Sigma-Aldrich, St. Louis, Mo., USA), allyl bromide (17.0 g, 138.0 mmol) and potassium carbonate (45.0 g, 329.0 mmol) in DMSO (30.0 mL) was stirred at room temperature for 8 hours. EtOAc (150 mL) was added, and the organic layer was washed with water (30×3 mL) and then dried over MgSO$_4$. After filtration, the solvent was removed. The product was used in the next step without further purification, (25.0 g, yield 99%). ¹H NMR (400 MHz, CDCl$_3$) δ ppm 7.91 (2H, m), 6.86 (2H, m), 5.98 (1H, dt, J=17.2, 5.3 Hz), 5.35 (1H, dd, J=17.2, 1.6 Hz), 5.24 (1H, dd, J=10.6, 1.6 Hz), 4.52 (2H, d, J=5.5 Hz), 3.81 (3H, s).

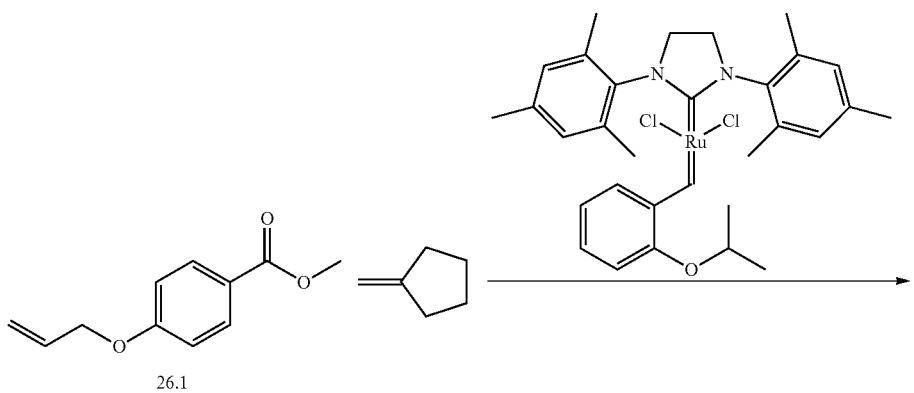

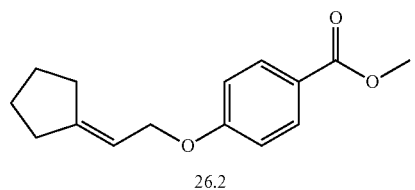

26.2

Methyl 4-(2-cyclopentylideneethoxy)benzoate (26.2)

To a solution of methyl 4-(allyloxy)benzoate 26.1 (3.00 g, 16.0 mmol) and methylenecyclopentane (1.9 g, 23.0 mmol) (commercially available from Sigma-Aldrich, St. Louis, Mo., USA) in DCM (5.0 mL) was added Hoveyda-Grubbs reagent (0.39 g, 0.62 mmol), (commercially available from Sigma-Aldrich, St. Louis, Mo., USA) at room temperature. The resulting reaction mixture was degassed three times and then stirred at 55° C. under nitrogen overnight. The reaction mixture was purified by CombiFlash® silica gel column chromatography (hexane/EtOAc 95/5) to give 26.2, (2.60 g, yield 68%). $^1$H NMR (500 MHz, CDCl$_3$) δ ppm 7.82-7.93 (2H, m), 6.80-6.88 (2H, m), 5.44-5.56 (1H, m), 4.47 (2H, d, J=6.6 Hz), 3.80 (3H, s), 2.20-2.31 (4H, m), 1.50-1.71 (4H, m).

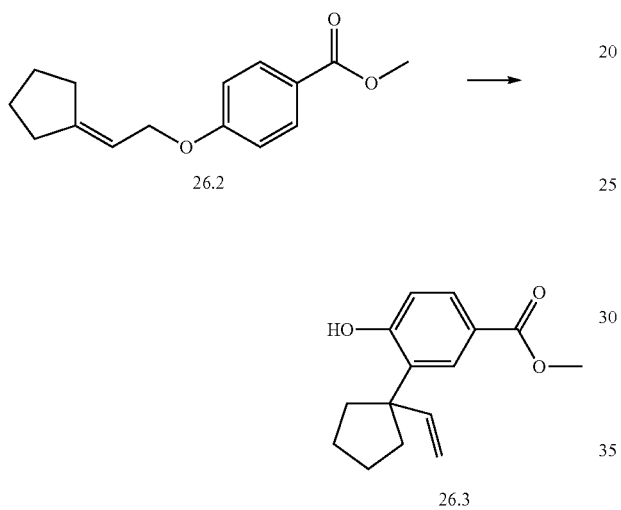

26.2

Methyl 4-hydroxy-3-(1-vinylcyclopentyl)benzoate (26.3)

The reaction mixture of methyl 4-(2-cyclopentylideneethoxy)benzoate 26.2 (0.50 g, 2.0 mmol), N,N-diethylaniline (3.2 mL, 20 mmol) and N,O-bis(trimethylsilyl)acetamide (2.5 mL, 10 mmol) in a 20 mL seal tube was heated at 240° C. for 48 hours. The reaction was then cooled to room temperature. Diethyl ether (60 mL) was added, and the organic layer was washed with HCl (3N, 20 mL). The organic layer was separated and the solvent was removed. The residue was dissolved in MeOH (10 mL) and HCl (3N, 2 mL) and stirred at room temperature for 30 minutes. Diethyl ether (80 mL) was added, and the organic layer was washed with NaHCO$_3$ (30 mL) and brine (15 mL). The organic layer was dried over MgSO$_4$. After filtration, the solvent was removed, and the residue was purified by CombiFlash® silica gel column chromatography, eluting with hexane/EtOAc, 95/5 to give 26.3 (0.15 g, yield 30%). $^1$H NMR (500 MHz, CDCl$_3$) δ ppm 7.90 (1H, d, J=2.2 Hz), 7.80 (1H, dd, J=8.3, 2.0 Hz), 6.81 (1H, d, J=8.3 Hz), 5.99 (1H, dd, J=17.6, 10.5 Hz), 5.77 (1H, s), 5.18 (1H, dd, J=10.5, 1.0 Hz), 5.08 (1H, d, J=17.6 Hz), 3.82 (3H, s), 1.89-2.03 (4H, m), 1.56-1.78 (4H, m). MS ESI (neg.) m/e: 245.1 (M−H)$^+$.

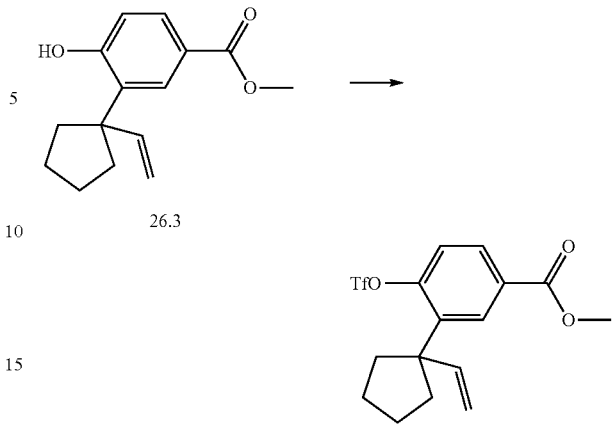

Methyl 4-(trifluoromethylsulfonyloxy)-3-(1-vinylcyclopentyl)benzoate (26.4)

To a solution of methyl 4-hydroxy-3-(1-vinylcyclopentyl)benzoate (0.19 g, 0.77 mmol) and a catalytic amount of DMAP in pyridine (1.5 mL) was slowly added trifluoromethanesulfonic anhydride (0.17 mL, 1.0 mmol) at 0° C. After addition, the reaction mixture was stirred at ambient temperature overnight. EtOAc (70 mL) was added, and the mixture was washed with citric acid (15.0 mL, 1 M in water), brine (20.0 mL) and dried with magnesium sulfate. After filtration, the solvent was removed. The product 26.4 thus obtained was used in the next step without further purification. $^1$H NMR (400 MHz, CDCl$_3$) δ ppm 8.06 (1H, d, J=2.3 Hz), 7.87 (1H, dd, J=8.6, 2.0 Hz), 7.16 (1H, s), 5.85 (1H, dd, J=17.2, 10.6 Hz), 4.95 (1H, d, J=10.6 Hz), 4.72 (1H, d, J=17.2 Hz), 3.83 (3H, s), 2.12-2.28 (2H, m), 1.74-1.94 (2H, m), 1.66 (4H, m).

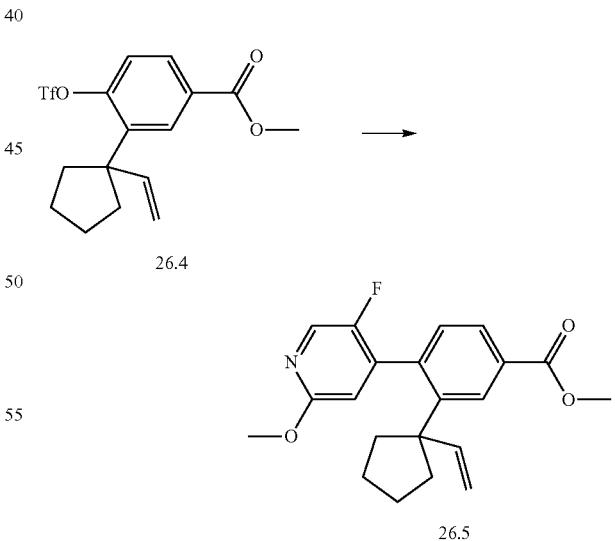

Methyl 4-(5-fluoro-2-methoxypyridin-4-yl)-3-(1-vinylcyclopentyl)benzoate (26.5)

The reaction mixture of methyl 4-(trifluoromethylsulfonyloxy)-3-(1-vinylcyclopentyl)benzoate 26.4 (0.29 g, 0.8 mmol), 5-fluoro-2-methoxypyridin-4-ylboronic acid (0.2 g, 1.0 mmol) (commercially available from Sigma-Aldrich, St. Louis, Mo., USA), potassium phosphate (0.5 g, 2.0 mmol), S-phos (0.06 g, 0.2 mmol) and palladium acetate (0.02 g, 0.08 mmol) in DMF (1.5 mL) was purged with nitrogen three times. The resulting mixture was heated at 90° C. for 2 hours. After work up, the product was purified by CombiFlash® silica gel column chromatography, eluting with hexane/EtOAc 9/1, to give the compound 26.5. $^1$H NMR (500 MHz, CDCl$_3$) δ ppm 8.20 (1H, d, J=1.7 Hz), 8.00 (1H, s), 7.91 (1H, dd, J=7.8, 1.7 Hz), 7.10 (1H, d, J=8.1 Hz), 6.63 (1H, d, J=4.9 Hz), 5.87 (1H, dd, J=17.4, 10.5 Hz), 4.97 (1H, d, J=10.5 Hz), 4.69 (1H, d, J=17.4 Hz), 3.98 (3H, s), 3.85 (3H, s), 2.00-2.20 (1H, m), 1.80-1.96 (1H, m), 1.51-1.75 (6H, m). MS ESI (pos.) m/e: 355.9 (M+H)$^+$.

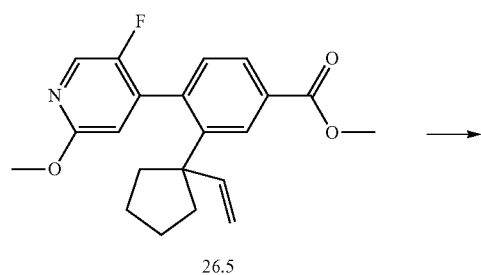

26.5

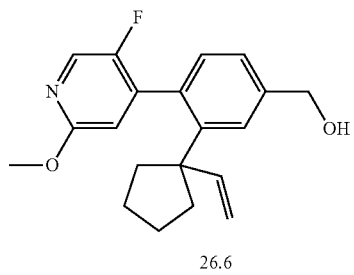

26.6

(4-(5-Fluoro-2-methoxypyridin-4-yl)-3-(1-vinylcyclopentyl)phenyl)methanol (26.6)

To a solution of methyl 4-(5-fluoro-2-methoxypyridin-4-yl)-3-(1-vinylcyclopentyl)benzoate 26.5 (51.0 mg, 143 µmol) in THF (2.0 mL) was slowly added LAH, (1.0 M solution in diethyl ether (0.30 mL, 287 µmol)) at room temperature. The resulting mixture was stirred at 50° C. for 1 hour. The product was obtained after work up and solvent removal. The desired product was used in the next step without further purification. MS ESI (pos.) m/e: 328.2 (M+H)$^+$.

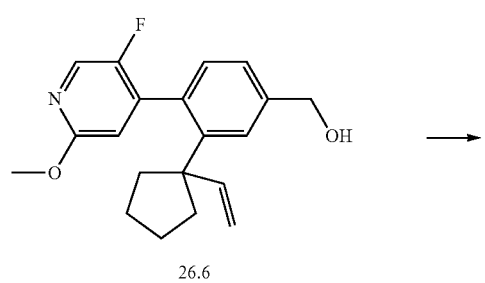

26.6

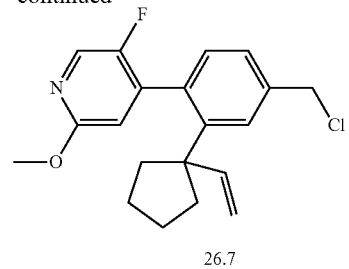

26.7

4-(4-(Chloromethyl)-2-(1-vinylcyclopentyl)phenyl)-5-fluoro-2-methoxypyridine (26.7)

To a solution of (4-(5-fluoro-2-methoxypyridin-4-yl)-3-(1-vinylcyclopentyl)phenyl)methanol (47.0 mg, 144 µmol) in DMF (0.01 mL) and DCM (4.0 mL) was slowly added thionyl chloride (14.7 µL, 201 µmol) at 0° C. After addition, the resulting mixture was stirred at room temperature for 1 hour. The solvent was removed, and the product thus obtained was used in the next step without further purification. $^1$H NMR (400 MHz, CDCl$_3$) δ ppm 8.01-8.11 (1H, m), 7.98 (1H, m), 7.47 (1H, s), 6.94 (1H, d, J=7.8 Hz), 6.69-6.82 (1H, m), 5.80 (1H, dd, J=17.2, 10.6 Hz), 4.89 (1H, d, J=10.2 Hz), 4.52-4.69 (3H, m), 3.89 (3H, s), 1.68-1.84 (4H, m), 1.49-1.67 (4H, m).

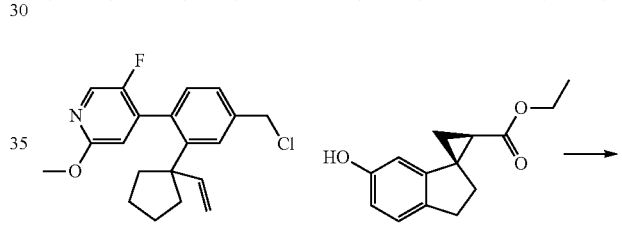

26.7  H1A

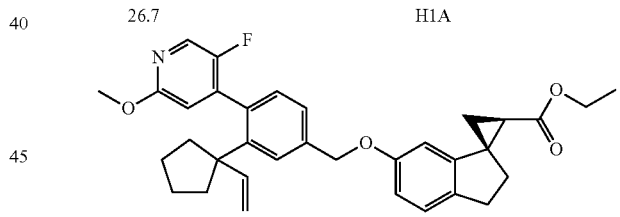

26.8

Compound 26.8

The reaction mixture of 4-(4-(chloromethyl)-2-(1-vinylcyclopentyl)phenyl)-5-fluoro-2-methoxypyridine (24.0 mg, 69.4 µmol) (commercially available from Sigma-Aldrich, St. Louis, Mo., USA), compound H1A (16.1 mg, 69.4 µmol) and Cs$_2$CO$_3$ (Cabot high purity grade) (33.9 mg, 104 µmol) in DMF (1.0 mL) was stirred at room temperature overnight. LCMS indicated that the reaction was complete. EtOAc (50 mL) was added, and the organic layer was washed with brine (15×2 mL) and dried with MgSO$_4$. After filtration and solvent removal, the product was obtained as a residue which was used in the next step without further purification. MS ESI (pos.) m/e: 542.2 (M+H)$^+$.

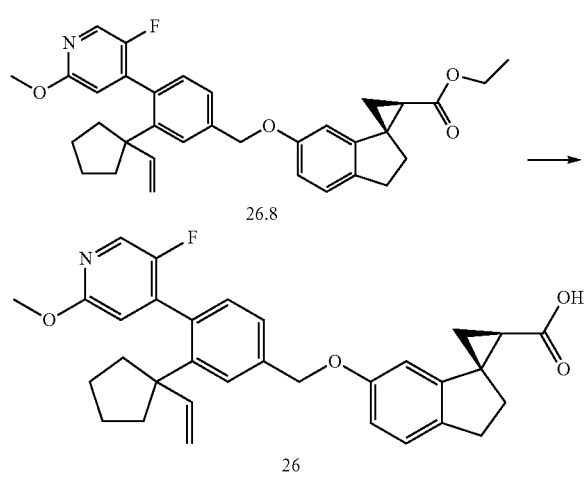

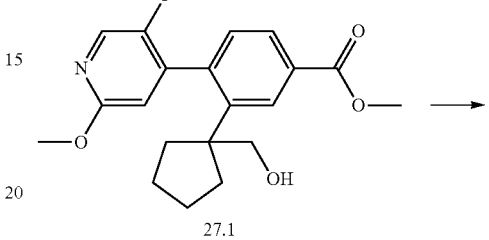

Example 26

The reaction mixture of compound 26.8 (37.6 mg, 69 µmol) and LiOH (0.20 mL, 3.33 mmol in water, 694.0 µmol) in MeOH (1.0 mL) was stirred at room temperature overnight. The reaction mixture was then neutralized by HCl (3.0 N in water) and purified by preparative HPLC (reverse phase) to give the product, 26. MS ESI (pos.) m/e: 514.2 (M+H)$^+$.

Example 27

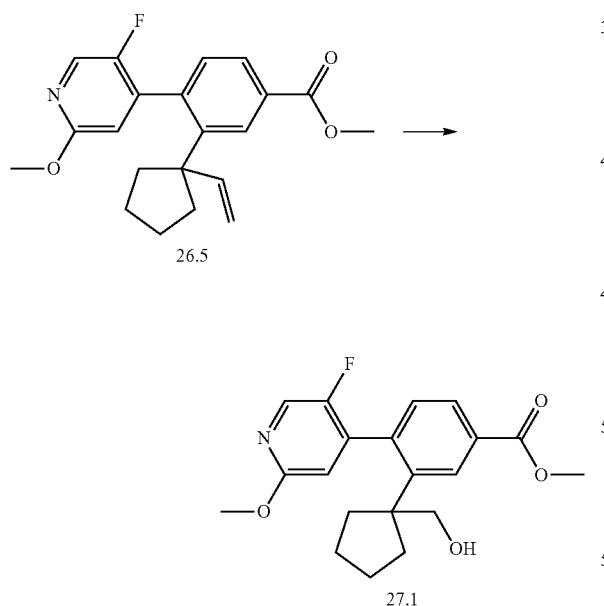

Methyl 4-(5-fluoro-2-methoxypyridin-4-yl)-3-(1-(hydroxymethyl)cyclopentyl)benzoate (27.1)

The mixture of methyl 4-(5-fluoro-2-methoxypyridin-4-yl)-3-(1-formylcyclopentyl)benzoate (0.13 g, 0.36 mmol) in DCM (6.0 mL) and MeOH (1.5 mL) was reacted with ozone gas at −78° C. for 10 minutes. The excess ozone was removed by flushing with nitrogen, and dimethylsulfide (0.3 mL) was added. The resulting reaction mixture was stirred at room temperature for 30 minutes. Sodium borohydride (0.13 mL, 3.6 mmol) was added to the reaction mixture, and the reaction was stirred at room temperature overnight. EtOAc (50 mL) was added, and the organic layer was washed with brine (20×2 mL) and dried over Na$_2$SO$_4$. After filtration, the solvent was removed. The product thus obtained was used in the next step without further purification. MS ESI (pos.) m/e: 360.2 (M+H)$^+$.

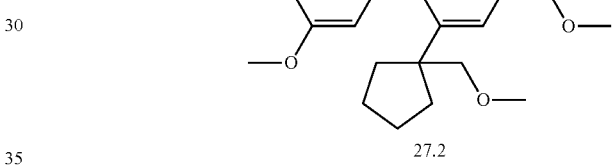

Methyl 4-(5-fluoro-2-methoxypyridin-4-yl)-3-(1-(methoxymethyl)cyclopentyl)benzoate (27.2)

To a suspension of sodium hydride (20.0 mg 60% in oil, 522 µmol) in DMF (1.0 mL) was slowly added methyl 4-(5-fluoro-2-methoxypyridin-4-yl)-3-(1-(hydroxymethyl)cyclopentyl)benzoate (75.0 mg, 209.0 µmol) at 0° C. The resulting mixture was stirred at room temperature for 30 minutes and then methyl iodide (296.0 mg, 2087 µmol) was added to the reaction mixture. The resulting mixture was stirred at room temperature overnight. EtOAc (60.0 mL) was added, and the organic layers were washed with brine (20×2 mL) and dried over MgSO$_4$. The product was obtained after filtration and solvent removal. The product was used in the next step. MS ESI (pos.) m/e: 374.0 (M+H)$^+$.

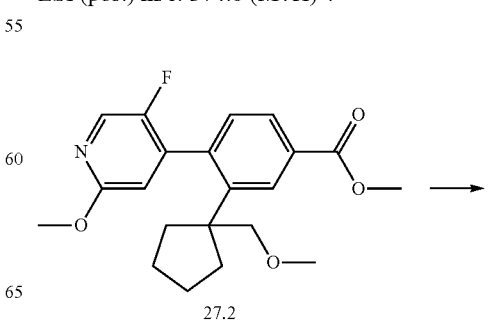

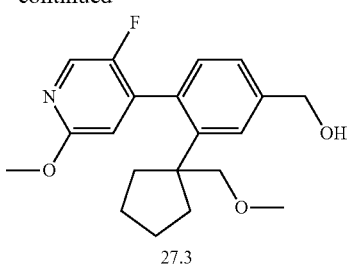

(4-(5-Fluoro-2-methoxypyridin-4-yl)-3-(1-(methoxymethyl)cyclopentyl)phenyl) methanol (27.3)

To a solution of methyl 4-(5-fluoro-2-methoxypyridin-4-yl)-3-(1-(methoxymethyl)cyclopentyl)benzoate (77.0 mg, 206 μmol) in THF (4.0 mL) was added LAH (0.42 mL, 1.0 M solution in diethyl ether, 412.0 μmol) at 0° C. The reaction mixture was stirred at 45° C. for 3 hours. After work up, the solvent was removed to provide the product which was used in the next step. MS ESI (pos.) m/e: 346.2 (M+H)+.

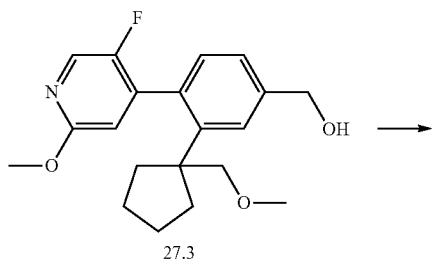

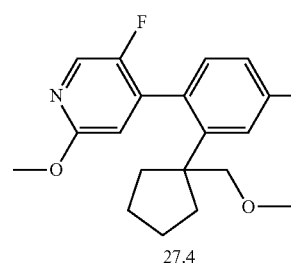

4-(4-(Chloromethyl)-2-(1-(methoxymethyl)cyclopentyl)phenyl)-5-fluoro-2-methoxypyridine (27.4)

To a solution of (4-(5-fluoro-2-methoxypyridin-4-yl)-3-(1-(methoxymethyl)cyclopentyl)phenyl)methanol (71.0 mg, 206 μmol) DMF (10 uL), and DCM (4.0 mL) was slowly added thionyl chloride (15.0 μL, 206 μmol) at 0° C. After addition, the resulting mixture was stirred at room temperature for 1 hour. The solvent was removed providing the product which was used in the next step. MS ESI (pos.) m/e: 364.2 (M+H)+.

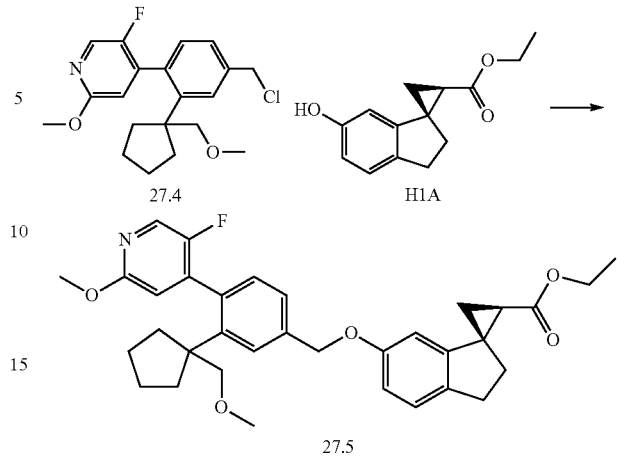

Compound (27.5)

The reaction mixture of 4-(4-(chloromethyl)-2-(1-(methoxymethyl)cyclopentyl)phenyl)-5-fluoro-2-methoxypyridine (25.0 mg, 68.7 μmol), compound H1A (19.2 mg, 82.5 μmol) and Cs2CO3 (Cabot high purity grade)(56.0 mg, 172 μmol) in DMSO (1.0 mL) was stirred at room temperature overnight. The LCMS results indicated that the reaction was complete. EtOAc (50 mL) was added, and the organic layer was washed with brine (15×2 mL), dried with MgSO4, and then filtered. The solvent was removed providing the product as a residue which was used in the next step without further purification. MS ESI (pos.) m/e: 560.3 (M+H)+.

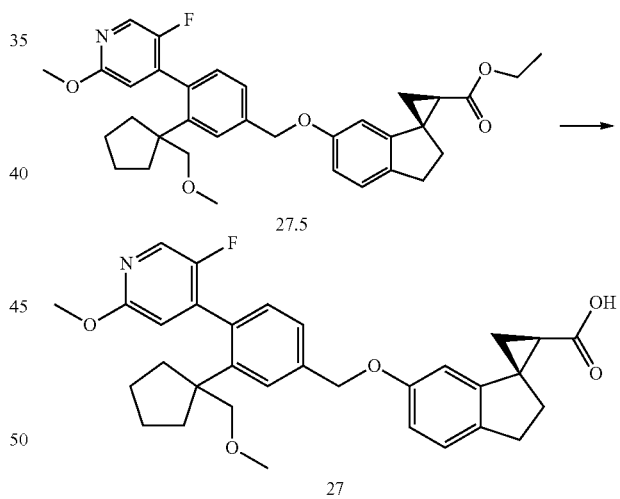

Example 27

The reaction mixture of compound 27.5 (38.5 mg, 69 μmol) and LiOH (0.1 mL LiOH, 3.33 mmol in water, 344.0 μmol) in MeOH (0.6 mL) was stirred at room temperature for 3 hours. The reaction mixture was purified by CombiFlash® silica gel column chromatography, eluting with hexane/EtOAc, 95/5, to provide 27. $^1$H NMR (400 MHz, CDCl$_3$) δ ppm 7.93 (1H, s), 7.41 (1H, s), 7.19-7.30 (1H, m), 7.06 (1H, d, J=8.2 Hz), 6.92 (1H, d, J=7.8 Hz), 6.76 (1H, dd, J=8.2, 2.3 Hz), 6.65 (1H, d, J=5.1 Hz), 6.27 (1H, s), 4.97 (2H, s), 3.87 (3H, s), 3.16-3.27 (2H, m), 3.12 (3H, s), 2.76-2.99 (3H, m), 2.15-2.37 (3H, m), 1.80-1.96 (3H, m), 1.47-1.70 (6H, m), 1.42 (1H, dd, J=8.3, 4.8 Hz). MS ESI (pos.) m/e: 532.2 (M+H)+.

Example 28

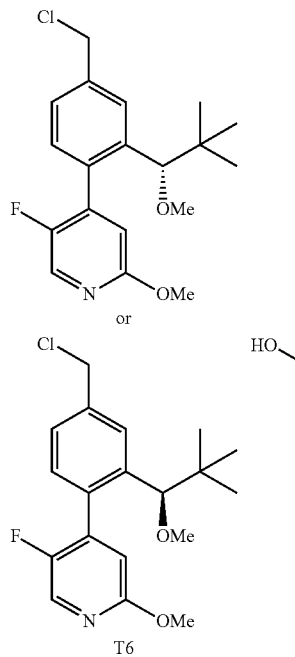

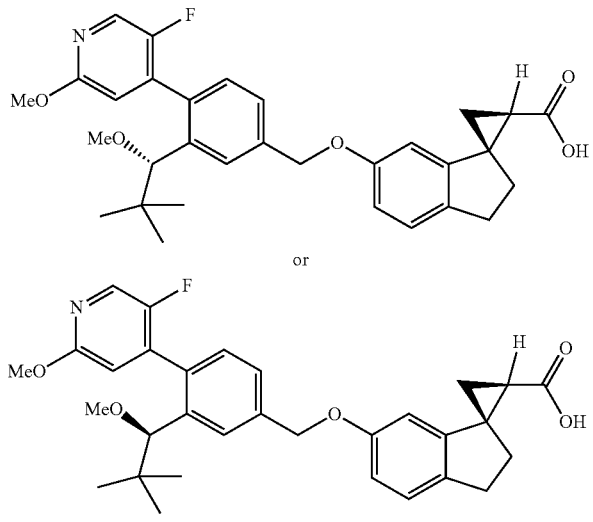

Example 28

The title compound was prepared from H1A and T6 according to the procedure described above to provide 28 as colorless solid (46 mg, 84%). $^1$H NMR (400 MHz, CDCl$_3$) δ ppm 7.97 (br. s., 1H), 7.51 (br. s., 1H), 7.36 (d, J=7.43 Hz, 1H), 6.99-7.17 (m, 2H), 6.75 (dd, J=8.22, 2.35 Hz, 1H), 6.55 (br. s., 1H), 6.25 (d, J=2.35 Hz, 1H), 5.02 (s, 2H), 3.88 (s, 3H), 3.19 (br. s., 3H), 2.89 (t, J=7.43 Hz, 2H), 2.25-2.38 (m, 1H), 2.15-2.25 (m, 1H), 1.93 (dd, J=8.22, 5.87 Hz, 1H), 1.61 (t, J=5.48 Hz, 1H), 1.40 (dd, J=8.22, 4.70 Hz, 1H), 0.63 (s, 9H), MS ESI (pos) m/e: 520.2 (M+H).

Example 29

2'-Fluoro-4-(hydroxymethyl)-5'-(methyloxy)-1,1'-biphenyl-2-carboxylic acid (29.1)

To a room temperature solution of T4.4 (1.30 g, 4.5 mmol) in dioxane (15 mL) was added LiOH (2.0 M, 6.7 mL, 13.4 mol). The mixture was heated at 55° C. for 2.5 hours, cooled to room temperature, and then acidified with 1.0 N HCl to a pH of 4.0. The resulting mixture was diluted with water (10 mL). The resulting mixture was extracted with 30% IPA/chloroform (3×20 mL). The organic layers were combined. After removal of organic solvents under reduced pressure, purification of the residue by flash chromatography on silica gel with 0-10% MeOH/DCM for elution gave 29.1 as colorless solid (1.18 g, 95%).

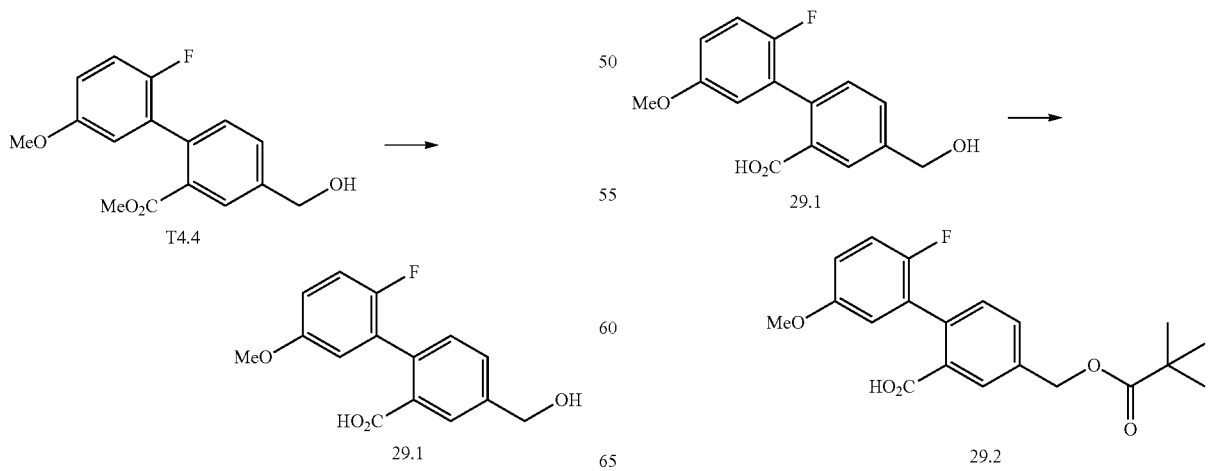

4-(((2,2-Dimethylpropanoyl)oxy)methyl)-2'-fluoro-5'-(methyloxy)-1,1'-biphenyl-2-carboxylic acid (29.2)

To a 0° C. mixture of 29.1 (2.2 g, 7.9 mmol) in THF (20 mL) was added pyridine (1.56 g, 19.8 mmol) followed by pivaloyl chloride (0.96 g, 7.9 mmol) (commercially available from Sigma-Aldrich, St. Louis, Mo., USA). The resulting solution was stirred at 0-25° C. overnight and was then quenched with water and treated with 2.0 N HCl (15 mL). The mixture was extracted with EtOAc (3×30 mL). The organic layers were combined and washed with water (10 mL) and brine (10 mL). After removal of organic solvents under reduced pressure, purification of the residue by flash chromatography on silica gel with 0-65% EtOAc/hexanes for elution gave 29.2 as white solid (1.60 g, 56%).

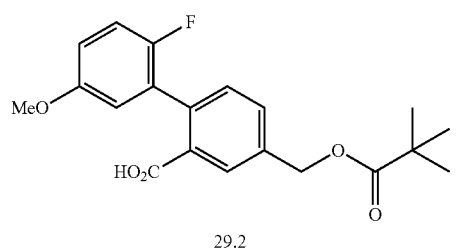

29.2

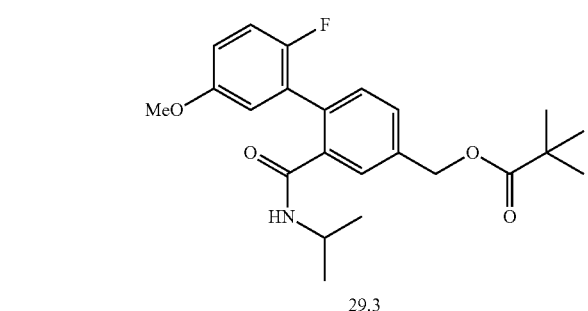

29.3

(2'-Fluoro-2-(((1-methylethyl)amino)carbonyl)-5'-(methyloxy)-1,1'-biphenyl-4-yl)methyl 2,2-dimethylpropanoate (29.3)

To a room temperature solution of 29.2 (432 mg, 1199 µmol) in DCM (6.0 mL) was added two drops of DMF followed by thionyl chloride (0.26 mL, 3596 µmol). The mixture was refluxed under N₂ for 1.5 hours, cooled to room temperature, and the organic solvent was removed under reduced pressure. The residue was treated with neat isopropylamine (2.0 mL, 23515 µmol) (commercially available from Sigma-Aldrich, St. Louis, Mo., USA), and the mixture was heated at 50° C. for 45 minutes. The reaction was then quenched with water (5 mL) and extracted with (3×5 mL) EtOAc. After removal of organic solvents under reduced pressure, purification of the residue by flash chromatography on silica gel with 0-50% EtOAc/hexanes for elution gave 29.3 as white solid (378 mg, 79%).

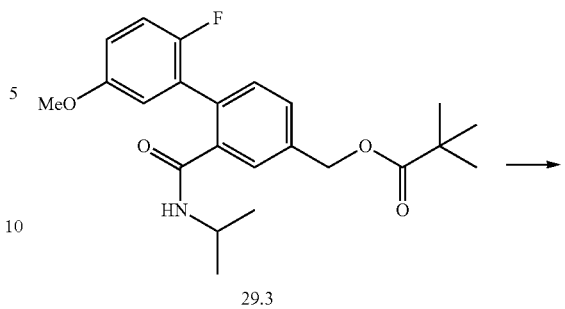

29.3

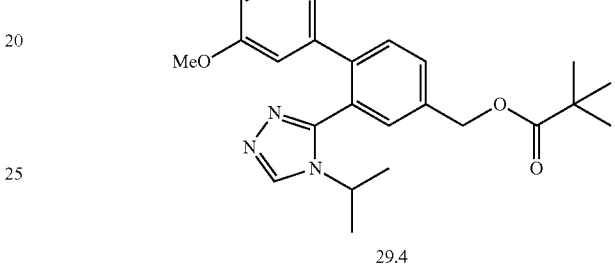

29.4

(2'-Fluoro-2-(4-(1-methylethyl)-4H-1,2,4-triazol-3-yl)-5'-(methyloxy)-1,1'-biphenyl-4-yl)methyl 2,2-dimethylpropanoate (29.4)

To a room temperature solution of 29.3 (244 mg, 608 µmol) in toluene was added 2,4-bis(4-methoxyphenyl)-1,3-dithia-2,4-diphosphetane-2,4-disulfide (369 mg, 912 µmol, Acros Organics). The mixture was heated at 120° C. for 1.0 hour, cooled to room temperature, treated with water, and then extracted with EtOAc. After removal of organic solvent under reduced pressure, the residue was dissolved in dioxane (4 mL). To the solution was added formohydrazide (208 mg, 3461 µmol) (commercially available from Sigma-Aldrich, St. Louis, Mo., USA) and mercuric acetate (202 µL, 2076 µmol, Acros Organics). The resulting mixture was heated at 130° C. for 1.5 hours, cooled to room temperature, treated with water, and extracted with 30% IPA. After removal of organic solvents under reduced pressure, purification of the residue by flash chromatography on silica gel with 0-60% EtOAc/hexanes for elution gave 29.4 as a colorless oil (135 mg, 52%).

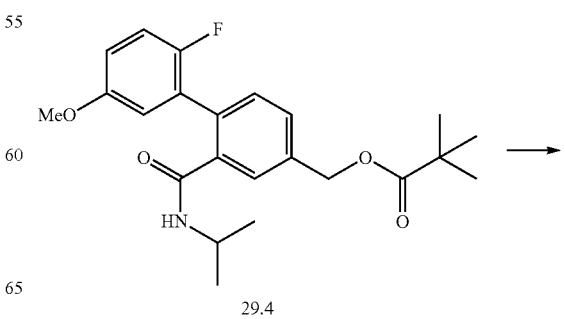

29.4

327

-continued

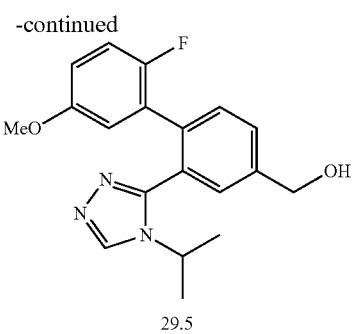
29.5

(2'-Fluoro-2-(4-(1-methylethyl)-4H-1,2,4-triazol-3-yl)-5'-(methyloxy)-1,1'-biphenyl-4-yl)methanol (29.5)

To a room temperature solution of 29.4 (50 mg, 118 μmol) in MeOH (3.0 mL) was added LiOH monohydrate (1.0 M, 494 μL, 494 μmol). The mixture was stirred at room temperature for 30 minutes, diluted with water, and extracted with 30% IPA/chloroform. After removal of organic solvents under reduced pressure, purification of the residue by flash chromatography on silica gel with 0-10% MeOH/DCM for elution gave 29.5 as colorless solid (86 mg, 89%)

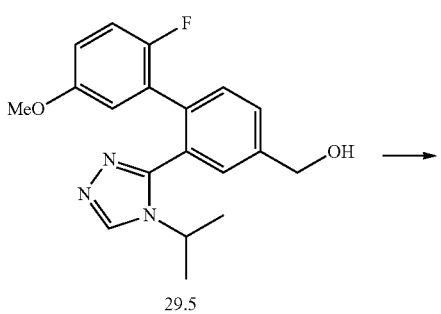
29.5

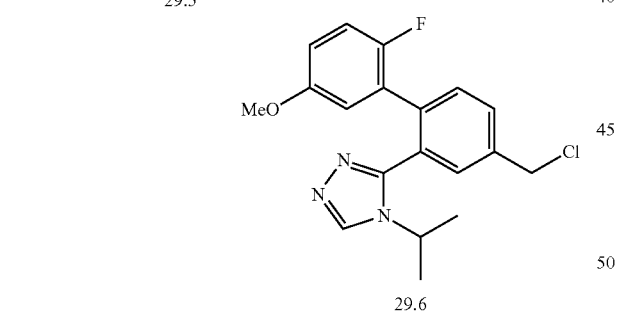
29.6

328

3-(4-(Chloromethyl)-2'-fluoro-5'-(methyloxy)-1,1'-biphenyl-2-yl)-4-(1-methylethyl)-4H-1,2,4-triazole (29.6)

To a room temperature solution of 29.5 (60 mg, 176 μmol) in DCM was added one drop of DMF followed by SOCl₂ (63 mg, 527 μmol). The mixture was stirred at room temperature for 2.0 hours. After removal of organic solvents under reduced pressure, purification of the residue by flash chromatography on silica gel with 0-5% MeOH/EtOAc provided 29.6 as a colorless oil (44 mg, 70%).

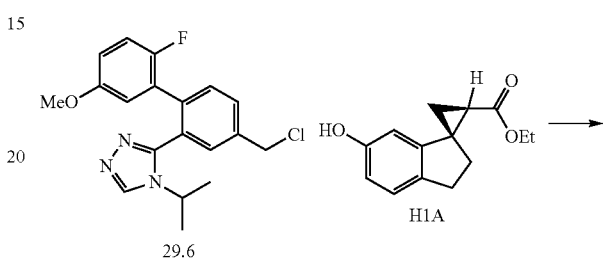
29.6      H1A

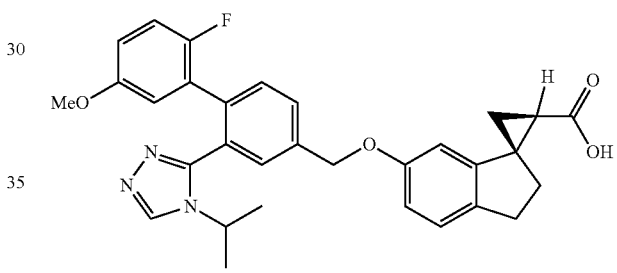
29

Compound 29

The title compound was prepared from 29.6 and H1A according to the procedure described above to provide 29 as colorless solid. (MS ESI (pos.) m/e: 536.2 (M+H).

Example 30

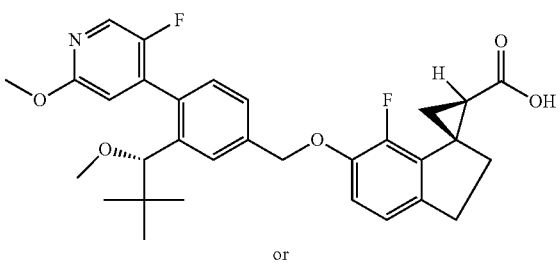

or

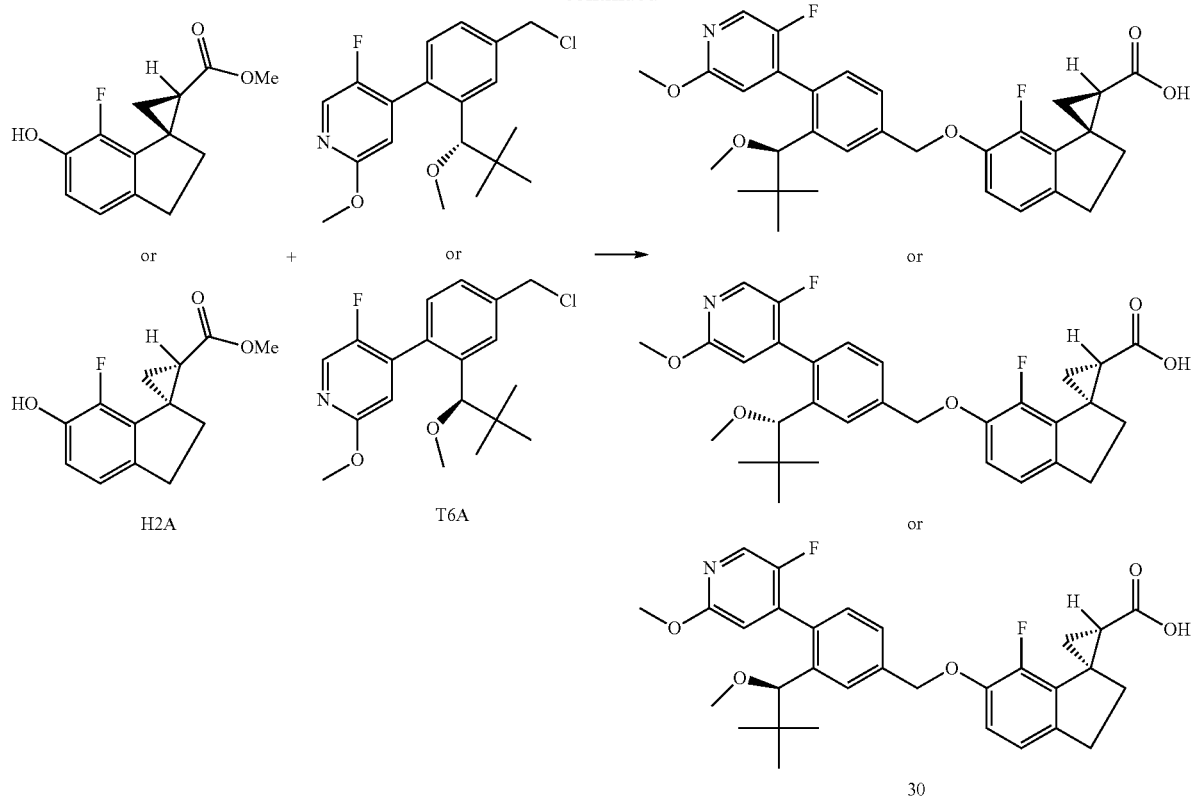
Example 30
To a stirred solution of H2A (28 mg, 119 μmol) and T6A (42 mg, 119 μmol) in DMSO (0.5 mL), was added Cs$_2$CO$_3$ (78 mg, 239 μmol). The resulting mixture was stirred at room temperature overnight and then 2N LiOH (0.5 mL) and MeOH (1 mL) were added and the reaction was stirred for another 16 hours at 50° C. The mixture was acidified with 2N HCl (0.8 mL) and then purified by HPLC to give 30 (41 mg, 64%). MS ESI m/e: 538.2 (M+1)$^+$.
Example 31
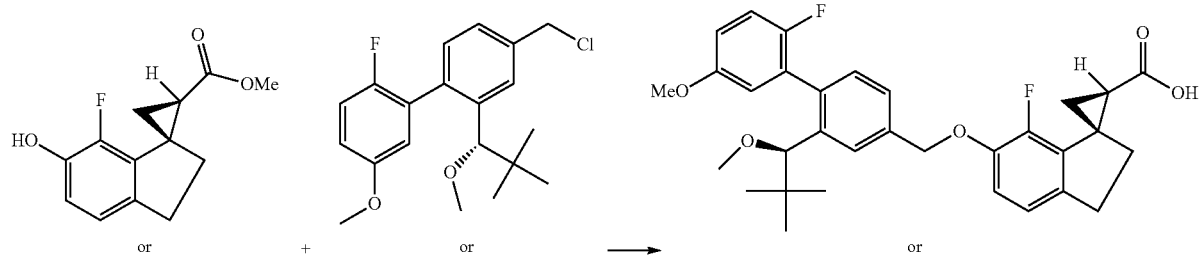

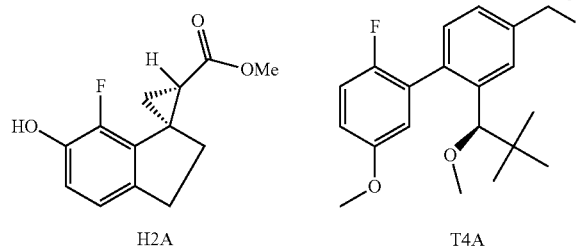

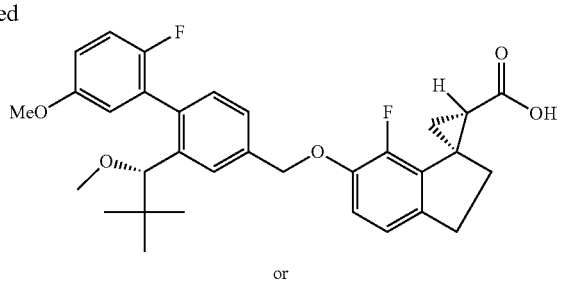

Example 31

Example 31 was synthesized from H2A and T4A by a method analogous to the method used for compound 30. MS ESI m/e: 537.2 (M+1)⁺. $^1$H NMR (400 MHz, CDCl$_3$) δ ppm 7.57 (m, 1H,), 7.44 (m, 1H), 7.19 (m, 1H), 7.04 (m, 1H), 6.87 (m, 3H), 6.75 (m 1H), 5.16 (s, 2H), 4.20 (s, 0.3H) 3.96 (s, 0.7H), 3.81 (s, 3H), 3.31 (s, 0.9H), 3.25 (s, 2.1H), 2.98 (m, 2H), 2.59 (m, 1H), 2.35 (m, 1H), 2.30 (m, 1H), 2.00 (m, 1H), 1.61 (m, 1H), 0.71 (s, 9H).

Example 32

Example 32

Compound 32 was synthesized from H2A and T5 by a method analogous to the method used for compound 30. MS ESI m/e: 534.2 (M+1)⁺. $^1$H NMR (400 MHz, CDCl$_3$) δ ppm 8.12 (m, 1H,), 7.44 (m, 1H), 7.36 (m, 1H), 7.17 (m, 1H), 6.86 (m, 2H), 6.75 (m, 0.67H), 6.62 (m, 0.23H), 5.14 (s, 2H), 3.99 (s, 3H) 2.99 (m, 2H), 2.86 (m, 0.3H), 2.70 (m, 0.7H), 2.61 (dd, J=8 Hz, J=4 Hz, 1H), 2.38 (m, 1H), 2.30 (m, 1H), 2.13 (m, 1H), 2.02 (m, 2H), 1.82 (m, 1H), 1.72 (m, 1H), 1.63 (m, 1H), 1.54 (m, 1H), 1.41 (m, 1H), 0.70 (s, 0.9H), 0.68 (s, 2.1H), 0.64 (s, 0.9H), 0.59 (s, 2.1H).

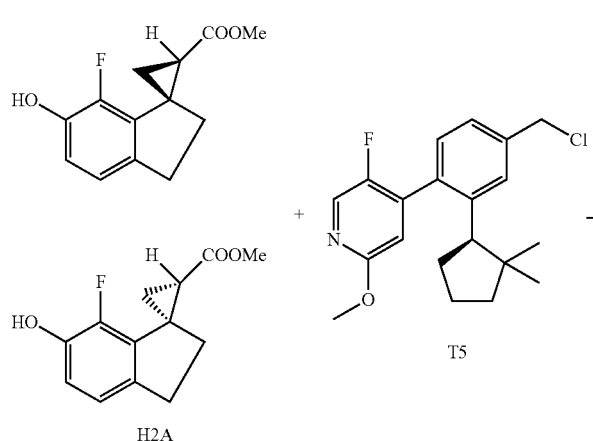

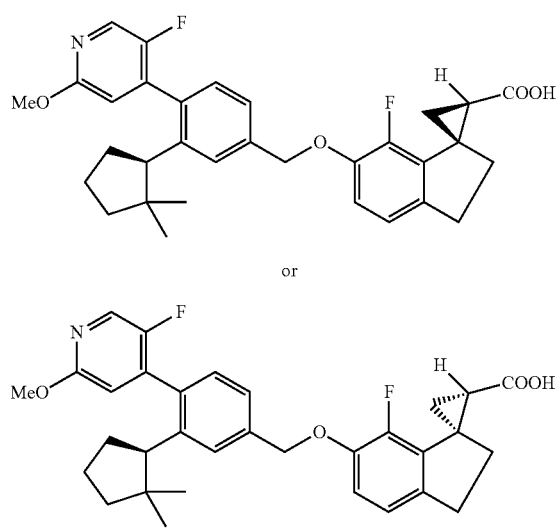

Example 33

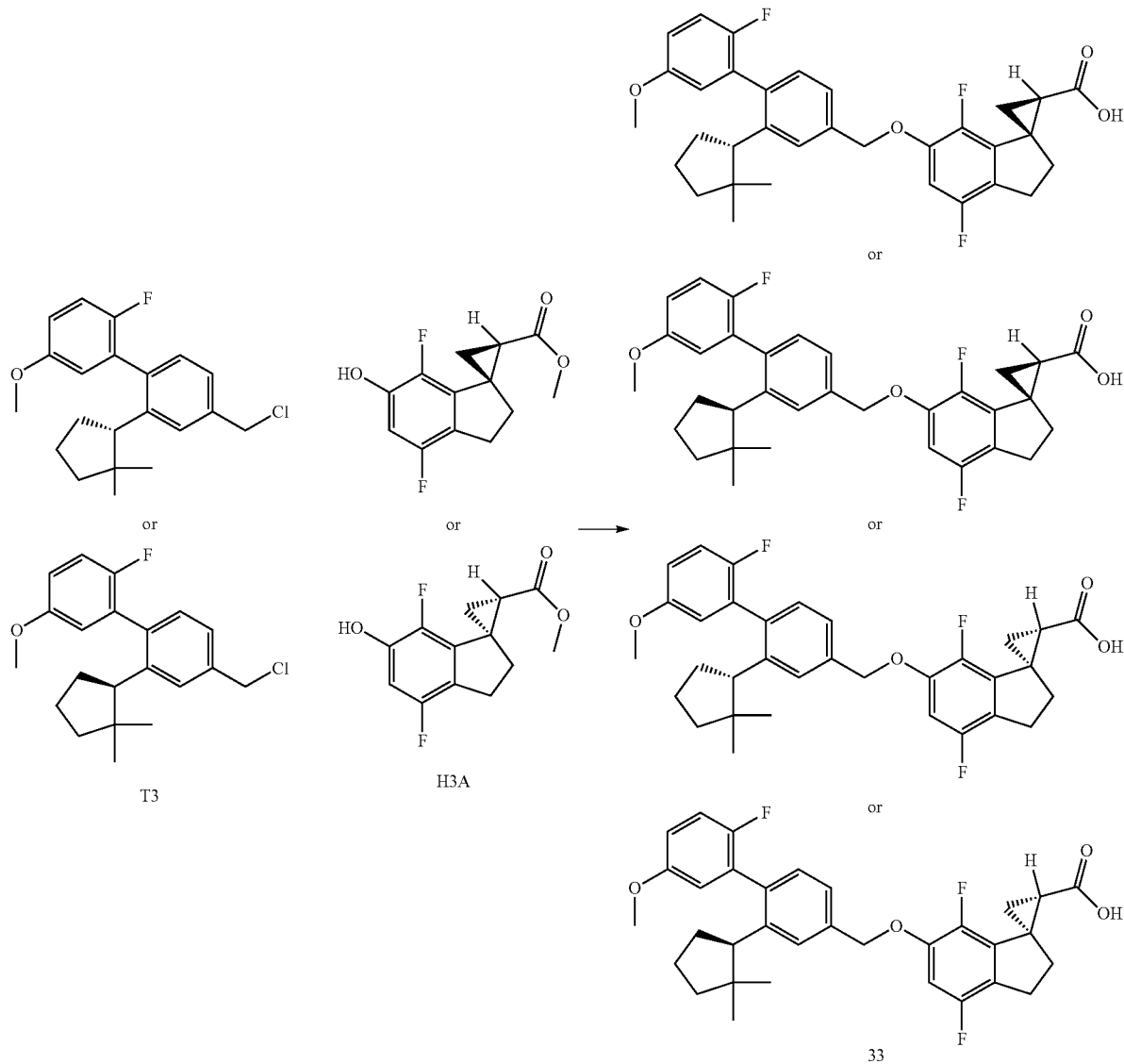

Example 33

A screw-cap vial was charged with H3A (0.015 g, 0.059 mmol), T3 (0.023 g, 0.065 mmol), DMF (1 mL), and Cs$_2$CO$_3$ (0.029 g, 0.089 mmol). The mixture was stirred overnight at room temperature, diluted with water, and extracted with EtOAc. The combined organic layers were dried (MgSO$_4$), filtered, and concentrated. The crude product was purified by silica gel flash chromatography (0-10% EtOAc/hexane) to afford the desired alkylation product as a colorless oil.

A screw-cap vial was charged with the above alkylation product, 2:1 THF/MeOH (1.5 mL), and 1 N LiOH (0.500 mL, 0.50 mmol). The mixture was stiffed overnight at room temperature, concentrated, quenched with a slight excess of 1 N HCl (0.60 mL), and extracted with EtOAc. The combined organic layers were dried (MgSO$_4$), filtered, and concentrated to afford 33 (0.0310 g, 95% yield) as a white solid. MS ESI (neg.) m/e: 549.2 (M–H).

Example 34

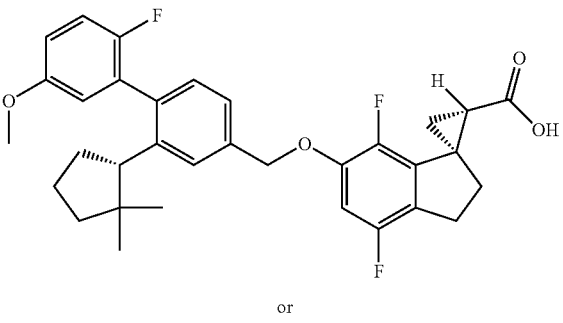

335
-continued
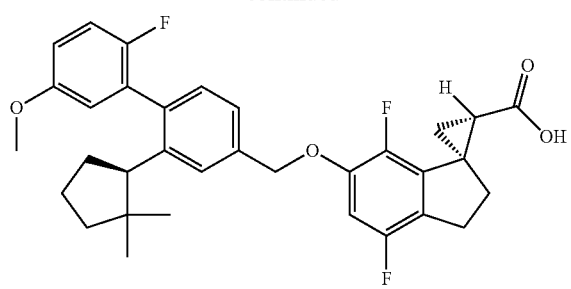
or
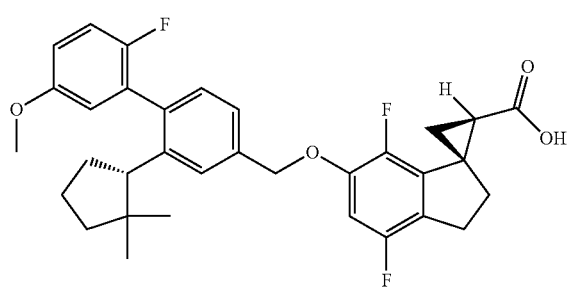
or
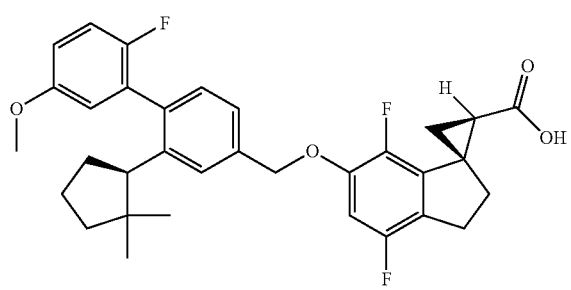
Example 34
The title compound was prepared from T3 and H3B according to the analogous methods described for the synthesis of compound 33. MS ESI (neg.) m/e: 549.2 (M−H).
Example 35
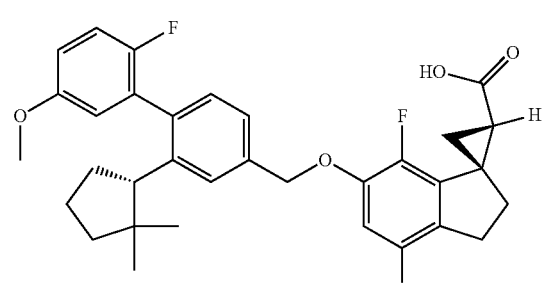
or
336
-continued
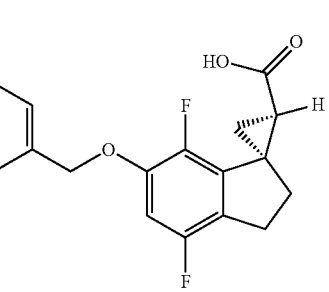
or
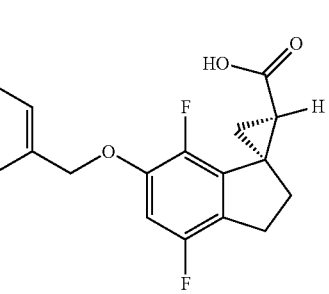
or
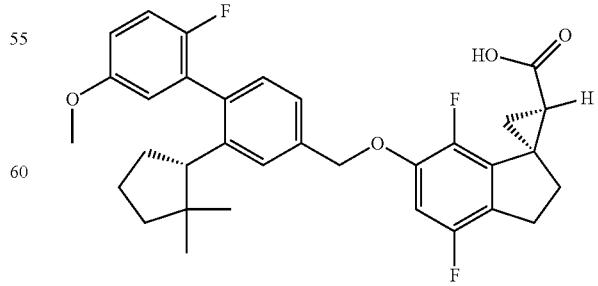
Example 35
The title compound was prepared from T3 and H3C according to the analogous methods described for the synthesis of compound 33. MS ESI (neg.) m/e: 549.2 (M−H).
Example 36
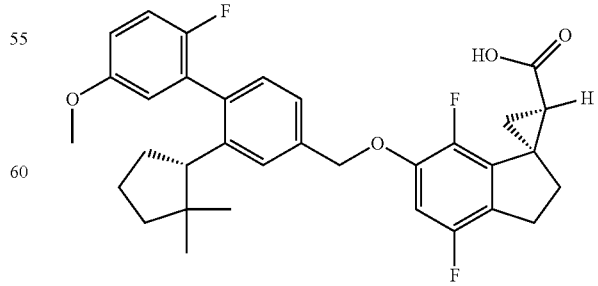
or

337
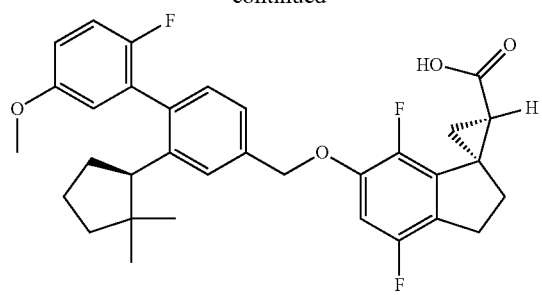
or
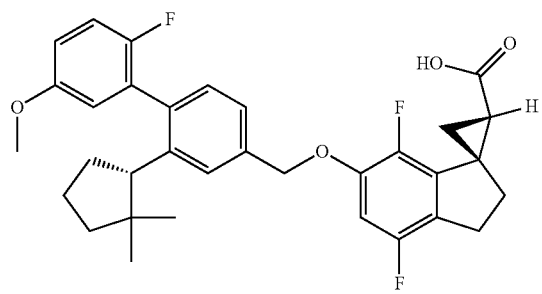
or
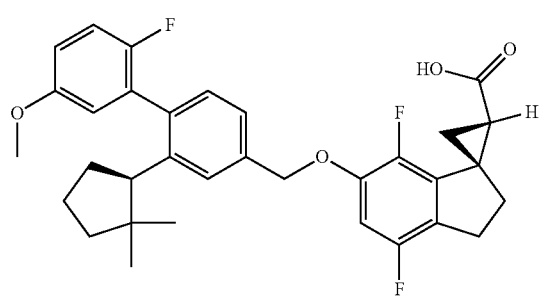
Example 36
The title compound was prepared from T3 and H3D according to the analogous methods described for the synthesis of compound 33. MS ESI (neg.) m/e: 549.2 (M–H).
Example 37
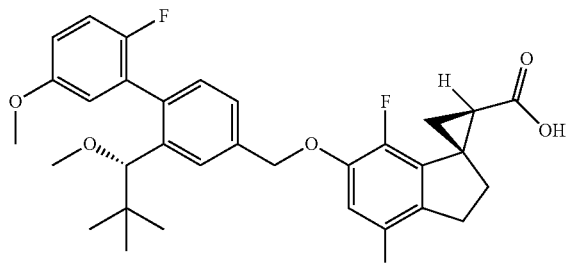
or
338
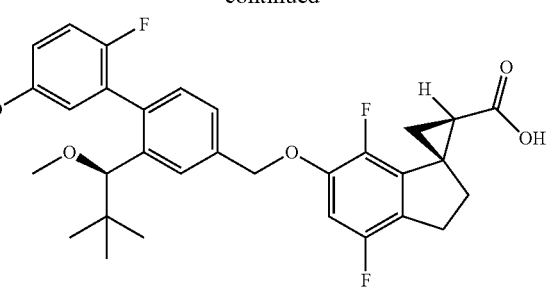
or
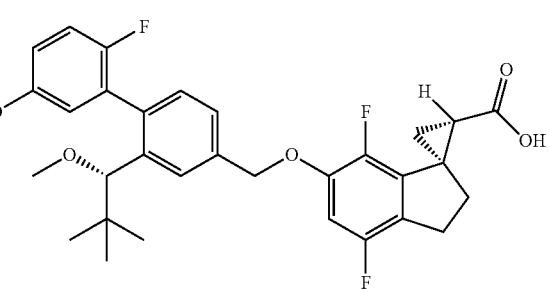
or
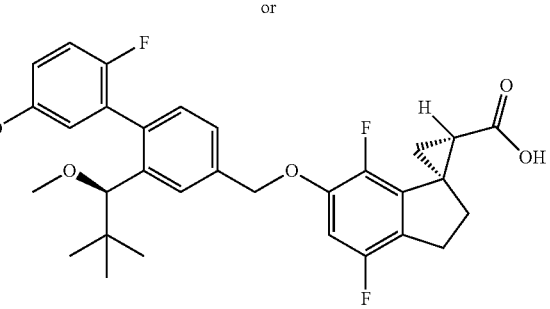
Example 37
The title compound was prepared from T4 and H3A according to the analogous methods described for the synthesis of compound 33. MS ESI (neg.) m/e: 553.2 (M–H).
Example 38
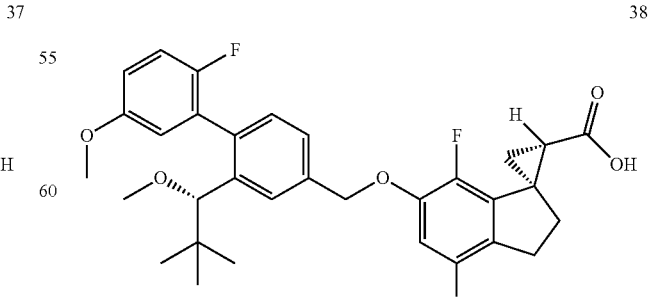
or 339
-continued
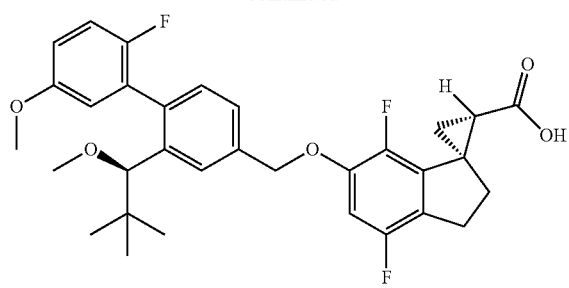
or
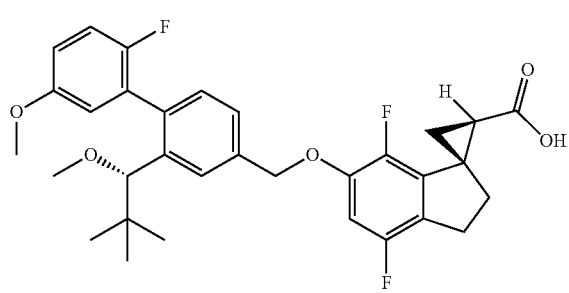
or
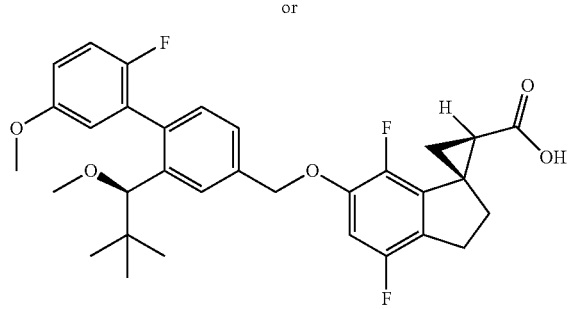
Example 38
The title compound was prepared from T4 and H3B according to the analogous methods described for the synthesis of compound 33. MS ESI (neg.) m/e: 553.2 (M−H).
Example 39
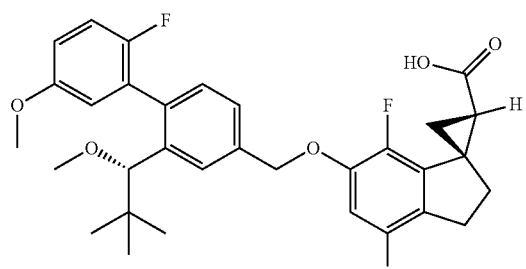
or
340
-continued
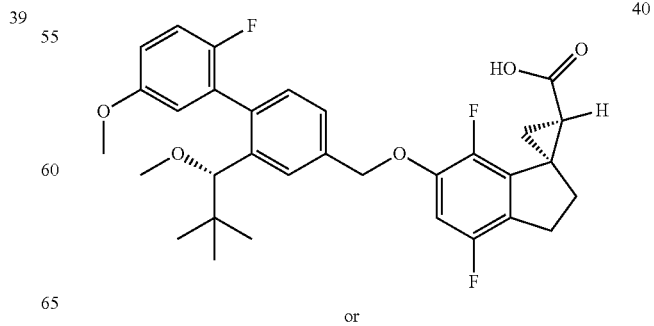
Example 39
The title compound was prepared from T4 and H3C according to the analogous methods described for the synthesis of compound 33. MS ESI (neg.) m/e: 553.2 (M−H).
Example 40

341

-continued

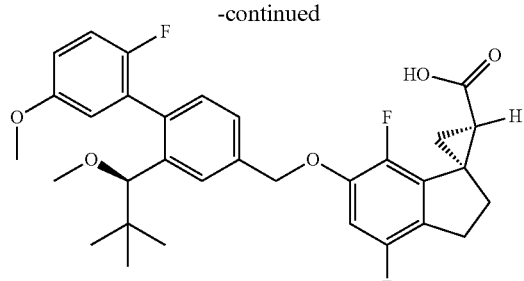

or

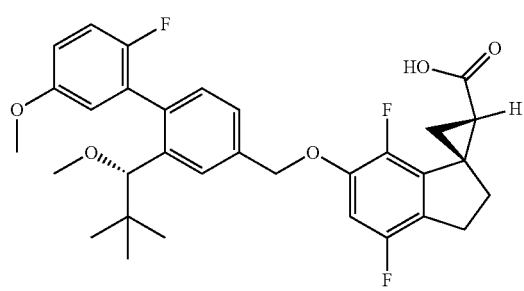

or

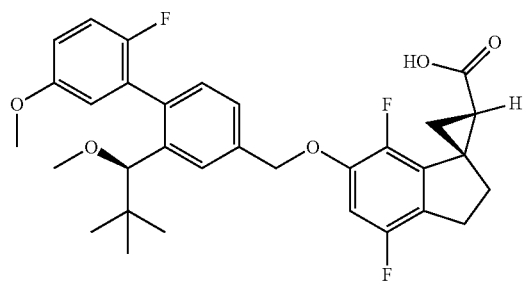

Example 40

The title compound was prepared from T4 and H3D according to the analogous methods described for the synthesis of compound 33. MS ESI (neg.) m/e: 553.2 (M–H).

Example 41

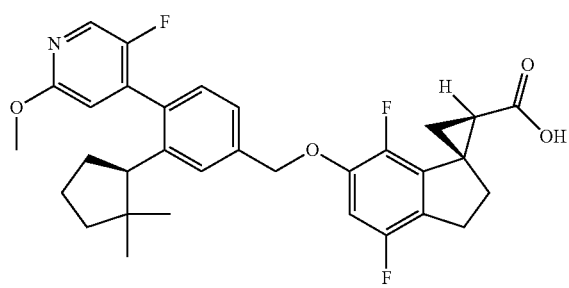

or

342

-continued

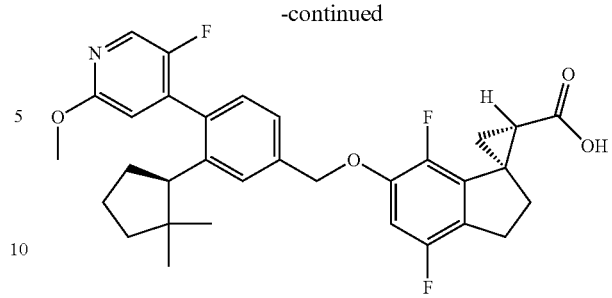

(1R,2R)-6'-(3-((R)-2,2-dimethylcyclopentyl)-4-(5-fluoro-2-methoxypyridin-4-yl)benzyloxy)-4',7'-difluoro-2',3'-dihydrospiro[cyclopropane-1,1'-indene]-2-carboxylic acid or (1S,2S)-6'-(3-((R)-2,2-dimethylcyclopentyl)-4-(5-fluoro-2-methoxypyridin-4-yl)benzyloxy)-4',7'-difluoro-2',3'-dihydrospiro[cyclopropane-1,1'-indene]-2-carboxylic acid 41

The title compound was prepared from T5 and H3A according to the analogous methods described for the synthesis of compound 33. MS ESI (neg.) m/e: 550.2 (M–H).

Example 42

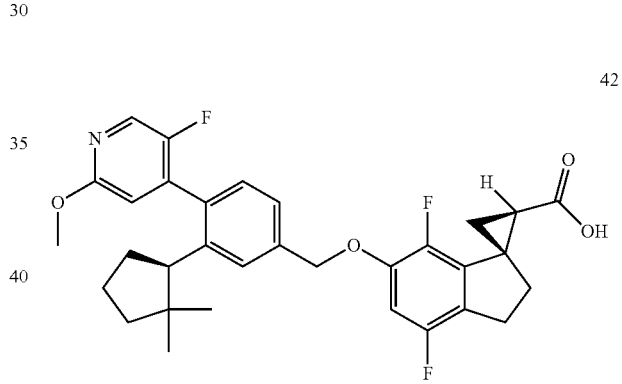

42 or

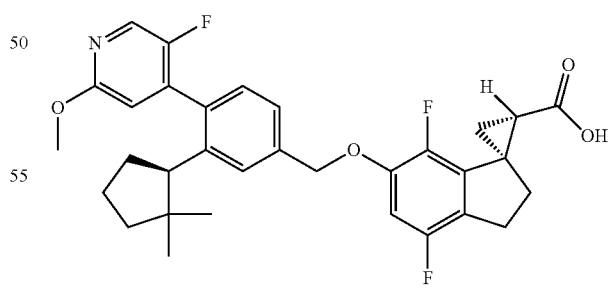

Example 42

The title compound was prepared from T5 and H3B according to the analogous methods described for the synthesis of compound 33. MS ESI (neg.) m/e: 550.2 (M–H).

Example 43

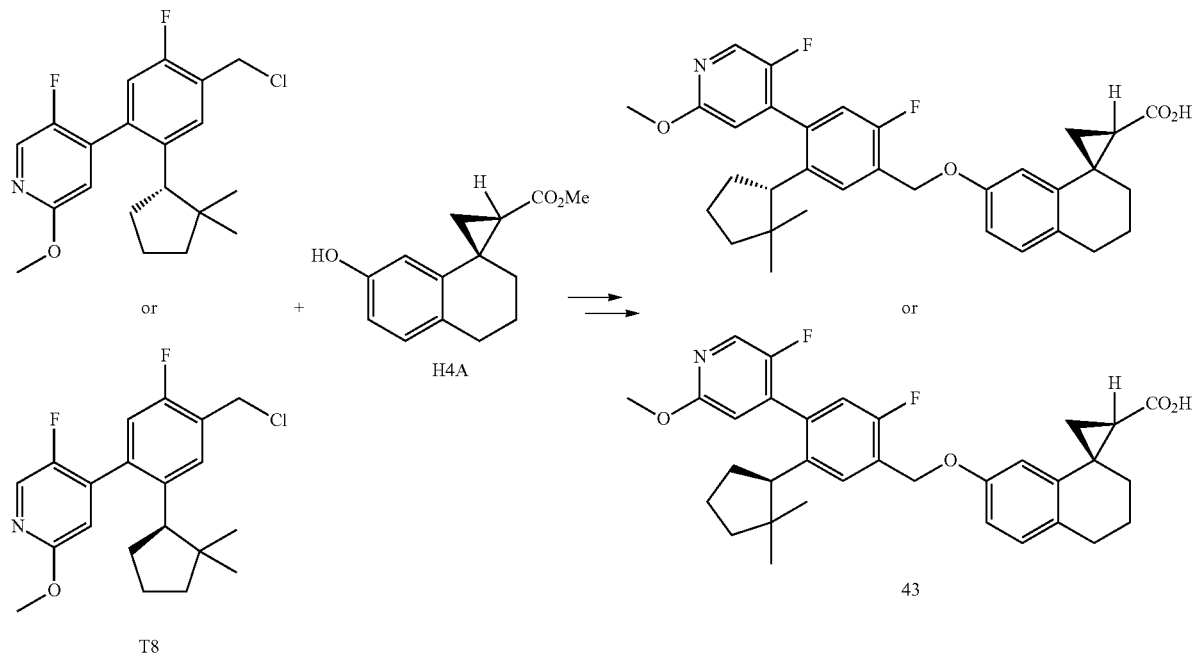

Example 43

The alkylation and hydrolysis were conducted in an analogous manner to Example 15 using T8 and H4A to yield 43 as a TFA salt. MS ESI (pos.) m/e: 548.2 (M+H)[1]. MS ESI (neg.) m/e: 546.1 (M−H)+.

Example 44

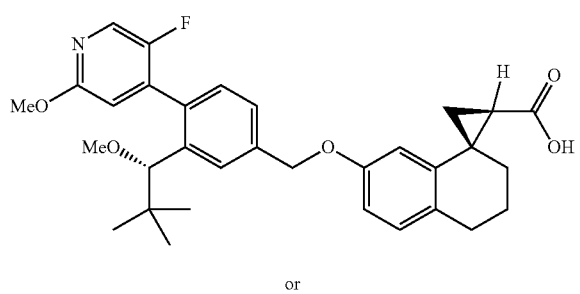

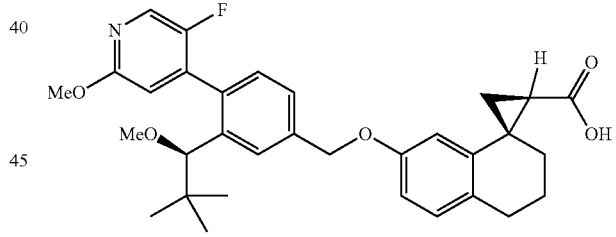

Example 44

The title compound was prepared starting from compound T6 and H4A according to the procedure described above to provide 44 as colorless solid (46 mg, 84%). $^1$H NMR (400 MHz, CDCl$_3$) δ ppm 7.97 (br. s., 1H), 7.50 (br. s., 1H), 7.36 (d, J=7.43 Hz, 1H), 7.08 (d, J=7.43 Hz, 1H), 6.94 (d, J=8.22 Hz, 1H), 6.71 (dd, J=8.41, 2.54 Hz, 1H), 6.55 (br. s., 1H), 6.26 (d, J=2.74 Hz, 1H), 5.02 (s, 2H), 3.88 (s, 3H), 3.18 (br. s., 3H), 2.74 (t, J=6.46 Hz, 2H), 1.85-2.02 (m, 4H), 1.63-1.85 (m, 2H), 1.45-1.59 (m, 2H), 1.13-1.25 (m, 1H), 0.63 (s, 9H); (MS ESI (pos.) m/e: 534.2 (M+H).

Example 45
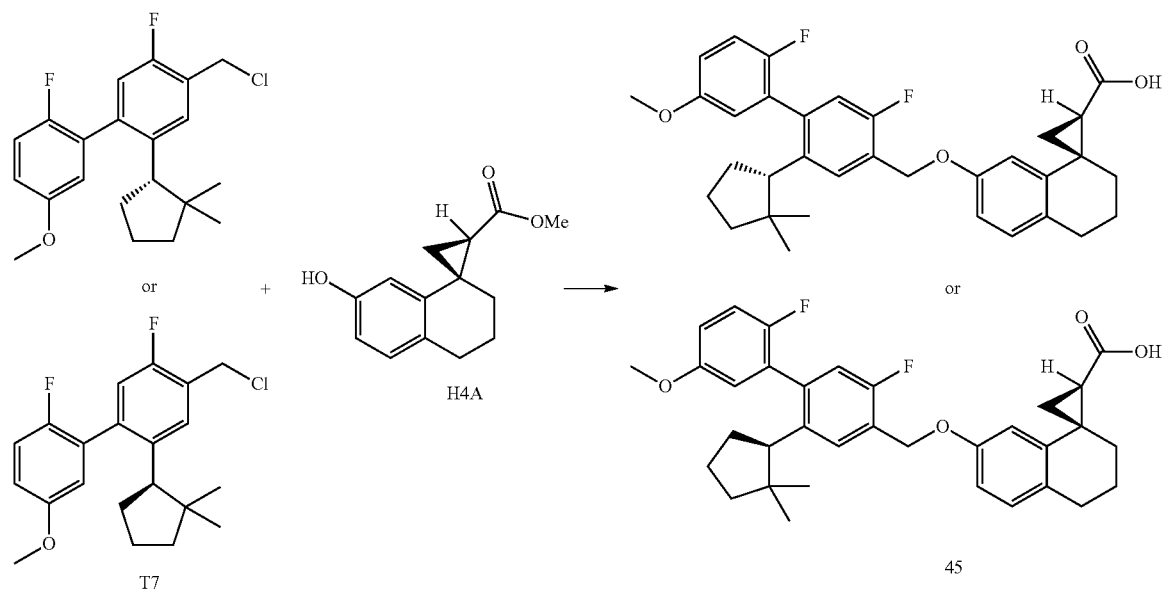
Example 45
The title compound was synthesized from H4A and T7 using a procedure analogous to that described for synthesizing 9. MS ESI (pos.) M/E: 569 (M+Na).
Example 46
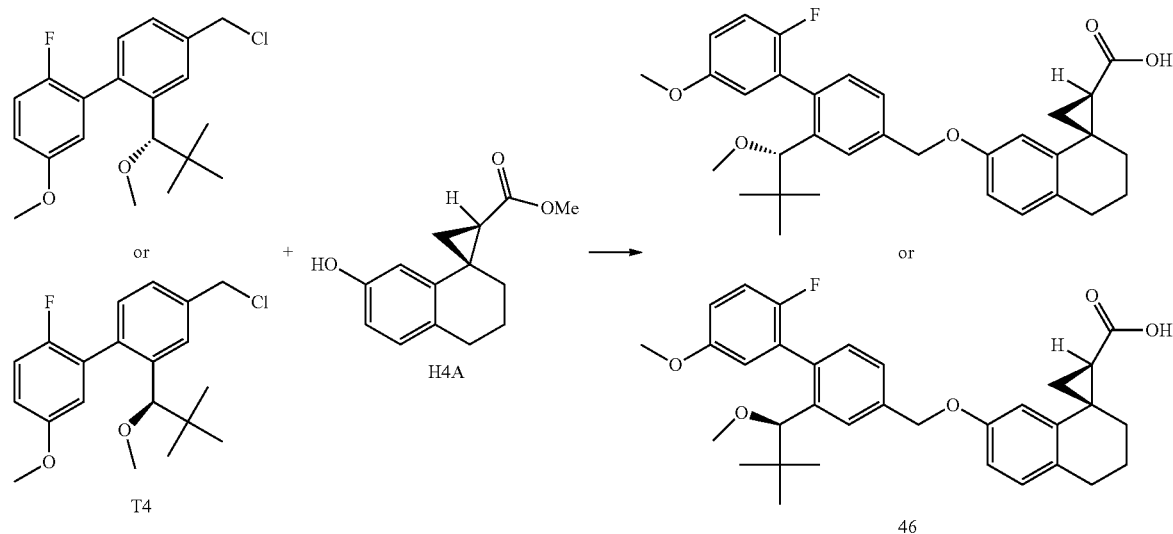
Example 46
The title compound was synthesized from H4A and T4 using a procedure analogous to that described for synthesizing 9. MS ESI (pos.) M/E: 555 (M+Na).

Example 47
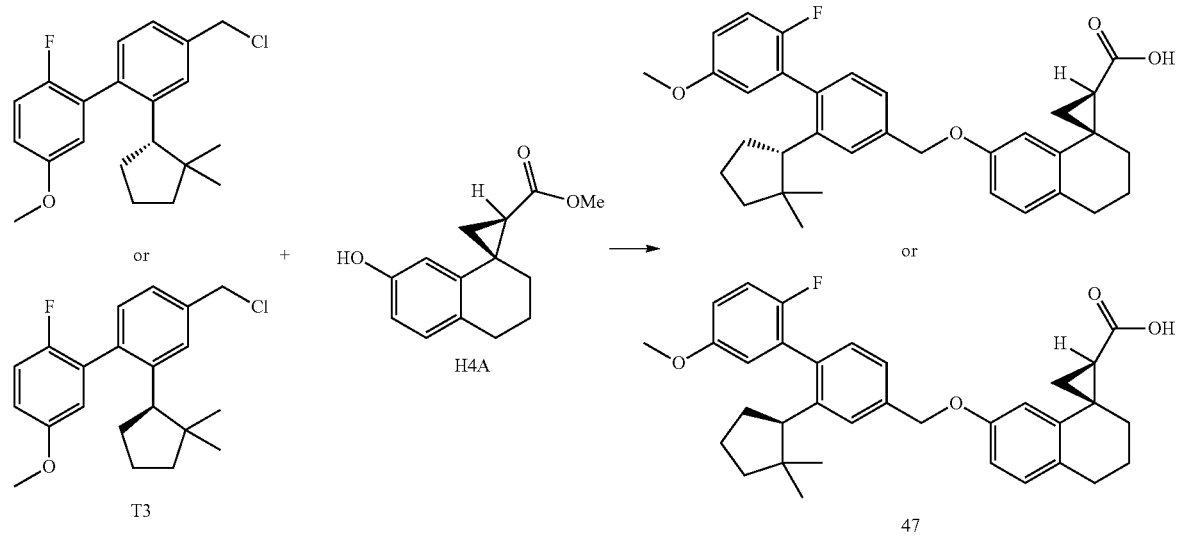
Example 47
The title compound was synthesized from T3 and H4A using a procedure analogous to that described for synthesizing 9. MS ESI (pos.) M/E: 551 (M+Na).
Example 48
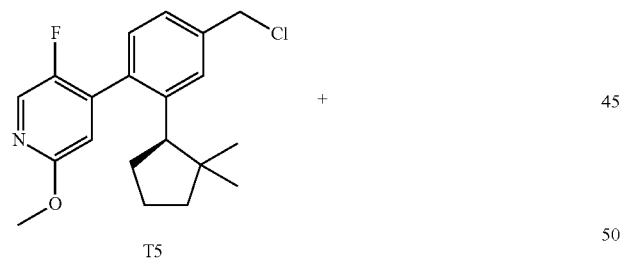
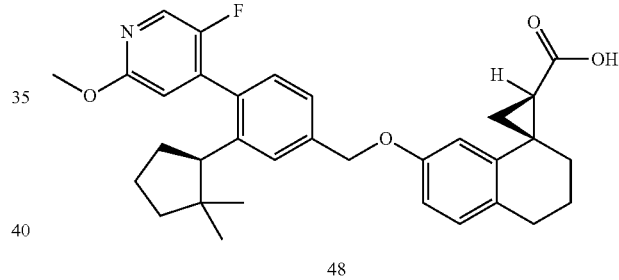
Example 48
The title compound was synthesized from T5 and H4A using a procedure analogous to that described for synthesizing 9. MS ESI (pos.) M/E: 552 (M+Na).
Example 49
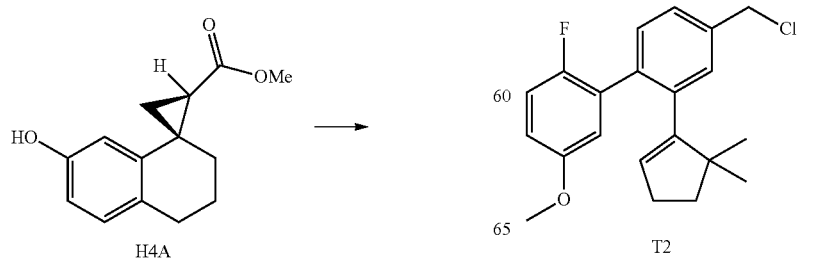

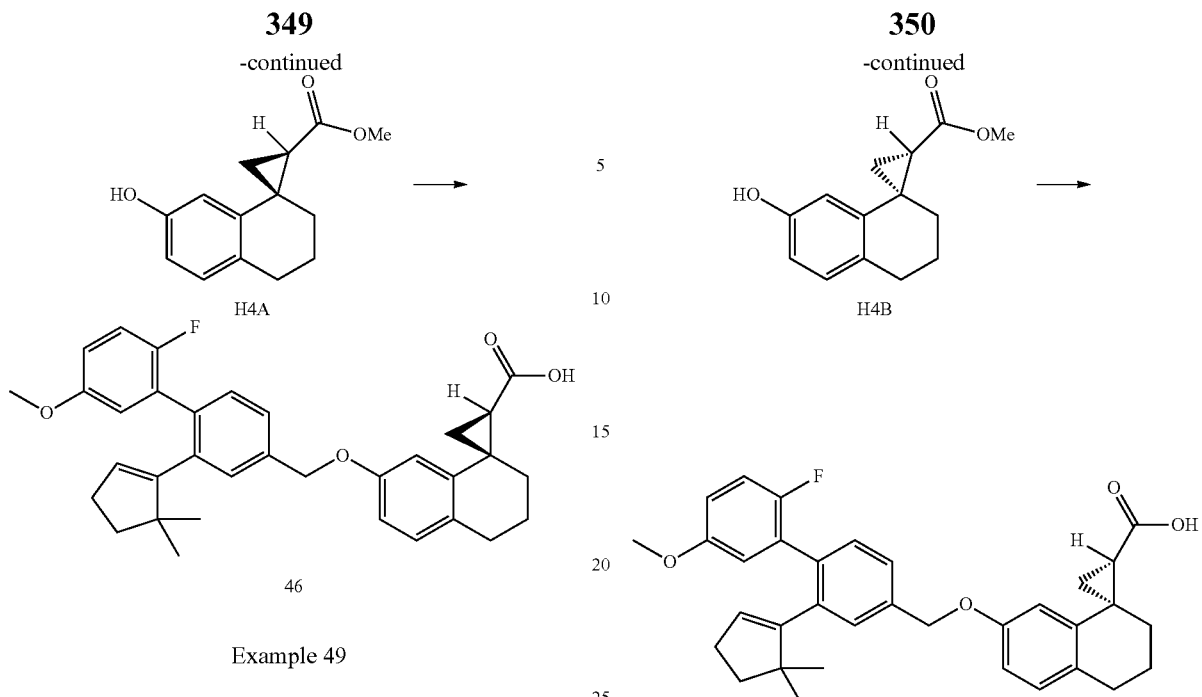
Example 49
The title compound was synthesized from H4A and T2 using a procedure analogous to that described for synthesizing 9. MS ESI (pos.) M/E: 549 (M+Na).
Example 50
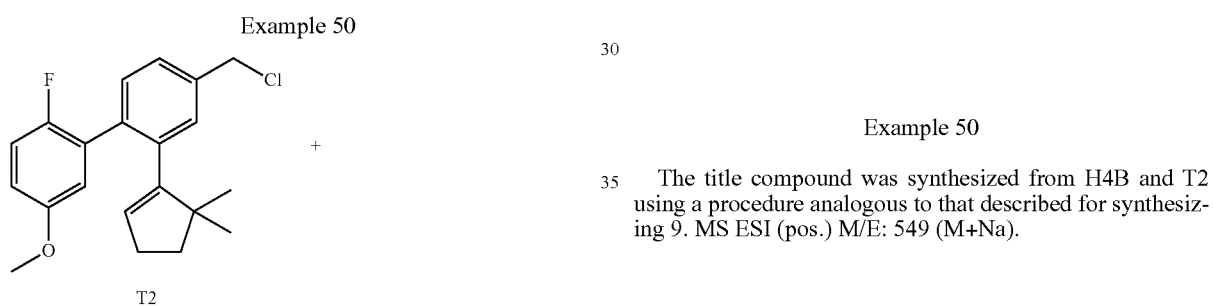
Example 50
The title compound was synthesized from H4B and T2 using a procedure analogous to that described for synthesizing 9. MS ESI (pos.) M/E: 549 (M+Na).
Example 51
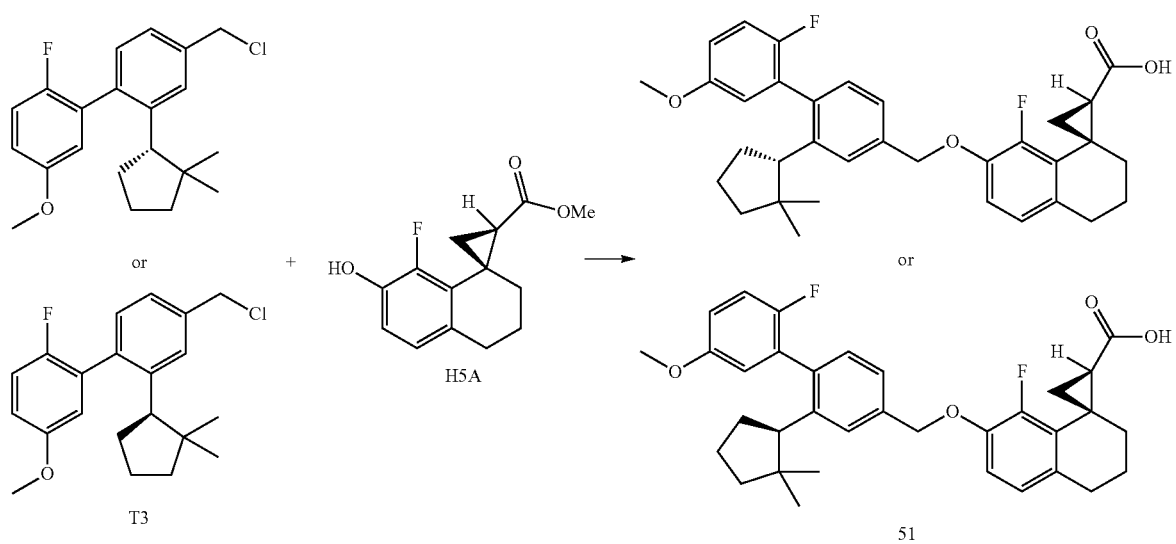

Example 51

The title compound was synthesized from H5A and T3 using a procedure analogous to that described for synthesizing 9. MS ESI (pos.) M/E: 569 (M+Na).

Example 52

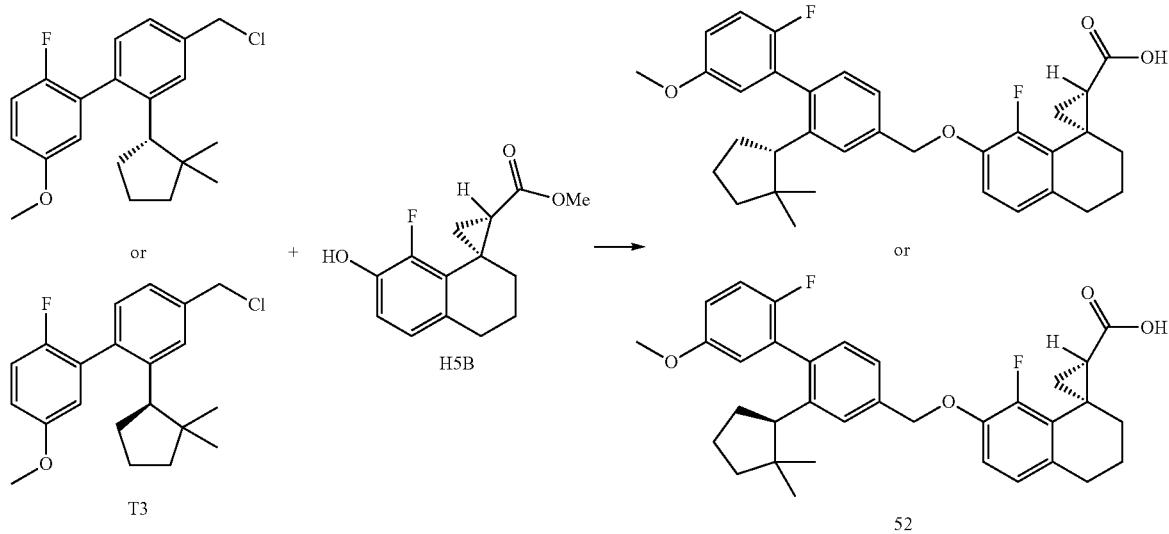

Example 52

The title compound was synthesized from H5B and T3 using a procedure analogous to that described for synthesizing 9. MS ESI (pos.) M/E: 569 (M+Na).

Example 53

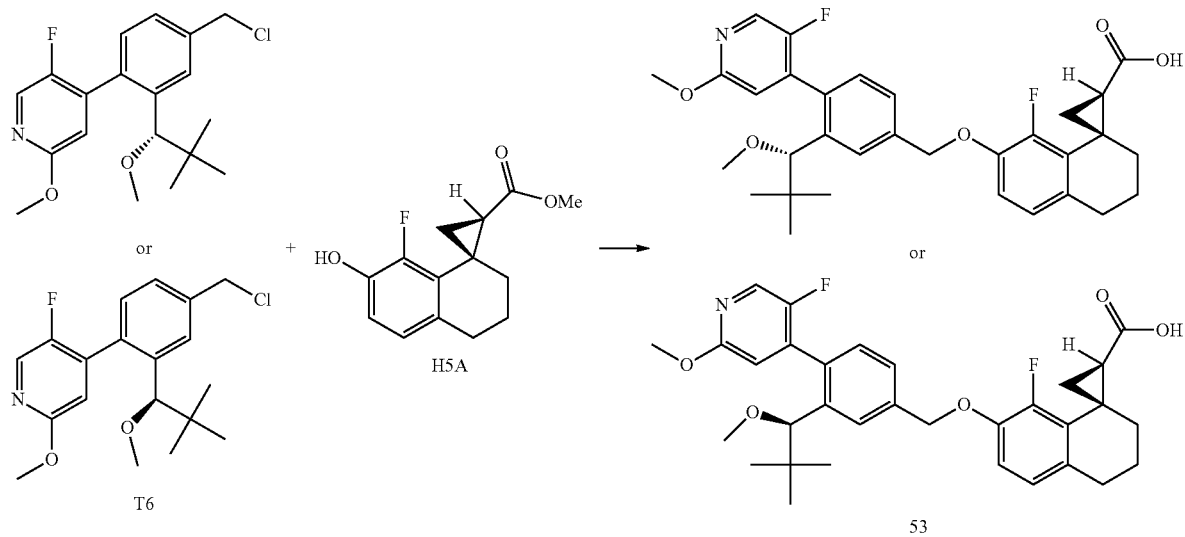

Example 53

The title compound was synthesized from H5A and T6 using a procedure analogous to that described for synthesizing 9. MS ESI (pos.) M/E: 574 (M+Na).

Example 54
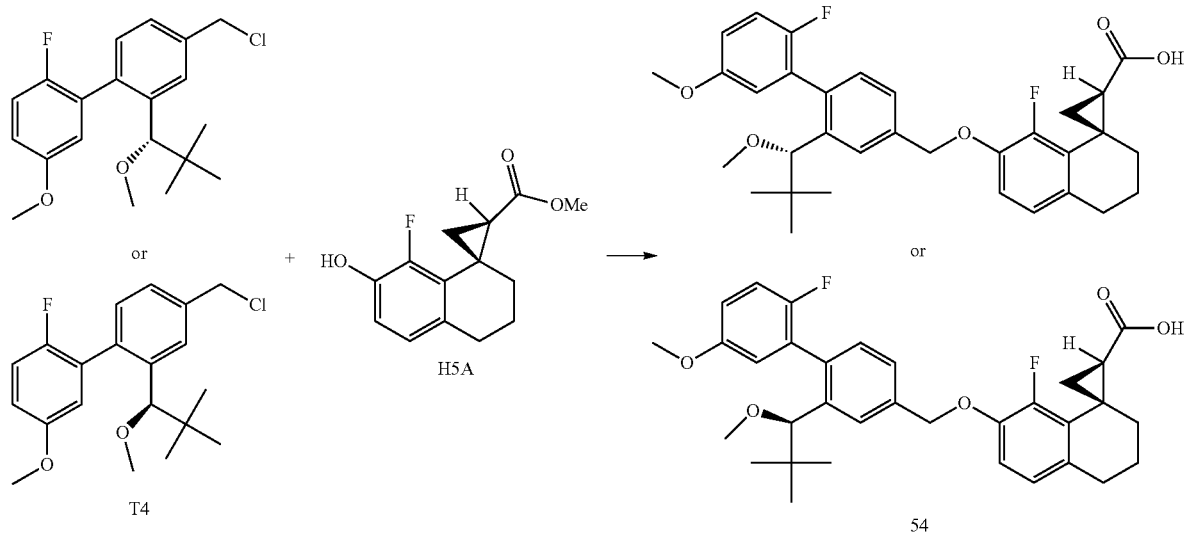
Example 54
The title compound was synthesized from H5A and T4 using a procedure analogous to that described for synthesizing 9. MS ESI (pos.) M/E: 573 (M+Na).
Example 55
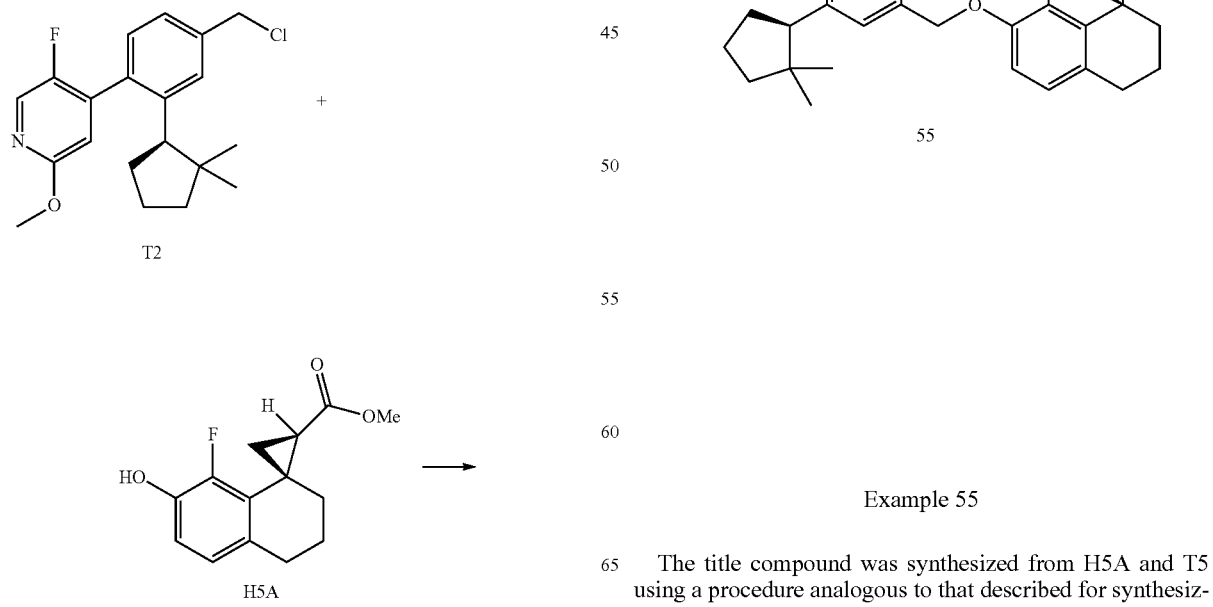
Example 55
The title compound was synthesized from H5A and T5 using a procedure analogous to that described for synthesizing Example 9. MS ESI (pos.) M/E: 548 (M+H).

Example 56
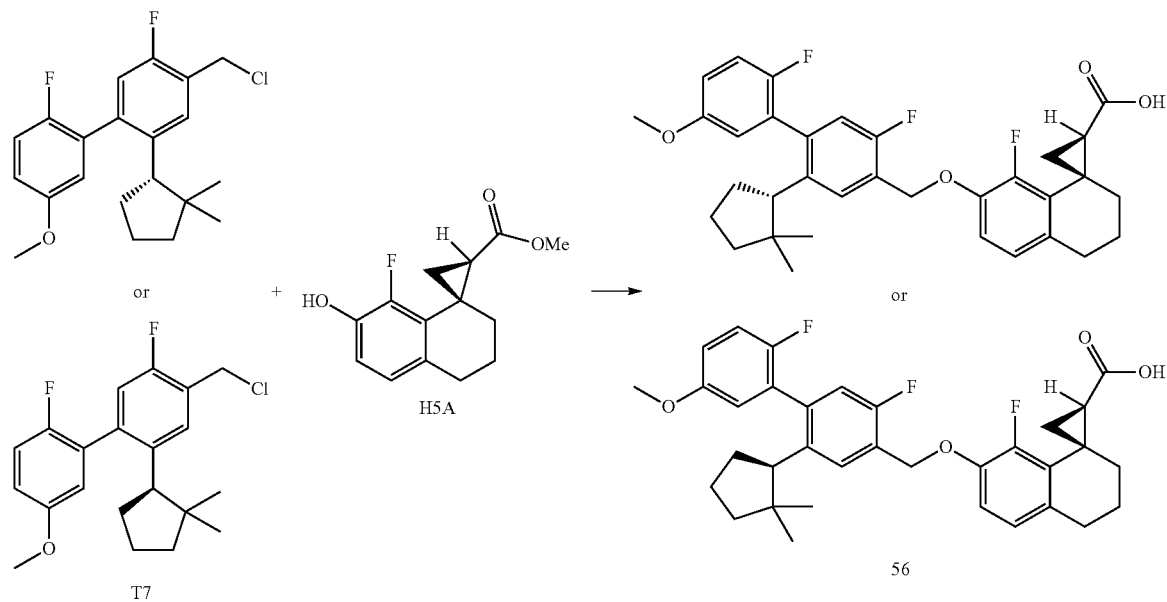
Example 56
The title compound was synthesized from H5A & T7 using a procedure analogous to that described for synthesizing 9. MS ESI (pos.) M/E: 587 (M+Na).
Example 57
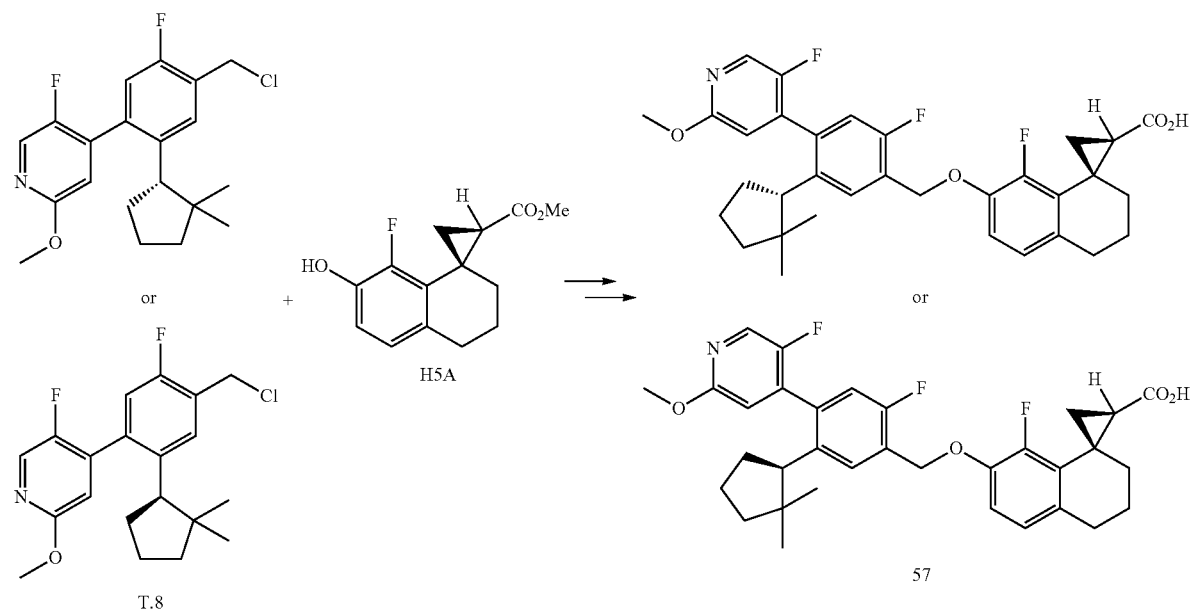

Example 57

The alkylation and hydrolysis were conducted in an analogous manner to Example 15 using T11 and H5A to yield 57 (38.7 mg). MS ESI (pos.) m/e: 566.2 (M+H)⁺. MS ESI (neg.) m/e: 564.1 (M−H)⁺.

Example 58

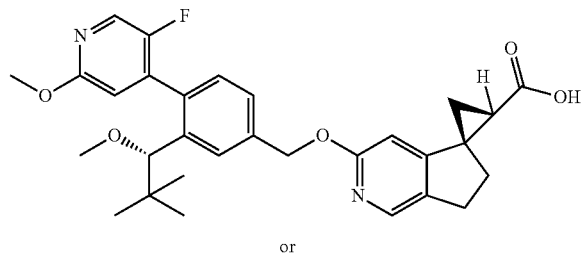

or

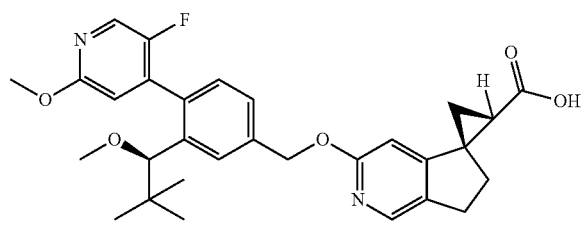

(2'R,5R)-3-({4-(5-Fluoro-2-methoxypyridin-4-yl)-3-1[(1S)-1-methoxy-2,2-dimethylpropyl]phenyl}methoxy)-6,7-dihydrospiro[cyclopenta[c]pyridine-5,1'-cyclopropane]-2'-carboxylic acid or (2'R,5R)-3-({4-(5-fluoro-2-methoxypyridin-4-yl)-3-[(1R)-1-methoxy-2,2-dimethylpropyl]phenyl}methoxy)-6,7-dihydrospiro[cyclopenta[c]pyridine-5,1'-cyclopropane]-2'-carboxylic acid (58)

Compound 58 was synthesized from compounds H6A and T6 using the same method used to prepare compound 33. MS ESI (pos.) m/e: 521.1 (M+H)⁺. ¹H NMR (400 MHz, CDCl₃) δ ppm 8.24 (1H, s), 8.11 (1H, s), 7.60 (1H, s), 7.46 (1H, s), 6.66 (1H, s) 6.41 (1H, s), 5.48 (2H, s), 3.98 (3H, s), 3.27 (3H, br. s.), 3.14 (2H, m), 2.47 (2H, m), 2.22 (1H, dd, J=8.7, 6.4 Hz), 1.91 (1H, t, J=5.9 Hz), 1.61 (1H, m), 0.71 (9H, s).

Example 59

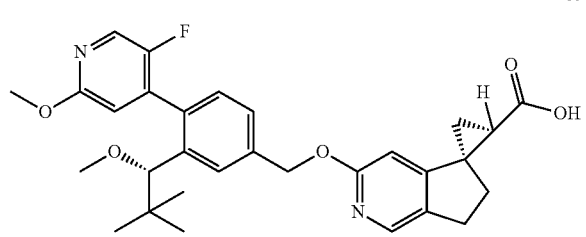

or

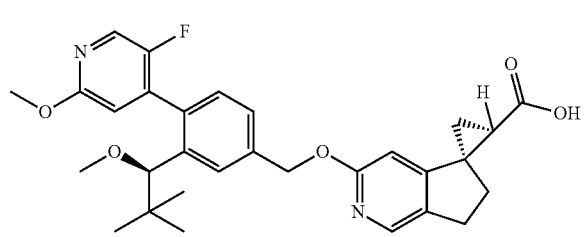

(2'S,5S)-3-({4-(5-Fluoro-2-methoxypyridin-4-yl)-3-[(1S)-1-methoxy-2,2-dimethylpropyl]phenyl}methoxy)-6,7-dihydrospiro[cyclopenta[c]pyridine-5,1'-cyclopropane]-2'-carboxylic acid or (2'S,5S)-3-({4-(5-fluoro-2-methoxypyridin-4-yl)-3-[(1R)-1-methoxy-2,2-dimethylpropyl]phenyl}methoxy)-6,7-dihydrospiro[cyclopenta[c]pyridine-5,1'-cyclopropane]-2'-carboxylic acid (59)

Example 59 was synthesized from compounds H6B and T6 using the same method used to prepare compound 33. MS ESI (pos.) m/e: 521.1 (M+H)⁺. ¹H NMR (400 MHz, CDCl₃) δ ppm 8.24 (1H, s), 8.21 (1H, s), 7.61 (1H, s), 7.46 (1H, s), 7.22 (1H, s), 6.66 (1H, s) 6.41 (1H, s), 5.49 (2H, s), 3.98 (3H, s), 3.28 (3H, br. s.), 3.14 (2H, m), 2.47 (2H, m), 2.23 (1H, dd, J=8.7, 6.4 Hz), 1.92 (1H, t, J=5.9 Hz), 1.63 (1H, m), 0.71 (9H, s).

Example 60

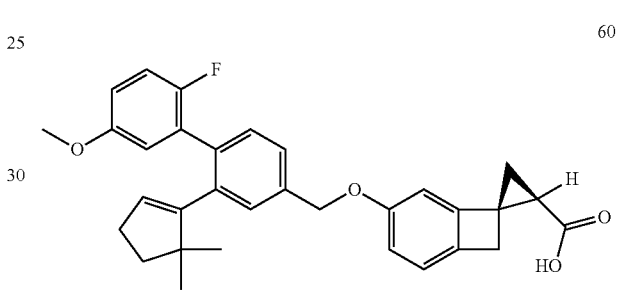

(2'R,7S)-4-(3-(((2-(5,5-Dimethyl-1-cyclopenten-1-yl)-2'-fluoro-5'-(methyloxy)-1,1'-biphenyl-4-yl)methyl)oxy)hydroxyspiro[bicyclo[4.2.0]octane-7,1'-cyclopropane]-1,3,5-triene-2'-carboxylic acid (60)

Example 60 was synthesized from compounds H7A and T2 using the same method used to prepare compound 33. MS ESI (pos.) m/e: 499.2 (M+H)⁺. ¹H NMR (400 MHz, CDCl₃) δ ppm 7.38 (1H, m), 7.26-7.34 (2H, m), 6.93-7.02 (2H, m), 6.87-6.91 (2H, m), 6.80-6.78 (2H, m), 5.52 (1H, s), 5.03 (2H, s), 3.76 (3H, s), 3.31 (2H, m), 2.25 (3H, br.), 1.81 (1H, d, J=5.5 Hz), 1.64-1.69 (2H, m), 0.85 (6H, d, J=3.9 Hz).

Example 61

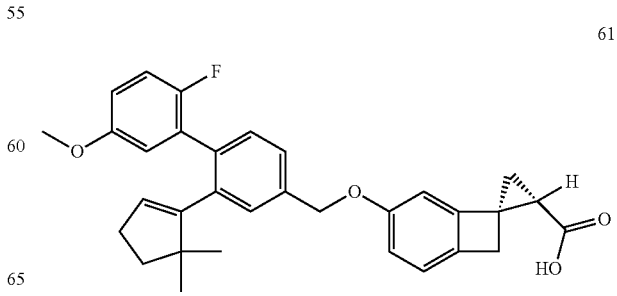

(2'S,7R)-4-(3-(((2-(5,5-Dimethyl-1-cyclopenten-1-yl)-2'-fluoro-5'-(methyloxy)-1,1'-biphenyl-4-yl)methyl)oxy)hydroxyspiro[bicyclo[4.2.0]octane-7,1'-cyclopropane]-1,3,5-triene-2'-carboxylic acid (61)

Example 61 was synthesized from compounds H7B and T2 using the same method used to prepare compound 33. MS ESI (pos.) m/e: 499.2 (M+H)⁺. ¹H NMR (400 MHz, CDCl₃) δ ppm 7.38 (1H, m), 7.26-7.34 (2H, m), 6.93-7.02 (2H, m), 6.87-6.91 (2H, m), 6.80-6.78 (2H, m), 5.52 (1H, s), 5.03 (2H, s), 3.76 (3H, s), 3.31 (2H, m), 2.25 (3H, br.), 1.81 (1H, d, J=5.5 Hz), 1.64-1.69 (2H, m), 0.85 (6H, d, J=3.9 Hz).

Example 62

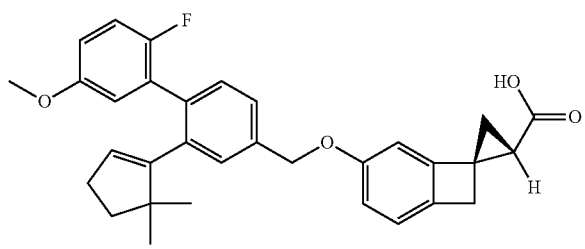

62

(2'S,7S)-4-(3-(((2-(5,5-Dimethyl-1-cyclopenten-1-yl)-2'-fluoro-5'-(methyloxy)-1,1'-biphenyl-4-yl)methyl)oxy)hydroxyspiro[bicyclo[4.2.0]octane-7,1'-cyclopropane]-1,3,5-triene-2'-carboxylic acid (62)

Compound 62 was synthesized from compounds H7C and T2 using the same method used to prepare compound 33. MS ESI (pos.) m/e: 499.2 (M+H)⁺. ¹H NMR (400 MHz, CDCl₃) δ ppm 7.37 (2 Hm), 7.04 (1H, d, J=8.2 Hz), 6.99-6.93 (1H, m), 6.90 (1H, dd, J=8.0, 2.2 Hz), 6.80 (2H, m), 6.56 (1H, d, J=2.3 Hz), 5.53 (1H, s), 5.05 (2H, s), 3.76 (3H, s), 3.36 (2H, s), 2.27 (3H, m), 1.82 (1H, t, J=5.5 Hz), 1.63 (1H, d, J=3.1 Hz), 1.66 (2H, t, J=7.0 Hz), 0.86 (6H, s).

Example 63

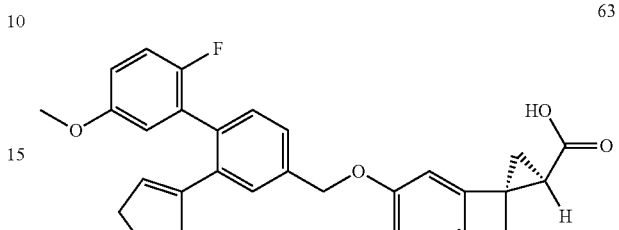

63

(2R,7R)-4-(3-(((2-(5,5-Dimethyl-1-cyclopenten-1-yl)-2'-fluoro-5'-(methyloxy)-1,1'-biphenyl-4-yl)methyl)oxy)hydroxyspiro[bicyclo[4.2.0]octane-7,1'-cyclopropane]-1,3,5-triene-2'-carboxylic acid (63)

Compound 63 was synthesized from compounds H7D and T2 using the same method used to prepare compound 33. MS ESI (pos.) m/e: 499.2 (M+H)⁺. 1H NMR (400 MHz, CDCl₃) δ ppm 7.37 (2 Hm), 7.04 (1H, d, J=8.2 Hz), 6.99-6.93 (1H, m), 6.90 (1H, dd, J=8.0, 2.2 Hz), 6.80 (2H, m), 6.56 (1H, d, J=2.3 Hz), 5.53 (1H, s), 5.05 (2H, s), 3.76 (3H, s), 3.36 (2H, s), 2.27 (3H, m), 1.82 (1H, t, J=5.5 Hz), 1.63 (1H, d, J=3.1 Hz), 1.66 (2H, t, J=7.0 Hz), 0.86 (6H, s).

Examples 64-67

Examples 64-67 are synthesized according to the following scheme:

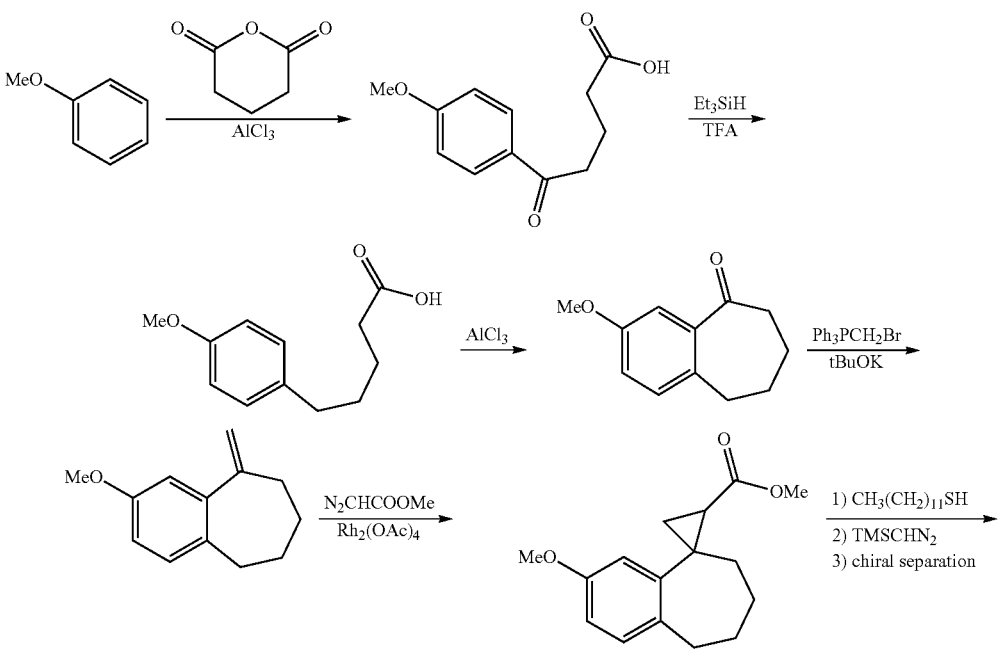

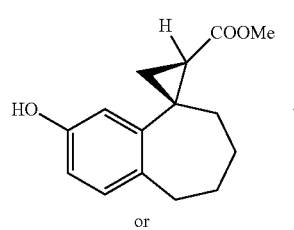 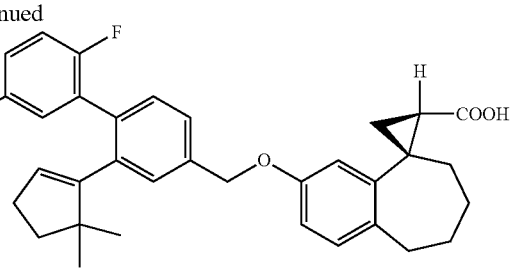
64
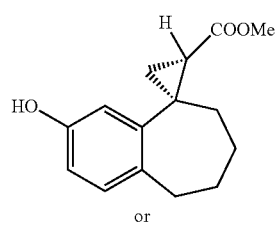 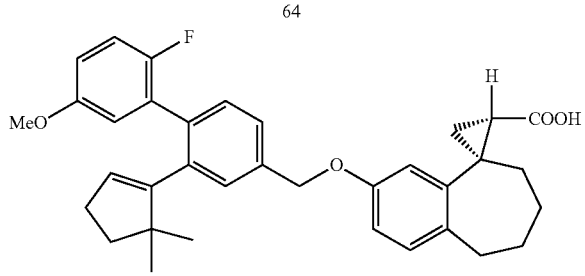
65
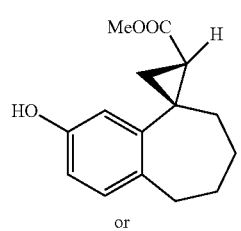 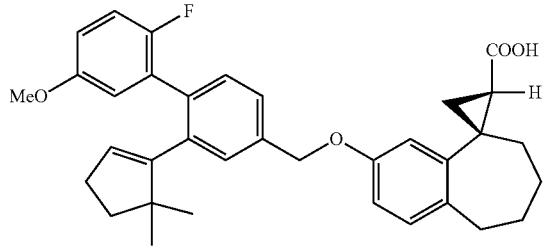
66
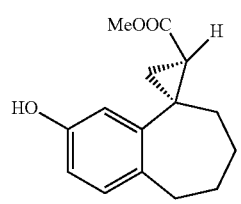 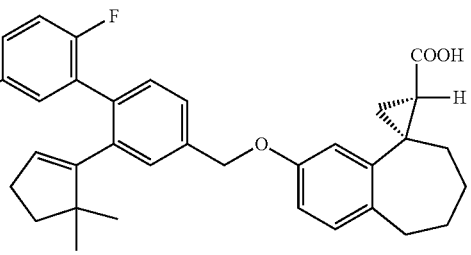
67
Examples 68-71
Examples 68-71 are synthesized according to the following scheme. One of the four stereoisomers was synthesized as described in Example 151.
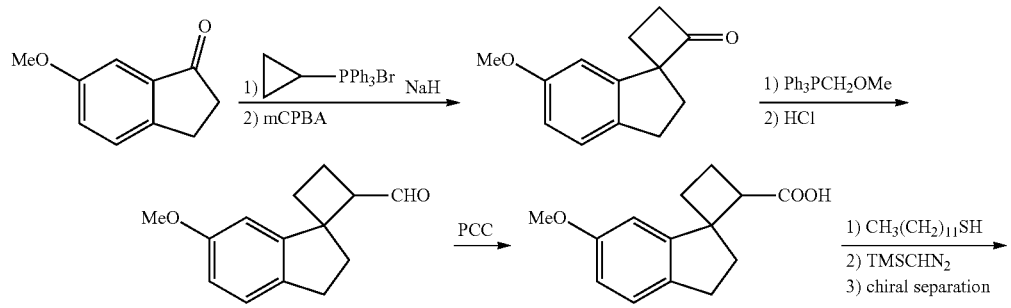

-continued
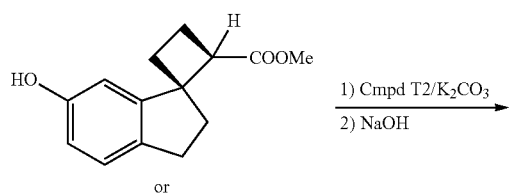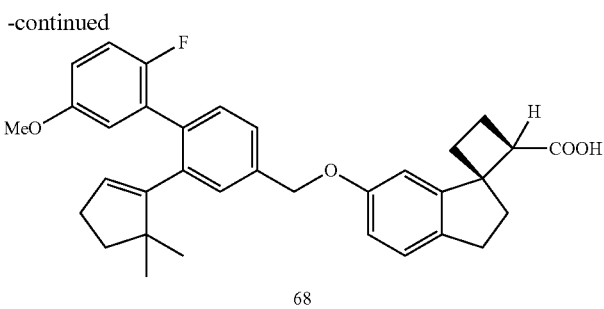
68
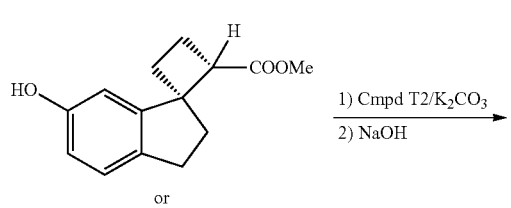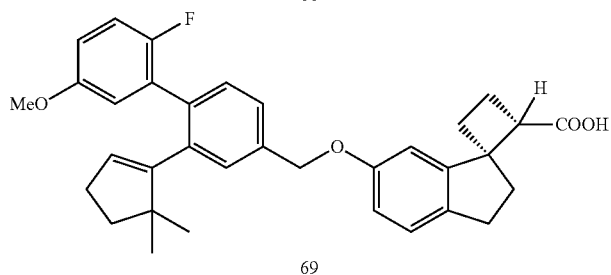
69
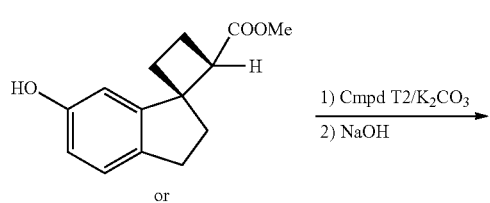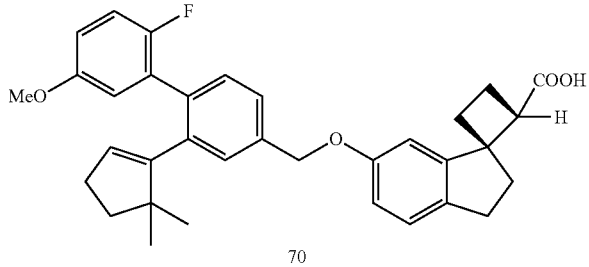
70
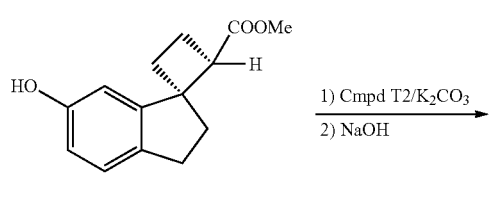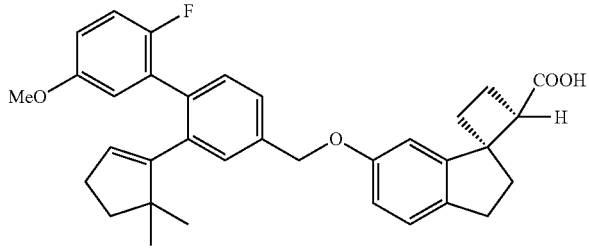
71
See Nemoto et al., Org. Lett., 1(3), pp. 517-519 (1999).
Examples 72-75
Examples 72-75 are synthesized according to the following scheme:
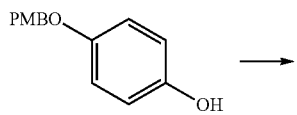
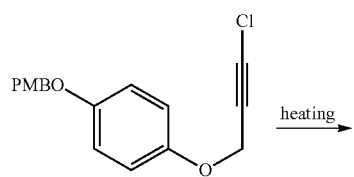
-continued
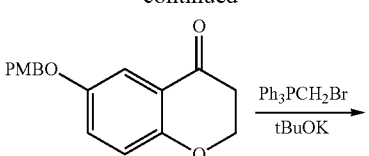
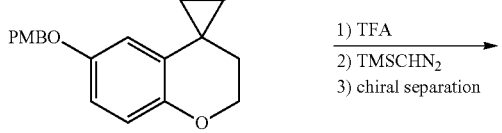

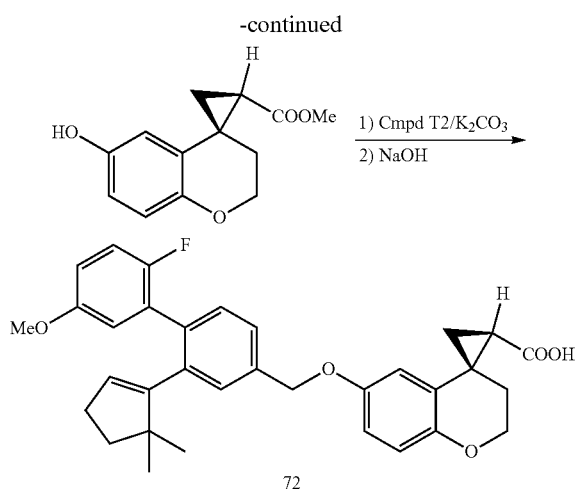
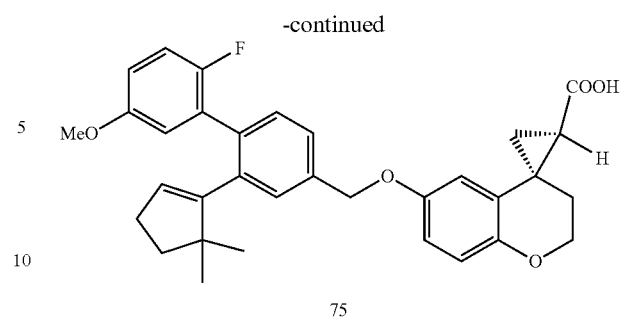
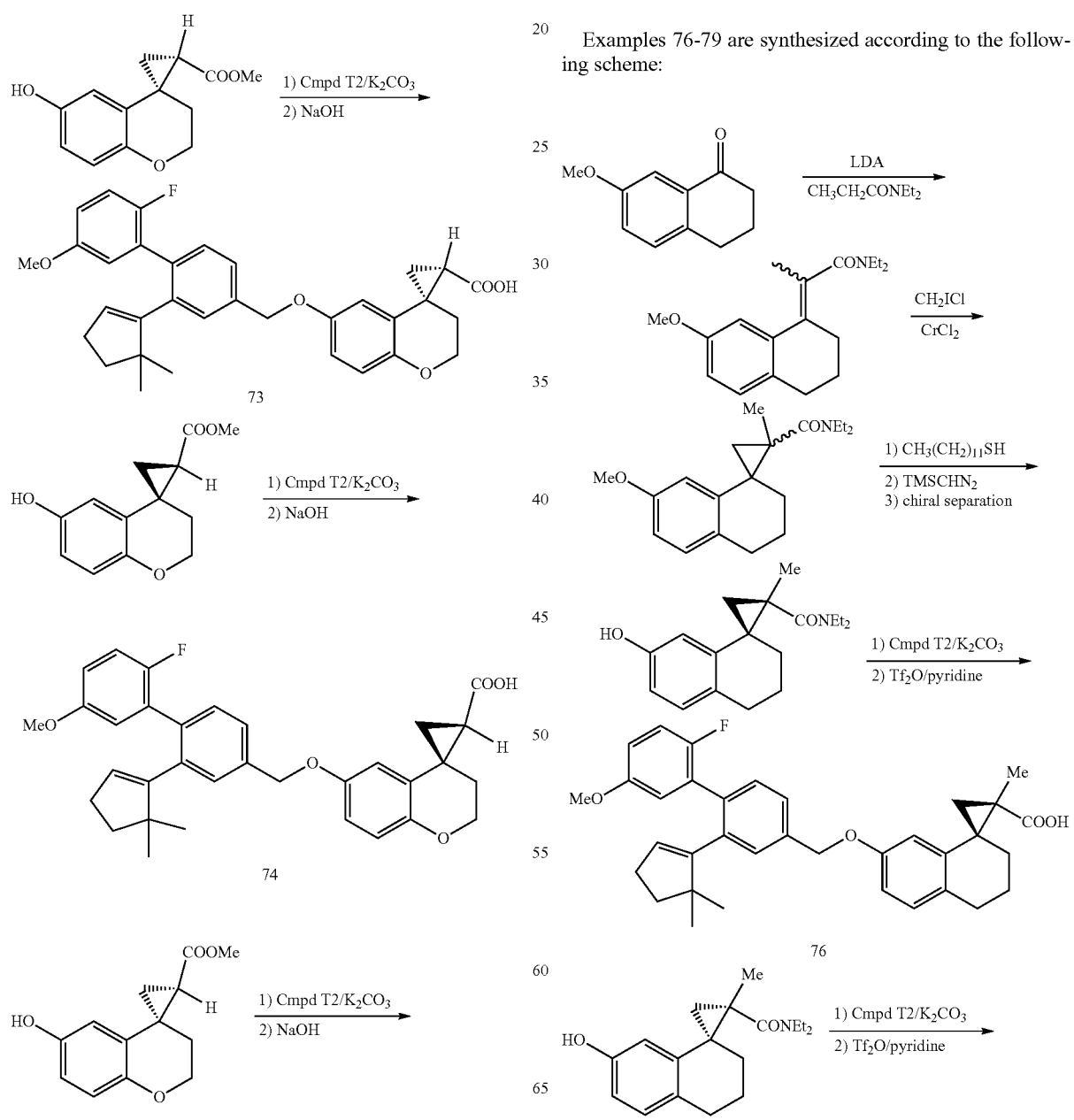
See Ariamala, G. et al., Tetrahedron, 45(1), pp 309-318 (1989).
Examples 76-79
Examples 76-79 are synthesized according to the following scheme:

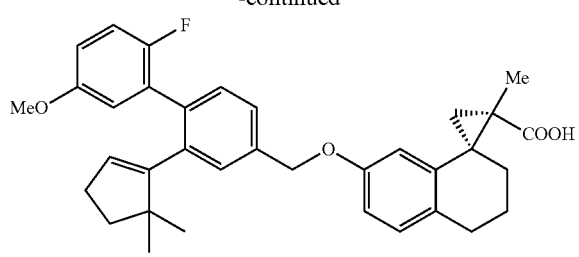
77
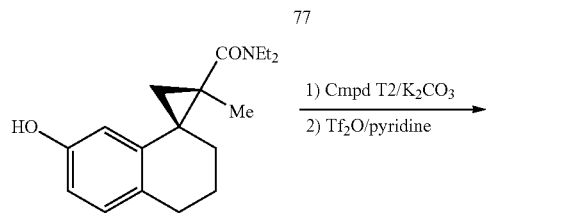
78
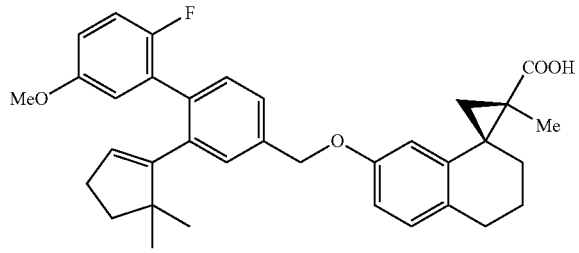
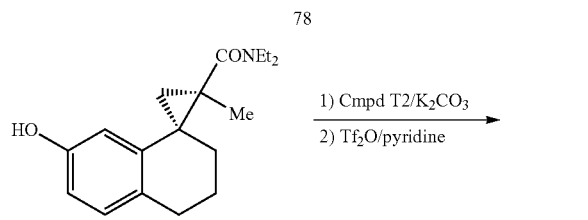
79
See Concellón et al. Org. Lett., 9(16), pp. 2981-2984 (2007).
Examples 80-83
Examples 80-83 are synthesized according to the following scheme:
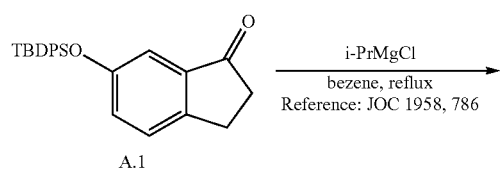
A.1
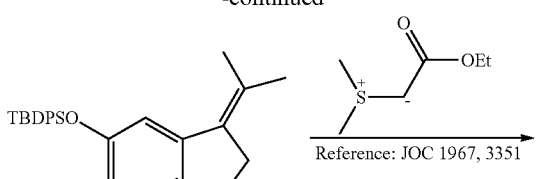
80.1
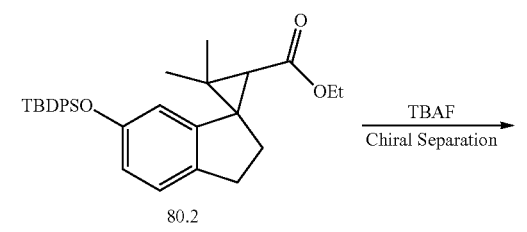
80.2
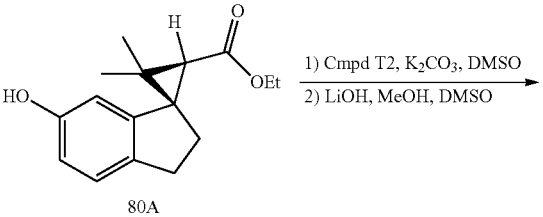
80A
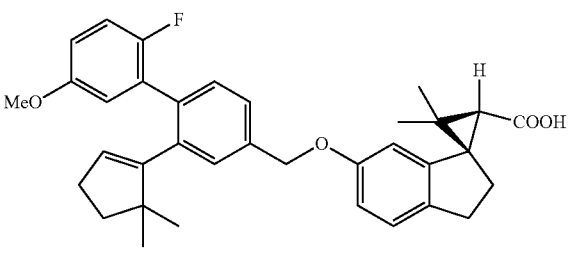
80
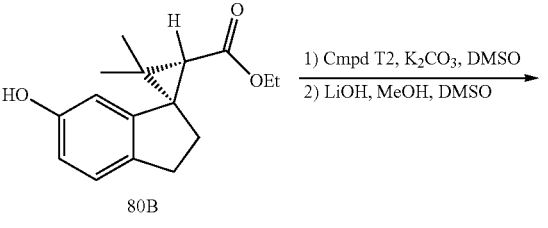
80B
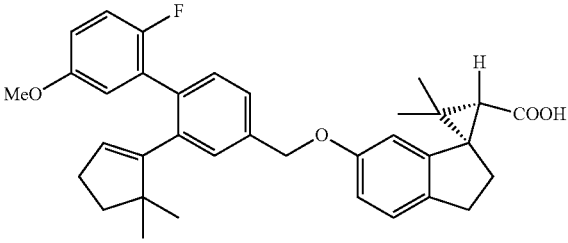
81
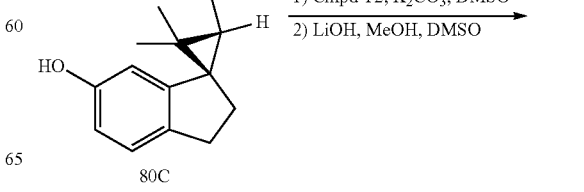
80C

369
-continued
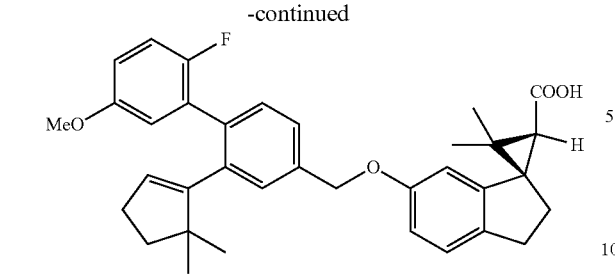
82
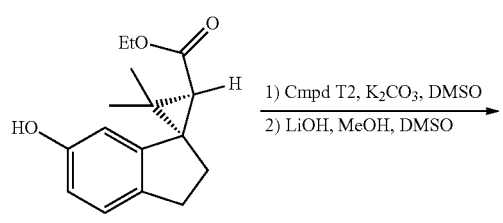
80D
1) Cmpd T2, K$_2$CO$_3$, DMSO
2) LiOH, MeOH, DMSO
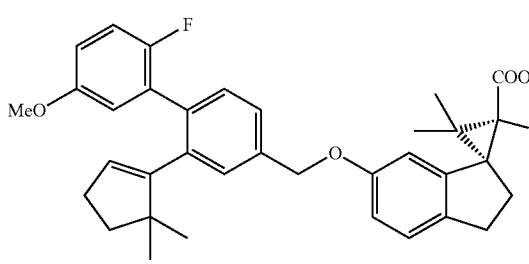
83
Examples 84-87
Examples 84-87 are synthesized according to the following scheme:
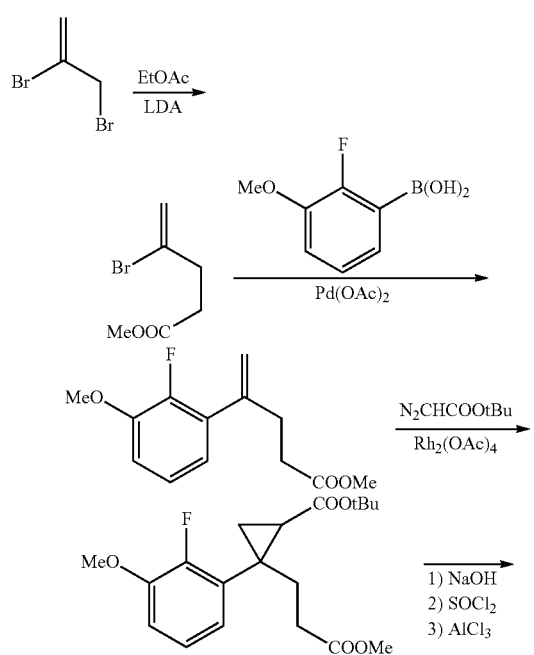
370
-continued
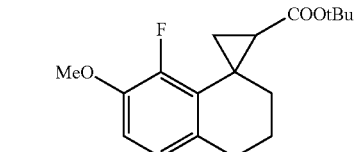
DAST →
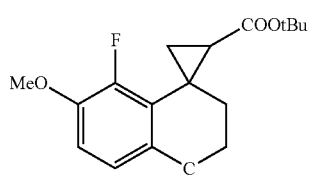
1) CH$_3$(CH$_2$)$_{11}$SH
2) chiral separation →
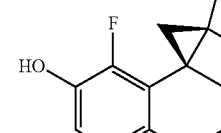
1) Cmpd T2/K$_2$CO$_3$
2) TFA →
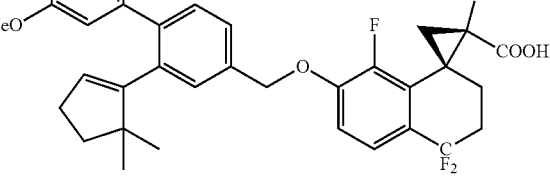
84
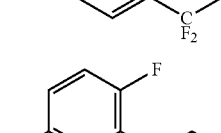
1) Cmpd T2/K$_2$CO$_3$
2) TFA →
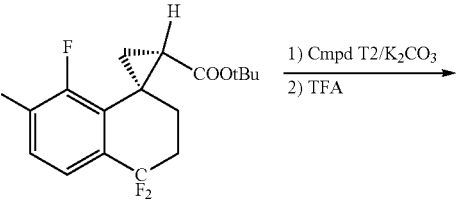
85
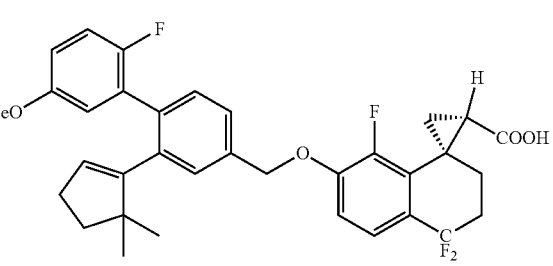
1) Cmpd T2/K$_2$CO$_3$
2) TFA →

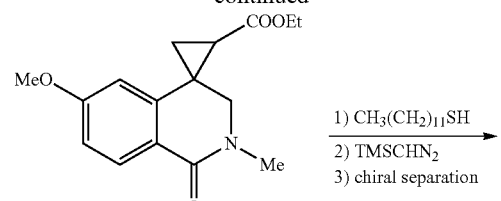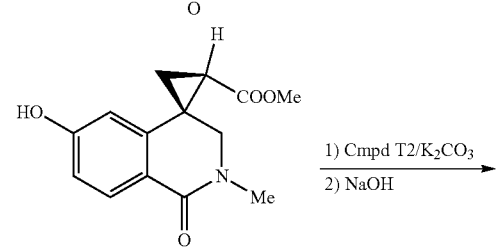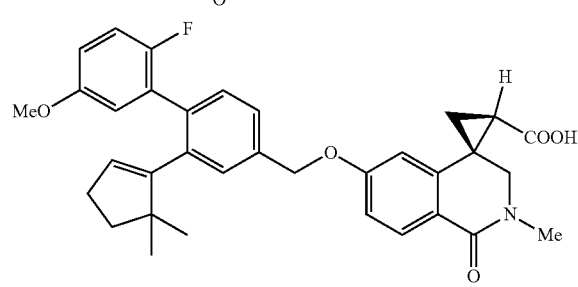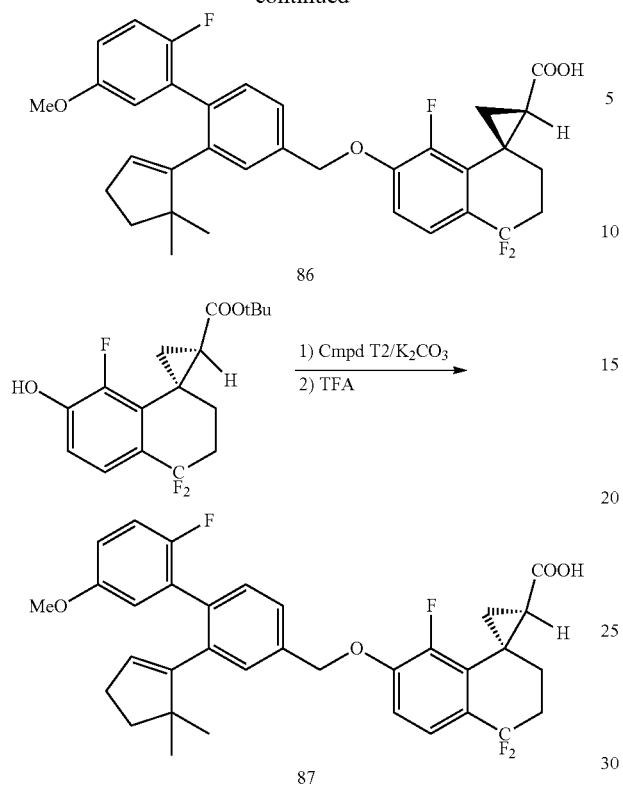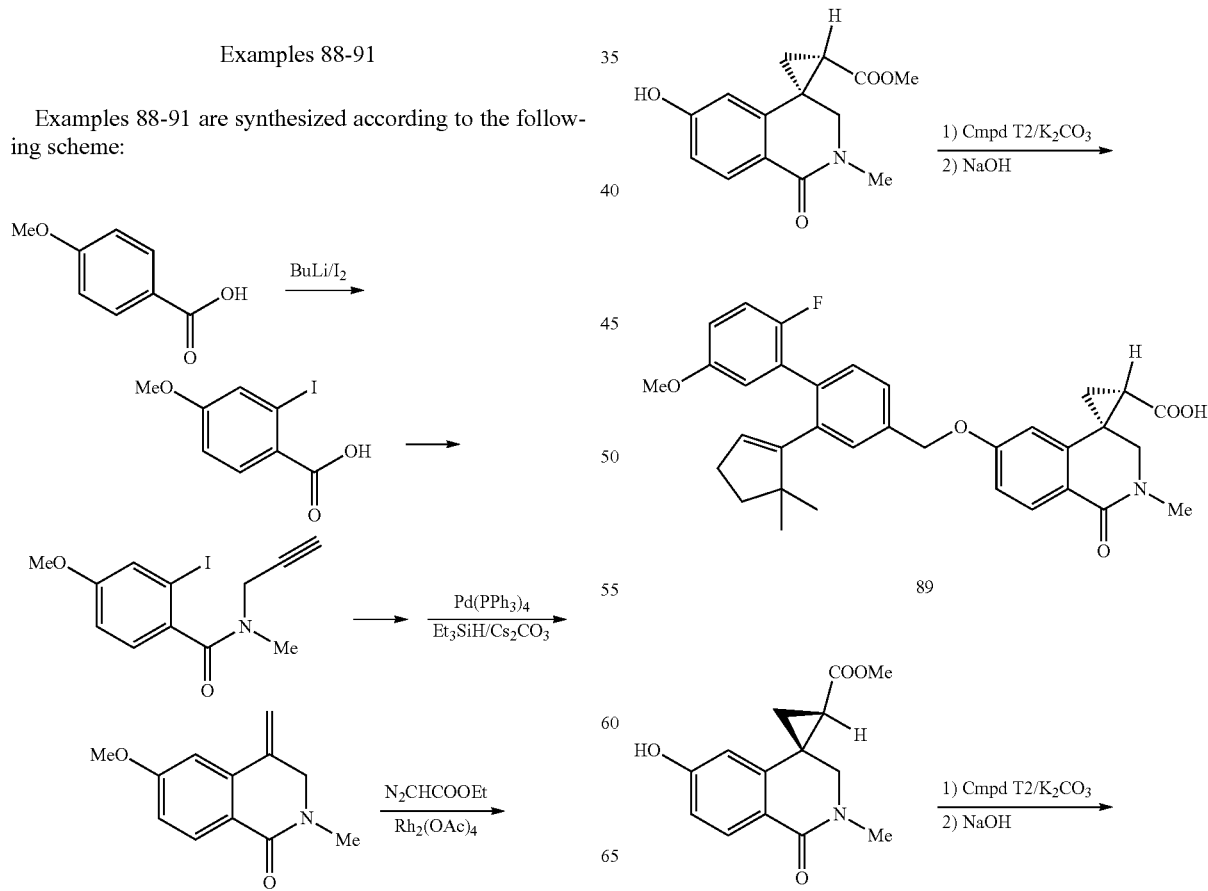

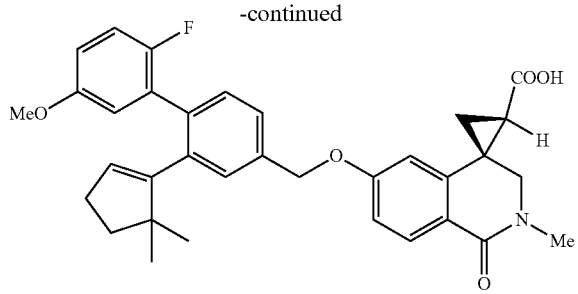

90

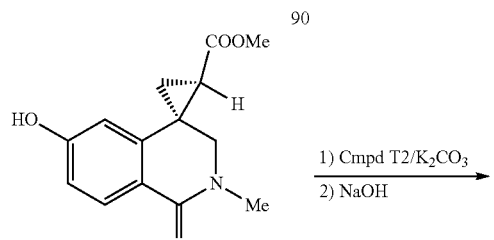

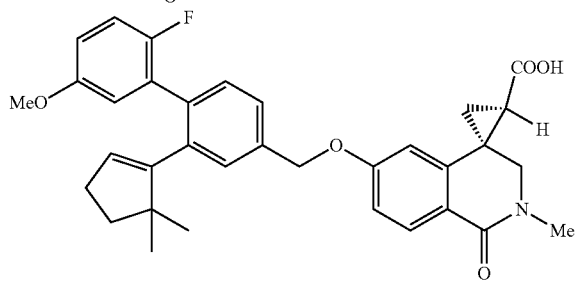

91

References:
1) JOC 2007, 72(9), 3419;
2) TL 2003, 44(19), 3785.

Examples 92-107

Examples 92-103 and 105-107 are synthesized by reacting compound H1A with commercially available starting materials or chloro or hydroxy reagents described herein or in various patent applications including U.S. Patent Application Publication No. US 2006/0004012; U.S. Patent Application Publication No. US 2006/0270724; U.S. Patent Application Publication No. US 2007/0066647; U.S. Patent Application Publication No. US 2007/0244155; U.S. Patent Application Publication No. US 2008/0090840; and U.S. Patent Application Publication No. US 2008/0119511 and then hydrolyzing the ester obtained using the methodology described herein.

Example 92

Example 92 is synthesized from H1A and the appropriate biphenyl reagent.

Example 93

Example 93 is synthesized from H1A and the appropriate tail reagents and boronic acid reagents using the method described in Examples 47, 59, and 62 of US 2007/0066647.

Example 94

Example 94 is synthesized from H1A and the appropriate tail reagents and boronic acid reagents using a method analogous to that described in Examples 47, 59, and 62 of US 2007/0066647 starting with the appropriate indane compound.

Example 95

Example 95 is synthesized from H1A and 1-indanol (commercially available from Sigma-Aldrich, St. Louis, Mo., USA) using the method described in Example 46 of US 2007/0066647.

Example 96

Example 96 is synthesized from H1A and 2-indanol (commercially available from Sigma-Aldrich, St. Louis, Mo., USA) using the method described in Example 27 of US 2007/0066647.

Example 97

Example 97 is synthesized from H1A and the appropriate chloromethyl thiazole phenyl compound (commercially available) which is prepared using the method described in Example 3.1 of US 2006/0004012.

Example 98

Example 98 is synthesized from H1A and the appropriate oxadiazole phenyl compound which is prepared using the method described in Example 27.1 of US 2006/0004012.

Example 99

Example 99 is synthesized according to the following scheme:

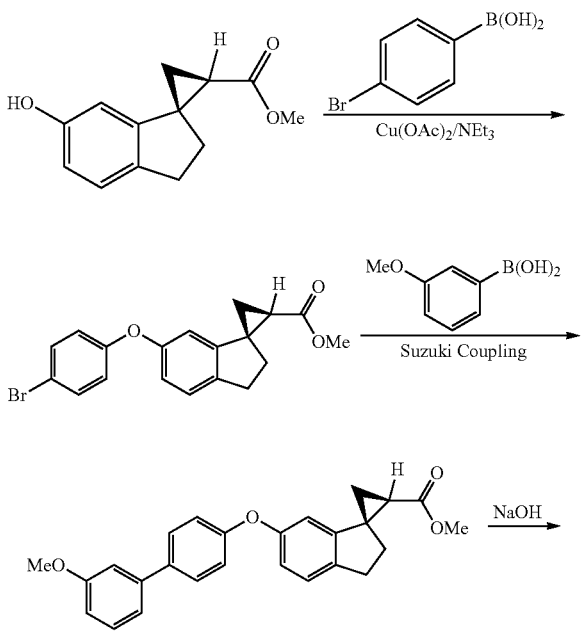

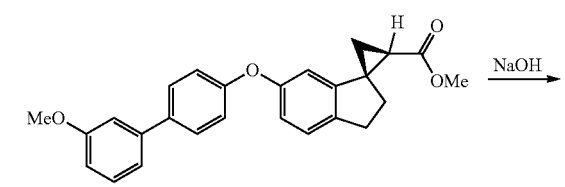

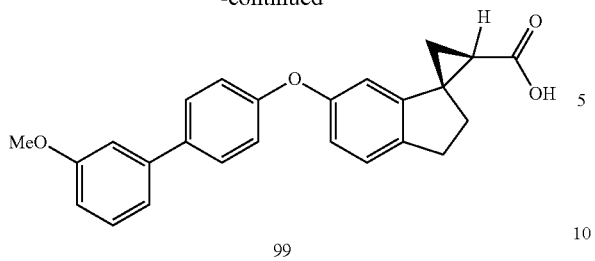

99

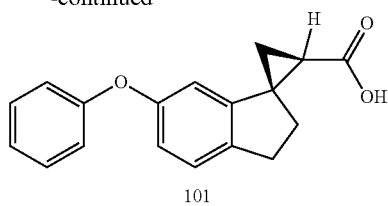

101

Example 100

Example 100 is synthesized according to the following scheme:

Example 102

Example 102 is synthesized from H1A and commercially available benzyl chloride or benzyl bromide using the method described herein.

Example 103

Example 103 is synthesized from H1A and 2-(bromomethyl)naphthalene or 2-(hydroxymethyl)naphthalene (which are commercially available from Sigma-Aldrich, St. Louis, Mo., USA) using the methods described herein.

Example 104

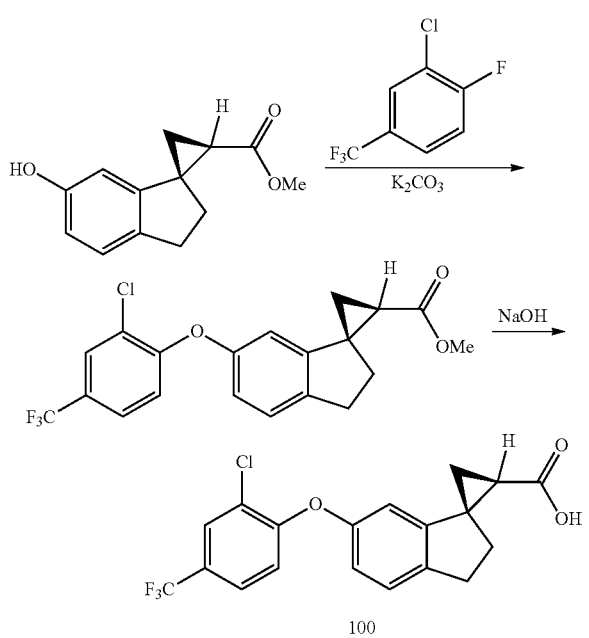

100

Example 101

Example 101 is synthesized according to the following scheme:

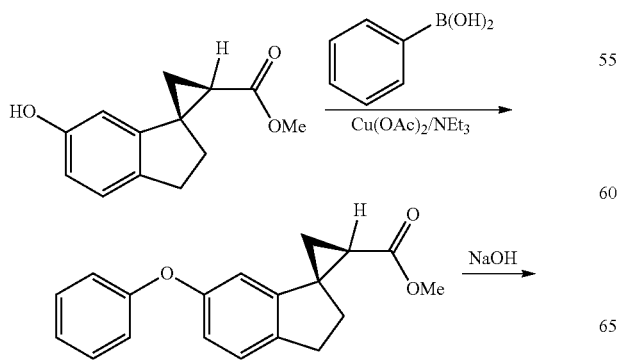

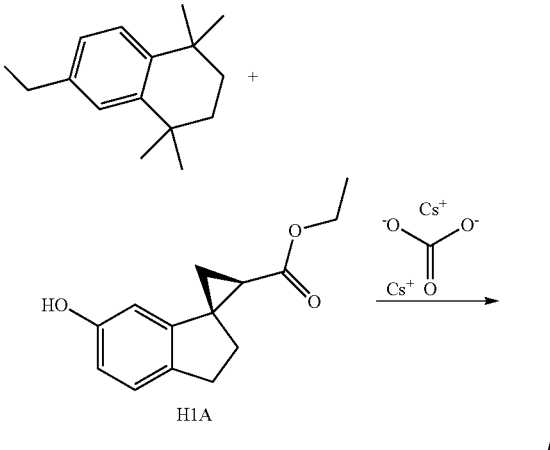

H1A 104.1

Compound 104.1

Compound 104.1 was synthesized from 6-(chloromethyl)-1,1,4,4-tetramethyl-1,2,3,4-tetrahydronaphthalene (commercially available from Maybridge) and compound H1A using a procedure analogous to that described for synthesizing 1.1.

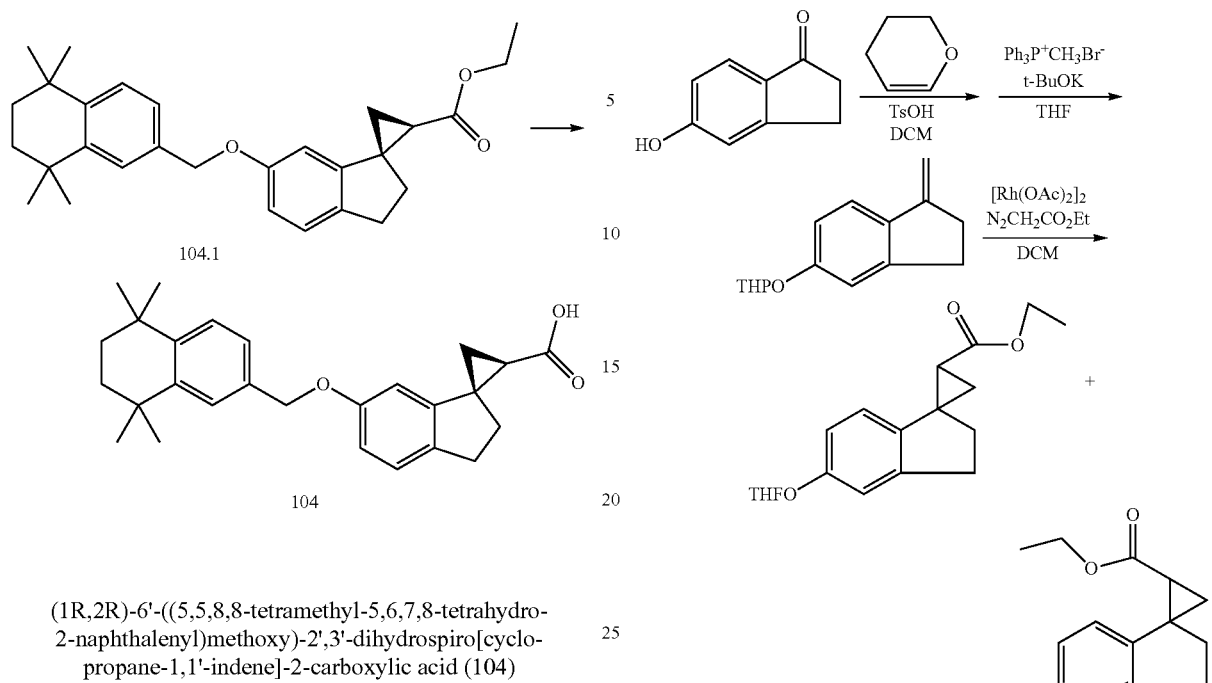

104.1

104

(1R,2R)-6'-((5,5,8,8-tetramethyl-5,6,7,8-tetrahydro-2-naphthalenyl)methoxy)-2',3'-dihydrospiro[cyclopropane-1,1'-indene]-2-carboxylic acid (104)

Example 104 was synthesized from 104.1 using a procedure analogous to that described for synthesizing 1 from 1.1. MS ESI (neg.) m/e: 403 (M−H).

Example 105

Example 105 is synthesized from H1A and commercially available cyclohexylmethyl bromide using the methods described herein or in Example 68 of US 2007/0066647.

Example 106

Example 106 is synthesized from H1A and either (2-bromoethyl)benzene or 2-phenylethanol (which are both commercially available from Sigma-Aldrich, St. Louis, Mo., USA) using the methods described herein.

Example 107

Example 107 is synthesized from H1A and either (3-bromopropyl)benzene or 3-phenyl-1-propanol (which are both commercially available from Sigma-Aldrich, St. Louis, Mo., USA) using the methods described herein.

Examples 108-122 are synthesized by reacting intermediate H8A (shown in the scheme below) with commercially available starting materials or biphenyl reagents described herein or in various patent applications including U.S. Patent Application Publication No. US 2006/0004012; U.S. Patent Application Publication No. US 2006/0270724; U.S. Patent Application Publication No. US 2007/0066647; U.S. Patent Application Publication No. US 2007/0244155; U.S. Patent Application Publication No. US 2008/0090840; and U.S. Patent Application Publication No. US 2008/0119511 and then hydrolyzing the ester obtained using the methodology described herein.

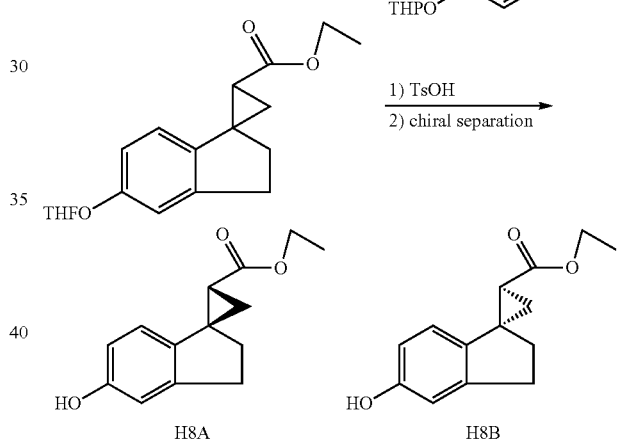

H8A H8B

Example 108

Example 108 is synthesized from H8A and commercially available starting materials.

Example 109

Example 109 is synthesized from H8A and Ti using the method described herein.

Example 110

Example 110 is synthesized from H8A and commercially available starting materials.

Examples 111-112

Examples 111 and 112 are synthesized using a procedure similar to that used to prepare Example 99 using intermediate H8A and commercially available starting materials.

Example 113

Example 113 is synthesized using a procedure similar to that used to prepare Example 100 using intermediate H8A and commercially available starting materials.

Example 114

Example 114 is synthesized using a procedure similar to that used to prepare Example 101 using intermediate H8A and commercially available starting materials.

Example 115

Example 115 is synthesized from H8A and the appropriate chloromethyl thiazole phenyl compound (commercially available) which is prepared using the method described in Example 3.1 of US 2006/0004012.

Example 116

Example 116 is synthesized from H8A and the appropriate oxadiazole phenyl compound which is prepared using the method described in Example 27.1 of US 2006/0004012.

Example 117

Example 117 is synthesized from H8A and 6-bromomethyl-1,1,4,4-tetramethyl-1,2,3,4-tetrahydronaphthalene or 6-chloromethyl-1,1,4,4-tetramethyl-1,2,3,4-tetrahydronaphthalene which are commercially available using the method described herein. See also General Procedure E of US 2007/0066647.

Example 118

Example 118 is synthesized from H8A and commercially available cyclohexylmethyl bromide using the methods described herein or in Example 68 of US 2007/0066647.

Example 119

Example 119 is synthesized from H8A and commercially available benzyl chloride or benzyl bromide using the methods described herein.

Example 120

Example 120 is synthesized from H8A and commercially available 1-bromomethylnaphthalene using the methods described herein.

Example 121

Example 121 is synthesized from H8A and either (2-bromoethyl)benzene or 2-phenylethanol (which are both commercially available from Sigma-Aldrich, St. Louis, Mo., USA) using the methods described herein.

Example 122

Example 122 is synthesized from H8A and either (3-bromopropyl)benzene or 3-phenyl-1-propanol (which are both commercially available from Sigma-Aldrich, St. Louis, Mo., USA) using the methods described herein.

The following scheme may be used to synthesize intermediates necessary to synthesize tetrahydronaphthalene analogs of Examples 108-122.

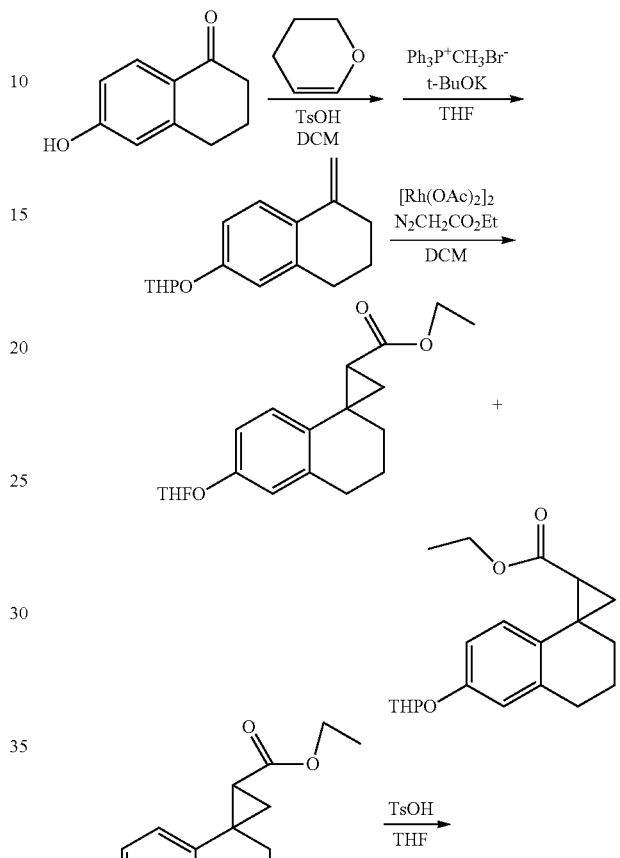

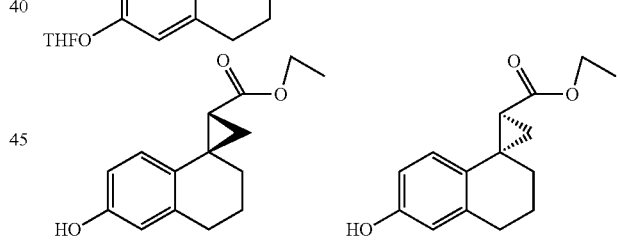

Example 123

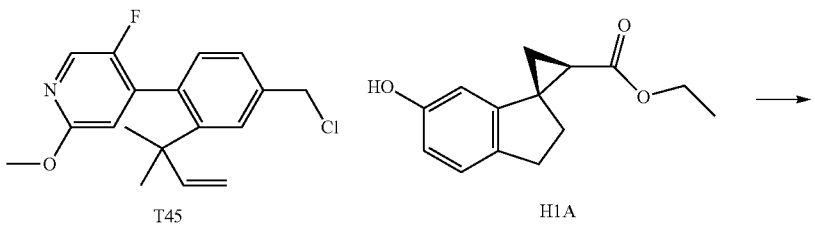

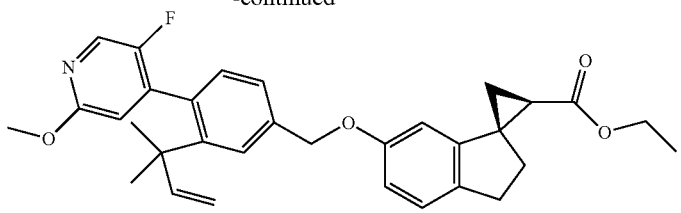

123.1

(1R,2R)-Ethyl 6'-(4-(5-fluoro-2-methoxypyridin-4-yl)-3-(2-methylbut-3-en-2-yl)benzyloxy)-2',3'-dihydrospiro[cyclopropane-1,1'-indene]-2-carboxylate (123.1)

The reaction mixture of T45 (30.0 mg, 93.8 μmol), H1A (21.8 mg, 93.8 μmol) and $Cs_2CO_3$ (76.4 mg, 235 μmol) in DMSO (1.0 mL) was stirred at room temperature overnight. The LCMS results indicated that the reaction was complete. The reaction mixture was used in the next step without further purification. MS ESI (pos.) M/E: 516.2 (M+H).

Example 124

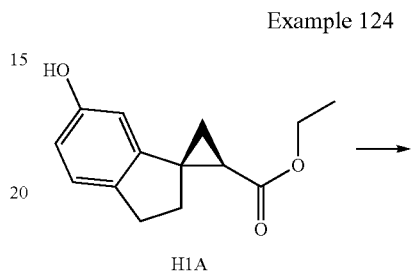

H1A

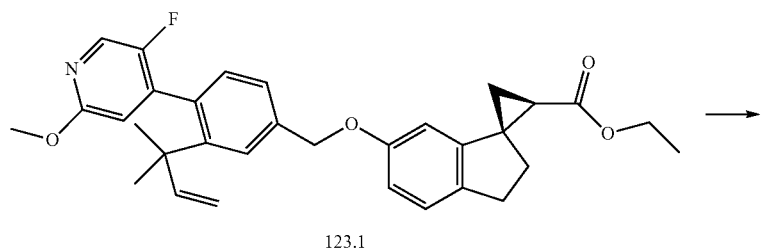

123.1

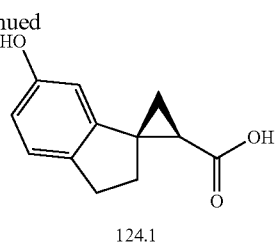

123

(1R,2R)-6'-(4-(5-Fluoro-2-methoxypyridin-4-yl)-3-(2-methylbut-3-en-2-yl)benzyloxy)-2',3'-dihydrospiro[cyclopropane-1,1'-indene]-2-carboxylic acid (123)

The reaction mixture of compound 123.1 (48.4 mg, 94 μmol) and lithium hydroxide (0.25 mL 3.3 M $LiOH_{(aq)}$, 0.75 mmol) in MeOH (0.6 m 1) was stirred at room temperature for 3 hours. The resulting mixture was purified by preparative HPLC (reverse phase) to give Example 123 (30.0 mg, 66% yield over two steps). MS ESI (pos.) M/E: 488.2 (M+H). $^1$H-NMR (500 MHz, $CDCl_3$) δ ppm 7.94 (1H, s), 7.58 (1H, s), 7.33 (1H, d, J=7.8 Hz), 7.15 (1H, d, J=8.1 Hz), 7.00 (1H, d, J=7.8 Hz), 6.85 (1H, dd, J=8.3, 2.4 Hz), 6.62 (1H, d, J=4.9 Hz), 6.36 (1H, d, J=2.2 Hz), 5.96 (1H, dd, J=17.5, 10.6 Hz), 5.05 (2H, s), 4.71-4.86 (2H, m), 3.88 (3H, s), 2.93-3.05 (2H, m), 2.39 (1H, dd, J=8.3, 6.2 Hz), 2.32 (1H, dd, J=8.3, 6.2 Hz), 1.96-2.06 (1H, m), 1.70 (1H, t, J=5.4 Hz), 1.51 (1H, dd, J=8.3, 4.8 Hz), 1.27 (3H, s), 1.25 (3H, s).

-continued

Compound 124.1

The title compound was synthesized from H1A using a procedure analogous to that described for synthesizing 1 from 1.1.

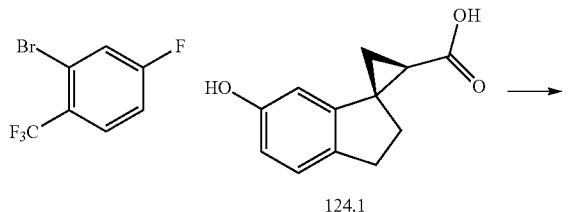

(1R,2R)-6'-(3-Bromo-4-(trifluoromethyl)phenoxy)-2',3'-dihydrospiro[cyclopropane-1,1'-indene]-2-carboxylic acid (124)

A mixture of 2-bromo-4-fluoro-1-(trifluoromethyl)benzene (0.030 g, 0.12 mmol) (commercially available from Oakwood), compound 124.1 (0.017 g, 0.083 mmol), and $Cs_2CO_3$ (0.081 g, 0.25 mmol) in DMF (1 mL) were stirred at 120° C. for 18 hours. The reaction mixture was loaded directly onto a silica gel cartridge and purified using column chromatography (1:1 EtOAc:hexanes) to obtain product 124 (0.024 g, 67% yield). MS ESI (neg.) m/e: 853.0 (2M−H). $^1$HNMR (CDCl$_3$) δ ppm 7.60 (1H, d, J=8.8 Hz), 7.22-7.26 (2H, m), 6.84-6.94 (2H, m), 6.42 (1H, d, J=2.2 Hz), 3.00-3.13 (2H, m), 2.40-2.48 (1H, m), 2.31-2.39 (1H, m), 2.01 (1H, dd, J=8.3, 6.1 Hz), 1.73 (1H, t, J=5.5 Hz), 1.49 (1H, dd, J=8.4, 5.0 Hz).

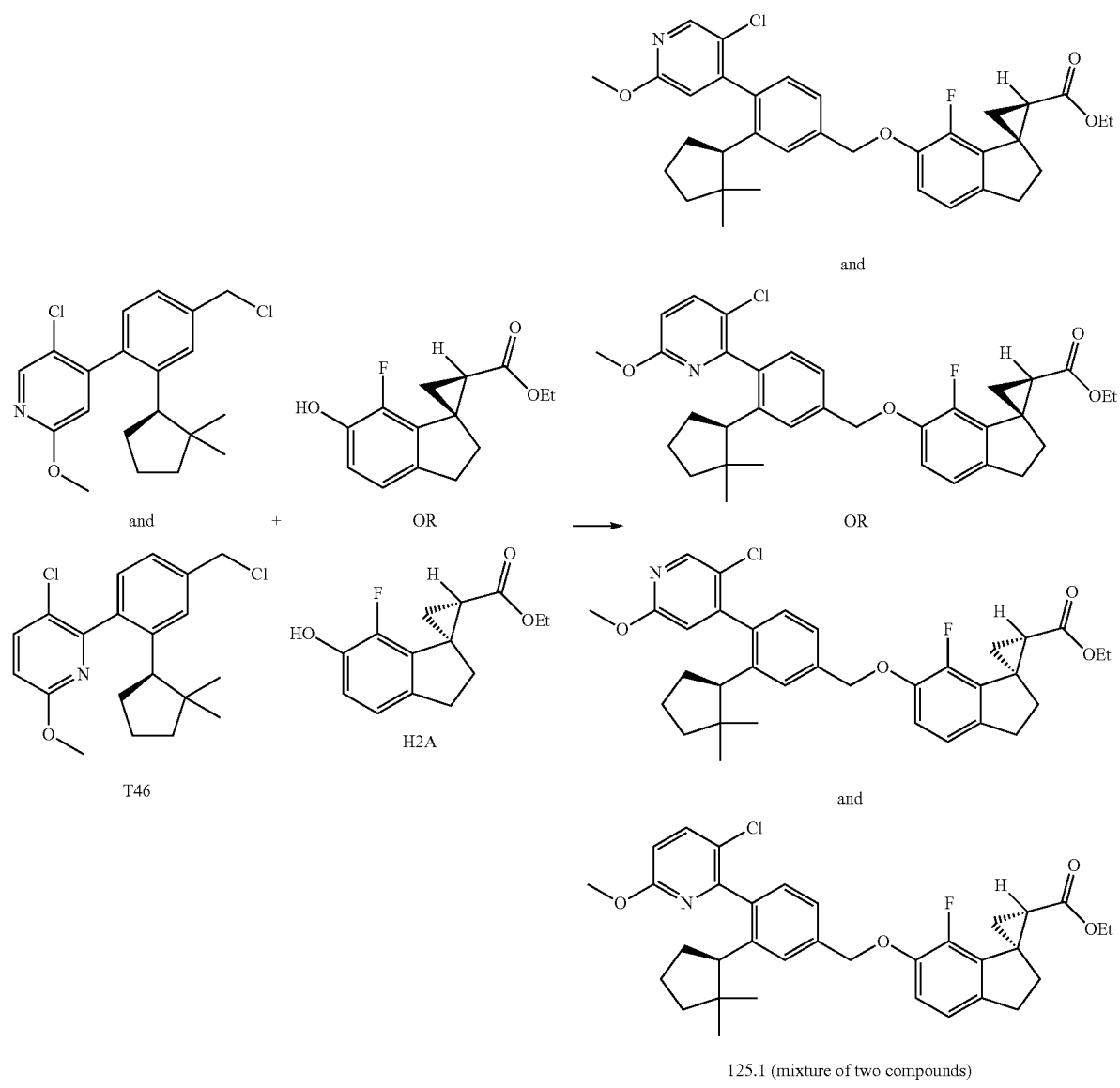

385

(1R,2R)-Ethyl 6'-(4-(5-chloro-2-methoxypyridin-4-yl)-3-(R)-2,2-dimethylcyclopentyl)benzyloxy)-7'-fluoro-2',3'-dihydrospiro[cyclopropane-1,1'-indene]-2-carboxylate and (1R,2R)-ethyl 6'-(4-(3-chloro-6-methoxypyridin-2-yl)-3-((R)-2,2-dimethylcyclopentyl)benzyloxy)-7'-fluoro-2',3'-dihydrospiro[cyclopropane-1,1'-indene]-2-carboxylate, or (1S,2S)-ethyl 6'-(4-(5-chloro-2-methoxypyridin-4-yl)-3-(R)-2,2-dimethylcyclopentyl)benzyloxy)-7'-fluoro-2',3'-dihydrospiro[cyclopropane-1,1'-indene]-2-carboxylate and (1S,2S)-ethyl 6'-(4-(3-chloro-6-methoxypyridin-2-yl)-3-(R)-2,2-dimethylcyclopentyl)benzyloxy)-7'-fluoro-2',3'-dihydrospiro[cyclopropane-1,1'-indene]-2-carboxylate (125.1)

The title compounds were synthesized from the mixture of compounds T46 and compound H2A using a procedure analogous to that described for synthesizing 1.1.

386

Examples 125 and 126

The title compounds were synthesized from 125.1 using a procedure analogous to that described for synthesizing 1 from 1.1. Purification of the product using prep-HPLC provided pure compound 125. [MS ESI (pos.) M/E: 550.2 (M+1)] and pure compound 126 [MS ESI (pos.) M/E: 550.2 (M+1)].

Example 127

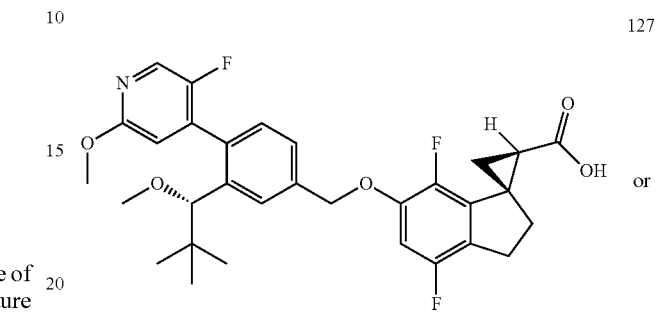

127 or

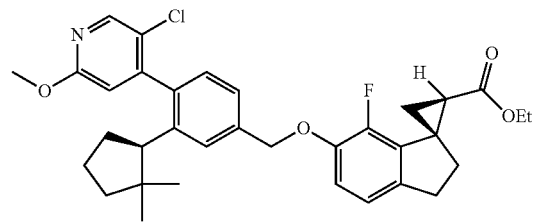

and

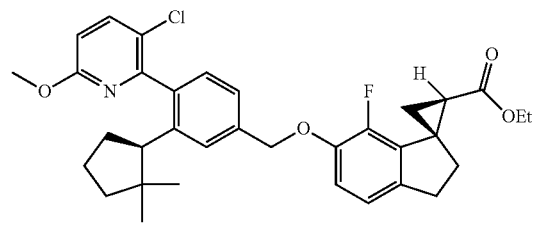

OR

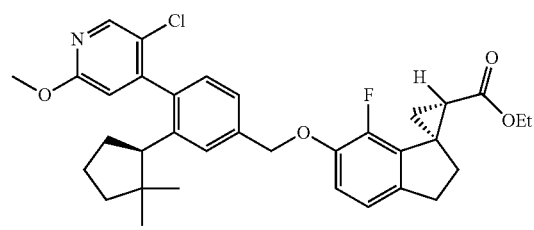

and

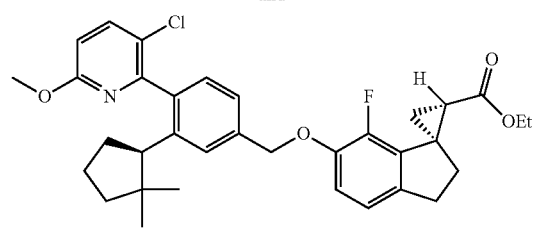

125.1 (mixture of two compounds)

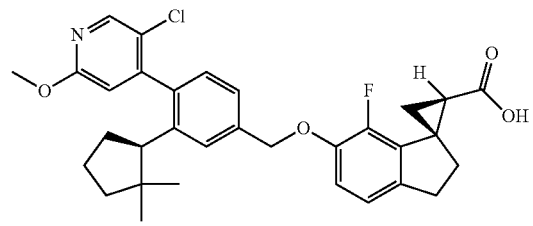

and

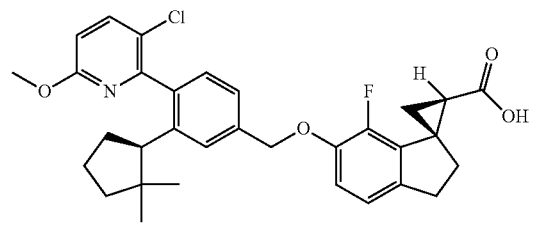

OR

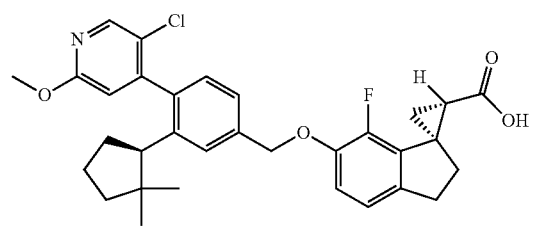

and

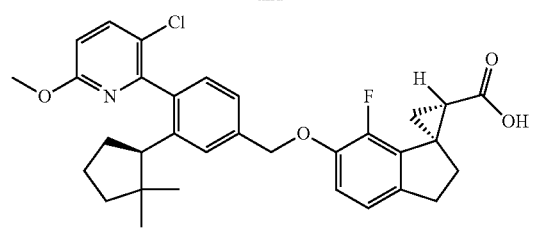

125 and 126

-continued

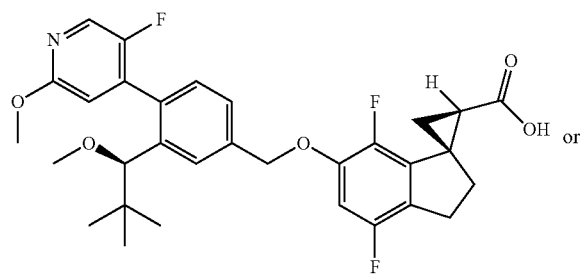

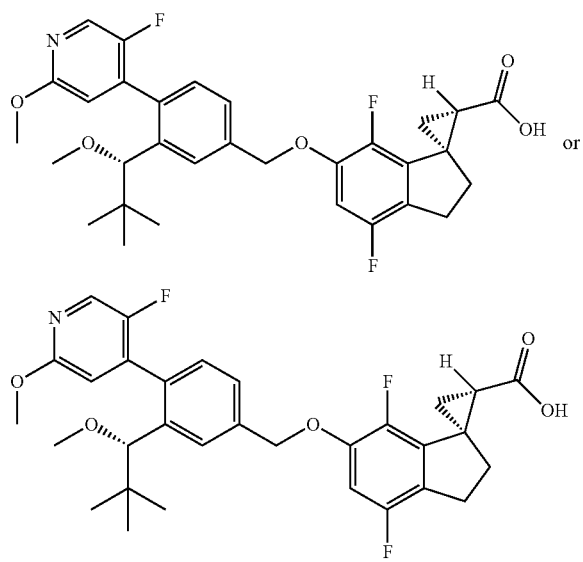

Example 127

The title compound was prepared from T6 and H3A according to the analogous methods described for the synthesis of compound 33. MS ESI (neg.) m/e: 554.2 (M−H).

Example 128

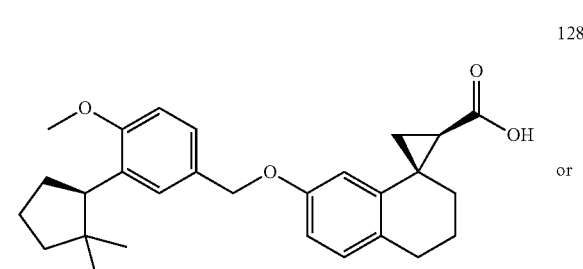

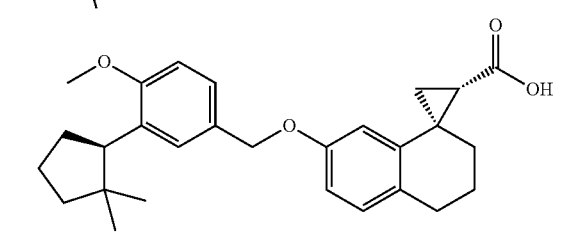

Example 128

128 was synthesized from T47 and H4A according to the procedure utilized for 13.1 followed by the ester hydrolysis method utilized for 1. MS ESI (neg.) m/e: 433.3 (M−H)$^+$.

Example 129

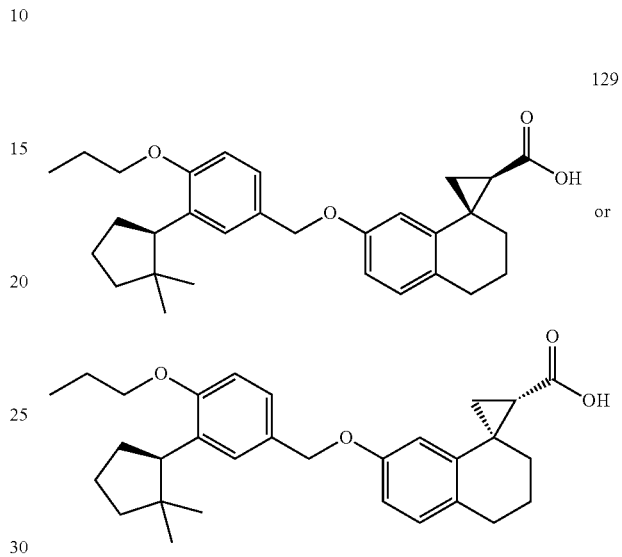

Example 129

129 was synthesized from T48 and H4A according to the procedure utilized for 13.1 followed by the ester hydrolysis method utilized for 1. MS ESI (neg.) m/e: 461.2 (M−H)$^+$.

Example 130

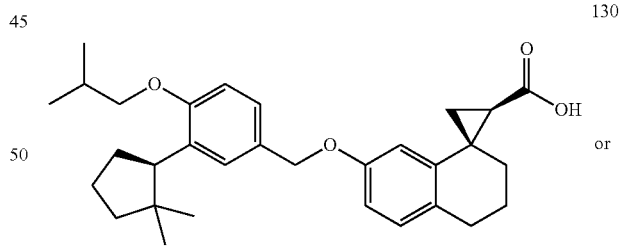

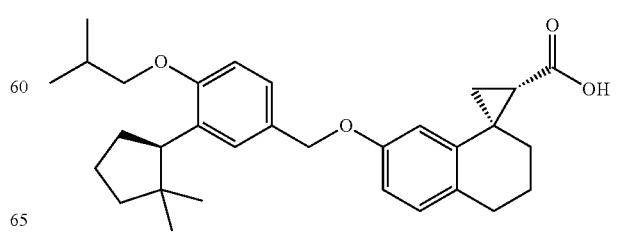

Example 130

130 was synthesized from T48 and H4A according to the procedure utilized for 13.1 followed by the ester hydrolysis method utilized for 1. MS ESI (neg.) m/e: 475.3 (M–H)+.

Example 131

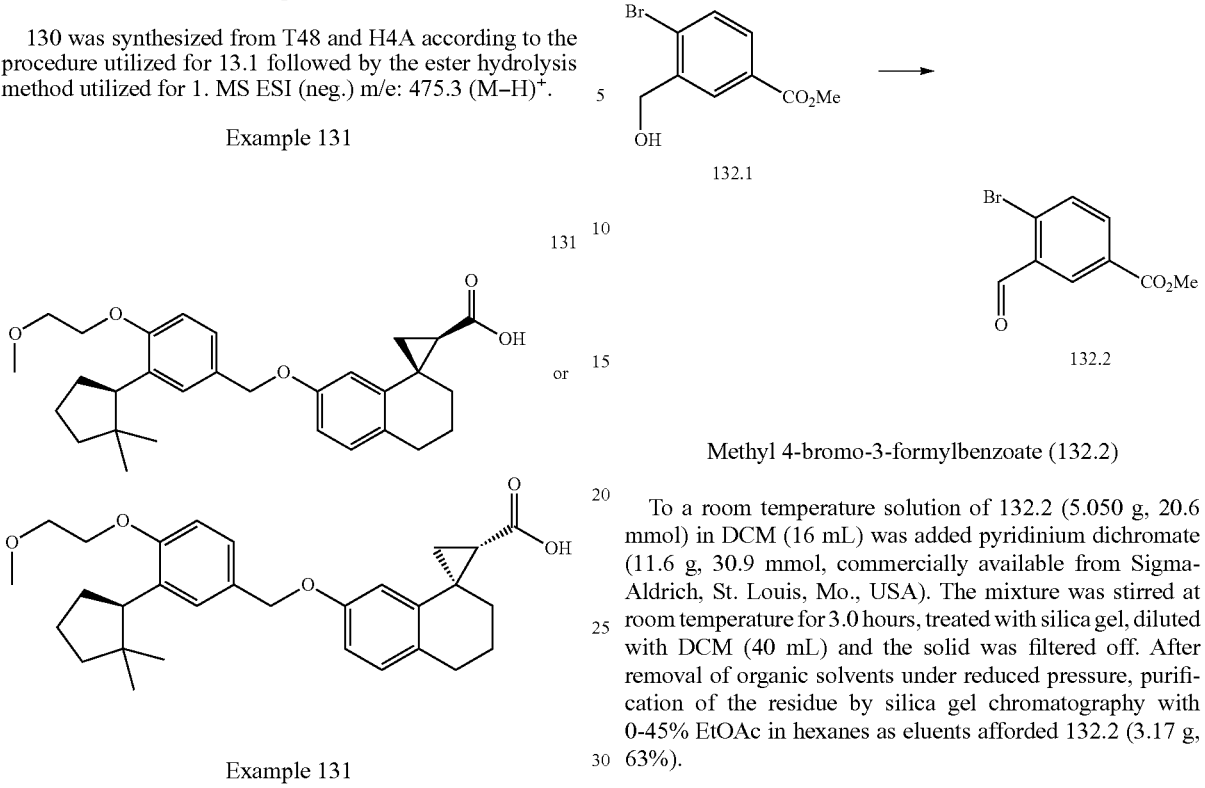

Example 131

Example 131

131 was synthesized from T48 and H4A according to the procedure utilized for 13.1 followed by the ester hydrolysis method utilized for 1. MS ESI (neg.) m/e: 477. (M–H)+.

Example 132

Methyl 4-bromo-3-(hydroxymethyl)benzoate (132.1)

To a –78° C. solution of dimethyl 4-bromoisophthalate (21.0 g, 77 mmol)(commercially available from Maybridge) in THF (100 mL) was slowly added diisobutylaluminum hydride (269 mL, 269 mol, 1.0 M solution in hexane, commercially available from Sigma-Aldrich, St. Louis, Mo., USA) over 20 minutes. After stirring at –78° C. for 3 hours, the resulting mixture was treated with MeOH. Organic solvents were removed under reduced pressure and the residue was redissolved in EtOAc and washed with 1.0 N HCl. After removal of organic solvents under reduced pressure, purification of the residue through silica gel chromatography with 0-35% EtOAc in hexanes as eluents afforded 132.1 (7.1 g, 38%).

Methyl 4-bromo-3-formylbenzoate (132.2)

To a room temperature solution of 132.2 (5.050 g, 20.6 mmol) in DCM (16 mL) was added pyridinium dichromate (11.6 g, 30.9 mmol, commercially available from Sigma-Aldrich, St. Louis, Mo., USA). The mixture was stirred at room temperature for 3.0 hours, treated with silica gel, diluted with DCM (40 mL) and the solid was filtered off. After removal of organic solvents under reduced pressure, purification of the residue by silica gel chromatography with 0-45% EtOAc in hexanes as eluents afforded 132.2 (3.17 g, 63%).

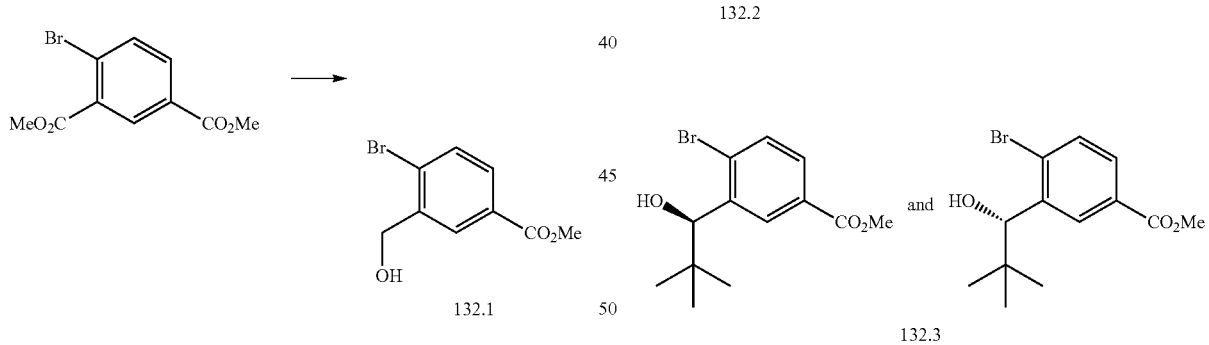

(S)-Methyl 4-bromo-3-(1-hydroxy-2,2-dimethylpropyl)benzoate and (R)-methyl 4-bromo-3-(1-hydroxy-2,2-dimethylpropyl)benzoate (132.3)

To a –78° C. solution of 132.2 (2.35 g, 9.67 mmol) in THF (35 mL) was added tert-butylmagnesium chloride (5318 μL, 10635 μmol, 2.0 M solution in diethyl ether, commercially available from Sigma-Aldrich, St. Louis, Mo., USA). The mixture was allowed to warm to 0° C. over 3.0 hours. The reaction mixture was quenched with saturated aqueous NH₄Cl solution (15 mL), diluted with water (30 mL) and extracted with EtOAc. After removal of organic solvents under reduced pressure, purification of the residue through silica gel chromatography with 0-65% EtOAc in hexanes as eluents afforded 132.3 (1.50 g, 52%).

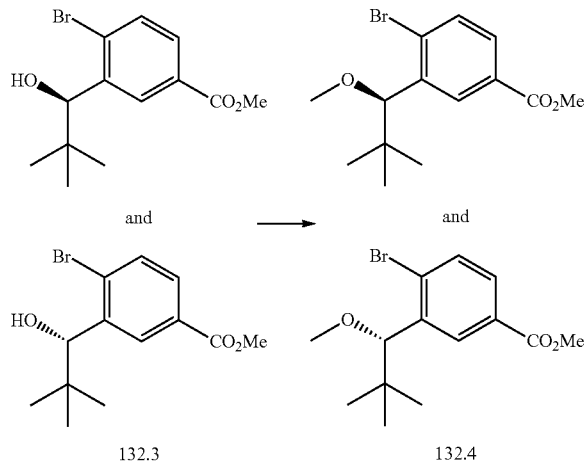 [SMILES: COC(=O)c1ccc(Br)c([C@H](O)C(C)(C)C)c1 ; COC(=O)c1ccc(Br)c([C@H](OC)C(C)(C)C)c1 ; COC(=O)c1ccc(Br)c([C@@H](O)C(C)(C)C)c1 ; COC(=O)c1ccc(Br)c([C@@H](OC)C(C)(C)C)c1]

132.3                132.4

(R)-Methyl 4-bromo-3-(1-methoxy-2,2-dimethylpropyl)benzoate and (S)-methyl 4-bromo-3-(1-methoxy-2,2-dimethylpropyl)benzoate (132.4)

To a 0° C. solution of 132.3 (1660 mg, 5.51 mmol) and iodomethane (1.57 g, 11.0 mmol) in DMF (20 mL) was added sodium hydride (530 mg, 13.8 mmol, 60% in mineral oil, commercially available from Strem Chemicals). The mixture was allowed to warm to room temperature over 20 minutes, and quenched carefully with water, saturated aqueous NH$_4$Cl. The mixture was then extracted with EtOAc. The combined organic layers were then washed with water and brine. After removal of organic solvents under reduced pressure, purification of the residue through silica gel chromatography with 0-50% EtOAc in hexanes as eluents afforded 132.4 (1.50 g, 52%).

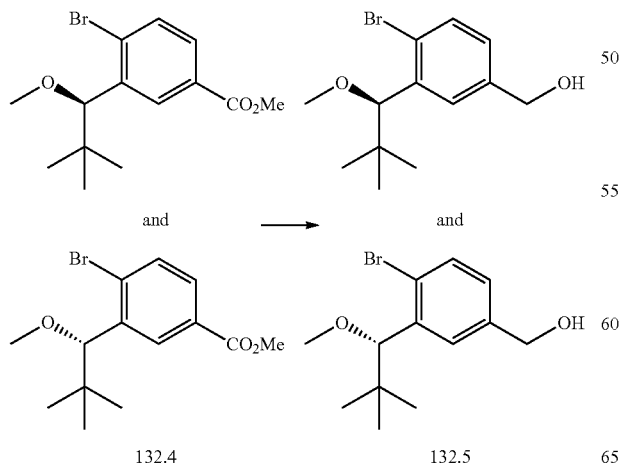

132.4                132.5

(R)-(4-Bromo-3-(1-methoxy-2,2-dimethylpropyl)phenyl)methanol and (S)-(4-bromo-3-(1-methoxy-2,2-dimethylpropyl)phenyl)methanol (132.5)

To a 0° C. solution of 132.4 (1135 mg, 3601 μmol) in THF (18 mL) was added diisobutylaluminum hydride (12.6 mL, 12.6 mmol, 1.0 M solution in toluene, commercially available from Sigma-Aldrich, St. Louis, Mo., USA) over 20 minutes. The resulting mixture was stirred at 0-10° C. for 1.5 hours and was then quenched with MeOH. Organic solvents were removed under reduced pressure and the residue was redissolved in EtOAc and washed with 1.0 N HCl. After removal of organic solvents under reduced pressure, purification of the residue through silica gel chromatography with 50-70% EtOAc in hexanes as eluent afforded 132.5 (910 mg, 88%).

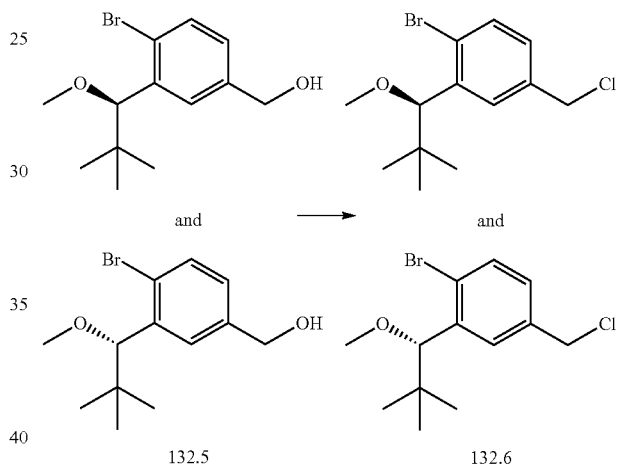

132.5                132.6

(R)-1-Bromo-4-(chloromethyl)-2-(1-methoxy-2,2-dimethylpropyl)benzene and (S)-1-bromo-4-(chloromethyl)-2-(1-methoxy-2,2-dimethylpropyl)benzene (132.6)

To a room temperature solution of 132.5 (190 mg, 662 μmol) in DCM (5 mL) was added DMF (51.0 μL, 662 μmol) followed by thionyl chloride (96.5 μL, 1323 μmol, commercially available from Sigma-Aldrich, St. Louis, Mo., USA). The resulting mixture was stirred at room temperature 50° C. for 35 minutes. After removal of organic solvents under reduced pressure, purification of the residue through silica gel chromatography with 0-30% EtOAc in hexanes as eluent afforded 132.6 (198 mg, 98%).

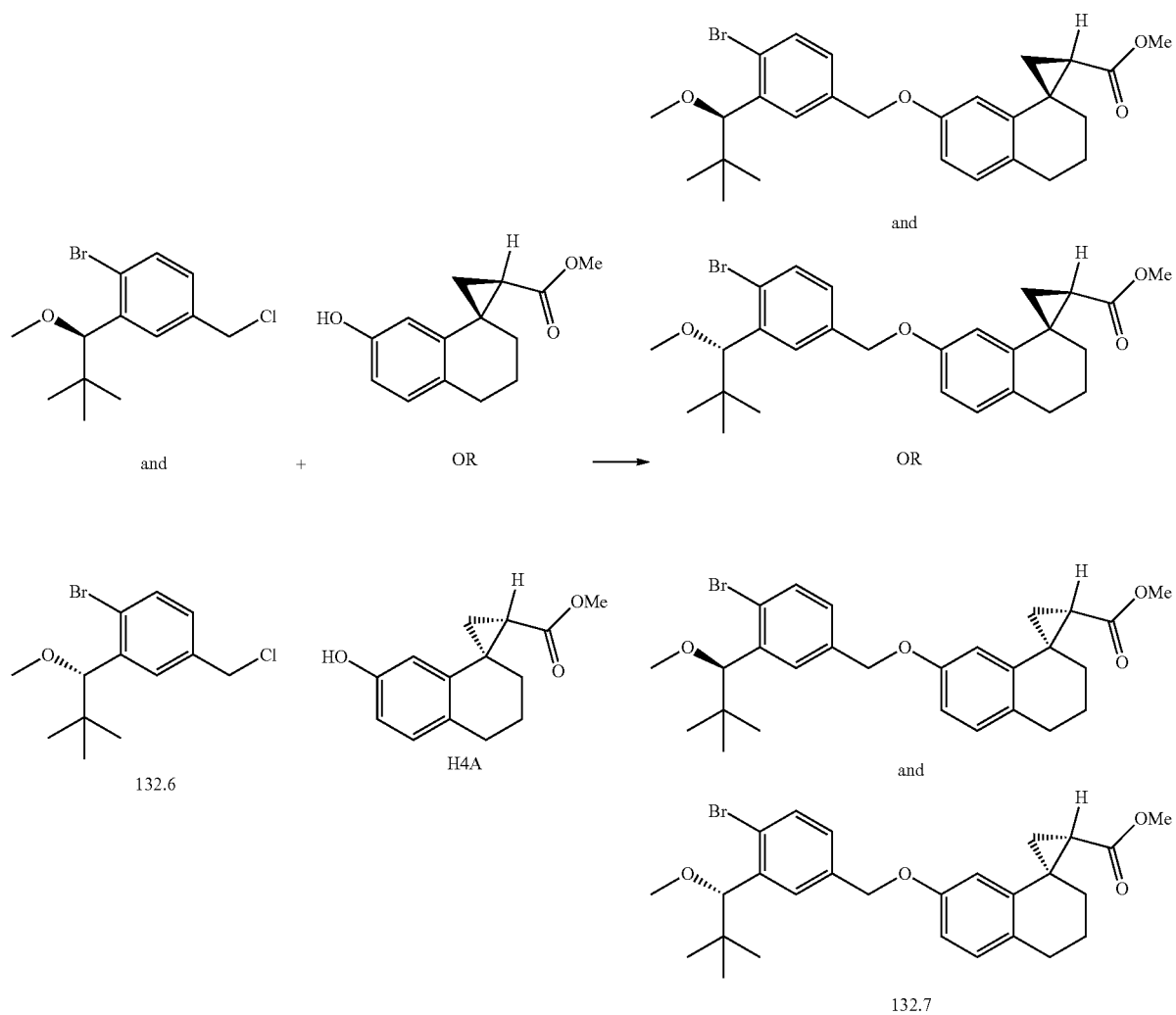

(1R,2R)-Methyl 7'-(4-bromo-3-(((R)-1-methoxy-2,2-dimethylpropyl)benzyloxy)-3',4'-dihydro-2'H-spiro[cyclopropane-1,1'-naphthalene]-2-carboxylate and (1R,2R)-methyl 7'-(4-bromo-3-(((S)-1-methoxy-2,2-dimethylpropyl)benzyloxy)-3',4'-dihydro-2'H-spiro[cyclopropane-1,1'-naphthalene]-2-carboxylate, or (1S,2S)-methyl 7'-(4-bromo-3-(((S)-1-methoxy-2,2-dimethylpropyl)benzyloxy)-3',4'-dihydro-2'H-spiro[cyclopropane-1,1'-naphthalene]-2-carboxylate and (1S,2S)-methyl 7'-(4-bromo-3-(((R)-1-methoxy-2,2-dimethylpropyl)benzyloxy)-3',4'-dihydro-2'H-spiro[cyclopropane-1,1'-naphthalene]-2-carboxylate (132.7)

To a room temperature solution of 132.6 (950 mg, 3108 µmol) and H4A (794 mg, 3419 µmol) in DMSO (10 mL) was added $Cs_2CO_3$ (497 µL, 6216 µmol). The mixture was stirred at room temperature for 2.5 hours, diluted with water, treated with 1.0 N HCl (0.2 mL), and extracted with EtOAc. After removal of organic solvents under reduced pressure, purification of the residue using silica gel chromatography with 0-50% EtOAc in hexanes as eluents afforded 132.7 (970 mg, 62%).

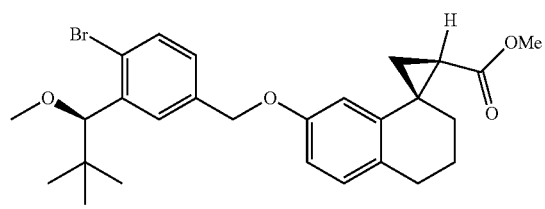

and

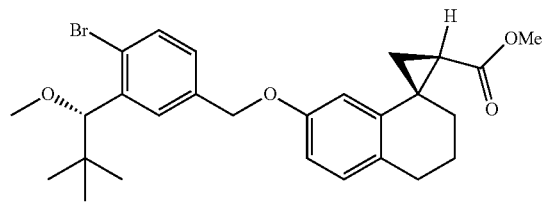

OR

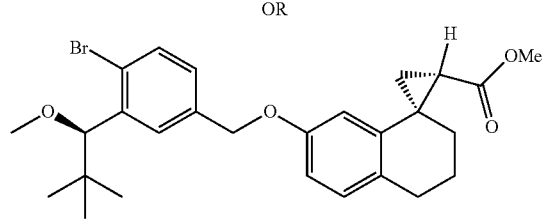

and

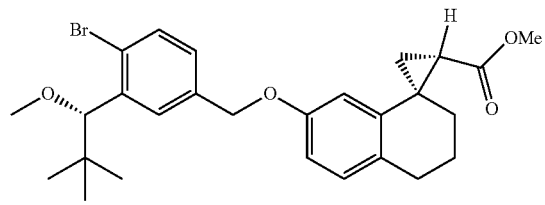

132.7

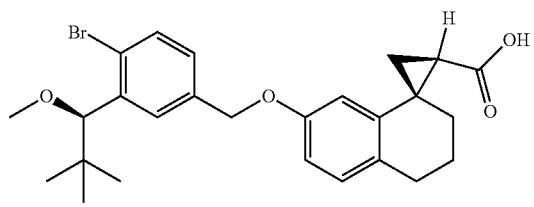

and

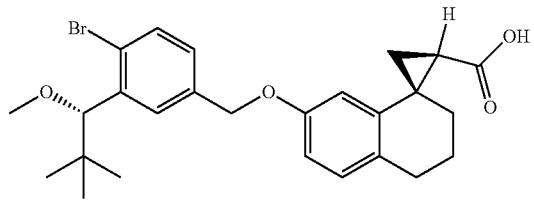

OR

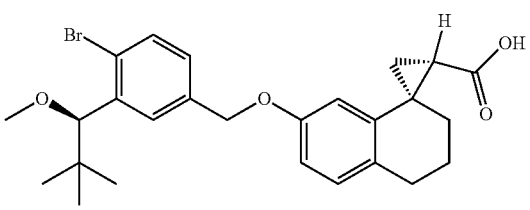

and

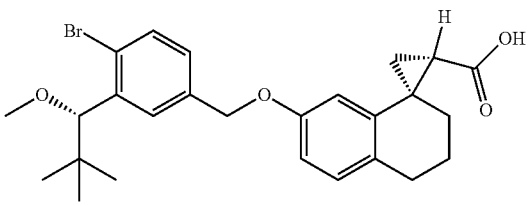

132

(1R,2R)-7'-(4-Bromo-3-((R)-1-methoxy-2,2-dimethylpropyl)benzyloxy)-3',4'-dihydro-2'H-spiro[cyclopropane-1,1'-naphthalene]-2-carboxylic acid and (1R,2R)-7'-(4-bromo-3-((S)-1-methoxy-2,2-dimethylpropyl)benzyloxy)-3',4'-dihydro-2'H-spiro[cyclopropane-1,1'-naphthalene]-2-carboxylic acid, or (1S,2S)-7'-(4-bromo-3-((R)-1-methoxy-2,2-dimethylpropyl)benzyloxy)-3',4'-dihydro-2'H-spiro[cyclopropane-1,1'-naphthalene]-2-carboxylic acid and (1S,2S)-7'-(4-bromo-3-((S)-1-methoxy-2,2-dimethylpropyl)benzyloxy)-3',4'-dihydro-2'H-spiro[cyclopropane-1,1'-naphthalene]-2-carboxylic acid (132)

To a room temperature solution of 132.7 (260 mg, 518 µmol) in dioxane/MeOH (1:1, 8 mL) was added lithium hydroxide, monohydrate (2592 µL, 5185 µmol, commercially available from Sigma-Aldrich, St. Louis, Mo., USA). The mixture was stirred at 50° C. for 30 minutes and was then treated with 3.0 N HCl to bring the pH to 4. After removal of solvents under reduced pressure, purification of the residue using silica gel chromatography with 50-75% EtOAc in hexanes as eluent afforded 132 (231 mg, 91%). MS ESI (neg.) m/e: 485.4, 487.4 (M−H)⁻.

Example 133

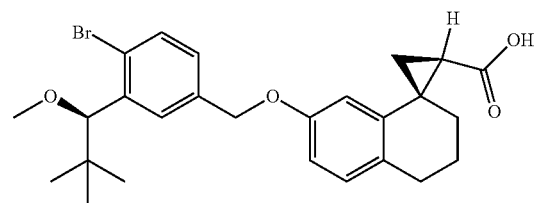

and

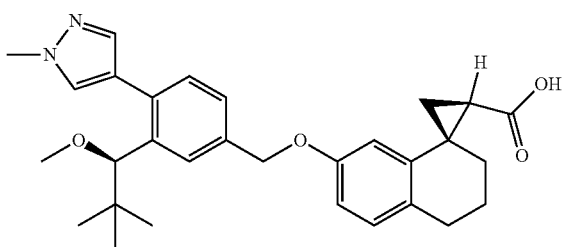

and 397                                                                                                   398

-continued

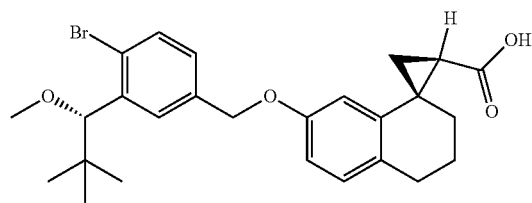

OR

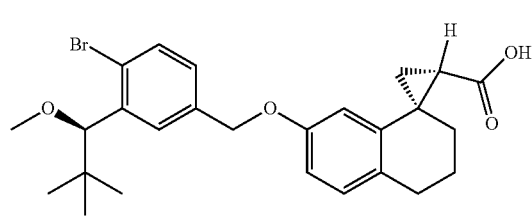

and

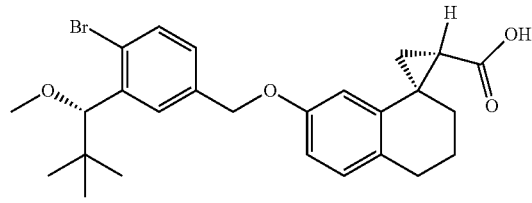

132

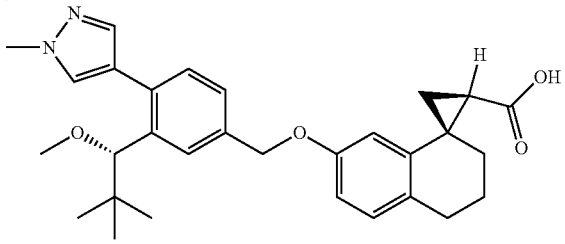

OR

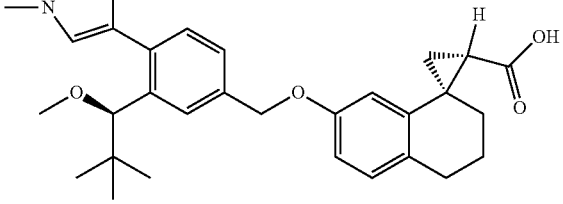

and

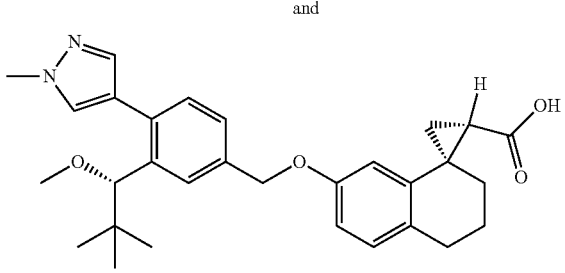

133

(1R,2R)-7'-(3-((R)-1-Methoxy-2,2-dimethylpropyl)-4-(1-methyl-1H-pyrazol-4-yl)benzyloxy)-3',4'-dihydro-2'H-spiro[cyclopropane-1,1'-naphthalene]-2-carboxylic acid and (1R,2R)-7'-(3-((S)-1-methoxy-2,2-dimethylpropyl)-4-(1-methyl-1H-pyrazol-4-yl)benzyloxy)-3',4'-dihydro-2'H-spiro[cyclopropane-1,1'-naphthalene]-2-carboxylic acid, or (1S,2S)-7'-(3-((R)-1-methoxy-2,2-dimethylpropyl)-4-(1-methyl-1H-pyrazol-4-yl)benzyloxy)-3',4'-dihydro-2'H-spiro[cyclopropane-1,1'-naphthalene]-2-carboxylic acid and (1S,2S)-7'-(3-((S)-1-methoxy-2,2-dimethylpropyl)-4-(1-methyl-1H-pyrazol-4-yl)benzyloxy)-3',4'-dihydro-2'H-spiro[cyclopropane-1,1'-naphthalene]-2-carboxylic acid (133)

To a room temperature solution of 133 (34 mg, 70 µmol) and 1-methyl-4-(4,4,5,5-tetramethyl-1,3,2-dioxaborolan-2-yl)-1H-pyrazole (29 mg, 140 µmol, commercially available from Oakwood Products) and trans-dichlorobis(triphenylphosphine)palladium (II) (9.8 mg, 14 µmol, commercially available from Alfa Aeser) in DMF (2.5 mL) was added saturated aqueous NaHCO$_3$ (0.3 mL). The mixture was purged with N$_2$ for 5 minutes and heated at 80° C. for 30 minutes. After cooling to room temperature, the reaction mixture was purified by HPLC (reverse phase, C18, 0.1% TFA in water/0.1% TFA in ACN, 30-95%) to afford 133 (6.7 mg, 20%) MS ESI (pos.) M/E: 487.3 (M+H).

Example 134

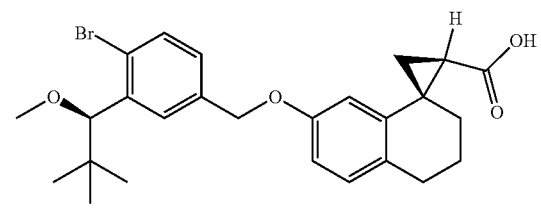

and

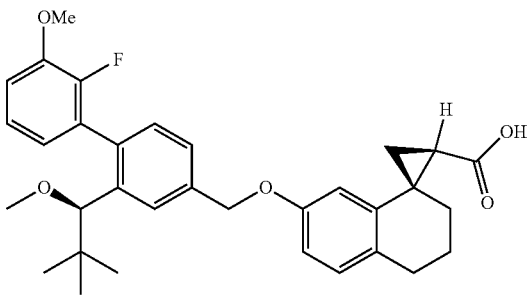

and

-continued

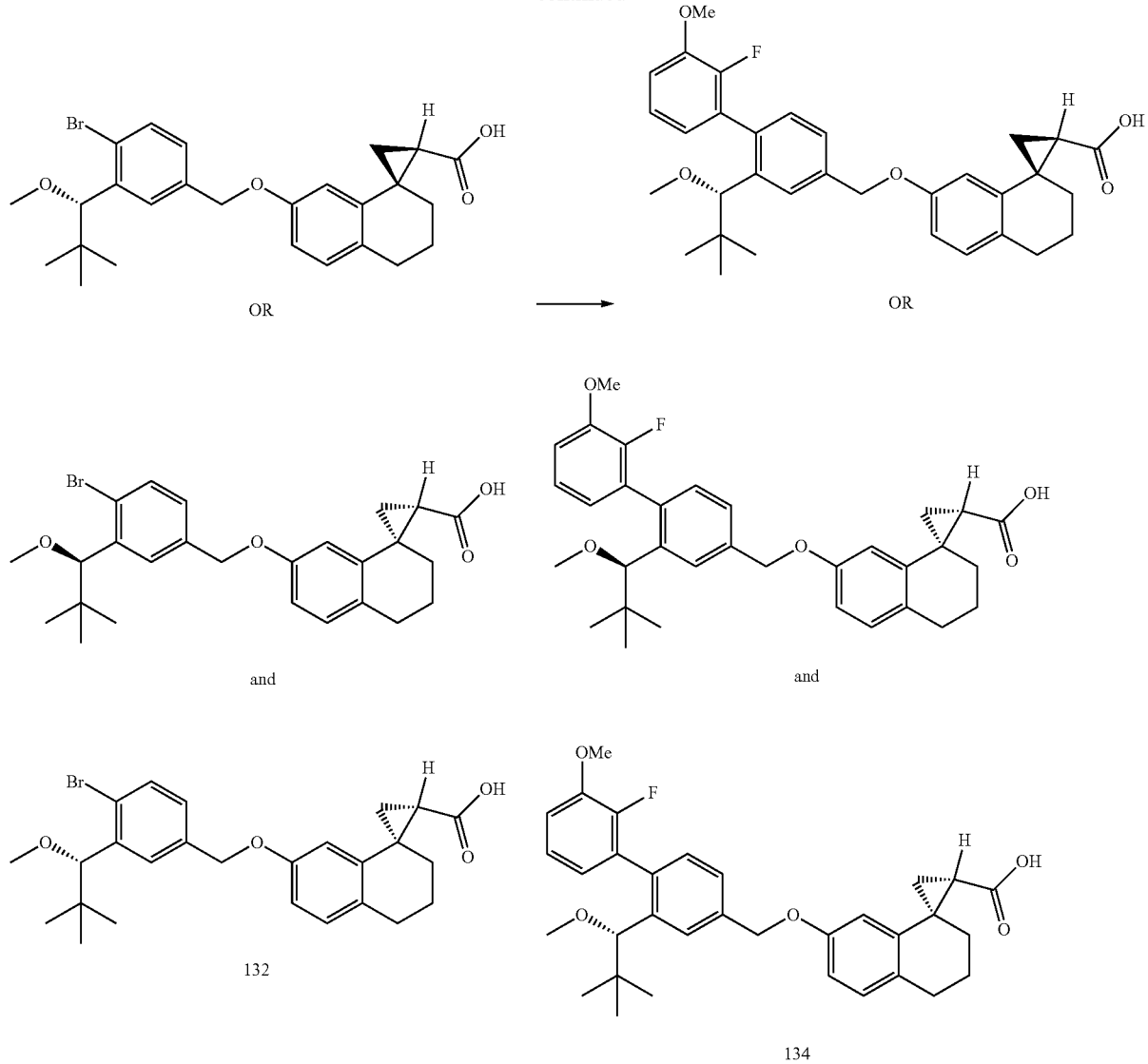

132

134

(1R,2R)-7'-((2'-Fluoro-3'-methoxy-2-((R)-1-methoxy-2,2-dimethylpropyl)biphenyl-4-yl)methoxy)-3',4'-dihydro-2'H-spiro[cyclopropane-1,1'-naphthalene]-2-carboxylic acid and (1R,2R)-7'-((2'-fluoro-3'-methoxy-2-((S)-1-methoxy-2,2-dimethylpropyl)biphenyl-4-yl)methoxy)-3',4'-dihydro-2'H-spiro[cyclopropane-1,1'-naphthalene]-2-carboxylic acid, or (1S,2S)-7'-((2'-fluoro-3'-methoxy-2-((R)-1-methoxy-2,2-dimethylpropyl)biphenyl-4-yl)methoxy)-3',4'-dihydro-2'H-spiro[cyclopropane-1,1'-naphthalene]-2-carboxylic acid and (1S,2S)-7'-((2'-fluoro-3'-methoxy-2-((S)-1-methoxy-2,2-dimethylpropyl)biphenyl-4-yl)methoxy)-3',4'-dihydro-2'H-spiro[cyclopropane-1,1'-naphthalene]-2-carboxylic acid (134)

The title compound 134 was synthesized from 132 by the method described for preparation of 133 from 132, except that 2-fluoro-3-methoxyphenylboronic acid (commercially available from Oakwood Products) was used. MS ESI (neg.) m/e: 530.9 (M−H)⁻.

Example 135

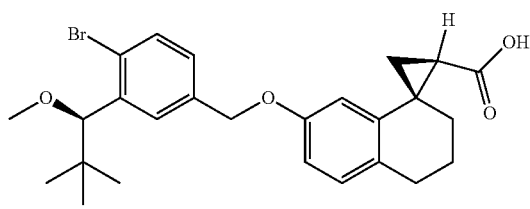

and

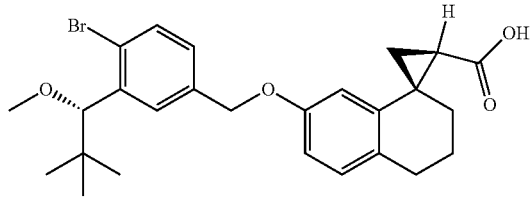

OR

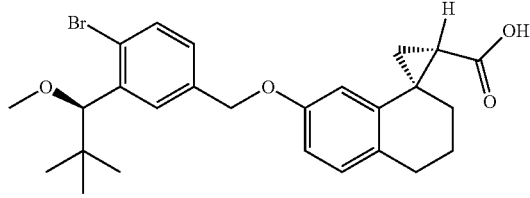

and

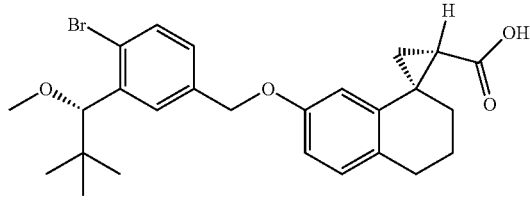

132

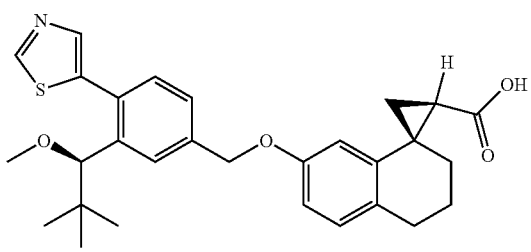

and

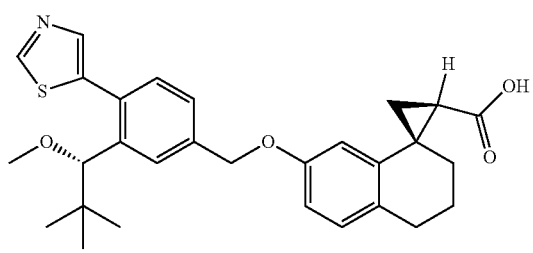

OR

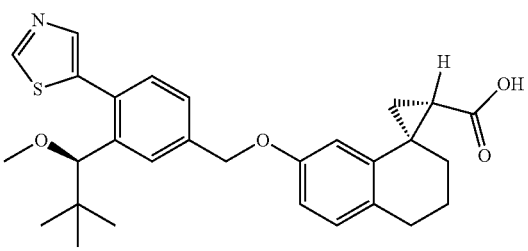

and

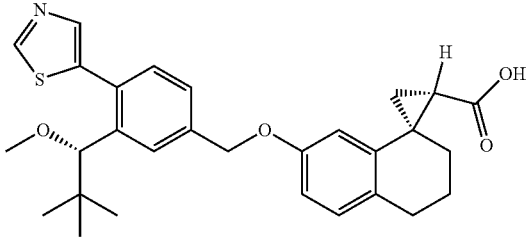

135

(1R,2R)-7'-(3-((R)-1-Methoxy-2,2-dimethylpropyl)-4-(thiazol-5-yl)benzyloxy)-3',4'-dihydro-2'H-spiro[cyclopropane-1,1'-naphthalene]-2-carboxylic acid and (1R,2R)-7'-(3-((S)-1-methoxy-2,2-dimethylpropyl)-4-(thiazol-5-yl)benzyloxy)-3',4'-dihydro-2'H-spiro[cyclopropane-1,1'-naphthalene]-2-carboxylic acid, or (1S,2S)-7'-(3-((R)-1-methoxy-2,2-dimethylpropyl)-4-(thiazol-5-yl)benzyloxy)-3',4'-dihydro-2'H-spiro[cyclopropane-1,1'-naphthalene]-2-carboxylic acid and (1S,2S)-7'-(3-((S)-1-methoxy-2,2-dimethylpropyl)-4-(thiazol-5-yl)benzyloxy)-3',4'-dihydro-2'H-spiro[cyclopropane-1,1'-naphthalene]-2-carboxylic acid (135)

To a room temperature solution of 132 (30 mg, 62 µmol) and 5-(tributylstannyl)thiazole (69 mg, 185 µmol, commercially available from Maybridge Chemical Company) and trans-dichlorobis(triphenyl-phosphine)palladium (II) (4.3 mg, 6 µmol, commercially available from Alfa Aeser) in DMF (2 mL) was added aqueous $Cs_2CO_3$ (1.23 µL, 123 µmol, 1.0 M in water). The mixture was purged with $N_2$ for 5 minutes and then heated at 80° C. for 35 minutes. After cooling to room temperature, the reaction mixture was purified by HPLC (reverse phase, C18, 0.1% TFA in water/0.1% TFA in ACN, 35-95%) to afford 135 (4.0, 13%). MS ESI (pos.) m/e: 492.2 $(M+H)^+$.

403

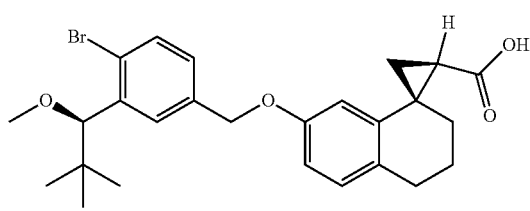

and

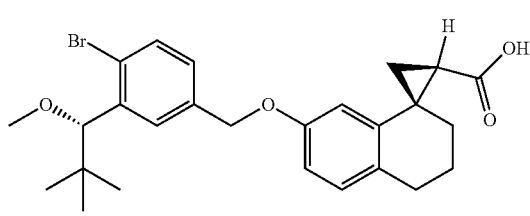

OR

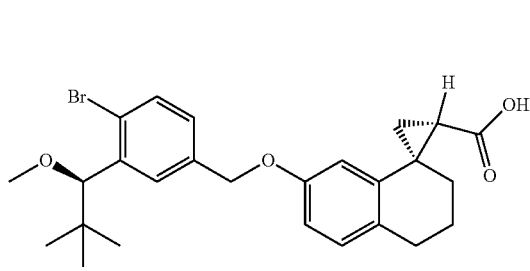

and

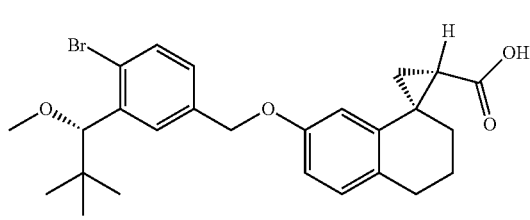

132

404

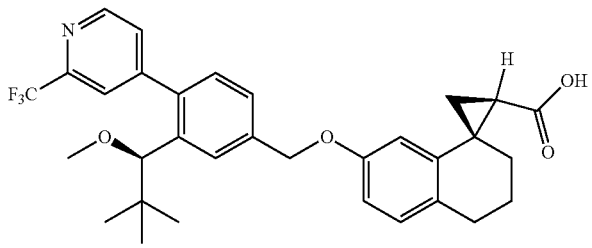

and

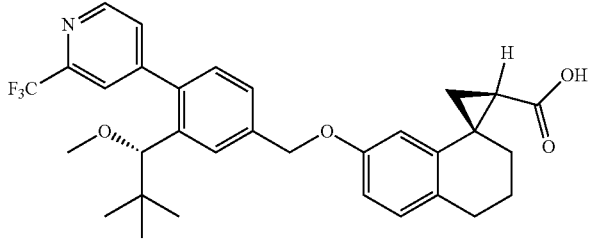

OR

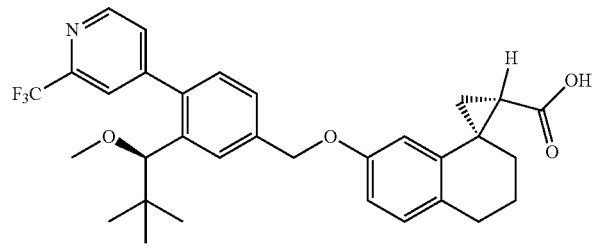

and

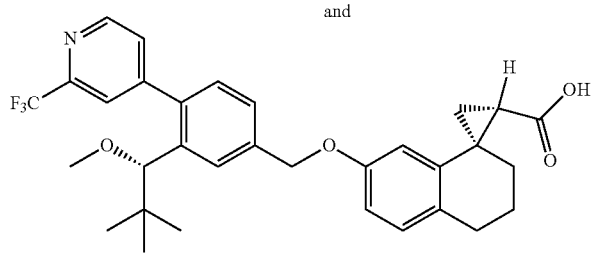

136

(1R,2R)-7'-(3-((R)-1-Methoxy-2,2-dimethylpropyl)-4-(2-(trifluoromethyl)pyridin-4-yl)benzyloxy)-3',4'-dihydro-2'H-spiro[cyclopropane-1,1'-naphthalene]-2-carboxylic acid and (1R,2R)-7'-(3-((S)-1-methoxy-2,2-dimethylpropyl)-4-(2-(trifluoromethyl)pyridin-4-yl)benzyloxy)-3',4'-dihydro-2'H-spiro[cyclopropane-1,1'-naphthalene]-2-carboxylic acid, or (1S,2S)-7'-(3-((R)-1-methoxy-2,2-dimethylpropyl)-4-(2-(trifluoromethyl)pyridin-4-yl)benzyloxy)-3',4'-dihydro-2'H-spiro[cyclopropane-1,1'-naphthalene]-2-carboxylic acid and (1S,2S)-7'-(3-((S)-1-methoxy-2,2-dimethylpropyl)-4-(2-(trifluoromethyl)pyridin-4-yl)benzyloxy)-3',4'-dihydro-2'H-spiro[cyclopropane-1,1'-naphthalene]-2-carboxylic acid (136)

The title compound 136 was synthesized from 132 using a procedure analogous to the method described for preparation of 133 from 132, except that 2-(trifluoromethyl)pyridin-4-ylboronic acid (commercially available from CombiPhos Catalysts) was used. MS ESI (pos.) m/e: 554.2 (M+H)$^+$.

Example 137

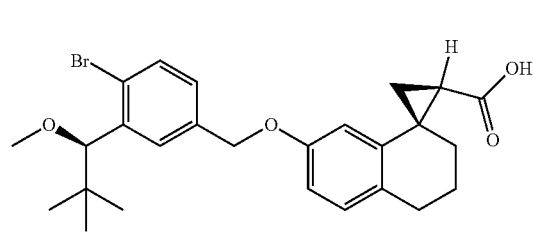

and

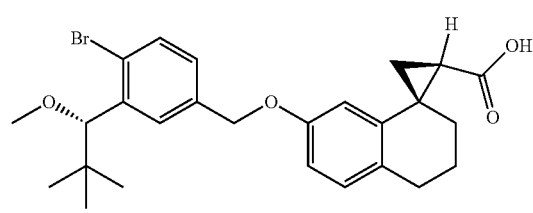

OR

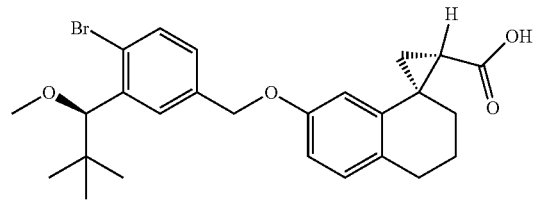

and

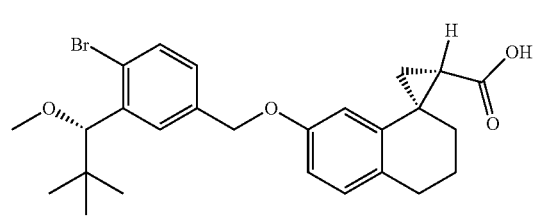

132

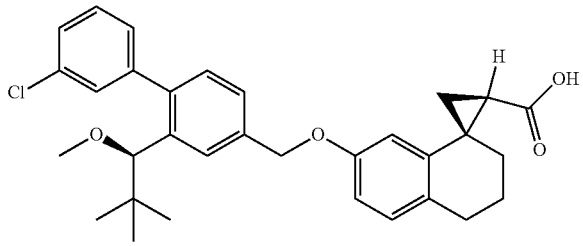

and

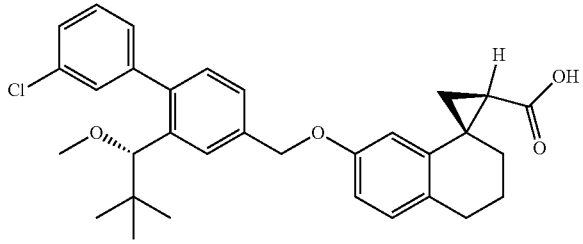

OR

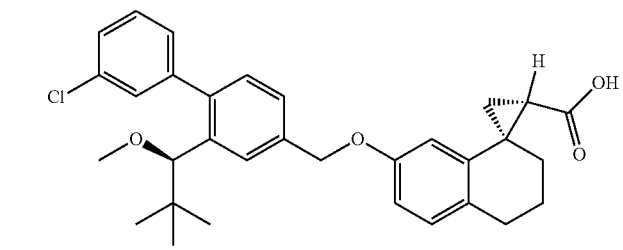

and

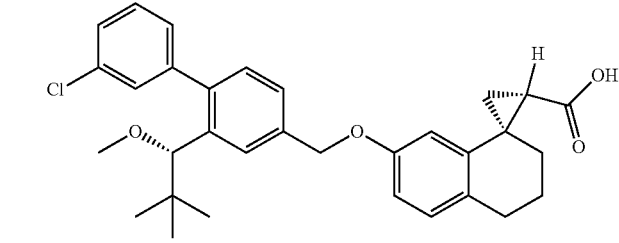

137

(1R,2R)-7'-((3'-Chloro-2-((R)-1-methoxy-2,2-dimethylpropyl)biphenyl-4-yl)methoxy)-3',4'-dihydro-2'H-spiro[cyclopropane-1,1'-naphthalene]-2-carboxylic acid and (1R,2R)-7'-((3'-chloro-2-((S)-1-methoxy-2,2-dimethylpropyl)biphenyl-4-yl)methoxy)-3',4'-dihydro-2'H-spiro[cyclopropane-1,1'-naphthalene]-2-carboxylic acid, or (1S,2S)-7'-((3'-chloro-2-((R)-1-methoxy-2,2-dimethylpropyl)biphenyl-4-yl)methoxy)-3',4'-dihydro-2'H-spiro[cyclopropane-1,1'-naphthalene]-2-carboxylic acid and (1S,2S)-7'-((3'-chloro-2-((S)-1-methoxy-2,2-dimethylpropyl)biphenyl-4-yl)methoxy)-3',4'-dihydro-2'H-spiro[cyclopropane-1,1'-naphthalene]-2-carboxylic acid (137)

The title compound 137 was synthesized from 132 using a procedure analogous to the method described for preparation of 133 from 132, except that 3-chlorophenylboronic acid (commercially available from Sigma-Aldrich, St. Louis, Mo., USA) was used. MS ESI (neg.) m/e: 517.3 (M−H)⁻.

Example 138

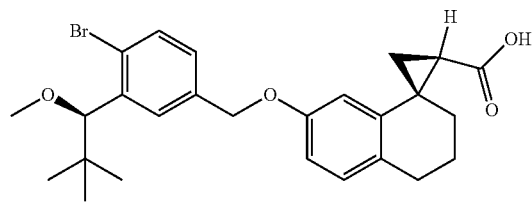

and

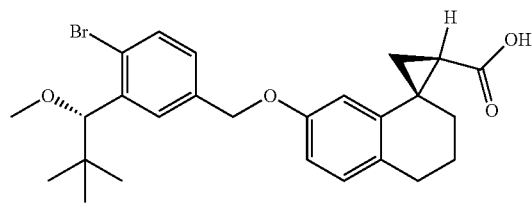

OR

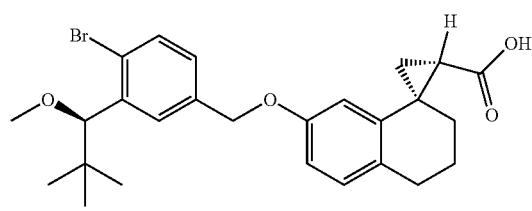

and

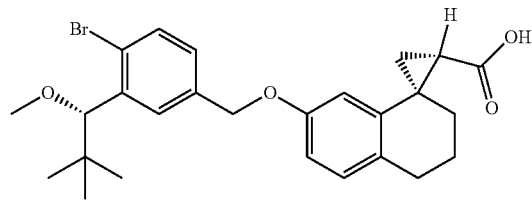

132

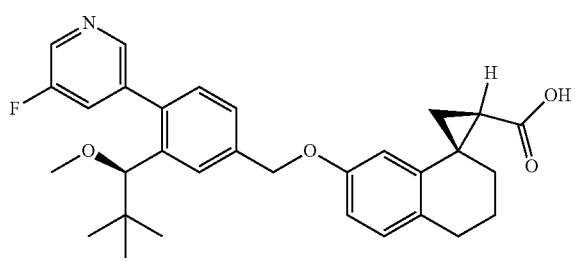

and

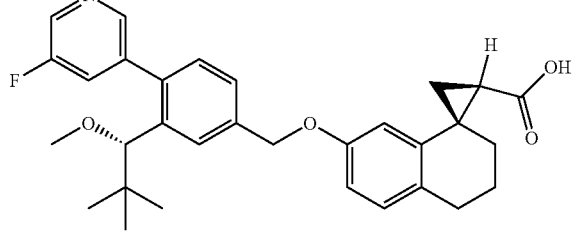

OR

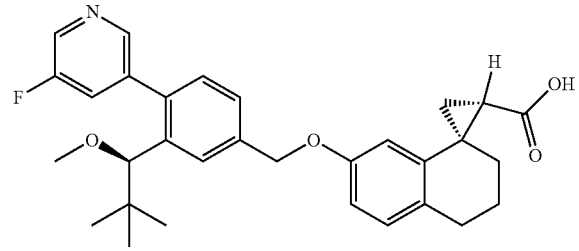

and

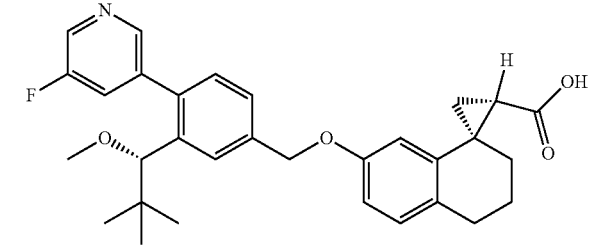

138

(1R,2R)-7'-(4-(5-Fluoropyridin-3-yl)-3-(R)-1-methoxy-2,2-dimethylpropyl)benzyloxy)-3',4'-dihydro-2'H-spiro[cyclopropane-1,1'-naphthalene]-2-carboxylic acid and (1R,2R)-7'-(4-(5-fluoropyridin-3-yl)-3-(S)-1-methoxy-2,2-dimethylpropyl)benzyloxy)-3',4'-dihydro-2'H-spiro[cyclopropane-1,1'-naphthalene]-2-carboxylic acid, or (1S,2S)-7'-(4-(5-fluoropyridin-3-yl)-3-(R)-1-methoxy-2,2-dimethylpropyl)benzyloxy)-3',4'-dihydro-2'H-spiro[cyclopropane-1,1'-naphthalene]-2-carboxylic acid and (1S,2S)-7'-(4-(5-fluoropyridin-3-yl)-3-(S)-1-methoxy-2,2-dimethylpropyl)benzyloxy)-3',4'-dihydro-2'H-spiro[cyclopropane-1,1'-naphthalene]-2-carboxylic acid (138)

The title compound 138 was synthesized from 132 using a procedure analogous to the method described for preparation of 133 from 132, except that 5-fluoropyridine-3-boronic acid (commercially available from Combi-Blocks) was used. MS ESI (pos.) m/e: 504.2 (M+H)$^+$.

Example 139

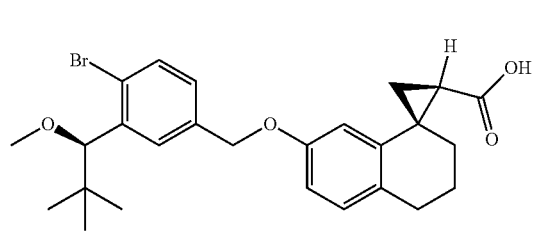

and

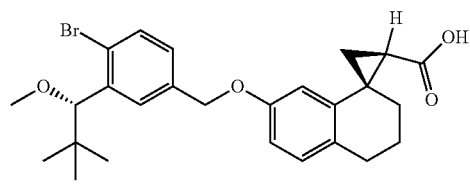

OR

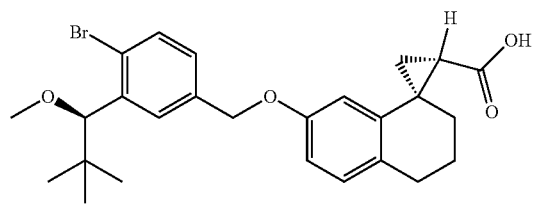

and

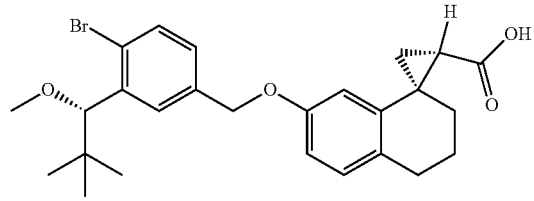

132

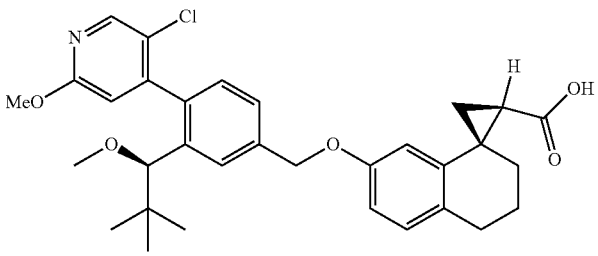

and

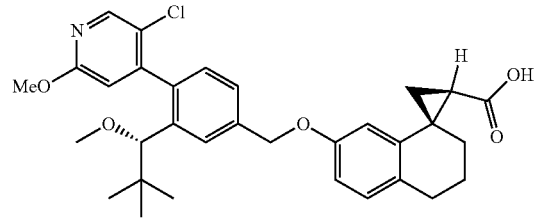

OR

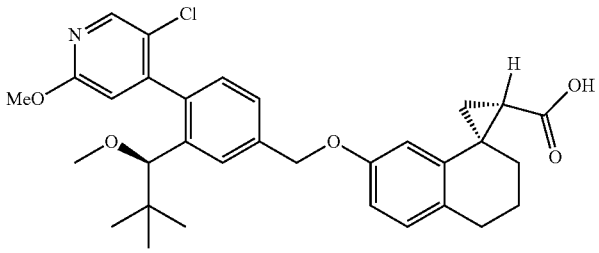

and

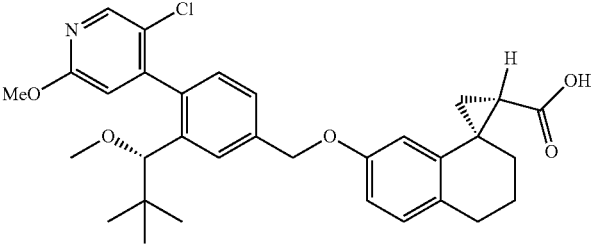

139

(1R,2R)-7'-(4-(5-Chloro-2-methoxypyridin-4-yl)-3-((R)-1-methoxy-2,2-dimethylpropyl)benzyloxy)-3',4'-dihydro-2'H-spiro[cyclopropane-1,1'-naphthalene]-2-carboxylic acid and (1R,2R)-7'-(4-(5-chloro-2-methoxypyridin-4-yl)-3-(S)-1-methoxy-2,2-dimethylpropyl)benzyloxy)-3',4'-dihydro-2'H-spiro[cyclopropane-1,1'-naphthalene]-2-carboxylic acid, or (1S,2S)-7'-(4-(5-chloro-2-methoxypyridin-4-yl)-3-((R)-1-methoxy-2,2-dimethylpropyl)benzyloxy)-3',4'-dihydro-2'H-spiro[cyclopropane-1,1'-naphthalene]-2-carboxylic acid and (1S,2S)-7'-(4-(5-chloro-2-methoxypyridin-4-yl)-3-((S)-1-methoxy-2,2-dimethylpropyl)benzyloxy)-3',4'-dihydro-2'H-spiro[cyclopropane-1,1'-naphthalene]-2-carboxylic acid (139)

The title compound 139 was synthesized from 132 using a procedure analogous to the method described for preparation of 133 from 132, except that 5-chloro-2-methoxypyridin-4-ylboronic acid (commercially available from Chem Impex International) was used. MS ESI (neg.) m/e: 548.2 (M−H)−.

Example 140

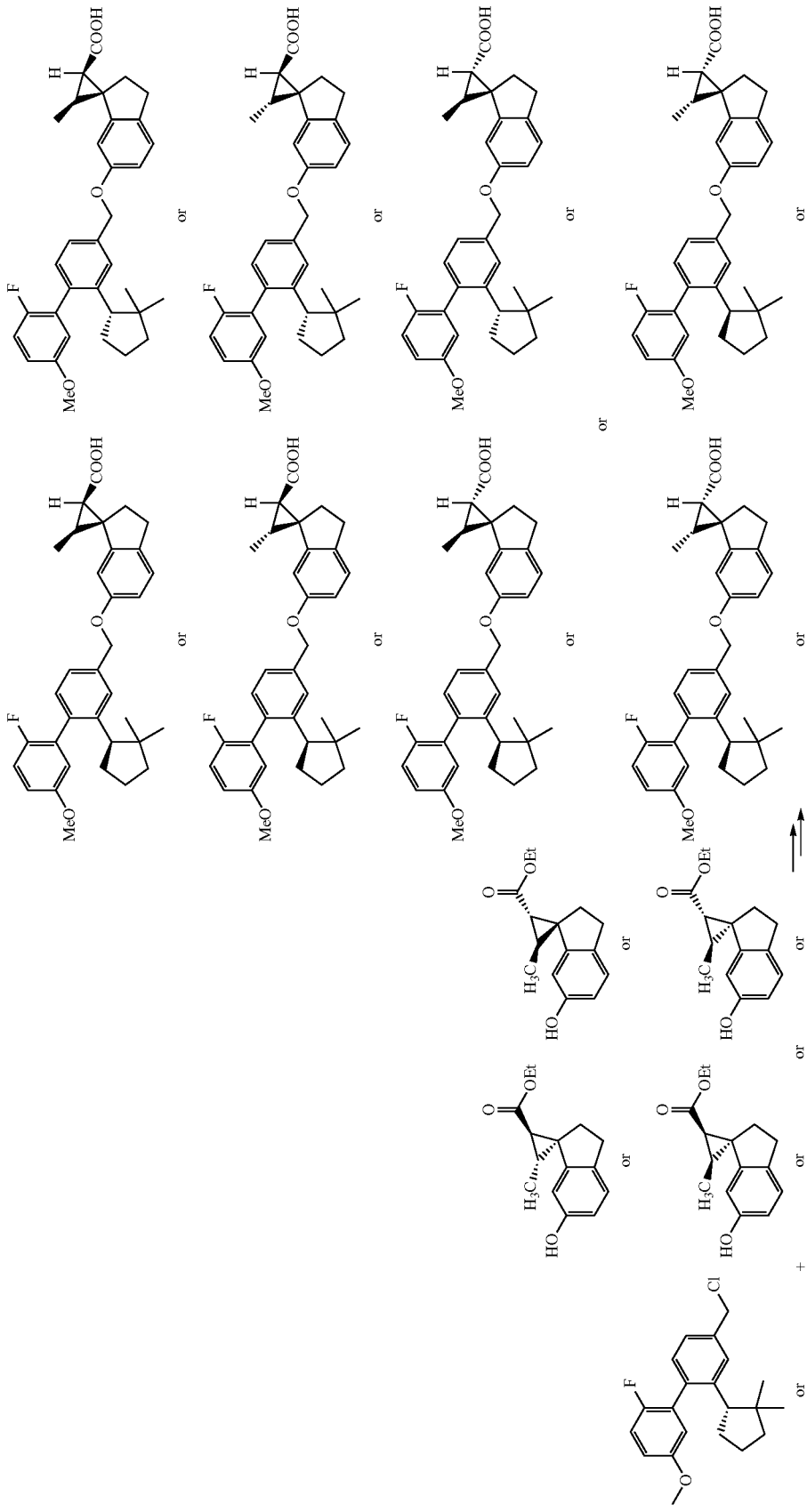

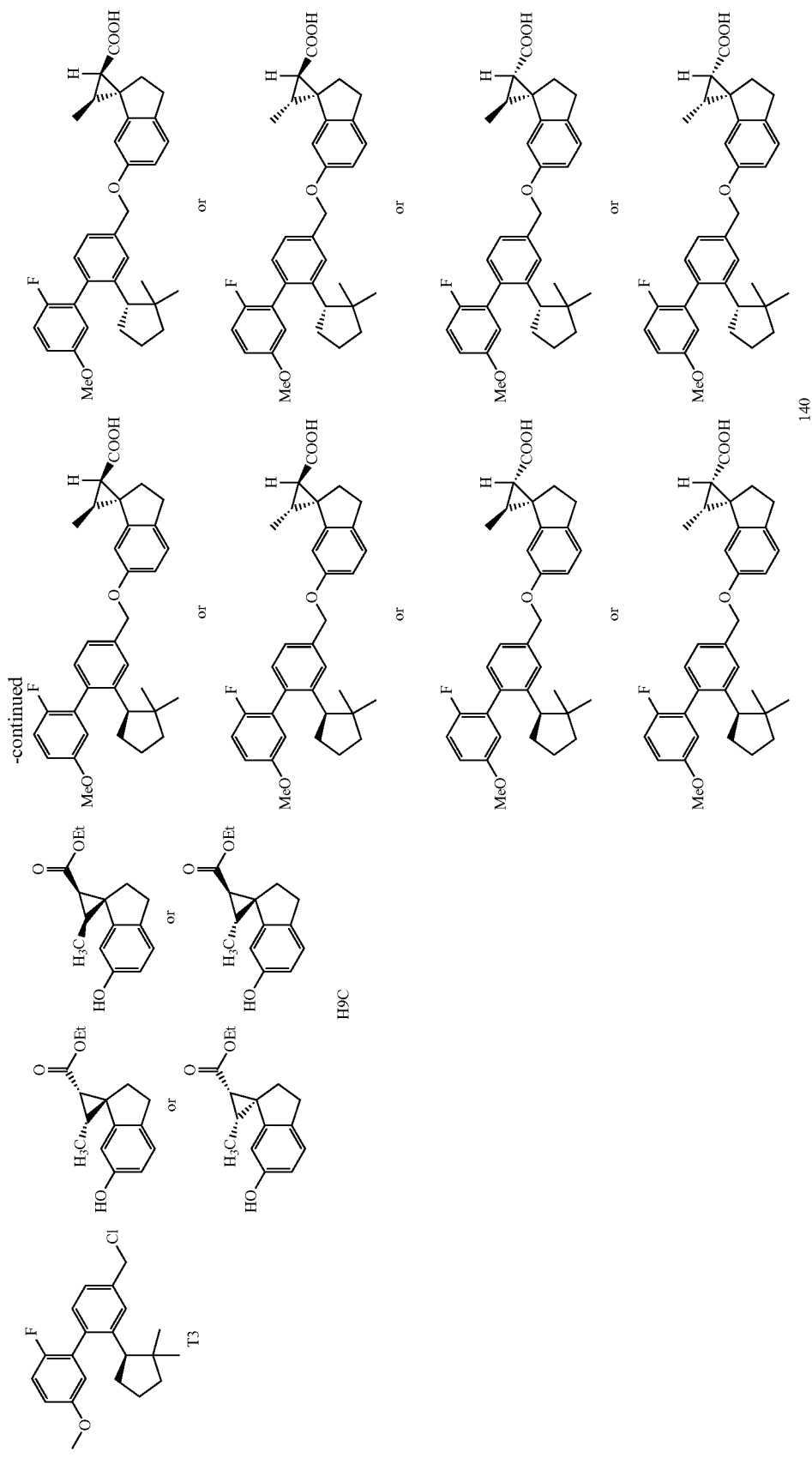

Example 140

Cs$_2$CO$_3$ (26.5 mg, 81.2 µmol) was added to a stirred solution of H9C (10.0 mg, 40.6 µmol) and T3 (14.1 mg, 40.6 µmol), and the resulting mixture was stirred at 50° C. for 3 hours. To the mixture was added 2N LiOH (0.2 mL) and MeOH (0.5 mL), and the resulting mixture was stirred for 15 hours at 50° C. The reaction mixture was acidified with 2N HCl (0.3 mL), diluted with ACN, purified by HPLC (reverse phase, C18, 0.1% TFA in water/0.1% TFA in ACN, 10-95%) to give 140 (13.3 mg, 62.0% yield) as a white solid. MS ESI (pos.) M/E: 551 (M+Na).

Example 141

The title compound (12.6 mg, 58.6% yield) is a diastereomer of 140 was synthesized as a white solid from T3 and H9G using a procedure analogous to that described for synthesizing 140. MS ESI (pos.) M/E: 551 (M+Na).

Example 142

The title compound (13.7 mg, 63.8% yield) is a diastereomer of 140 and was synthesized as a white solid from T3 and H9D using a procedure analogous to that described for synthesizing 140. MS ESI (pos.) M/E: 551 (M+Na).

Example 143

The title compound (13.0 mg, 60.6% yield) is a diastereomer of 140 and was synthesized as a white solid from T3 and H9F using a procedure analogous to that described for synthesizing 140. MS ESI (pos.) M/E: 551 (M+Na).

Example 144

The title compound (14.1 mg, 65.7% yield) is a diastereomer of 140 and was synthesized as a white solid from T3 and H9H using a procedure analogous to that described for synthesizing 140. MS ESI (pos.) M/E: 551 (M+Na).

Example 145

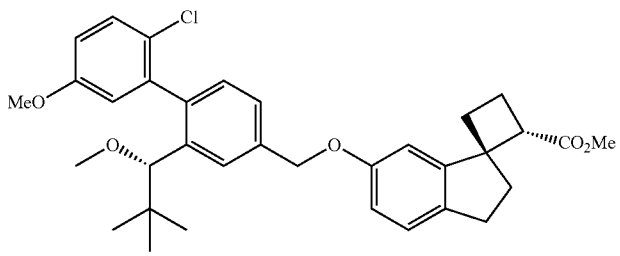

or

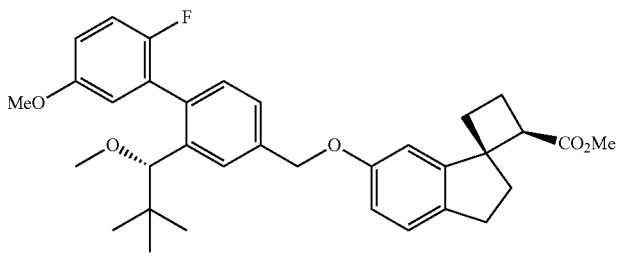

or

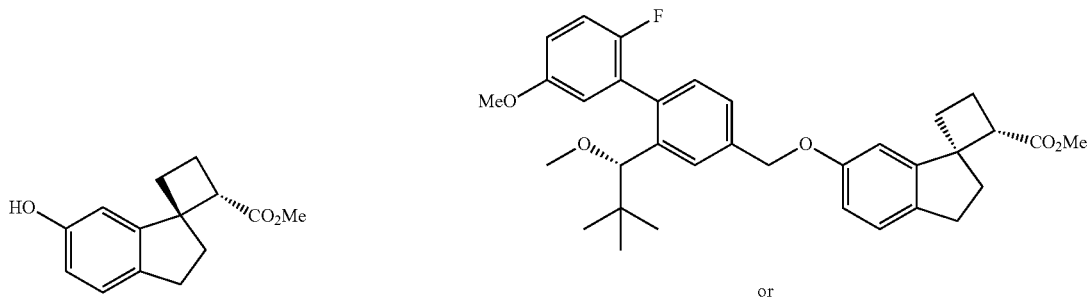

or 417
or
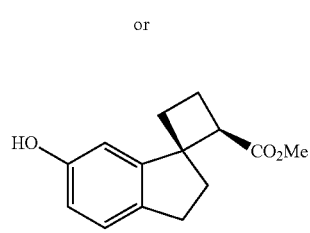
or
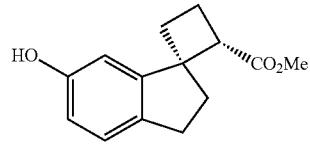
or
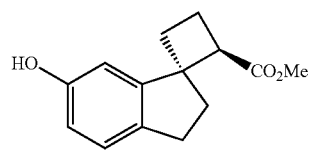
H12
→
418
-continued
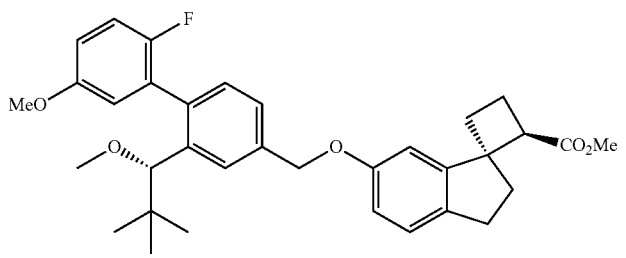
or
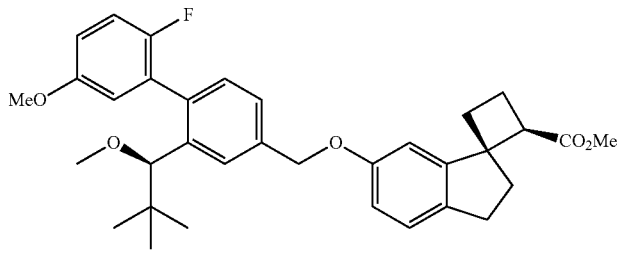
or
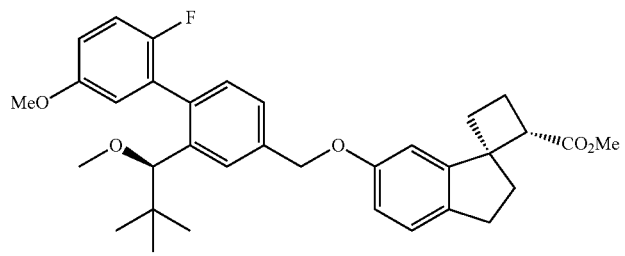
or
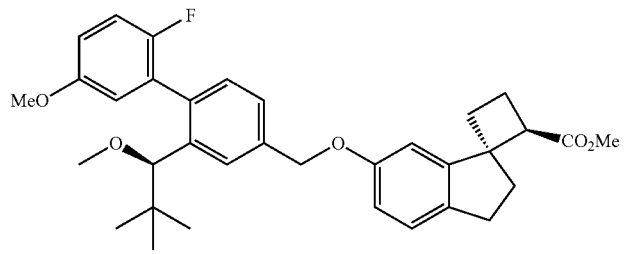
145.1

(1S,2S)-Methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1S,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1R,2S)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1R,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1S,2S)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1S,2R)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1R,2S)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1R,2R)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate (145.1)

A mixture of H12 (0.010 g, 0.043 mmol), T4 (0.018 g, 0.052 mmol) and $Cs_2CO_3$ (0.028 g, 0.086 mmol) in DMF (1.5 mL) was stirred at room temperature for 20 hours. The reaction mixture was concentrated, and the residue was purified by chromatography (silica gel, eluting with 1:9 EtOAc/hexane) to give 20 mg of 145.1. MS ESI (pos.) M/E: 564.3 ($M+H_2O$).

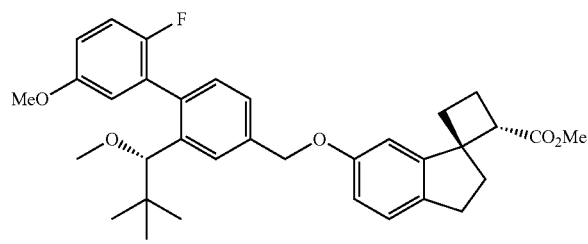

or

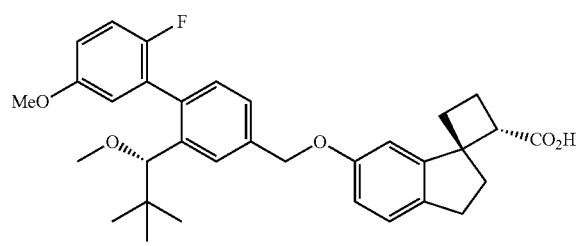

or

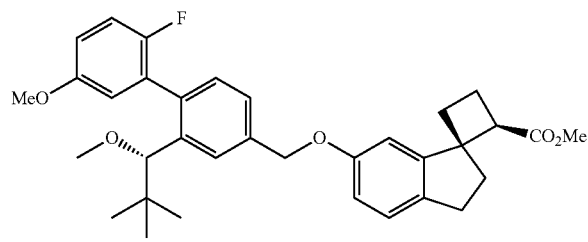

or

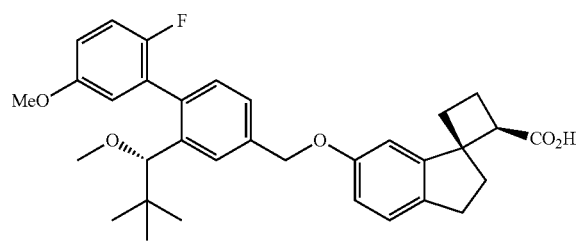

or

421
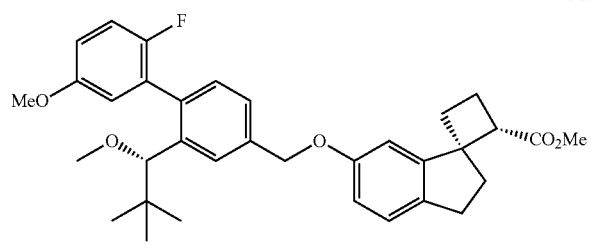
or
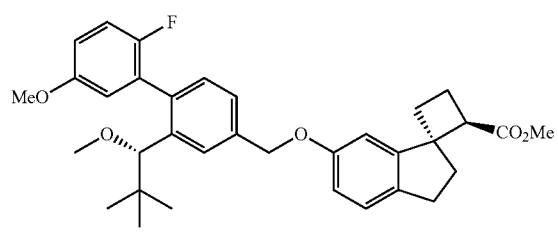
or
422
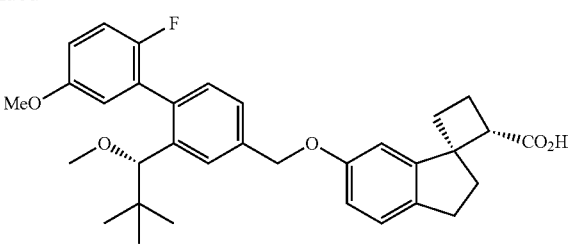
or
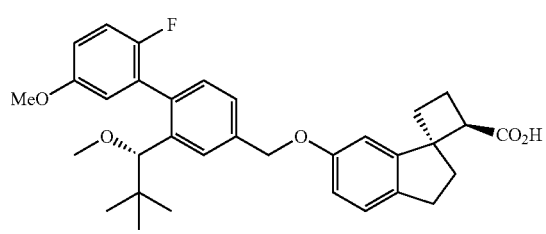
or
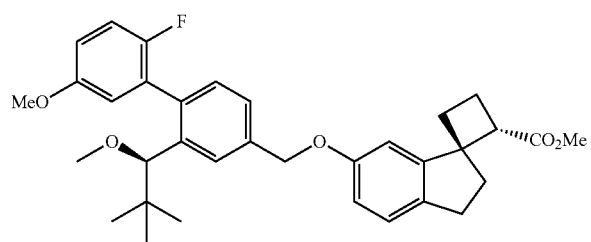
or
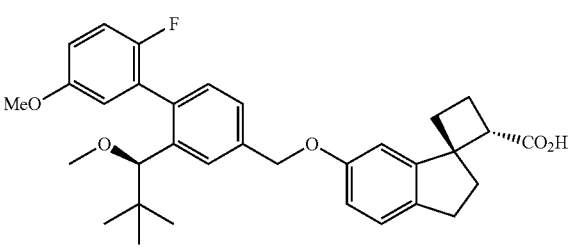
or
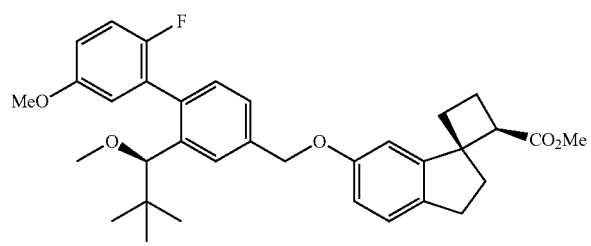
or
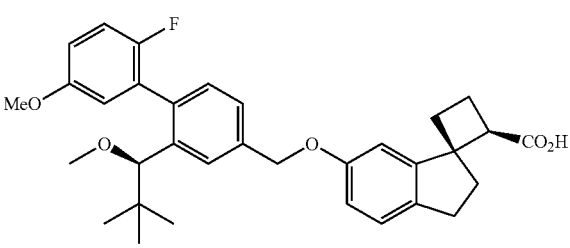
or
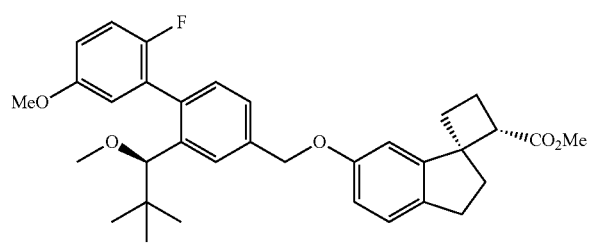
or
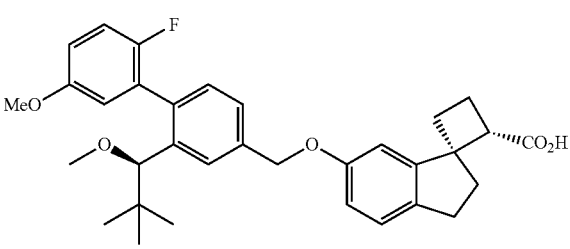
or 423 424

-continued

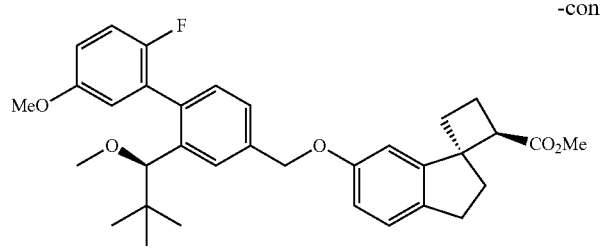

145.1

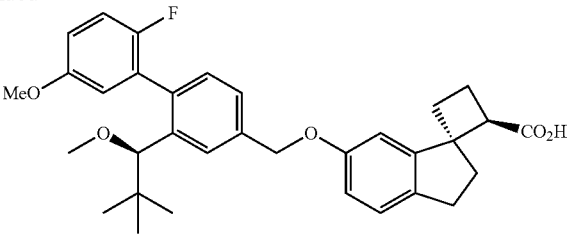

145

(1S,2S)-6'-((2'-Fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1S,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1R,2S)-6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1R,2R)-6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1S,2S)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1S,2R)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1R,2S)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1R,2R)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid (145)

A mixture of 145.1 (0.020 g, 0.037 mmol), NaOH (aqueous, 10%) (0.7 mL) and EtOH (2 mL) was stirred at room temperature for 24 hours. The mixture was then concentrated and acidified with 1N HCl to pH 3-5. The mixture was extracted with EtOAc (120 mL). The organic phase was washed with brine and then dried over anhydrous sodium sulfate. The organic phase was then concentrated and the residue was purified by chromatography (silica gel, eluting with 1:4 EtOAc/DCM) to give 16 mg of 145. MS ESI (neg.) M/E: 531 (M−H). $^1$H NMR (400 MHz, CDCl$_3$) δ ppm 7.60 (1H, m), 7.46 (1H, m), 7.20 (1H, m), 7.11 (1H, m), 7.03 (1H, m), 6.85-6.89 (2H, m), 6.74 (1H, m), 5.17 (2H, s), 3.97-4.20 (1H, m), 3.80 (3H, s), 3.26-3.38 (4H, m), 2.75-2.89 (2H, m), 2.20-2.24 (2H, m), 2.13 (1H, m), 2.09-2.13 (3H, m), 0.72 (9H, s).

Example 146

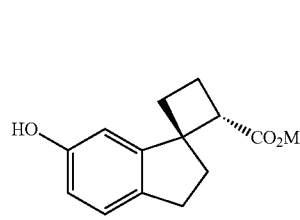

or

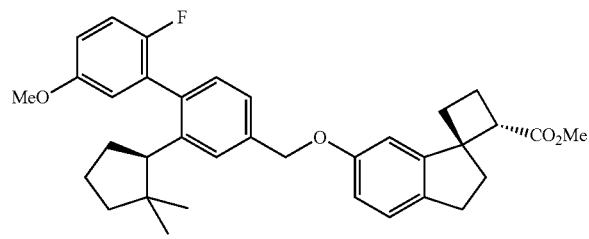

or

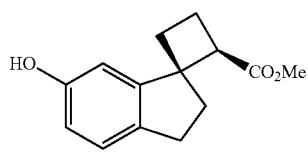

or

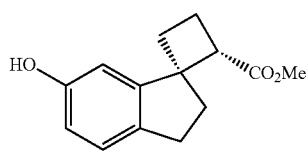

or

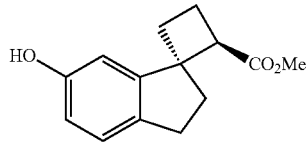

H10

-continued

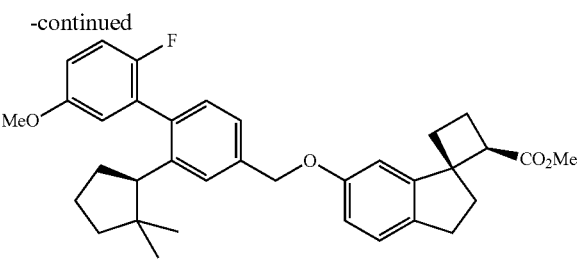

or

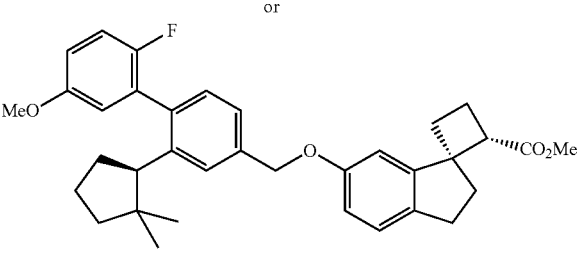

or

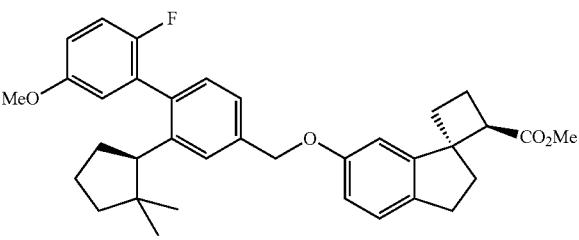

146.1

(1S,2S)-Methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate or (1S,2R)-methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate or (1R,2S)-methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate or (1R,2R)-methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate (146.1)

A mixture of H10 (0.034 mmol), T3 (0.041 mmol) and $Cs_2CO_3$ (0.069 mmol) in DMF (1.5 mL) was stirred at room temperature for 20 hours. The reaction mixture was concentrated and the residue was purified by chromatography (silica gel, eluting with 1:9 EtOAc/hexane) to give 12 mg of 146.1. MS ESI (pos.) M/E: 560 (M+$H_2O$).

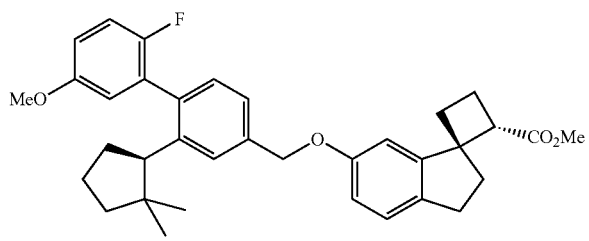

or

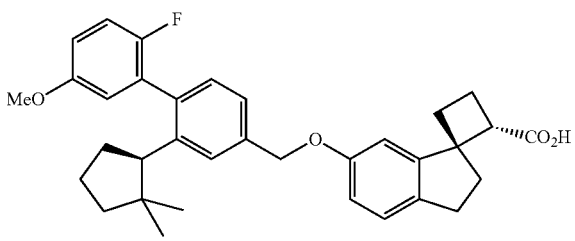

or

-continued

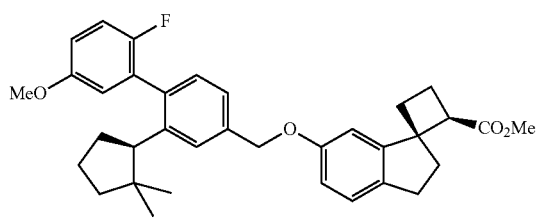

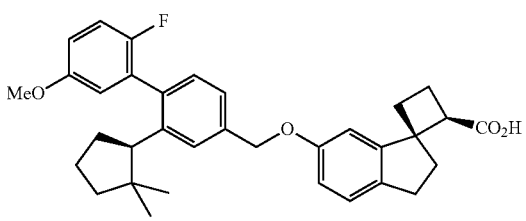

or

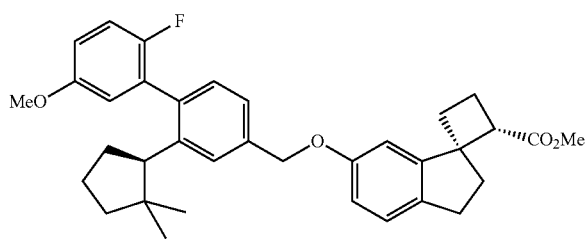

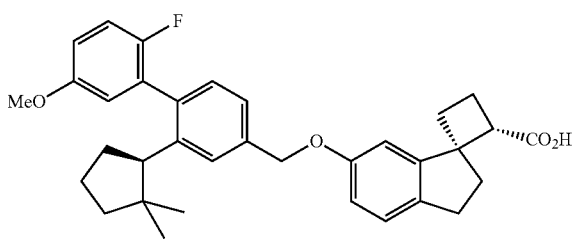

or

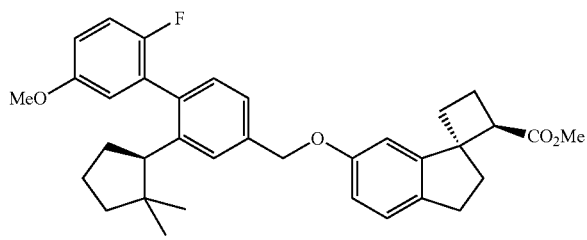

146.1

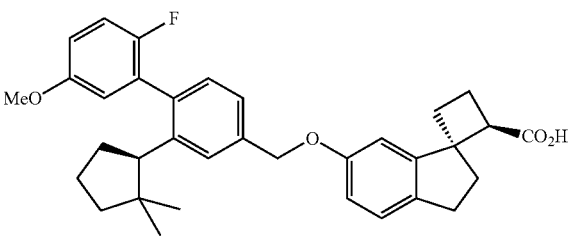

146

(1S,2S)-6'-((2-((R)-2,2-Dimethylcyclopentyl)-2'-fluoro-5'-methoxybiphenyl-4-yl)methoxy)-2',3'-dihydrospiro[cyclobutane-1,1'-indene]-2-carboxylic acid or (1S,2R)-6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylic acid or (1R,2S)-6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylic acid or (1R,2R)-6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylic acid (146)

Example 146 was prepared from 146.1 using the same method used to prepare 145. MS ESI (neg.) M/E: 527 (M–H). $^1$H NMR (400 MHz, CDCl$_3$) δ ppm 7.43 (1H, m), 7.34 (1H, m), 7.21 (1H, m), 7.03-7.09 (3H, m), 6.84 (2H, m), 6.65-6.77 (1H, m), 5.09 (2H, s), 3.80 (3H, s), 3.36 (1H, m), 2.83-2.91 (2H, m), 2.70 (1H, m), 2.30-2.50 (3H, m), 2.10-2.24 (3H, m), 2.00-2.10 (1H, m), 1.75-1.80 (1H, m), 1.60-1.70 (2H, m), 1.50-1.56 (1H, m), 1.30-1.40 (1H, m), 0.71 (3H, m), 0.58 (3H, m).

429
Example 147
430
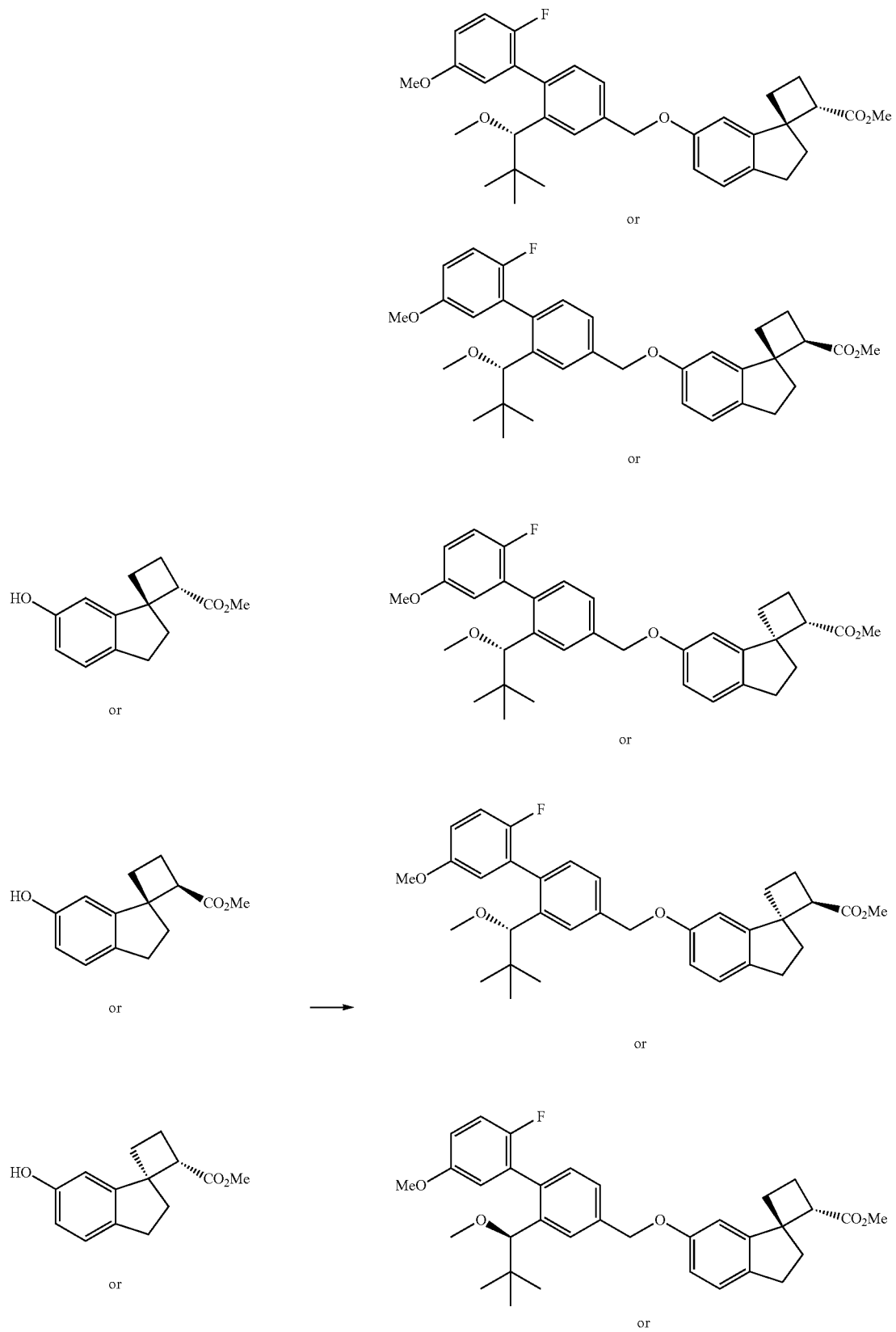

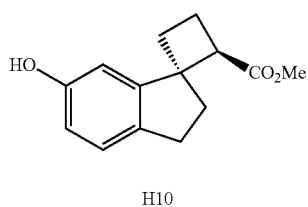

H10

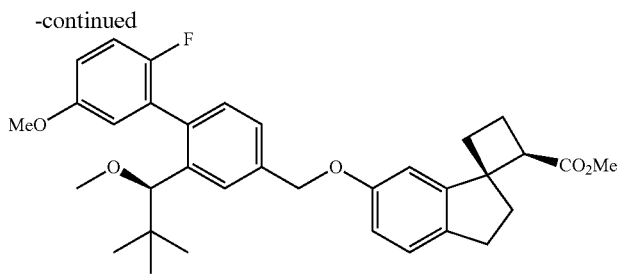

or

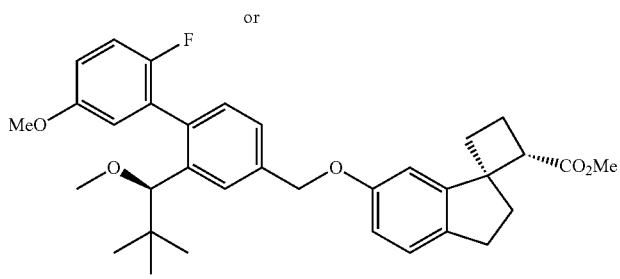

or

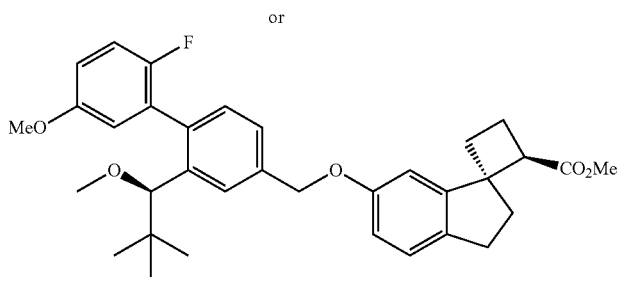

147.1

(1S,2S)-Methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1S,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1R,2S)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1R,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1S,2S)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1S,2R)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1R,2S)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1R,2R)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate (147.1)

A mixture of H10 (0.034 mmol), T4 (0.041 mmol) and $Cs_2CO_3$ (0.069 mmol) in DMF (1.5 mL) was stirred at room temperature for 20 hours. The reaction mixture was concentrated and the residue was purified by chromatography (silica gel, eluting with 1:9 EtOAc/hexane) to give 14 mg of 147.1. MS ESI (pos.) M/E: 569 (M+Na).

433                                    434
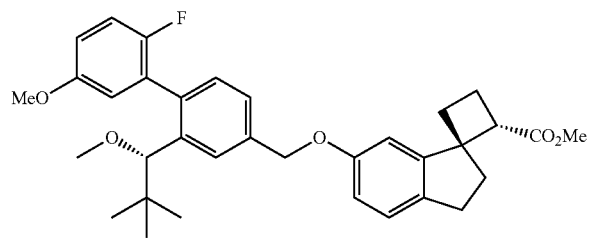
or
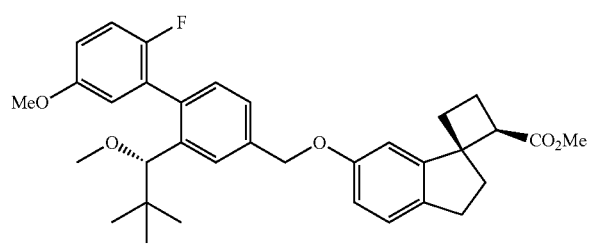
or
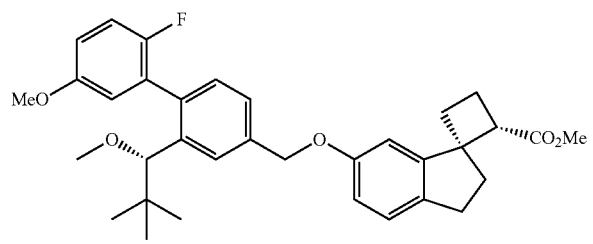
or
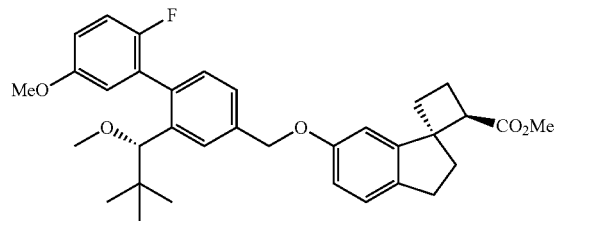
or
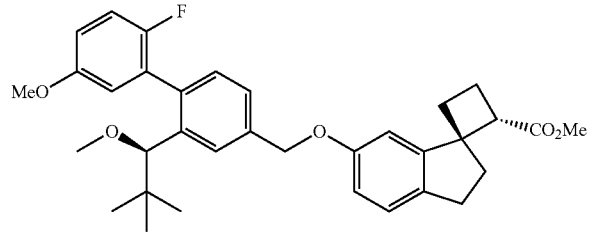
or
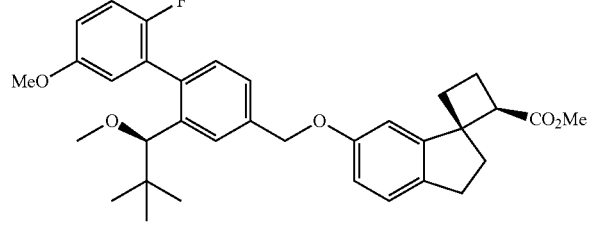
or
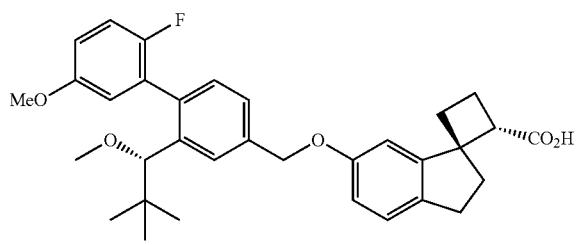
or
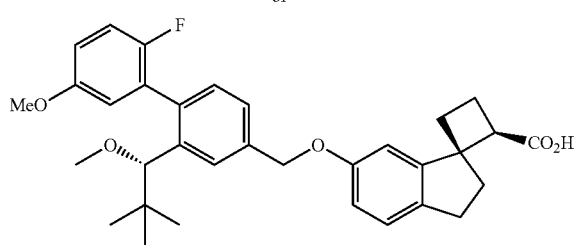
or
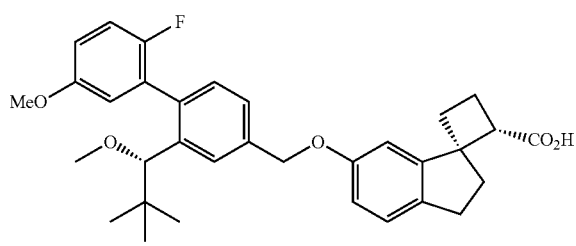
or
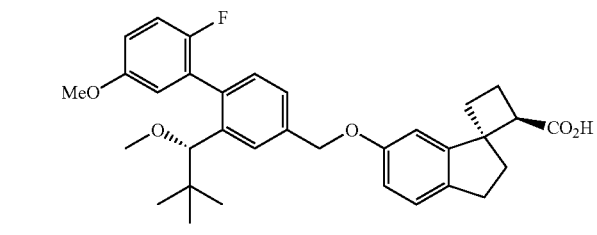
or
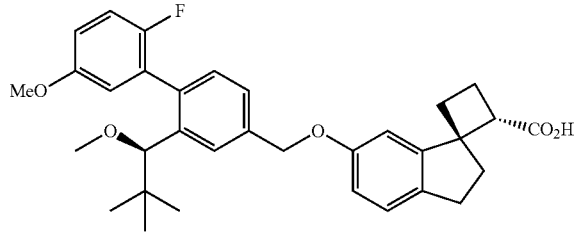
or
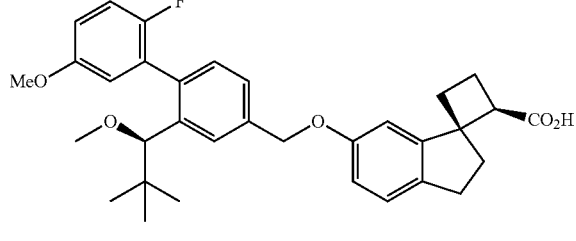
or

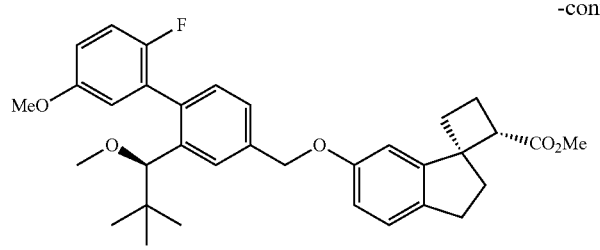

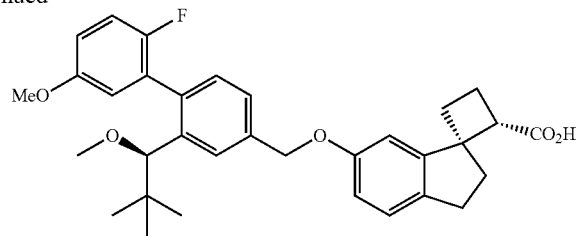

or

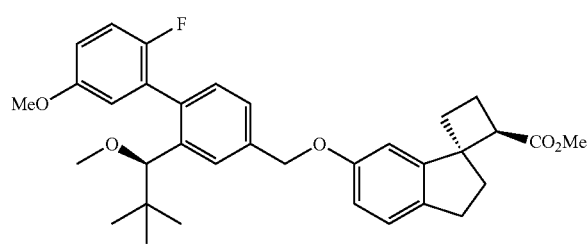

147.1

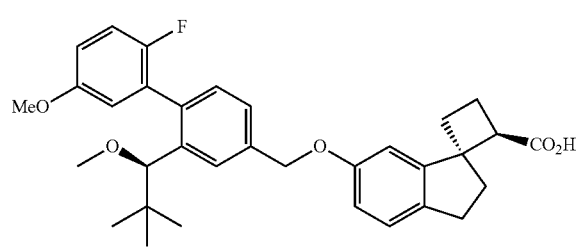

147

(1S,2S)-6'-((2'-Fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1S,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1R,2S)-6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1R,2R)-6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1S,2S)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1S,2R)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1R,2S)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1R,2R)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid (147)

Example 147 was prepared from 147.1 using the same method used to prepare 145. MS ESI (neg.) M/E: 531 (M−H). $^1$H NMR (400 MHz, CDCl$_3$) δ ppm 7.38-7.43 (2H, m), 7.20 (2H, m), 6.96-7.04 (2H, m), 6.87 (1H, m), 6.71 (1H, m), 6.59 (1H, m), 5.21 (2H, s), 3.94-4.16 (1H, m), 3.79 (3H, s), 3.41 (1H, m), 3.02-3.09 (3H, m), 2.89 (1H, m), 2.73 (1H, m), 2.57 (1H, m), 2.42 (1H, m), 2.15-2.26 (3H, m), 0.73 (9H, s).

Example 148

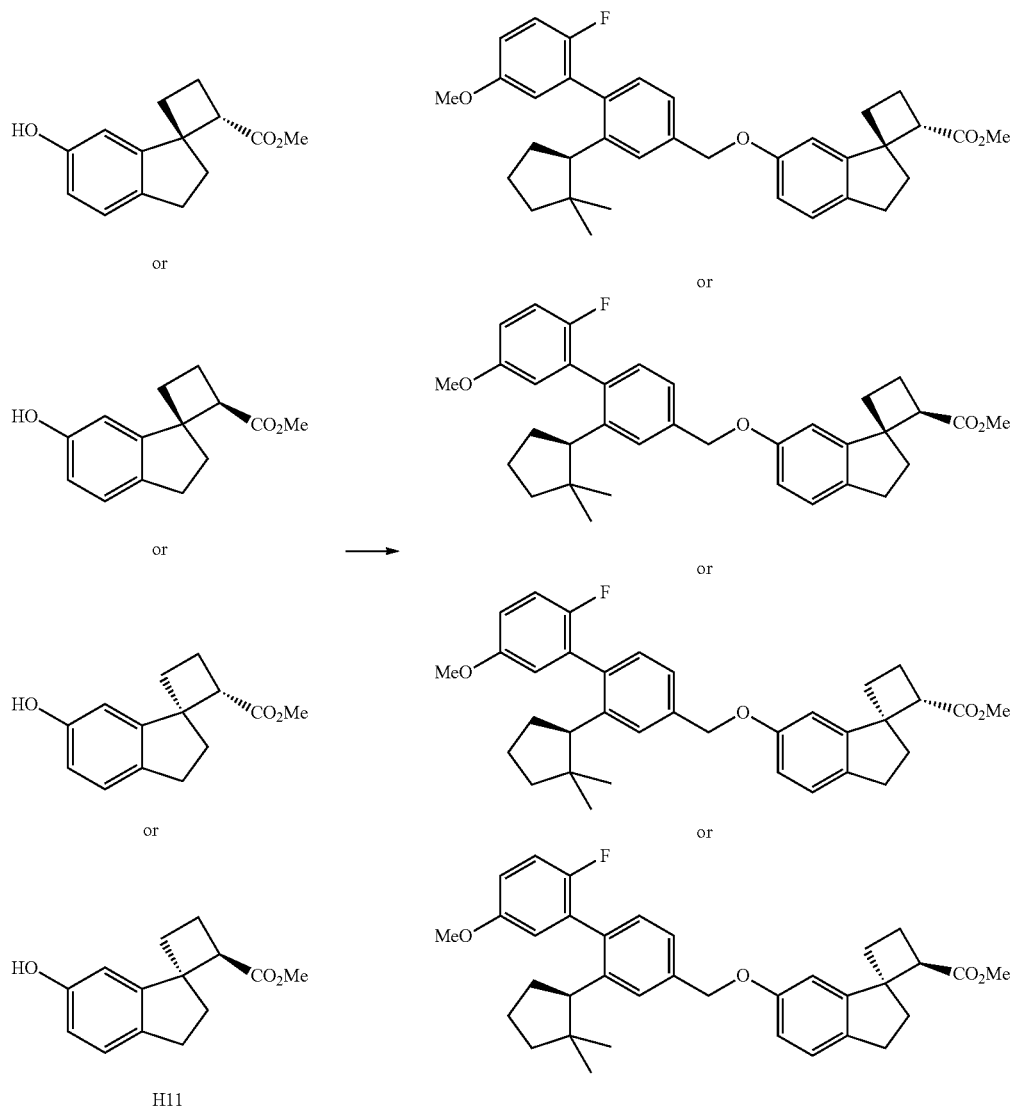

(1S,2S)-Methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate or (1S,2R)-methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate or (1R,2S)-methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate or (1R,2R)-methyl 6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylate (148.1)

A mixture of H11 (0.052 mmol), T3 (0.062 mmol) and $Cs_2CO_3$ (0.10 mmol) in DMF (2 mL) was stirred at room temperature for 20 hours. The reaction mixture was concentrated and the residue was purified by chromatography (silica gel, eluting with 1:9 EtOAc/hexane) to give 24 mg of 148.1. M/E: 560 (M+$H_2O$).

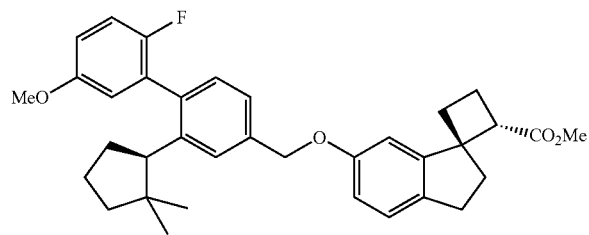

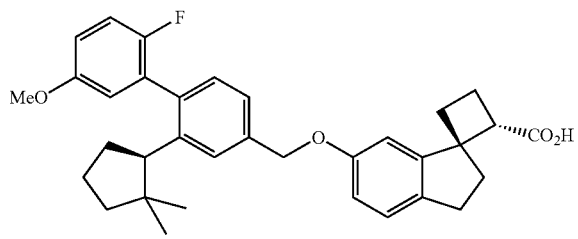

or

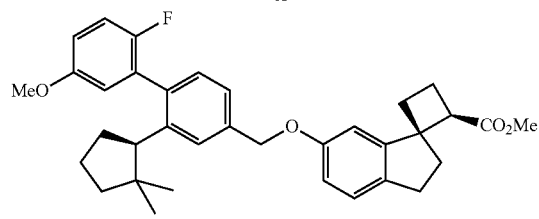

or

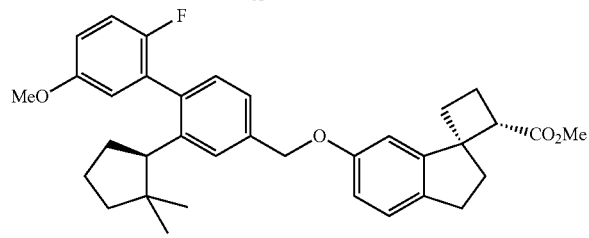

or

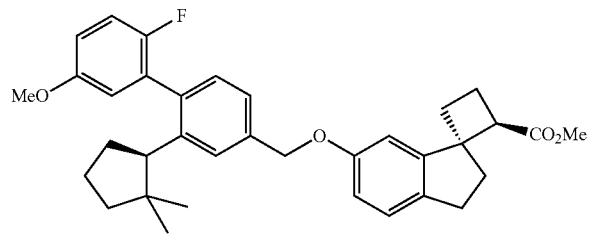

148.1

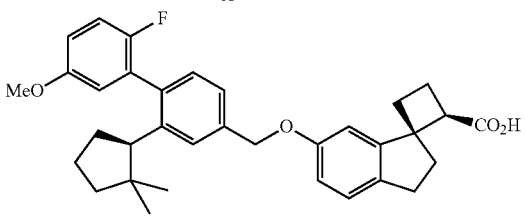

or

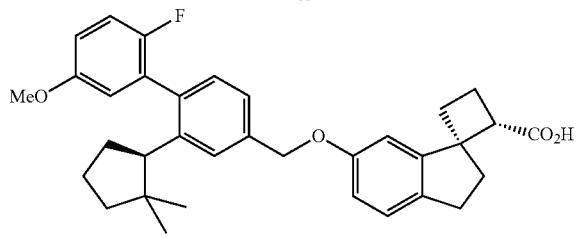

or

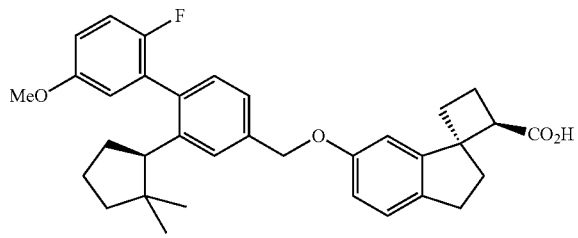

148

(1S,2S)-6'-((2-((R)-2,2-Dimethylcyclopentyl)-2'-fluoro-5'-methoxybiphenyl-4-yl)methoxy)-2',3'-dihydrospiro[cyclobutane-1,1'-indene]-2-carboxylic acid or (1S,2R)-6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylic acid or (1R,2S)-6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylic acid or (1R,2R)-6'-((2-((R)-2,2-dimethylcyclopentyl)-2'-fluoro-5'-methoxybiphenyl-4-yl)methoxy)-2',3'-dihydrospiro[cyclobutane-1,1'-indene]-2-carboxylic acid (148)

Example 148 was prepared from 148.1 using the same method used to prepare 145. MS ESI (neg.) M/E: 527 (M–H). $^1$H NMR (400 MHz, CDCl$_3$) δ ppm 7.43 (1H, m), 7.34 (1H, m), 7.21 (1H, m), 7.03-7.09 (3H, m), 6.84 (2H, m), 6.65-6.77 (1H, m), 5.09 (2H, s), 3.80 (3H, s), 3.36 (1H, m), 2.83-2.91 (2H, m), 2.70 (1H, m), 2.30-2.50 (3H, m), 2.10-2.24 (3H, m), 2.00-2.10 (1H, m), 1.75-1.80 (1H, m), 1.60-1.70 (2H, m), 1.50-1.56 (1H, m), 1.30-1.40 (1H, m), 0.71 (3H, m), 0.58 (3H, m).

441
Example 149
442
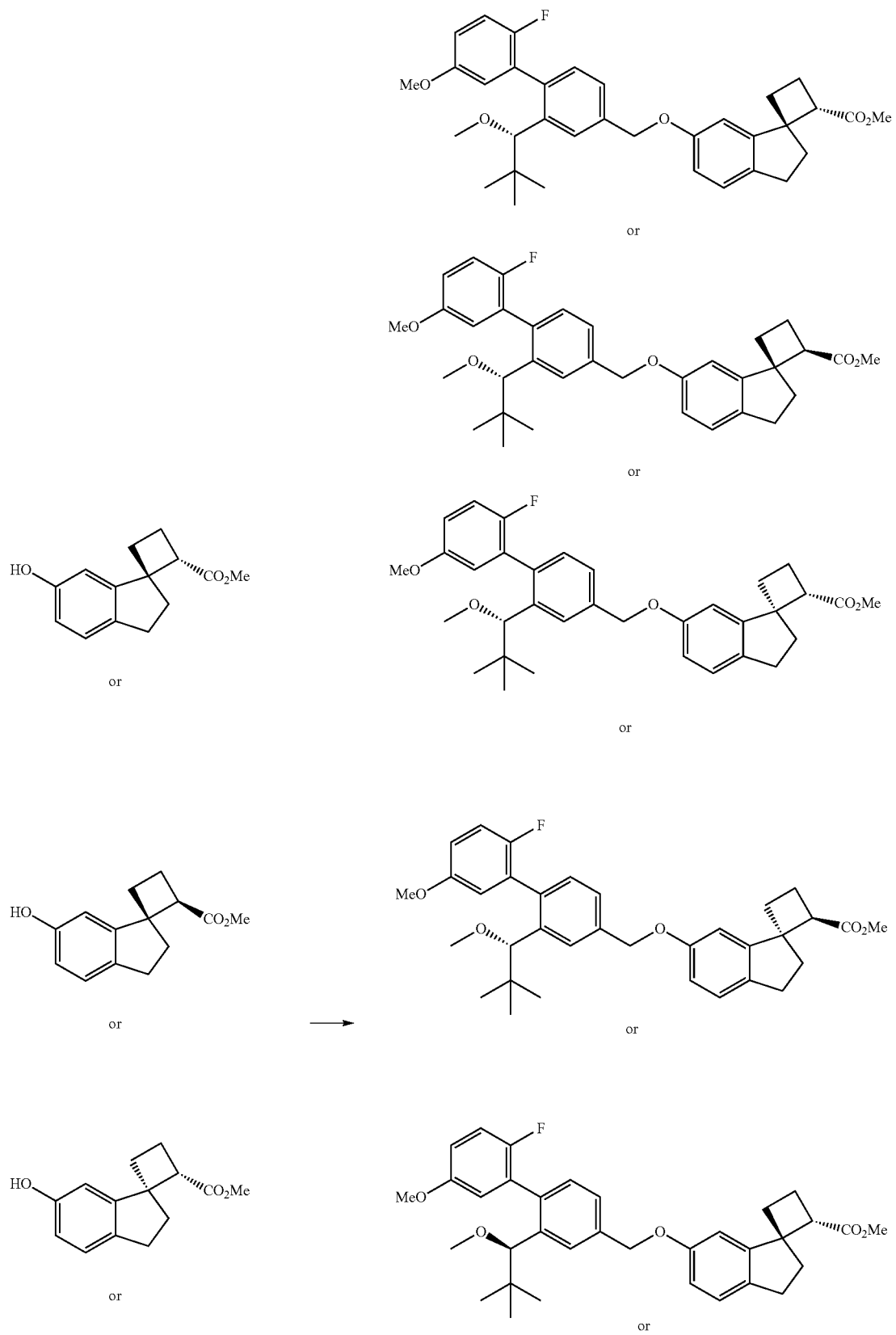

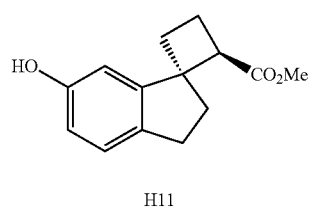

H11

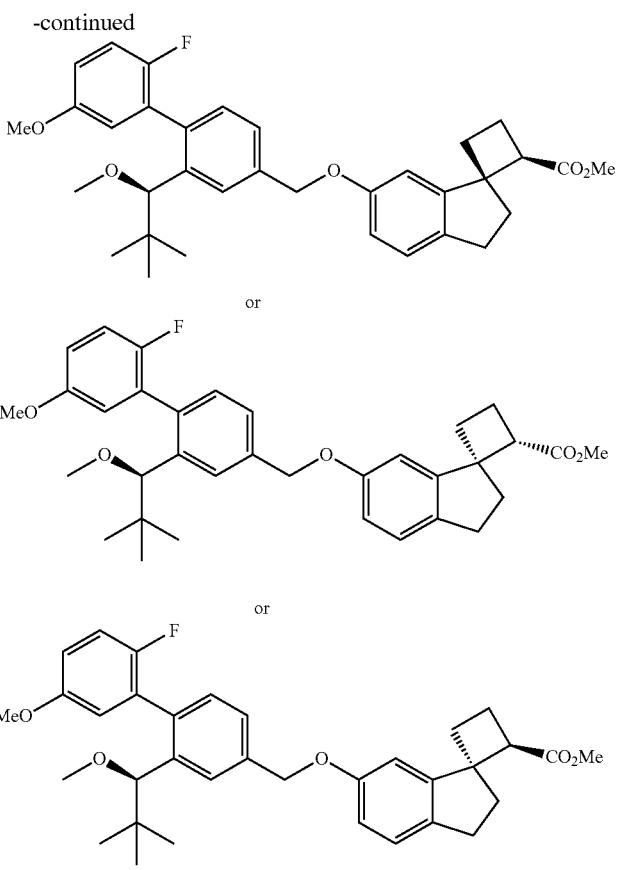

149.1

(1S,2S)-Methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1S,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1R,2S)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1R,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylate or (1S,2S)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1S,2R)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1R,2S)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate or (1R,2R)-methyl 6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylate (149.1)

A mixture of H11 (0.052 mmol), T4 (0.062 mmol) and $Cs_2CO_3$ (0.10 mmol) in DMF (2 mL) was stirred at room temperature for 20 hours. The reaction mixture was concentrated and the residue was purified by chromatography (silica gel, eluting with 1:9 EtOAc/hexane) to give 22 mg of 149.1. MS ESI (pos.) M/E: 546 (M+H).

445
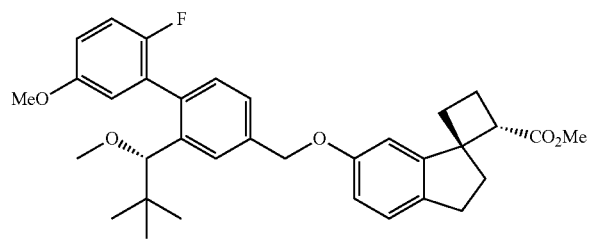
or
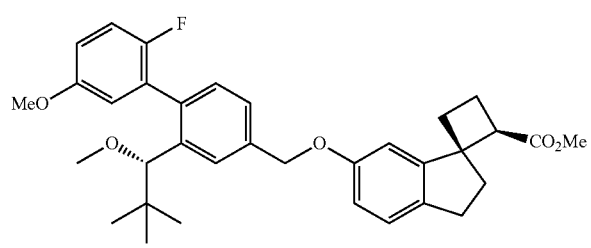
or
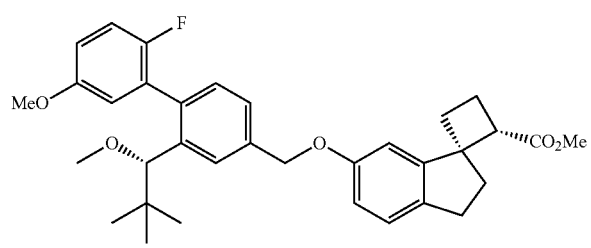
or
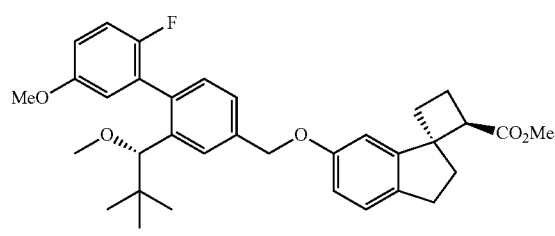
or
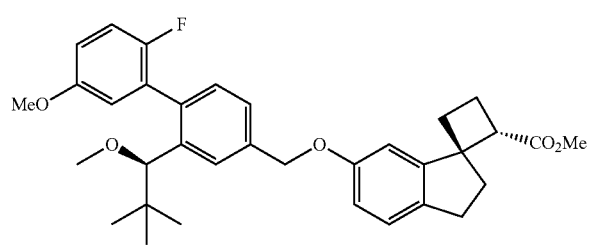
or
446
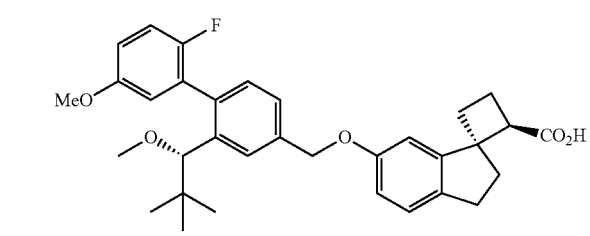
or
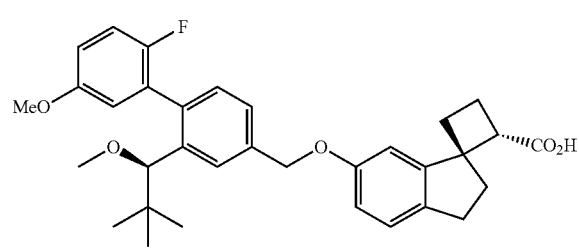
or

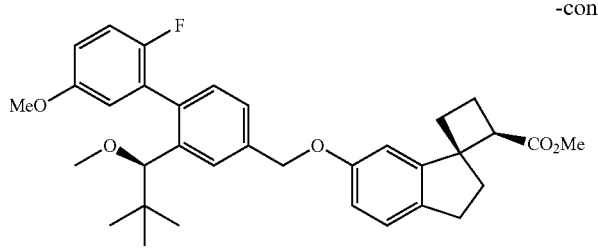

or

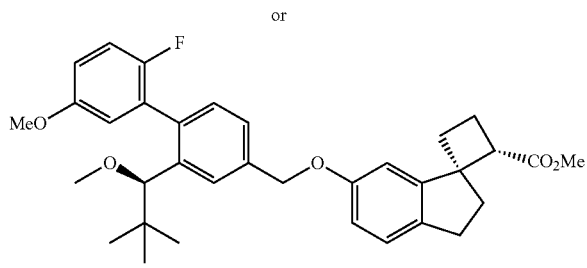

or

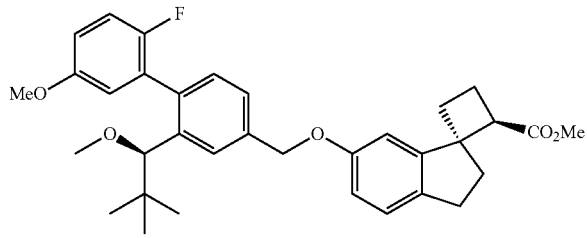

149.1

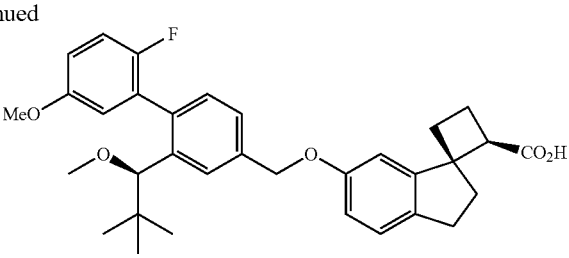

or

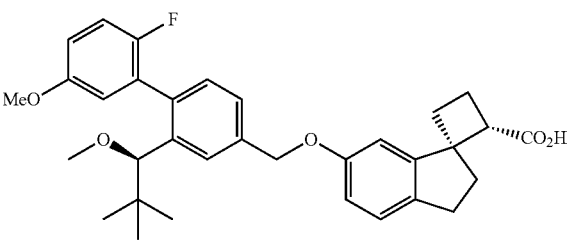

or

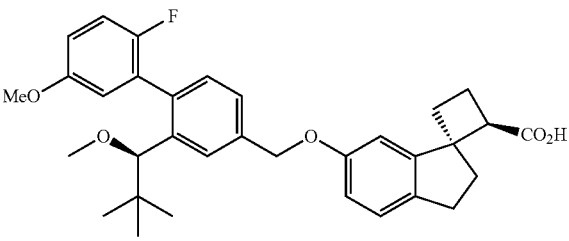

149

(1S,2S)-6'-((2'-Fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1S,2R)-methyl 6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1R,2S)-6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1R,2R)-6'-((2'-fluoro-5'-methoxy-2-((S)-1-methoxy-2,2-dimethylpropyl)biphenyl-4-yl)methoxy)-2',3'-dihydrospiro[cyclobutane-1,1'-indene]-2-carboxylic acid or (1S,2S)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1S,2R)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1R,2S)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid or (1R,2R)-6'-((2'-fluoro-5'-methoxy-2-((R)-1-methoxy-2,2-dimethylpropyl)biphenyl-4-yl)methoxy)-2',3'-dihydrospiro[cyclobutane-1,1'-indene]-2-carboxylic acid (149)

Example 149 was prepared from 149.1 using the same method used to prepare 145. MS ESI (neg.) M/E: 531 (M−H). $^1$H NMR (400 MHz, CDCl$_3$) δ ppm 7.38-7.43 (2H, m), 7.20 (2H, m), 6.96-7.04 (2H, m), 6.87 (1H, m), 6.71 (1H, m), 6.59 (1H, m), 5.21 (2H, s), 3.94-4.16 (1H, m), 3.79 (3H, s), 3.41 (1H, m), 3.02-3.09 (3H, m), 2.89 (1H, m), 2.73 (1H, m), 2.57 (1H, m), 2.42 (1H, m), 2.15-2.26 (3H, m), 0.73 (9H, s).

Example 150

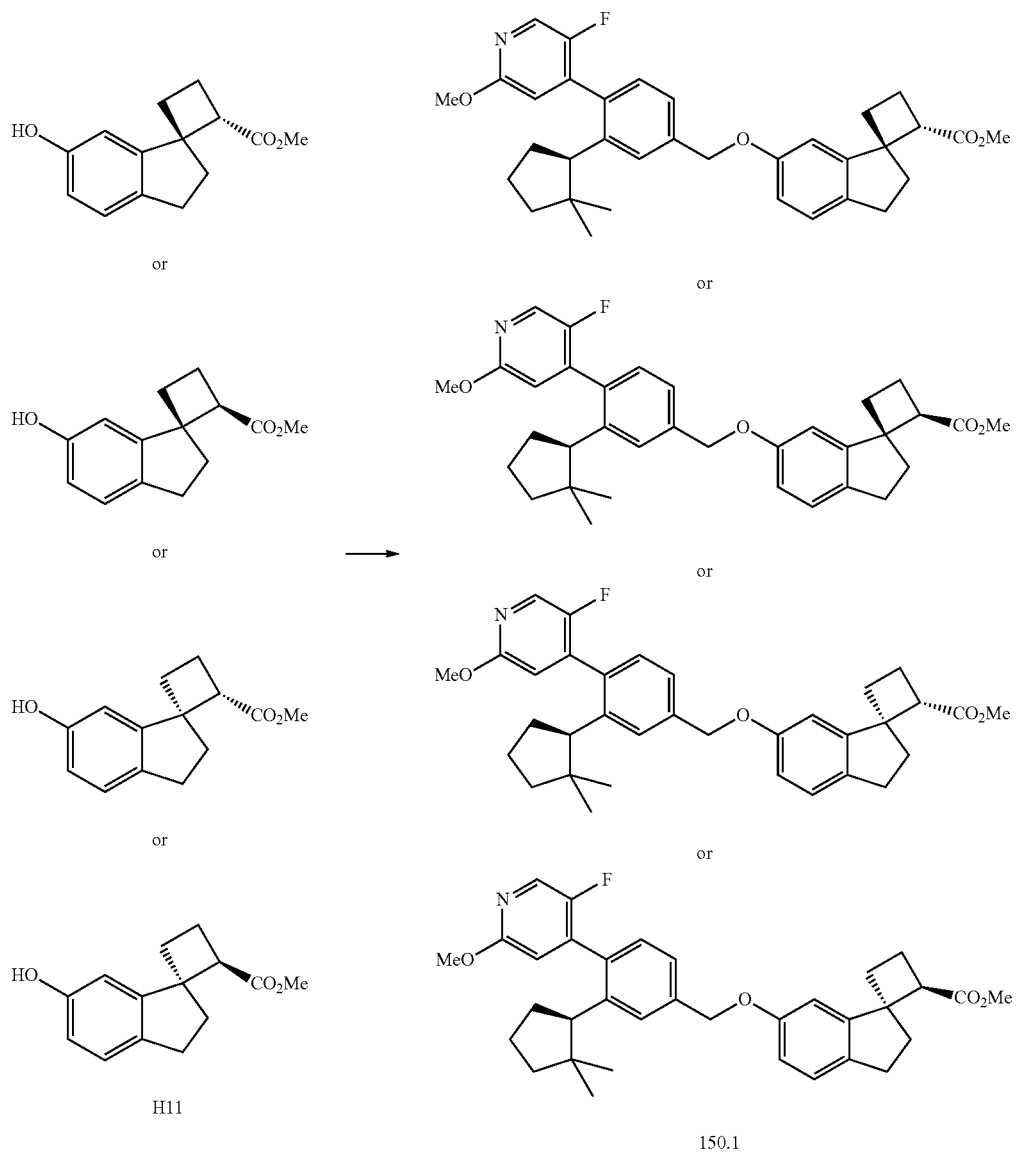

(1S,2S)-Methyl 6'-(3-((R)-2,2-dimethylcyclopentyl)-4-(5-fluoro-2-methoxypyridin-4-yl)benzyloxy)-2',3'-dihydrospiro[cyclobutane-1,1'-indene]-2-carboxylate or (1S,2R)-methyl 6'-(3-((R)-2,2-dimethylcyclopentyl)-4-(5-fluoro-2-methoxypyridin-4-yl)benzyloxy)-2',3'-dihydrospiro[cyclobutane-1,1'-indene]-2-carboxylate or (1R,2S)-methyl 6'-(3-((R)-2,2-dimethylcyclopentyl)-4-(5-fluoro-2-methoxypyridin-4-yl)benzyloxy)-2',3'-dihydrospiro[cyclobutane-1,1'-indene]-2-carboxylate or (1R,2R)-methyl 6'-(3-((R)-2,2-dimethylcyclopentyl)-4-(5-fluoro-2-methoxypyridin-4-yl)benzyloxy)-2',3'-dihydrospiro[cyclobutane-1,1'-indene]-2-carboxylate (150.1)

A mixture of H11 (0.052 mmol), T5 (0.062 mmol) and $Cs_2CO_3$ (0.10 mmol) in DMF (2 mL) was stirred at room temperature for 20 hours. The reaction mixture was concentrated and the residue was purified by chromatography (silica gel, eluting with 1:9 EtOAc/hexane) to give 23 mg of 150.1. MS ESI (pos.) M/E: 544 (M+H).

451

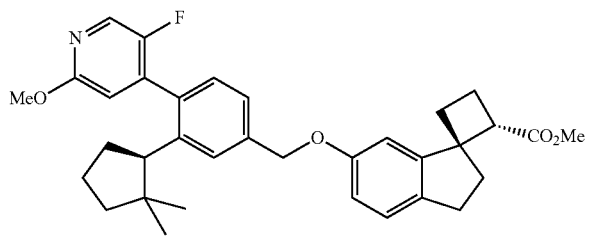

or

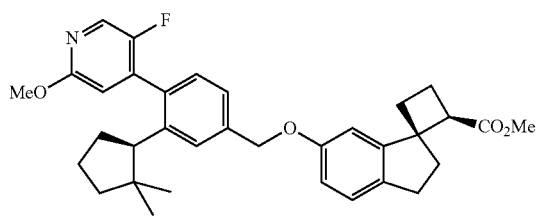

or

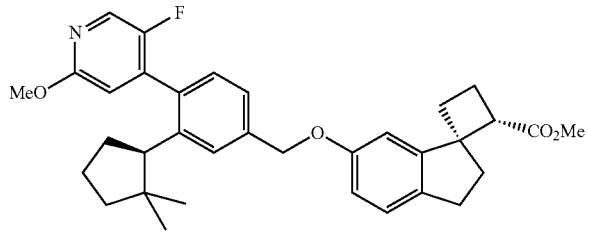

or

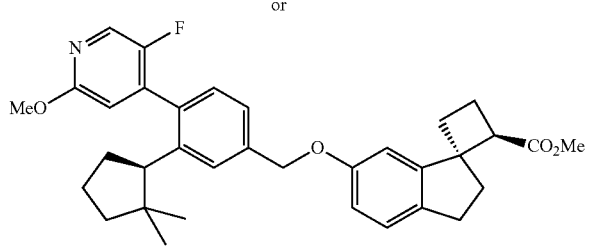

150.1

452

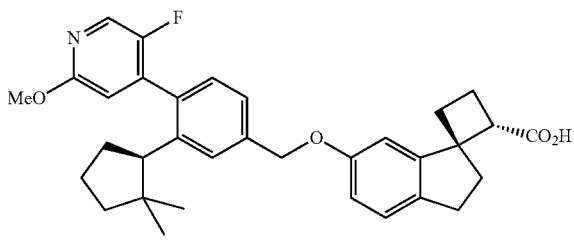

or

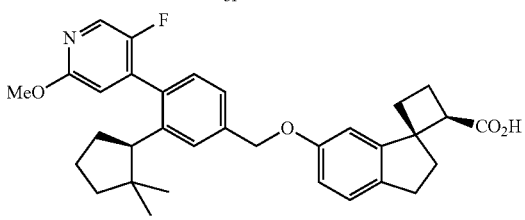

or

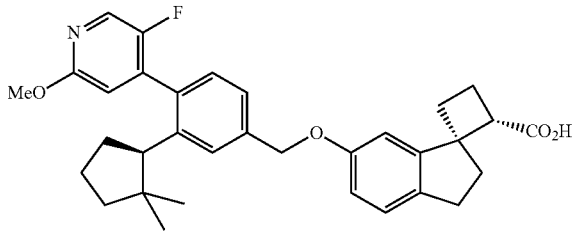

or

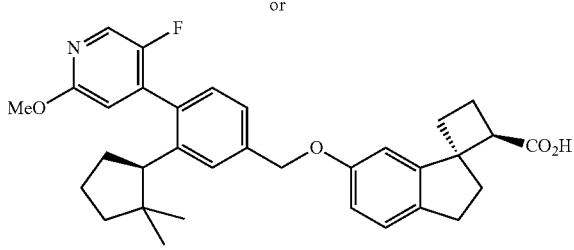

150

(1S,2S)-6'-(3-((R)-2,2-Dimethylcyclopentyl)-4-(5-fluoro-2-methoxypyridin-4-yl)benzyloxy)-2',3'-dihydrospiro[cyclobutane-1,1'-indene]-2-carboxylic acid or (1S,2R)-6'-(3-((R)-2,2-dimethylcyclopentyl)-4-(5-fluoro-2-methoxypyridin-4-yl)benzyloxy)-2',3'-dihydrospiro[cyclobutane-1,1'-indene]-2-carboxylic acid or (1R,2S)-6'-(3-((R)-2,2-dimethylcyclopentyl)-4-(5-fluoro-2-methoxypyridin-4-yl)benzyloxy)-2',3'-dihydrospiro[cyclobutane-1,1'-indene]-2-carboxylic acid or (1R,2R)-6'-(3-((R)-2,2-dimethylcyclopentyl)-4-(5-fluoro-2-methoxypyridin-4-yl)benzyloxy)-2',3'-dihydrospiro[cyclobutane-1,1'-indene]-2-carboxylic acid (150)

Example 150 was prepared from 150.1 using the same method used to prepare 145. MS ESI (neg.) M/E: 528 (M–H). $^1$H NMR (400 MHz, CDCl$_3$) δ ppm 8.03 (1H, m), 7.46 (1H, m), 7.36 (1H, m), 7.13 (1H, m), 7.11 (1H, m), 7.02 (1H, m), 6.86 (1H, m), 6.55-6.69 (1H, m), 5.13 (2H, s), 3.98 (3H, m), 3.36 (1H, m), 2.70-2.90 (3H, m), 2.35-2.45 (2H, m), 2.25 (1H, m), 2.00-2.20 (6H, m), 1.60-1.90 (2H, m), 1.52 (1H, m), 1.43 (1H, m), 0.60-0.70 (6H, m).

Example 151

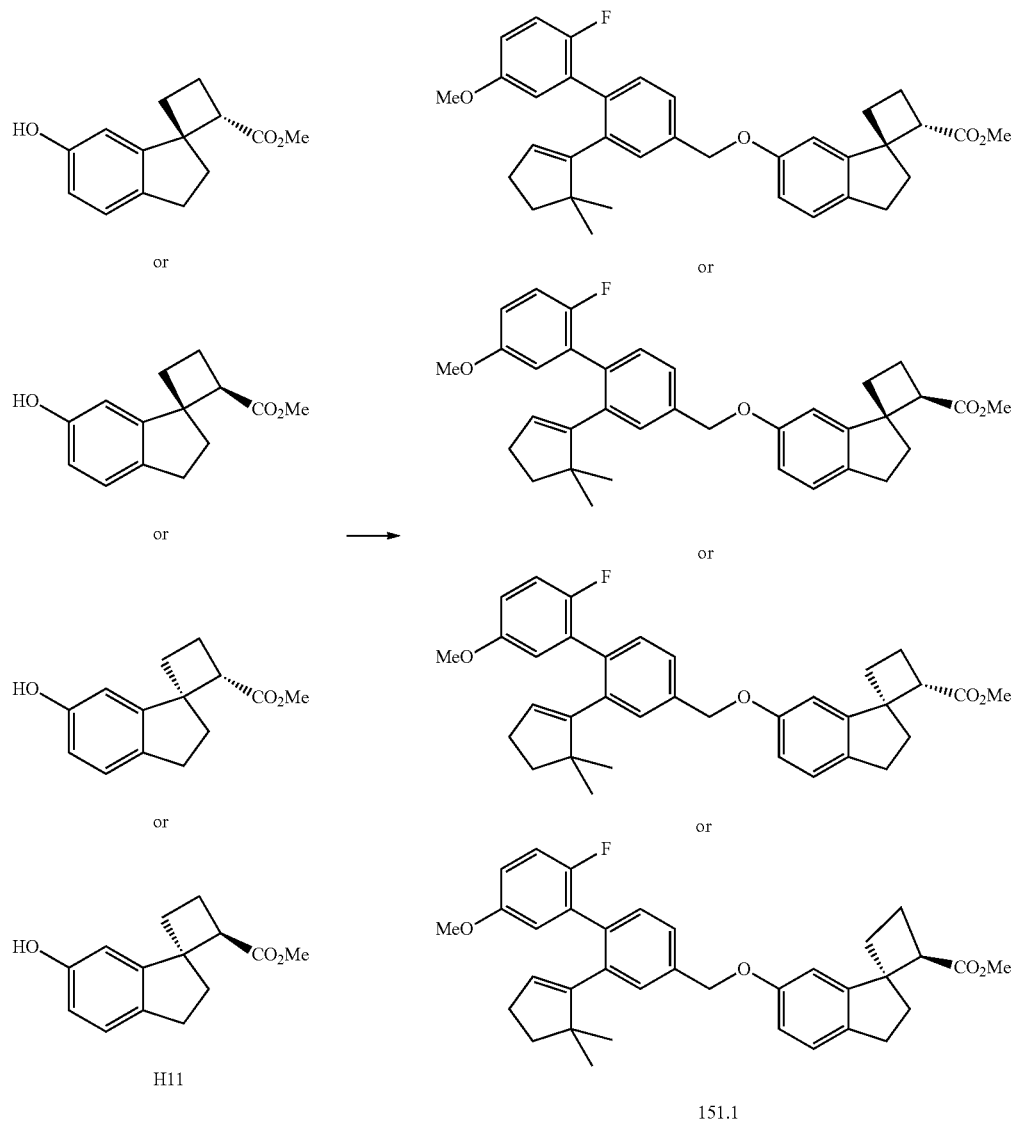

(1S,2S)-Methyl 6'-((2-(5,5-dimethylcyclopent-1-enyl)-2'-fluoro-5'-methoxybiphenyl-4-yl)methoxy)-2',3'-dihydrospiro[cyclobutane-1,1'-indene]-2-carboxylate or (1S,2R)-methyl 6'-((2-(5,5-dimethylcyclopent-1-enyl)-2'-fluoro-5'-methoxybiphenyl-4-yl)methoxy)-2',3'-dihydrospiro[cyclobutane-1,1'-indene]-2-carboxylate or (1R,2S)-methyl 6'-((2-(5,5-dimethylcyclopent-1-enyl)-2'-fluoro-5'-methoxybiphenyl-4-yl)methoxy)-2',3'-dihydrospiro[cyclobutane-1,1'-indene]-2-carboxylate or (1R,2R)-methyl 6'-((2-(5,5-dimethylcyclopent-1-enyl)-2'-fluoro-5'-methoxybiphenyl-4-yl)methoxy)-2',3'-dihydrospiro[cyclobutane-1,1'-indene]-2-carboxylate (151.1)

A mixture of H11 (0.052 mmol), T2 (0.062 mmol) and $Cs_2CO_3$ (0.10 mmol) in DMF (2 mL) was stirred at room temperature for 20 hours. The reaction mixture was concentrated and the residue was purified by chromatography (silica gel, eluting with 1:9 EtOAc/hexane) to give 18 mg of 151.1. MS ESI (pos.) M/E: 558 (M+$H_2O$).

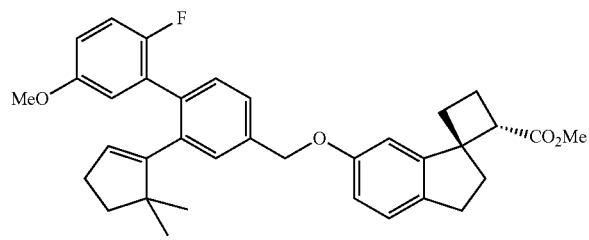

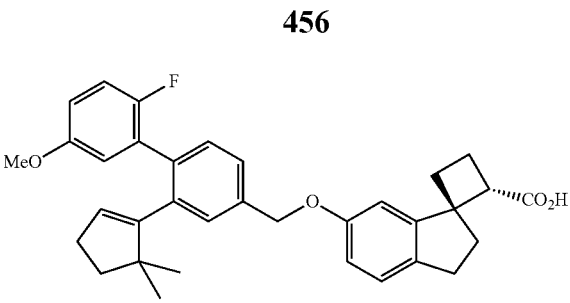

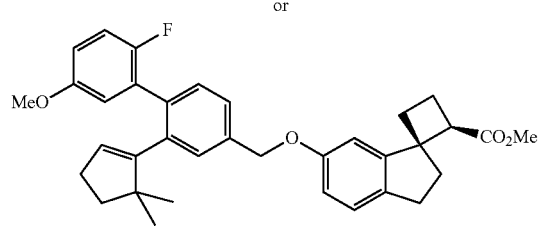

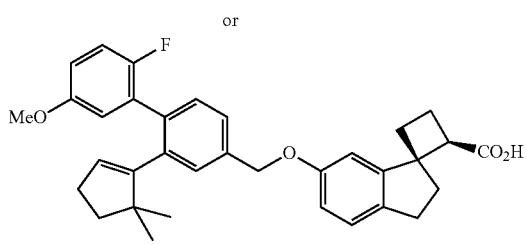

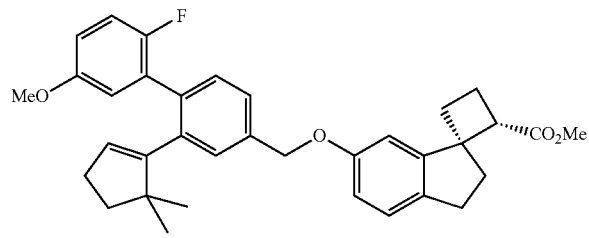

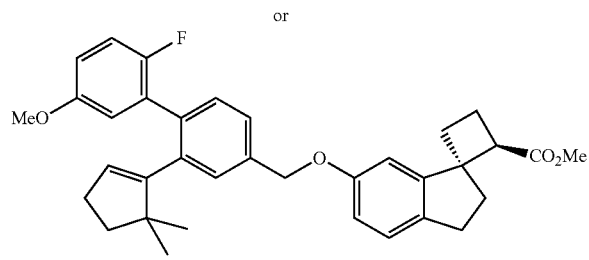

151.1

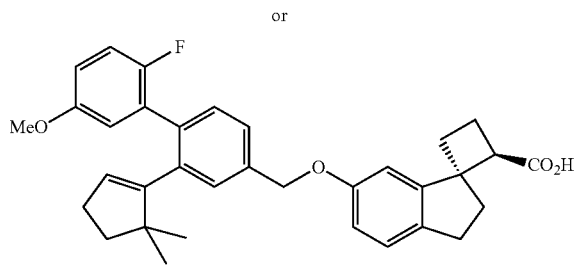

151

(1S,2S)-6'-((2-(5,5-Dimethylcyclopent-1-enyl)-2'-fluoro-5'-methoxybiphenyl-4-yl)methoxy)-2',3'-dihydrospiro[cyclobutane-1,1'-indene]-2-carboxylic acid or (1S,2R)-6'-((2-(5,5-dimethylcyclopent-1-enyl)-2'-fluoro-5'-methoxybiphenyl-4-yl)methoxy)-2',3'-dihydrospiro[cyclobutane-1,1'-indene]-2-carboxylic acid or (1R,2S)-6'-((2-(5,5-dimethylcyclopent-1-enyl)-2'-fluoro-5'-methoxybiphenyl-4-yl)methoxy)-2',3'-dihydrospiro[cyclobutane-1,1'-indene]-2-carboxylic acid or (1R,2R)-6'-((2-(5,5-dimethylcyclopent-1-enyl)-2'-fluoro-5'-methoxybiphenyl-4-yl)methoxy)-2',3'-dihydrospiro[cyclobutane-1,1'-indene]-2-carboxylic acid (151)

Example 151 was prepared from 151.1 using the same method used to prepare 145. MS ESI (neg.) M/E: 525 (M–H). $^1$H NMR (400 MHz, CDCl$_3$) δ ppm 7.36 (1H, m), 7.32-7.36 (2H, s), 7.12 (1H, m), 7.04 (1H, m), 7.03 (2H, m), 6.95 (1H, m), 6.85 (1H, m), 6.81 (2H, m), 5.53 (1H, m), 5.12 (2H, s), 3.76 (3H, s), 3.37 (1H, m), 2.82 (2H, m), 2.40-2.50 (2H, m), 2.20-2.55 (3H, m), 2.05-2.15 (3H, m), 1.67 (2H, m), 0.87 (6H, s).

457
Example 152
458
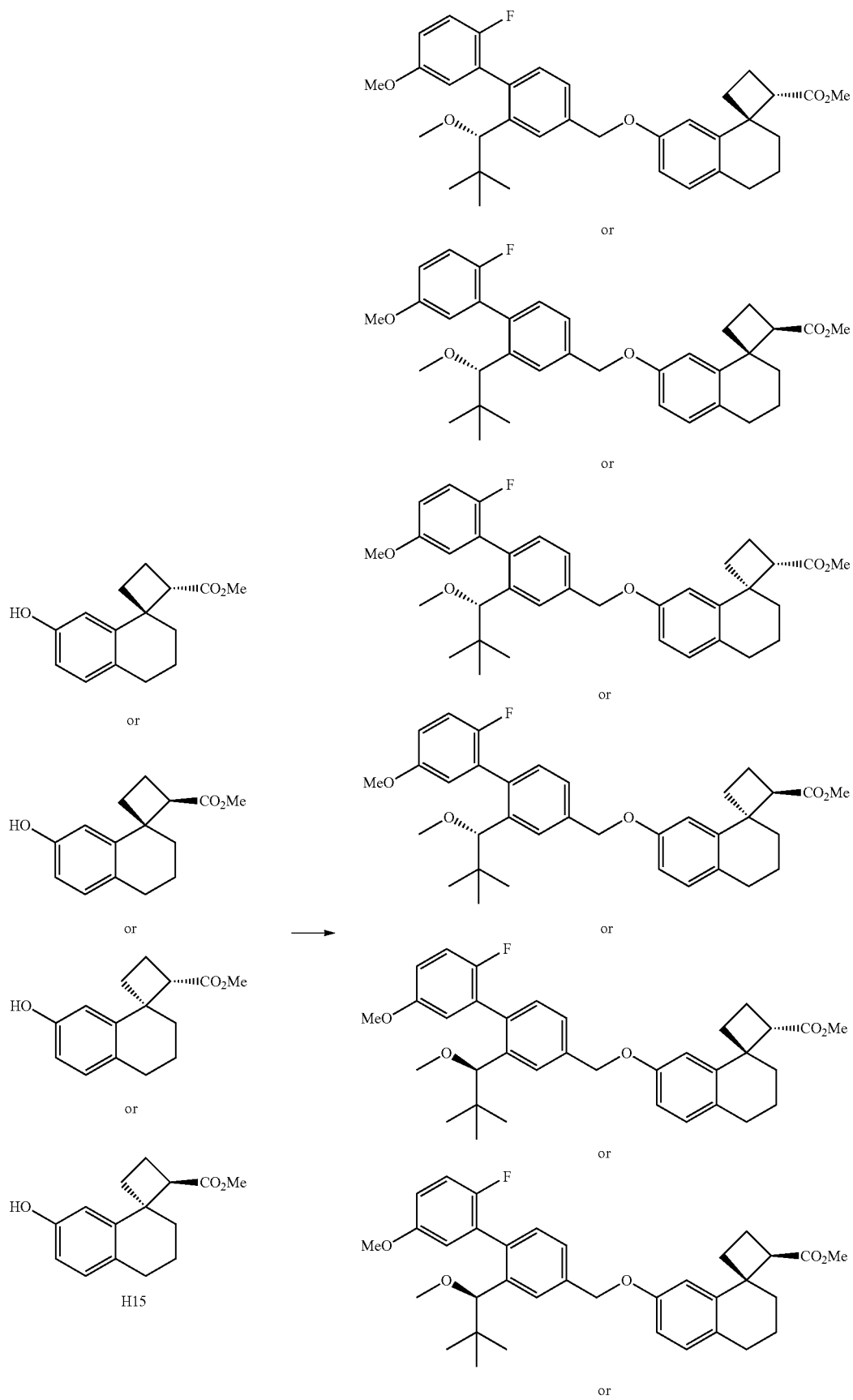

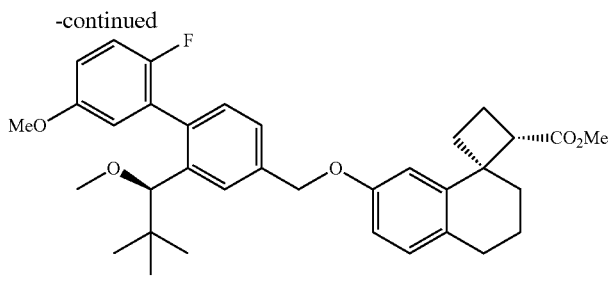

or

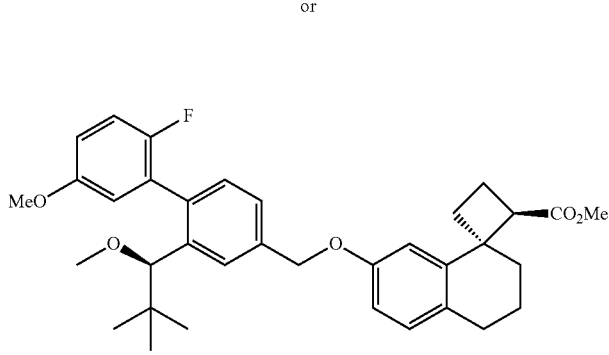

152.1

(1R,2S)-Methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1R,2R)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1S,2S)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1S,2R)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1R,2S)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1R,2R)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1S,2S)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1S,2R)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate (152.1)

A mixture of H15 (0.043 mmol), T4 (0.051 mmol) and $Cs_2CO_3$ (0.085 mmol) in DMF (2 mL) was stirred at room temperature for 20 hours. The reaction mixture was concentrated and the residue was purified by chromatography (silica gel, eluting with 1:9 EtOAc/hexane) to give 152.1.

461
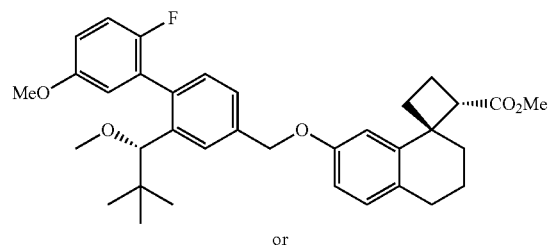
or
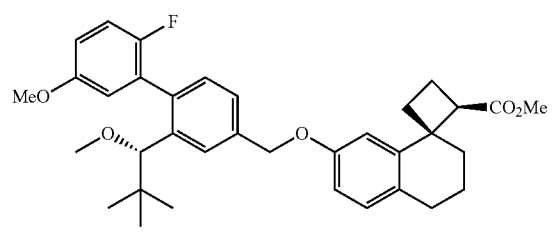
or
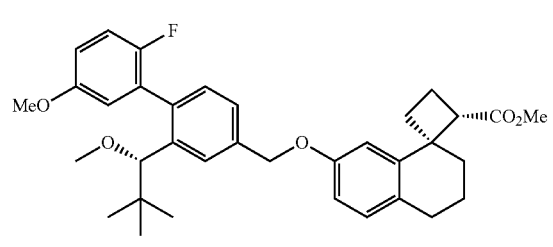
or
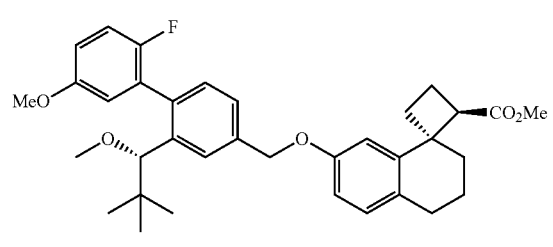
or
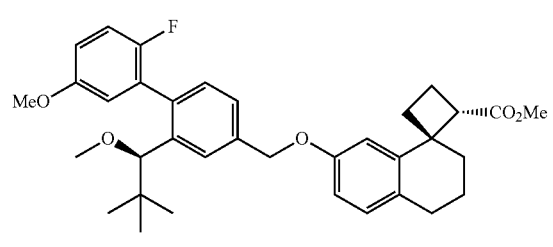
or
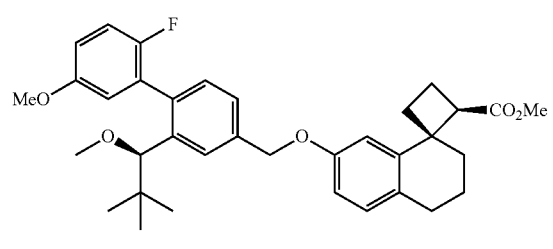
or
462
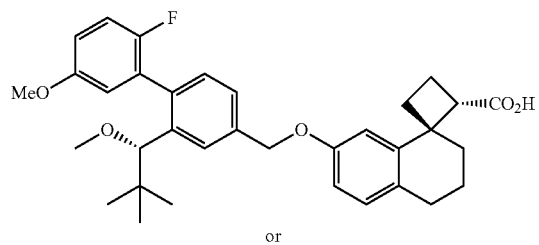
or
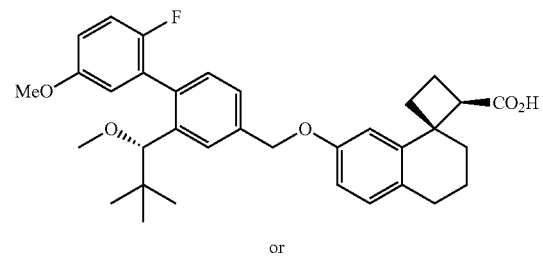
or
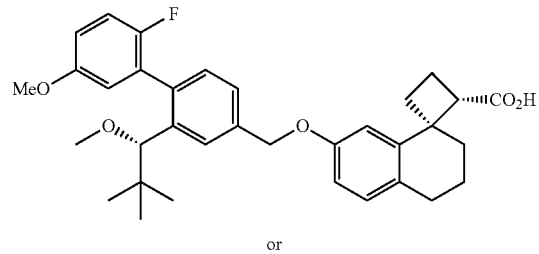
or
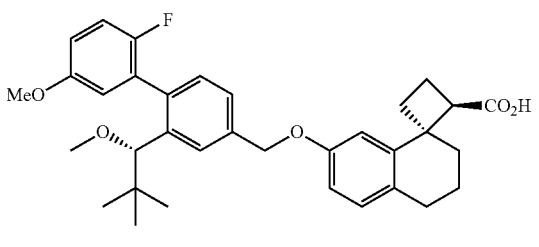
or
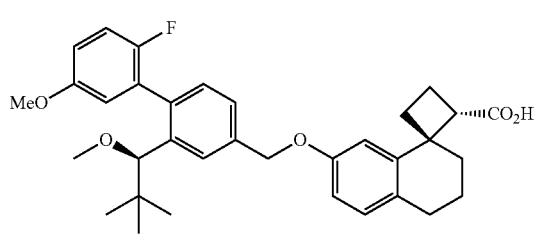
or
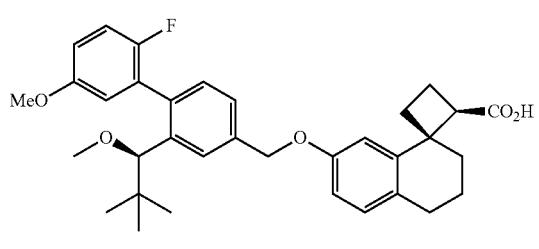
or

463

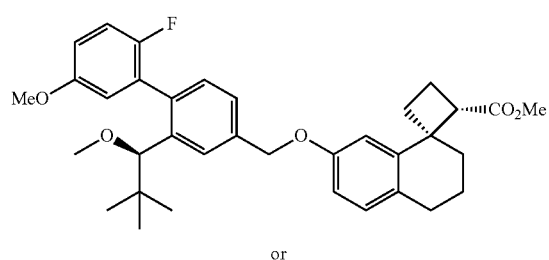

or

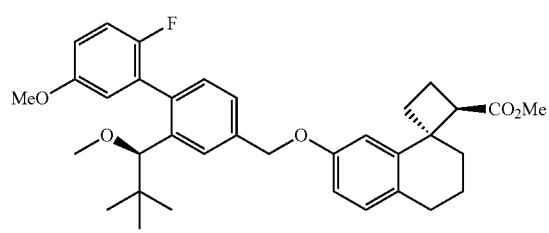

152.1

-continued

464

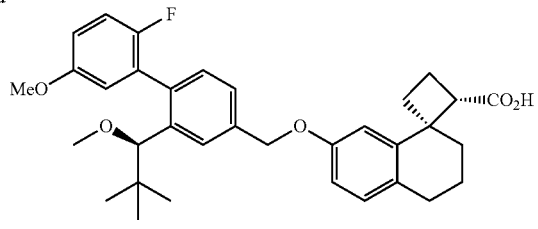

or

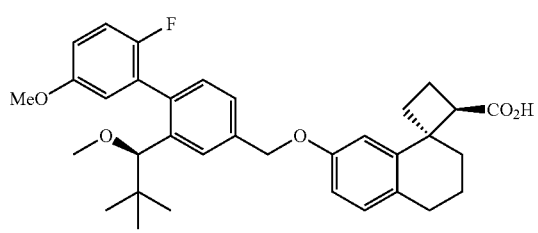

152

(1R,2S)-7'-((2'-Fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2R)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2S)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2R)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2S)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2R)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2S)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2R)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid (152)

Example 152 was prepared from 152.1 using the same method used to prepare 145. MS ESI (neg.) M/E: 545 (M−H). $^1$H NMR (400 MHz, CDCl$_3$) δ ppm 7.60 (1H, m), 7.46 (1H, m), 7.19 (2H, m), 6.98-7.10 (2H, m), 6.82-6.98 (2H, m), 6.74-6.82 (1H, m), 5.16 (2H, s), 3.96-4.20 (1H, m), 3.64 (1H, m), 3.26-3.31 (3H, m), 2.68 (2H, m), 2.38-2.45 (1H, m), 2.06-2.19 (2H, m), 1.97 (3H, m), 1.65-1.80 (2H, m), 0.72 (9H, s).

Example 153

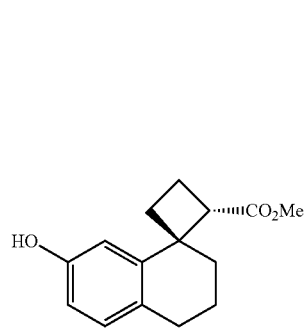

or

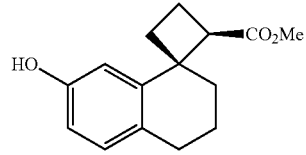

or

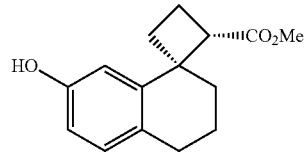

or

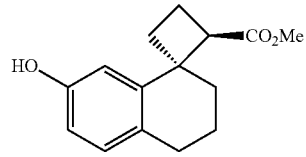

H15

→

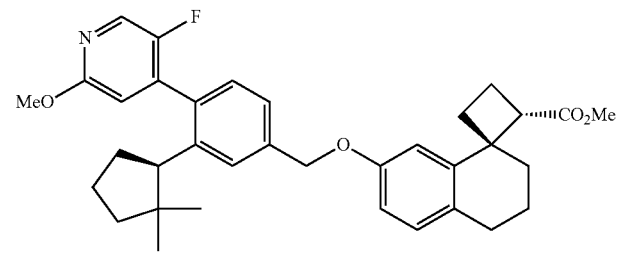

or

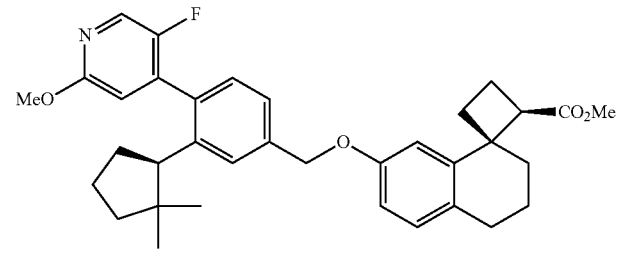

or

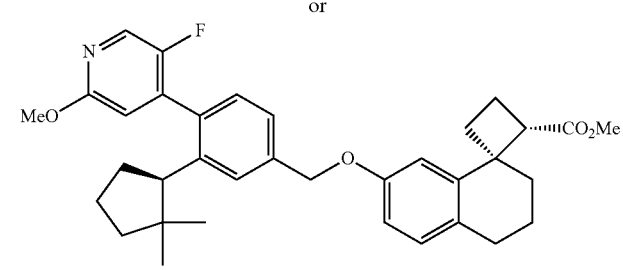

or

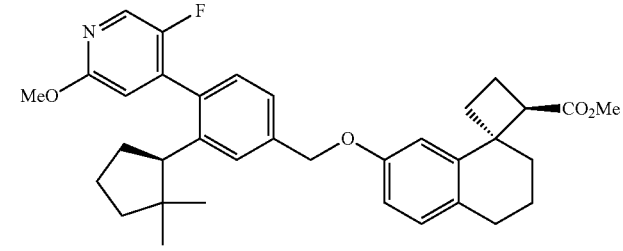

153.1

(1R,2S)-Methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate or (1R,2R)-methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate or (1S,2S)-methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate or (1S,2R)-methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate (153.1)

A mixture of H15 (0.043 mmol), T5 (0.051 mmol) and $Cs_2CO_3$ (0.085 mmol) in DMF (2 mL) was stirred at room temperature for 20 hours. The reaction mixture was concentrated and the residue was purified by chromatography (silica gel, eluting with 1:9 EtOAc/hexane) to give 153.1.

467

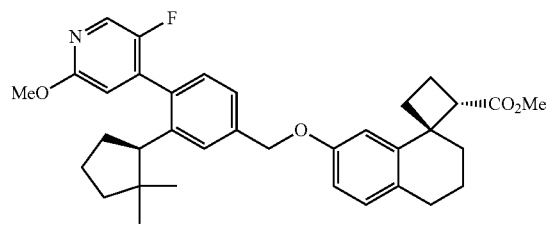

or

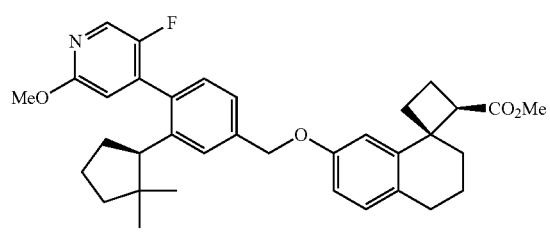

or

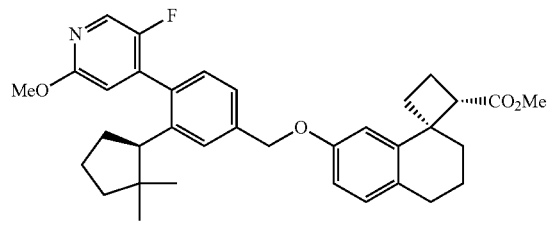

or

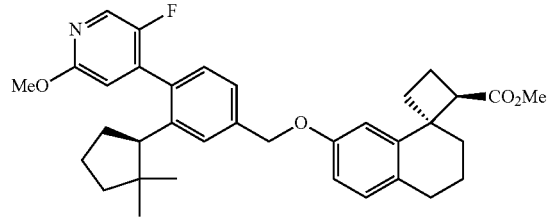

153.1

468

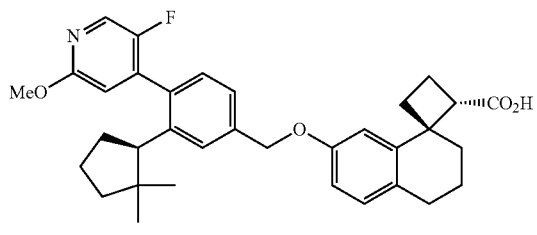

or

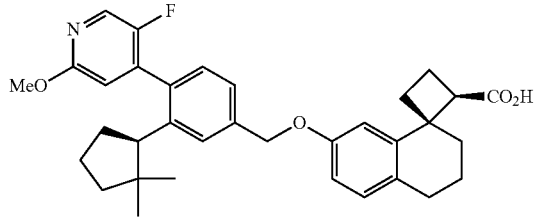

or

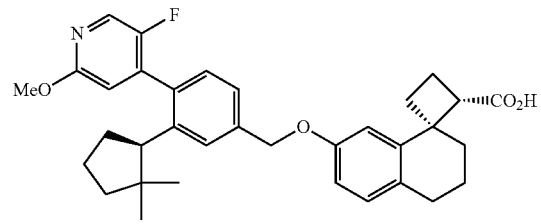

or

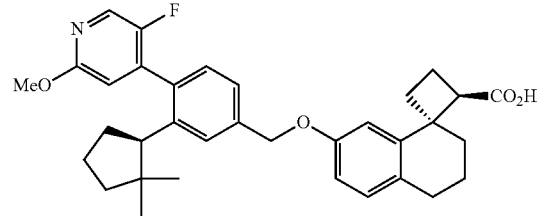

153

(1R,2S)-7'-(3-((R)-2,2-Dimethylcyclopentyl)-4-(5-fluoro-2-methoxypyridin-4-yl)benzyloxy)-3',4'-dihydro-2'H-spiro[cyclobutane-1,1'-naphthalene]-2-carboxylic acid or (1R,2R)-7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylic acid or (1S,2S)-7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylic acid or (1S,2R)-7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylic acid (153)

Example 153 was prepared from 153.1 using the same method used to prepare 145 MS ESI (neg.) M/E: 542 (M–H). $^1$H NMR (400 MHz, CDCl$_3$) δ ppm 8.04-8.10 (1H, m), 7.46 (1H, m), 7.37 (1H, m), 7.18 (2H, m), 7.00 (1H, m), 6.80-6.83 (1H, m), 6.55-6.70 (1H, m), 5.13 (1H, s), 3.99 (3H, s), 3.64 (1H, m), 2.66-2.73 (3H, m), 2.0-2.50 (1H, m), 2.00-2.20 (3H, m), 1.90-2.00 (2H, m), 1.65-1.85 (4H, m), 1.55 (2H, m), 1.40 (2H, m), 0.69 (3H, 3), 2.00 (1H, m), 0.59-0.61 (3H, m).

Example 154

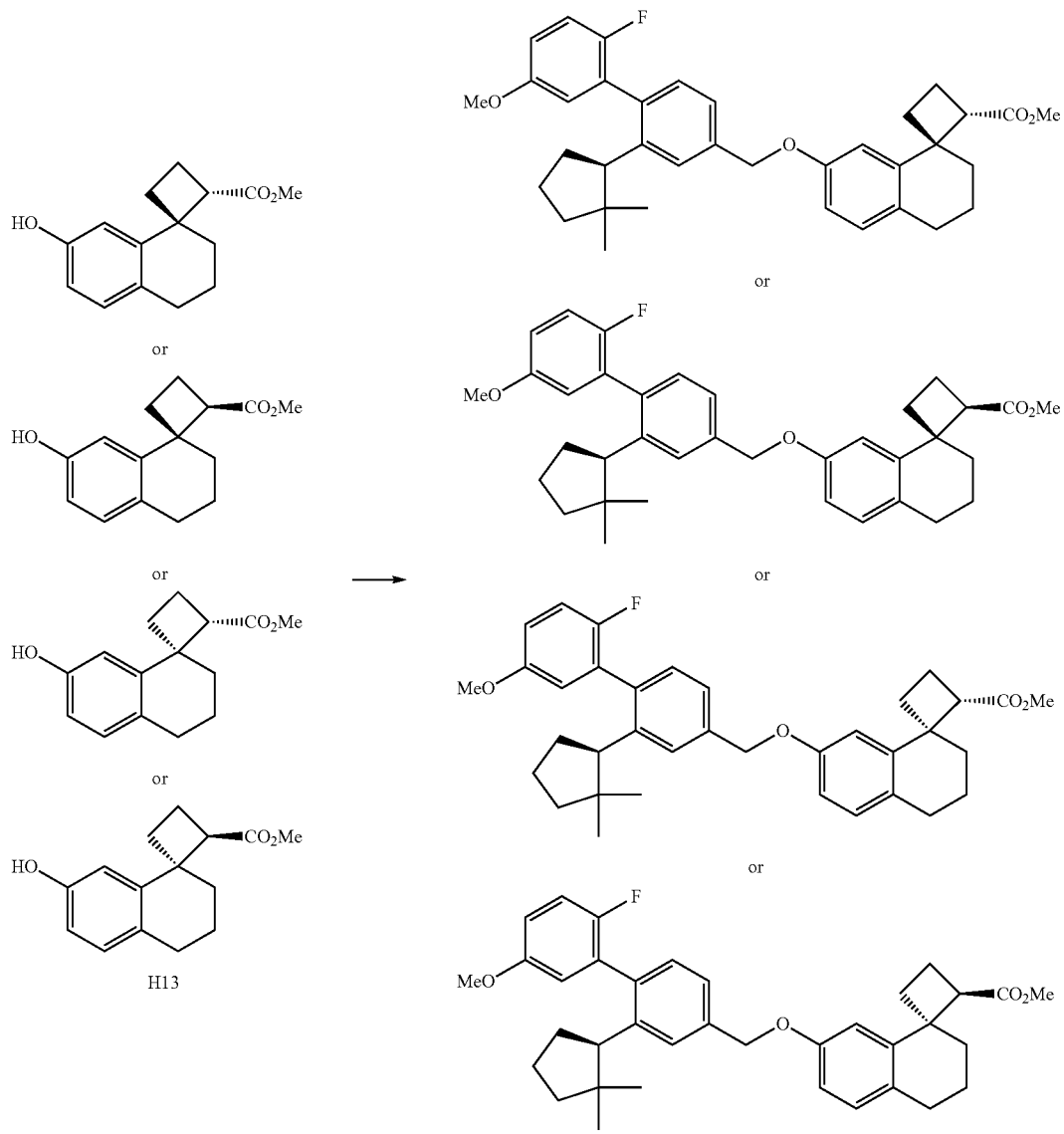

(1R,2S)-Methyl 7'-((2-((R)-2,2-dimethylcyclopentyl)-2'-fluoro-5'-methoxybiphenyl-4-yl)methoxy)-3',4'-dihydro-2'H-spiro[cyclobutane-1,1'-naphthalene]-2-carboxylate or (1R,2R)-methyl 7'-((2-((R)-2,2-dimethylcyclopentyl)-2'-fluoro-5'-methoxybiphenyl-4-yl)methoxy)-3',4'-dihydro-2'H-spiro[cyclobutane-1,1'-naphthalene]-2-carboxylate or (1S,2S)-methyl 7'-((2-((R)-2,2-dimethylcyclopentyl)-2'-fluoro-5'-methoxybiphenyl-4-yl)methoxy)-3',4'-dihydro-2'H-spiro[cyclobutane-1,1'-naphthalene]-2-carboxylate or (1S,2R)-methyl 7'-((2-((R)-2,2-dimethylcyclopentyl)-2'-fluoro-5'-methoxybiphenyl-4-yl)methoxy)-3',4'-dihydro-2'H-spiro[cyclobutane-1,1'-naphthalene]-2-carboxylate (154.1)

A mixture of H13 (0.045 mmol), T3 (0.054 mmol) and $Cs_2CO_3$ (0.10 mmol) in DMF (2 mL) was stirred at room temperature for 20 hours. The reaction mixture was concentrated and the residue was purified by chromatography (silica gel, eluting with 1:9 EtOAc/hexane) to give 24 mg of 154.1. MS ESI (pos.) M/E: 556 (M+$H_2O$).

471

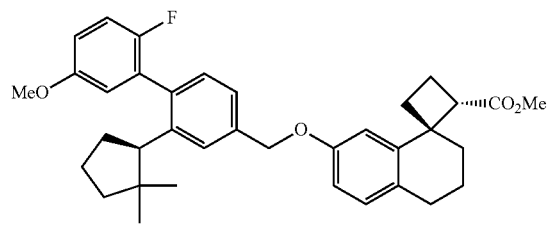

or

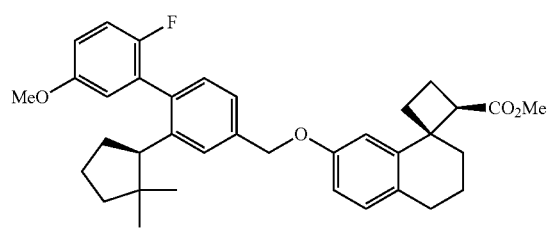

or

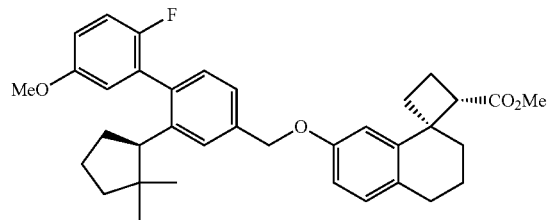

or

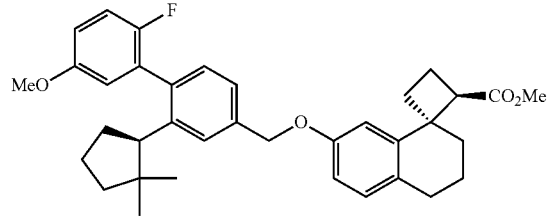

154.1

472

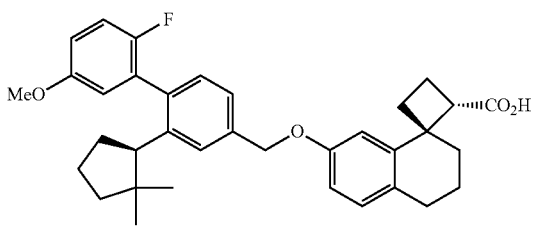

or

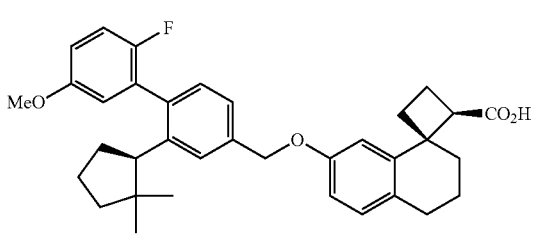

or

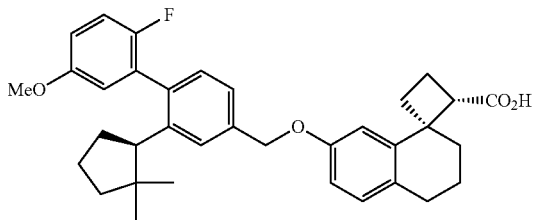

or

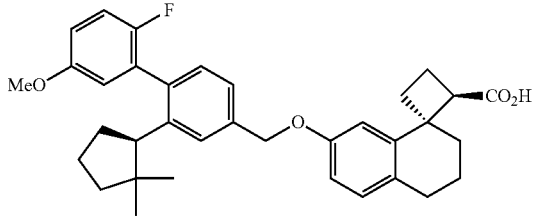

154

(1R,2S)-7'-((2-((R)-2,2-Dimethylcyclopentyl)-2'-fluoro-5'-methoxybiphenyl-4-yl)methoxy)-3',4'-dihydro-2'H-spiro[cyclobutane-1,1'-naphthalene]-2-carboxylic acid or (1R,2R)-7'-((2-((R)-2,2-dimethylcyclopentyl)-2'-fluoro-5'-methoxybiphenyl-4-yl)methoxy)-3',4'-dihydro-2'H-spiro[cyclobutane-1,1'-naphthalene]-2-carboxylic acid or (1S,2S)-7'-((2-((R)-2,2-dimethylcyclopentyl)-2'-fluoro-5'-methoxybiphenyl-4-yl)methoxy)-3',4'-dihydro-2'H-spiro[cyclobutane-1,1'-naphthalene]-2-carboxylic acid or (1S,2R)-7'-((2-((R)-2,2-dimethylcyclopentyl)-2'-fluoro-5'-methoxybiphenyl-4-yl)methoxy)-3',4'-dihydro-2'H-spiro[cyclobutane-1,1'-naphthalene]-2-carboxylic acid (154)

Example 154 was prepared from 154.1 using the same method used to prepare 145. MS ESI (neg.) M/E: 541 (M–H). $^1$H NMR (400 MHz, CDCl$_3$) δ ppm 7.43-7.47 (1H, m), 7.35 (1H, m), 7.19-7.25 (2H, m), 6.95-7.10 (2H, m), 6.80-6.90 (2H, m), 6.65-6.80 (1H, m), 5.13 (2H, s), 5.17 (1H, s), 3.80 (3H, s), 3.63 (1H, m), 2.80-3.00 (1H, m), 2.69 (2H, m), 2.40 (1H, m), 1.90-2.20 (4H, m), 1.60-1.85 (4H, m), 1.45-1.60 (1H, m), 1.32-1.40 (1H, m), 1.71 (3H, m), 0.57-0.62 (3H, m).

473
Example 155
474
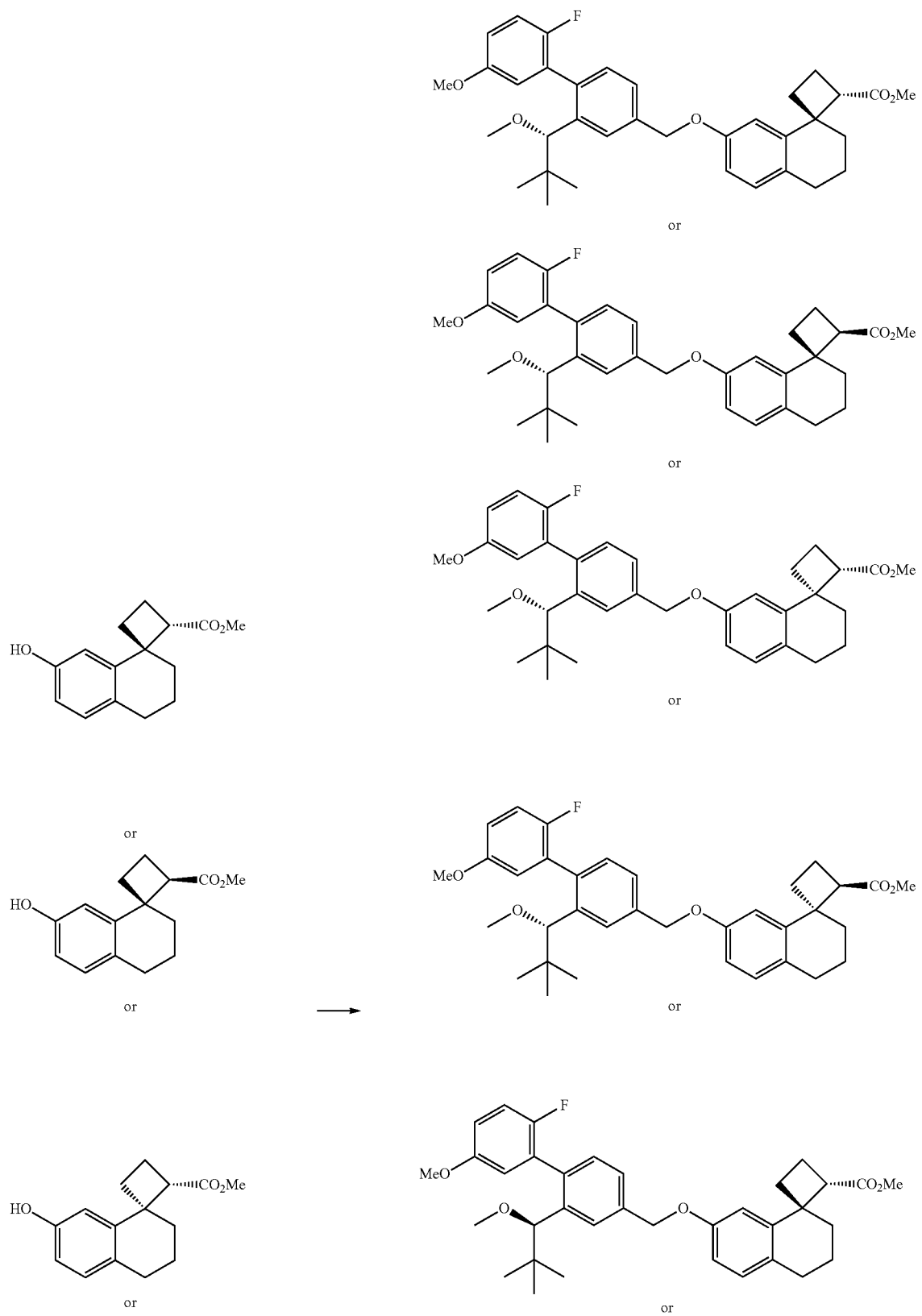

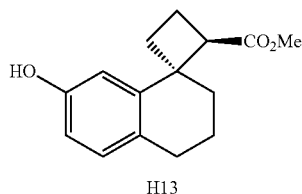

H13

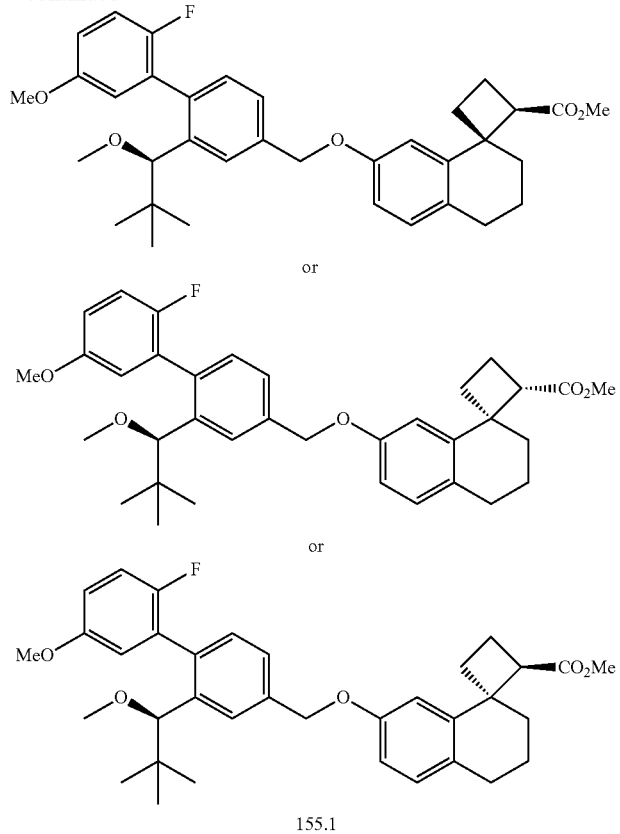

155.1

(1R,2S)-Methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1R,2R)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1S,2S)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1S,2R)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1R,2S)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1R,2R)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1S,2S)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1S,2R)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate (155.1)

A mixture of H13 (0.053 mmol), T4 (0.063 mmol) and $Cs_2CO_3$ (0.13 mmol) in DMF (2 mL) was stirred at room temperature for 22 hours. The reaction mixture was then concentrated, and the residue was purified by chromatography (silica gel, eluting with 1:9 EtOAc/hexane) to give 155.1.

477
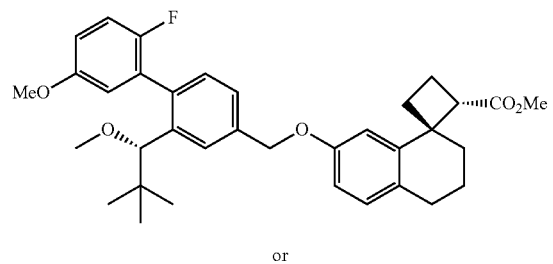
or
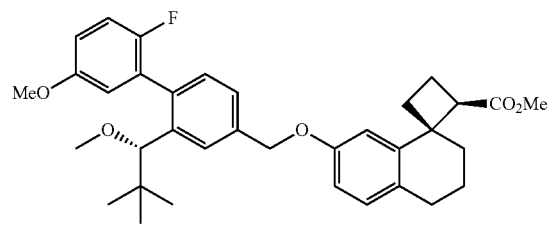
or
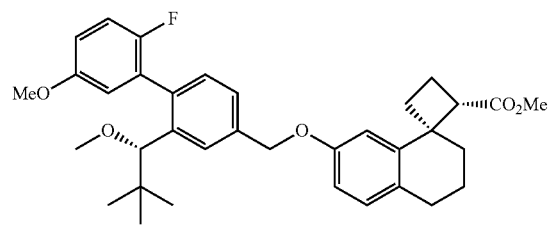
or
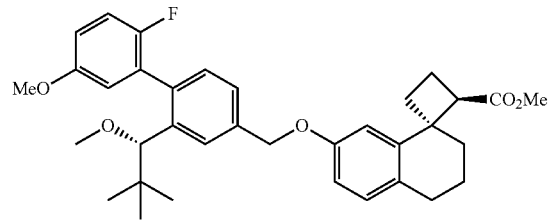
or
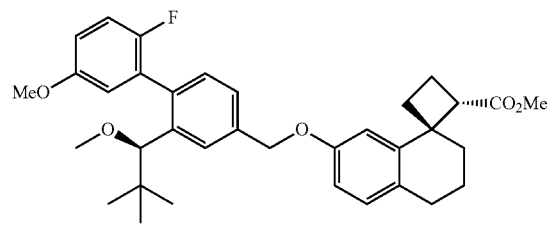
or
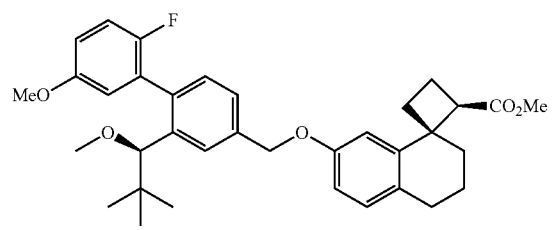
or
478
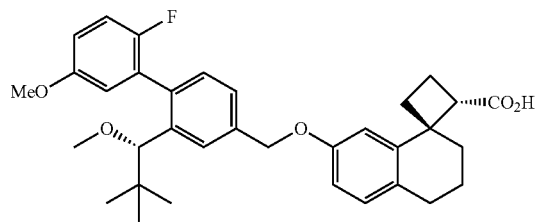
or
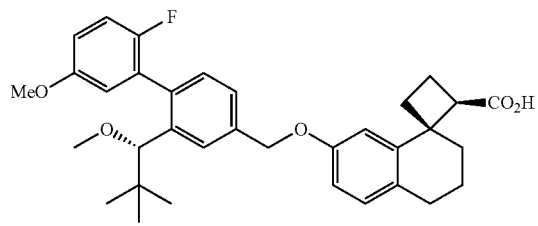
or
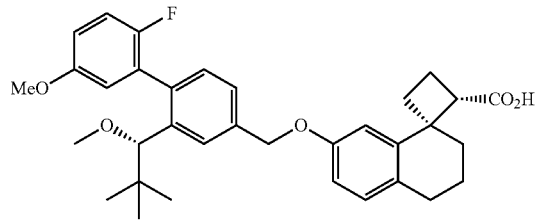
or
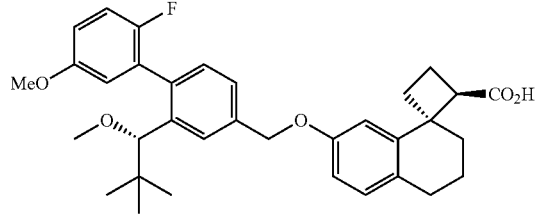
or
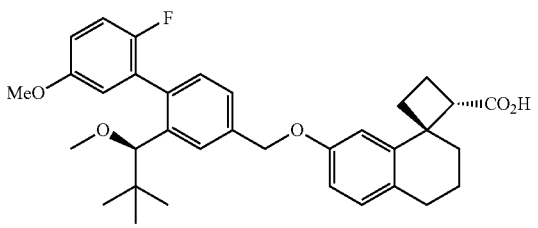
or
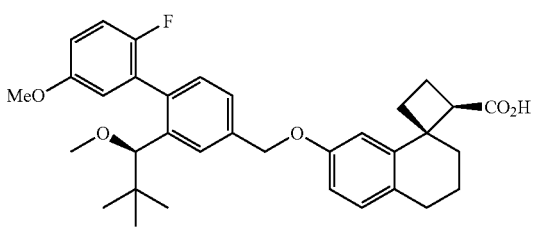
or -continued

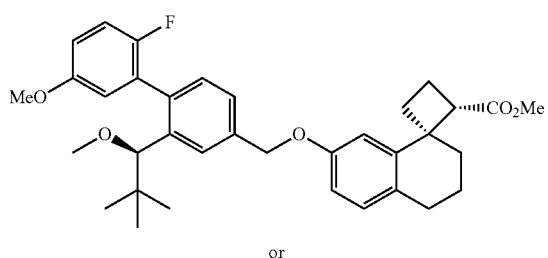

or

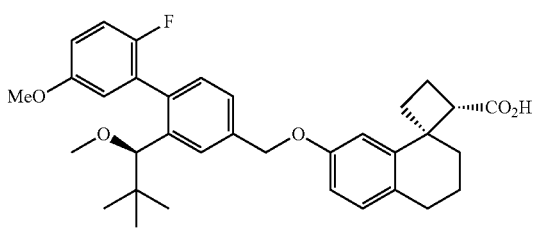

or

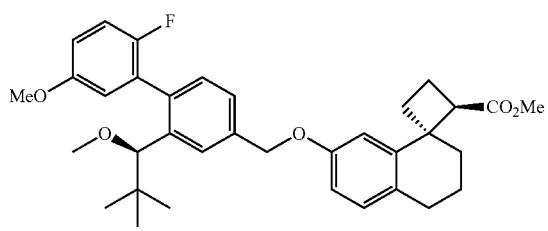

155.1

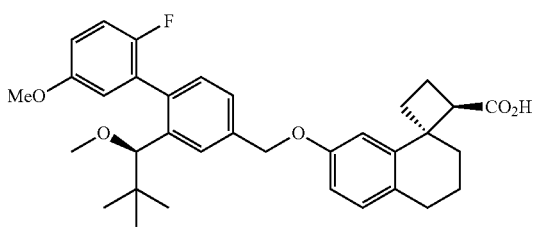

155

(1R,2S)-7'-((2'-Fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2R)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2S)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2R)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2S)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2R)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2S)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2R)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid (155)

Example 155 was prepared from 155.1 using the same method used to prepare 145. MS ESI (neg.) M/E: 545 (M−H). $^1$H NMR (400 MHz, CDCl$_3$) δ ppm 7.60-7.65 (1H, m), 7.46 (1H, m), 7.20 (2H, m), 6.95-7.10 (2H, m), 6.80-6.90 (2H, m), 6.74 (1H, m), 5.16 (1H, s), 3.96-4.20 (1H, m), 3.80 (3H, s), 3.65 (1H, m), 3.26-3.31 (3H, m), 2.61-2.73 (2H, m), 2.38-2.45 (1H, m), 2.05-2.20 (2H, m), 1.96-1.99 (3H, m), 1.65-1.85 (2H, m), 0.72 (9H, s).

Example 156

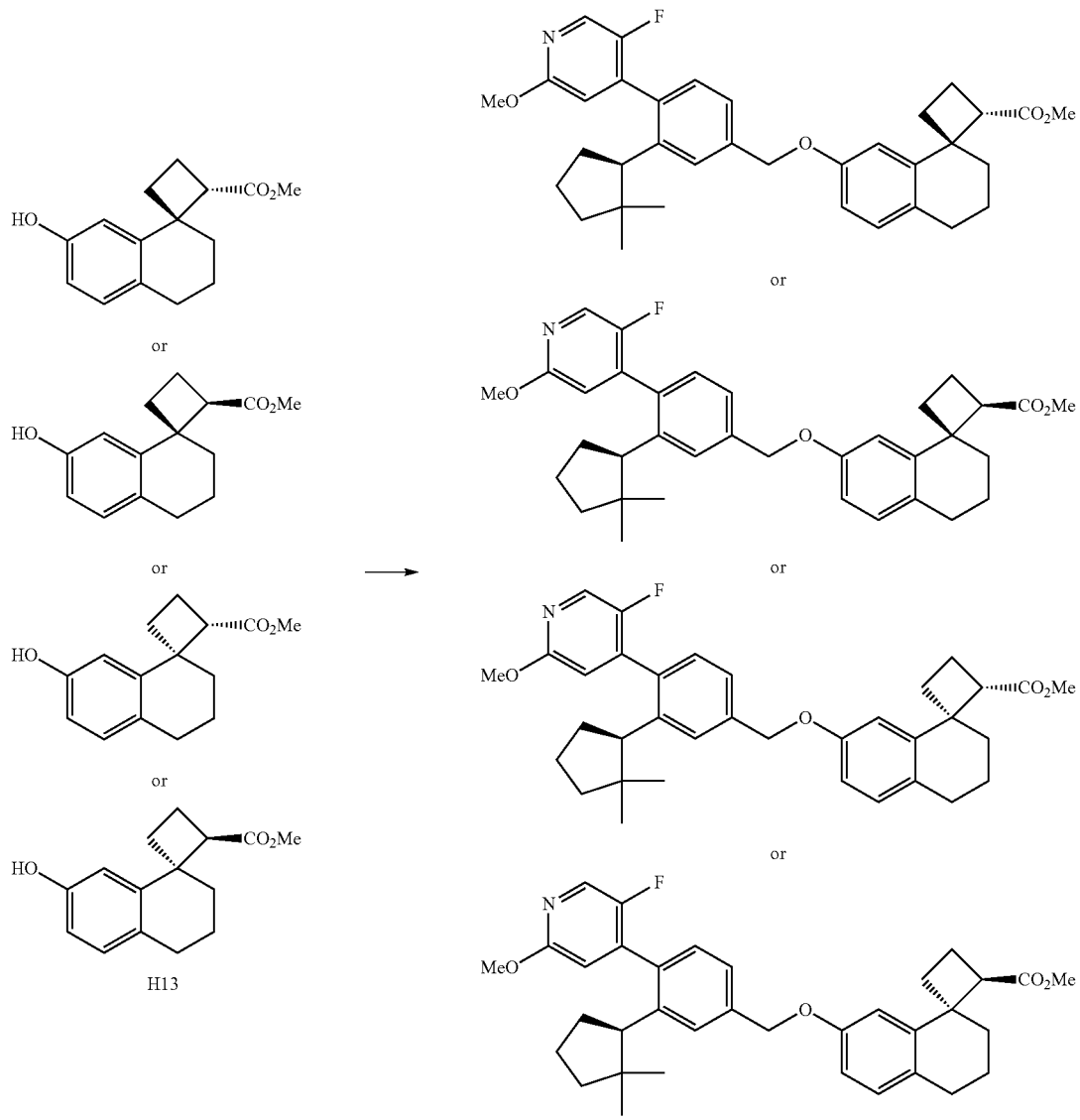

(1R,2S)-Methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate or (1R,2R)-methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate or (1S,2S)-methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate or (1S,2R)-methyl 7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylate (156.1)

A mixture of H13 (0.037 mmol), T5 (0.044 mmol) and Cs$_2$CO$_3$ (0.091 mmol) in DMF (2 mL) was stirred at room temperature for 22 hours. The reaction mixture was concentrated and the residue was purified by chromatography (silica gel, eluting with 1:9 EtOAc/hexane) to give 20 mg of 156.1. MS ESI (pos.) M/E: 558 (M+H).

483

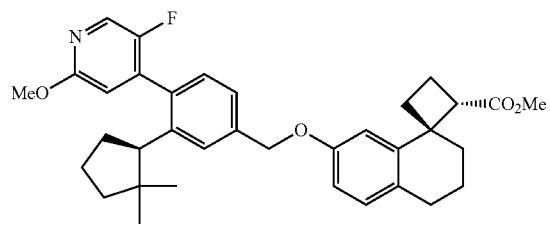

or

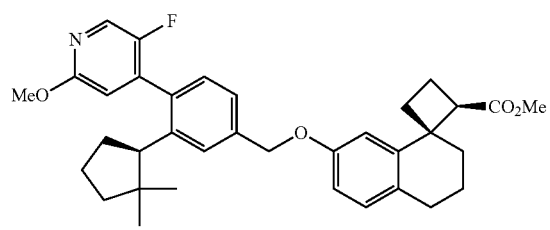

or

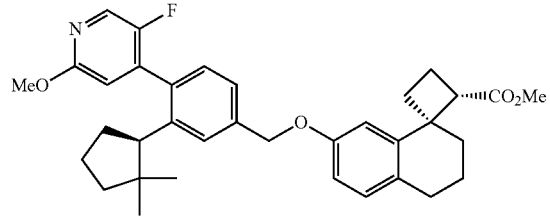

or

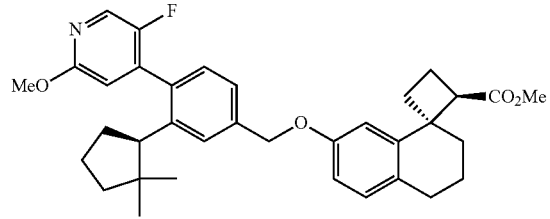

156.1

484

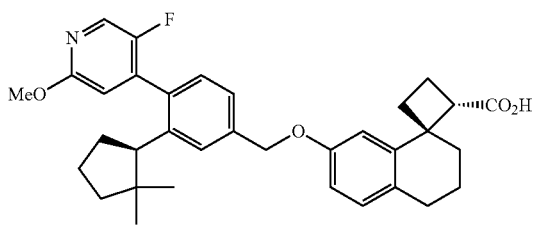

or

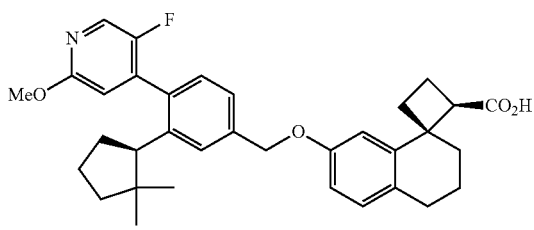

or

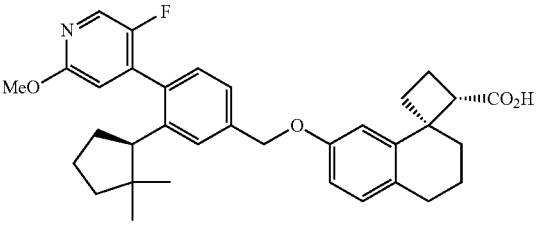

or

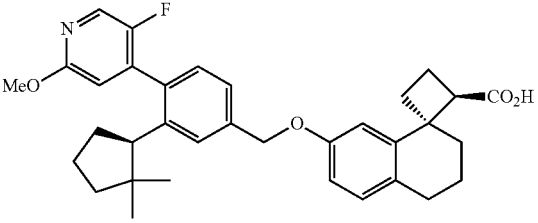

156

(1R,2S)-7'-(3-((R)-2,2-Dimethylcyclopentyl)-4-(5-fluoro-2-methoxypyridin-4-yl)benzyloxy)-3',4'-dihydro-2'H-spiro[cyclobutane-1,1'-naphthalene]-2-carboxylic acid or (1R,2R)-7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylic acid or (1S,2S)-7'-(3-((R)-2,2-dimethylcyclopentyl)-4-(5-fluoro-2-methoxypyridin-4-yl)benzyloxy)-3',4'-dihydro-2'H-spiro[cyclobutane-1,1'-naphthalene]-2-carboxylic acid or (1S,2R)-7'-(3-((R)-2,2-dimethylcyclopentyl)-4-(5-fluoro-2-methoxypyridin-4-yl)benzyloxy)-3',4'-dihydro-2'H-spiro [cyclobutane-1,1'-naphthalene]-2-carboxylic acid (156)

Example 156 was prepared from 156.1 using the same method used to prepare 145. MS ESI (neg.) M/E: 542 (M–H). $^1$H NMR (400 MHz, CDCl$_3$) δ ppm 8.06-8.15 (1H, m), 7.46 (1H, m), 7.35-7.39 (1H, m), 7.18 (1H, m), 6.98 (1H, m), 6.81 (1H, m), 6.55-6.74 (1H, m), 5.13 (2H, s), 3.97 (3H, s), 3.64 (1H, m), 2.60-2.95 (3H, m), 2.35-2.50 (1H, m), 2.10-2.25 (3H, m), 1.95-2.05 (4H, m), 1.65-1.90 (4H, m), 1.55 (1H, m), 1.40 (1H, m), 0.70 (3H, m), 0.59 (3H, m).

485
Example 157
486
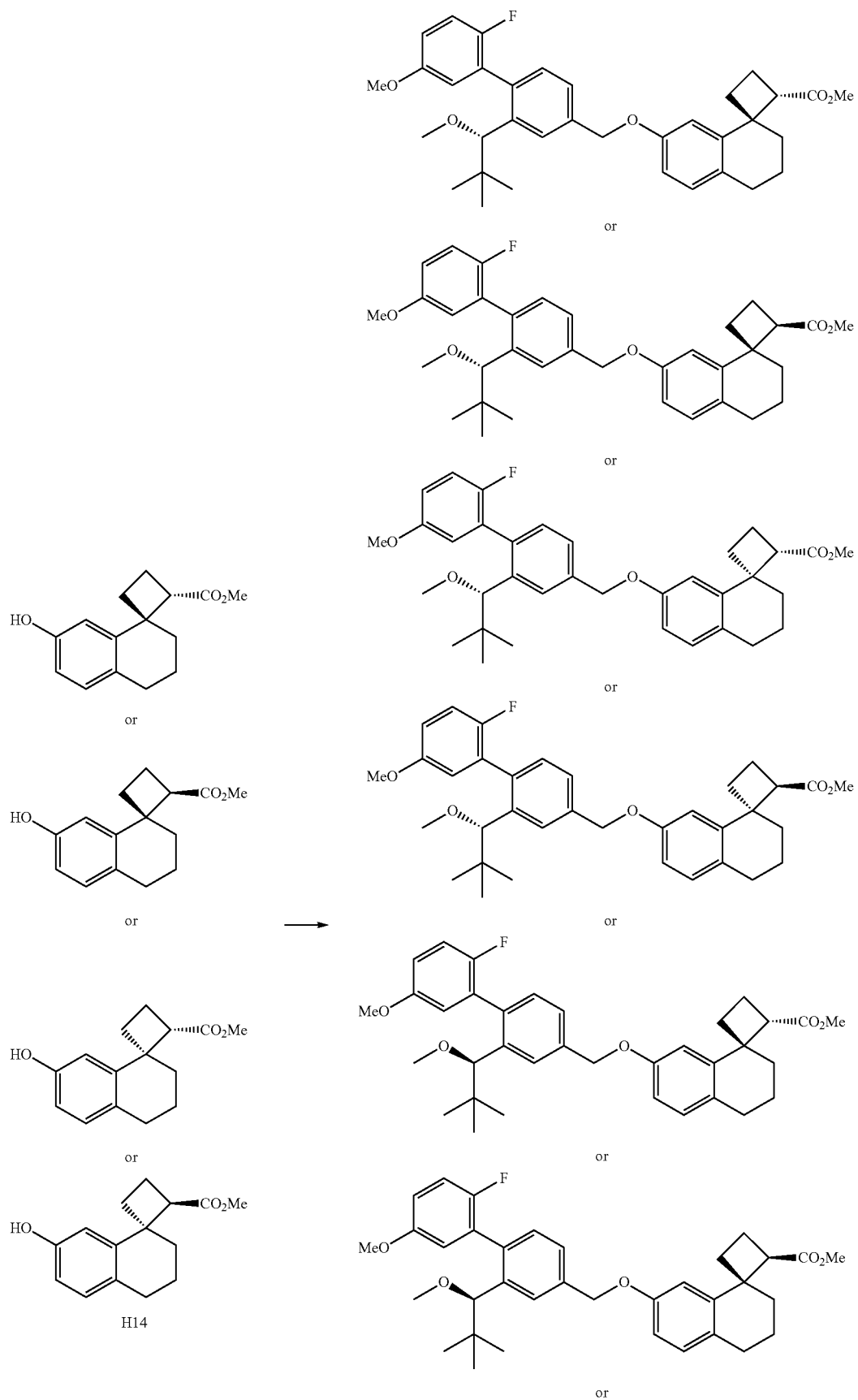

-continued

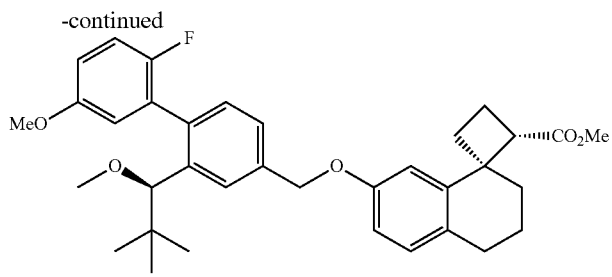

or

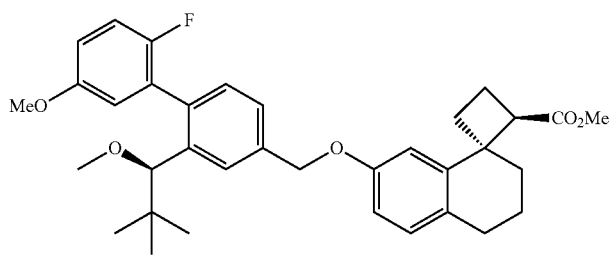

157.1

(1R,2S)-Methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1R,2R)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1S,2S)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1S,2R)-methyl 7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylate or (1R,2S)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1R,2R)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1S,2S)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate or (1S,2R)-methyl 7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylate (157.1)

A mixture of H14 (0.022 mmol), T4 (0.026 mmol) and $Cs_2CO_3$ (0.054 mmol) in DMF (2 mL) was stirred at room temperature for 22 hours. The reaction mixture was concentrated and the residue was purified by chromatography (silica gel, eluting with 1:9 EtOAc/hexane) to give 12 mg of 157.1.

489  490
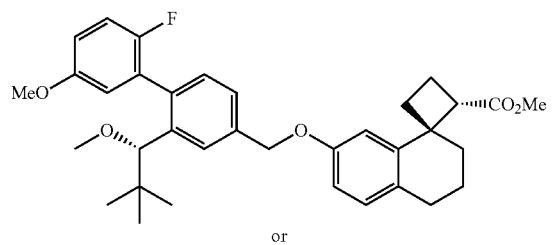
or
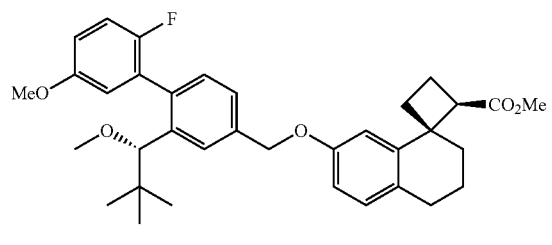
or
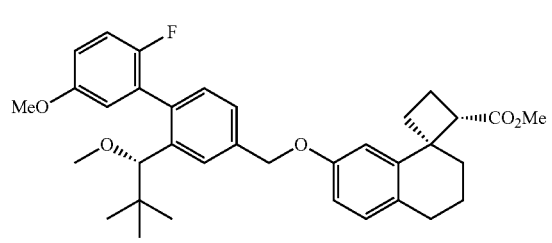
or
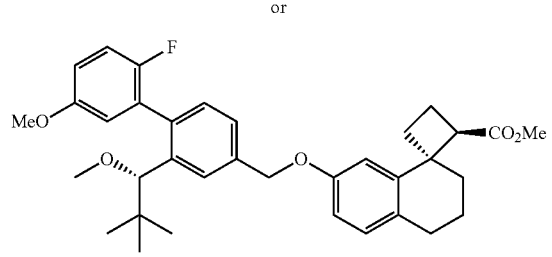
or
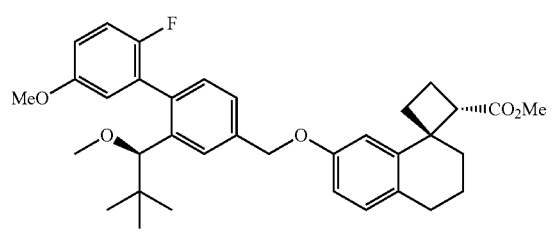
or
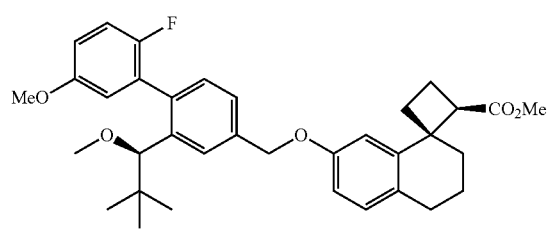
or
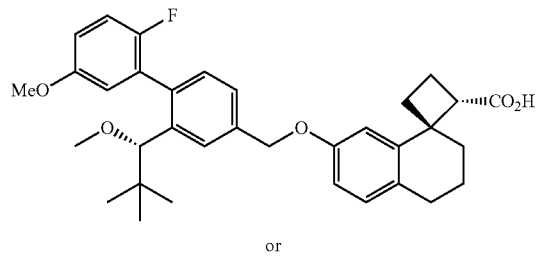
or
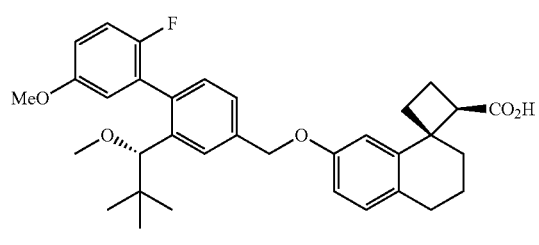
or
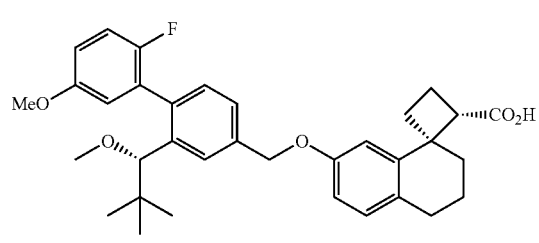
or
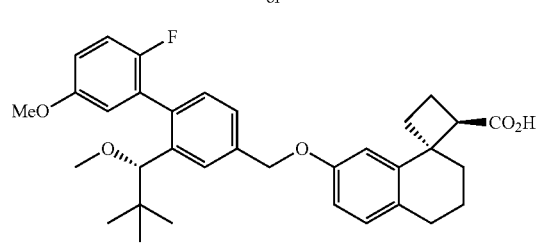
or
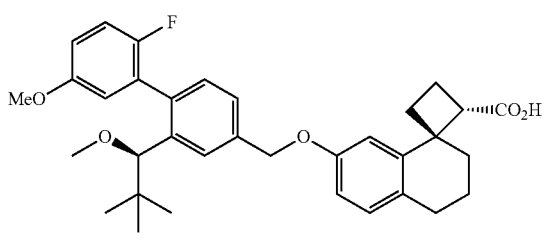
or
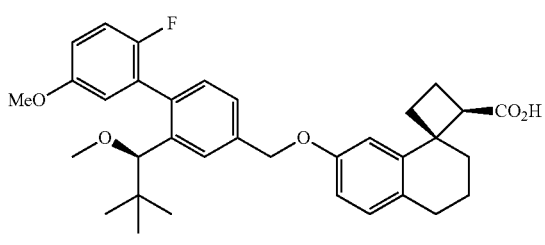
or

491

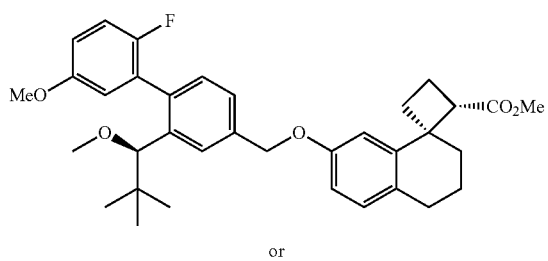

or

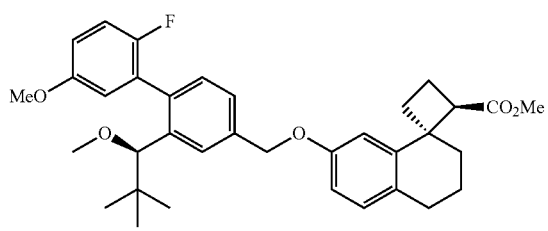

157.1

492

-continued

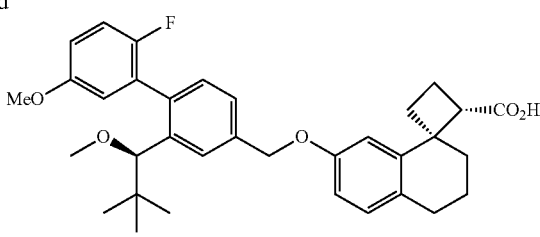

or

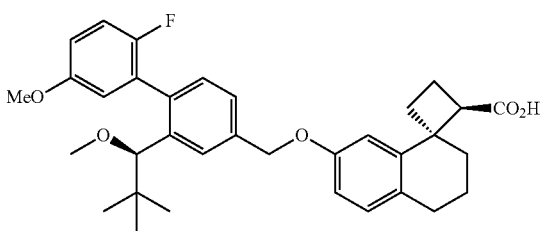

157

(1R,2S)-7'-((2'-Fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2R)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2S)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2R)-7'-((2'-fluoro-5'-methoxy-2-((S)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2S)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1R,2R)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2S)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid or (1S,2R)-7'-((2'-fluoro-5'-methoxy-2-((R)-1-methoxy-2,2-dimethylpropyl)biphenyl-4-yl)methoxy)-3',4'-dihydro-2'H-spiro[cyclobutane-1,1'-naphthalene]-2-carboxylic acid (157)

Example 157 was prepared from 157.1 using the same method used to prepare 145. MS ESI (neg.) M/E: 545 (M−H). $^1$H NMR (400 MHz, CDCl$_3$) δ ppm 7.36-7.43 (2H, m), 7.29 (1H, m), 7.19 (1H, m), 6.95-7.10 (1H, m), 6.80-6.90 (2H, m), 6.71 (1H, m), 6.45 (1H, m), 5.22 (2H, m), 4.14 (1H, m), 3.79 (3H, s), 3.20-3.24 (1H, m), 2.93-3.00 (3H, m), 2.55-2.75 (4H, m), 2.15-2.30 (2H, m), 2.00-2.10 (2H, m), 1.75-1.90 (2H, m), 0.72 (9H, s).

Example 158

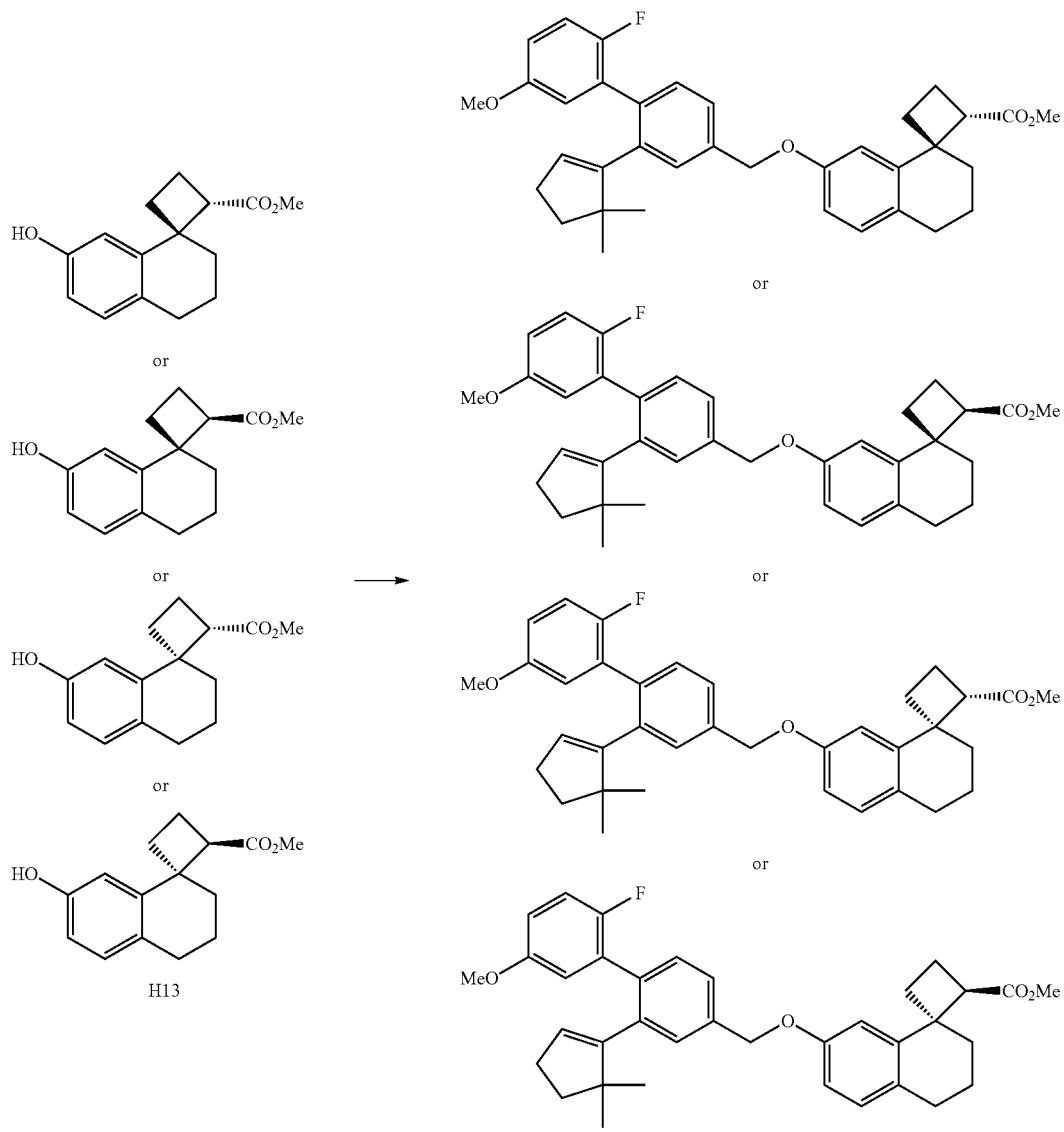

(1R,2S)-Methyl 7'-((2-(5,5-dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylate or (1R,2R)-methyl 7'-((2-(5,5-dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylate or (1S,2S)-methyl 7'-((2-(5,5-dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylate or (1S,2R)-methyl 7'-((2-(5,5-dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylate (158.1)

A mixture of H13 (0.045 mmol), T2 (0.054 mmol) and $Cs_2CO_3$ (0.112 mmol) in DMF (2 mL) was stirred at room temperature for 22 hours. The reaction mixture was concentrated and the residue was purified by chromatography (silica gel, eluting with 1:9 EtOAc/hexane) to give 24 mg of 158.1.

495

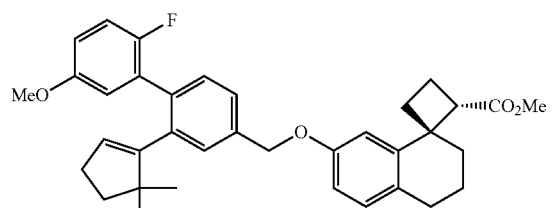

or

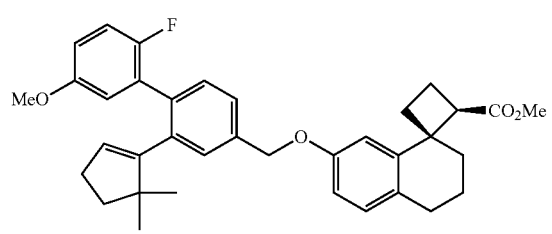

or

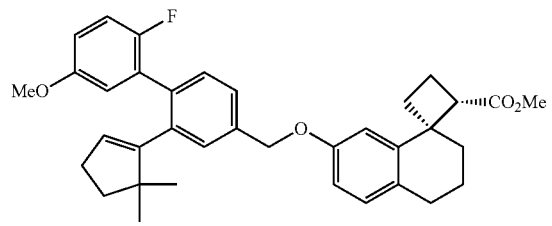

or

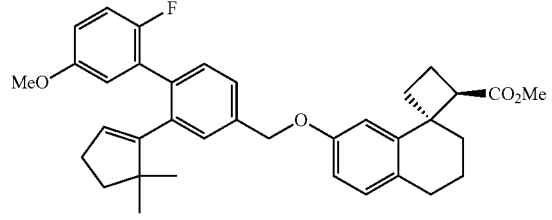

158.1

(1R,2S)-7'-((2-(5,5-Dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylic acid or (1R,2R)-7'-((2-(5,5-dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylic acid or (1S,2S)-7'-((2-(5,5-dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylic acid or (1S,2R)-7'-((2-(5,5-dimethylcyclopent-1-enyl)-2'-fluoro-5'-methoxybiphenyl-4-yl)methoxy)-3',4'-dihydro-2'H-spiro[cyclobutane-1,1'-naphthalene]-2-carboxylic acid (158)

Example 158 was prepared from 158.1 using the same method used to prepare 145. MS ESI (neg.) M/E: 539 (M−H). $^1$H NMR (400 MHz, CDCl$_3$) δ ppm 7.42 (1H, m), 7.32-7.36 (2H, m), 7.20 (1H, m), 6.92-7.03 (2H, m), 6.76-6.85 (3H, m), 5.53 (1H, s), 5.12 (2H, s), 3.76 (3H, s), 3.64 (1H, s), 2.69 (2H, m), 2.43 (1H, m), 2.25 (2H, m), 2.10-2.20 (2H, m), 1.94-2.05 (3H, m), 1.65-1.85 (4H, m), 0.86 (6H, s).

496

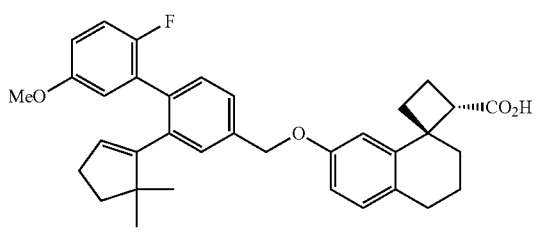

or

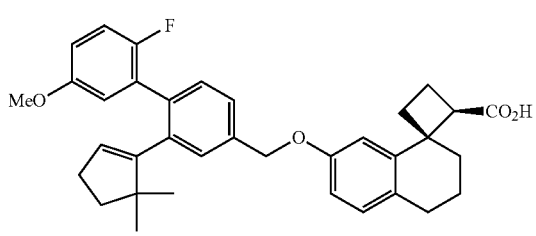

or

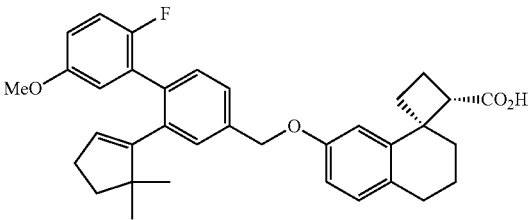

or

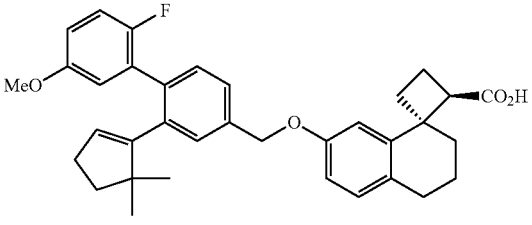

158

Cell-Based Aequorin Assay

Cell-based aequorin assays were employed to characterize the modulatory activity of compounds on the GPR40 signaling pathway. In an exemplary assay, CHO cells were stably transfected with both GPR40 and Aequorin (Euroscreen). Cells were detached from the tissue culture dish with 2 mL of trypsin (0.25% (w/v)). Trypsinization was halted with 28 mL of Hanks Buffered Salt Solution containing 20 mM Hepes (H/HBSS) and 0.01% fatty acid-free human serum albumin (HSA). Coelantrazine is added to 1 ug/mL, and the cells were incubated for 2 hours at room temperature. Compounds were dissolved in DMSO for preparation of 10 mM stock solutions. Compounds were diluted in H/HBSS containing 0.01% HSA. Serial dilutions of the test compounds were prepared to determine dose response.

Aequorin luminescence measurements were made using an EG&G Berthold 96-well luminometer, and the response was measured over a 20 second interval after cells and compounds were mixed. The maximum relative light units was plotted to determine dose response. The EC$_{50}$ (effective concentration to reach 50% maximal response) was determined from the dose response plot.

The following table presents representative data (EC$_{50}$ values) obtained for exemplary compounds of the invention for the activation of human GPR40.

Inositol Phosphate Accumulation Assay

An A9 cell line stably transfected with GPR40 (A9_GPR40) was used in IP accumulation assays. A9_GPR40 cells were plated in 96-well plates containing 20,000 cells/well in DMEM containing 10% FBS. After the cells attached to the well surface, the media was replaced with inositol free DMEM containing 10% dialyzed FBS and 1 µCi, mL $^3$H-inositol and incubated for 16 hours. Compounds were diluted in HBSS/10 mM LiCl containing a desired amount of HSA and added directly to cells. Following 1 hour incubation at 37° C., the media was replaced with 100 µL of 20 mM formic acid to quench the reaction. 50 µL of the extract was then added to 100 µL of SPA beads, incubated overnight, and measured on a TopCount the following day.

The stereoisomers in the following table are as specified, i.e., S-enantiomers or R-enantiomers, and if not specified, or if shown with wavy bonds, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

TABLE

| | Assay Data For Human GPR40 | | |
|---|---|---|---|
| No. | Structure$^a$ | Aequorin EC$_{50}$$^{b,c}$ | IP3 EC$_{50}$$^{c,d}$ |
| 1 | | +++ | +++++ |
| 2 | | + | ND$^e$ |
| 3 | | + | ND |
| 4 | | ++ | ND |

TABLE-continued

Assay Data For Human GPR40

| No. | Structure[a] | Aequorin EC$_{50}$[b,c] | IP3 EC$_{50}$[c,d] |
|---|---|---|---|
| 5 | | ++ | ND |
| 6 | | + | ND |
| 7 | | + | ND |
| 8 | | + | ND |
| 9 | | +++ | ++++ | or

TABLE-continued
Assay Data For Human GPR40
| No. | Structure[a] | Aequorin EC$_{50}$[b,c] | IP3 EC$_{50}$[c,d] |
|---|---|---|---|
| 10 | 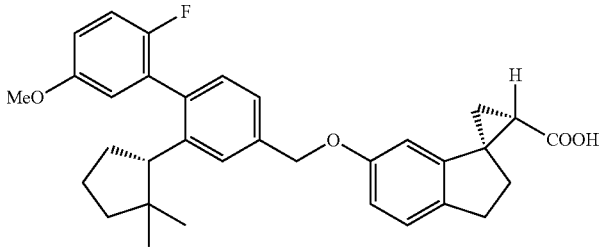 [SMILES: COc1ccc(F)c(-c2ccc(COc3ccc4c(c3)[C@@]3(CC4)C[C@@H]3C(=O)O)cc2[C@H]2CCCC2(C)C)c1] or 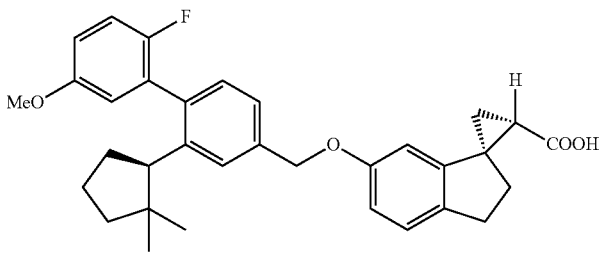 [SMILES: COc1ccc(F)c(-c2ccc(COc3ccc4c(c3)[C@@]3(CC4)C[C@@H]3C(=O)O)cc2[C@@H]2CCCC2(C)C)c1] | + | ND |
| 11 | 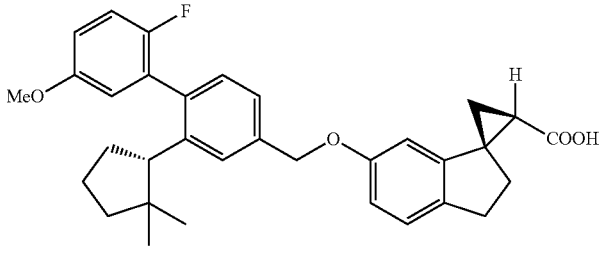 [SMILES: COc1ccc(F)c(-c2ccc(COc3ccc4c(c3)[C@]3(CC4)C[C@H]3C(=O)O)cc2[C@H]2CCCC2(C)C)c1] or 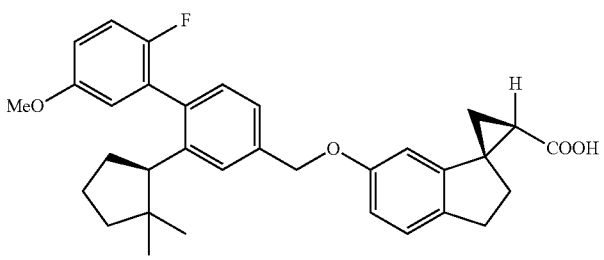 | ++++ | +++++ |
| 12 | 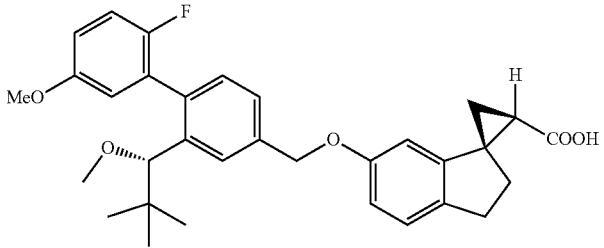 [SMILES: COc1ccc(F)c(-c2ccc(COc3ccc4c(c3)[C@]3(CC4)C[C@H]3C(=O)O)cc2[C@@H](OC)C(C)(C)C)c1] or | ++++ | +++++ |

TABLE-continued

Assay Data For Human GPR40

| No. | Structure$^a$ | Aequorin EC$_{50}$$^{b,c}$ | IP3 EC$_{50}$$^{c,d}$ |
|---|---|---|---|
| | (structure: 2'-F, 5'-MeO biphenyl with (R)-1-methoxy-2,2-dimethylpropyl substituent, linked via CH$_2$O to indane-spirocyclopropane carboxylic acid) | | |
| 13 | (structure: 2'-F, 5'-MeO biphenyl with neopentyl substituent, linked via CH$_2$O to indane-spirocyclopropane carboxylic acid) | ++++ | +++++ |
| 14 | (structure: 2'-F, 5'-MeO biphenyl, 5-F, with (R)-2,2-dimethylcyclopentyl substituent, linked via CH$_2$O to indane-spirocyclopropane carboxylic acid) | +++ | +++++ |
| | or | | |
| | (structure: 2'-F, 5'-MeO biphenyl, 5-F, with (S)-2,2-dimethylcyclopentyl substituent, linked via CH$_2$O to indane-spirocyclopropane carboxylic acid) | | |
| 15 | (structure: 2'-F, 5'-MeO biphenyl with (R)-2,2-dimethylcyclohexyl substituent, linked via CH$_2$O to indane-spirocyclopropane carboxylic acid) | ++++ | +++++ |
| | or | | |

TABLE-continued

Assay Data For Human GPR40

| No. | Structure[a] | Aequorin EC$_{50}$[b,c] | IP3 EC$_{50}$[c,d] |
|---|---|---|---|
| | (structure) | | |
| 16 | (structure) or (structure) | ++++ | +++++ |
| 17 | (structure) or (structure) | ++++ | +++++ |

TABLE-continued
Assay Data For Human GPR40
| No. | Structure[a] | Aequorin EC$_{50}$[b,c] | IP3 EC$_{50}$[c,d] |
|---|---|---|---|
| 18 | 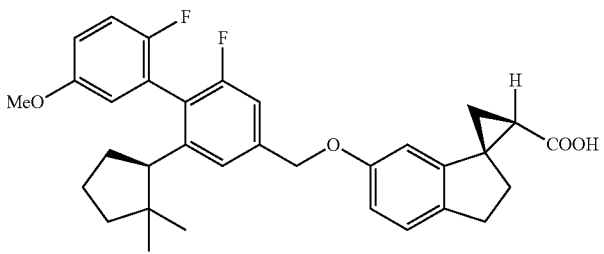 [SMILES: COc1ccc(F)c(-c2c(F)cc(COc3ccc4c(c3)[C@]3(CC4)C[C@H]3C(=O)O)cc2[C@@H]2CCCC2(C)C)c1] or 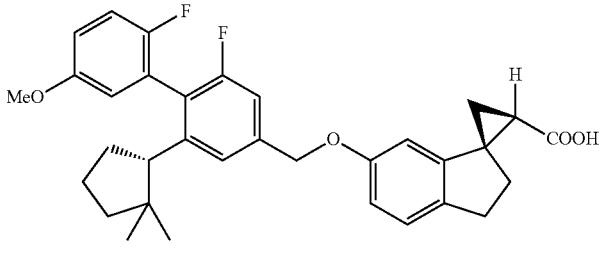 [SMILES: COc1ccc(F)c(-c2c(F)cc(COc3ccc4c(c3)[C@]3(CC4)C[C@H]3C(=O)O)cc2[C@H]2CCCC2(C)C)c1] | +++ | +++++ |
| 19 | 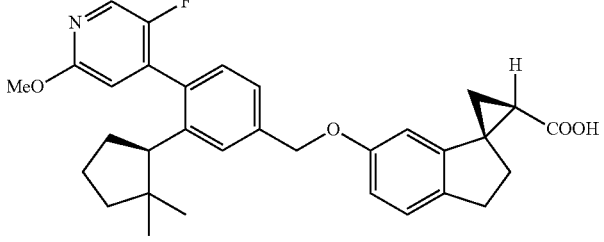 | ++++ | +++++ |
| 20 | 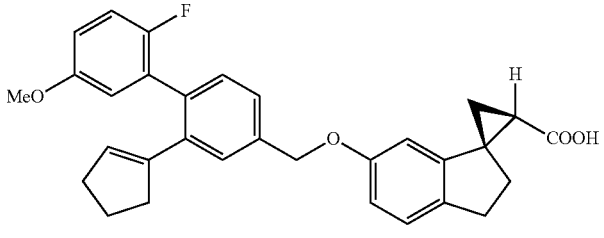 [SMILES: COc1ccc(F)c(-c2ccc(COc3ccc4c(c3)[C@]3(CC4)C[C@H]3C(=O)O)cc2C2=CCCC2)c1] | +++ | ++++ |
| 21 | 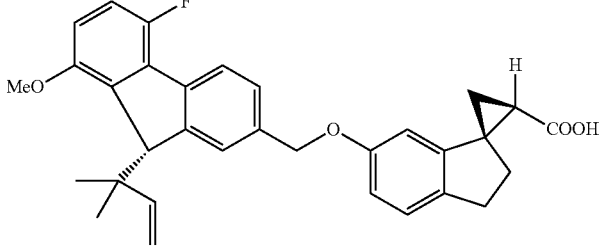 and | +++ | ND |

TABLE-continued

Assay Data For Human GPR40

| No. | Structure[a] | Aequorin EC$_{50}$[b,c] | IP3 EC$_{50}$[c,d] |
|---|---|---|---|
| 22 | | +++ | ++++ |
| 23 | or | ++ | ND |
| 24 | | +++ | ++++ |

TABLE-continued

Assay Data For Human GPR40

| No. | Structure$^a$ | Aequorin EC$_{50}$$^{b,c}$ | IP3 EC$_{50}$$^{c,d}$ |
|---|---|---|---|
| 25 | | +++ | +++ |
| 26 | | ++ | ND |
| 27 | | ++ | ND |
| 28 | (two structures shown, "or" between them) | +++ | +++++ |
| 29 | | + | ND |

TABLE-continued
Assay Data For Human GPR40
| No. | Structure[a] | Aequorin EC$_{50}$[b,c] | IP3 EC$_{50}$[c,d] |
|---|---|---|---|
| 30 | 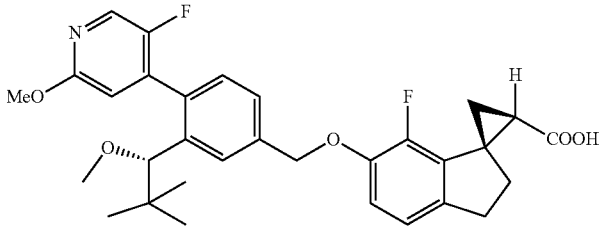 [SMILES: COc1cc(-c2ccc(COc3ccc4c(c3F)[C@]3(CC4)C[C@H]3C(=O)O)cc2[C@@H](OC)C(C)(C)C)c(F)cn1] or 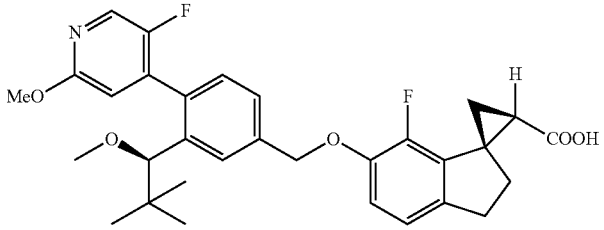 [SMILES: COc1cc(-c2ccc(COc3ccc4c(c3F)[C@]3(CC4)C[C@H]3C(=O)O)cc2[C@H](OC)C(C)(C)C)c(F)cn1] or 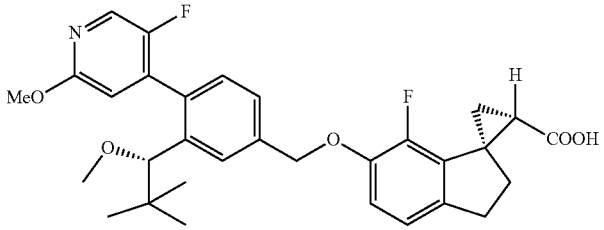 [SMILES: COc1cc(-c2ccc(COc3ccc4c(c3F)[C@@]3(CC4)C[C@@H]3C(=O)O)cc2[C@@H](OC)C(C)(C)C)c(F)cn1] or 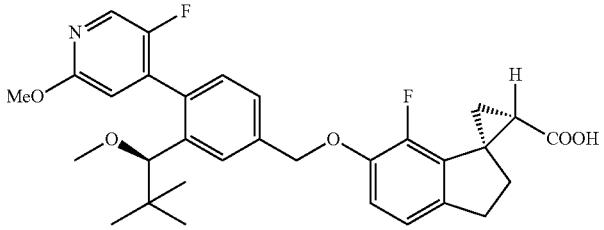 [SMILES: COc1cc(-c2ccc(COc3ccc4c(c3F)[C@@]3(CC4)C[C@@H]3C(=O)O)cc2[C@H](OC)C(C)(C)C)c(F)cn1] | ++++ | +++++ |
| 31 | 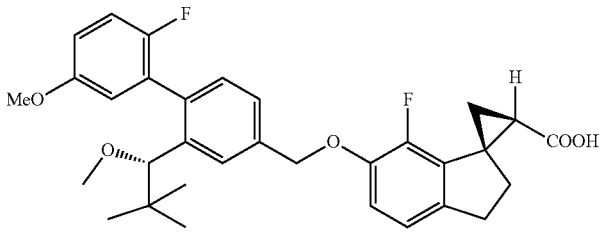 [SMILES: COc1ccc(F)c(-c2ccc(COc3ccc4c(c3F)[C@]3(CC4)C[C@H]3C(=O)O)cc2[C@@H](OC)C(C)(C)C)c1] or | ++++ | +++++ |

TABLE-continued

Assay Data For Human GPR40

| No. | Structure[a] | Aequorin EC$_{50}$[b,c] | IP3 EC$_{50}$[c,d] |
|---|---|---|---|
| | *(structure)* or *(structure)* or *(structure)* | | |
| 32 | *(structure)* or *(structure)* | +++ | +++++ |

TABLE-continued

Assay Data For Human GPR40

| No. | Structure[a] | Aequorin EC$_{50}$[b,c] | IP3 EC$_{50}$[c,d] |
|---|---|---|---|
| 33 | | +++ | +++++ |
| 34 | | ++ | ND |

| No. | Structure[a] | Aequorin EC$_{50}$[b,c] | IP3 EC$_{50}$[c,d] |
|---|---|---|---|
| | or 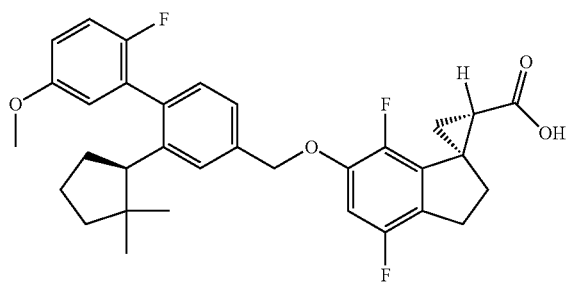 [SMILES: COc1ccc(F)c(-c2ccc(COc3cc(F)c4c(c3F)[C@@]3(CC4)C[C@@H]3C(=O)O)cc2[C@@H]2CCCC2(C)C)c1] | | |
| | or 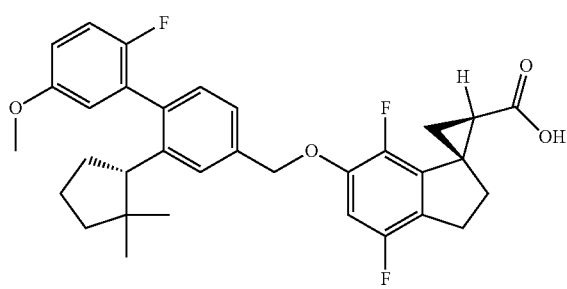 [SMILES: COc1ccc(F)c(-c2ccc(COc3cc(F)c4c(c3F)[C@]3(CC4)C[C@H]3C(=O)O)cc2[C@H]2CCCC2(C)C)c1] | | |
| | or 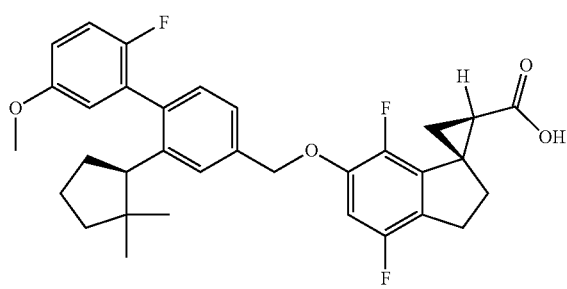 [SMILES: COc1ccc(F)c(-c2ccc(COc3cc(F)c4c(c3F)[C@]3(CC4)C[C@H]3C(=O)O)cc2[C@@H]2CCCC2(C)C)c1] | | |
| 35 | 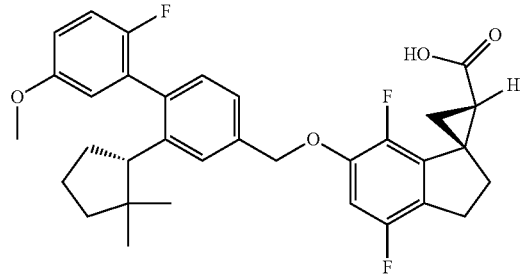 [SMILES: COc1ccc(F)c(-c2ccc(COc3cc(F)c4c(c3F)[C@]3(CC4)C[C@@H]3C(=O)O)cc2[C@H]2CCCC2(C)C)c1] | + | ND |
| | or | | |

TABLE-continued
Assay Data For Human GPR40
| No. | Structure[a] | Aequorin EC$_{50}$[b,c] | IP3 EC$_{50}$[c,d] |
|---|---|---|---|
| | 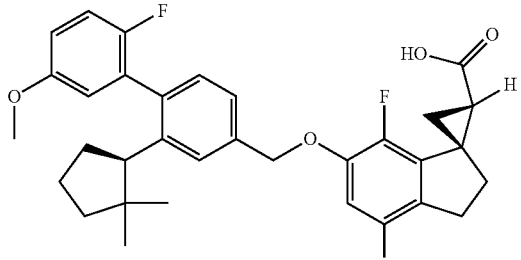 or 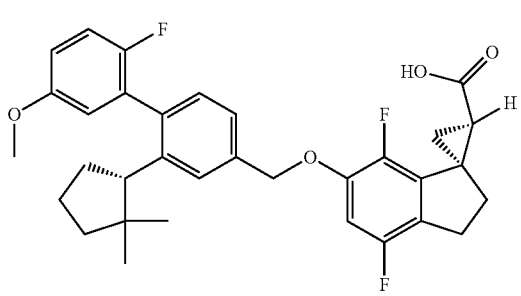 or 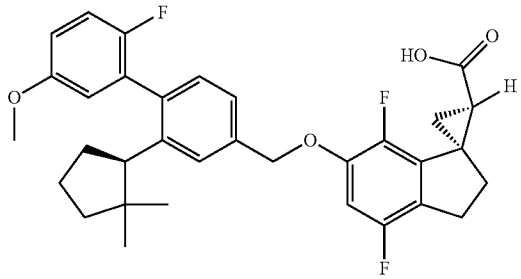 [SMILES: COc1ccc(F)c(-c2ccc(COc3cc(F)c4c(c3F)[C@@]3(CC4)C[C@H]3C(=O)O)cc2[C@@H]2CCCC2(C)C)c1] | | |
| 36 | 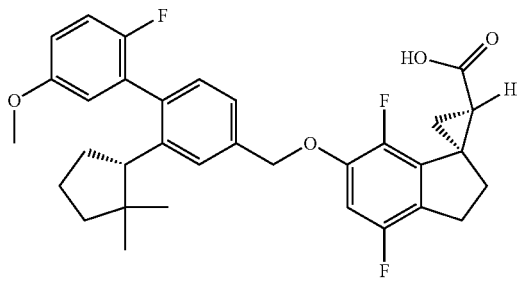 [SMILES: COc1ccc(F)c(-c2ccc(COc3cc(F)c4c(c3F)[C@@]3(CC4)C[C@H]3C(=O)O)cc2[C@H]2CCCC2(C)C)c1] or 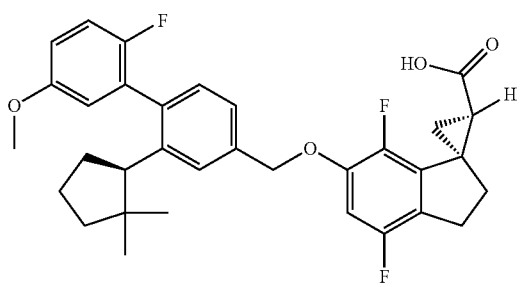 [SMILES: COc1ccc(F)c(-c2ccc(COc3cc(F)c4c(c3F)[C@@]3(CC4)C[C@H]3C(=O)O)cc2[C@@H]2CCCC2(C)C)c1] | + | ND |

TABLE-continued
Assay Data For Human GPR40
| No. | Structure[a] | Aequorin EC$_{50}$[b,c] | IP3 EC$_{50}$[c,d] |
|---|---|---|---|
or
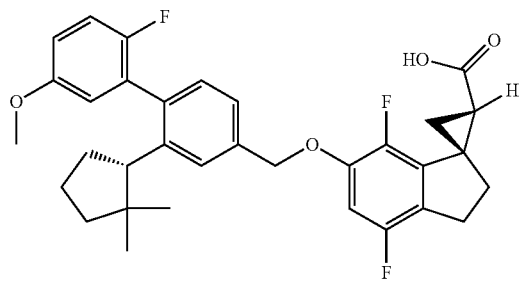 [SMILES: COc1ccc(F)c(-c2ccc(COc3cc(F)c4c(c3F)[C@]3(CC4)C[C@@H]3C(=O)O)cc2[C@H]2CCCC2(C)C)c1]
or
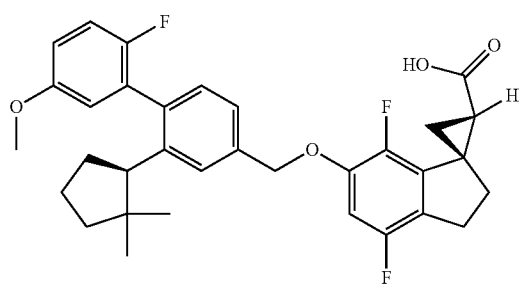 [SMILES: COc1ccc(F)c(-c2ccc(COc3cc(F)c4c(c3F)[C@]3(CC4)C[C@@H]3C(=O)O)cc2[C@@H]2CCCC2(C)C)c1]
| 37 | | ++++ | ND |
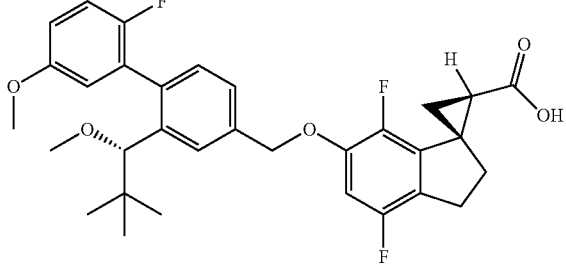
or
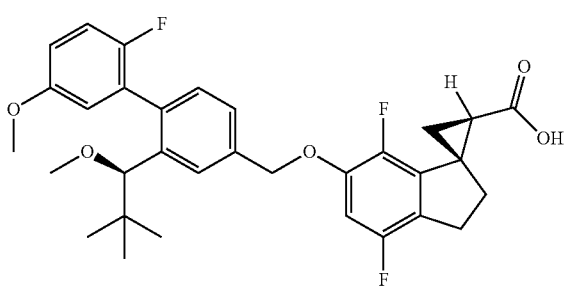 [SMILES: COc1ccc(F)c(-c2ccc(COc3cc(F)c4c(c3F)[C@]3(CC4)C[C@H]3C(=O)O)cc2[C@H](OC)C(C)(C)C)c1]
or

| No. | Structure[a] | Aequorin EC$_{50}$[b,c] | IP3 EC$_{50}$[c,d] |
|---|---|---|---|
|  | 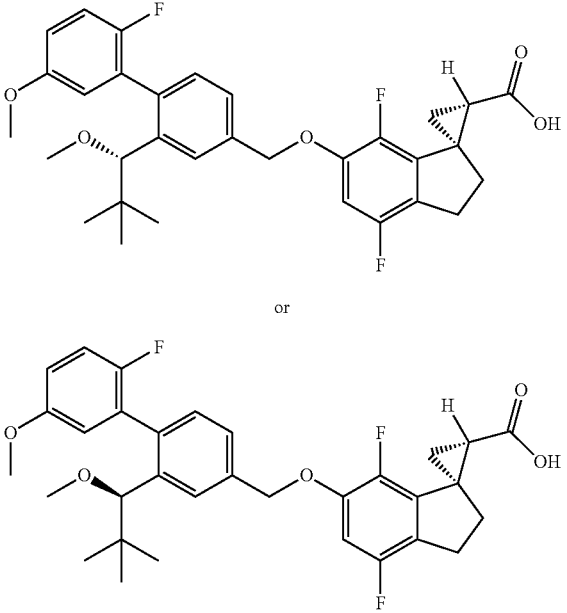 or 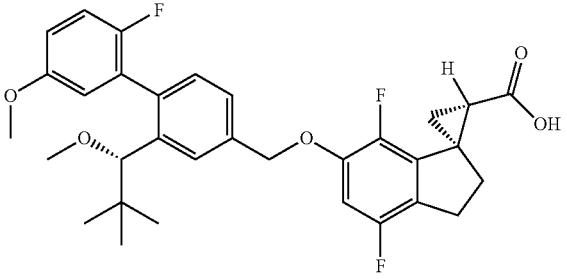 [SMILES: COc1ccc(F)c(-c2ccc(COc3cc(F)c4c(c3F)[C@@]3(CC4)C[C@@H]3C(=O)O)cc2[C@@H](OC)C(C)(C)C)c1] |  |  |
| 38 | 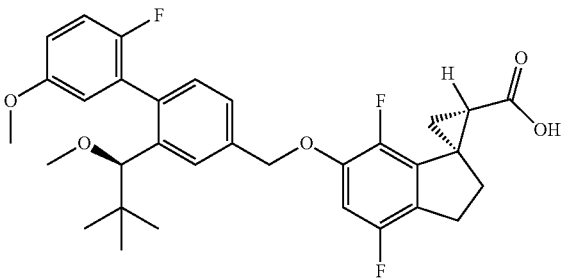 [SMILES: COc1ccc(F)c(-c2ccc(COc3cc(F)c4c(c3F)[C@@]3(CC4)C[C@@H]3C(=O)O)cc2[C@H](OC)C(C)(C)C)c1] or 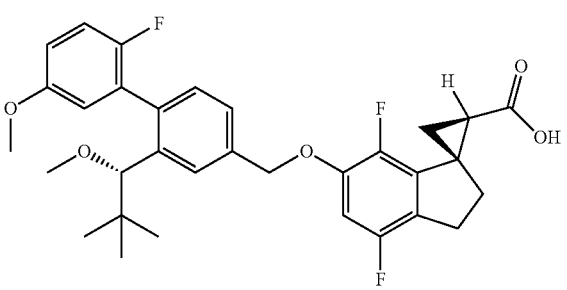 [SMILES: COc1ccc(F)c(-c2ccc(COc3cc(F)c4c(c3F)[C@]3(CC4)C[C@H]3C(=O)O)cc2[C@@H](OC)C(C)(C)C)c1] | ++ | ND |

| No. | Structure[a] | Aequorin EC$_{50}$[b,c] | IP3 EC$_{50}$[c,d] |
|---|---|---|---|
or
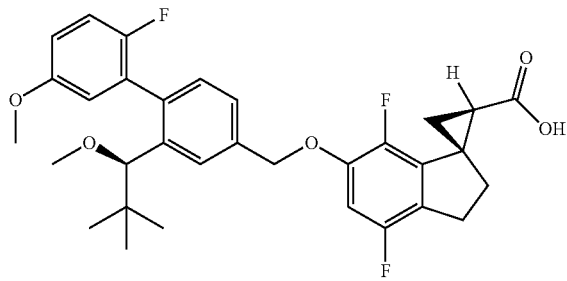 [SMILES: COc1ccc(F)c(-c2ccc(COc3cc(F)c4c(c3F)[C@]3(CC4)C[C@H]3C(=O)O)cc2[C@H](OC)C(C)(C)C)c1]
| 39 | | ++ | ND |
|---|---|---|---|
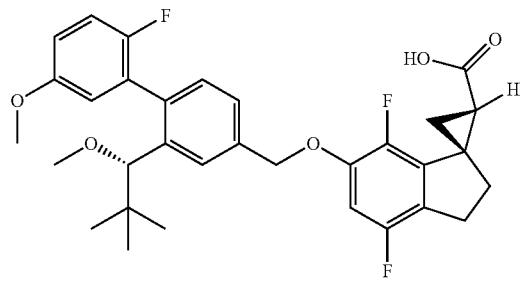 [SMILES: COc1ccc(F)c(-c2ccc(COc3cc(F)c4c(c3F)[C@]3(CC4)C[C@@H]3C(=O)O)cc2[C@@H](OC)C(C)(C)C)c1]
or
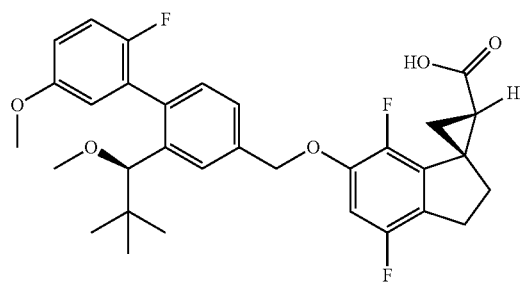 [SMILES: COc1ccc(F)c(-c2ccc(COc3cc(F)c4c(c3F)[C@]3(CC4)C[C@@H]3C(=O)O)cc2[C@H](OC)C(C)(C)C)c1]
or
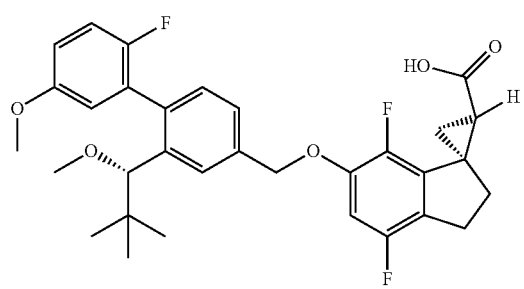
or

TABLE-continued

Assay Data For Human GPR40

| No. | Structure[a] | Aequorin EC$_{50}$[b,c] | IP3 EC$_{50}$[c,d] |
|-----|--------------|-------------------------|---------------------|
| 40  | (structure) or (structure) or (structure) or (structure) | ++ | ND |

TABLE-continued
Assay Data For Human GPR40
| No. | Structure[a] | Aequorin EC$_{50}$[b,c] | IP3 EC$_{50}$[c,d] |
|---|---|---|---|
| 41 | 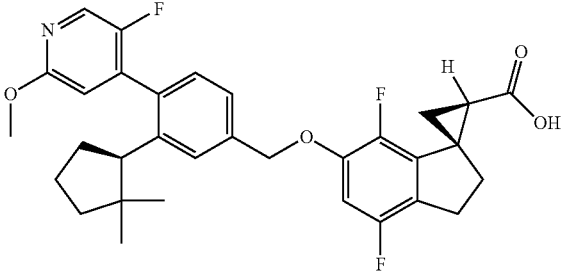 [SMILES: COc1cc(-c2ccc(COc3cc(F)c4c(c3F)[C@]3(CC4)C[C@H]3C(=O)O)cc2[C@@H]2CCCC2(C)C)c(F)cn1] or 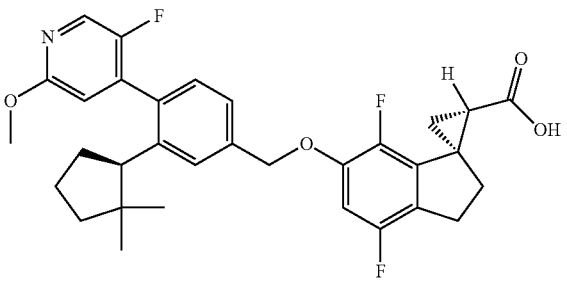 | +++ | +++++ |
| 42 | 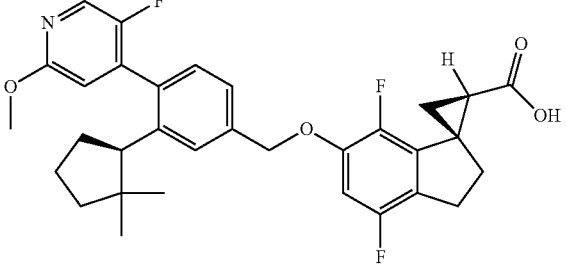 or 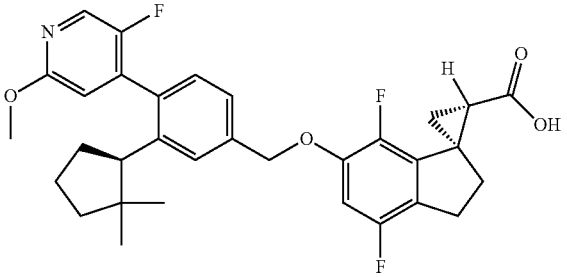 [SMILES: COc1cc(-c2ccc(COc3cc(F)c4c(c3F)[C@@]3(CC4)C[C@@H]3C(=O)O)cc2[C@@H]2CCCC2(C)C)c(F)cn1] (Alternate diastereomer of 41) | ++ | ND |
| 43 | 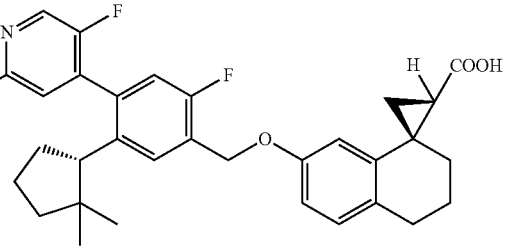 | ++++ | ND |

TABLE-continued
Assay Data For Human GPR40
| No. | Structure[a] | Aequorin EC$_{50}$[b,c] | IP3 EC$_{50}$[c,d] |
|---|---|---|---|
| | or 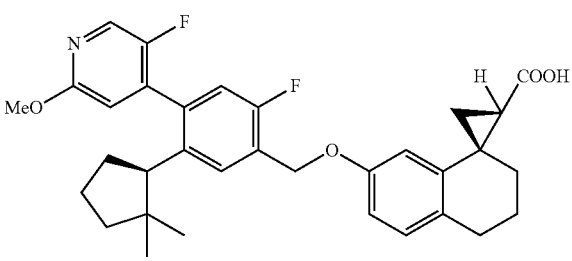 [SMILES: COc1cc(-c2cc(F)c(COc3ccc4c(c3)[C@]3(CCC4)C[C@H]3C(=O)O)cc2[C@@H]2CCCC2(C)C)c(F)cn1] | | |
| 44 | 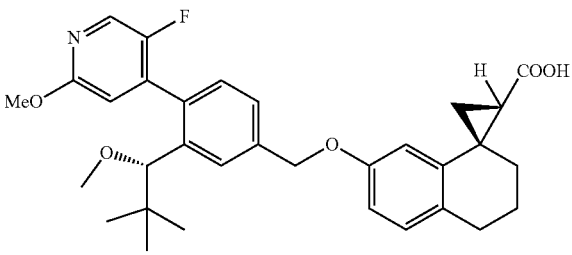 [SMILES: COc1cc(-c2ccc(COc3ccc4c(c3)[C@]3(CCC4)C[C@H]3C(=O)O)cc2[C@@H](OC)C(C)(C)C)c(F)cn1] or 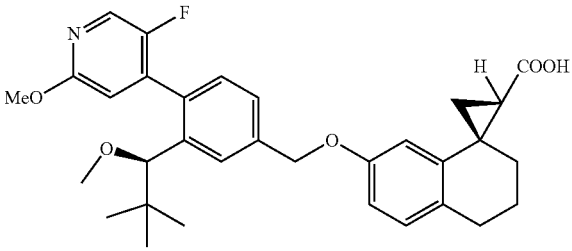 [SMILES: COc1cc(-c2ccc(COc3ccc4c(c3)[C@]3(CCC4)C[C@H]3C(=O)O)cc2[C@H](OC)C(C)(C)C)c(F)cn1] | ++++ | +++++ |
| 45 | 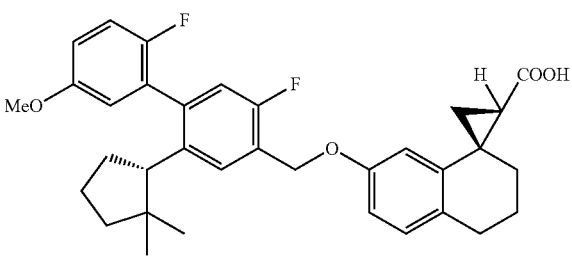 [SMILES: COc1ccc(F)c(-c2cc(F)c(COc3ccc4c(c3)[C@]3(CCC4)C[C@H]3C(=O)O)cc2[C@H]2CCCC2(C)C)c1] or 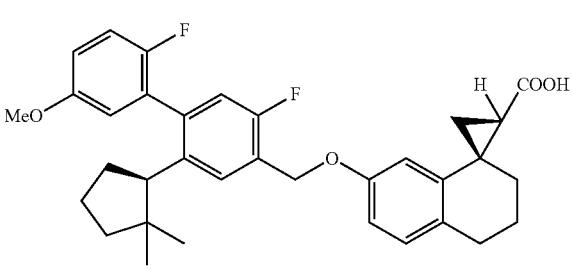 [SMILES: COc1ccc(F)c(-c2cc(F)c(COc3ccc4c(c3)[C@]3(CCC4)C[C@H]3C(=O)O)cc2[C@@H]2CCCC2(C)C)c1] | +++ | +++++ |

TABLE-continued
Assay Data For Human GPR40
| No. | Structure[a] | Aequorin EC$_{50}$[b,c] | IP3 EC$_{50}$[c,d] |
|---|---|---|---|
| 46 | 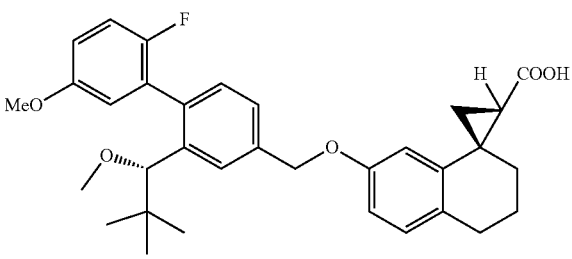 [SMILES: COc1ccc(F)c(-c2ccc(COc3ccc4c(c3)[C@]3(CCC4)C[C@H]3C(=O)O)cc2[C@@H](OC)C(C)(C)C)c1]<br>or<br>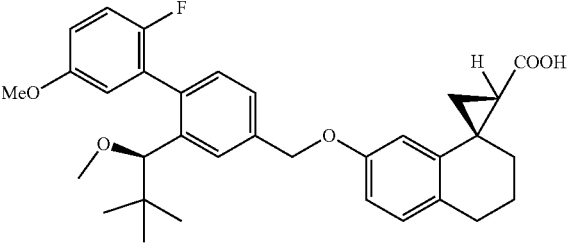 [SMILES: COc1ccc(F)c(-c2ccc(COc3ccc4c(c3)[C@]3(CCC4)C[C@H]3C(=O)O)cc2[C@H](OC)C(C)(C)C)c1] | ++++ | +++++ |
| 47 | 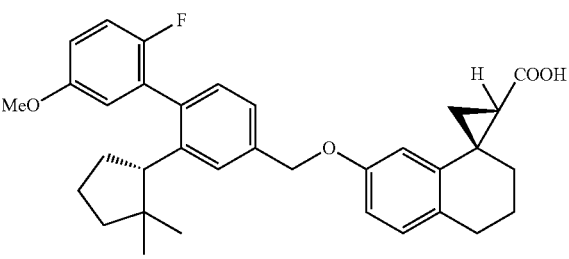 [SMILES: COc1ccc(F)c(-c2ccc(COc3ccc4c(c3)[C@]3(CCC4)C[C@H]3C(=O)O)cc2[C@H]2CCCC2(C)C)c1]<br>or<br>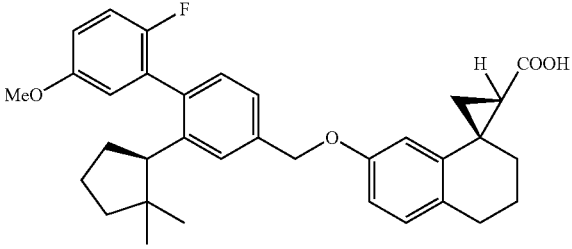 [SMILES: COc1ccc(F)c(-c2ccc(COc3ccc4c(c3)[C@]3(CCC4)C[C@H]3C(=O)O)cc2[C@@H]2CCCC2(C)C)c1] | ++++ | +++++ |
| 48 | 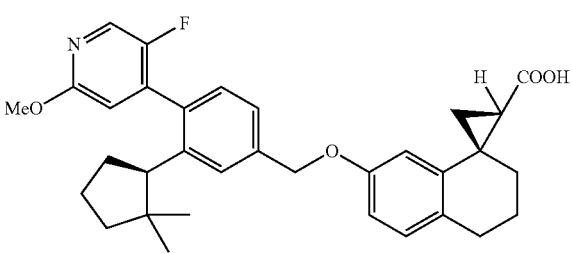 [SMILES: COc1cc(-c2ccc(COc3ccc4c(c3)[C@]3(CCC4)C[C@H]3C(=O)O)cc2[C@@H]2CCCC2(C)C)c(F)cn1] | ++++ | +++++ |

TABLE-continued

Assay Data For Human GPR40

| No. | Structure[a] | Aequorin EC$_{50}$[b,c] | IP3 EC$_{50}$[c,d] |
|---|---|---|---|
| 49 | | +++ | ++++ |
| 50 | | + | ND |
| 51 | | ++++ | +++++ |
|  | or |  |  |
| 52 | | + | ++ |
|  | or |  |  |

TABLE-continued

Assay Data For Human GPR40

| No. | Structure[a] | Aequorin EC$_{50}$[b,c] | IP3 EC$_{50}$[c,d] |
|---|---|---|---|
| | (structure) | | |
| 53 | (structure) or (structure) | ++++ | +++++ |
| 54 | (structure) or (structure) | ++++ | +++++ |

TABLE-continued

Assay Data For Human GPR40

| No. | Structure[a] | Aequorin EC$_{50}$[b,c] | IP3 EC$_{50}$[c,d] |
|---|---|---|---|
| 55 | | +++ | +++++ |
| 56 | | +++ | +++++ |
| 57 | | +++ | +++++ |

TABLE-continued

Assay Data For Human GPR40

| No. | Structure<sup>a</sup> | Aequorin EC<sub>50</sub><sup>b,c</sup> | IP3 EC<sub>50</sub><sup>c,d</sup> |
|---|---|---|---|
| 58 | | +++ | +++++ |
| 59 | | +++ | +++ |
| 60 | | +++ | ++++ |

TABLE-continued

Assay Data For Human GPR40

| No. | Structure[a] | Aequorin EC$_{50}$[b,c] | IP3 EC$_{50}$[c,d] |
|---|---|---|---|
| 61 | | ++ | ND |
| 62 | | + | ND |
| 63 | | ++ | ND |

Compounds 64-103 are synthesized using the methodology described herein from the intermediates described herein or synthesized using intermediates analogous to those described herein and synthesized using analogous routes from commercially available starting materials.[f]

| 64 | 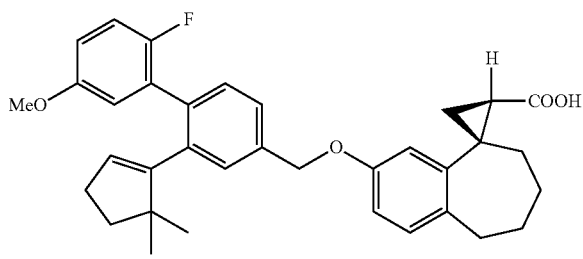 [SMILES: COc1ccc(F)c(-c2ccc(COc3ccc4c(c3)[C@]3(CCCC4)C[C@H]3C(=O)O)cc2C2=CCCC2(C)C)c1] | ND | ND |
| 65 | 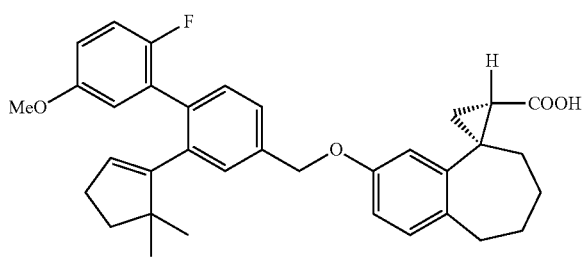 [SMILES: COc1ccc(F)c(-c2ccc(COc3ccc4c(c3)[C@@]3(CCCC4)C[C@@H]3C(=O)O)cc2C2=CCCC2(C)C)c1] | ND | ND |

TABLE-continued

Assay Data For Human GPR40

| No. | Structure[a] | Aequorin EC$_{50}$[b,c] | IP3 EC$_{50}$[c,d] |
|---|---|---|---|
| 66 | | ND | ND |
| 67 | | ND | ND |
| 68 | | ND[f] | ND[f] |
| 69 | | ND[f] | ND[f] |
| 70 | | ND[f] | ND[f] |
| 71 | | ND[f] | ND[f] |

TABLE-continued

Assay Data For Human GPR40

| No. | Structure[a] | Aequorin EC$_{50}$[b,c] | IP3 EC$_{50}$[c,d] |
|---|---|---|---|
| 72 | | ND | ND |
| 73 | | ND | ND |
| 74 | | ND | ND |
| 75 | | ND | ND |
| 76 | | ND | ND |

TABLE-continued

Assay Data For Human GPR40

| No. | Structure[a] | Aequorin EC$_{50}$[b,c] | IP3 EC$_{50}$[c,d] |
|---|---|---|---|
| 77 | | ND | ND |
| 78 | | ND | ND |
| 79 | | ND | ND |
| 80 | | ND | ND |
| 81 | | ND | ND |
| 82 | | ND | ND |

TABLE-continued
Assay Data For Human GPR40
| No. | Structure[a] | Aequorin EC$_{50}$[b,c] | IP3 EC$_{50}$[c,d] |
|---|---|---|---|
| 83 | 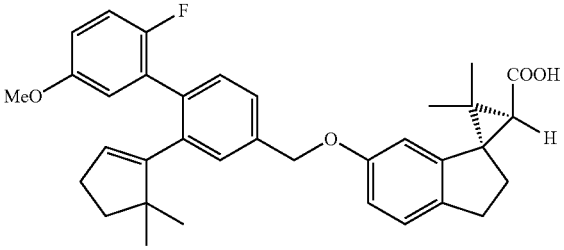 [SMILES: COc1ccc(F)c(-c2ccc(COc3ccc4c(c3)[C@]3(CC4)[C@H](C(=O)O)C3(C)C)cc2C2=CCCC2(C)C)c1] | ND | ND |
| 84 | 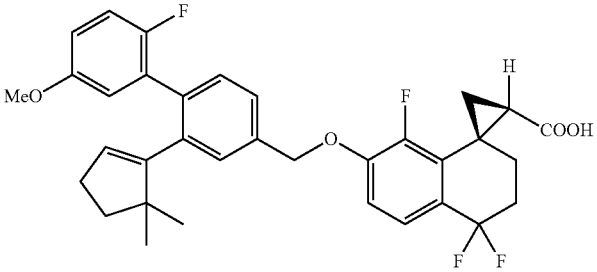 [SMILES: COc1ccc(F)c(-c2ccc(COc3ccc4c(c3F)[C@]3(CCC4(F)F)C[C@H]3C(=O)O)cc2C2=CCCC2(C)C)c1] | ND | ND |
| 85 | 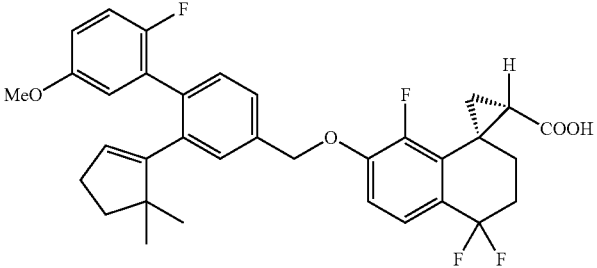 [SMILES: COc1ccc(F)c(-c2ccc(COc3ccc4c(c3F)[C@@]3(CCC4(F)F)C[C@@H]3C(=O)O)cc2C2=CCCC2(C)C)c1] | ND | ND |
| 86 | 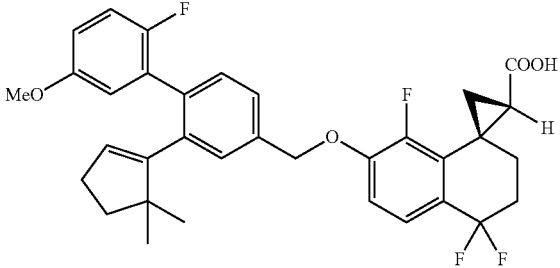 [SMILES: COc1ccc(F)c(-c2ccc(COc3ccc4c(c3F)[C@]3(CCC4(F)F)C[C@@H]3C(=O)O)cc2C2=CCCC2(C)C)c1] | ND | ND |
| 87 | 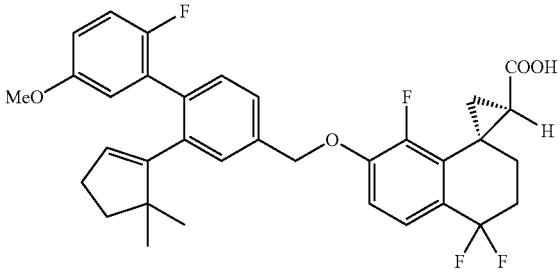 [SMILES: COc1ccc(F)c(-c2ccc(COc3ccc4c(c3F)[C@@]3(CCC4(F)F)C[C@H]3C(=O)O)cc2C2=CCCC2(C)C)c1] | ND | ND |

TABLE-continued

Assay Data For Human GPR40

| No. | Structure[a] | Aequorin EC$_{50}$[b,c] | IP3 EC$_{50}$[c,d] |
|---|---|---|---|
| 88 | | ND | ND |
| 89 | | ND | ND |
| 90 | | ND | ND |
| 91 | | ND | ND |
| 92 | | ND | ND |
| 93 | | ND | ND |

TABLE-continued

Assay Data For Human GPR40

| No. | Structure[a] | Aequorin EC$_{50}$[b,c] | IP3 EC$_{50}$[c,d] |
|---|---|---|---|
| 94 | | ND | ND |
| 95 | | ND | ND |
| 96 | | ND | ND |
| 97 | | ND | ND |
| 98 | | ND | ND |
| 99 | | ND | ND |
| 100 | | ND | ND |
| 101 | | ND | ND |

TABLE-continued

Assay Data For Human GPR40

| No. | Structure[a] | Aequorin EC$_{50}$[b,c] | IP3 EC$_{50}$[c,d] |
|---|---|---|---|
| 102 | | ND | ND |
| 103 | | ND | ND |

Example 104 was synthesized as described herein.

| | | | |
|---|---|---|---|
| 104 | | + | ND |

Compounds 105-122 are synthesized using the methodology described herein from the intermediates described herein or synthesized using intermediates analogous to those described herein and synthesized using analogous routes from commercially available starting materials.[f]

| | | | |
|---|---|---|---|
| 105 | | ND | ND |
| 106 | | ND | ND |
| 107 | | ND | ND |
| 108 | | ND | ND |

TABLE-continued

Assay Data For Human GPR40

| No. | Structure$^a$ | Aequorin EC$_{50}$$^{b,c}$ | IP3 EC$_{50}$$^{c,d}$ |
|---|---|---|---|
| 109 | | ND | ND |
| 110 | | ND | ND |
| 111 | | ND | ND |
| 112 | | ND | ND |
| 113 | | ND | ND |
| 114 | | ND | ND |

TABLE-continued

Assay Data For Human GPR40

| No. | Structure[a] | Aequorin EC$_{50}$[b,c] | IP3 EC$_{50}$[c,d] |
|---|---|---|---|
| 115 | | ND | ND |
| 116 | | ND | ND |
| 117 | | ND | ND |
| 118 | | ND | ND |
| 119 | | ND | ND |
| 120 | | ND | ND |
| 121 | | ND | ND |

TABLE-continued
Assay Data For Human GPR40
| No. | Structure[a] | Aequorin EC$_{50}$[b,c] | IP3 EC$_{50}$[c,d] |
|---|---|---|---|
| 122 | 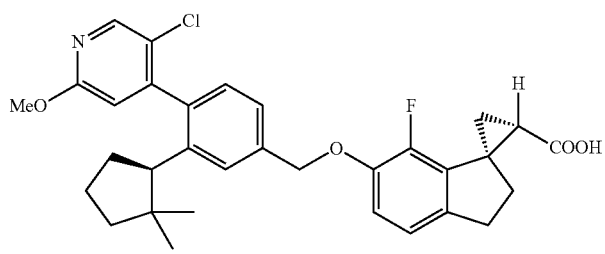 [SMILES: COc1cc(-c2ccc(COc3ccc4c(c3F)[C@@]3(CC4)C[C@@H]3C(=O)O)cc2[C@@H]2CCCC2(C)C)c(Cl)cn1] | ND | ND |
The following compounds were synthesized as described herein.
| 123 | | ++ | ND |
| 124 | | ++ | ND |
| 125 | | +++ | ++++ |
or
| 126 | | ++ | ND |
or

TABLE-continued

Assay Data For Human GPR40

| No. | Structure[a] | Aequorin EC$_{50}$[b,c] | IP3 EC$_{50}$[c,d] |
|---|---|---|---|
| 127 | | +++ | +++++ |

TABLE-continued
Assay Data For Human GPR40
| No. | Structure[a] | Aequorin EC$_{50}$[b,c] | IP3 EC$_{50}$[c,d] |
|---|---|---|---|
| 128 | 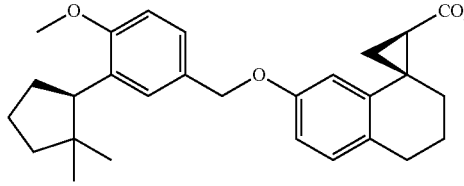 or 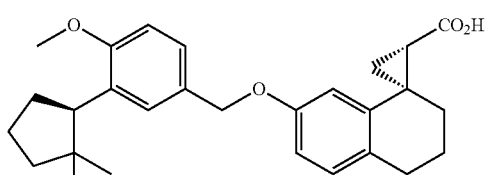 | ++ | ND |
| 129 | 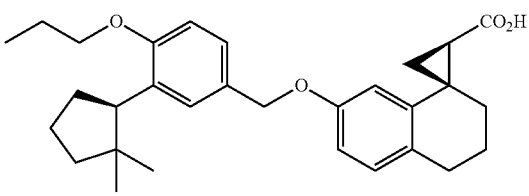 [SMILES: CCCOc1ccc(COc2ccc3c(c2)[C@]2(CCC3)C[C@H]2C(=O)O)cc1[C@@H]1CCCC1(C)C] or 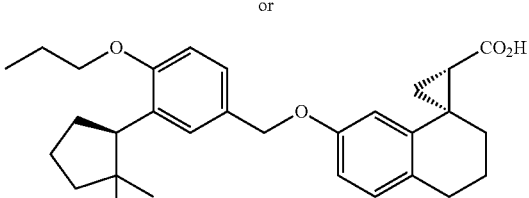 | ++ | +++ |
| 130 | 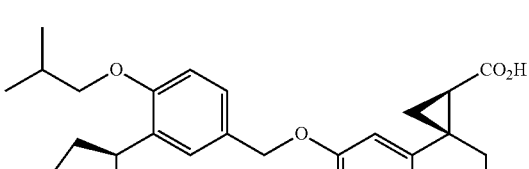 or 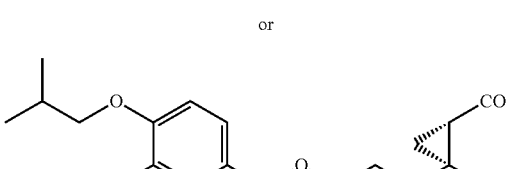 | ++ | +++ |
| 131 | 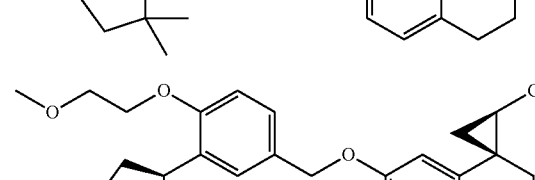 | ++ | +++ |

TABLE-continued
Assay Data For Human GPR40
| No. | Structure[a] | Aequorin EC$_{50}$[b,c] | IP3 EC$_{50}$[c,d] |
|---|---|---|---|
| | or 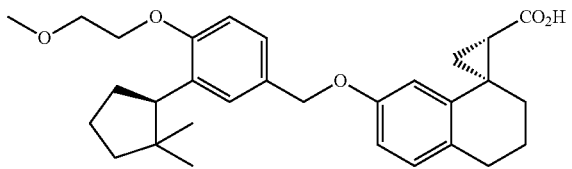 [SMILES: COCCOc1ccc(COc2ccc3c(c2)[C@@]2(CCC3)C[C@@H]2C(=O)O)cc1[C@@H]1CCCC1(C)C] | | |
| 132 | 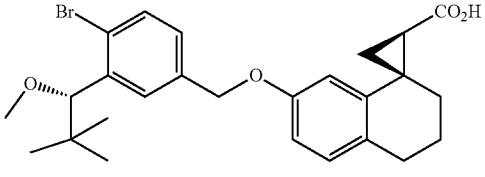 [SMILES: CO[C@H](c1cc(COc2ccc3c(c2)[C@]2(CCC3)C[C@H]2C(=O)O)ccc1Br)C(C)(C)C] and 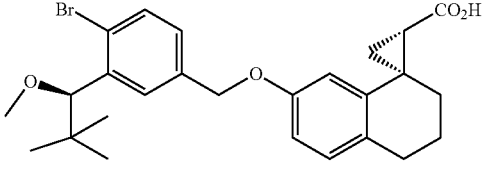 [SMILES: CO[C@@H](c1cc(COc2ccc3c(c2)[C@@]2(CCC3)C[C@@H]2C(=O)O)ccc1Br)C(C)(C)C] or 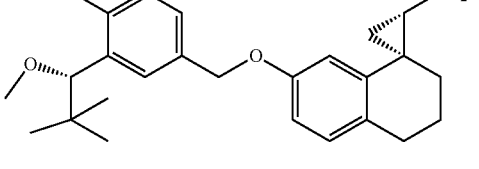 and 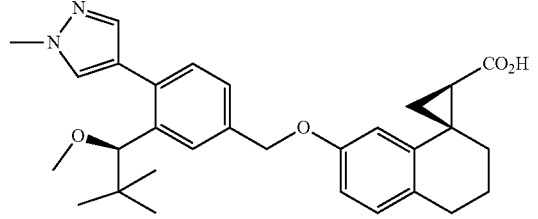 [SMILES: CO[C@@H](c1cc(COc2ccc3c(c2)[C@]2(CCC3)C[C@H]2C(=O)O)ccc1-c1cnn(C)c1)C(C)(C)C] | ++ | ND |
| 133 | 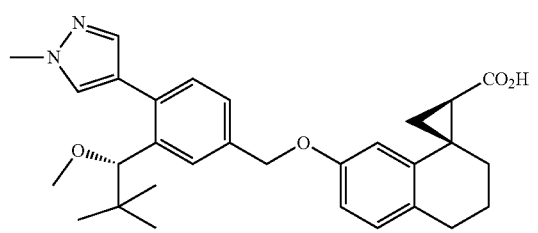 [SMILES: CO[C@H](c1cc(COc2ccc3c(c2)[C@]2(CCC3)C[C@H]2C(=O)O)ccc1-c1cnn(C)c1)C(C)(C)C] and | ++ | ND |

TABLE-continued
Assay Data For Human GPR40
| No. | Structure[a] | Aequorin EC$_{50}$[b,c] | IP3 EC$_{50}$[c,d] |
|-----|-----------|------|------|
| | or 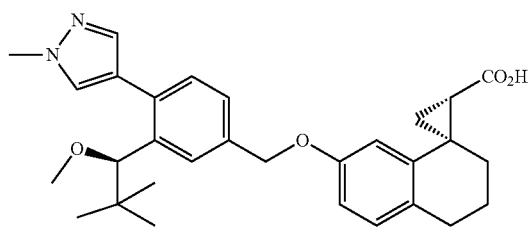 [SMILES: CO[C@@H](c1cc(COc2ccc3c(c2)[C@@]2(CCC3)C[C@@H]2C(=O)O)ccc1-c1cnn(C)c1)C(C)(C)C] and 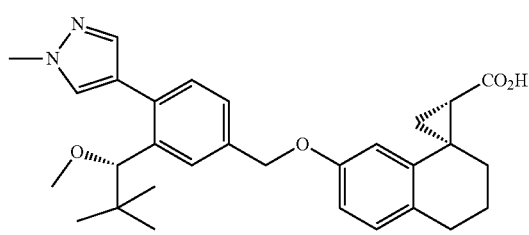 [SMILES: CO[C@H](c1cc(COc2ccc3c(c2)[C@@]2(CCC3)C[C@@H]2C(=O)O)ccc1-c1cnn(C)c1)C(C)(C)C] | | |
| 134 | 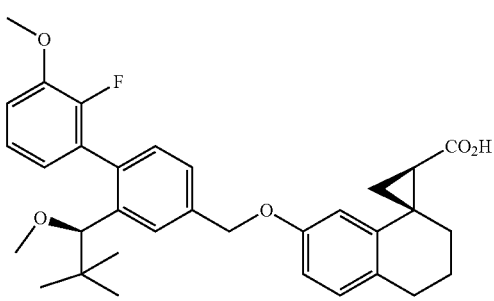 [SMILES: COc1cccc(-c2ccc(COc3ccc4c(c3)[C@]3(CCC4)C[C@H]3C(=O)O)cc2[C@H](OC)C(C)(C)C)c1F] and 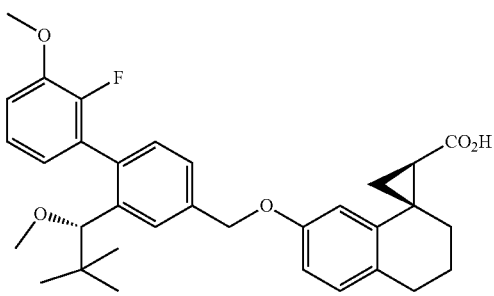 [SMILES: COc1cccc(-c2ccc(COc3ccc4c(c3)[C@]3(CCC4)C[C@H]3C(=O)O)cc2[C@@H](OC)C(C)(C)C)c1F] or 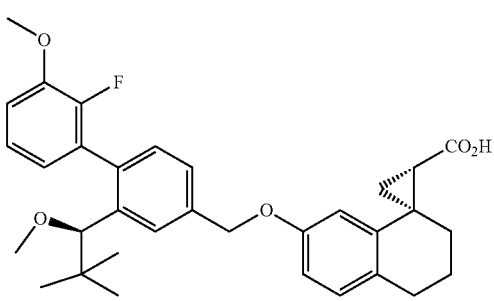 [SMILES: COc1cccc(-c2ccc(COc3ccc4c(c3)[C@@]3(CCC4)C[C@@H]3C(=O)O)cc2[C@H](OC)C(C)(C)C)c1F] | +++ | ++++ |

TABLE-continued

Assay Data For Human GPR40

| No. | Structure[a] | Aequorin $EC_{50}$[b,c] | IP3 $EC_{50}$[c,d] |
|---|---|---|---|
| 135 | and (structures shown) or (structures shown) and (structures shown) | ++ | ND |

TABLE-continued
Assay Data For Human GPR40
| No. | Structure[a] | Aequorin EC$_{50}$[b,c] | IP3 EC$_{50}$[c,d] |
|---|---|---|---|
| 136 | 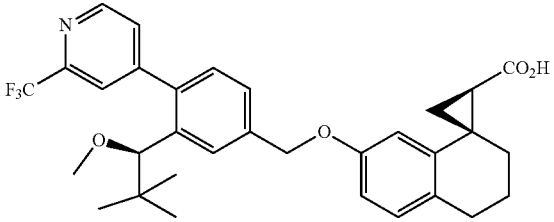 [SMILES: CO[C@@H](c1cc(COc2ccc3c(c2)[C@]2(CCC3)C[C@H]2C(=O)O)ccc1-c1ccnc(C(F)(F)F)c1)C(C)(C)C] and 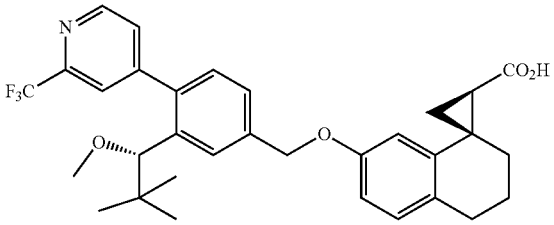 [SMILES: CO[C@H](c1cc(COc2ccc3c(c2)[C@]2(CCC3)C[C@H]2C(=O)O)ccc1-c1ccnc(C(F)(F)F)c1)C(C)(C)C] or 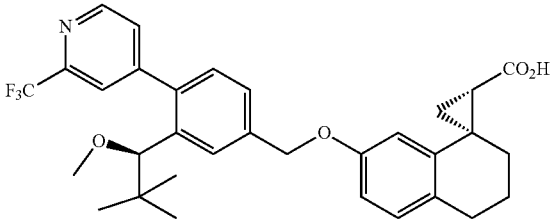 [SMILES: CO[C@@H](c1cc(COc2ccc3c(c2)[C@@]2(CCC3)C[C@@H]2C(=O)O)ccc1-c1ccnc(C(F)(F)F)c1)C(C)(C)C] and 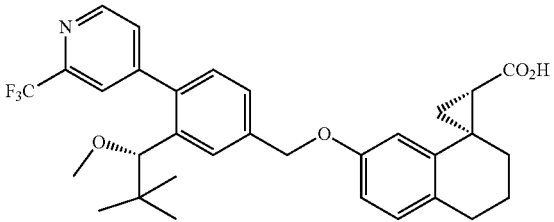 [SMILES: CO[C@H](c1cc(COc2ccc3c(c2)[C@@]2(CCC3)C[C@@H]2C(=O)O)ccc1-c1ccnc(C(F)(F)F)c1)C(C)(C)C] | ++ | ND |
| 137 | 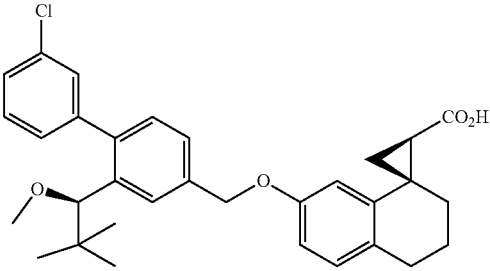 [SMILES: CO[C@@H](c1cc(COc2ccc3c(c2)[C@]2(CCC3)C[C@H]2C(=O)O)ccc1-c1cccc(Cl)c1)C(C)(C)C] and | +++ | ++++ |

TABLE-continued
Assay Data For Human GPR40
| No. | Structure[a] | Aequorin EC$_{50}$[b,c] | IP3 EC$_{50}$[c,d] |
|---|---|---|---|
| | 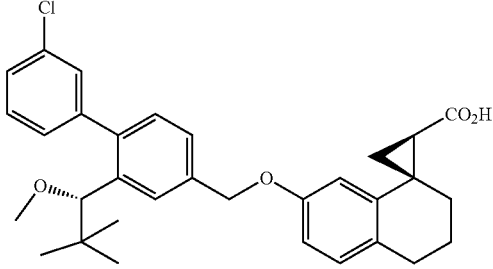 [SMILES: CO[C@H](c1cc(COc2ccc3c(c2)[C@]2(CCC3)C[C@H]2C(=O)O)ccc1-c1cccc(Cl)c1)C(C)(C)C] or 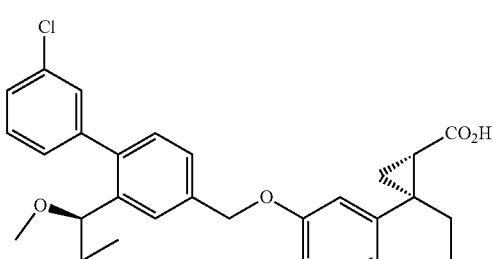 and 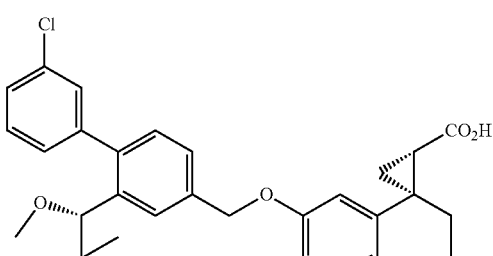 | | |
| 138 | 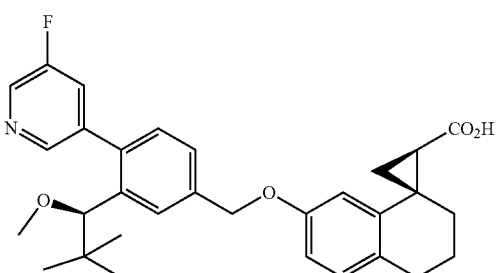 and 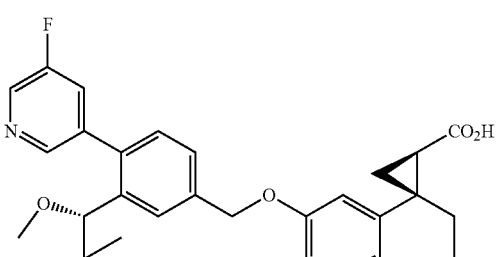 | ++ | ND |

| No. | Structure | Aequorin EC$_{50}$[b,c] | IP3 EC$_{50}$[c,d] |
|---|---|---|---|
TABLE-continued
Assay Data For Human GPR40
or
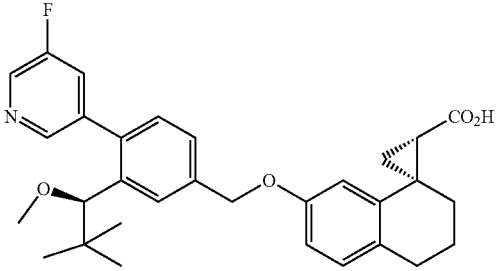 [SMILES: CO[C@@H](c1cc(COc2ccc3c(c2)[C@@]2(CCC3)C[C@@H]2C(=O)O)ccc1-c1cncc(F)c1)C(C)(C)C]
and
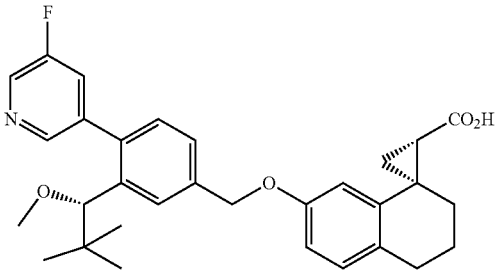 [SMILES: CO[C@H](c1cc(COc2ccc3c(c2)[C@@]2(CCC3)C[C@@H]2C(=O)O)ccc1-c1cncc(F)c1)C(C)(C)C]
139
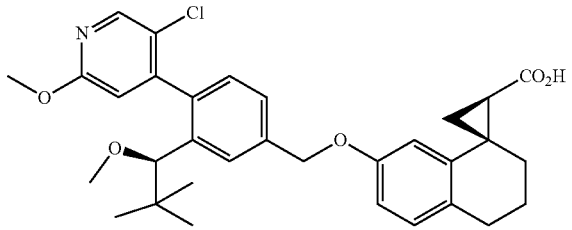 [SMILES: COc1cc(-c2ccc(COc3ccc4c(c3)[C@]3(CCC4)C[C@H]3C(=O)O)cc2[C@H](OC)C(C)(C)C)c(Cl)cn1]
+++ +++++
and
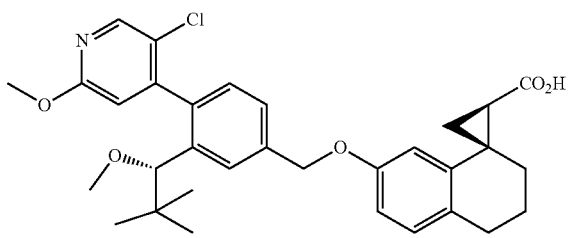 [SMILES: COc1cc(-c2ccc(COc3ccc4c(c3)[C@]3(CCC4)C[C@H]3C(=O)O)cc2[C@@H](OC)C(C)(C)C)c(Cl)cn1]
or
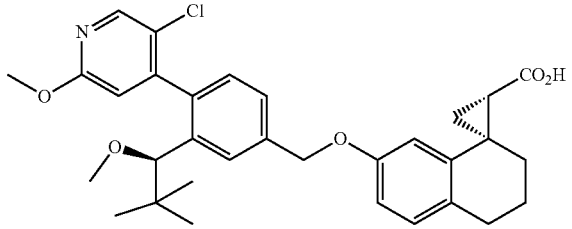 [SMILES: COc1cc(-c2ccc(COc3ccc4c(c3)[C@@]3(CCC4)C[C@@H]3C(=O)O)cc2[C@H](OC)C(C)(C)C)c(Cl)cn1]
and

TABLE-continued

Assay Data For Human GPR40

| No. | Structure[a] | Aequorin EC$_{50}$[b,c] | IP3 EC$_{50}$[c,d] |
|---|---|---|---|
| 140 | | +++ | ND | or or or or

TABLE-continued
Assay Data For Human GPR40
| No. | Structure[a] | Aequorin EC$_{50}$[b,c] | IP3 EC$_{50}$[c,d] |
|---|---|---|---|
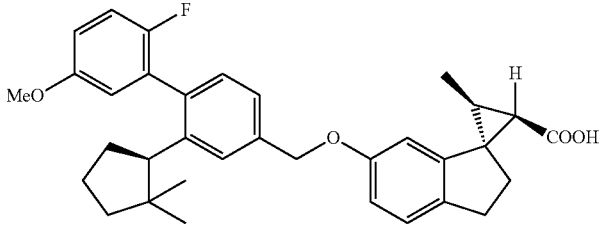 [SMILES: COc1ccc(F)c(-c2ccc(COc3ccc4c(c3)[C@]3(CC4)[C@H](C(=O)O)[C@@H]3C)cc2[C@@H]2CCCC2(C)C)c1]
or
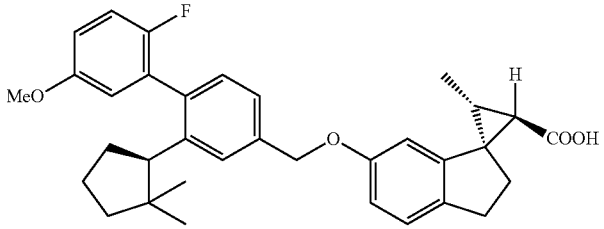 [SMILES: COc1ccc(F)c(-c2ccc(COc3ccc4c(c3)[C@@]3(CC4)[C@H](C)[C@H]3C(=O)O)cc2[C@@H]2CCCC2(C)C)c1]
or
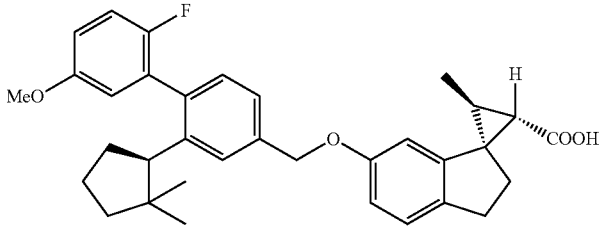 [SMILES: COc1ccc(F)c(-c2ccc(COc3ccc4c(c3)[C@@]3(CC4)[C@@H](C)[C@@H]3C(=O)O)cc2[C@@H]2CCCC2(C)C)c1]
or
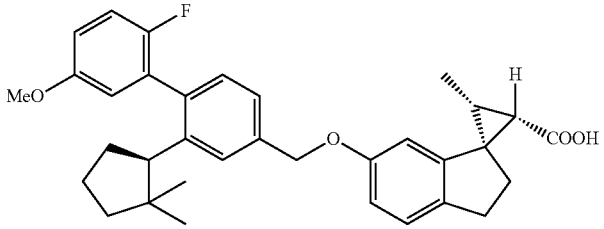 [SMILES: COc1ccc(F)c(-c2ccc(COc3ccc4c(c3)[C@@]3(CC4)[C@H](C)[C@@H]3C(=O)O)cc2[C@@H]2CCCC2(C)C)c1]
or
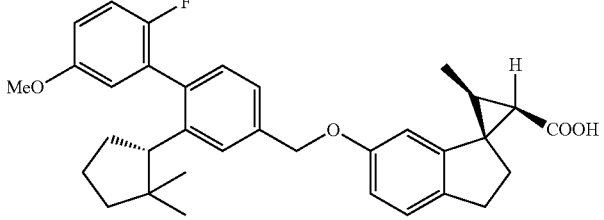
or

TABLE-continued
Assay Data For Human GPR40
| No. | Structure[a] | Aequorin EC$_{50}$[b,c] | IP3 EC$_{50}$[c,d] |
|---|---|---|---|
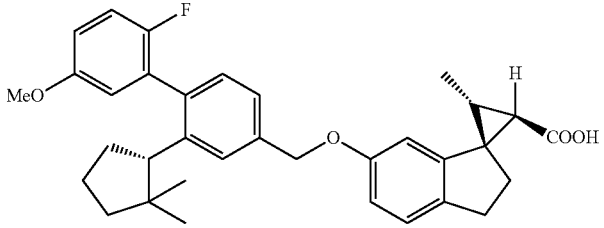 [SMILES: COc1ccc(F)c(-c2ccc(COc3ccc4c(c3)[C@]3(CC4)[C@H](C)[C@H]3C(=O)O)cc2[C@H]2CCCC2(C)C)c1]
or
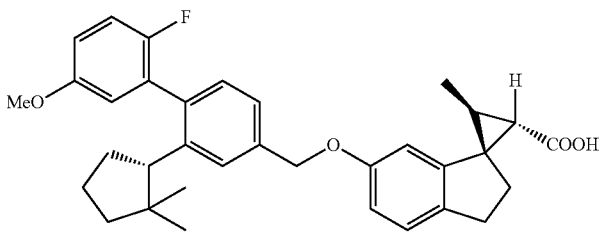 [SMILES: COc1ccc(F)c(-c2ccc(COc3ccc4c(c3)[C@]3(CC4)[C@@H](C)[C@@H]3C(=O)O)cc2[C@H]2CCCC2(C)C)c1]
or
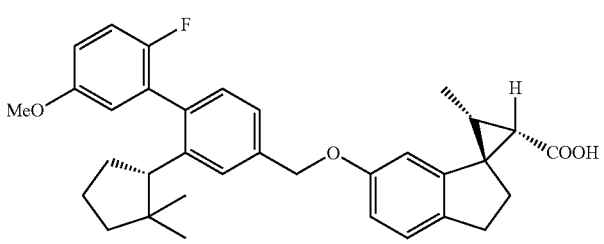 [SMILES: COc1ccc(F)c(-c2ccc(COc3ccc4c(c3)[C@]3(CC4)[C@H](C)[C@@H]3C(=O)O)cc2[C@H]2CCCC2(C)C)c1]
or
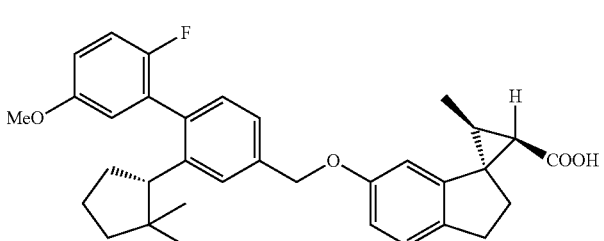
or
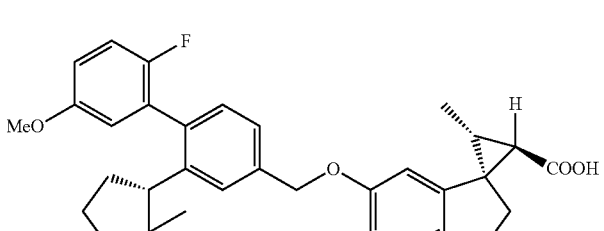
or

TABLE-continued

Assay Data For Human GPR40

| No. | Structure[a] | Aequorin EC$_{50}$[b,c] | IP3 EC$_{50}$[c,d] |
|---|---|---|---|
| 141 | Diastereomer of 140 | +++ | ND |
| 142 | Diastereomer of 140 | +++ | ND |
| 143 | Diastereomer of 140 | ++ | ND |
| 144 | Diastereomer of 140 | +++ | ++++ |
| 145 | | ++ | ND | or

TABLE-continued
Assay Data For Human GPR40
| No. | Structure[a] | Aequorin EC$_{50}$[b,c] | IP3 EC$_{50}$[c,d] |
|---|---|---|---|
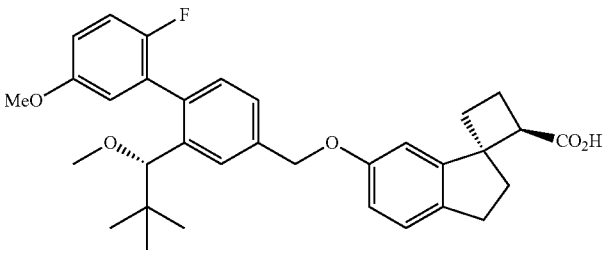 [SMILES: COc1ccc(F)c(-c2ccc(COc3ccc4c(c3)[C@@]3(CC4)CC[C@H]3C(=O)O)cc2[C@@H](OC)C(C)(C)C)c1]
or
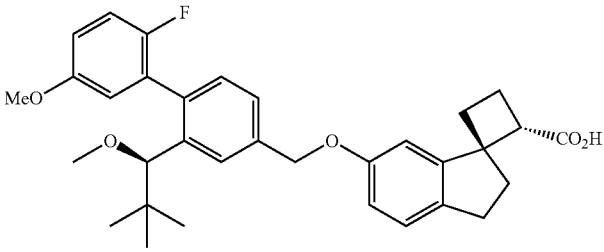 [SMILES: COc1ccc(F)c(-c2ccc(COc3ccc4c(c3)[C@]3(CC4)CC[C@@H]3C(=O)O)cc2[C@H](OC)C(C)(C)C)c1]
or
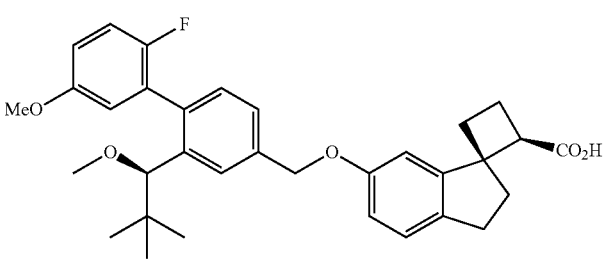 [SMILES: COc1ccc(F)c(-c2ccc(COc3ccc4c(c3)[C@]3(CC4)CC[C@H]3C(=O)O)cc2[C@H](OC)C(C)(C)C)c1]
or
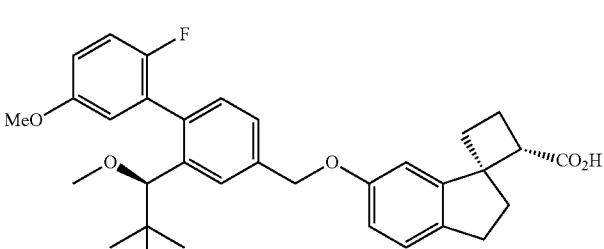
or
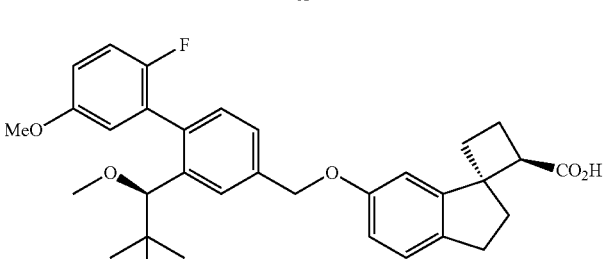

TABLE-continued

Assay Data For Human GPR40

| No. | Structure[a] | Aequorin EC$_{50}$[b,c] | IP3 EC$_{50}$[c,d] |
|---|---|---|---|
| 146 | [structure] | +++ | ND |
| | or [structure] | | |
| | or [structure] | | |
| | or [structure] | | |
| 147 | Diastereomer of 145 | +++ | |
| 148 | Diastereomer of 146 | +++ | ++++ |
| 149 | Diastereomer of 145 | +++ | +++++ |
| 150 | [structure] | +++ | +++++ |
| | or | | |

TABLE-continued
Assay Data For Human GPR40
| No. | Structure[a] | Aequorin EC$_{50}$[b,c] | IP3 EC$_{50}$[c,d] |
|---|---|---|---|
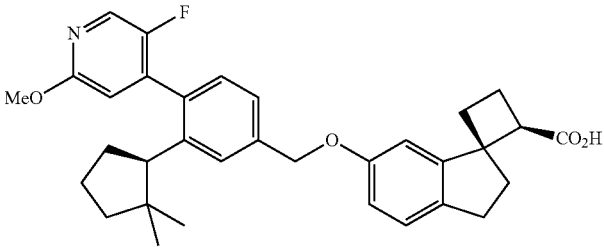 [SMILES: COc1cc(-c2ccc(COc3ccc4c(c3)[C@]3(CC4)CC[C@H]3C(=O)O)cc2[C@@H]2CCCC2(C)C)c(F)cn1]
or
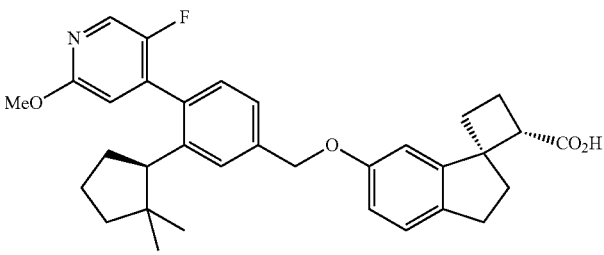 [SMILES: COc1cc(-c2ccc(COc3ccc4c(c3)[C@@]3(CC4)CC[C@@H]3C(=O)O)cc2[C@@H]2CCCC2(C)C)c(F)cn1]
or
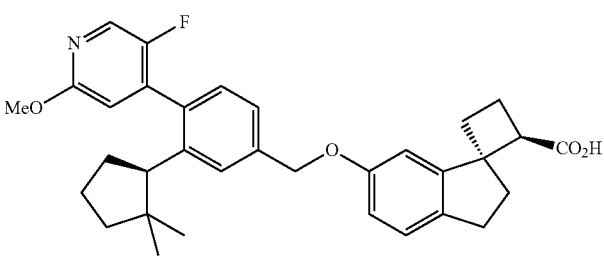 [SMILES: COc1cc(-c2ccc(COc3ccc4c(c3)[C@@]3(CC4)CC[C@H]3C(=O)O)cc2[C@@H]2CCCC2(C)C)c(F)cn1]
| 151 | | +++ | ++++ |
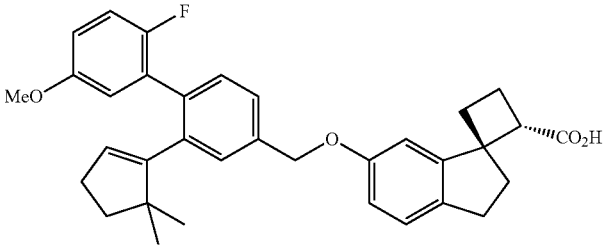 [SMILES: COc1ccc(F)c(-c2ccc(COc3ccc4c(c3)[C@]3(CC4)CC[C@@H]3C(=O)O)cc2C2=CCCC2(C)C)c1]
or
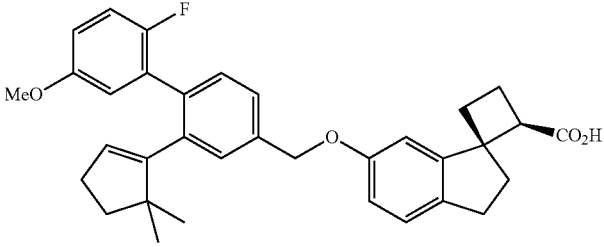 [SMILES: COc1ccc(F)c(-c2ccc(COc3ccc4c(c3)[C@]3(CC4)CC[C@H]3C(=O)O)cc2C2=CCCC2(C)C)c1]
or

| No. | Structure[a] | Aequorin EC$_{50}$[b,c] | IP3 EC$_{50}$[c,d] |
|---|---|---|---|
| | 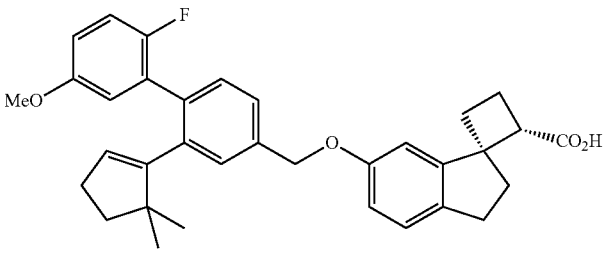 [SMILES: COc1ccc(F)c(-c2ccc(COc3ccc4c(c3)[C@@]3(CC4)CC[C@@H]3C(=O)O)cc2C2=CCCC2(C)C)c1] or 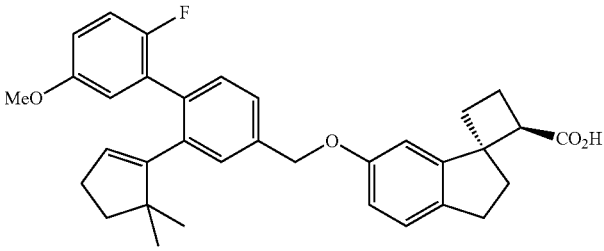 [SMILES: COc1ccc(F)c(-c2ccc(COc3ccc4c(c3)[C@@]3(CC4)CC[C@H]3C(=O)O)cc2C2=CCCC2(C)C)c1] | | |
| 152 | 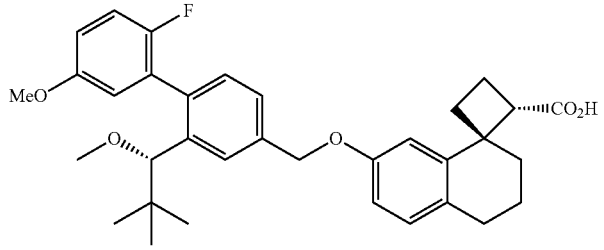 [SMILES: COc1ccc(F)c(-c2ccc(COc3ccc4c(c3)[C@]3(CCC4)CC[C@@H]3C(=O)O)cc2[C@@H](OC)C(C)(C)C)c1] or 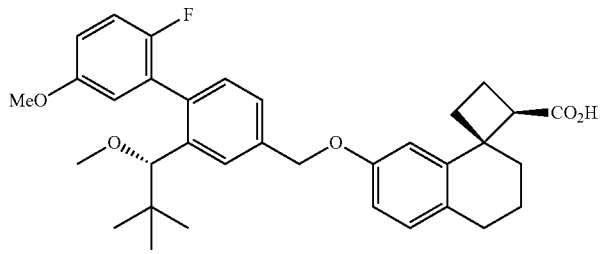 [SMILES: COc1ccc(F)c(-c2ccc(COc3ccc4c(c3)[C@]3(CCC4)CC[C@H]3C(=O)O)cc2[C@@H](OC)C(C)(C)C)c1] or 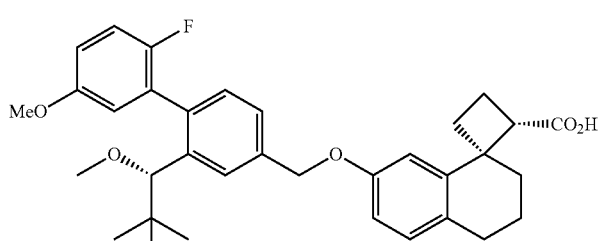 or | ++ | ND |

TABLE-continued
Assay Data For Human GPR40
| No. | Structure[a] | Aequorin EC$_{50}$[b,c] | IP3 EC$_{50}$[c,d] |
|---|---|---|---|
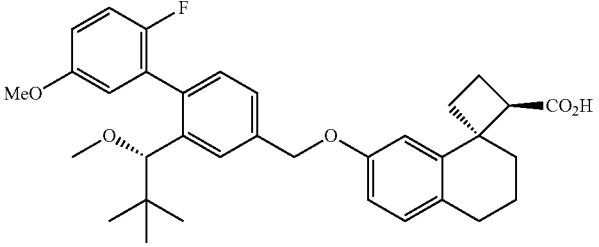 [SMILES: COc1ccc(F)c(-c2ccc(COc3ccc4c(c3)[C@@]3(CCC4)CC[C@H]3C(=O)O)cc2[C@@H](OC)C(C)(C)C)c1]
or
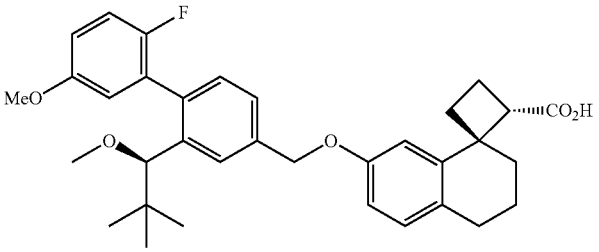 [SMILES: COc1ccc(F)c(-c2ccc(COc3ccc4c(c3)[C@]3(CCC4)CC[C@@H]3C(=O)O)cc2[C@H](OC)C(C)(C)C)c1]
or
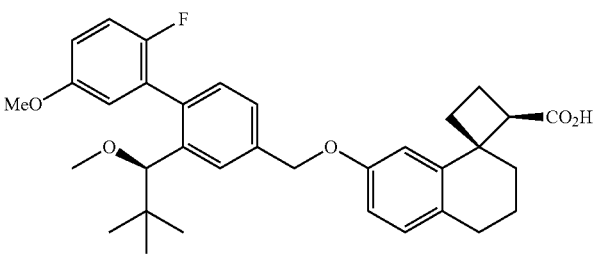 [SMILES: COc1ccc(F)c(-c2ccc(COc3ccc4c(c3)[C@]3(CCC4)CC[C@H]3C(=O)O)cc2[C@H](OC)C(C)(C)C)c1]
or
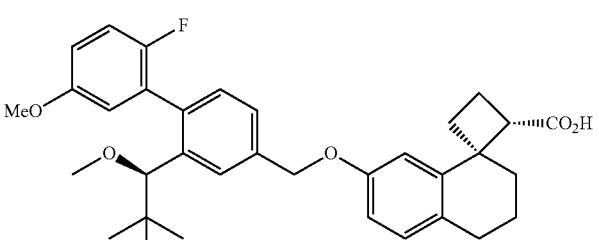
or
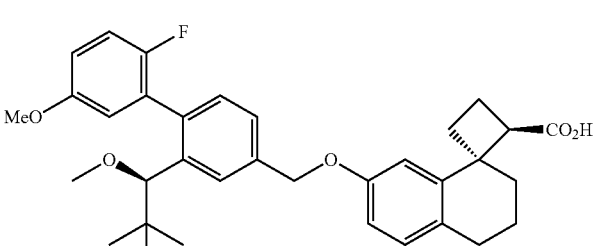

TABLE-continued
Assay Data For Human GPR40
| No. | Structure[a] | Aequorin EC50[b,c] | IP3 EC50[c,d] |
|---|---|---|---|
| 153 | 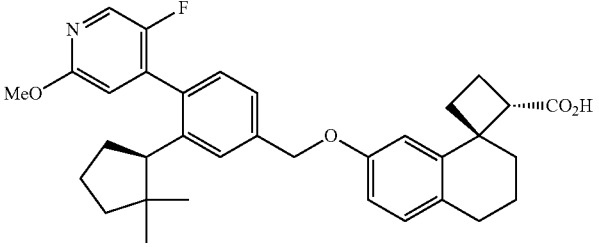 [SMILES: COc1cc(-c2ccc(COc3ccc4c(c3)[C@]3(CCC4)CC[C@@H]3C(=O)O)cc2[C@@H]2CCCC2(C)C)c(F)cn1] or 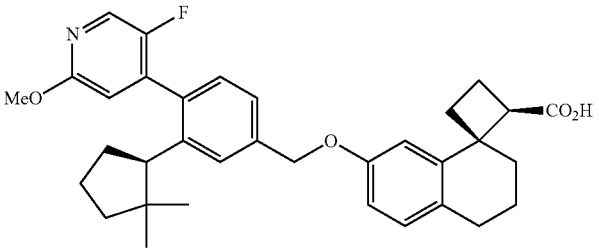 [SMILES: COc1cc(-c2ccc(COc3ccc4c(c3)[C@]3(CCC4)CC[C@H]3C(=O)O)cc2[C@@H]2CCCC2(C)C)c(F)cn1] or 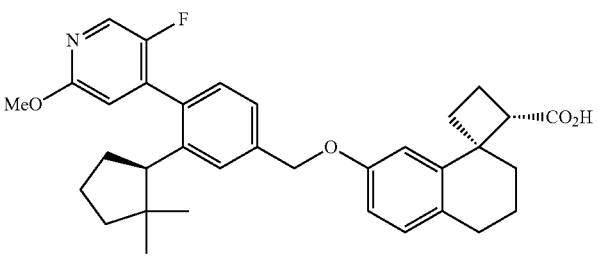 [SMILES: COc1cc(-c2ccc(COc3ccc4c(c3)[C@@]3(CCC4)CC[C@@H]3C(=O)O)cc2[C@@H]2CCCC2(C)C)c(F)cn1] or 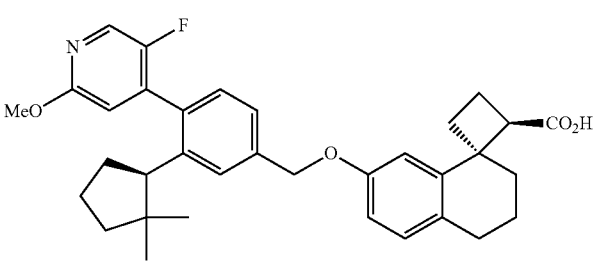 [SMILES: COc1cc(-c2ccc(COc3ccc4c(c3)[C@@]3(CCC4)CC[C@H]3C(=O)O)cc2[C@@H]2CCCC2(C)C)c(F)cn1] | ++ | ND |
| 154 | 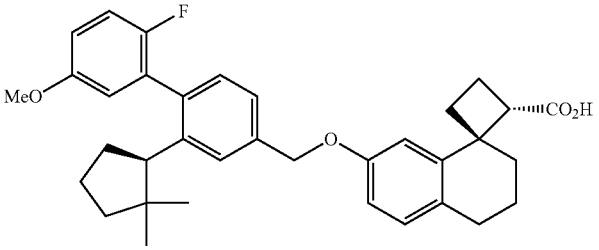 [SMILES: COc1ccc(F)c(-c2ccc(COc3ccc4c(c3)[C@]3(CCC4)CC[C@@H]3C(=O)O)cc2[C@@H]2CCCC2(C)C)c1] or | +++ | ++++ |

TABLE-continued

Assay Data For Human GPR40

| No. | Structure[a] | Aequorin EC$_{50}$[b,c] | IP3 EC$_{50}$[c,d] |
|---|---|---|---|
| 155 | Diastereomer of 152 | +++ | +++++ |
| 156 | Diastereomer of 153 | +++ | ++++ |
| 157 | Diastereomer of 152 | ++ | ND |
| 158 | | +++ | ++++ |

TABLE-continued

Assay Data For Human GPR40

| No. | Structure[a] | Aequorin $EC_{50}$[b,c] | IP3 $EC_{50}$[c,d] |
|---|---|---|---|

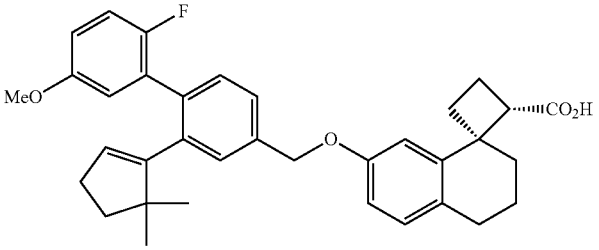 [SMILES: COc1ccc(F)c(-c2ccc(COc3ccc4c(c3)[C@@]3(CCC4)CC[C@@H]3C(=O)O)cc2C2=CCCC2(C)C)c1]

or

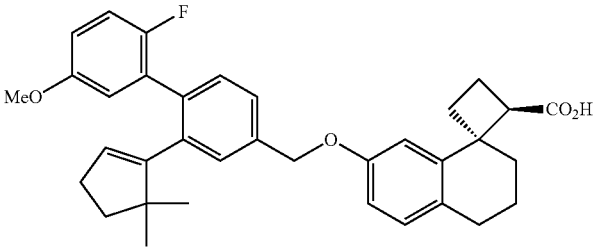 [SMILES: COc1ccc(F)c(-c2ccc(COc3ccc4c(c3)[C@@]3(CCC4)CC[C@H]3C(=O)O)cc2C2=CCCC2(C)C)c1]

[a]When present, the "⌇⌇" bond indicates a mixture of stereoisomers are present in the exemplary compound or indicates a mixture of cis and trans isomers when attached to a double bond.
[b]Aequorin assay data
[c]$EC_{50}$ Ranges:
+ $EC_{50} > 10$ μM
++ $1$ μM ≤ $EC_{50}$ ≤ $10$ μM
+++ $0.1$ μM ≤ $EC_{50}$ < $1$ μM
++++ $0.01$ μM ≤ $EC_{50}$ < $0.1$ μM
+++++ $EC_{50}$ > $0.01$ μM
[d]Inositol phosphate assay data
[e]ND means not determined
[f]One of Examples of 68, 69, 70, and 71 was synthesized (see Example 151)

All publications and patent applications cited in this specification are hereby incorporated by reference as if each individual publication or patent application were specifically and individually indicated to be incorporated by reference. Each publication and patent application cited herein is incorporated in its entirety as if fully set forth herein. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:
1. A compound of formula I'A or I'B:

I'A

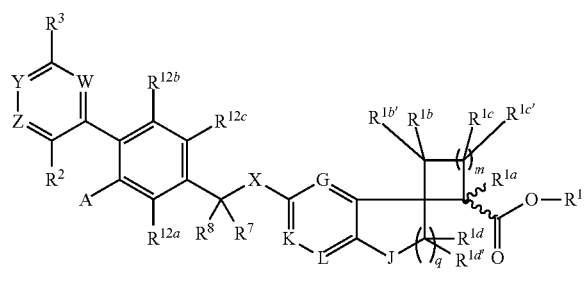

-continued

I'B

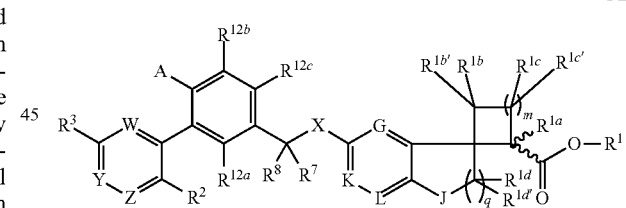

or a pharmaceutically acceptable salt, stereoisomer, or a mixture thereof,
wherein
G is $CR^{11a}$;
K is $CR^{11b}$;
L is $CR^{11c}$;
X is O;
J is $CR^cR^d$; wherein $R^c$ and $R^d$ are H;
W is CH;
Y is CH or N;
Z is CH;
A is selected from —H, —$(C_1-C_{12})$alkyl; —$(C_2-C_{12})$alkenyl; —$(C_1-C_{12})$alkyl-O—$(C_1-C_4)$alkyl; —$(C_1-C_{12})$alkyl-OH; —$(C_1-C_{12})$alkyl-O—$(C_2-C_4)$alkenyl; —$(C_2-C_{12})$alkenyl-O—$(C_1-C_4)$alkyl; —$(C_2-C_{12})$alkenyl-OH; —$(C_2-C_{12})$alkenyl-O—$(C_2-C_4)$alkenyl; —O—$(C_1-C_{12})$alkyl; —O—$(C_2-C_{12})$alkenyl; $S(C_1-C_{12})$alkyl;

—S—(C$_2$-C$_{12}$)alkenyl; —S(O)—(C$_1$-C$_{12}$)alkyl; —S(O)—(C$_2$-C$_{12}$)alkenyl; —S(O)$_2$—(C$_1$-C$_{12}$)alkyl; or —S(O)$_2$—(C$_2$-C$_{12}$)alkenyl; further wherein the alkyl and alkenyl groups of —(C$_1$-C$_{12}$)alkyl, —(C$_2$-C$_{12}$)alkenyl, —(C$_1$-C$_{12}$)alkyl-O—(C$_1$-C$_4$)alkyl, —(C$_1$-C$_{12}$) alkyl-O—H, —(C$_1$-C$_{12}$)alkyl-O—(C$_2$-C$_4$)alkenyl, —(C$_2$-C$_{12}$)alkenyl-O—(C$_1$-C$_4$)alkyl, —(C$_2$-C$_{12}$)alkenyl-OH, —(C$_2$-C$_{12}$)alkenyl-O—(C$_2$-C$_4$)alkenyl, —O—(C$_1$-C$_{12}$)alkyl, and —O—(C$_2$-C$_{12}$)alkenyl are unsubstituted or are substituted with from 1 to 4 substituents selected from —F, —Cl, —OH, (═O), —NH$_2$, NH(C$_1$-C$_4$)alkyl, —N((C$_1$-C$_4$)alkyl)$_2$, unsubstituted —(C$_1$-C$_2$)alkyl, or unsubstituted —O—(C$_1$-C$_2$)alkyl;

R$^1$ is H or —(C$_1$-C$_6$)alkyl;
R$^{1a}$ is —H;
R$^{1b}$ is —H;
R$^{1b'}$ is —H;
R$^{1d}$ is —H;
R$^{1d'}$ is —H;
R$^2$ is —F or —Cl;
R$^3$ is —O—(C$_1$-C$_3$)alkyl;
R$^7$ and R$^8$ are —H;
R$^{11a}$ is selected from —H, —F, —Cl, —(C$_1$-C$_4$)alkyl, or —O(C$_1$-C$_4$)alkyl;
R$^{11b}$ and R$^{11c}$ are —H;
R$^{12a}$ and R$^{12b}$ are —H;
R$^{12c}$ is selected from —H, —F, —Cl, —(C$_1$-C$_4$)alkyl, or —O(C$_1$-C$_4$)alkyl;
m is 0; and
q is selected from 0, 1, or 2;
wherein the ~~ indicates that the R$^{1a}$ and —C(═O)—O—R$^1$ may be attached to either side of the ring to which the ~~ is attached and either R or S stereochemistry is allowed.

2. The compound of claim 1, wherein R$^3$ is —O(C$_1$-C$_2$) alkyl.

3. The compound of claim 2, wherein R$^3$ is methoxy.

4. The compound of claim 1, wherein A is (C$_3$-C$_{10}$)alkyl or (C$_4$-C$_{10}$)alkenyl.

5. The compound of claim 1, wherein A is a group of formula A'

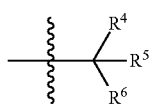

where the wavy line indicates the point of attachment; and R$^4$, R$^5$, and R$^6$ are independently selected from H, F, (C$_1$-C$_4$)alkyl, wherein at least two of R$^4$, R$^5$, and R$^6$ are other than H; or two or three of R$^4$, R$^5$, and R$^6$ join together to form an optionally substituted saturated or partially unsaturated 3-8 membered monocyclic or bicyclic ring.

6. The compound of claim 1, wherein A is —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-OH, —(C$_3$-C$_{12}$)alkenyl-O—(C$_1$-C$_4$)alkyl, —(C$_3$-C$_{12}$)alkenyl-OH, —O—(C$_4$-C$_{12}$)alkyl, or —O—(C$_4$-C$_{12}$)alkenyl, further wherein the alkyl and alkenyl groups of —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-O—H, —(C$_3$-C$_{12}$)alkenyl-O—(C$_1$-C$_4$)alkyl, —(C$_3$-C$_{12}$)alkenyl-OH, —O—(C$_4$-C$_{12}$) alkyl, or —O—(C$_4$-C$_{12}$)alkenyl are unsubstituted or are substituted with from 1 to 3 substituents selected from —F, —Cl, —OH, (═O), —NH$_2$, NH(C$_1$-C$_4$)alkyl, —N((C$_1$-C$_4$) alkyl)$_2$, or unsubstituted —O—(C$_1$-C$_2$)alkyl.

7. The compound of claim 1, wherein A is selected from

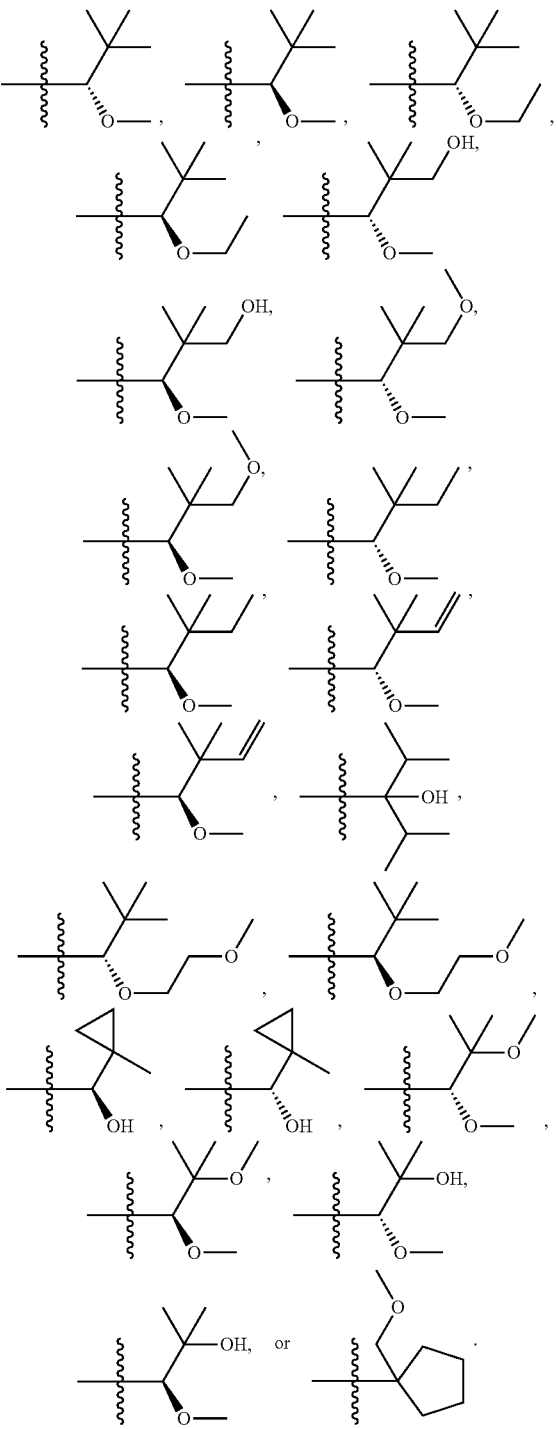

8. The compound of claim 1, wherein A is

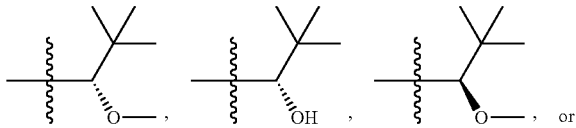

-continued

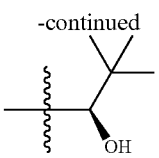

9. The compound of claim 1, wherein A is a $(C_5-C_7)$cycloalkyl group or a $(C_5-C_7)$cycloalkenyl group optionally substituted with 1, 2, 3, or 4 methyl groups.

10. The compound of claim 9, wherein A has the formula

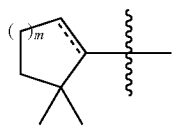

wherein m is 1, 2, or 3, and the dashed line indicates a single or double bond.

11. The compound of claim 1, wherein the compound has the formula I'A.

12. The compound of claim 1, wherein the compound has the formula I'B.

13. The compound of claim 1, wherein Y is C—H.

14. The compound of claim 1, wherein Y is N.

15. The compound of claim 1, wherein $R^{12c}$ is H.

16. The compound of claim 1, wherein $R^{12c}$ is F.

17. The compound of claim 1, wherein $R^{11a}$ is H or F.

18. The compound of claim 1, wherein $R^2$ is —Cl.

19. The compound of claim 1, wherein $R^2$ is F and $R^3$ is methoxy.

20. The compound of claim 19, wherein Y is C—H.

21. The compound of claim 19, wherein Y is N.

22. The compound of claim 19, wherein $R^{12c}$ is H or F.

23. The compound of claim 19, wherein $R^{11a}$ is H or F.

24. The compound of claim 19, wherein $R^1$ is H.

25. A pharmaceutical composition, comprising: a pharmaceutically acceptable carrier, diluent, or excipient, and the compound of claim 1.

* * * * *